United States Patent
Imamura et al.

(10) Patent No.: US 11,442,051 B2
(45) Date of Patent: Sep. 13, 2022

(54) METHOD AND DEVICE FOR IDENTIFYING SAMPLE USING CHEMICAL SENSOR

(71) Applicant: NATIONAL INSTITUTE FOR MATERIALS SCIENCE, Tsukuba (JP)

(72) Inventors: Gaku Imamura, Tsukuba (JP); Genki Yoshikawa, Tsukuba (JP); Takashi Washio, Suita (JP)

(73) Assignee: NATIONAL INSTITUTE FOR MATERIALS SCIENCE, Ibaraki (JP)

(*) Notice: Subject to any disclaimer, the term of this patent is extended or adjusted under 35 U.S.C. 154(b) by 261 days.

(21) Appl. No.: 16/488,866

(22) PCT Filed: Feb. 16, 2018

(86) PCT No.: PCT/JP2018/005551
§ 371 (c)(1),
(2) Date: Aug. 26, 2019

(87) PCT Pub. No.: WO2018/155344
PCT Pub. Date: Aug. 30, 2018

(65) Prior Publication Data
US 2019/0391122 A1    Dec. 26, 2019

(30) Foreign Application Priority Data

Feb. 27, 2017    (JP) .............................. JP2017-034419

(51) Int. Cl.
*G01N 33/00* (2006.01)
*G01N 19/00* (2006.01)
(Continued)

(52) U.S. Cl.
CPC ..... *G01N 33/0022* (2013.01); *G01N 33/0062* (2013.01); *G01N 2033/0068* (2013.01)

(58) Field of Classification Search
CPC .............. G01N 33/0022; G01N 19/00; G01N 2033/0068; G01N 33/0034;
(Continued)

(56) References Cited

U.S. PATENT DOCUMENTS 3,849,653 A * 11/1974 Sakaide ............. G01N 33/0022
250/361 C
6,089,206 A * 7/2000 Suzuki .................. F02D 41/307
123/295

(Continued)

FOREIGN PATENT DOCUMENTS

JP    2003-506714 A    2/2003
JP    2014-139557 A    7/2014
(Continued)

OTHER PUBLICATIONS

Llobet, E., et al., "Quantitative Vapor Analysis Using the Transient Response of Non-Selective Thick-Film Tin Oxide Gas Sensors," Proceedings of International Solid-State Sensors and Actuators Conference (Transducers '97), vol. 2, Jun. 16-19, 1997, pp. 971-974. (Year: 1997).*

(Continued)

*Primary Examiner* — Jeffrey P Aiello
(74) *Attorney, Agent, or Firm* — Crowell & Moring LLP

(57) ABSTRACT

Provided is a novel analysis method which, when a chemical sensor is used to perform a measurement, makes it possible to identify a sample without controlling or monitoring a change in the time the sample is introduced. According to the present invention, a sample can be identified without knowing a change in the time the sample is introduced, by using a chemical sensor having a plurality of channels each having different characteristics to perform a measurement, and performing an analysis on the basis of responses obtained from each channel.

13 Claims, 13 Drawing Sheets

(51) Int. Cl.
   *G01N 29/00* (2006.01)
   *G01N 35/00* (2006.01)
   *G06K 9/00* (2022.01)

(58) Field of Classification Search
   CPC ......... G01N 33/0062; G01N 35/00693; G06K 9/00536; G06K 9/627
   USPC ............ 435/287.1; 436/161; 506/9; 702/19, 702/22–23, 30, 188
   See application file for complete search history.

(56) References Cited

U.S. PATENT DOCUMENTS

| | | | |
|---|---|---|---|
| 6,285,807 B1* | 9/2001 | Walt | G01N 21/7703 250/227.14 |
| 2001/0029774 A1* | 10/2001 | Grate | G01N 29/022 73/23.35 |
| 2002/0141901 A1 | 10/2002 | Lewis et al. | |
| 2006/0229820 A1* | 10/2006 | Kemp | G01N 33/0034 702/19 |
| 2011/0097740 A1* | 4/2011 | Paek | G01N 33/54366 435/7.9 |
| 2011/0244584 A1* | 10/2011 | Haick | G01N 33/497 436/71 |
| 2014/0165702 A1* | 6/2014 | Tanabe | G01N 29/022 73/24.06 |
| 2014/0233039 A1* | 8/2014 | Takahashi | G01N 21/253 356/519 |
| 2017/0248514 A1* | 8/2017 | Pavey | G01N 33/0036 |
| 2017/0325724 A1* | 11/2017 | Wang | A61B 5/14521 |

FOREIGN PATENT DOCUMENTS

| | | |
|---|---|---|
| JP | 2017-156254 A | 9/2017 |
| WO | WO 2011/148774 A1 | 12/2011 |

OTHER PUBLICATIONS

Gardner, J.W, et al., "Prediction of health of dairy cattle from breath samples using neural network with parametric model of dynamic response of array of semiconducting gas sensors," Science, Measurement and Technology, IEE Proceedings), vol. 146, No. 2, Mar. 1997, pp. 102-106. (Year: 1997).*

Extended European Search Report for Europe Application No. 18756666.6, dated Nov. 10, 2020, 11 pages.

Llobet et al., "Quantitative Vapor Analysis Using the Transient Response of Non-Selective Thick-Film Tin Oxide Gas Sensors" Int'l Conference on Solid-State Sensors and Actuators, Digest of Technical Papers; New York, NY: IEEE; US, vol. 2, dated Jun. 16, 1997, pp. 971-974, XP010240638.

Gardner et al., "Prediction of Health of Dairy Cattle from Breath Samples Using Neural Network with Parametric Model of Dynamic Response of Array of Semiconducting Gas Sensors" IEE Proceedings: Science, Measurement and Technology, IEE, Stevenage, Herts, GB, vol. 146, No. 2, dated Mar. 4, 1999, pp. 102-106, XP006013745.

Yoshikawa et al., "Nanomechanical Membrane-type Surface Stress Sensor," Nano Letters, vol. 11, 2011, American Chemical Society, ACS Publications, pp. 1044-1048.

International Search Report in International Application No. PCT/JP2018/005551, dated May 22, 2018, 1 page.

* cited by examiner

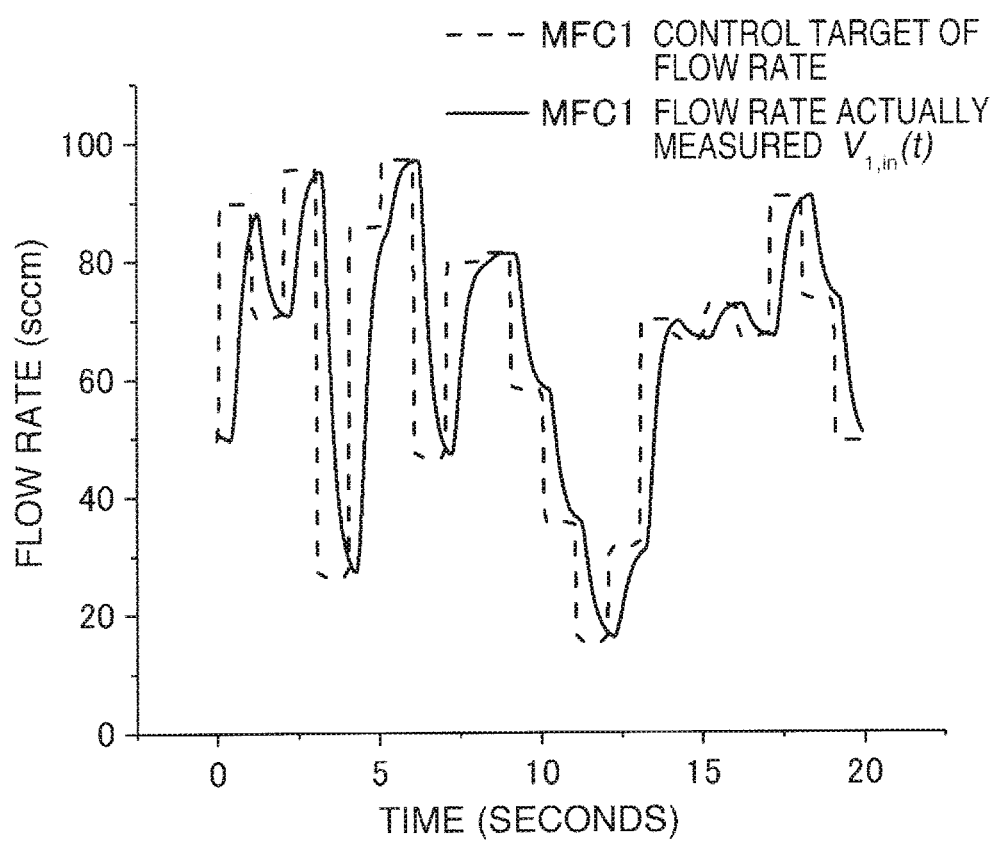

METHOD AND DEVICE FOR IDENTIFYING SAMPLE USING CHEMICAL SENSOR

This application is a 371 application of PCT/JP2018/005551 having an international filing date of Feb. 16, 2018, which claims priority to JP2017-034419 filed Feb. 27, 2017, the entire content of each of which is incorporated herein by reference.

RELATED APPLICATIONS

This application is a 371 application of PCT/JP2018/005551 having an international filing date of Feb. 16, 2018, which claims priority to JP2017-034419 filed Feb. 27, 2017, the entire content of each of which is incorporated herein by reference.

TECHNICAL FIELD

The present invention relates to a measurement analysis mode using a chemical sensor, or more specifically, to a method of identifying a sample by using a chemical sensor provided with multiple channels. The present invention also relates to a device configured to identify a sample based on the aforementioned identification method.

BACKGROUND ART

Nowadays, various devices are connected to one another through networks and allowed to mutually exchange massive data. Given the situation, cloud computing, big data analyses, the Internet of things (IoT), and so forth have been drawing attention as new services and systems based on this technology. Sensors are extremely important pieces of hardware for utilizing these new techniques. Among other things, chemical sensors designed to analyze liquid and gas samples are in high demand in the fields of food, safety, environment, and so forth. Meanwhile, advances in MEMS technologies have brought micro chemical sensor elements into realization. Accordingly, it is expected that a mobile terminal or the like equipped with such a micro chemical sensor will be able to automatically conduct or allow anybody to easily conduct a measurement of a sample and enable various analyses by combining data thus obtained with the new IT techniques mentioned above.

Flow rate control of a sample is often a problem in the measurement using the chemical sensor. In an ordinary measurement using the sensor, a sample is introduced into the sensor element while controlling its flow rate by using a pump, a mass flow controller, and the like and the sample is identified by analyzing signals obtained as a consequence. Since this measurement method requires installation of the pump and the mass flow controller in a measurement device, a measurement system cannot be reduced in size as a whole even though the sensor element is very small. On the other hand, there is also a measurement method in which the flow rate to introduce the sample is just monitored without controlling it, and the sample is identified based on a correspondence between the signal and a change in flow rate to introduce the sample with time. Nevertheless, even in this case, it is still necessary to monitor the flow rate and a component such as a flowmeter for monitoring the flow rate needs to be installed in a flow passage.

CITATION LIST

Patent Literature

Patent Literature 1: WO 2011/148774

Non-Patent Literature

Non-patent Literature 1: G. Yoshikawa, T. Akiyama, S. Gautsch, P. Vettiger, and H. Rohrer, "Nanomechanical Membrane-type Surface Stress Sensor", Nano Letters, Vol. 11, pp. 1044-1048 (2011).

SUMMARY OF INVENTION

Technical Problem

An object of the present invention is to provide a novel analysis method that enables identification of a sample without controlling or monitoring a change in sample introduction with time when a measurement using a chemical sensor takes place.

Solution to Problem

According to an aspect of the present invention, there is provided a sample identification method using a chemical sensor, comprising providing a sample to be identified to a chemical sensor having a plurality of channels as inputs in accordance with identical first functions that vary with time, and thus obtaining a group of outputs for the sample to be identified including a plurality of time-varying outputs from the plurality of channels; providing a control sample to as an input in accordance with identical second functions that vary with time to a chemical sensor having a plurality of channels which chemical sensor is identical to or has the same characteristics as the formerly mentioned chemical sensor, and obtaining a group of outputs for a control sample including a plurality of time-varying outputs from the plurality of channels; performing a first comparison or a second comparison, the first comparison being obtaining relationships between the group of the outputs for the sample to be identified and the group of the outputs for the control sample for each of the corresponding channels, and then comparing the relationships between the plurality of channels, and the second comparison being obtaining relationships between the outputs corresponding to the channels within each of the group of the outputs for sample to be identified and the group of the outputs for the control sample, and then comparing the thus obtained relationships between the outputs for the sample to be identified and the outputs for the control sample; and identifying the sample to be identified and the control sample based on a result of the first or the second comparisons Here, in each of the channels of the chemical sensor, the output from the channel may be describable in a separative form of a multiplication or an addition of an input to the channel and a transfer function (h) of the channel.

Meanwhile, each of the outputs for the sample to be identified and the outputs for the control sample may be expressed by the following formula (A) using a transfer function of the corresponding one of the plurality of channels, $$y_{q,c}(t) = h_{q,c}(t) * x_q(t) \qquad (A),$$

(where $x_q(t)$ represents any of the first function and the second function expressed as a time function, $y_{q,c}(t)$ represents the outputs for the sample to be identified and the outputs for the control sample expressed as a time function, $h_{q,c}(t)$ represents the transfer function expressed as a time function, the suffix q indicates discrimination of the control sample and the sample to be identified, c indicates a channel number in a range from 1 to C, and * represents a convolution operation). Moreover, each of the first and second comparisons may be a comparison where, with respect to simultaneous expressions including C polynomial concerning the sample to be identified and C polynomials concerning the control sample obtained by transforming the formula (A) so that the formula (A) is expressed in polynomials, an identification is made whether or not the transfer function in the formula (A) concerning the sample to be identified is the same as the transfer function in the formula (A) concerning the control sample.

In the meantime, the polynomials of the transform so that the formula (A) is expressed in polynomials may be expressed by a multiplication formula (B) in the form of $$Y=HX \tag{B},$$

where X and Y are the input to and the output from the channel respectively, and H is a variable or a constant corresponding to the transfer function between the input and the output.

Meanwhile, the first comparison may comprise obtaining ratios between each pair of the corresponding channels among the C polynomial expressions in the form of the formula (B) concerning the sample to be identified and the C polynomial expressions in the form of the formula (B) concerning the control sample; and comparing the obtained ratios among the multiple channels.

On the other hand, the second comparison may comprise obtaining first ratios between the C polynomial expressions in the form of the formula (B) concerning the sample to be identified; obtaining second ratios between the C polynomial expressions in the form of the formula (B) concerning the control sample; and comparing the first ratios and the second ratios between the corresponding channels.

Meanwhile, the transform of the formula (A) so that the formula (A) is expressed in polynomials may be a transform of the convolution operation in the formula (A) into a multiplication of matrices or vectors.

Alternatively, the transform from the formula (A) so that the formula (A) is expressed in polynomials may be a transform of the formula (A) from a function in the time domain into a function in the frequency domain.

Meanwhile, the first function and the second function may be determined independently of each other.

In the meantime, at least one of the first function and the second function may be a random function.

Meanwhile, the outputs for the sample to be identified and the outputs for the control sample may be subjected to time discretization.

According to another aspect of the present invention, there is provided a sample identification device which includes multiple chemical sensors; and an information processing device connected to the chemical sensors. Here, the sample identification device conducts the sample identification method using any one of the above-mentioned chemical sensors.

Advantageous Effects of Invention

According to the present invention, the same input is measured with the sensor provided with the multiple channels having different characteristics. Thus, it is possible to perform identification based on features of the sample (a chemical species, a concentration, a temperature, and the like of the sample) without controlling or monitoring a change in sample introduction with time. To be more precise, the present invention makes it possible to evaluate whether or not an unknown sample matches a known sample by comparing measurement data obtained from the unknown sample with data of the known sample measured in advance.

BRIEF DESCRIPTION OF DRAWINGS

FIG. 6 is a graph showing changes in control flow rate and actually measured flow rate of MFC1 in the example.

DESCRIPTION OF EMBODIMENTS

An aspect of the present invention provides a mode of identifying a sample in which, when the sample is introduced into a chemical sensor provided with multiple channels having different characteristics, the sample is identified by performing an analysis based on responses from the respective channels. In this way, there is provided an identification mode based on features of the sample (a chemical species, a concentration, a temperature, and the like of the sample) without controlling or monitoring a change in sample introduction with time.

The present invention is configured to analyze a sample by a measurement using a chemical sensor. The chemical sensor is a broad concept which signifies a sensor designed to identify and detect various molecules and ions existing in a gas phase, a liquid phase, and the like. As an example of the chemical sensor, this specification will pick up and describe a membrane-type surface stress sensor (MSS), which is one of nanomechanical sensors designed to detect very small expansions or contractions of a membrane attributed to adsorption of a chemical substance representing a particular chemical species and to convert the expansions or contractions into electrical signals. Nevertheless, the chemical sensor represents the concept based on the detection target and an operating principle, a structure, and the like thereof do not matter. For instance, various other principles are applied as the operating principles of chemical sensors, including those that utilize various chemical reactions, those that utilize electrochemical phenomena, those that utilize interactions between a semiconductor element and various substances present in the vicinity thereof, those that utilize biological functions such as enzymes, and so forth. A sensor body usable in the present invention is not limited to any particular structures, operating principles, and the like as long as the sensor body is designed to show a response of some sort to a sample.

<Theoretical Backgrounds>

Figure 1:
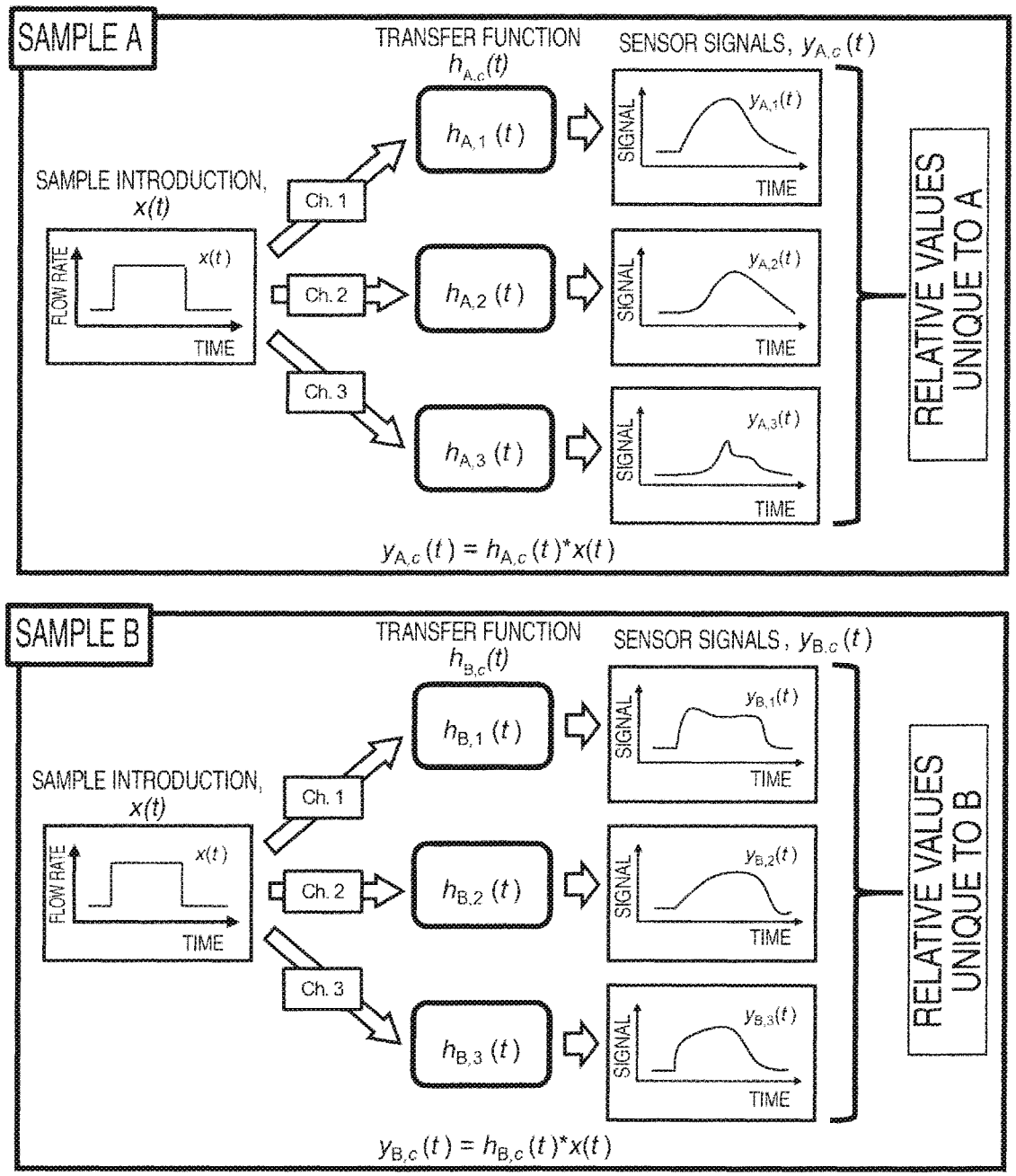
FIG. 1 is a diagram illustrating a case of performing measurements of samples A and B by using a chemical sensor provided with multiple channels, which depicts relations among inputs of the samples, outputs obtained in the respective channels, and transfer functions to connect the inputs to the corresponding outputs in the time domain.

FIG. 1 shows a conceptual diagram of the present invention. When there is an input to the chemical sensor provided with the multiple channels having different characteristics, different signals are obtained from the respective channels. Now, a connection between the input and each signal will be defined as a "transfer function". In many cases, such a transfer function is unique to a combination of a sensor and a sample, which does not change with an input of a time or frequency function of any kind. Accordingly, it is possible to identify the sample by calculating the transfer function in which introduction of the sample is defined as an input while the signal is defined as an output. Now, a case of conducting a measurement by using the sensor formed from the multiple channels having the different characteristics will be considered. In this case, all the channels have the same input whereas the signals obtained therefrom vary among the channels since the respective channels have different transfer functions with respect to the sample. Since all the channels have the same input, it is possible to compare the transfer functions among the channels by comparing the signals among the channels in response to an arbitrary input. Here, relationships of the transfer functions among the channels are also unique to the sample, so that the sample can be identified based on the relationships. In this way, it is possible to identify the sample without controlling or monitoring the input but solely by using relative values of the signals among the channels.

Figure 2:
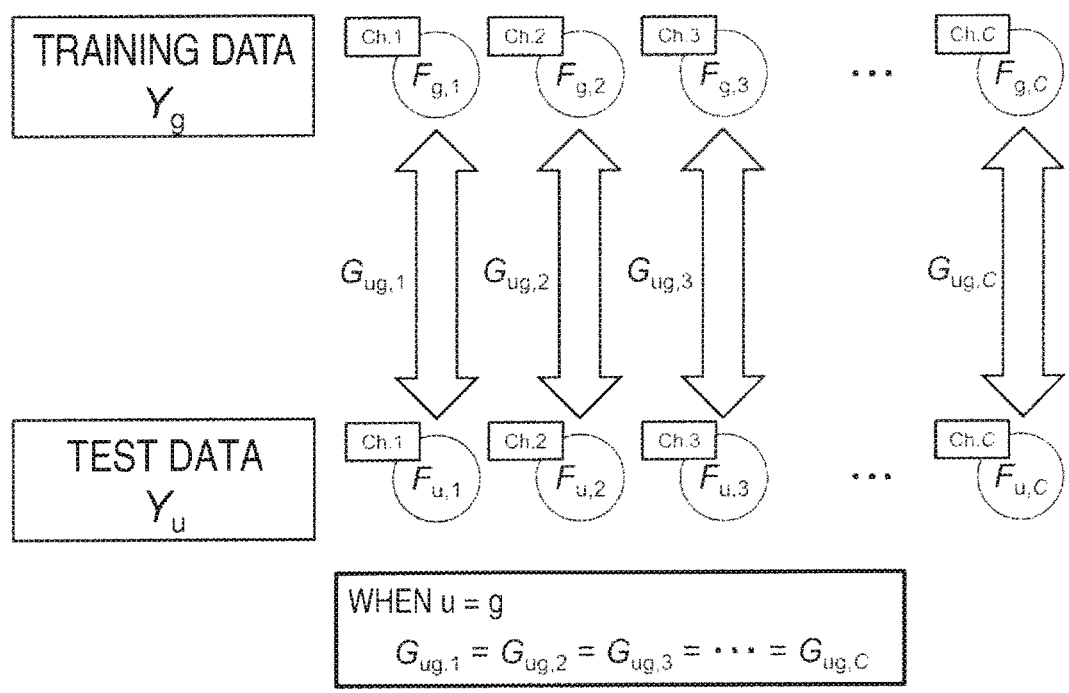
FIG. 2 is a diagram illustrating a concept of an analysis method in which a sample is identified by comparing features obtained from test data with features obtained from training data with respect to each of the channels.
Figure 3:
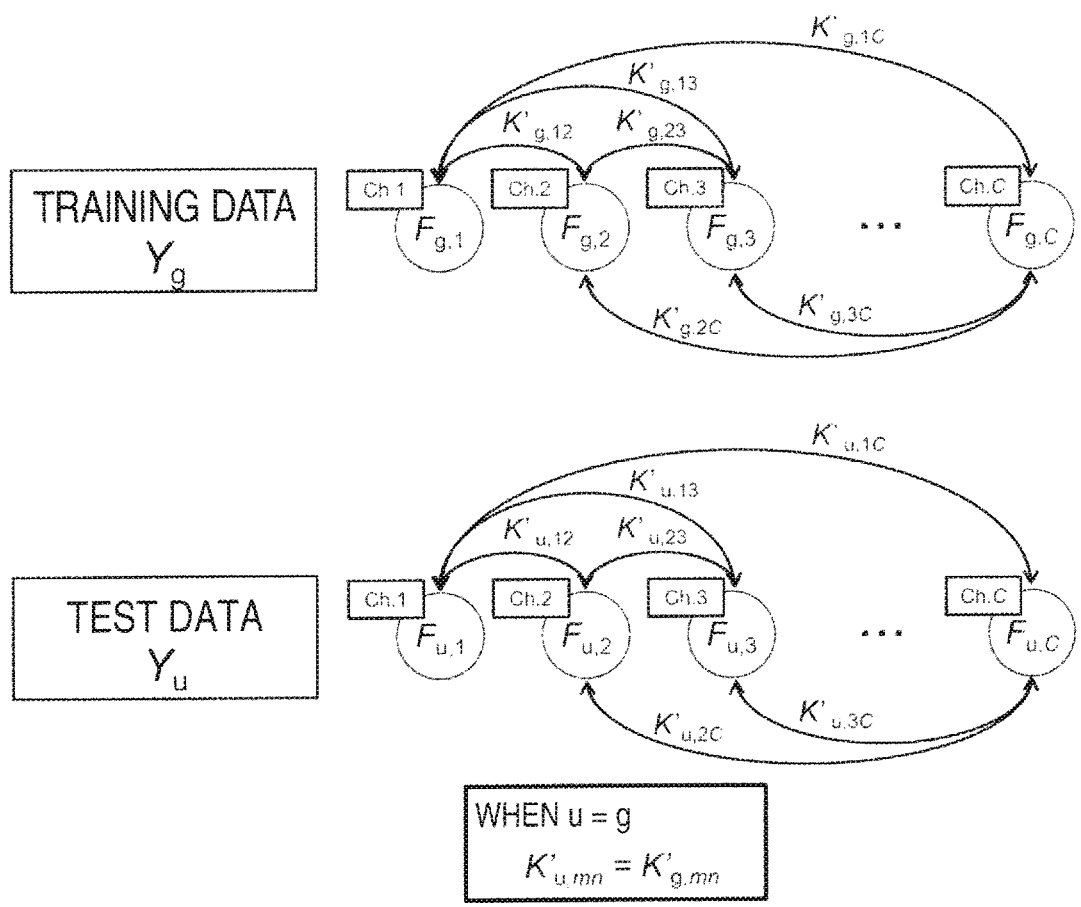
FIG. 3 is a diagram illustrating a concept of an analysis method in which a sample is identified by comparing features between two channels.

When the sample is identified by using the chemical sensor provided with the multiple channels as described above, the identification method falls roughly into two conceivable ways. Now, let us consider a case where a measurement is performed on a sample (also referred to as a sample to be measured) u, of which chemical species, concentration, temperature, and the like are unknown, by using a chemical sensor provided with C pieces of channels so as to evaluate whether or not the sample u matches a known sample g that is measured in advance. As shown in FIGS. 2 and 3, regarding training data $Y_g$ obtained by the measurement of the known sample g and data $Y_u$ (which will be referred to as test data in this specification according to the terminology to call data for verifying an estimation as test data, which is in heavy usage in the fields of the machine learning and the like) obtained by the measurement of the unknown sample u, it is assumed that features $F_{q,c}$ (where q is either g or u) is obtained in a c-th channel. Here, a first method is a method of obtaining new features $G_{ug,c}$ from the amounts $F_{u,c}$ and $F_{g,c}$ and comparing the features $G_{ug,c}$ among the respective channels as shown in FIG. 2. In this instance, the functions to be inputted need to be considered different depending on the measurement. Accordingly, the features $G_{ug,c}$ to be obtained are values which are not determined solely by the sample but are values that vary depending on the measurement even in the case of the same combination of the samples g and u. However, when the unknown sample u matches the learned sample g, the values $G_{ug,c}$ are the same among all the channels. Accordingly, it is possible to evaluate whether or not the unknown sample u is the same as the known sample g by comparing the values $G_{ug,c}$ among the channels. Another method is a method of calculating new features $K'_{g,mn}$ in terms of arbitrary channels m and n from features $F_{q,m}$ and $F_{q,n}$ to be obtained from the respective channels as shown in FIG. 3. The features $K'_{g,mn}$ obtained in this instance are unique to the sample, and the values are always the same regardless of any measurement as long as the sample is the same. Accordingly, it is possible to evaluate whether or not the unknown sample u is the same as the known sample g by obtaining features $K'_{u,mn}$ concerning the unknown sample u from the two arbitrary channels m and n and comparing the amounts with learned amounts $K'_{g,mn}$ of the sample g.

The above-described identification of the sample is feasible when an output (y) can be described in the form of either a multiplication or an addition of an input (x) and a transfer function (h) thereof separately from the other outputs. Here, if it is possible to describe the form of the multiplication, the multiplication is transformed into the addition by taking the logarithm, and vice versa. Therefore, it is sufficient just by explaining one of these forms. Accordingly, the case of the multiplication will be described in the following. A system in which a relationship between the input and the output is linear will be considered as an example. First, an inflow amount of the sample g into a sensor element is defined as $x_g(t)$ and a sensor signal $y_{g,c}(t)$ is assumed to be obtained in the channel c as a consequence. Note that t represents the time. Here, assuming that $x_g(t)$ and $y_{g,c}(t)$ have linearity, the sensor signal $y_{g,c}(t)$ can be expressed by the following convolution while using a time transfer function $h_{g,c}(t)$:

[MATH. 1]

$$y_{g,c}(t) = \int_0^t h_{g,c}(t-\tau) x_g(t-\tau) d\tau = h_{g,c}(t) * x_g(t) \quad (1)$$

In the convolution integral, an integration interval is usually set from $-\infty$ to $+\infty$. However, according to the law of casualty, $x_g(t)$ in the future after the time t will not have an effect on current $y_{g,c}(t)$. Accordingly, $\tau<0$ is excluded from the integration interval. In the meantime, the measurement is performed for a period that is sufficiently longer than the time required for transfer of the signal from $x_g(t)$ to $y_{g,c}$ and an effect of the inflow amount $x_g(t)$ in the past before the measurement start time t=0 on current $y_{g,c}(t)$ is assumed to be negligible. Thus, t−τ<0, or more specifically, τ>t is excluded from the integration interval. As a consequence, the integration interval can be defined as [0: t]. This time transfer function $h_{g,c}(t)$ does not depend on the inflow amount $x_g(t)$ of the sample g as long as it is the linear system, but varies depending on features of the sample on the other hand.

Next, this will be considered with an expression in terms of a frequency domain. The input $x_g(t)$, the output $y_{g,c}(t)$, and the time transfer function $h_{g,c}(t)$ in the case of considering with the time domain can be expressed as $X_g(f)$, $Y_{g,c}(f)$, and $H_{g,c}(f)$, respectively, as functions of the frequency f by conducting the Fourier transform or the Laplace transform. In this instance, $Y_{g,c}(f)$ can be described in the form of a multiplication by using $X_g(f)$ and the frequency transfer function $H_{g,c}(f)$ as:

[MATH. 2]

$$Y_{g,c}(f) = H_{g,c}(f)X_g(f) \qquad (2)$$

As with the time transfer function, the frequency transfer function $H_{g,c}(f)$ also varies depending on the features of the sample. Accordingly, the sample can be identified by obtaining $H_{g,c}(f)$ by the measurement. Note that the formula (1) and the formula (2) are the expressions in terms of the time domain and the frequency domain, respectively, and are mathematically equivalent to each other.

Here, the measurement with multiple channels will be considered. According to the formula (1), when the sample g is inputted at $x_g(t)$, the signals $y_g,1(t), y_g,2(t), \ldots, y_{g,c}(t)$ to be obtained in the channels $c=1, 2, \ldots, C$ can be expressed by using the time transfer functions $h_{g,1}(t), h_{g,2}(t), \ldots, h_{g,c}(t)$ applicable to the respective channels as:

[MATH. 3]

$$\begin{bmatrix} y_{g,1}(t) \\ y_{g,2}(t) \\ \vdots \\ y_{g,C}(t) \end{bmatrix} = \begin{bmatrix} h_{g,1}(t) * x_g(t) \\ h_{g,2}(t) * x_g(t) \\ \vdots \\ h_{g,C}(t) * x_g(t) \end{bmatrix}. \qquad (3)$$

Next, a case of inputting a different sample u into the same sensor will be considered. If the input in this case is $x_u(t)$ while a signal obtained in each channel c is $y_{u,c}(t)$ and the frequency transfer function applicable to each channel c is $h_{u,c}(t)$, then the following expression is obtained as with the formula (3):

[MATH. 4]

$$\begin{bmatrix} y_{u,1}(t) \\ y_{u,2}(t) \\ \vdots \\ y_{u,C}(t) \end{bmatrix} = \begin{bmatrix} h_{u,1}(t) * x_u(t) \\ h_{u,2}(t) * x_u(t) \\ \vdots \\ h_{u,C}(t) * x_u(t) \end{bmatrix}. \qquad (4)$$

Let us consider the same concept in light of the frequency domain. According to the formula (2), each signal $Y_{g,c}(f)$ to be obtained in each channel c in response to the input $X_g(f)$ of the sample g can be expressed by using the frequency transfer function $H_{g,c}(f)$ applicable to each channel as:

[MATH. 5]

$$\begin{bmatrix} Y_{g,1}(f) \\ Y_{g,2}(f) \\ \vdots \\ Y_{g,C}(f) \end{bmatrix} = \begin{bmatrix} H_{g,1}(f) \\ H_{g,2}(f) \\ \vdots \\ H_{g,C}(f) \end{bmatrix} X_g(f). \qquad (5)$$

Meanwhile, if a different sample u is inputted to the same sensor at $X_u(f)$, each signal $Y_{u,c}(f)$ obtained in each channel c can be expressed by using the frequency transfer function $H_{u,c}(f)$ applicable to each channel c concerning the sample u as:

[MATH. 6]

$$\begin{bmatrix} Y_{u,1}(f) \\ Y_{u,2}(f) \\ \vdots \\ Y_{u,C}(f) \end{bmatrix} = \begin{bmatrix} H_{u,1}(f) \\ H_{u,2}(f) \\ \vdots \\ H_{u,C}(f) \end{bmatrix} X_u(f). \qquad (6)$$

Now, assuming that u is the unknown sample that is expected to be identified and g is the measurement sample for training, let us consider a way to evaluate whether or not u matches g by using only $y_{u,c}(t)$ and $y_{g,c}(t)$ or using only $Y_{u,c}(f)$ and $Y_{g,c}(f)$ but without using the input $x_q(t)$ or $X_q(f)$.

Here, it is to be noted that the act of not using the input function for obtaining the training data and not using any of the inputs $x_q(t)$ and $X_q(f)$ for obtaining the test data is equivalent to a situation where information indicating what these functions are is not used in the processing for identifying the sample. This is indicated more specifically in the following evaluation methods 1 to 3. This means that these two functions may be different from each other or may happen to be the same, or in other words, these functions may be determined independently and separately from each other.

<Evaluation Method 1: Analysis in Time Domain>

An evaluation in the time domain will be conducted in accordance with the analysis mode (FIG. 2) in which the sample is identified by comparing the features obtained from the test data with the features obtained from the training data for the respective channels. The formula (1) is subjected to time discretization to obtain the following:

[MATH. 7]

$$y'_{g,c}(i \times \Delta t) = \sum_{j=1}^{p} h'_{g,c}((j-1) \times \Delta t) x_g(i \times \Delta t - (j-1) \times \Delta t), \qquad (7)$$

where $h'_{g,c}(j \times \Delta t) = h_{g,c}(j \times \Delta t) \times \Delta t$, $c=1, 2, \ldots, C$, $p \times \Delta t = t$, and $i=1, 2, \ldots, 2I-1$. In this instance, the following holds true for each channel:

[MATH. 8]

$$\begin{bmatrix} y'_{g,c}(\Delta t) & y'_{g,c}(2\Delta t) & \cdots & y'_{g,c}(I\Delta t) \\ y'_{g,c}(2\Delta t) & y'_{g,c}(3\Delta t) & \cdots & y'_{g,c}((I+1)\Delta t) \\ \vdots & \vdots & \ddots & \vdots \\ y'_{g,c}((I-1)\Delta t) & y'_{g,c}(I\Delta t) & \cdots & y'_{g,c}((2I-2)\Delta t) \\ y'_{g,c}(I\Delta t) & y'_{g,c}((I+1)\Delta t) & \cdots & y'_{g,c}((2I-1)\Delta t) \end{bmatrix} \cong \qquad (8)$$

$$x_g \begin{bmatrix} h'_{g,c}(0) & h'_{g,c}(\Delta t) & \cdots & 0 & 0 \\ 0 & h'_{g,c}(0) & \cdots & \vdots & \vdots \\ \vdots & \vdots & \ddots & \vdots & h'_{g,c}((p-1)\Delta t) \\ 0 & 0 & \cdots & h'_{g,c}(0) & \vdots \\ 0 & 0 & \cdots & 0 & h'_{g,c}(0) \end{bmatrix},$$

therefore:

[MATH. 9]

$$x_g^{-1} \begin{bmatrix} y'_{g,c}(\Delta t) & y'_{g,c}(2\Delta t) & \ldots & y'_{g,c}(I\Delta t) \\ y'_{g,c}(2\Delta t) & y'_{g,c}(3\Delta t) & \ldots & y'_{g,c}((I+1)\Delta t) \\ \vdots & \vdots & \ddots & \vdots \\ y'_{g,c}((I-1)\Delta t) & y'_{g,c}(I\Delta t) & \ldots & y'_{g,c}((2I-2)\Delta t) \\ y'_{g,c}(I\Delta t) & y'_{g,c}((I+1)\Delta t) & \ldots & y'_{g,c}((2I-1)\Delta t) \end{bmatrix} \cong \begin{bmatrix} h'_{g,c}(0) & h'_{g,c}(\Delta t) & \ldots & 0 & 0 \\ 0 & h'_{g,c}(0) & \ldots & \vdots & \vdots \\ \vdots & \vdots & \ddots & \vdots & h'_{g,c}((p-1)\Delta t) \\ 0 & 0 & \ldots & h'_{g,c}(0) & \vdots \\ 0 & 0 & \ldots & 0 & h'_{g,c}(0) \end{bmatrix} \tag{9}$$

holds true on condition that:

[MATH. 10]

$$x_g = \begin{bmatrix} x_g(\Delta t) & x_g(2\Delta t) & \ldots & x_g(I\Delta t) \\ x_g(2\Delta t) & x_g(3\Delta t) & \ldots & x_g((I+1)\Delta t) \\ \vdots & \vdots & \ddots & \vdots \\ x_g((I-1)\Delta t) & x_g(I\Delta t) & \ldots & x_g((2I-2)\Delta t) \\ x_g(I\Delta t) & x_g((I+1)\Delta t) & \ldots & x_g((2I-1)\Delta t) \end{bmatrix}. \tag{10}$$

It is possible to assume that $x_g$ is substantially regular because elements therein are statistically random. Likewise, the following holds true for the measurement of the unknown sample u:

[MATH. 11]

$$\begin{bmatrix} y'_{u,c}(\Delta t) & y'_{u,c}(2\Delta t) & \ldots & y'_{u,c}(I\Delta t) \\ y'_{u,c}(2\Delta t) & y'_{u,c}(3\Delta t) & \ldots & y'_{u,c}((I+1)\Delta t) \\ \vdots & \vdots & \ddots & \vdots \\ y'_{u,c}((I-1)\Delta t) & y'_{u,c}(I\Delta t) & \ldots & y'_{u,c}((2I-2)\Delta t) \\ y'_{u,c}(I\Delta t) & y'_{u,c}((I+1)\Delta t) & \ldots & y'_{u,c}((2I-1)\Delta t) \end{bmatrix} \cong x_u \begin{bmatrix} h'_{u,c}(0) & h'_{u,c}(\Delta t) & \ldots & 0 & 0 \\ 0 & h'_{u,c}(0) & \ldots & \vdots & \vdots \\ \vdots & \vdots & \ddots & \vdots & h'_{u,c}((p-1)\Delta t) \\ 0 & 0 & \ldots & h'_{u,c}(0) & \vdots \\ 0 & 0 & \ldots & 0 & h'_{u,c}(0) \end{bmatrix}, \tag{11}$$

therefore:

[MATH. 12]

$$x_u^{-1} \begin{bmatrix} y'_{u,c}(\Delta t) & y'_{u,c}(2\Delta t) & \ldots & y'_{u,c}(I\Delta t) \\ y'_{u,c}(2\Delta t) & y'_{u,c}(3\Delta t) & \ldots & y'_{u,c}((I+1)\Delta t) \\ \vdots & \vdots & \ddots & \vdots \\ y'_{u,c}((I-1)\Delta t) & y'_{u,c}(I\Delta t) & \ldots & y'_{u,c}((2I-2)\Delta t) \\ y'_{u,c}(I\Delta t) & y'_{u,c}((I+1)\Delta t) & \ldots & y'_{u,c}((2I-1)\Delta t) \end{bmatrix} \cong \begin{bmatrix} h'_{u,c}(0) & h'_{u,c}(\Delta t) & \ldots & 0 & 0 \\ 0 & h'_{u,c}(0) & \ldots & \vdots & \vdots \\ \vdots & \vdots & \ddots & \vdots & h'_{u,c}((p-1)\Delta t) \\ 0 & 0 & \ldots & h'_{u,c}(0) & \vdots \\ 0 & 0 & \ldots & 0 & h'_{u,c}(0) \end{bmatrix} \tag{12}$$

holds true on condition that:

[MATH. 13]

$$x_u = \begin{bmatrix} x_u(\Delta t) & x_u(2\Delta t) & \ldots & x_u(I\Delta t) \\ x_u(2\Delta t) & x_u(3\Delta t) & \ldots & x_u((I+1)\Delta t) \\ \vdots & \vdots & \ddots & \vdots \\ x_u((I-1)\Delta t) & x_u(I\Delta t) & \ldots & x_u((2I-2)\Delta t) \\ x_u(I\Delta t) & x_u((I+1)\Delta t) & \ldots & x_u((2I-1)\Delta t) \end{bmatrix}. \tag{13}$$

It is possible to assume that $x_u$ is substantially regular because elements therein are statistically random.

If u=g, then the respective channels satisfy the following:

[MATH. 14]

$$\begin{bmatrix} h'_{u,c}(0) & h'_{u,c}(\Delta t) & \ldots & 0 & 0 \\ 0 & h'_{u,c}(0) & \ldots & \vdots & \vdots \\ \vdots & \vdots & \ddots & \vdots & h'_{u,c}((p-1)\Delta t) \\ 0 & 0 & \ldots & h'_{u,c}(0) & \vdots \\ 0 & 0 & \ldots & 0 & h'_{u,c}(0) \end{bmatrix} = \begin{bmatrix} h'_{g,c}(0) & h'_{g,c}(\Delta t) & \ldots & 0 & 0 \\ 0 & h'_{g,c}(0) & \ldots & \vdots & \vdots \\ \vdots & \vdots & \ddots & \vdots & h'_{g,c}((p-1)\Delta t) \\ 0 & 0 & \ldots & h'_{g,c}(0) & \vdots \\ 0 & 0 & \ldots & 0 & h'_{g,c}(0) \end{bmatrix}. \tag{14}$$

Therefore, the following is derived from the formula (9) and the formula (12):

[MATH. 15]

$$x_u^{-1} \begin{bmatrix} y'_{u,c}(\Delta t) & y'_{u,c}(2\Delta t) & \ldots & y'_{u,c}(I\Delta t) \\ y'_{u,c}(2\Delta t) & y'_{u,c}(3\Delta t) & \ldots & y'_{u,c}((I+1)\Delta t) \\ \vdots & \vdots & \ddots & \vdots \\ y'_{u,c}((I-1)\Delta t) & y'_{u,c}(I\Delta t) & \ldots & y'_{u,c}((2I-2)\Delta t) \\ y'_{u,c}(I\Delta t) & y'_{u,c}((I+1)\Delta t) & \ldots & y'_{u,c}((2I-1)\Delta t) \end{bmatrix} \cong x_g^{-1} \begin{bmatrix} y'_{g,c}(\Delta t) & y'_{g,c}(2\Delta t) & \ldots & y'_{g,c}(I\Delta t) \\ y'_{g,c}(2\Delta t) & y'_{g,c}(3\Delta t) & \ldots & y'_{g,c}((I+1)\Delta t) \\ \vdots & \vdots & \ddots & \vdots \\ y'_{g,c}((I-1)\Delta t) & y'_{g,c}(I\Delta t) & \ldots & y'_{g,c}((2I-2)\Delta t) \\ y'_{g,c}(I\Delta t) & y'_{g,c}((I+1)\Delta t) & \ldots & y'_{g,c}((2I-1)\Delta t) \end{bmatrix}. \tag{15}$$

Accordingly, the following holds true:

[MATH. 16]

$$R_{ug,c} \equiv \begin{bmatrix} y'_{u,c}(\Delta t) & y'_{u,c}(2\Delta t) & \cdots & y'_{u,c}(I\Delta t) \\ y'_{u,c}(2\Delta t) & y'_{u,c}(3\Delta t) & \cdots & y'_{u,c}((I+1)\Delta t) \\ \vdots & \vdots & \ddots & \vdots \\ y'_{u,c}((I-1)\Delta t) & y'_{u,c}(I\Delta t) & \cdots & y'_{u,c}((2I-2)\Delta t) \\ y'_{u,c}(I\Delta t) & y'_{u,c}((I+1)\Delta t) & \cdots & y'_{u,c}((2I-1)\Delta t) \end{bmatrix} \times$$

$$\begin{bmatrix} y'_{g,c}(\Delta t) & y'_{g,c}(2\Delta t) & \cdots & y'_{g,c}(I\Delta t) \\ y'_{g,c}(2\Delta t) & y'_{g,c}(3\Delta t) & \cdots & y'_{g,c}((I+1)\Delta t) \\ \vdots & \vdots & \ddots & \vdots \\ y'_{g,c}((I-1)\Delta t) & y'_{g,c}(I\Delta t) & \cdots & y'_{g,c}((2I-2)\Delta t) \\ y'_{g,c}(I\Delta t) & y'_{g,c}((I+1)\Delta t) & \cdots & y'_{g,c}((2I-1)\Delta t) \end{bmatrix}^{-1} \cong x_u x_g^{-1}.$$

(16)

The rightmost side of the formula (16) depends only on the $x_u$ and $x_g$ (i=1, 2, ..., 2I-1) but does not depend on the channels. Accordingly, the values $R_{ug,c}$ are equal among all the channels.

On the other hand, the following holds true if u≠g:

[MATH. 17]

$$\begin{bmatrix} h'_{u,c}(0) & h'_{u,c}(\Delta t) & \cdots & 0 & 0 \\ 0 & h'_{u,c}(0) & \cdots & \vdots & \vdots \\ \vdots & \vdots & \ddots & \vdots & h'_{u,c}((p-1)\Delta t) \\ 0 & 0 & \cdots & h'_{u,c}(0) & \vdots \\ 0 & 0 & \cdots & 0 & h'_{u,c}(0) \end{bmatrix} \neq$$

$$\begin{bmatrix} h'_{g,c}(0) & h'_{g,c}(\Delta t) & \cdots & 0 & 0 \\ 0 & h'_{g,c}(0) & \cdots & \vdots & \vdots \\ \vdots & \vdots & \ddots & \vdots & h'_{g,c}((p-1)\Delta t) \\ 0 & 0 & \cdots & h'_{g,c}(0) & \vdots \\ 0 & 0 & \cdots & 0 & h'_{g,c}(0) \end{bmatrix}.$$

(17)

Therefore, the values $R_{ug,c}$ are not equal among many of the channels. Accordingly, it is possible to determine whether or not the unknown sample u is the training sample g without controlling or monitoring the input $x_q(t)$ but instead by comparing the values $R_{ug,c}$ among the respective channels.

Here, in the above-described example, the transform of the above-described formula (1) into the polynomial expressions in the case of time discretization of the continuous function was expressed as the multiplication of matrices. It is to be noted, however, that the expressions do not always have to be composed of the matrices but may be expressed as a multiplication of vectors instead.

<Evaluation Method 2: Analysis in Frequency Domain (No. 1)>

An evaluation in the frequency domain will be conducted in accordance with the analysis mode (FIG. 2) in which the sample is identified by comparing the features obtained from the test data with the features obtained from the training data for the respective channels. If u=g, the frequency transfer function $H_{q,c}(f)$ is invariant with any input $X_q(f)$. The following therefore holds true:

[MATH. 18]

$$\begin{bmatrix} H_{u,1}(f) \\ H_{u,2}(f) \\ \vdots \\ H_{u,C}(f) \end{bmatrix} = \begin{bmatrix} H_{g,1}(f) \\ H_{g,2}(f) \\ \vdots \\ H_{g,C}(f) \end{bmatrix}.$$

(18)

Accordingly, the following is derived from the formulae (5) and (6):

[MATH. 19]

$$\frac{1}{X_u(f)} \begin{bmatrix} Y_{u,1}(f) \\ Y_{u,2}(f) \\ \vdots \\ Y_{u,C}(f) \end{bmatrix} = \frac{1}{X_g(f)} \begin{bmatrix} Y_{g,1}(f) \\ Y_{g,2}(f) \\ \vdots \\ Y_{g,C}(f) \end{bmatrix} \iff C_{ug}(f) \begin{bmatrix} Y_{u,1}(f) \\ Y_{u,2}(f) \\ \vdots \\ Y_{u,C}(f) \end{bmatrix} = \begin{bmatrix} Y_{g,1}(f) \\ Y_{g,2}(f) \\ \vdots \\ Y_{g,C}(f) \end{bmatrix},$$

(19)

where $C_{ug}(f) = X_g(f)/X_u(f)$. Here, assuming that:

$$C_{ug}(f) = X_g(f)/X_u(f) = A_{ug}(f) e^{i\theta_{ug}(f)},$$

the formula (19) can also be notated as:

[MATH. 20]

$$A_{ug}(f) e^{i\theta_{ug}(f)} \begin{bmatrix} Y_{u,1}(f) \\ Y_{u,2}(f) \\ \vdots \\ Y_{u,C}(f) \end{bmatrix} = \begin{bmatrix} Y_{g,1}(f) \\ Y_{g,2}(f) \\ \vdots \\ Y_{g,C}(f) \end{bmatrix},$$

(20)

where $A_{ug}(f) = |X_g(f)/X_u(f)|$. In this case, absolute values of both sides in the formula (20) satisfy the following:

[MATH. 21]

$$A_{ug}(f) \begin{bmatrix} |Y_{u,1}(f)| \\ |Y_{u,2}(f)| \\ \vdots \\ |Y_{u,C}(f)| \end{bmatrix} = \begin{bmatrix} |Y_{g,1}(f)| \\ |Y_{g,2}(f)| \\ \vdots \\ |Y_{g,C}(f)| \end{bmatrix}.$$

(21)

Accordingly, the following holds true:

[MATH. 22]

$$\log|Y_{u,1}(f)| - \log|Y_{g,1}(f)| = \log|Y_{u,2}(f)| - \log|Y_{g,2}(f)|$$
$$= \ldots = \log|Y_{u,C}(f)| - \log|Y_{g,C}(f)| = -\log A_{ug}(f) \quad (22)$$

Meanwhile, phase components of both sides in the formula (20) satisfy the following:

[MATH. 23]

$$\arg Y_{u,1}(f) - \arg Y_{g,1}(f) = \arg Y_{u,2}(f) - \arg Y_{g,2}(f) = \ldots = \arg Y_{u,C}(f) - \arg Y_{g,C}(f) = -\theta_{ug}(f) \quad (23)$$

On the other hand, the following holds true if u≠g:

[MATH. 24]

$$\begin{bmatrix} H_{u,1}(f) \\ H_{u,2}(f) \\ \vdots \\ H_{u,C}(f) \end{bmatrix} \neq \begin{bmatrix} H_{g,1}(f) \\ H_{g,2}(f) \\ \vdots \\ H_{g,C}(f) \end{bmatrix}, \quad (24)$$

which leads to:

[MATH. 25]

$$\frac{1}{X_u(f)}\begin{bmatrix} Y_{u,1}(f) \\ Y_{u,2}(f) \\ \vdots \\ Y_{u,C}(f) \end{bmatrix} \neq \frac{1}{X_g(f)}\begin{bmatrix} Y_{g,1}(f) \\ Y_{g,2}(f) \\ \vdots \\ Y_{g,C}(f) \end{bmatrix} \iff C_{ug}(f)\begin{bmatrix} Y_{u,1}(f) \\ Y_{u,2}(f) \\ \vdots \\ Y_{u,C}(f) \end{bmatrix} \neq \begin{bmatrix} Y_{g,1}(f) \\ Y_{g,2}(f) \\ \vdots \\ Y_{g,C}(f) \end{bmatrix}, \quad (25)$$

whereby the equations of the formulae (22) and (23) do not hold true any longer.

Accordingly, it is possible to evaluate whether or not the unknown sample u is the same as the training sample g without controlling or monitoring the input $X_q(f)$ but instead by comparing $\log|Y_{u,c}(f)| - \log|Y_{g,c}(f)|$ and $\arg Y_{u,c}(f) - \arg Y_{g,c}(f)$ among the channels, respectively, based on the measurement of the unknown sample u and the measurement of the training sample g.

<Evaluation Method 3: Analysis Based on Frequency Domain (No. 2)>

An evaluation in the frequency domain will be conducted in accordance with the analysis mode (FIG. 3) in which the features are compared between the channels for the respective measurements. Since the following is derived from the formula (5):

[MATH. 26]

$$X_g(f) = Y_{g,1}(f)/H_{g,1}(f) = Y_{g,2}(f)/H_{g,2}(f) = \ldots = Y_{g,C}(f)/H_{g,C}(f) \quad (26),$$

the following holds true for the arbitrary channels m and n:

[MATH. 27]

$$Y_{g,m}(f)/Y_{g,n}(f) = H_{g,m}(f)/H_{g,n}(f) = K'_{g,mn}(f) \quad (27)$$

Likewise, regarding the measurement of the unknown sample u, the following is derived from the formula (6):

[MATH. 28]

$$Y_{u,m}(f)/Y_{u,n}(f) = H_{u,m}(f)/H_{u,n}(f) = K'_{u,mn}(f) \quad (28)$$

If the sample is the same, the frequency transfer function $H_{q,c}(f)$ is invariant with any input $X_q(f)$. Accordingly, $K'_{u,mn}(f) = K'_{g,mn}(f)$ holds true when u=g while $K'_{u,mn}(f) \neq K'_{g,mn}(f)$ holds true when u≠g. As a consequence, it is possible to determine whether or not the unknown sample u is the same as the training sample g without controlling or monitoring the input $X_q(f)$ but instead by comparing the values $K'_{u,mn}(f)$ obtained by the measurement of the unknown sample u with the values $K'_{g,mn}(f)$ obtained in advance in the measurement for training.

As described above, when the sample is identified by using the multiple chemical sensors, there are two conceivable ways, namely, the analysis mode (FIG. 2) in which the sample is identified by comparing the features obtained from the test data with the features obtained from the training data for the respective channels, and the analysis mode (FIG. 3) in which the sample is identified by comparing the features between the channels for the respective measurements. The evaluation methods 1 and 2 showed the specific analysis modes in the time domain and the frequency domain, respectively, based on the concept of the former mode (FIG. 2) while the evaluation method 3 showed the specific analysis mode in the frequency domain based on the concept of the latter mode (FIG. 3). Though it is of course possible to think about an analysis mode (FIG. 3) to identify the sample by comparing the features between the channels for the respective measurements in the time domain, the description thereof will be omitted because the availability of this mode is obvious from the evaluation methods 1 to 3.

Note that the input function for obtaining the training data and the input function for obtaining the test data are not limited to particular functions as long as the functions can satisfy the theoretical explanation described above. It is possible to achieve the analyses theoretically when each function is a function containing various frequency components or a time-varying function. Accordingly, such a function may for example be any of a function that varies randomly with time, a function in which frequency components are distributed to a predetermined range, and the like. Those functions may be generated in some way as needs arise, or may be such functions that seem to be random but are actually preset such as patterns stored in a memory or the like.

In the meantime, the above-described evaluation method 1 is designed to perform the processing on the outputs from the chemical sensors subjected to the time discretization. However, the evaluation method is not limited to the foregoing. Even in a case of conducting an evaluation in accordance with a method other than the evaluation method 1, such an evaluation is thought to be accomplished in fact by using an information processing device that applies a digital computer in most cases. Therefore, it is also possible to conduct the analysis based on the formula (1) or on the formula (2) obtained by the time discretization of results of the outputs from the chemical sensors even in the case of the evaluation method other than the evaluation method 1. Modes for performing the information processing by way of the time discretization, instruments used therefor, and the like are matters known to those skilled in the art and specific explanations thereof will be omitted.

Furthermore, it is to be noted that a sample identification device according to the present invention does not always require a pump for providing the sample to the chemical sensors, instruments for controlling flow rates thereof, and so forth. For example, a source of generation of the sample may provide a flow of the sample by itself in accordance with an appropriate input function. Meanwhile, any of a source of the sample and the chemical sensors may be held at a proper position by hand instead of completely fixing a positional relationship therebetween with a fixture or the like. Moreover, the input function may further be optimized for example by moving the hand or the sample when appropriate. It should be understood that these measures are sufficiently practical. Accordingly, the minimum required elements of the sample identification device according to the present invention consist of the chemical sensors and the information processing device that receives the outputs therefrom and conducts analyses.

EXAMPLES

The present invention will be described further in detail below based on examples. However, it is needless to say that the present invention shall not be limited only to these examples. For instance, a membrane-type surface stress sensor (MSS) (Patent Literature 1 and Non-patent Literature 1) is used as an example of the chemical sensor in the following description. However, it is also possible to use chemical sensors of other types depending on the situation.

Figure 4:
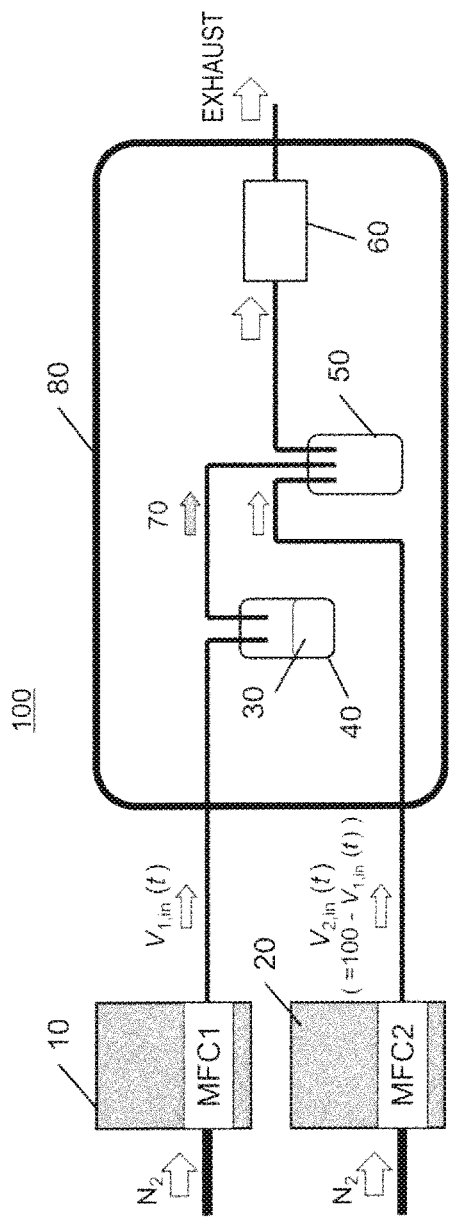
FIG. 4 is a diagram illustrating flow lines for a gas when conducting a measurement in an example.

FIG. 4 shows an outline of an experimental system 100 used in the examples. Nitrogen gas was supplied from two mass flow controllers (MFCs) 10 and 20. An MFC (MFC1) 10 out of the two was connected to a vial 40 containing a solvent 30 as the sample. The vial 40 containing the solvent 30 is further connected to another empty vial 50. Meanwhile, the other MFC (MFC2) 20 is also connected directly to the empty vial 50. The empty vial 50 was further connected to a sensor chamber 60 to which an MSS chip was set, and a gas that passed through the sensor chamber 60 was then exhausted. This experimental system can supply a head space gas 70 to the sensors while variously changing the concentration of the gas. Since the saturated vapor pressure varies depending on the solvent, a specific saturated vapor concentration $x_i$ is used as an input herein. In a case where water ($H_2O$) is used as the solvent and a flow rate of the MFC1 10 is set to 30 sccm while a flow rate of the MFC2 20 is set to 70 sccm, the specific saturated vapor concentration $x_{H2O}$ of water is equal to 30%.

Figure 5:
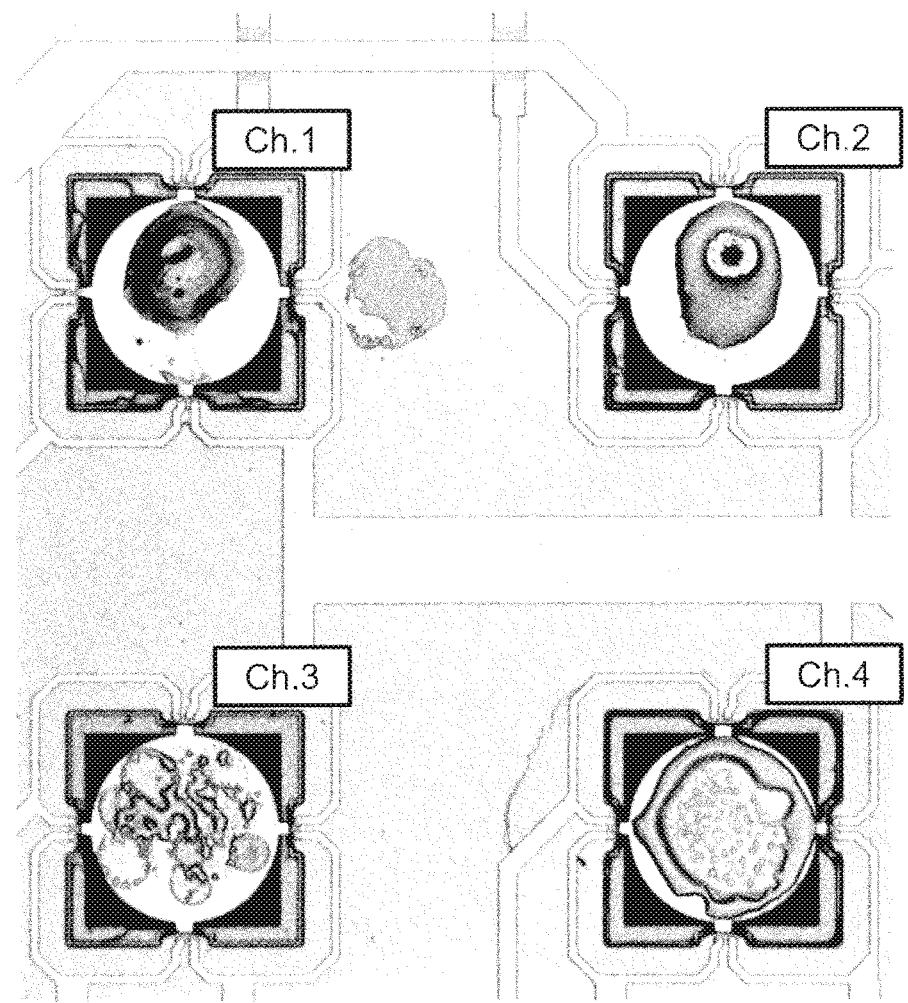
FIG. 5 is an optical photomicrograph of a four-channel MSS (membrane-type surface stress sensor) chip used in the example.
Figure 7A:
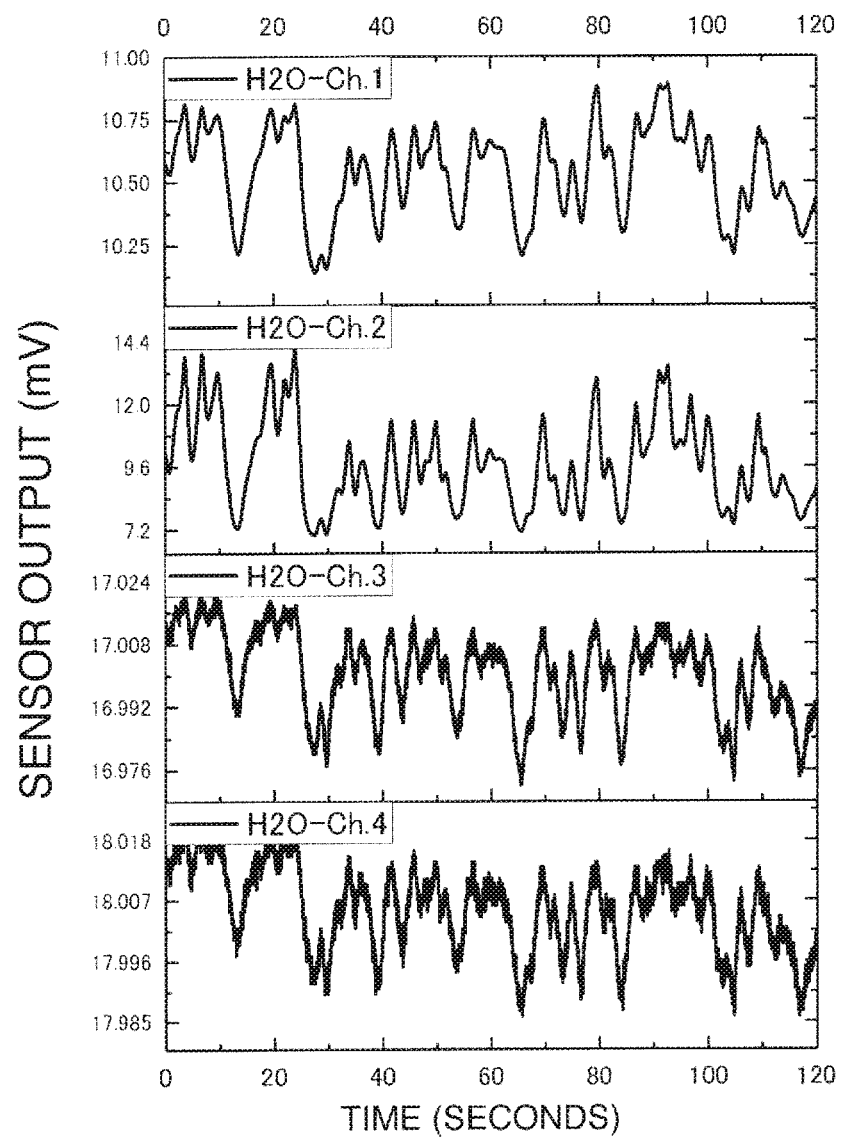
FIG. 7A is a graph showing sensor outputs (signals) obtained in respective channels in a case of a measurement of water vapor.
Figure 7B:
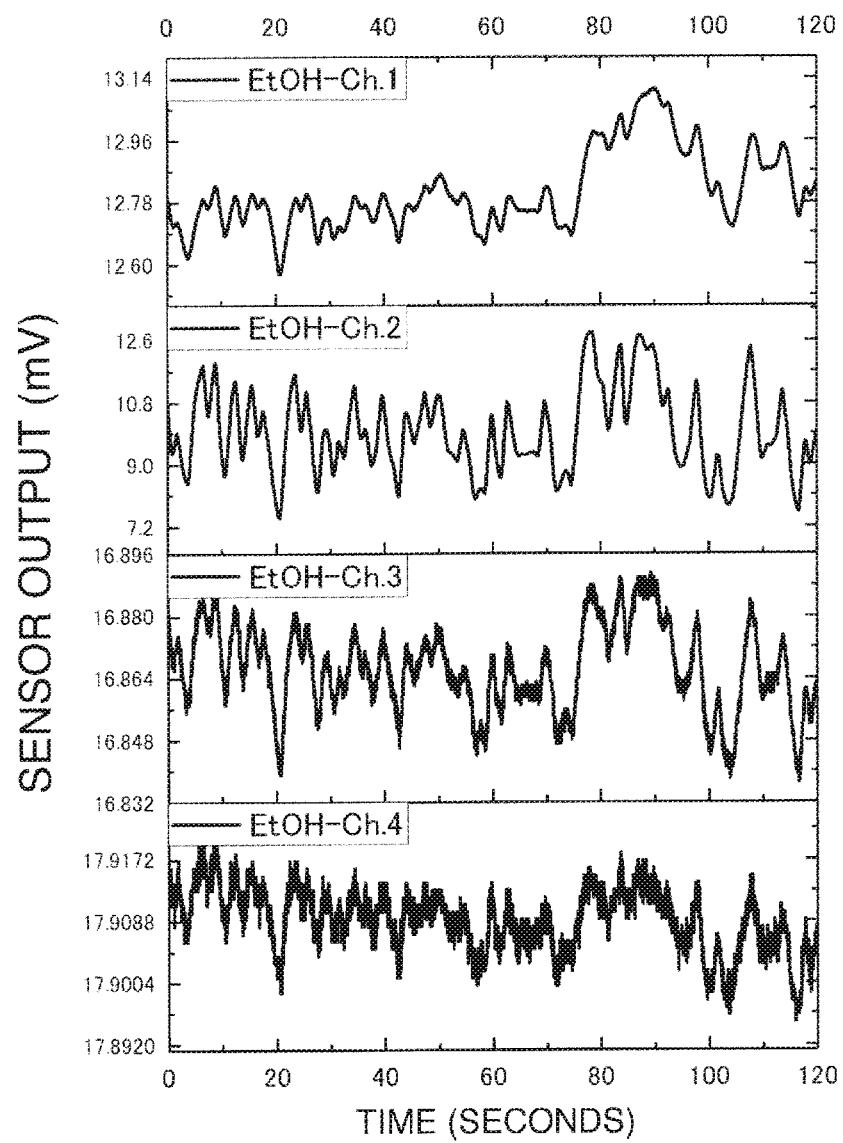
FIG. 7B is a graph showing sensor outputs (signals) obtained in the respective channels in a case of a measurement of ethanol.
Figure 7C:
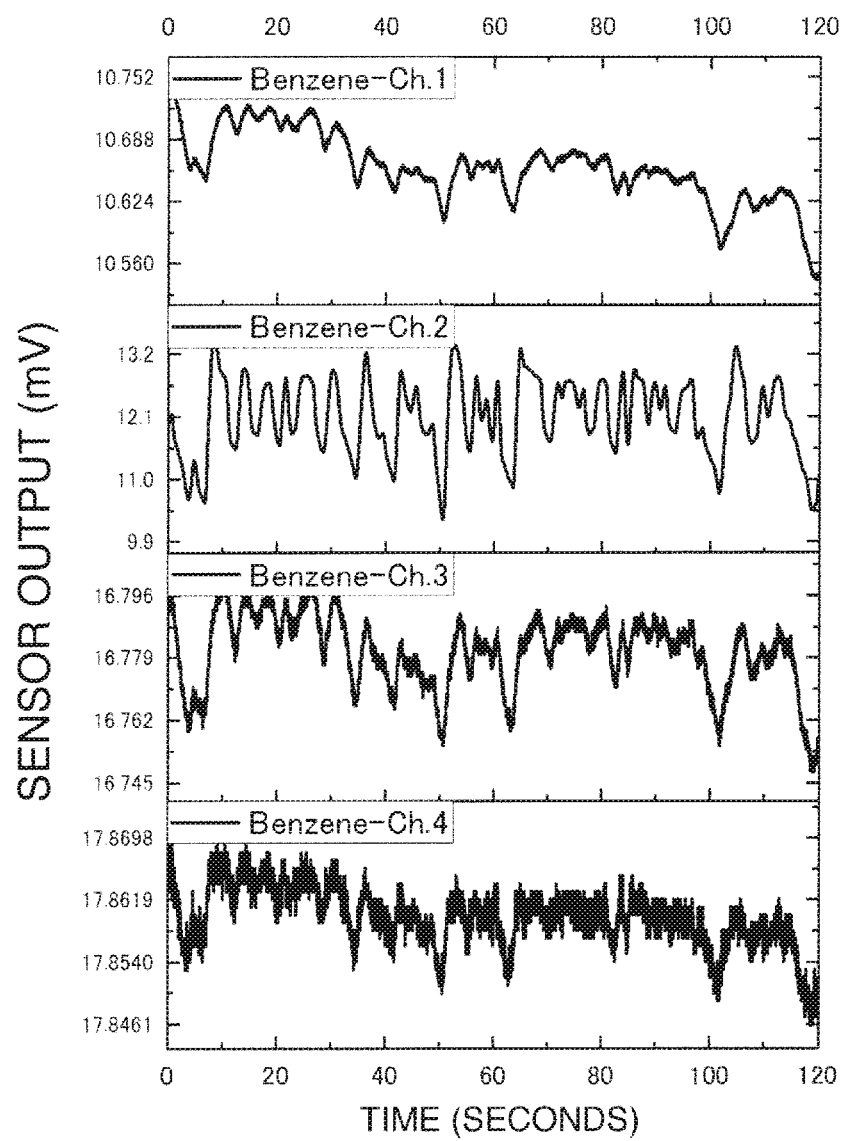
FIG. 7C is a graph showing sensor outputs (signals) obtained in the respective channels in the case of a measurement of benzene.
Figure 7D:
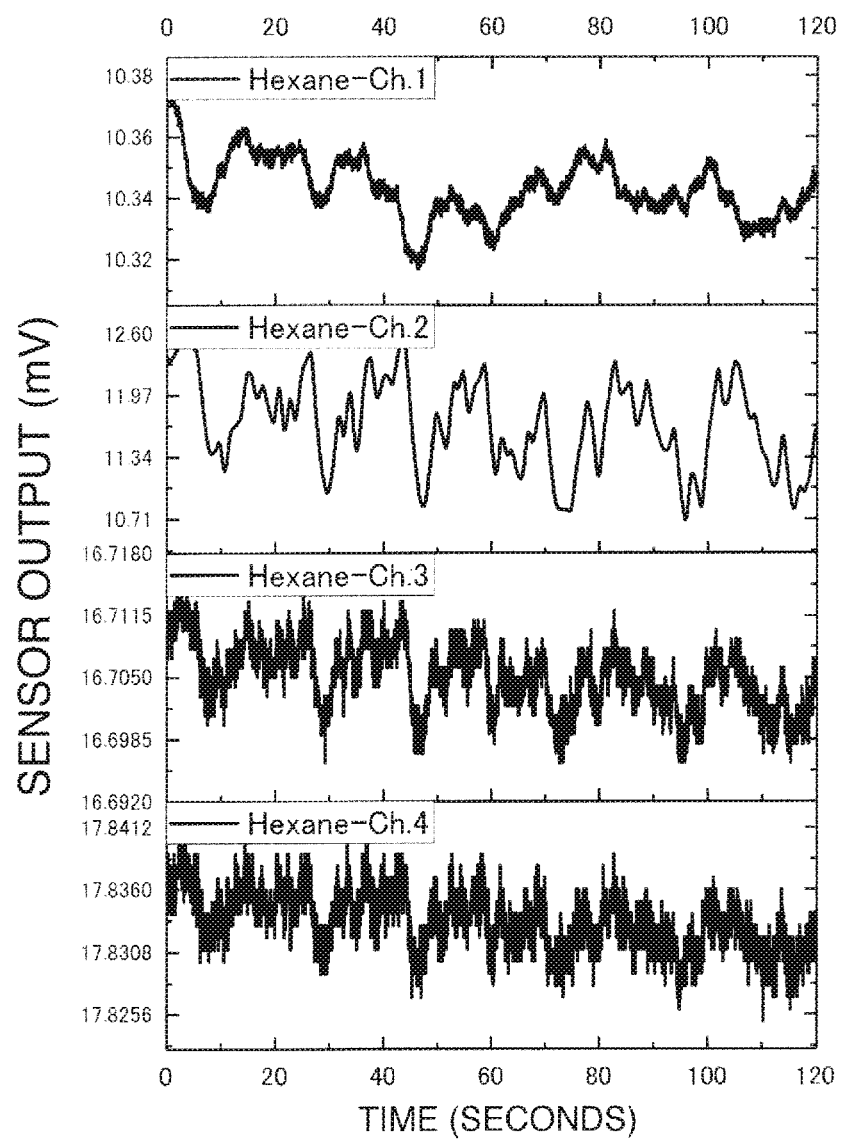
FIG. 7D is a graph showing sensor outputs (signals) obtained in the respective channels in the case of a measurement of hexane.
Figure 7E:
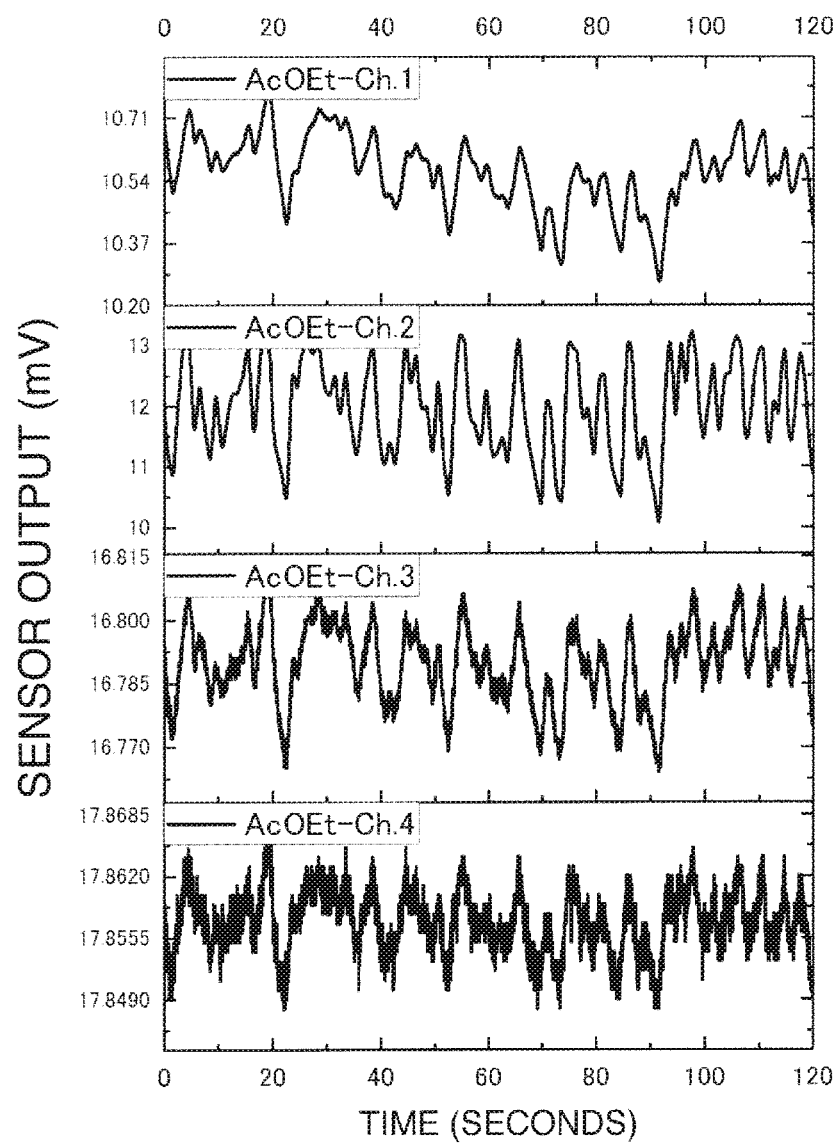
FIG. 7E is a graph showing sensor outputs (signals) obtained in the respective channels in the case of a measurement of ethyl acetate.
Figure 7F:
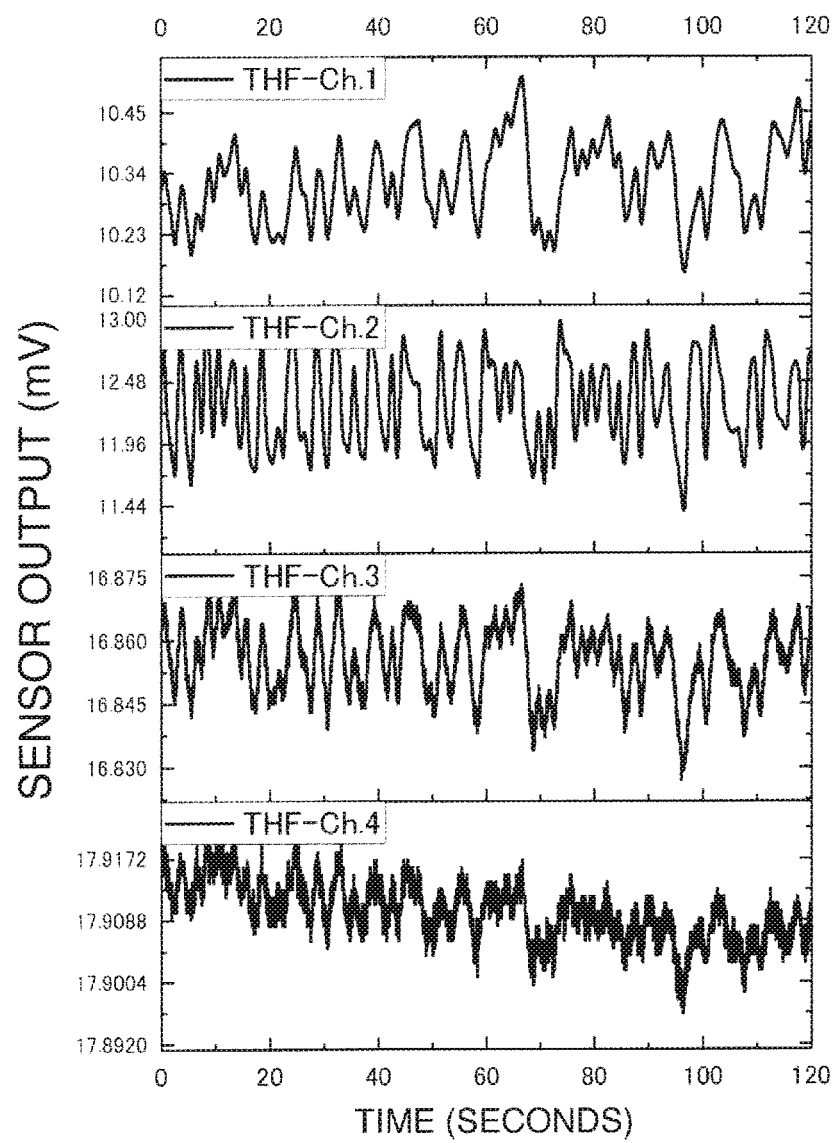
FIG. 7F is a graph showing sensor outputs (signals) obtained in the respective channels in the case of a measurement of tetrahydrofuran.

FIG. 5 shows an optical photomicrograph of an MSS chip used in this example. The MSS chip used here had four channels, and channels 1 to 4 (Ch. 1 to 4) were coated with polymethylmethacrylate, polyethylene oxide, polyepichlorohydrin, and poly(styrene-co-butadiene), respectively, as gas-sensitive membranes. The vials and the sensor chamber were installed in an incubator and a temperature was kept constant (25° C.).

In this example, the measurement was conducted by randomly changing the flow rate of the MFC1 10. In principle, the frequency transfer function can be obtained by applying an impulse (a pulse having an infinitely small temporal width and an infinitely large height) as an input and observing a response thereto. Nonetheless, it is difficult to apply such an impulse with the actual experimental system. There is also another problem of a difficulty in extracting only the response to the impulse from an output signal if the output contains noise. Accordingly, in this example, the frequency transfer function was obtained by applying white noise as the input instead of the impulse. The white noise has the constant value across the entire frequency range. It is therefore possible to seek the frequency transfer function by evaluating the response to the white noise. In the actual experimental system, the input-controllable frequency range is limited. Hence, the responses to a half bandwidth of the aforementioned frequency are significant for the analysis according to the Nyquist's theorem. In this example, the flow rate of the MFC1 10 was randomly changed every second (1 Hz) within a range from 0 to 100 sccm as shown in FIG. 6. When the flow rate of the MFC1 was set to $V_{1,in}(t)$ sccm, the flow rate of the MFC2 20 was set to $V_{2,in}(t)=100-V_{1,in}(t)$ sccm such that a sum of the flow rates of the MFC1 10 and the MFC2 20 was always equal to 100 sccm. A measurement period was set to 120 seconds for each sample, and 2400 pieces of data were acquired at a sampling frequency of 20 Hz (every 0.05 second from 0 second to 119.95 seconds). Six solvents, namely, water ($H_2O$), ethanol (EtOH), benzene (Benzene), hexane (Hexane), ethyl acetate (AcOEt), and tetrahydrofuran (THF) were used as the samples. Results of measurements of these solvents are shown in FIGS. 7A to 7F.

Example 1

Analysis Example 1: Analysis Based on Time Transfer Function (Evaluation Method 1)

This analysis was conducted based on <Evaluation method 1> in <Theoretical backgrounds>. The measurement data corresponding to 20 Hz and 120 seconds were divided into K=2400/(2I) sessions and then K−1 sessions (measurement number k=1, 2, . . . , K−1) were used as the training data while the last session (k=K) was used as the test data. The formulae (16) and (17) enable identification of a gas by evaluating whether or not the values $R_{ug,c}$ are equal to one another. In the case where the determination as to whether or not the values $R_{ug,c}$ are equal to one another is made based on the magnitude of variance of the values $R_{ug,c}$ across channels of (i, j) elements, even if structures of $R_{ug,c}$ are not similar in general, the structures are possibly determined to be similar if the respective elements of $R_{ug,c}$ are small in general due to combinations of scales of $y_{g,c}(t)$ and $y_{u,c}(t)$. To avoid this, the determination as to whether or not the values $R_{ug,c}$ are equal to one another is made based on differences in logarithm and sign among the respective element values. If u=g, then:

[MATH. 29]

$$\log|R_{ug,1}(i,j)|=\log|R_{ug,2}(i,j)|=\ldots=\log|R_{ug,C}(i,j)| \quad (29); \text{ and}$$

[MATH. 30]

$$\text{sign}(R_{ug,1}(i,j))=\text{sign}(R_{ug,2}(i,j))=\ldots=\text{sign}(R_{ug,C}(i,j)) \quad (30)$$

are derived from the formula (16). Here, $R_{ug,c}(i, j)$ denotes the (i, j) elements of $R_{ug,\ c}$, and sign(x) is a sign of x which has any of values of −1, 0, and 1 when x<0, x=0, and x>0, respectively. In the meantime, when u≠g, the values $\log|R_{ug,c}(i,j)|$ and $\text{sign}(R_{ug,c}(i, j))$ do not match among the channels in terms of many of $R_{ug,c}(i, j)$.

Here, regarding a value $R_{ug,ck}$ to be obtained from the test data and the training data of the measurement number k, values $LR_{ug,k}(i, j)$ and $SR_{ug,k}(i, j)$ are defined as follows:

[MATH. 31]

$$LR_{ug,k}(i, j) \equiv \frac{1}{C}\sum_{c=1}^{C}\log|R_{ug,ck}(i, j)|; \text{ and} \quad (31)$$

[MATH. 32]

$$SR_{ug,k}(i, j) \equiv \frac{1}{C}\sum_{c=1}^{C}\text{sign}(R_{ug,ck}(i, j)). \quad (32)$$

If u=g, then the values $R_{ug,k}(i, j)$ have averages $LR_{ug,k}$ and $SR_{ug,k}$ in common irrespective of the value of c. Here, values $\log|R_{ug,ck}(i,j)|$ and $\text{sign}(R_{ug,c}k(i,j))$ are assumed to be in conformity to common distributions $N(LR_{ug,k}(i,j), \sigma_{Lg,c}^2(i,$ j)) and $N(SR_{ug,k}(i,j), \sigma_{Sg,c}^2(i,j))$, respectively, regardless of the value k on condition that $N(\mu, \sigma^2)$ is a normal distribution with the mean $\mu$ and the variance $\sigma^2$. Meanwhile, assuming that $R_{g,ck1k2}$ is a matrix to be obtained by conducting a calculation similar to the case of $R_{ug,c}$ in the formula (16) by using K pieces of the measurement values $y_{g,ck1}$ and $y_{g,ck2}$ concerning the respective channels, values $\sigma_{Lg,c}^2(i,j)$ and $\sigma_{Sg,c}^2(i,j)$ are defined as follows:

[MATH. 33]

$$\sigma_{Lg,c}^2(i,j) = \frac{2}{(K-1)(K-2)} \sum_{k_1,k_2(k_1<k_2)}^{K-1} \Delta LR_{g,ck_1k_2}^2(i,j); \quad (33)$$

and

[MATH. 34]

$$\sigma_{Sg,c}^2(i,j) = \frac{2}{(K-1)(K-2)} \sum_{k_1,k_2(k_1<k_2)}^{K-1} \Delta SR_{g,ck_1k_2}^2(i,j), \quad (34)$$

on condition that:

[MATH. 35]

$$\Delta LR_{g,ck_1k_2}(i,j) \equiv \log|R_{g,ck_1k_2}(i,j)| - \frac{1}{C}\sum_{c=1}^{C} \log|R_{g,ck_1k_2}(i,j)|; \quad (35)$$

and

[MATH. 36]

$$\Delta SR_{g,ck_1k_2}(i,j) \equiv \text{sign}(R_{g,ck_1k_2}(i,j)) - \frac{1}{C}\sum_{c=1}^{C} \text{sign}(R_{g,ck_1k_2}(i,j)). \quad (36)$$

Accordingly, in the comparison between the test data $y_{u,c}(t)$ and the training data $y_{g,ck}(t)$, a consistent probability $L(u, g)$ with a substance g across all the channels c, all the training data (the measurement number k), and respective transfer matrix elements (i, j) is defined as:

[MATH. 37]

$$L(u,g) = P(R_{ug,1k}(i,j) = R_{ug,2k}(i,j) = \ldots = R_{ug,Ck}(i,j) | i, \quad (37)$$
$$j = 1, \ldots, I, \quad k = 1, \ldots K-1) =$$
$$\prod_{i,j=1,k=1,c=1}^{I,K-1,C} \frac{1}{\sqrt{2\pi}\sigma_{Lg,c}(i,j)} \exp\left\{-\frac{(\log|R_{ug,ck}(i,j)| - LR_{ug,k}(i,j))^2}{\sigma_{Lg,c}^2(i,j)}\right\} \times$$
$$\frac{1}{\sqrt{2\pi}\sigma_{Sg,c}(i,j)} \exp\left\{-\frac{(\text{sign}(R_{ug,ck}(i,j)) - SR_{ug,k}(i,j))^2}{\sigma_{Sg,c}^2(i,j)}\right\}.$$

A logarithmic likelihood $LL(u, g)$ obtained by taking the logarithm of the formula (37) is defined as:

[MATH. 38]

$$LL(u,g) = \quad (38)$$
$$\sum_{i,j=1,k=1,c=1}^{I,K-1,C} \log P(R_{ug,1k}(i,j) = R_{ug,2k}(i,j) = \ldots = R_{ug,Ck}(i,j)) \propto$$
$$\sum_{i,j=1,k=1,c=1}^{I,K-1,C} -\frac{(\log|R_{ug,ck}(i,j)| - LR_{ug,k}(i,j))^2}{\sigma_{Lg,c}^2(i,j)} -$$
$$\sum_{i,j=1,k=1,c=1}^{I,K-1,C} -\frac{(\text{sign}(R_{ug,ck}(i,j)) - SR_{ug,k}(i,j))^2}{\sigma_{Sg,c}^2(i,j)} -$$
$$C(K-1)\sum_{i,j=1}^{I} \log \sigma_{Lg,c}(i,j) - C(K-1)\sum_{i,j=1}^{I} \log \sigma_{Sg,c}(i,j).$$

As a consequence, it is possible to evaluate the consistent probability of the training data with each gas type by calculating the rightmost side of the formula (38) regarding each piece of the test data.

Calculations of $LL(u, g)$ were conducted in accordance with the above discussion. While tables of data used for calculations in other analysis examples (analysis examples 2 and 3) are quoted near the end of this specification, this analysis example involved enormous data pieces that ran into several millions and the quotation thereof was therefore omitted. As for the data preprocessing, high-frequency noise was removed by using a finite response (FIR) low-pass filter set to a cut-off frequency of 0.5 Hz. Results in the case of setting I=10 and K=120 are shown in Table 1. Note that actual values of $LL(u, g)$ are given by multiplying The values on the Table by $10^7$. The case that brings about the largest value of $LL(u, g)$ in each row was indicated in bold. As for four types of the solvents, namely, water, ethanol, and ethyl acetate, the pieces of the training data that brought about the largest likelihood coincided with those of the test data. In other words, the identification of those samples was successful. As for hexane, the piece of the training data that brought about the largest likelihood turned out to be that of benzene which was incorrect. Nonetheless, the piece of the training data representing hexane as the correct answer showed the second largest likelihood. However, as for THF, the logarithmic likelihood of the piece of training data representing THF as the correct answer was the fifth largest and showed poor accuracy. A possible reason why the analysis in the time domain based on the concept in FIG. 2 showed the poor accuracy does not lie in a problem of the principle of <Evaluation method 1> but is attributable to a non-essential reason that the analysis in the time domain requires estimation of the matrices linked with all time steps and a resultant increase in the number of quantities to be estimated is likely to cause statistical instability. To solve this problem, it is necessary to optimize the size of I, the cut-off frequency of the FIR low-pass filter, and so forth.

TABLE 1

| | | TRAINING DATA | | | | | |
|---|---|---|---|---|---|---|---|
| | | WATER | ETHANOL | BENZENE | HEXANE | ETHYL ACETATE | THF |
| TEST DATA | WATER | −1.6227 | −1.6688 | −1.7271 | −1.8138 | −1.7131 | −1.7602 |
| | ETHANOL | −1.6203 | −1.5981 | −1.6044 | −1.7229 | −1.6281 | −1.7019 |

TABLE 1-continued

| | TRAINING DATA | | | | | |
|---|---|---|---|---|---|---|
| | WATER | ETHANOL | BENZENE | HEXANE | ETHYL ACETATE | THF |
| BENZENE | −1.6665 | −1.5886 | −1.5283 | −1.6386 | −1.5949 | −1.6973 |
| HEXANE | −1.6681 | −1.5917 | −1.5336 | −1.5796 | −1.6160 | −1.7083 |
| ETHYL ACETATE | −1.7747 | −1.7555 | −1.6653 | −1.7507 | −1.5821 | −1.7365 |
| THF | −1.5620 | −1.5506 | −1.5768 | −1.6981 | −1.5522 | −1.6093 |

Example 2

Analysis Example 2: Analysis Based on Frequency Transfer Function (Evaluation Method 2)

This analysis was conducted based on <Evaluation method 2> in <Theoretical backgrounds>. The measurement data corresponding to 120 seconds were divided by six (K=6) and then 5 sessions (the measurement number k=1, 2, 3, 4, 5) were used as the training data while the last session (k=6) was used as the test data. First, the measurement data were subjected to the Fourier transform to seek the frequency components of the sensor signal. In this example, the measurement was conducted for 20 seconds at the sampling frequency of 20 Hz (400 pieces). Accordingly, the frequency characteristics are obtained at 0.05-Hz intervals. Since the flow rate is randomly changed every second (1 Hz) in this example, the frequency components up to 0.5 Hz, which is a half of 1 Hz, are useful in the analysis according to the Nyquist's theorem. As mentioned earlier, the input-controllable frequency range is limited in the actual experimental system. In this example, the system could hardly follow in an attempt to switch the flow rate at a frequency higher than 1 Hz due to a restriction in responsiveness of the MFCs and the like. As a consequence, ten components at 0.05, 0.1, 0.15, . . . , and 0.5 Hz are used in the analysis. Hence, $Y_{q,c}(f)$ is obtained as a 10-dimensional complex vector per channel in each measurement.

Based on the above, let us consider a case of identifying the gas type of the test data by comparing Fourier components $Y_{u,c}(f)$ of the test data obtained based on Evaluation method 2 with Fourier components $Y_{g,ck}(f)$ of the training data. Here, the gas is identified based on a probability defined as $$A_{ug}(f)e^{i\theta_{ug}(f)}Y_{u,c}(f)=Y_{g,ck}(f) \ (k=1, 2, \ldots, K-1)$$

that is derived from the formula (20).

Based on the formulae (22) and (23), the values $\log|Y_{u,c}(f)|-\log|Y_{g,c}(f)|$ and $\arg Y_{u,c}(f)-\arg Y_{g,c}(f)$ take the same values in all the channels when u=g. Accordingly, based on $Y_{u,c}(f)$ of the test data with the channel c obtained by the measurement and $Y_{g,ck}(f)$ of the k-th piece of the training data, values $\hat{L}_{ug,k}(f)$ and $\hat{\theta}_{ug,k}(f)$ are defined respectively as:

[MATH. 39]

$$\hat{L}_{ug,k}(f) \equiv \frac{1}{C}\sum_{c=1}^{C}\{\log|Y_{u,c}(f)|-\log|Y_{g,ck}(f)|\}; \tag{39}$$

and

[MATH. 40]

$$\hat{\theta}_{ug,k}(f) \equiv \frac{1}{C}\sum_{c=1}^{C}\{\arg Y_{u,c}(f)-\arg Y_{g,ck}(f)\}. \tag{40}$$

Here, the values $\log|Y_{u,c}(f)|-\log|Y_{g,c}(f)|$ and $\arg Y_{u,c}(f)-\arg Y_{g,c}(f)$ are assumed to be in conformity to common distributions $N(\hat{L}_{ug,k}(f), \sigma_{Lg,c}^2(f))$ and $N(\hat{\theta}_{ug,k}(f), \sigma_{\theta g,c}^2(f))$, respectively. Here, if $Y_{u,c}(f)$ is assumed to be in conformity to a population distribution similar to $Y_{g,ck}(f)$, then variances of $\log|Y_{u,c}(f)|$ and $\arg Y_{u,c}(f)$ are thought to be equivalent to variances $s_{Lg,c}^2(f)$ and $s_{\theta g,c}^2(f)$ of $\log|Y_{g,ck}(f)|$ and $\arg Y_{g,ck}(f)$ Accordingly, values $\sigma_{Lg,c}^2(f)$ and $\sigma_{\theta g,c}^2(f)$ are defined as:

[MATH. 41]

$$\sigma_{Lg,c}^2(f)=2s_{Lg,c}^2(f) \tag{41}$$

and

[MATH. 42]

$$\sigma_{\theta g,c}^2(f)=2s_{\theta g,c}^2(f) \tag{42}$$

on condition that:

[MATH. 43]

$$s_{Lg,c}^2(f) = \frac{1}{K-2}\sum_{k=1}^{K-1}\{\log|Y_{g,ck}(f)|-\log|Y_{g,c}(f)|\}^2; \tag{43}$$

and

[MATH. 44]

$$s_{\theta g,c}^2(f) = \frac{1}{K-2}\sum_{k=1}^{K-1}\{\arg Y_{g,ck}(f)-\arg Y_{g,c}(f)\}^2, \tag{44}$$

where $\log|Y_{g,c}(f)|$ and $\arg Y_{g,c}(f)$ are defined as:

[MATH. 45]

$$\log|Y_{g,c}(f)| = \frac{1}{K-1}\sum_{k=1}^{K-1}\log|Y_{g,ck}(f)|; \tag{45}$$

and

[MATH. 46]

$$\arg Y_{g,c}(f) = \frac{1}{K-1}\sum_{k=1}^{K-1}\arg Y_{g,ck}(f), \tag{46}$$

respectively.

Accordingly, a probability that $Y_{u,c}(f)$ of the test data match the training data $Y_{g,ck}(f)$ notated as $$P(A_{ug}(f)e^{i\theta_{ug}(f)}Y_{u,c}(f)=Y_{g,ck}(f))$$

is defined as:

[MATH. 47]

$$P(A_{ug}(f)e^{i\theta_{ug}(f)}Y_{u,c}(f) = Y_{g,ck}(f)) = \qquad (47)$$
$$\frac{1}{\sqrt{2\pi}\,\sigma_{Lg,c}(f)}\exp\left\{-\frac{(\log|Y_{u,c}(f)| - \log|Y_{g,ck}(f)| - \hat{L}_{ug,k}(f))^2}{\sigma_{Lg,c}^2(f)}\right\} \times$$
$$\frac{1}{\sqrt{2\pi}\,\sigma_{\theta g,c}(f)}\exp\left\{-\frac{(\arg Y_{u,c}(f) - \arg Y_{g,ck}(f) - \hat{\theta}_{ug,k}(f))^2}{\sigma_{\theta g,c}^2(f)}\right\}.$$

Therefore, a probability $L(u, g)$ that the unknown sample u matches the substance g across all the channels c, all the training data (the measurement number k), and all the frequency components f (from the lowest frequency $f_L$ to the highest frequency $f_H$) is obtained by:

[MATH. 48]

$$L(u, g) = \prod_{k=1, f=f_L, c=1}^{K-1, f_H, C} P(A_{ug}(f)e^{i\theta_{ug}(f)}Y_{u,c}(f) = Y_{g,ck}(f)). \qquad (48)$$

The logarithmic likelihood $LL(u, g)$ obtained by taking the logarithm of the formula (48) is obtained by:

[MATH. 49]

$$LL(u, g) = \log L(u, g) = \sum_{k=1, f=f_L, c=1}^{K-1, f_H, C} \log P(A_{ug}(f)e^{i\theta_{ug}(f)}Y_{u,c}(f) = \qquad (49)$$
$$Y_{g,ck}(f)) \propto -\sum_{k=1, f=f_L, c=1}^{K-1, f_H, C} \frac{(\log|Y_{u,c}(f)| - \log|Y_{g,ck}(f)| - \hat{L}_{ug,k}(f))^2}{\sigma_{Lg,c}^2(f)} -$$
$$\sum_{k=1, f=f_L, c=1}^{K-1, f_H, C} \frac{(\arg Y_{u,c}(f) - \arg Y_{g,ck}(f) - \hat{\theta}_{ug,k}(f))^2}{\sigma_{\theta g,c}^2(f)} -$$
$$(K-1)\sum_{f=f_L, c=1}^{f_H, C} \log \sigma_{Lg,c}(f) - (K-1)\sum_{f=f_L, c=1}^{f_H, C} \log \sigma_{\theta g,c}(f)$$

As a consequence, it is possible to evaluate the probability that a test data matches the training data of each gas type by calculating the rightmost side of the formula (49) regarding each piece of the test data.

Results are shown in Table 2. If needed, please refer to tables of data used for the calculations that are quoted near the end of this specification together with tables of data for the analysis example 3. The case that brings about the largest value of LL(u, g) in each row was indicated in bold. As for five types of the solvents, namely, water, ethanol, hexane, ethyl acetate, and THF, the pieces of the training data that brought about the largest likelihood coincided with those of the test data. In other words, the identification of those samples was successful. The piece of the training data that brought about the largest likelihood was incorrect only in the case of the benzene, which turned out to be that of ethanol. Nonetheless, the piece of the training data representing benzene as the correct answer showed the second largest likelihood. Thus, the analysis method based on Evaluation method 2 showed the possibility to identify the gasses.

TABLE 2

|  |  | TRAINING DATA | | | | | |
| --- | --- | --- | --- | --- | --- | --- | --- |
|  |  | WATER | ETHANOL | BENZENE | HEXANE | ETHYL ACETATE | THF |
| TEST DATA | WATER | −761.2 | −1158.9 | −2620.2 | −2915.6 | −843.9 | −1307.6 |
|  | ETHANOL | −1360.4 | −915.1 | −1555.8 | −3434.6 | −1138.8 | −1275.4 |
|  | BENZENE | −1761.2 | −897.2 | −1024.8 | −1246.6 | −1469.9 | −1389.4 |
|  | HEXANE | −4956.3 | −3232.7 | −2052.9 | −1377.5 | −10743.1 | −8332.3 |
|  | ETHYL ACETATE | −1234.7 | −946.1 | −2180.7 | −4436.1 | −607.9 | −815.2 |
|  | THF | −1315.1 | −1205.7 | −2563.0 | −3267.5 | −847.2 | −677.9 |

Example 3

Analysis Example 3: Analysis Based on Frequency Transfer Function (Evaluation Method 3)

This analysis was conducted based on <Evaluation method 3> in <Theoretical backgrounds>. The measurements corresponding to 120 seconds were divided by six (K=6) and then 5 sessions (the measurement number k=1, 2, 3, 4, 5) were used as the training data while the last session (k=6) was used as the test data. First, the measurement data were subjected to the Fourier transform to seek the frequency components of the sensor signal. In this analysis example as well, ten components at 0.05, 0.1, 0.15, . . . , 0.5 Hz are used in the analysis as with <Analysis example 2>. Hence, $Y_{q,c}(f)$ is obtained as a 10-dimensional complex vector per channel in each measurement.

Being the complex number, $K'_{q,mn}(f)$ can be notated as:

[MATH. 50]

$$K'_{q,mn}(f) = r_{q,mn}(f)\exp[i\theta_{q,mn}(f)] \qquad (50)$$

In this case, regarding the training data, values $r_{g,mnk}(f)$ and $\theta_{g,mnk}(f)$ are assumed to be in conformity to common distributions $N(\hat{r}_{g,mn}(f), \sigma_{r_{g,mn}}^2(f))$ and $N(\hat{\theta}_{g,mn}(f), \sigma_{\theta_{g,mn}}^2(f))$, respectively, regardless of the value k on condition that:

[MATH. 51]

$$\hat{r}_{g,mn}(f) \equiv \frac{1}{K-1}\sum_{k=1}^{K-1} r_{g,mnk}(f); \qquad (51)$$

and

[MATH. 52]

$$\hat{\theta}_{g,mn}(f) \equiv \frac{1}{K-1}\sum_{k=1}^{K-1} \theta_{g,mnk}(f). \qquad (52)$$

Here, if $K'_{u,mn}(f)$ is assumed to be in conformity to a population distribution similar to $K'_{g,mnk}(f)$, then variances of $r_{u,mn}(f)$ and $\theta_{u,mn}(f)$ are thought to be equivalent to variances $s_{r_{g,mn}}^2(f)$ and $s_{\theta_{g,mn}}^2(f)$ of $r_{g,mn}(f)$ and $\theta_{g,mnk}(f)$. Accordingly, values $\sigma_{r_{g,mn}}^2(f)$ and $\sigma_{\theta_{g,mn}}^2(f)$ are defined as:

[MATH. 53]

$$\sigma_{r_{g,mn}}^2(f) = 2s_{r_{g,mn}}^2(f) \quad (53);\text{ and}$$

[MATH. 54]

$$\sigma_{\theta_{g,mn}}^2(f) = 2s_{\theta_{g,mn}}^2 \quad (54),$$

on condition that:

[MATH. 55]

$$s_{r_{g,mn}}^2(f) = \frac{1}{K-2} \sum_{k=1}^{K-1} \{r_{g,mnk}(f) - \hat{r}_{g,mn}(f)\}^2; \quad (55)$$

and

[MATH. 56]

$$s_{\theta_{g,mn}}^2(f) = \frac{1}{K-2} \sum_{k=1}^{K-1} \{\theta_{g,mnk}(f) - \hat{\theta}_{g,mn}(f)\}^2. \quad (56)$$

Accordingly, a probability that $K'_{u,mn}(f)$ obtained from the test data match the training data $K'_{g,mnk}(f)$ (the measurement number k) notated as $$P(K'_{u,mn}(f) = K'_{g,mnk}(f))$$

is defined as:

[MATH. 57]

$$P(K'_{u,mn}(f) = K'_{g,mnk}(f)) = \quad (57)$$

$$\frac{1}{\sqrt{2\pi}\,\sigma_{r_{g,mn}}(f)} \exp\left\{-\frac{(r_{u,mn}(f) - r_{g,mnk}(f))^2}{\sigma_{r_{g,mn}}^2(f)}\right\} \times$$

$$\frac{1}{\sqrt{2\pi}\,\sigma_{\theta_{g,mn}}(f)} \exp\left\{-\frac{(\theta_{u,mn}(f) - \theta_{g,mnk}(f))^2}{\sigma_{\theta_{g,mn}}^2(f)}\right\}.$$

Therefore, the probability L(u, g) that u matches the substance g across all combinations of the channels (m, n, m<n), all the training data (the measurement number k), and all the frequencies f (from the lowest frequency $f_L$ to the highest frequency $f_H$) is obtained by:

[MATH. 58]

$$L(u, g) = \prod_{\substack{m,n,m<n \\ k=1, f=f_L}}^{C, K-1, f_H} \frac{1}{\sqrt{2\pi}\,\sigma_{r_{g,mn}}(f)} \exp\left\{-\frac{(r_{u,mn}(f) - r_{g,mnk}(f))^2}{\sigma_{r_{g,mn}}^2(f)}\right\} \times \quad (58)$$

$$\frac{1}{\sqrt{2\pi}\,\sigma_{\theta_{g,mn}}(f)} \exp\left\{-\frac{(\theta_{u,mn}(f) - \theta_{g,mnk}(f))^2}{\sigma_{\theta_{g,mn}}^2(f)}\right\}.$$

The logarithmic likelihood LL(u, g) obtained by taking the logarithm of the formula (58) is obtained by:

[MATH. 59]

$$LL(u, g) = \log L(u, g) \propto -\sum_{\substack{m,n,m<n \\ k=1, f=f_L}}^{C, K-1, f_H} \frac{(r_{u,mn}(f) - r_{g,mnk}(f))^2}{\sigma_{r_{g,mn}}^2(f)} - \quad (59)$$

$$\sum_{\substack{m,n,m<n \\ k=1, f=f_L}}^{C, K-1, f_H} \frac{(\theta_{u,mn}(f) - \theta_{g,mnk}(f))^2}{\sigma_{\theta_{g,mn}}^2(f)} -$$

$$(K-1) \sum_{\substack{m,n,m<n \\ f_L}}^{C, f_H} \log \sigma_{r_{g,mn}}(f) - (K-1) \sum_{\substack{m,n,m<n \\ f_L}}^{C, f_H} \log \sigma_{\theta_{g,mn}}(f).$$

As a consequence, it is possible to evaluate the probability that the unknown sample u matches the training data of each gas type by calculating the rightmost side of the formula (59) regarding each piece of the test data.

Results are shown in Table 3. If needed, please refer to the tables of data used for the calculations that are quoted near the end of this specification together with the tables of data for the analysis example 2. The case that brings about the largest value of LL(u, g) in each row was indicated in bold. Regarding all the solvents, the pieces of the training data that brought about the largest likelihood coincided with those of the test data. In other words, the identification of those samples was successful with the best accuracy among the analyses conducted in the examples. A reason why <Analysis example 3> based on the concept of FIG. 3 showed the better accuracy than <Analysis example 2> based on the concept of FIG. 2 in spite of being the analyses in the same frequency domain lies in the difference in statistical stability. In the analysis based on the concept of FIG. 2, the features are evaluated for the respective channels. Accordingly, when there are C channels, it is possible to conduct the evaluations based on C ways of indices at the maximum. On the other hand, the analysis based on the concept of FIG. 3 evaluates each feature amount between two channels. Accordingly, when there are C channels, it is possible to conduct the evaluations based on $_CC_2 = C(C-1)/2$ ways of indices at the maximum. In this example, C=4 and the evaluations are conducted by using the probability P (u=g) that u becomes equal to g as the index. Therefore, while the number of the indices $$P(A_{ug}(f) e^{i\theta_{ug}(f)} Y_{u,c}(f) = Y_{g,ck}(f))$$

used for the evaluations in <Analysis example 2> based on the concept of FIG. 2 is four while the number of the indices $$P(K'_{u,mn}(f) = K'_{g,mnk}(f))$$

used for the evaluations in <Analysis example 3> based on the concept of FIG. 3 is six. Thus, the latter analysis was more statistically stabilized and presumably showed the improved accuracy.

TABLE 3

|  |  | TRAINING DATA | | | | | |
| --- | --- | --- | --- | --- | --- | --- | --- |
|  |  | WATER | ETHANOL | BENZENE | HEXANE | ETHYL ACETATE | THF |
| TEST | WATER | −1192.1 | −8292.8 | −19127.9 | −13069.7 | −7120.0 | −15637 |
| DATA | ETHANOL | −18615.3 | −920.6 | −1932.6 | −3241.7 | −1782.4 | −5330.7 |
|  | BENZENE | −34140.7 | −3906.1 | −3753.3 | −9697.2 | −23344.2 | −7566.6 |
|  | HEXANE | −5174.1 | −5024.5 | −2169.2 | −800.6 | −8011.4 | −12966.1 |
|  | ETHYL ACETATE | −11680.0 | −2295.9 | −9623.3 | −8535.8 | −1621.8 | −2484.9 |
|  | THF | −27021.1 | −13157.8 | −16002.5 | −27201.9 | −4171.5 | −1077.6 |

<Data in Calculation Processes>

The whole tables of data in the process of the calculations used for calculating the logarithmic likelihood LL from the actual measurement data in the analysis examples 2 and 3 are shown below. In each of the analysis example 2 and the analysis example 3, the data for each of the solvents measured were organized into one table. It is to be noted, however, that each Table is extremely long in a horizontal direction and is therefore divided into four segments in the horizontal direction and listed accordingly. A code appearing on the upper left and below each Table indicates a Table identification code formed from [one-digit number (an analysis example number)]−[an abbreviation indicating the solvent]−[one-digit number (a Table segment number)]. The Table segment number indicates which segment on the original Table the relevant segmented Table corresponds to when it is counted from the left end thereof. For example, a segmented Table with a Table identification of "2-H2O-4" indicates a segmented Table on the right end among the four segmented tables obtained from the original Table organizing the data on water in Analysis example 2.

(A) Data in Analysis Example 2

TABLE 4

| 2-H2O-1 | | | | | | | | | | |
| --- | --- | --- | --- | --- | --- | --- | --- | --- | --- | --- |
| | | $\log|Y_{u,c}|$ | $(\log|Y_{u,c}|-\log|Y_{g,ck}|-L_{ug,k})^2/\sigma_{Lg,c}^2$ | | | | | | | |
| | | $H_2O$ | $H_2O$ | | | | | EtOH | | |
| f | c | $k_6$ | $k_1$ | $k_2$ | $k_3$ | $k_4$ | $k_5$ | $k_1$ | $k_2$ | $k_3$ |
| 0.05 Hz | Ch. 1 | 2.932448 | 0.015528 | 0.061257 | 0.007598 | 0.012343 | 0.002632 | 0.082277 | 0.33508 | 0.061385 |
|  | Ch. 2 | 4.807255 | 0.253899 | 0.196401 | 0.006815 | 0.055687 | 0.257109 | 0.167735 | 0.10927 | 0.104259 |
|  | Ch. 3 | 0.214059 | 0.282552 | 0.302889 | 0.018644 | 0.075247 | 0.251072 | 0.033428 | 0.042129 | 0.074088 |
|  | Ch. 4 | −0.15075 | 0.22161 | 0.269001 | 0.013513 | 0.071738 | 0.176866 | 0.141532 | 0.041189 | 0.198302 |
| 0.1 Hz | Ch. 1 | 3.15177 | 0.028493 | 0.241935 | 0.030046 | 0.083013 | 0.001193 | 0.327646 | 0.336982 | 0.458025 |
|  | Ch. 2 | 5.095017 | 0.315946 | 0.02812 | 0.000803 | 4.83E−06 | 1.87E−06 | 0.225991 | 0.066558 | 0.040657 |
|  | Ch. 3 | 0.102954 | 0.06614 | 0.003893 | 0.002774 | 0.011445 | 0.000161 | 0.176814 | 0.364407 | 0.312016 |
|  | Ch. 4 | −0.30613 | 0.030136 | 0.018826 | 0.00234 | 0.011087 | 0.000137 | 0.03381 | 0.034793 | 0.003291 |
| 0.15 Hz | Ch. 1 | 2.445173 | 0.404382 | 0.023972 | 1.299293 | 0.027642 | 0.007997 | 0.180952 | 0.056679 | 0.135192 |
|  | Ch. 2 | 4.518538 | 0.262701 | 0.309177 | 0.191865 | 0.323546 | 0.112863 | 0.38733 | 0.118136 | 0.149124 |
|  | Ch. 3 | −0.0373 | 0.5658 | 0.295941 | 0.639018 | 0.302057 | 0.126915 | 0.323844 | 0.382738 | 0.343264 |
|  | Ch. 4 | −0.43583 | 0.494061 | 0.11102 | 0.872339 | 0.11598 | 0.102996 | 1.34342 | 1.251611 | 0.701806 |
| 0.2 Hz | Ch. 1 | 2.739805 | 0.066057 | 0.340039 | 0.012297 | 0.000646 | 1.5E−05 | 3.682749 | 2.213634 | 2.225391 |
|  | Ch. 2 | 4.884092 | 0.881861 | 0.026965 | 0.013381 | 0.071721 | 0.064853 | 1.03967 | 1.224021 | 0.805373 |
|  | Ch. 3 | −0.03027 | 0.017451 | 0.169163 | 6.69E−05 | 0.011982 | 0.012865 | 3.812753 | 2.823364 | 2.778195 |
|  | Ch. 4 | −0.39468 | 0.082344 | 0.099176 | 0.002849 | 0.007218 | 0.010161 | 0.132148 | 0.494451 | 0.251361 |
| 0.25 Hz | Ch. 1 | 1.304614 | 0.083381 | 0.053683 | 0.178045 | 0.06335 | 0.126283 | 0.21969 | 0.010341 | 0.077039 |
|  | Ch. 2 | 3.974741 | 0.189864 | 0.056947 | 0.062641 | 0.023908 | 0.021632 | 0.003946 | 0.024046 | 0.018486 |
|  | Ch. 3 | −1.08519 | 0.292937 | 0.017939 | 0.283765 | 0.000882 | 0.519068 | 1.049757 | 0.934272 | 0.962281 |
|  | Ch. 4 | −1.30175 | 0.536128 | 0.061673 | 0.536718 | 0.099586 | 0.061731 | 0.120168 | 1.169053 | 0.585128 |
| 0.3 Hz | Ch. 1 | 1.77906 | 0.017229 | 0.121454 | 0.003508 | 7.96E−05 | 0.103669 | 5.385901 | 3.212201 | 4.127876 |
|  | Ch. 2 | 3.969648 | 19.77757 | 0.447483 | 0.022152 | 0.436747 | 0.285548 | 1.237518 | 0.493951 | 0.871189 |
|  | Ch. 3 | −1.10723 | 0.691018 | 0.001425 | 0.00523 | 0.003042 | 0.001418 | 2.811423 | 3.487934 | 2.908687 |
|  | Ch. 4 | −1.38584 | 0.281316 | 0.009429 | 0.000254 | 0.027503 | 0.00379 | 0.098454 | 0.431133 | 0.22032 |
| 0.35 Hz | Ch. 1 | 1.991224 | 0.007782 | 0.831335 | 0.856439 | 0.095316 | 0.032772 | 0.662734 | 1.08776 | 0.673883 |
|  | Ch. 2 | 4.402223 | 0.891123 | 1.259555 | 0.10718 | 0.466628 | 0.04784 | 0.13307 | 0.168194 | 0.105433 |
|  | Ch. 3 | −0.48774 | 0.168365 | 0.117823 | 0.181619 | 0.13284 | 0.008554 | 0.302263 | 0.284196 | 0.498945 |
|  | Ch. 4 | −0.84129 | 0.19811 | 0.01879 | 0.116577 | 0.14708 | 7.66E−07 | 0.084399 | 0.026987 | 0.140524 |
| 0.4 Hz | Ch. 1 | 1.671233 | 0.375403 | 0.778679 | 0.977055 | 0.160357 | 0.366523 | 0.002541 | 0.04599 | 0.075243 |
|  | Ch. 2 | 4.034196 | 4.499357 | 0.616937 | 1.35635 | 1.451181 | 1.98444 | 0.450383 | 0.226996 | 0.741311 |
|  | Ch. 3 | −0.41272 | 2.253397 | 0.003096 | 1.714624 | 0.54077 | 1.190717 | 0.22827 | 0.054912 | 0.025177 |
|  | Ch. 4 | −0.84991 | 1.638972 | 0.113672 | 1.046523 | 0.897661 | 1.028717 | 0.895005 | 0.106178 | 0.242065 |
| 0.45 Hz | Ch. 1 | 1.0326 | 0.293257 | 0.354489 | 0.132529 | 0.496565 | 0.263738 | 2.714157 | 2.569215 | 3.067098 |
|  | Ch. 2 | 3.45847 | 0.018455 | 0.684412 | 0.163855 | 0.310662 | 0.049393 | 0.144457 | 0.264787 | 0.190736 |
|  | Ch. 3 | −3.08209 | 0.73181 | 1.517527 | 0.720607 | 1.472133 | 0.378617 | 1.376256 | 1.208661 | 1.490575 |
|  | Ch. 4 | −2.69591 | 0.005479 | 0.098794 | 1.11E−05 | 0.034243 | 0.041934 | 0.000424 | 0.008054 | 0.000233 |
| 0.5 Hz | Ch. 1 | 0.623116 | 0.203752 | 0.008503 | 0.064501 | 9.59E−07 | 0.149319 | 11.70239 | 7.946248 | 9.91867 |
|  | Ch. 2 | 2.83636 | 1.150344 | 0.24782 | 0.206593 | 0.828952 | 0.194315 | 0.004016 | 0.022699 | 0.008735 |
|  | Ch. 3 | −2.27069 | 0.05016 | 0.000626 | 0.001055 | 0.029994 | 0.005476 | 0.317226 | 0.279423 | 0.407181 |
|  | Ch. 4 | −2.5256 | 0.002452 | 0.048259 | 0.000489 | 0.194428 | 0.025902 | 0.041662 | 8.4E−05 | 0.001052 |

TABLE 4-continued

2-H2O-1

$(\log|Y_{u,c}| - \log|Y_{g,ck}| - L_{ug,k})^2 / \sigma_{Lg,c}^2$

| | | EtOH | | Benzene | | | | | |
|---|---|---|---|---|---|---|---|---|---|
| f | c | $k_4$ | $k_5$ | $k_1$ | $k_2$ | $k_3$ | $k_4$ | $k_5$ | $k_1$ |
| 0.05 Hz | Ch. 1 | 0.126445 | 0.076843 | 1.649683 | 0.496517 | 1.236384 | 1.135342 | 2.567349 | 4.046843 |
| | Ch. 2 | 0.211516 | 0.169844 | 0.079576 | 0.179251 | 0.070754 | 0.034197 | 0.291957 | 1.381176 |
| | Ch. 3 | 0.069527 | 0.060545 | 1.815624 | 1.762462 | 2.557034 | 1.959455 | 1.417671 | 0.305101 |
| | Ch. 4 | 0.20259 | 0.238038 | 0.000167 | 0.00941 | 0.035678 | 0.060009 | 0.106044 | 0.000655 |
| 0.1 Hz | Ch. 1 | 0.311539 | 0.001309 | 1.482032 | 0.490013 | 1.92649 | 1.659878 | 2.287115 | 6.481283 |
| | Ch. 2 | 0.125353 | 1.190082 | 0.033674 | 0.260209 | 0.260377 | 0.092826 | 0.592061 | 1.372616 |
| | Ch. 3 | 0.313963 | 0.590839 | 0.486679 | 0.074454 | 0.355842 | 0.55665 | 0.300288 | 2.45065 |
| | Ch. 4 | 0.042587 | 1.026679 | 0.012286 | 0.008016 | 0.01788 | 0.000635 | 0.011043 | 2.383702 |
| 0.15 Hz | Ch. 1 | 0.019925 | 0.670243 | 6.694773 | 15.42012 | 9.153566 | 9.865874 | 0.929161 | 0.621689 |
| | Ch. 2 | 0.647196 | 0.676467 | 0.327445 | 0.743509 | 0.702182 | 0.635333 | 0.148967 | 0.043792 |
| | Ch. 3 | 0.152742 | 0.213666 | 0.539817 | 0.900582 | 0.620828 | 0.654247 | 0.689521 | 0.009099 |
| | Ch. 4 | 3.78553 | 0.195488 | 0.011957 | 0.001751 | 0.05593 | 0.028981 | 0.360247 | 0.097804 |
| 0.2 Hz | Ch. 1 | 0.395651 | 3.25061 | 3.910434 | 3.331296 | 4.397251 | 4.941173 | 2.370107 | 2.288185 |
| | Ch. 2 | 0.661149 | 1.75222 | 1.752434 | 0.329824 | 0.979184 | 0.80768 | 1.011595 | 0.222188 |
| | Ch. 3 | 1.705178 | 2.250791 | 1.628749 | 1.655137 | 1.268445 | 1.081111 | 1.491309 | 0.461202 |
| | Ch. 4 | 1.224301 | 0.148506 | 0.166106 | 0.000528 | 0.007571 | 0.118604 | 0.25082 | 0.010314 |
| 0.25 Hz | Ch. 1 | 0.048653 | 0.273525 | 4.658813 | 2.067987 | 8.575946 | 9.061227 | 2.450557 | 3.283795 |
| | Ch. 2 | 0.00554 | 0.217376 | 0.773978 | 3.101811 | 5.165864 | 1.177992 | 2.806897 | 0.009744 |
| | Ch. 3 | 0.55285 | 2.517766 | 1.068557 | 0.10894 | 0.315497 | 1.046344 | 1.332725 | 0.208665 |
| | Ch. 4 | 1.544012 | 0.049261 | 0.024976 | 0.045536 | 0.017001 | 0.038524 | 0.709337 | 0.084774 |
| 0.3 Hz | Ch. 1 | 4.904303 | 4.471869 | 6.004123 | 3.280892 | 7.069575 | 7.361276 | 3.700611 | 1.234569 |
| | Ch. 2 | 0.772502 | 1.52879 | 0.2166 | 0.079105 | 1.57134 | 0.210588 | 0.258738 | 0.000106 |
| | Ch. 3 | 3.523438 | 3.247666 | 2.844729 | 3.033213 | 1.498373 | 3.303834 | 3.390104 | 2.11598 |
| | Ch. 4 | 0.159557 | 0.583094 | 0.316986 | 0.002258 | 0.104836 | 0.532337 | 0.02993 | 0.381888 |
| 0.35 Hz | Ch. 1 | 0.028054 | 0.922258 | 2.997888 | 4.128365 | 2.093287 | 2.747367 | 1.4836 | 8.805812 |
| | Ch. 2 | 0.018826 | 0.101264 | 5.233506 | 4.455679 | 1.088861 | 9.554294 | 1.844267 | 1.510488 |
| | Ch. 3 | 0.19929 | 0.297975 | 0.68058 | 1.097048 | 0.9845 | 0.713113 | 0.962923 | 2.050922 |
| | Ch. 4 | 0.120707 | 0.017708 | 0.059448 | 0.192286 | 0.072707 | 0.027987 | 0.008372 | 0.550144 |
| 0.4 Hz | Ch. 1 | 0.612533 | 0.090324 | 3.820468 | 2.381472 | 3.461294 | 4.201941 | 4.031053 | 2.038086 |
| | Ch. 2 | 0.465237 | 0.451061 | 2.347553 | 6.785044 | 0.586211 | 1.889497 | 0.452262 | 0.206035 |
| | Ch. 3 | 0.046856 | 0.062114 | 0.092352 | 0.175908 | 0.249641 | 0.450247 | 0.248643 | 0.206266 |
| | Ch. 4 | 0.015775 | 0.156318 | 0.000398 | 1.16E−05 | 0.015732 | 0.117774 | 0.079635 | 0.148375 |
| 0.45 Hz | Ch. 1 | 0.050813 | 2.851424 | 6.563217 | 2.122993 | 13.56992 | 16.03969 | 14.49123 | 1.108909 |
| | Ch. 2 | 0.097663 | 0.985223 | 0.461907 | 0.077316 | 0.008882 | 0.005119 | 0.066247 | 0.044487 |
| | Ch. 3 | 0.623549 | 1.46337 | 1.244469 | 0.169385 | 0.902767 | 0.922616 | 1.169577 | 0.961478 |
| | Ch. 4 | 0.444963 | 0.090701 | 0.052596 | 0.012512 | 0.14405 | 0.217042 | 0.162256 | 0.236798 |
| 0.5 Hz | Ch. 1 | 4.520826 | 8.848809 | 13.17834 | 8.79552 | 19.85639 | 16.56784 | 9.075497 | 0.900141 |
| | Ch. 2 | 0.171546 | 0.013193 | 2.424845 | 0.822181 | 1.668586 | 3.975087 | 2.527241 | 0.000183 |
| | Ch. 3 | 0.08433 | 0.336942 | 11.14977 | 7.251999 | 11.87231 | 12.80431 | 5.740116 | 0.155094 |
| | Ch. 4 | 0.088525 | 0.000425 | 0.053684 | 0.202759 | 2.119544 | 0.234567 | 0.07145 | 0.35384 |

TABLE 5

2-H2O-2

$(\log|Y_{u,c}| - \log|Y_{g,ck}| - L_{ug,k})^2 / \sigma_{Lg,c}^2$

| Hexane | | | | AcOEt | | | | | THF |
|---|---|---|---|---|---|---|---|---|---|
| $k_2$ | $k_3$ | $k_4$ | $k_5$ | $k_1$ | $k_2$ | $k_3$ | $k_4$ | $k_5$ | $k_1$ |
| 10.07774 | 7.343268 | 2.606222 | 8.337645 | 0.022548 | 0.002416 | 0.006139 | 0.035771 | 0.000161 | 0.023632 |
| 1.452162 | 1.583796 | 0.408543 | 1.781462 | 0.093098 | 0.010997 | 0.63979 | 0.03627 | 0.008268 | 0.353331 |
| 1.099164 | 0.587407 | 0.162378 | 0.654298 | 0.026879 | 0.090262 | 0.00029 | 0.061909 | 0.05161 | 0.446262 |
| 0.905118 | 0.33302 | 0.371687 | 0.404851 | 0.051379 | 0.046287 | 0.169111 | 0.113091 | 0.086563 | 0.000144 |
| 5.834411 | 7.121482 | 6.003362 | 9.869387 | 1.126352 | 1.892097 | 1.473798 | 1.68482 | 1.004888 | 0.034417 |
| 1.788889 | 2.2992 | 3.625222 | 2.67085 | 0.129682 | 0.000894 | 0.072834 | 0.000361 | 0.044435 | 0.764931 |
| 2.645601 | 2.848241 | 2.494947 | 3.544518 | 4.875101 | 4.030122 | 4.35298 | 3.6002 | 3.584921 | 1.022593 |
| 1.251974 | 1.682393 | 0.446188 | 3.121042 | 0.246713 | 0.193739 | 0.120292 | 0.166814 | 0.194933 | 0.070464 |
| 10.45288 | 4.750302 | 5.987154 | 1.569412 | 0.017205 | 0.026443 | 0.028167 | 0.089105 | 0.031711 | 0.013891 |
| 1.967169 | 0.484784 | 0.900543 | 1.036687 | 0.00138 | 0.021985 | 0.010905 | 0.171088 | 0.058726 | 0.450252 |
| 0.368758 | 0.236879 | 0.26 | 0.00078 | 0.128555 | 0.08874 | 0.07792 | 0.03484 | 0.055371 | 0.783337 |
| 0.270001 | 0.264739 | 0.203611 | 0.002348 | 0.042863 | 0.09974 | 0.098797 | 0.135732 | 0.115255 | 0.087302 |
| 5.728559 | 10.7524 | 2.313693 | 8.850467 | 0.270672 | 0.510395 | 0.174497 | 0.150516 | 0.112187 | 0.244788 |
| 0.285201 | 0.671265 | 0.282362 | 0.894463 | 0.000137 | 0.02552 | 0.03214 | 0.010105 | 0.360528 | 0.853633 |
| 0.512058 | 0.938176 | 0.12961 | 0.77037 | 0.523398 | 0.522785 | 0.423782 | 0.387564 | 0.396807 | 1.721049 |
| 0.368853 | 0.604856 | 0.104393 | 0.312287 | 0.021969 | 0.011044 | 0.089739 | 0.061774 | 0.395054 | 0.01182 |
| 4.748248 | 8.456597 | 21.88148 | 20.35875 | 0.000178 | 0.196188 | 0.002588 | 0.000101 | 0.000178 | 0.026857 |
| 0.024026 | 0.0197 | 0.122687 | 0.324019 | 0.061068 | 0.1268 | 0.00048 | 0.013546 | 0.006864 | 0.232353 |

TABLE 5-continued

2-H2O-2

| | | | | | | | | |
|---|---|---|---|---|---|---|---|---|
| 0.082563 | 0.37254 | 0.835265 | 0.743887 | 0.091803 | 0.036041 | 0.066251 | 0.052277 | 0.057394 | 3.683439 |
| 0.974846 | 0.403316 | 0.911865 | 0.448149 | 0.038039 | 0.122 | 0.075125 | 0.039434 | 0.064796 | 0.667874 |
| 3.963878 | 4.608531 | 0.714937 | 1.220821 | 1.198109 | 0.169662 | 0.593198 | 1.314485 | 0.512644 | 0.066046 |
| 0.344913 | 0.770878 | 0.002503 | 0.180059 | 0.222327 | 0.006765 | 0.081014 | 0.109654 | 0.003862 | 0.239986 |
| 2.829433 | 6.444794 | 0.731561 | 1.572389 | 1.821216 | 1.858886 | 2.411171 | 2.187729 | 1.575976 | 0.705213 |
| 1.122962 | 0.137395 | 0.333066 | 1.469056 | 0.834385 | 1.293352 | 2.936058 | 1.231997 | 0.288108 | 0.002607 |
| 19.84914 | 12.09916 | 8.550761 | 20.48575 | 2.67978 | 2.269058 | 1.988926 | 0.334702 | 1.237108 | 0.965949 |
| 1.435227 | 0.701491 | 1.683512 | 3.54148 | 0.145983 | 0.293028 | 0.022217 | 0.027001 | 0.001182 | 0.262831 |
| 4.122937 | 2.369113 | 2.817053 | 5.526473 | 0.951903 | 1.061777 | 0.96717 | 0.699007 | 0.832624 | 3.60233 |
| 2.62063 | 1.84727 | 0.24395 | 1.028466 | 0.882741 | 0.314577 | 0.009781 | 0.69175 | 0.121876 | 0.628132 |
| 1.698785 | 0.817325 | 0.506226 | 1.061669 | 0.001958 | 0.077766 | 0.058701 | 0.074052 | 0.021171 | 0.001923 |
| 0.388182 | 0.363319 | 0.477823 | 0.482599 | 0.011662 | 0.210658 | 0.661106 | 0.029968 | 0.322697 | 0.005858 |
| 0.319207 | 5.33E−05 | 0.380862 | 0.480652 | 0.031153 | 0.040146 | 0.02818 | 0.019981 | 0.071441 | 0.120801 |
| 0.015904 | 0.066183 | 0.221106 | 0.035104 | 0.09896 | 0.180953 | 0.607222 | 0.283492 | 0.501807 | 0.072845 |
| 3.920121 | 2.757216 | 2.519565 | 4.980514 | 0.599075 | 0.061603 | 0.635124 | 0.079553 | 0.956636 | 0.959772 |
| 0.060583 | 0.306026 | 0.410681 | 0.441816 | 0.127681 | 0.192719 | 0.097079 | 0.3037 | 0.078131 | 1.83989 |
| 3.029191 | 1.532743 | 1.769039 | 2.734207 | 0.561221 | 0.489656 | 0.561385 | 0.116808 | 0.576508 | 15.31597 |
| 0.757144 | 1.813982 | 1.544664 | 3.020211 | 0.00173 | 0.034499 | 1.54E−05 | 0.183583 | 0.007477 | 0.010509 |
| 0.103894 | 1.897864 | 1.179989 | 4.003272 | 0.052948 | 0.009164 | 0.73259 | 0.029799 | 0.052948 | 0.383418 |
| 0.031976 | 0.00877 | 0.001974 | 0.040724 | 0.010019 | 0.216525 | 0.094689 | 0.000176 | 0.070847 | 0.004453 |
| 0.022378 | 0.290971 | 0.125147 | 0.471049 | 0.352756 | 0.07434 | 0.692435 | 0.204761 | 0.11861 | 0.218839 |
| 0.686681 | 0.686148 | 0.796547 | 1.619872 | 0.02375 | 3.06E−05 | 0.158275 | 0.039158 | 0.070961 | 0.003264 |

| THF | | | | argY$_{u,c}$ H$_2$O | H$_2$O | | | |
|---|---|---|---|---|---|---|---|---|
| k$_2$ | k$_3$ | k$_4$ | k$_5$ | k$_6$ | k$_1$ | k$_2$ | k$_3$ | k$_4$ |
| 0.055763 | 0.013319 | 0.04502 | 0.000139 | 2.796509 | 4.017292 | 3.670154 | 4.301342 | 3.796275 |
| 0.985796 | 0.972339 | 0.320363 | 0.572303 | −3.11269 | 0.51617 | 0.357417 | 0.689627 | 0.450227 |
| 0.442992 | 0.753087 | 0.51529 | 0.570567 | −3.02643 | 0.568519 | 0.629654 | 0.584118 | 0.586821 |
| 0.557219 | 0.37792 | 0.048568 | 0.245254 | −2.95369 | 0.486703 | 0.467971 | 0.422542 | 0.452904 |
| 0.050693 | 0.050416 | 0.00011 | 0.001121 | −0.19158 | 0.000549 | 0.000268 | 6.33E−07 | 0.001226 |
| 0.947678 | 0.423364 | 0.717639 | 0.636148 | −0.02059 | 0.001268 | 6.21E−05 | 0.000723 | 0.002504 |
| 0.910748 | 0.817723 | 0.901448 | 0.874819 | −0.09212 | 0.000114 | 1.8E−05 | 1.58E−07 | 2.2E−05 |
| 0.293396 | 0.016919 | 0.002254 | 0.000696 | −0.10392 | 0.002082 | 1.8E−05 | 0.00062 | 7.41E−05 |
| 0.017373 | 0.178265 | 0.029318 | 0.031499 | −1.09626 | 0.580052 | 4.26E−06 | 1.357032 | 0.004328 |
| 0.389936 | 0.546421 | 1.74E−06 | 0.065987 | −1.01917 | 0.767595 | 0.000447 | 0.126619 | 0.006098 |
| 0.886926 | 0.903606 | 0.792828 | 0.755088 | −0.71826 | 4.10314 | 0.007891 | 1.214384 | 0.000112 |
| 0.179201 | 0.38096 | 0.559691 | 0.664279 | −0.76987 | 3.649552 | 0.001098 | 1.003897 | 2.17E−05 |
| 0.068677 | 0.005398 | 0.077764 | 0.525973 | −0.50722 | 0.199437 | 0.251872 | 0.005952 | 0.00018 |
| 1.62994 | 4.616609 | 1.780879 | 0.095797 | −0.12618 | 0.107269 | 1.77054 | 0.000326 | 0.004894 |
| 1.887096 | 2.138744 | 1.546253 | 1.770265 | −0.13157 | 0.278647 | 0.388678 | 0.002213 | 0.005117 |
| 0.066493 | 0.00027 | 0.002681 | 0.05359 | −0.14665 | 0.325135 | 0.398722 | 0.00753 | 0.002411 |
| 0.09144 | 0.124042 | 1.098178 | 0.006918 | −2.48277 | 0.005062 | 0.004607 | 0.046837 | 0.006563 |
| 0.646629 | 1.055208 | 2.179844 | 0.452437 | −2.14734 | 0.009286 | 0.001184 | 0.025688 | 0.008596 |
| 2.991335 | 2.892913 | 3.879155 | 2.42223 | −2.61724 | 0.004351 | 0.001687 | 0.031236 | 0.00509 |
| 0.034562 | 0.16424 | 0.420455 | 0.103014 | −2.58758 | 0.008377 | 0.003277 | 0.033177 | 0.008573 |
| 0.074969 | 0.114515 | 0.408355 | 0.002879 | −0.43502 | 0.036211 | 0.094221 | 0.02601 | 0.006019 |
| 0.267594 | 0.001505 | 0.358732 | 1.097421 | −0.01557 | 0.000346 | 0.065615 | 0.00092 | 0.013965 |
| 0.828378 | 0.587664 | 0.754821 | 1.060858 | 0.654159 | 0.002077 | 0.050271 | 0.004732 | 0.000999 |
| 0.005843 | 0.140624 | 0.261399 | 0.000358 | 0.67298 | 0.015136 | 0.047647 | 0.007176 | 2.39E−05 |
| 0.031767 | 0.850176 | 0.291719 | 1.61109 | −1.3954 | 0.071407 | 0.004641 | 0.000286 | 0.01378 |
| 0.272675 | 0.410484 | 0.850429 | 0.005683 | −1.11989 | 0.079894 | 0.00711 | 0.004117 | 0.009298 |
| 3.673789 | 2.827257 | 1.81335 | 2.778873 | −1.07357 | 0.063412 | 0.006182 | 0.000685 | 0.012282 |
| 2.239591 | 0.115626 | 0.064068 | 1.539037 | −1.04083 | 0.189793 | 0.012463 | 0.005697 | 0.024365 |
| 0.094607 | 0.005817 | 0.172033 | 0.033416 | −2.8133 | 5.37E−07 | 4.189622 | 0.073703 | 0.001581 |
| 0.025761 | 0.010754 | 0.163305 | 0.003441 | −2.48483 | 0.011014 | 5.678081 | 0.06064 | 0.003204 |
| 0.127736 | 0.097828 | 0.016026 | 0.095513 | −2.39591 | 1.93E−05 | 1.214079 | 0.01027 | 6.57E−05 |
| 0.783049 | 0.193158 | 0.001569 | 0.190379 | −2.24821 | 0.002325 | 1.253492 | 0.026386 | 0.001503 |
| 1.267557 | 0.885196 | 2.465928 | 0.733585 | −0.87061 | 0.000322 | 0.002066 | 0.006113 | 0.152573 |
| 2.975927 | 2.012552 | 3.983075 | 1.504136 | −0.71379 | 0.002019 | 0.030151 | 0.002396 | 0.318352 |
| 15.95825 | 14.16483 | 18.42565 | 13.61758 | 0.012324 | 0.014569 | 0.041192 | 0.017418 | 0.383604 |
| 0.882846 | 0.090318 | 3.651201 | 0.013948 | −0.39248 | 0.003376 | 0.006787 | 0.027756 | 0.114678 |
| 0.199824 | 0.104825 | 0.118078 | 0.063761 | −1.34856 | 0.120862 | 0.02763 | 0.040295 | 0.135557 |
| 1.19559 | 0.016385 | 0.009266 | 0.028408 | −1.31643 | 0.15703 | 0.129667 | 0.017268 | 0.154493 |
| 0.628969 | 0.065865 | 0.237851 | 0.007757 | −0.23093 | 0.265506 | 0.163355 | 0.040927 | 0.329221 |
| 0.214536 | 0.041174 | 0.048762 | 0.005854 | −0.2891 | 0.103101 | 0.037774 | 0.027938 | 0.079427 |

TABLE 6

2-H2O-3

$(argY_{u,c}-argY_{g,ck}-\theta_{ug,k})^2/\sigma_{\theta g,c}^2$

| | EtOH | | | | | Benzene | | | |
|---|---|---|---|---|---|---|---|---|---|
| $k_5$ | $k_1$ | $k_2$ | $k_3$ | $k_4$ | $k_5$ | $k_1$ | $k_2$ | $k_3$ | $k_4$ |
| 3.794932 | 0.022258 | 0.284158 | 0.001617 | 1.649574 | 2.082616 | 2.701516 | 2.205939 | 2.576857 | 2.474891 |
| 0.57792 | 0.005126 | 0.363788 | 0.002337 | 0.731433 | 0.758826 | 0.301387 | 0.240556 | 0.34933 | 0.332914 |
| 0.501907 | 0.007073 | 0.022506 | 0.001135 | 0.641893 | 0.796067 | 0.265977 | 0.234577 | 0.298734 | 0.213964 |
| 0.409438 | 0.018027 | 0.047053 | 0.003814 | 0.606677 | 0.988323 | 0.245779 | 0.191988 | 0.146967 | 0.196391 |
| 0.014515 | 0.067652 | 5.556974 | 0.010286 | 0.001116 | 0.005863 | 0.033838 | 0.2058 | 1.669124 | 0.016578 |
| 0.022096 | 0.001138 | 0.291893 | 0.032691 | 4.08E-05 | 0.012209 | 0.005304 | 0.415577 | 0.917234 | 0.022811 |
| 0.015281 | 0.000452 | 0.336346 | 0.002793 | 4.86E-05 | 0.002144 | 0.000107 | 0.08429 | 2.302073 | 0.003894 |
| 0.018167 | 0.015003 | 0.250931 | 0.002817 | 0.001271 | 7.57E-05 | 0.004453 | 0.01911 | 0.938576 | 0.000386 |
| 0.006654 | 0.002245 | 0.019074 | 0.007131 | 0.010142 | 0.018404 | 0.000351 | 0.043163 | 0.025761 | 0.012919 |
| 0.065593 | 0.031042 | 0.01078 | 0.003199 | 0.00693 | 0.023493 | 9.45E-05 | 0.044458 | 0.050367 | 0.014225 |
| 0.067511 | 0.005992 | 0.004382 | 0.006039 | 0.003861 | 0.000405 | 0.020843 | 0.029004 | 0.018789 | 0.014734 |
| 0.01652 | 0.017518 | 0.007359 | 0.008988 | 0.004734 | 5.19E-05 | 0.023184 | 0.008383 | 2.41E-05 | 0.005435 |
| 1.82E-06 | 0.00047 | 1.89E-05 | 0.00303 | 0.000505 | 0.27426 | 0.041217 | 0.000152 | 0.003311 | 0.000608 |
| 0.002945 | 5.87E-05 | 0.001106 | 3.23E-05 | 0.00059 | 0.288956 | 0.094281 | 0.007738 | 0.004152 | 0.001237 |
| 0.000256 | 0.000505 | 0.000401 | 0.001218 | 0.001739 | 0.315911 | 0.013807 | 0.011133 | 0.011777 | 0.00103 |
| 0.003895 | 0.002388 | 0.002095 | 0.00636 | 1.98E-05 | 2.330767 | 0.000195 | 2.59E-07 | 0.008188 | 0.007905 |
| 0.048154 | 0.005243 | 0.012211 | 0.02021 | 0.026669 | 0.003749 | 0.005477 | 0.013474 | 0.124757 | 0.141706 |
| 0.222572 | 0.005517 | 0.010022 | 0.000185 | 0.003817 | 0.006284 | 0.02585 | 0.215572 | 0.001948 | 0.014085 |
| 0.112184 | 0.004321 | 0.005532 | 0.001352 | 0.002994 | 0.004288 | 0.010061 | 0.001987 | 0.058617 | 0.020827 |
| 0.094737 | 0.005421 | 0.015487 | 0.011399 | 0.023897 | 0.004689 | 0.163518 | 0.31487 | 0.34893 | 0.091437 |
| 0.000125 | 0.00731 | 0.032304 | 0.018352 | 0.097276 | 0.05716 | 0.022919 | 0.000107 | 0.015183 | 1.214415 |
| 0.002082 | 0.012079 | 0.013645 | 0.023946 | 0.00853 | 0.069546 | 0.00618 | 0.046543 | 0.011915 | 1.421455 |
| 1.35E-05 | 0.029925 | 0.035106 | 0.041815 | 0.061531 | 0.033339 | 0.022825 | 0.02496 | 0.03933 | 0.65884 |
| 0.000489 | 0.000104 | 0.007374 | 0.004052 | 0.015715 | 0.072112 | 0.008302 | 0.00037 | 0.000634 | 1.468107 |
| 0.027556 | 3.41E-05 | 3.8E-06 | 0.001843 | 0.024391 | 0.00014 | 0.019877 | 0.010878 | 0.001158 | 0.011045 |
| 0.000759 | 0.0005 | 0.001043 | 0.01244 | 0.001376 | 0.000476 | 0.00197 | 0.009032 | 8.88E-05 | 0.020115 |
| 0.006995 | 0.000938 | 0.001787 | 0.000241 | 0.001897 | 0.000574 | 0.006035 | 0.006026 | 0.000515 | 0.01647 |
| 0.02521 | 0.00023 | 0.007107 | 0.042784 | 0.037953 | 0.000254 | 0.053137 | 0.00269 | 0.003374 | 0.103507 |
| 0.014888 | 0.000153 | 2.23E-05 | 0.00483 | 1.046974 | 0.000141 | 0.020728 | 0.878865 | 0.000611 | 0.00855 |
| 0.022666 | 0.002277 | 0.001906 | 0.006 | 0.074699 | 0.002376 | 0.003231 | 0.065433 | 0.020632 | 9.83E-05 |
| 4.52E-05 | 0.02079 | 0.003398 | 0.004466 | 0.235813 | 0.002562 | 0.009954 | 0.022085 | 0.008949 | 0.002571 |
| 2.97E-06 | 0.042071 | 9.77E-05 | 0.004947 | 0.176533 | 0.000121 | 0.00537 | 0.11937 | 0.00094 | 0.018037 |
| 0.015278 | 3.12E-06 | 0.004581 | 0.005296 | 1.391084 | 0.011007 | 1.678165 | 1.225861 | 0.101906 | 0.00694 |
| 0.037981 | 0.038333 | 0.049317 | 0.040744 | 0.400589 | 0.001117 | 0.00493 | 0.283764 | 0.000466 | 0.00641 |
| 0.012559 | 0.086199 | 0.111718 | 0.089909 | 1.045404 | 0.062824 | 0.257425 | 2.770248 | 0.313453 | 0.608985 |
| 0.002844 | 0.003388 | 0.000404 | 0.02436 | 0.39237 | 0.046292 | 0.021951 | 0.27111 | 0.009898 | 0.043541 |
| 0.098239 | 0.04269 | 0.037773 | 2.55E-05 | 0.556388 | 0.009094 | 0.507553 | 0.395552 | 0.141462 | 0.024243 |
| 0.019182 | 0.041683 | 0.061825 | 0.042912 | 0.745744 | 0.0688 | 0.451238 | 0.023639 | 0.11449 | 0.175129 |
| 0.092298 | 0.058139 | 0.076344 | 0.091353 | 0.034482 | 0.084252 | 0.289067 | 0.139977 | 0.137348 | 0.111708 |
| 0.038499 | 0.029087 | 0.02941 | 0.002808 | 2.508948 | 0.007344 | 0.089196 | 0.146668 | 0.009082 | 0.006192 |

$(argY_{u,c}-argY_{g,ck}-\theta_{ug,k})^2/\sigma_{\theta g,c}^2$

| Benzene | | Hexane | | | | AcOEt | | |
|---|---|---|---|---|---|---|---|---|
| $k_5$ | $k_1$ | $k_2$ | $k_3$ | $k_4$ | $k_5$ | $k_1$ | $k_2$ | $k_3$ |
| 4.067596 | 9.099628 | 12.22306 | 9.470432 | 2.815597 | 7.812348 | 3.591476 | 1.678801 | 4.666848 |
| 0.000384 | 0.83056 | 1.09004 | 0.875665 | 0.323741 | 0.524195 | 0.557366 | 1.123811 | 1.69E-05 |
| 4.610081 | 0.953257 | 1.392764 | 1.086559 | 0.287728 | 0.861117 | 0.235967 | 0.924243 | 0.026893 |
| 0.003192 | 1.169767 | 1.475339 | 1.097053 | 0.294244 | 1.223209 | 0.277519 | 1.787751 | 6.546657 |
| 0.598071 | 0.225753 | 0.125798 | 0.063886 | 0.052376 | 0.062761 | 0.14546 | 0.295503 | 0.170598 |
| 0.050504 | 0.042513 | 1.565254 | 0.022434 | 0.034293 | 0.049996 | 0.296058 | 0.208705 | 0.076942 |
| 0.00404 | 0.007262 | 0.477662 | 0.001713 | 1.2E-05 | 0.000544 | 0.02978 | 0.004756 | 0.006227 |
| 0.142648 | 0.004457 | 0.378049 | 0.000161 | 0.001197 | 0.008559 | 0.004439 | 0.051522 | 0.068655 |
| 0.000785 | 0.140071 | 0.16268 | 0.05141 | 1.757708 | 0.093797 | 0.000893 | 0.01138 | 9.89E-05 |
| 0.025546 | 0.008357 | 0.013656 | 1.400347 | 0.176947 | 0.016335 | 0.045166 | 0.040457 | 0.249985 |
| 0.000666 | 0.058485 | 0.023242 | 0.622112 | 0.377202 | 0.019853 | 0.00693 | 0.006385 | 0.030252 |
| 0.044515 | 0.012804 | 0.044888 | 0.58339 | 0.26006 | 0.004626 | 0.00373 | 6.46E-05 | 0.052754 |
| 0.000158 | 0.066857 | 0.093607 | 1.261447 | 0.895558 | 1.939862 | 0.000346 | 0.005835 | 0.000529 |
| 0.001873 | 0.000716 | 0.047344 | 0.046964 | 0.954089 | 0.09378 | 0.003622 | 0.015648 | 0.000777 |
| 0.004925 | 0.008041 | 0.002648 | 0.101542 | 0.697157 | 0.126194 | 0.002384 | 0.002366 | 0.00141 |
| 0.001172 | 0.018397 | 3.28E-07 | 0.139488 | 0.577109 | 0.220365 | 0.001153 | 1.22E-06 | 0.0012 |
| 0.707728 | 0.001032 | 0.161774 | 0.000219 | 2.113918 | 0.003932 | 0.009846 | 0.063434 | 0.013129 |
| 0.073241 | 0.521418 | 4.065741 | 3.95603 | 15.26224 | 3.265185 | 0.0001 | 0.267723 | 0.002346 |
| 0.011991 | 0.027285 | 0.100399 | 0.308394 | 2.977814 | 0.082274 | 0.001088 | 0.149928 | 0.001911 |
| 0.115164 | 0.039861 | 0.036115 | 0.655484 | 0.857233 | 1.19566 | 0.003499 | 1.38565 | 0.010301 |
| 0.008722 | 1.754388 | 0.101814 | 0.434917 | 0.321932 | 0.317802 | 0.011099 | 0.034029 | 0.022303 |
| 0.069285 | 0.392755 | 2.42E-05 | 0.014647 | 0.182366 | 0.072997 | 0.000849 | 2.3E-05 | 0.020679 |
| 0.0446 | 0.038002 | 0.045743 | 0.169233 | 0.094458 | 0.005012 | 0.013527 | 0.020837 | 0.029734 |
| 0.01989 | 0.124704 | 0.006299 | 0.085453 | 0.036755 | 0.024946 | 0.000321 | 0.002074 | 0.014185 |
| 0.002357 | 0.035665 | 0.035495 | 0.246686 | 3.321278 | 0.062602 | 0.350013 | 0.000384 | 0.00254 |

TABLE 6-continued

2-H2O-3

| | | | | | | | | |
|---|---|---|---|---|---|---|---|---|
| 0.005937 | 0.026971 | 0.025182 | 0.03208 | 0.404326 | 0.051122 | 0.206182 | 0.004475 | 0.001564 |
| 0.00812 | 0.007302 | 0.000434 | 0.02448 | 0.340395 | 0.01026 | 0.435043 | 0.002374 | 0.00036 |
| 0.000682 | 0.004308 | 5.67E−06 | 0.015277 | 0.215025 | 0.006887 | 2.329201 | 0.014541 | 0.000752 |
| 0.025907 | 1.94E−05 | 0.564523 | 0.420965 | 0.012488 | 0.035464 | 0.001174 | 0.870284 | 0.001017 |
| 0.000519 | 0.002228 | 1.199943 | 0.885024 | 0.010028 | 0.001078 | 2.58E−05 | 1.119615 | 0.005198 |
| 0.008183 | 0.035515 | 1.895019 | 1.576902 | 8.85E−05 | 1.02281 | 0.000751 | 0.878167 | 0.014092 |
| 0.000259 | 0.004588 | 0.982097 | 0.202142 | 3.2E−05 | 0.457205 | 7.84E−05 | 0.703666 | 0.021116 |
| 0.332233 | 0.109625 | 0.015363 | 0.224795 | 0.208275 | 0.849081 | 0.004981 | 2.005473 | 0.002639 |
| 0.01584 | 0.044698 | 0.001199 | 0.019294 | 0.064478 | 0.630868 | 0.011236 | 1.219989 | 0.023687 |
| 0.429768 | 0.167926 | 0.090013 | 0.099957 | 0.095673 | 1.758448 | 0.071163 | 1.076517 | 0.040014 |
| 0.001685 | 0.05953 | 0.030432 | 0.00569 | 0.004315 | 0.562031 | 0.005599 | 1.655844 | 0.001732 |
| 0.205228 | 0.442846 | 0.495782 | 0.201741 | 0.547255 | 1.782961 | 0.02565 | 0.038269 | 2.021329 |
| 0.192162 | 4.17E−05 | 1.01777 | 0.001583 | 0.010859 | 0.168756 | 0.062123 | 0.810775 | 0.018426 |
| 0.275085 | 0.061009 | 0.542438 | 0.058229 | 0.065371 | 0.024893 | 0.074731 | 0.020627 | 0.461727 |
| 0.065408 | 0.026701 | 1.206761 | 0.007397 | 0.012789 | 0.070544 | 0.010961 | 0.747086 | 0.428034 |

TABLE 7

2-H2O-4

| | | THF | | | | | $\log\sigma_{Lg,c}$ | | |
|---|---|---|---|---|---|---|---|---|---|
| $k_4$ | $k_5$ | $k_1$ | $k_2$ | $k_3$ | $k_4$ | $k_5$ | $H_2O$ | EtOH | Benzene |
| 4.304673 | 3.917203 | 1.144109 | 0.031146 | 2.173876 | 2.294106 | 1.963776 | −0.27945 | 0.398827 | −0.12502 |
| 0.640647 | 0.418868 | 1.081464 | 0.003388 | 0.241227 | 0.391809 | 0.300455 | −0.0226 | 0.248584 | −0.25239 |
| 0.204385 | 0.234234 | 1.00002 | 0.003103 | 0.236814 | 0.221728 | 0.20685 | −0.55571 | 0.239137 | −0.39623 |
| 0.493774 | 0.539481 | 4.514255 | 0.175043 | 1.350119 | 0.942368 | 0.865381 | −0.53188 | −0.1312 | −0.52282 |
| 0.144491 | 0.124644 | 0.01352 | 0.053619 | 0.09793 | 0.602355 | 0.014619 | −0.7076 | −0.13743 | 0.044038 |
| 0.017039 | 0.056794 | 0.068713 | 0.207095 | 5.289527 | 2.098837 | 0.105317 | −0.42382 | −0.15439 | −0.11099 |
| 0.001273 | 0.003207 | 0.002287 | 0.002238 | 0.185782 | 0.771452 | 0.002393 | −0.42179 | −0.09534 | 0.33566 |
| 0.107433 | 0.046273 | 0.000643 | 0.001514 | 0.273111 | 0.84151 | 8.43E−06 | −0.40275 | 0.458128 | 0.175373 |
| 0.007276 | 0.003122 | 0.016785 | 0.01104 | 0.04952 | 0.003666 | 0.082222 | −0.91872 | −0.22917 | −0.95407 |
| 0.016898 | 0.003319 | 0.241956 | 0.305071 | 0.342569 | 0.007125 | 0.352814 | −0.17315 | −0.39424 | −0.01421 |
| 0.012897 | 0.002981 | 0.082936 | 0.064555 | 0.056877 | 0.009721 | 0.039784 | −0.83614 | −0.65358 | −0.29561 |
| 0.005507 | 0.002669 | 0.148218 | 0.069018 | 0.041298 | 0.002954 | 0.036106 | −0.6724 | −1.1222 | 0.043835 |
| 0.000498 | 0.009437 | 0.00219 | 7.57E−05 | 0.005373 | 0.01038 | 0.000529 | 0.371859 | −0.99151 | −0.41346 |
| 0.000374 | 0.005514 | 0.043862 | 0.006543 | 0.040386 | 0.236158 | 0.008919 | −0.16865 | −1.23994 | −0.55346 |
| 0.001736 | 0.003056 | 0.002897 | 0.00313 | 0.006828 | 0.017799 | 0.003582 | −0.0813 | −1.29443 | −0.40318 |
| 0.002261 | 0.007045 | 0.005437 | 1.05E−05 | 0.000146 | 0.028691 | 1.3E−05 | 0.04032 | −1.12337 | −0.28638 |
| 0.022094 | 3.528758 | 0.033175 | 0.023341 | 0.040891 | 0.04225 | 0.018843 | 0.191785 | −0.22819 | −0.94597 |
| 0.012119 | 0.320189 | 0.0074 | 0.028387 | 0.004016 | 0.043683 | 0.008624 | −0.11037 | −0.07316 | −1.25623 |
| 0.002895 | 0.245921 | 0.001396 | 0.000915 | 0.001401 | 0.000102 | 0.004439 | −0.54554 | −0.75784 | −0.37232 |
| 0.034229 | 0.20628 | 0.003556 | 0.001296 | 0.009821 | 1.08E−05 | 0.022744 | −0.54083 | −0.73936 | −0.23667 |
| 0.040113 | 0.026161 | 0.03681 | 0.015148 | 0.000762 | 1.155999 | 0.032136 | −1.05253 | −1.09551 | −0.50347 |
| 0.006665 | 0.001788 | 0.041657 | 0.06052 | 0.099186 | 0.00127 | 0.028272 | −1.54088 | −1.18116 | −0.45473 |
| 0.023799 | 0.02755 | 0.048287 | 0.054079 | 0.054179 | 0.135429 | 0.051929 | −0.16437 | −1.13825 | −0.67257 |
| 0.016251 | 0.001429 | 0.033065 | 0.023946 | 0.009446 | 0.016217 | 0.015117 | −0.59311 | −1.11749 | −0.54994 |
| 6.59E−05 | 0.006625 | 0.000573 | 1.366152 | 0.000567 | 0.011531 | 0.002878 | −0.791 | −1.48094 | −0.13148 |
| 0.012103 | 0.001436 | 0.000343 | 0.109977 | 0.000995 | 0.060151 | 0.012324 | −0.30458 | −1.04454 | −1.15475 |
| 0.002756 | 0.000305 | 0.00079 | 0.258943 | 0.000648 | 0.005618 | 0.00028 | −0.14548 | −0.29639 | −0.3181 |
| 0.00175 | 0.003042 | 0.001441 | 0.233412 | 0.00049 | 0.001932 | 0.001017 | −0.15455 | −1.13279 | −0.21329 |
| 0.00033 | 0.00022 | 0.000493 | 0.01269 | 0.002941 | 0.010006 | 0.001244 | −0.62735 | 0.089626 | −0.60433 |
| 0.013464 | 0.001271 | 0.007039 | 0.009301 | 0.02815 | 0.040457 | 0.010214 | −0.90372 | −0.23395 | −0.70282 |
| 0.000406 | 0.002042 | 0.001876 | 0.013831 | 0.002861 | 0.017005 | 0.001593 | −0.75676 | −0.16047 | 0.069012 |
| 0.009097 | 0.000672 | 0.003792 | 0.011547 | 0.004566 | 5.33E−05 | 0.001005 | −0.97667 | 0.048629 | −0.20526 |
| 0.479913 | 0.066823 | 0.000511 | 0.085402 | 0.00021 | 0.193291 | 0.001294 | −0.10314 | −0.45305 | −0.63388 |
| 0.410123 | 0.026024 | 0.382249 | 0.127624 | 0.14389 | 0.321726 | −0.20565 | −0.12083 | 0.069844 | |
| 0.383249 | 0.097605 | 0.201329 | 0.185464 | 0.210585 | 0.226276 | 0.317346 | −0.25904 | 1.189343 | 0.446272 |
| 0.682763 | 0.014321 | 0.050649 | 0.070486 | 0.11253 | 0.019427 | 0.003674 | −0.1905 | 0.489136 | 0.408102 |
| 0.040752 | 0.138196 | 0.017974 | 0.091846 | 2.59E−06 | 0.024097 | 0.006933 | −0.18367 | −1.36604 | −0.93406 |
| 0.024848 | 0.098948 | 0.094072 | 0.340473 | 2.05703 | 0.103407 | 1.298381 | −0.56828 | 0.228993 | −0.9417 |
| 0.097647 | 0.057888 | 0.042345 | 0.005078 | 0.196049 | 0.046692 | 0.114918 | −0.16197 | 0.020417 | −1.34016 |
| 0.000274 | 0.137937 | 0.02041 | 0.006733 | 0.363733 | 0.026353 | 0.175747 | −0.17728 | 0.066696 | −1.43918 |

| $\log\sigma_{Lg,c}$ | | | $\log\sigma_{\theta g,c}$ | | | | | |
|---|---|---|---|---|---|---|---|---|
| Hexane | AcOEt | THF | $H_2O$ | EtOH | Benzene | Hexane | AeOEt | THF |
| −0.55113 | 0.32871 | −0.08107 | 0.801234 | 1.207714 | 1.079374 | 0.189762 | 0.866507 | 1.150356 |
| −0.32497 | −0.10168 | 0.215972 | 0.729341 | 0.669981 | 1.252097 | 0.229823 | 0.939489 | 1.183314 |
| −0.61155 | 0.447759 | −0.12574 | 0.714165 | 0.547871 | 0.999054 | 0.229044 | 1.090265 | 1.080704 |
| −0.89179 | 0.355916 | −0.55732 | 0.722126 | 0.465178 | 1.117856 | 0.1627 | 0.785955 | 0.3326 |
| −0.64421 | −1.19739 | −0.06096 | 0.5606 | 0.605007 | 0.795256 | 0.743116 | −0.2618 | 1.272964 |
| −1.14907 | −1.08912 | −0.0579 | 0.53307 | 0.957349 | 1.134892 | 1.126302 | −0.39762 | 0.636763 |

TABLE 7-continued

| 2-H2O-4 | | | | | | | | |
|---|---|---|---|---|---|---|---|---|
| −1.22368 | −1.29606 | −0.19802 | 0.576843 | 0.985589 | 0.696795 | 0.874959 | −0.37434 | 1.23767 |
| −1.11758 | −1.11766 | −0.44338 | 0.594635 | 0.995588 | 1.106001 | 0.863036 | −0.35685 | 1.205117 |
| −0.36169 | −0.08808 | −0.54633 | 1.378727 | 0.870049 | 0.644553 | 1.15028 | 0.84218 | 0.11585 |
| −0.13507 | 0.117575 | −0.50368 | 1.295079 | 0.951724 | 0.980232 | 1.301856 | 0.750527 | 0.170075 |
| −0.0715 | 1.061467 | −0.58296 | 0.444318 | 0.974456 | 0.722887 | 0.901578 | 0.922287 | 0.046107 |
| −0.11942 | 0.057921 | −0.63334 | 0.472307 | 1.012596 | 0.702096 | 0.794673 | 1.032039 | 0.070549 |
| −0.38187 | −0.37755 | −0.48677 | 0.961614 | 1.035338 | 0.756087 | 0.997163 | 0.862225 | 0.689686 |
| −0.28183 | −0.55965 | −1.19113 | 1.01892 | 1.0191 | 0.857216 | 1.099827 | 0.859037 | 0.505935 |
| −0.17188 | −0.38782 | −0.72924 | 0.654436 | 1.034736 | 0.789613 | 1.216735 | 0.834254 | 0.678971 |
| 0.033897 | −0.15015 | −0.82075 | 0.619903 | 1.091146 | 0.840677 | 1.260704 | 0.774444 | 0.696334 |
| −1.15407 | 0.02776 | −0.90701 | 1.044944 | 0.990337 | −0.16622 | 0.883427 | 0.852136 | 0.731865 |
| −0.34122 | 0.011325 | −0.71451 | 0.951797 | 1.037002 | 0.532775 | −0.79673 | 1.082475 | 0.682279 |
| −0.33503 | 0.564229 | −0.99709 | 1.059034 | 1.038236 | 0.205231 | −0.45793 | 1.088727 | 0.735329 |
| −0.51182 | 0.321599 | −0.41743 | 1.050676 | 1.089144 | 0.128321 | −0.33163 | 1.021132 | 0.783396 |
| 0.125804 | −0.91843 | −0.05209 | 0.656551 | 0.717653 | 1.123837 | 0.642526 | 1.106472 | 0.682546 |
| −0.12365 | −0.52523 | −0.15205 | 0.594566 | 0.691442 | 0.946763 | 0.738585 | 1.084102 | 0.904087 |
| −0.61878 | −1.01393 | −0.17641 | 0.879033 | 0.762743 | 1.111363 | 0.709606 | 1.104812 | 0.776997 |
| −0.24084 | −1.39596 | −0.26371 | 0.860382 | 0.844861 | 0.831881 | 0.830535 | 1.095595 | 0.802764 |
| −0.8441 | −1.78544 | −1.54092 | 0.909549 | 0.899793 | 0.836804 | 0.622138 | 0.89432 | 1.315317 |
| −1.10002 | −0.25395 | −0.86242 | 0.906718 | 0.842321 | 0.733571 | 0.646614 | 0.880259 | 1.176445 |
| −1.07174 | −0.91017 | −1.11347 | 0.706513 | 0.779633 | 0.822822 | 0.725209 | 0.912419 | 1.213009 |
| −0.67837 | −0.81836 | −1.39507 | 0.671983 | 0.655389 | 0.947994 | 0.74445 | 1.008622 | 1.180359 |
| −0.2829 | −0.47458 | −0.25747 | 0.40447 | 0.757171 | 0.997815 | 0.85769 | 1.104346 | 0.999825 |
| −0.41213 | −0.27044 | 0.204271 | 0.071537 | 0.602741 | 1.225844 | 0.825294 | 1.052402 | 1.112113 |
| −0.27628 | −0.31088 | 0.087425 | 0.907564 | 0.618479 | 1.213651 | 0.576452 | 1.166429 | 1.023458 |
| 0.111701 | −0.27363 | −0.07046 | 0.950403 | 0.619702 | 1.220683 | 1.165549 | 1.218396 | 1.152418 |
| 0.038614 | 0.083506 | −0.32954 | 0.634833 | 0.739149 | −0.20836 | 0.812456 | 0.535362 | 0.228705 |
| −0.15347 | 0.56292 | −0.3326 | 0.551091 | 0.864869 | 0.855276 | 0.850432 | 0.930297 | 0.188121 |
| −0.10431 | 0.630582 | −0.87203 | 0.582188 | 0.645764 | 0.006498 | 0.60461 | 0.689769 | 0.163691 |
| −0.21624 | 0.388878 | −0.91419 | 0.584172 | 0.450962 | 0.931221 | 0.69898 | 0.643733 | 0.089592 |
| 0.227763 | 0.666495 | 0.047935 | 0.768615 | 0.7843 | 0.198057 | 0.592487 | 0.754077 | 0.893002 |
| 0.117962 | 0.073392 | 0.670118 | 0.838437 | 0.813008 | 0.568256 | 1.022759 | 0.875654 | 0.682506 |
| 0.391301 | 0.158097 | 0.439682 | 0.683124 | 0.702989 | 0.698645 | 0.987988 | 0.895158 | 0.95815 |
| −0.00175 | −0.09715 | −0.05799 | 0.699085 | 0.915385 | 1.181083 | 1.161702 | 0.945869 | 1.024418 |

TABLE 8

| 2-EtOH-1 | | | | | | | | | |
|---|---|---|---|---|---|---|---|---|---|
| | | $\log\|Y_{u,c}\|$ | \multicolumn{5}{c}{$(\log\|Y_{u,c}\|-\log\|Y_{g,ck}\|-L_{ug,k})^2/\sigma_{Lg,c}^2$} | | | |
| | | EtOH | $H_2O$ | | | | | EtOH | | |
| f | c | $k_6$ | $k_1$ | $k_2$ | $k_3$ | $k_4$ | $k_5$ | $k_1$ | $k_2$ | $k_3$ |
| 0.05 Hz | Ch. 1 | 2.685314 | 0.260054 | 0.522636 | 0.316521 | 0.34402 | 0.277452 | 0.002076 | 0.113961 | 4.2E−05 |
| | Ch. 2 | 5.306179 | 0.011775 | 0.002285 | 0.097854 | 0.025405 | 0.012475 | 0.011685 | 0.000847 | 0.000459 |
| | Ch. 3 | 0.707027 | 1.450332 | 1.473239 | 0.639936 | 0.879336 | 1.356032 | 0.013642 | 0.008907 | 0.000753 |
| | Ch. 4 | −0.44595 | 0.049732 | 0.030663 | 0.333523 | 0.181409 | 0.074642 | 0.007836 | 0.445796 | 0.000377 |
| 0.1 Hz | Ch. 1 | 1.725596 | 1.50278 | 0.815064 | 1.491673 | 1.22447 | 1.849979 | 0.046736 | 0.0433 | 0.012502 |
| | Ch. 2 | 4.641248 | 0.016017 | 0.07174 | 0.165815 | 0.187779 | 0.188501 | 0.020369 | 0.001479 | 0.017169 |
| | Ch. 3 | −1.11462 | 1.106595 | 0.536373 | 0.55071 | 0.473052 | 0.611675 | 0.023384 | 0.000915 | 0.00022 |
| | Ch. 4 | −1.16398 | 1.97E−05 | 0.099379 | 0.051291 | 0.080275 | 0.035996 | 0.011795 | 0.012378 | 0.000321 |
| 0.15 Hz | Ch. 1 | 2.453679 | 2.003186 | 0.390125 | 3.683689 | 0.894323 | 0.75491 | 0.001174 | 0.023423 | 0.000549 |
| | Ch. 2 | 5.275327 | 5.46E−05 | 0.001303 | 0.006709 | 1.185365 | 0.03385 | 0.000688 | 0.092947 | 0.068862 |
| | Ch. 3 | 0.533561 | 1.774654 | 1.263307 | 1.902607 | 0.000922 | 0.376501 | 0.007377 | 0.018353 | 0.010548 |
| | Ch. 4 | −0.49391 | 0.001354 | 0.165236 | 0.037733 | 1.166934 | 0.175358 | 5.86E−07 | 0.001687 | 0.10374 |
| 0.2 Hz | Ch. 1 | 1.491063 | 0.056882 | 0.007676 | 0.147936 | 0.220988 | 0.241709 | 0.000327 | 0.201874 | 0.198344 |
| | Ch. 2 | 4.736876 | 0.236129 | 0.083482 | 0.113884 | 0.03435 | 0.039395 | 0.0919 | 0.046845 | 0.180937 |
| | Ch. 3 | −0.07134 | 0.43887 | 0.014179 | 0.272681 | 0.409388 | 0.414471 | 0.02838 | 0.01079 | 0.013776 |
| | Ch. 4 | −1.07778 | 0.019563 | 0.213388 | 0.040158 | 0.003851 | 0.002136 | 0.011488 | 0.054041 | 0.00094 |
| 0.25 Hz | Ch. 1 | 1.028648 | 0.378856 | 0.31137 | 0.560569 | 0.334606 | 0.000818 | 0.000817 | 0.156508 | 0.048286 |
| | Ch. 2 | 4.10595 | 0.178991 | 0.063149 | 0.056464 | 0.027983 | 0.025516 | 0.002562 | 0.020412 | 0.015318 |
| | Ch. 3 | −0.4563 | 2.015132 | 0.554103 | 1.990957 | 0.719795 | 0.024917 | 0.00378 | 0.014276 | 0.011046 |
| | Ch. 4 | −1.30639 | 0.268706 | 0.00119 | 0.269124 | 0.01035 | 0.213718 | 0.007371 | 0.673101 | 0.254154 |
| 0.3 Hz | Ch. 1 | 0.995197 | 4.777366 | 2.910292 | 3.980962 | 4.18423 | 3.001503 | 0.031002 | 0.124199 | 0.01276 |
| | Ch. 2 | 3.924034 | 18.90965 | 0.325203 | 0.061261 | 0.316061 | 0.189827 | 1.089049 | 0.401897 | 0.747381 |
| | Ch. 3 | −0.59068 | 2.306692 | 0.422191 | 0.378458 | 0.551544 | 0.422304 | 0.020712 | 0.002205 | 0.013261 |
| | Ch. 4 | −1.33991 | 0.539196 | 0.090606 | 0.048328 | 0.136713 | 0.070474 | 0.433302 | 1.002181 | 0.662378 |
| 0.35 Hz | Ch. 1 | 0.090699 | 2.673995 | 6.045678 | 6.113061 | 1.533356 | 2.986163 | 0.102721 | 0.008396 | 0.098396 |
| | Ch. 2 | 3.516489 | 0.147005 | 2.832082 | 0.054381 | 1.546744 | 0.607315 | 0.004547 | 0.000489 | 0.01156 |
| | Ch. 3 | −1.3398 | 0.658912 | 0.003382 | 0.684887 | 0.001365 | 0.095434 | 0.006887 | 0.004396 | 0.05739 |
| | Ch. 4 | −2.09946 | 0.141509 | 0.042434 | 0.074264 | 0.204692 | 0.00453 | 0.049765 | 0.009378 | 0.094513 |

TABLE 8-continued

2-EtOH-1

| | | | | | | | | | | |
|---|---|---|---|---|---|---|---|---|---|---|
| 0.4 Hz | Ch. 1 | −1.06817 | 1.14764 | 0.179648 | 2.093922 | 0.737922 | 1.132074 | 0.075238 | 8.91E−05 | 0.002542 |
| | Ch. 2 | 1.702324 | 2.9571 | 0.147384 | 0.582288 | 0.644975 | 1.014611 | 0.216767 | 0.073397 | 0.429643 |
| | Ch. 3 | −3.12158 | 1.090561 | 0.262628 | 0.726934 | 0.077583 | 0.402422 | 0.532058 | 0.226176 | 0.168362 |
| | Ch. 4 | −3.04786 | 4.275782 | 0.202879 | 3.278163 | 3.010304 | 3.246591 | 1.509311 | 0.37008 | 0.599842 |
| 0.45 Hz | Ch. 1 | 0.269017 | 0.623621 | 0.541459 | 0.935443 | 0.392572 | 0.668592 | 0.058301 | 0.081825 | 0.018938 |
| | Ch. 2 | 3.415752 | 0.205778 | 0.056557 | 0.034109 | 0.001031 | 0.134858 | 0.026071 | 0.000727 | 0.010984 |
| | Ch. 3 | −1.11904 | 1.257948 | 0.555266 | 1.272736 | 0.583279 | 1.854289 | 0.008014 | 0.026656 | 0.001741 |
| | Ch. 4 | −2.10393 | 0.06828 | 0.016136 | 0.033841 | 5.01E−06 | 0.000306 | 0.013344 | 2.67E−05 | 0.006347 |
| 0.5 Hz | Ch. 1 | 0.129064 | 0.663161 | 1.377159 | 1.023668 | 1.604568 | 0.7732 | 0.501391 | 1.716248 | 0.959564 |
| | Ch. 2 | 3.58882 | 0.535211 | 0.024604 | 0.012897 | 0.32434 | 0.009971 | 0.008145 | 8.75E−06 | 0.003619 |
| | Ch. 3 | −1.08473 | 0.923156 | 0.580445 | 0.591854 | 0.82616 | 0.657467 | 0.002577 | 0.007292 | 0.000581 |
| | Ch. 4 | −1.73275 | 0.107819 | 0.248527 | 0.09057 | 0.518091 | 0.013902 | 0.000206 | 0.051821 | 0.03461 |

| | | $(\log|Y_{u,c}|-\log|Y_{g,ck}|-L_{ug,k})^2/\sigma_{Lg,c}^2$ | | | | | | | |
|---|---|---|---|---|---|---|---|---|---|
| | | EtOH | | Benzene | | | | | |
| f | c | $k_4$ | $k_5$ | $k_1$ | $k_2$ | $k_3$ | $k_4$ | $k_5$ | $k_1$ |
| 0.05 Hz | Ch. 1 | 0.013067 | 0.001291 | 0.769127 | 0.088351 | 0.496359 | 0.433126 | 1.427772 | 1.925051 |
| | Ch. 2 | 0.025106 | 0.012246 | 0.046404 | 0.848037 | 0.58294 | 0.097709 | 0.001834 | 0.409957 |
| | Ch. 3 | 0.001292 | 0.00287 | 0.611262 | 0.580582 | 1.068028 | 0.695868 | 0.390677 | 0.022247 |
| | Ch. 4 | 0.000214 | 0.000536 | 0.49059 | 0.615456 | 0.768062 | 0.195839 | 1.026468 | 1.040194 |
| 0.1 Hz | Ch. 1 | 0.053099 | 0.56611 | 0.313229 | 0.001788 | 0.533282 | 0.397712 | 0.730345 | 1.529736 |
| | Ch. 2 | 0.000457 | 0.574932 | 0.018234 | 0.036699 | 0.036762 | 0.000192 | 0.203327 | 0.074042 |
| | Ch. 3 | 0.000171 | 0.038122 | 0.105616 | 0.009955 | 0.050126 | 0.139466 | 0.030747 | 0.04272 |
| | Ch. 4 | 0.017185 | 0.879807 | 0.0444 | 0.000107 | 0.01564 | 0.054561 | 0.042007 | 3.639701 |
| 0.15 Hz | Ch. 1 | 0.062482 | 0.182811 | 3.168212 | 9.730451 | 4.919557 | 5.445317 | 0.024477 | 0.116916 |
| | Ch. 2 | 0.024306 | 0.03024 | 0.016564 | 0.175345 | 0.15558 | 0.124998 | 0.003314 | 0.08482 |
| | Ch. 3 | 0.008531 | 0.000439 | 0.157552 | 0.37356 | 0.202619 | 0.221899 | 0.242635 | 0.030479 |
| | Ch. 4 | 0.617511 | 0.515071 | 0.063532 | 0.102115 | 0.015602 | 0.036544 | 0.057027 | 0.54498 |
| 0.2 Hz | Ch. 1 | 1.711189 | 0.018006 | 0.793451 | 0.545324 | 1.020583 | 1.290841 | 0.205021 | 0.211375 |
| | Ch. 2 | 0.259775 | 8.51E−07 | 0.43293 | 0.008376 | 0.10479Z | 0.054237 | 0.115572 | 0.001301 |
| | Ch. 3 | 0.228808 | 0.080599 | 0.296438 | 0.307757 | 0.155622 | 0.094865 | 0.23954 | 0.009695 |
| | Ch. 4 | 0.40421 | 0.007283 | 0.041509 | 0.051436 | 0.084585 | 0.300537 | 0.088207 | 0.062261 |
| 0.25 Hz | Ch. 1 | 0.515345 | 0.00066 | 1.29737 | 0.175262 | 3.644528 | 3.963205 | 0.298136 | 0.310127 |
| | Ch. 2 | 0.003873 | 0.228899 | 0.705503 | 2.963142 | 4.986449 | 1.093144 | 2.675062 | 0.00685 |
| | Ch. 3 | 0.11732 | 0.250689 | 0.087075 | 0.169422 | 0.031306 | 0.080817 | 0.172899 | 0.064918 |
| | Ch. 4 | 0.963898 | 0.233046 | 7.89E−08 | 0.003095 | 0.083028 | 0.12534 | 0.468491 | 0.248887 |
| 0.3 Hz | Ch. 1 | 0.004884 | 0.0009 | 1.597438 | 0.390488 | 2.168062 | 2.330916 | 0.543558 | 0.22922 |
| | Ch. 2 | 0.656194 | 1.363242 | 0.186709 | 0.06148 | 1.488953 | 0.18113 | 0.225966 | 0.001172 |
| | Ch. 3 | 0.003185 | 0.000343 | 0.295711 | 0.358529 | 0.0066 | 0.455363 | 0.48774 | 0.13813 |
| | Ch. 4 | 0.553429 | 1.227861 | 0.135219 | 0.021837 | 0.01651 | 0.2855 | 0.135641 | 0.22525 |
| 0.35 Hz | Ch. 1 | 1.695411 | 0.030361 | 0.867651 | 1.517515 | 0.418423 | 0.735401 | 0.174781 | 1.78512 |
| | Ch. 2 | 0.324247 | 0.012996 | 0.952409 | 0.638523 | 0.071978 | 3.165662 | 0.002141 | 0.000166 |
| | Ch. 3 | 0.000415 | 0.006253 | 0.121055 | 0.325308 | 0.265407 | 0.134995 | 0.254261 | 0.175162 |
| | Ch. 4 | 0.078397 | 0.004308 | 0.10043 | 0.261726 | 0.117464 | 0.008875 | 0.000339 | 0.736309 |
| 0.4 Hz | Ch. 1 | 0.312207 | 0.005875 | 2.269422 | 1.199157 | 1.994629 | 2.565513 | 2.432372 | 1.215866 |
| | Ch. 2 | 0.22711 | 0.217238 | 1.448917 | 5.181764 | 0.191127 | 1.094332 | 0.118355 | 0.043391 |
| | Ch. 3 | 0.219126 | 0.250875 | 0.253955 | 0.048123 | 0.48956 | 0.758728 | 0.488152 | 0.542738 |
| | Ch. 4 | 0.024616 | 0.4595 | 0.147526 | 0.130128 | 0.056985 | 0.500307 | 0.006715 | 0.014393 |
| 0.45 Hz | Ch. 1 | 2.767266 | 0.040125 | 0.089122 | 0.650112 | 2.017514 | 3.033217 | 2.382052 | 0.010452 |
| | Ch. 2 | 0.7294 | 0.203442 | 0.053875 | 0.526473 | 0.124808 | 0.141358 | 0.036154 | 0.121512 |
| | Ch. 3 | 0.223735 | 0.002805 | 0.019318 | 0.319231 | 0.000698 | 0.000257 | 0.011004 | 0.508481 |
| | Ch. 4 | 0.580602 | 0.042538 | 0.015979 | 0.046133 | 0.076514 | 0.131732 | 0.089929 | 0.086701 |
| 0.5 Hz | Ch. 1 | 39.12739 | 1.332341 | 0.901726 | 0.081292 | 3.152205 | 1.93142 | 0.110191 | 0.01209 |
| | Ch. 2 | 0.3224 | 0.001502 | 1.127594 | 0.169277 | 0.634298 | 2.245362 | 1.197757 | 0.025009 |
| | Ch. 3 | 0.104717 | 0.001124 | 0.803972 | 0.089597 | 1.106694 | 1.403479 | 4.96E−06 | 0.000895 |
| | Ch. 4 | 0.266263 | 0.039152 | 1.480134 | 0.28582 | 0.2218 | 2.158635 | 1.568029 | 0.130242 |

TABLE 9

2-EtOH-2

$(\log|Y_{u,c}|-\log|Y_{g,ck}|-L_{ug,k})^2/\sigma_{Lg,c}^2$

| Hexane | | | | AcOEt | | | | | THF |
|---|---|---|---|---|---|---|---|---|---|
| $k_2$ | $k_3$ | $k_4$ | $k_5$ | $k_1$ | $k_2$ | $k_3$ | $k_4$ | $k_5$ | $k_1$ |
| 6.505031 | 4.351364 | 0.981141 | 5.124084 | 0.011803 | 0.043954 | 0.032564 | 0.200646 | 0.060569 | 0.295513 |
| 0.449036 | 0.523502 | 0.010861 | 0.639614 | 0.015076 | 0.283843 | 0.138357 | 0.382359 | 0.113552 | 0.820598 |
| 0.120336 | 0.004213 | 0.089134 | 0.011529 | 0.006283 | 0.003275 | 0.067731 | 3.14E−05 | 0.000257 | 0.055911 |
| 3.785664 | 2.469235 | 2.572697 | 2.658794 | 0.003464 | 0.004954 | 0.015801 | 0.002577 | 7.55E−05 | 0.523626 |
| 1.224212 | 1.848509 | 1.302256 | 3.358227 | 1.475677 | 0.810967 | 1.127996 | 0.956613 | 1.622136 | 0.297037 |

TABLE 9-continued

2-EtOH-2

| | | | | | | | | | |
|---|---|---|---|---|---|---|---|---|---|
| 0.191856 | 0.380481 | 1.009064 | 0.539921 | 1.457468 | 0.667881 | 1.247734 | 0.685805 | 1.119235 | 1.38455 |
| 0.021203 | 0.007135 | 0.037396 | 0.01222 | 0.091686 | 0.010476 | 0.032838 | 6E−05 | 0.000139 | 0.141236 |
| 2.198673 | 2.758744 | 1.064712 | 4.539128 | 0.017635 | 0.005814 | 0.000292 | 0.001982 | 0.006023 | 0.203282 |
| 7.764847 | 3.003204 | 4.001292 | 0.649988 | 0.043466 | 0.031343 | 0.257541 | 0.001693 | 0.026107 | 0.428967 |
| 0.813703 | 0.038322 | 0.201122 | 0.267987 | 0.181404 | 0.057835 | 0.243237 | 0.000618 | 0.021441 | 1.944911 |
| 0.113758 | 0.046971 | 0.057565 | 0.058584 | 0.014929 | 0.003786 | 0.00183 | 0.00247 | 1.1E−06 | 0.189071 |
| 0.893228 | 0.883636 | 0.768646 | 0.142156 | 0.022294 | 0.001643 | 0.001766 | 0.000146 | 0.000284 | 0.172958 |
| 1.796996 | 4.955813 | 0.219176 | 3.694289 | 0.278914 | 0.111532 | 0.397754 | 0.436155 | 0.508998 | 0.455107 |
| 0.000708 | 0.09726 | 0.000573 | 0.192123 | 0.464635 | 0.688412 | 0.240767 | 0.324256 | 0.004832 | 4.768512 |
| 0.018205 | 0.150495 | 0.048684 | 0.088239 | 8.13E−06 | 5.89E−06 | 0.004848 | 0.009617 | 0.008224 | 0.088823 |
| 0.570473 | 0.8569 | 0.2219 | 0.499554 | 0.000879 | 0.080064 | 0.014811 | 0.004996 | 0.203103 | 0.057157 |
| 0.853432 | 2.731712 | 11.71372 | 10.60696 | 0.138118 | 0.685469 | 0.111641 | 0.140573 | 0.158673 | 1.309502 |
| 0.029224 | 0.015478 | 0.111769 | 0.306118 | 0.066734 | 0.118942 | 0.001097 | 0.016281 | 0.008847 | 0.255221 |
| 0.179989 | 0.010247 | 0.040941 | 0.02277 | 0.000181 | 0.229794 | 0.001033 | 0.003707 | 0.002495 | 0.291177 |
| 1.428187 | 0.710307 | 1.351734 | 0.769418 | 0.010976 | 0.06709 | 0.03379 | 0.011731 | 0.026988 | 0.394661 |
| 1.845811 | 2.293427 | 0.045453 | 0.223318 | 0.492869 | 1.917469 | 1.053567 | 0.422653 | 1.167774 | 0.248465 |
| 0.317392 | 0.729451 | 0.000682 | 0.20093 | 0.257305 | 0.01392 | 0.061948 | 0.087263 | 0.009581 | 0.2647 |
| 0.358933 | 2.118998 | 0.051833 | 0.02923 | 0.056714 | 0.059734 | 0.003027 | 0.016568 | 0.124211 | 0.020718 |
| 0.839668 | 0.051666 | 0.188595 | 1.142079 | 0.210084 | 2.535593 | 4.702787 | 2.449386 | 0.983777 | 0.039102 |
| 7.974196 | 3.411442 | 1.671315 | 8.379543 | 6.476496 | 32.35606 | 7.681803 | 12.98424 | 9.422726 | 5.252959 |
| 0.001927 | 0.163508 | 0.00309 | 0.409561 | 0.022748 | 1.153956 | 0.465065 | 0.135853 | 0.321815 | 2.225884 |
| 1.034128 | 0.276267 | 0.441995 | 1.788276 | 0.012835 | 0.028245 | 0.014662 | 0.000691 | 0.002512 | 0.707627 |
| 3.010929 | 2.17713 | 0.372442 | 1.27803 | 0.649138 | 0.182346 | 0.001222 | 0.487013 | 0.046335 | 0.307212 |
| 0.95731 | 0.335366 | 0.149416 | 0.497618 | 0.191719 | 0.013166 | 0.0229 | 0.443204 | 0.061558 | 0.074497 |
| 0.142458 | 0.127558 | 0.877696 | 0.201679 | 0.01106 | 0.060425 | 0.359909 | 0.001604 | 0.125957 | 0.043739 |
| 0.718301 | 0.075758 | 0.809429 | 0.952251 | 0.219954 | 0.242907 | 0.21193 | 0.188221 | 0.313348 | 0.295892 |
| 0.019353 | 6.34E−05 | 0.042022 | 0.204834 | 0.496306 | 0.66471 | 1.366924 | 0.85073 | 1.206251 | 0.345884 |
| 0.68004 | 0.255229 | 0.186649 | 1.158685 | 0.109275 | 0.733365 | 0.094631 | 0.676534 | 0.016 | 0.475798 |
| 0.0982 | 3.98E−05 | 0.006616 | 0.011064 | 0.007056 | 0.027448 | 0.001463 | 0.077153 | 3.84E−05 | 0.472194 |
| 0.002193 | 0.207561 | 0.132187 | 0.001607 | 0.003975 | 0.012642 | 0.003961 | 0.221295 | 0.002799 | 0.069629 |
| 0.459644 | 1.333267 | 1.10392 | 2.389207 | 0.00401 | 0.084487 | 0.010202 | 0.104678 | 0.000341 | 0.080475 |
| 0.266748 | 0.290334 | 0.061241 | 1.350278 | 0.096598 | 0.198181 | 0.099231 | 0.135631 | 0.096597 | 0.148109 |
| 0.122836 | 0.006086 | 0.046693 | 0.000908 | 0.078164 | 0.081703 | 0.016443 | 0.037155 | 0.007515 | 0.02741 |
| 0.328704 | 0.03383 | 0.004896 | 0.068957 | 0.00347 | 0.65234 | 0.088271 | 0.006809 | 0.036337 | 0.004107 |
| 0.353679 | 0.353296 | 0.433677 | 1.079082 | 0.169318 | 0.063423 | 0.019731 | 0.207258 | 0.274322 | 0.036236 |

| $(\log\|Y_{u,c}\|-\log\|Y_{g,c k}\|-L_{ug,k})^2/\sigma_{Lg,c}^2$ THF | | | | | argY$_{u,c}$ EtOH | H$_2$O | | | |
|---|---|---|---|---|---|---|---|---|---|
| $k_2$ | $k_3$ | $k_4$ | $k_5$ | $k_6$ | $k_1$ | $k_2$ | $k_3$ | $k_4$ | |
| 0.39191 | 0.255322 | 0.362482 | 0.142958 | 2.732679 | 1.665157 | 1.444458 | 1.849761 | 1.523977 | |
| 1.701262 | 1.683569 | 0.769933 | 1.140536 | −3.05878 | 2.041456 | 1.711359 | 2.374014 | 1.908087 | |
| 0.054758 | 0.1903 | 0.081948 | 0.104838 | 3.097583 | 2.240156 | 2.13346 | 2.209508 | 2.20426 | |
| 2.126086 | 1.759313 | 0.241333 | 1.456535 | −2.95992 | 2.080355 | 2.041433 | 1.945286 | 2.009829 | |
| 0.255409 | 0.256032 | 0.58446 | 0.485869 | 0.167611 | 0.063847 | 0.067467 | 0.07668 | 0.058132 | |
| 1.627036 | 0.907695 | 1.320665 | 1.209241 | 1.258725 | 0.08851 | 0.064563 | 0.083436 | 0.044916 | |
| 0.101705 | 0.072286 | 0.098613 | 0.089939 | 0.743215 | 8.67E−05 | 8.2E−06 | 3.18E−06 | 3.69E−05 | |
| 0.528643 | 0.099535 | 0.054242 | 0.044861 | 0.763724 | 0.000699 | 0.000223 | 3.26E−05 | 0.000773 | |
| 0.447427 | 0.920273 | 0.133861 | 0.510618 | −0.92985 | 0.683898 | 0.004547 | 1.513606 | 1.74E−07 | |
| 1.817214 | 2.143728 | 0.5255 | 0.961324 | −0.36738 | 0.663025 | 0.001658 | 0.17447 | 0.000263 | |
| 0.241599 | 0.250342 | 0.193749 | 0.175325 | −0.43093 | 3.751019 | 1.17E−09 | 1.026422 | 0.006129 | |
| 0.082962 | 0.008961 | 0.001352 | 0.01075 | −0.17174 | 4.071382 | 0.005513 | 1.23062 | 0.012555 | |
| 0.823217 | 1.201011 | 0.793016 | 0.197256 | 2.081036 | 0.221697 | 0.228106 | 0.002797 | 0.000118 | |
| 6.433636 | 11.61719 | 6.730216 | 2.462643 | 2.546804 | 0.102302 | 1.75018 | 0.000661 | 0.006027 | |
| 0.1295 | 0.201232 | 0.052729 | 0.100272 | 2.472752 | 0.25324 | 0.358561 | 0.005138 | 0.009249 | |
| 0.008088 | 0.109811 | 0.087626 | 0.013526 | 2.594713 | 0.38245 | 0.461943 | 0.001487 | 7.82E−07 | |
| 0.459769 | 1.775954 | 4.114375 | 0.805104 | 2.34603 | 0.252393 | 0.24912 | 0.419465 | 0.262404 | |
| 0.684419 | 1.103334 | 2.248781 | 0.484136 | 2.55045 | 0.269505 | 0.209005 | 0.339932 | 0.265718 | |
| 0.122449 | 0.103192 | 0.348025 | 0.031234 | 2.726574 | 0.289262 | 0.316655 | 0.182375 | 0.283499 | |
| 9.64E−06 | 0.046764 | 0.211057 | 0.017409 | −3.04721 | 2.286516 | 2.184099 | 2.568784 | 2.28974 | |
| 0.231989 | 0.173936 | 0.013556 | 0.654666 | −2.88493 | 8.07E−06 | 0.014281 | 0.000685 | 0.012071 | |
| 0.293657 | 0.004019 | 0.388813 | 1.149581 | −2.40415 | 0.046088 | 0.000523 | 0.041185 | 0.123516 | |
| 0.045933 | 0.005007 | 0.029919 | 0.111654 | −2.67011 | 0.02602 | 0.000127 | 0.020786 | 0.059815 | |
| 0.049784 | 0.272151 | 0.132926 | 0.027421 | −2.4096 | 6.87E−05 | 0.010721 | 0.000902 | 0.012066 | |
| 9.588134 | 5.535249 | 7.478312 | 4.021924 | 0.144677 | 0.004876 | 0.01671 | 0.032576 | 0.006401 | |
| 2.254357 | 2.624267 | 3.615535 | 0.816999 | 1.197808 | 0.158996 | 0.040164 | 0.03249 | 0.045163 | |
| 0.739493 | 0.390213 | 0.084003 | 0.372369 | 1.008753 | 0.051132 | 0.002802 | 2.31E−07 | 0.007247 | |
| 1.583183 | 0.010355 | 0.241471 | 1.004603 | 1.140042 | 0.128684 | 0.001205 | 2.09E−06 | 0.006267 | |
| 0.389847 | 0.057852 | 0.535185 | 0.249594 | −0.79318 | 0.548538 | 7.77419 | 1.025864 | 0.610157 | |
| 0.000778 | 0.000835 | 0.288058 | 0.03658 | 1.295606 | 0.503366 | 3.162487 | 0.128366 | 0.300229 | |
| 0.306691 | 0.259254 | 0.104323 | 0.255477 | 1.099439 | 0.022917 | 1.5596 | 0.061666 | 0.024053 | |
| 1.447502 | 0.574138 | 0.077624 | 0.569339 | 0.980164 | 0.000112 | 1.339138 | 0.040021 | 0.005836 | |
| 0.295504 | 0.530876 | 0.009827 | 0.660912 | 0.145599 | 0.010417 | 0.001494 | 3.51E−05 | 0.225356 | |
| 1.114768 | 0.561574 | 1.759609 | 0.310439 | 0.844064 | 0.030895 | 0.002215 | 0.029498 | 0.118008 | |
| 0.119086 | 0.01298 | 0.41322 | 0.001641 | 0.742039 | 0.016387 | 0.002094 | 0.013628 | 0.137377 | |
| 0.306259 | 0.007338 | 2.324465 | 0.254311 | 1.00335 | 0.004235 | 0.001664 | 0.001885 | 0.21328 | |
| 2.105616 | 0.462794 | 0.436171 | 0.564824 | 0.475047 | 0.082418 | 0.011163 | 0.019648 | 0.094627 | |

TABLE 9-continued

2-EtOH-2

| | | | | | | | | |
|---|---|---|---|---|---|---|---|---|
| 1.421476 | 0.051452 | 0.038059 | 0.004861 | 1.051811 | 0.010878 | 0.00464 | 0.025781 | 0.010218 |
| 0.151597 | 0.021632 | 0.007052 | 0.241863 | 1.01894 | 0.084964 | 0.032539 | 0.000461 | 0.122494 |
| 0.046524 | 0.001987 | 0.219312 | 0.029234 | 1.041106 | 0.019819 | 0.000197 | 0.000173 | 0.010305 |

TABLE 10

2-EtOH-3

$(argY_{u,c} - argY_{g,ck} - \theta_{ug,k})^2 / \sigma_{\theta g,c}^2$

| | EtOH | | | | | Benzene | | | |
|---|---|---|---|---|---|---|---|---|---|
| $k_5$ | $k_1$ | $k_2$ | $k_3$ | $k_4$ | $k_5$ | $k_1$ | $k_2$ | $k_3$ | $k_4$ |
| 1.523126 | 0.106449 | 0.003319 | 0.189439 | 0.654321 | 0.936387 | 1.21675 | 0.892412 | 1.133574 | 1.066291 |
| 2.162535 | 0.681263 | 1.841276 | 0.643417 | 2.588965 | 2.640281 | 0.941172 | 0.831046 | 1.024537 | 0.996284 |
| 2.378576 | 6.624534 | 6.289543 | 7.244768 | 3.447467 | 3.117668 | 1.385399 | 1.460299 | 1.313761 | 1.513386 |
| 1.917051 | 1.203735 | 1.39193 | 1.04969 | 3.033793 | 3.82996 | 0.994182 | 0.88264 | 0.782673 | 0.892052 |
| 0.024223 | 1.62E−05 | 6.87198 | 0.026472 | 0.053227 | 0.035176 | 0.001184 | 0.05536 | 2.281037 | 0.00803 |
| 0.168607 | 0.01895 | 0.506465 | 8.86E−05 | 0.031605 | 0.003709 | 0.004996 | 0.251143 | 1.212717 | 5.66E−05 |
| 0.01494 | 0.000414 | 0.337414 | 0.002891 | 6.22E−05 | 0.00223 | 0.000134 | 0.085005 | 2.298347 | 0.004049 |
| 0.013363 | 0.012021 | 0.263969 | 0.004346 | 0.00052 | 0.000464 | 0.00305 | 0.022423 | 0.961002 | 0.000971 |
| 0.000263 | 0.024366 | 0.000864 | 0.000589 | 6.41E−05 | 0.000726 | 0.013799 | 0.005118 | 0.00059 | 0.000509 |
| 0.037733 | 0.007918 | 0.000276 | 0.000939 | 1.57E−05 | 0.004365 | 0.00563 | 0.015901 | 0.019508 | 0.001191 |
| 0.029228 | 0.00063 | 0.000193 | 0.000646 | 9.67E−05 | 0.001035 | 0.005946 | 0.010618 | 0.004874 | 0.002929 |
| 0.055657 | 0.037993 | 0.000539 | 0.00104 | 3.9E−05 | 0.004868 | 0.004479 | 3.87E−05 | 0.008145 | 0.000135 |
| 0.000656 | 7.39E−07 | 0.000723 | 0.001056 | 0.002027 | 0.298377 | 0.030005 | 0.001776 | 0.00077 | 2.65E−05 |
| 0.003836 | 0.000235 | 0.001675 | 3.94E−06 | 0.000276 | 0.280768 | 0.088823 | 0.006233 | 0.003071 | 0.001953 |
| 0.001651 | 3.17E−05 | 1.01E−05 | 0.000326 | 0.000618 | 0.235131 | 0.009212 | 0.007054 | 0.007569 | 0.000112 |
| 0.000201 | 0.000352 | 0.000245 | 0.002465 | 0.001193 | 2.423579 | 0.00277 | 0.001535 | 0.002685 | 0.002524 |
| 0.423388 | 0.278632 | 0.3203 | 0.357136 | 0.382855 | 0.26695 | 2.316023 | 1.773596 | 3.24379 | 3.328 |
| 0.8002 | 0.213914 | 0.23848 | 0.161484 | 0.202514 | 0.218561 | 0.645739 | 1.225866 | 0.471885 | 0.579851 |
| 0.072281 | 0.303319 | 0.293876 | 0.336061 | 0.315581 | 0.303595 | 2.305381 | 1.866396 | 2.756104 | 1.622381 |
| 2.987339 | 2.075363 | 2.224375 | 2.171945 | 2.315186 | 2.060549 | 15.82027 | 17.09185 | 17.33722 | 15.01936 |
| 0.031068 | 0.008252 | 1.15E−05 | 0.00167 | 0.018375 | 0.003937 | 0.00115 | 0.016335 | 3.3E−05 | 0.9693 |
| 0.077785 | 0.01037 | 0.009011 | 0.003248 | 0.014252 | 0.002702 | 0.007295 | 0.002674 | 0.003011 | 1.839479 |
| 0.046931 | 0.004387 | 0.002689 | 0.001207 | 7.8E−05 | 0.003207 | 0.000314 | 0.000117 | 0.000871 | 0.96138 |
| 0.018726 | 0.011305 | 0.00094 | 0.002796 | 7.79E−05 | 0.023105 | 0.000726 | 0.009766 | 0.008627 | 1.195958 |
| 0.000985 | 0.037436 | 0.040513 | 0.024459 | 0.126382 | 0.035156 | 0.005084 | 0.100226 | 0.031775 | 0.01149 |
| 0.020631 | 0.01029 | 0.024369 | 0.055388 | 0.007519 | 0.010401 | 0.033277 | 0.054321 | 0.021743 | 0.078321 |
| 0.003357 | 0.002971 | 0.004376 | 0.001552 | 0.004548 | 0.002289 | 0.010111 | 0.010101 | 0.002077 | 0.022864 |
| 0.006699 | 0.003975 | 3.71E−05 | 0.016546 | 0.074545 | 0.00388 | 0.029633 | 4.23E−05 | 8.37E−08 | 0.069355 |
| 0.383597 | 0.258734 | 0.276406 | 0.203872 | 2.28468 | 0.283979 | 0.306428 | 0.278669 | 0.148125 | 0.252057 |
| 0.2061 | 0.162505 | 0.097188 | 0.077253 | 0.395282 | 0.094043 | 0.017889 | 0.004252 | 0.002205 | 0.032646 |
| 0.019674 | 0.115903 | 0.064704 | 0.069213 | 0.464938 | 0.060946 | 0.043264 | 0.001631 | 0.04114 | 0.003309 |
| 0.001288 | 0.023333 | 0.001804 | 0.000323 | 0.223386 | 0.004013 | 0.010401 | 0.100357 | 0.003525 | 0.026573 |
| 0.00156 | 0.006014 | 0.020581 | 9.02E−06 | 1.575581 | 0.03265 | 2.222772 | 0.831251 | 0.264898 | 0.07771 |
| 0.000667 | 0.001192 | 0.003698 | 0.001647 | 0.63073 | 0.037902 | 0.054303 | 0.136808 | 0.019815 | 0.006848 |
| 0.018673 | 0.003624 | 0.01017 | 0.004416 | 0.62261 | 0.000298 | 0.004234 | 1.493538 | 0.013822 | 0.114293 |
| 0.00488 | 0.00081 | 0.025866 | 0.000235 | 0.235866 | 0.005539 | 0.055229 | 0.188027 | 0.000154 | 0.014787 |
| 0.063941 | 0.021507 | 0.018152 | 0.002979 | 0.470996 | 0.001277 | 0.366354 | 0.541821 | 0.072339 | 0.002357 |
| 0.023554 | 0.009088 | 0.002585 | 0.008527 | 0.318178 | 0.001383 | 0.083637 | 0.052347 | 0.001952 | 0.001292 |
| 0.006403 | 0.000472 | 0.00324 | 0.006866 | 0.164009 | 0.005024 | 0.100685 | 0.023653 | 0.02258 | 0.01297 |
| 0.000253 | 0.00064 | 0.000689 | 0.039296 | 2.069926 | 0.003545 | 0.035083 | 0.244357 | 0.000258 | 0.001067 |

$(argY_{u,c} - argY_{g,ck} - \theta_{ug,k})^2 / \sigma_{\theta g,c}^2$

| Benzene | Hexane | | | | | AcOEt | | |
|---|---|---|---|---|---|---|---|---|
| $k_5$ | $k_1$ | $k_2$ | $k_3$ | $k_4$ | $k_5$ | $k_1$ | $k_2$ | $k_3$ |
| 2.179353 | 2.892461 | 4.75377 | 3.103133 | 0.131144 | 2.188098 | 1.507746 | 0.392988 | 2.224544 |
| 0.161251 | 4.335482 | 4.905697 | 4.437768 | 3.026951 | 3.590434 | 1.748422 | 0.234634 | 0.336189 |
| 0.206434 | 7.180529 | 6.129812 | 6.831 | 9.731884 | 7.442179 | 1.12239 | 0.340843 | 2.921308 |
| 0.31117 | 5.68603 | 6.338399 | 5.52431 | 3.405591 | 5.803137 | 1.50174 | 4.144167 | 10.61254 |
| 0.30801 | 0.497288 | 0.015532 | 0.233105 | 0.210598 | 0.230951 | 0.061027 | 0.007196 | 0.046394 |
| 0.006597 | 0.123094 | 1.224207 | 0.086696 | 0.108798 | 0.135615 | 0.014475 | 0.043091 | 0.147041 |
| 0.004190 | 0.007438 | 0.479084 | 0.001799 | 5.93E−06 | 0.000593 | 0.03103 | 0.005264 | 0.006806 |
| 0.134089 | 0.00663 | 0.396305 | 3.89E−06 | 0.000397 | 0.00605 | 0.000287 | 0.031435 | 0.045087 |
| 0.02697 | 0.208308 | 0.235693 | 0.020907 | 1.982274 | 0.150862 | 0.006709 | 2.61E−05 | 0.014819 |
| 0.059822 | 0.023367 | 0.031792 | 1.258702 | 0.232415 | 0.035817 | 0.011211 | 0.00893 | 0.154721 |
| 0.001719 | 0.034441 | 0.009254 | 0.536537 | 0.311288 | 0.007165 | 0.000792 | 0.000615 | 0.01412 |
| 0.015787 | 0.036462 | 0.083904 | 0.708281 | 0.345456 | 0.02126 | 0.014989 | 0.002843 | 0.084704 |
| 0.000297 | 0.055296 | 0.108484 | 1.209395 | 0.940427 | 1.87518 | 0.002061 | 0.002459 | 1.44E−05 |
| 0.001173 | 0.001145 | 0.050474 | 0.043947 | 0.940315 | 0.089496 | 0.002619 | 0.013477 | 0.000356 |

TABLE 10-continued

2-EtOH-3

| | | | | | | | | |
|---|---|---|---|---|---|---|---|---|
| 0.002367 | 0.010756 | 0.0014 | 0.110689 | 0.673904 | 0.136368 | 0.000797 | 0.000787 | 0.000289 |
| 1.96E−05 | 0.012151 | 0.000575 | 0.121157 | 0.616354 | 0.197158 | 0.005667 | 0.001799 | 4.46E−05 |
| 5.240018 | 0.225345 | 0.010946 | 0.27209 | 0.896992 | 0.324377 | 0.387101 | 0.600325 | 0.406442 |
| 0.138511 | 9.930977 | 19.76354 | 19.52075 | 40.14436 | 17.94568 | 0.145152 | 0.789244 | 0.175903 |
| 2.333388 | 6.693177 | 9.419717 | 4.826657 | 20.05188 | 6.078508 | 0.305962 | 0.947376 | 0.294212 |
| 15.3073 | 34.33269 | 34.22015 | 41.85286 | 22.40599 | 45.60599 | 2.317537 | 6.97134 | 2.448246 |
| 0.00058 | 2.294105 | 0.016638 | 0.220323 | 0.14235 | 0.568269 | 0.000201 | 0.004217 | 0.000889 |
| 0.00984 | 0.180382 | 0.038836 | 0.006555 | 0.395678 | 0.00465 | 0.01296 | 0.019093 | 6.79E−07 |
| 0.001796 | 0.200005 | 0.001475 | 0.025313 | 0.003032 | 0.104377 | 0.002875 | 0.000654 | 6.32E−06 |
| 0.000528 | 0.222171 | 0.001509 | 0.030314 | 0.096057 | 0.076263 | 0.005294 | 0.002038 | 0.000807 |
| 0.068034 | 0.204276 | 0.203869 | 0.577285 | 4.34954 | 0.263499 | 0.153036 | 0.032693 | 0.022506 |
| 0.003719 | 0.099101 | 0.095644 | 0.10869 | 0.618488 | 0.141864 | 0.328642 | 0.034633 | 0.006344 |
| 0.012766 | 0.012248 | 0.00212 | 0.033007 | 0.370456 | 0.016004 | 0.463067 | 0.00485 | 0.001592 |
| 0.007137 | 3.5E−05 | 0.005466 | 0.038033 | 0.2865 | 0.000131 | 2.164528 | 0.00431 | 0.000758 |
| 0.325519 | 0.217891 | 0.078485 | 0.03155 | 0.339324 | 0.434959 | 0.161971 | 0.318878 | 0.16007 |
| 0.045528 | 0.110017 | 0.657604 | 1.501234 | 0.147941 | 0.100699 | 0.049113 | 1.650739 | 0.089274 |
| 0.039478 | 0.000263 | 1.373387 | 1.104741 | 0.045834 | 0.650690 | 0.019842 | 0.678387 | 0.053905 |
| 0.002006 | 0.009618 | 1.043141 | 0.175785 | 0.001296 | 0.499148 | 0.001416 | 0.656414 | 0.013582 |
| 0.595757 | 0.161218 | 0.03778 | 0.296534 | 0.277513 | 0.983824 | 0.026727 | 1.750961 | 0.020817 |
| 0.001366 | 0.002286 | 0.039296 | 0.091514 | 0.174334 | 0.397735 | 0.00203 | 0.909125 | 8.14E−06 |
| 0.045482 | 0.027752 | 0.003229 | 0.005323 | 0.004371 | 1.172598 | 0.001885 | 1.589868 | 0.000543 |
| 0.016412 | 0.125181 | 0.004176 | 0.036716 | 0.001947 | 0.738754 | 0.0017 | 1.568001 | 0.024861 |
| 0.313797 | 0.544196 | 0.602715 | 0.142074 | 0.445605 | 1.981072 | 0.009742 | 0.018002 | 1.850367 |
| 0.003116 | 0.055871 | 0.58679 | 0.041225 | 0.120431 | 0.028216 | 0.001028 | 0.383316 | 0.021189 |
| 0.092504 | 0.169729 | 0.812675 | 0.005826 | 0.008226 | 0.104171 | 0.008527 | 0.001398 | 0.248478 |
| 0.134764 | 0.076693 | 0.970215 | 0.000758 | 1.95E−07 | 0.143742 | 0.001309 | 0.523395 | 0.263541 |

TABLE 11

2-EtOH-4

| | | THF | | | | | $\log\sigma_{Lg,c}$ | | |
|---|---|---|---|---|---|---|---|---|---|
| $k_4$ | $k_5$ | $k_1$ | $k_2$ | $k_3$ | $k_4$ | $k_5$ | $H_2O$ | EtOH | Benzene |
| 1.976759 | 1.717133 | 0.320475 | 0.106957 | 0.942613 | 1.022336 | 0.806087 | −0.27945 | 0.398827 | −0.12502 |
| 1.89369 | 1.495508 | 2.223304 | 0.154399 | 0.887908 | 1.160116 | 0.998556 | −0.0226 | 0.248584 | −0.25239 |
| 1.194876 | 1.12618 | 0.31363 | 2.263025 | 1.152191 | 1.185264 | 1.221531 | −0.55571 | 0.239137 | −0.39623 |
| 1.963769 | 2.053914 | 1.051214 | 2.303632 | 5.113642 | 4.285506 | 4.119475 | −0.53188 | −0.1312 | −0.52282 |
| 0.061657 | 0.075834 | 0.000367 | 0.009241 | 0.201034 | 0.830916 | 0.000185 | −0.7076 | −0.13743 | 0.044038 |
| 0.285041 | 0.181571 | 0.000674 | 0.047972 | 6.431623 | 2.836901 | 0.007807 | −0.42382 | −0.15439 | −0.11099 |
| 0.001542 | 0.003626 | 0.002356 | 0.002306 | 0.185166 | 0.770196 | 0.002463 | −0.42179 | −0.09534 | 0.33566 |
| 0.077331 | 0.027366 | 0.000223 | 0.000812 | 0.262328 | 0.860736 | 0.000178 | −0.40275 | 0.458128 | 0.175373 |
| 0.000702 | 0.003127 | 0.148212 | 0.022607 | 0.001082 | 0.099839 | 0.000981 | −0.91872 | −0.22917 | −0.95407 |
| 0.000545 | 0.002404 | 0.090807 | 0.130888 | 0.155892 | 0.011266 | 0.162759 | −0.17315 | −0.39424 | −0.01421 |
| 0.003418 | 2.52E−07 | 0.024227 | 0.014821 | 0.011269 | 0.001138 | 0.004506 | −0.83614 | −0.65358 | −0.29561 |
| 0.000165 | 9.4E−05 | 0.297542 | 0.179095 | 0.13228 | 0.046152 | 0.12285 | −0.6724 | −1.1222 | 0.043835 |
| 2.01E−05 | 0.004948 | 0.000224 | 0.000536 | 0.001718 | 0.004905 | 7.82E−05 | 0.371859 | −0.99151 | −0.41346 |
| 0.000107 | 0.004258 | 0.038659 | 0.004634 | 0.035399 | 0.223867 | 0.006662 | −0.16865 | −1.23994 | −0.55346 |
| 0.000444 | 0.001204 | 0.000887 | 0.001018 | 0.003433 | 0.011962 | 0.001282 | −0.8813 | −1.29443 | −0.40318 |
| 3.89E−05 | 0.001817 | 0.014021 | 0.002295 | 0.003223 | 0.04582 | 0.001686 | 0.04032 | −1.12337 | −0.28638 |
| 0.451025 | 1.837526 | 0.595858 | 0.551392 | 0.627254 | 0.632563 | 0.528601 | 0.191785 | −0.22819 | −0.84597 |
| 0.231418 | 0.877646 | 0.218568 | 0.148267 | 0.240263 | 0.118704 | 0.417837 | −0.11037 | −0.07316 | −1.25623 |
| 0.283369 | 1.170792 | 0.635561 | 0.646964 | 0.635447 | 0.67979 | 0.75784 | −0.54554 | −0.75784 | −0.37232 |
| 2.716576 | 1.018107 | 3.669164 | 3.311954 | 3.821947 | 3.432096 | 4.026793 | −0.54083 | −0.73936 | −0.23667 |
| 0.00652 | 0.001782 | 8.5E−05 | 0.003548 | 0.044206 | 0.045083 | 1.14E−05 | −1.05253 | −1.09551 | −0.50347 |
| 0.003763 | 0.010139 | 0.001084 | 0.0056 | 0.020667 | 0.042775 | 9.2E−06 | −1.54088 | −1.18116 | −0.45473 |
| 0.000245 | 1.55E−05 | 0.000259 | 1.08E−05 | 9.45E−06 | 2.26E−05 | 6.33E−05 | −0.16437 | −1.13825 | −0.67257 |
| 0.001353 | 0.002798 | 0.003635 | 0.001102 | 0.000593 | 3.37E−05 | 1.98E−06 | −0.59311 | −1.11749 | −0.54994 |
| 0.036981 | 0.014168 | 0.011583 | 1.690988 | 0.011607 | 0.000584 | 0.00607 | −0.791 | −0.48094 | −0.13148 |
| 8.44E−05 | 0.006012 | 0.004916 | 0.175359 | 0.003258 | 0.024528 | 0.0005 | −0.30458 | −0.04454 | −1.15475 |
| 0.005389 | 0.001474 | 0.0019 | 0.27494 | 0.001676 | 0.008179 | 0.001038 | −0.14548 | −0.29039 | −0.3181 |
| 0.009366 | 4.56E−08 | 6.89E−05 | 0.280261 | 0.000583 | 0.008141 | 0.006109 | −0.15455 | −0.13279 | −0.21329 |
| 0.14928 | 0.124872 | 0.185732 | 0.087683 | 0.125691 | 0.095318 | 0.139495 | −0.62735 | 0.089626 | −0.60433 |
| 0.012246 | 0.036495 | 0.01681 | 0.013716 | 0.002095 | 0.000154 | 0.012654 | −0.90372 | −0.23395 | −0.70282 |
| 0.017849 | 0.025172 | 0.030349 | 0.061756 | 0.034001 | 0.068279 | 0.029178 | −0.75676 | −0.16047 | 0.069012 |
| 0.015414 | 8.09E−06 | 0.008521 | 0.005886 | 0.009664 | 0.000549 | 0.003898 | −0.97667 | 0.048629 | −0.20526 |
| 0.359819 | 0.123489 | 0.022158 | 0.175132 | 0.019805 | 0.320243 | 0.026315 | −0.10314 | −0.45305 | −0.63388 |
| 0.626407 | 0.000105 | 0.090589 | 0.001538 | 0.176016 | 0.191177 | 0.062464 | −0.20565 | −0.12083 | 0.069844 |
| 0.709666 | 0.007934 | 0.005003 | 0.002776 | 0.006568 | 0.009549 | 0.034362 | −0.25904 | 0.189343 | 0.446272 |
| 0.504435 | 0.055568 | 0.182369 | 0.218544 | 0.288851 | 0.003921 | 0.068964 | −0.1905 | 0.489136 | 0.408102 |
| 0.019717 | 0.096283 | 0.006494 | 0.06229 | 0.003035 | 0.010353 | 0.018699 | −0.18367 | −1.36604 | −0.93406 |
| 0.015295 | 0.001106 | 0.001192 | 0.855147 | 1.194537 | 0.000387 | 0.637163 | −0.56828 | 0.228993 | −0.9417 |
| 0.017281 | 0.003548 | 0.001282 | 0.058197 | 0.074418 | 0.002120 | 0.028567 | −0.16197 | 0.020417 | −1.34016 |
| 0.015458 | 0.053139 | 0.000159 | 0.045084 | 0.223601 | 0.00103 | 0.083511 | −0.17728 | 0.066696 | −1.43918 |

TABLE 11-continued

2-EtOH-4

| $\log\sigma_{Lg,c}$ | | | $\log\sigma_{\theta g,c}$ | | | | | |
|---|---|---|---|---|---|---|---|---|
| Hexane | AcOEt | THF | H$_2$O | EtOH | Benzene | Hexane | AcOEt | THF |
| −0.55113 | 0.32871 | −0.08107 | 0.8012324 | 1.207714 | 1.079374 | 0.189762 | 0.866207 | 1.150356 |
| −0.32497 | −0.10168 | 0.215972 | 0.729341 | 0.669981 | 1.252097 | 0.229623 | 0.939489 | 1.183314 |
| −0.61155 | 0.447759 | −0.12574 | 0.714165 | 0.547871 | 0.999054 | 0.229044 | 1.090265 | 1.080704 |
| −0.89179 | 0.355916 | −0.55732 | 0.722126 | 0.465178 | 1.117856 | 0.1627 | 0.785955 | 0.3326 |
| −0.64421 | −1.19739 | −0.06096 | 0.5606 | 0.605007 | 0.795256 | 0.743116 | −0.2618 | 1.272964 |
| −1.14907 | −1.08912 | −0.0579 | 0.53307 | 0.957349 | 1.134892 | 1.126902 | −0.39762 | 0.636763 |
| −1.22368 | −1.29606 | −0.19802 | 0.576843 | 0.985589 | 0.696795 | 0.874959 | −0.37434 | 1.23767 |
| −1.11758 | −1.11766 | −0.44338 | 0.594635 | 0.995588 | 1.106001 | 0.863036 | −0.35685 | 1.205117 |
| −0.36169 | −0.08808 | −0.54633 | 1.378727 | 0.870049 | 0.644553 | 1.15028 | 0.84218 | 0.01585 |
| −0.13507 | 0.117575 | −0.50368 | 1.295079 | 0.951724 | 0.980232 | 1.301856 | 0.750527 | 0.170075 |
| −0.0715 | 0.061467 | −0.58296 | 0.444318 | 0.974456 | 0.722887 | 0.901578 | 0.922287 | 0.046107 |
| −0.11942 | 0.057921 | −0.63334 | 0.472307 | 1.012596 | 0.702096 | 0.794673 | 1.032039 | 0.070549 |
| −0.38187 | −0.37755 | −0.48677 | 0.961614 | 1.035338 | 0.756087 | 0.997163 | 0.862225 | 0.689686 |
| −0.28183 | −0.55965 | −1.19113 | 1.01892 | 1.0191 | 0.857216 | 1.099827 | 0.859037 | 0.505935 |
| −0.17188 | −0.38782 | −0.72924 | 0.654436 | 1.034736 | 0.789613 | 1.216736 | 0.834254 | 0.678971 |
| 0.033897 | −0.15015 | −0.82075 | 0.619903 | 1.091146 | 0.840677 | 1.260704 | 0.774444 | 0.696334 |
| −1.15407 | 0.02776 | −0.90701 | 1.044944 | 0.990337 | −0.16622 | 0.883427 | 0.852136 | 0.731865 |
| −0.34122 | 0.011325 | −0.71451 | 0.951797 | 1.037002 | 0.532775 | −0.79673 | 1.082475 | 0.682279 |
| −0.33503 | 0.564229 | −0.99709 | 1.059034 | 1.038236 | 0.205231 | −0.45793 | 1.088727 | 0.735329 |
| −0.51182 | 0.321599 | −0.41743 | 1.050676 | 1.089144 | 0.128321 | −0.33163 | 1.021132 | 0.783396 |
| 0.125804 | −0.91843 | −0.05209 | 0.656551 | 0.717663 | 1.123837 | 0.642526 | 1.106472 | 0.682546 |
| −0.12365 | −0.52523 | −0.15205 | 0.594566 | 0.691442 | 0.946763 | 0.738585 | 1.084102 | 0.904087 |
| −0.61878 | −1.01393 | −0.17641 | 0.879033 | 0.762743 | 1.111363 | 0.709606 | 1.104812 | 0.776997 |
| −0.24084 | −1.39596 | −0.26371 | 0.860382 | 0.844861 | 0.831881 | 0.830535 | 1.095595 | 0.802764 |
| −0.8441 | −1.78544 | −1.54092 | 0.909549 | 0.899793 | 0.836804 | 0.622138 | 0.89432 | 1.315317 |
| −1.10002 | −0.25395 | −0.66242 | 0.906718 | 0.842321 | 0.733571 | 0.646614 | 0.880259 | 1.176445 |
| −1.07174 | −0.91017 | −1.11347 | 0.706513 | 0.779633 | 0.822822 | 0.725209 | 0.912419 | 1.213009 |
| −0.67837 | −0.81830 | −1.39507 | 0.671983 | 0.655389 | 0.947994 | 0.74445 | 1.008622 | 1.180359 |
| −0.2829 | −0.47458 | −0.25747 | 0.40447 | 0.757171 | 0.997815 | 0.85769 | 1.104346 | 0.999825 |
| −0.41213 | −0.27044 | 0.204271 | 0.071537 | 0.602741 | 1.225844 | 0.825294 | 1.052402 | 1.112113 |
| −0.27628 | −0.31088 | 0.087425 | 0.907564 | 0.618479 | 1.213651 | 0.576452 | 1.166429 | 1.023458 |
| 0.111701 | −0.27363 | −0.07046 | 0.950403 | 0.619702 | 1.220683 | 1.165549 | 1.218396 | 1.152418 |
| 0.038614 | 0.083506 | −0.32954 | 0.634833 | 0.739149 | −0.20836 | 0.812456 | 0.535362 | 0.228705 |
| −0.15347 | 0.56292 | −0.3326 | 0.551091 | 0.864869 | 0.855276 | 0.850432 | 0.930297 | 0.188121 |
| −0.10431 | 0.630582 | −0.87208 | 0.582188 | 0.645764 | 0.006498 | 0.60401 | 0.689769 | 0.163691 |
| −0.21624 | 0.388878 | −0.91419 | 0.584172 | 0.450962 | 0.931221 | 0.69898 | 0.643733 | 0.089592 |
| 0.227763 | 0.666495 | 0.047935 | 0.760615 | 0.7843 | 0.198057 | 0.592487 | 0.754077 | 0.893002 |
| 0.117962 | 0.073392 | 0.670118 | 0.838437 | 0.813008 | 0.568256 | 1.022759 | 0.875654 | 0.682508 |
| 0.391301 | 0.159097 | 0.439682 | 0.683124 | 0.702989 | 0.698645 | 0.987988 | 0.895158 | 0.95815 |
| −0.00175 | −0.09715 | −0.05799 | 0.699085 | 0.915385 | 1.181093 | 1.161702 | 0.945869 | 1.024418 |

TABLE 12

2-Benzene-1

| | | $\log|Y_{u,c}|$ | $(\log|Y_{u,c}|-\log|Y_{g,ck}|-L_{ug,k})^2/\sigma_{Lg,c}^2$ | | | | | | | |
|---|---|---|---|---|---|---|---|---|---|---|
| | | Benzene | H$_2$O | | | | | EtOH | | |
| f | c | k$_6$ | k$_1$ | k$_2$ | k$_3$ | k$_4$ | k$_5$ | k$_1$ | k$_2$ | k$_3$ |
| 0.05 Hz | Ch. 1 | 1.778002 | 2.357864 | 2.75037 | 2.244275 | 2.316548 | 2.138105 | 0.184206 | 0.018816 | 0.219279 |
| | Ch. 2 | 5.03543 | 0.032757 | 0.014467 | 0.057764 | 0.007554 | 0.033917 | 0.026686 | 0.007117 | 0.005882 |
| | Ch. 3 | 0.904478 | 3.598383 | 3.634413 | 2.227865 | 2.658114 | 3.448936 | 0.184581 | 0.165819 | 0.115785 |
| | Ch. 4 | −0.26491 | 0.180953 | 0.223998 | 0.005024 | 0.049493 | 0.140764 | 0.119588 | 0.054449 | 0.172158 |
| 0.1 Hz | Ch. 1 | 1.180901 | 6.911931 | 5.317566 | 6.888085 | 6.298761 | 7.63591 | 1.019249 | 1.002964 | 0.8194 |
| | Ch. 2 | 4.794564 | 0.013604 | 0.077153 | 0.173993 | 0.196475 | 0.197214 | 0.018263 | 0.002119 | 0.019212 |
| | Ch. 3 | 0.392694 | 2.566485 | 1.644682 | 1.669717 | 1.53231 | 1.774686 | 0.302267 | 0.13441 | 0.169494 |
| | Ch. 4 | −0.69292 | 0.230936 | 0.028833 | 0.066894 | 0.040691 | 0.087215 | 0.098393 | 0.100065 | 0.035033 |
| 0.15 Hz | Ch. 1 | 0.219302 | 5.074511 | 2.137234 | 7.598965 | 3.179142 | 2.911062 | 0.148925 | 0.32858 | 0.196788 |
| | Ch. 2 | 4.129586 | 0.818206 | 0.741415 | 0.958574 | 3.943809 | 1.158666 | 1.311858 | 2.027814 | 1.908697 |
| | Ch. 3 | −1.00143 | 4.730575 | 3.868288 | 4.938072 | 0.762469 | 3.164995 | 0.379821 | 0.321161 | 0.359379 |
| | Ch. 4 | −3.17983 | 2.483307 | 3.785165 | 1.808367 | 6.860759 | 3.833042 | 5.827379 | 6.0236 | 7.481964 |
| 0.2 Hz | Ch. 1 | 0.585413 | 0.136266 | 0.001851 | 0.265499 | 0.360883 | 0.387234 | 0.279636 | 0.92165 | 0.91409 |
| | Ch. 2 | 3.748405 | 0.65329 | 0.001116 | 0.000229 | 0.018768 | 0.015339 | 0.406772 | 0.524899 | 0.265813 |
| | Ch. 3 | −0.43422 | 1.393456 | 0.252293 | 0.819749 | 1.046623 | 1.054741 | 1.255874 | 1.940444 | 1.978223 |
| | Ch. 4 | −1.68544 | 0.059612 | 0.127965 | 0.00925 | 0.001777 | 0.003364 | 0.051297 | 0.320514 | 0.132733 |

TABLE 12-continued

| | | | | | 2-Benzene-1 | | | | | |
|---|---|---|---|---|---|---|---|---|---|---|
| 0.25 Hz | Ch. 1 | 0.03119 | 0.657463 | 0.568184 | 0.891209 | 0.598732 | 0.027796 | 0.106186 | 0.480089 | 0.267303 |
| | Ch. 2 | 3.751291 | 0.000931 | 0.496846 | 0.046637 | 0.385466 | 0.376156 | 0.149297 | 0.086518 | 0.098121 |
| | Ch. 3 | −1.15517 | 2.277797 | 0.695665 | 2.252091 | 0.880104 | 0.061274 | 0.029714 | 0.053074 | 0.046654 |
| | Ch. 4 | −2.28876 | 0.319017 | 0.11969 | 0.019129 | 0.077691 | 0.710247 | 0.14301 | 0.127027 | 0.001609 |
| 0.3 Hz | Ch. 1 | −0.44168 | 6.384968 | 4.190572 | 5.458605 | 5.696193 | 4.299881 | 0.032413 | 0.502014 | 0.22003 |
| | Ch. 2 | 2.686519 | 15.79029 | 0.038198 | 0.387298 | 0.035103 | 0.003705 | 0.611519 | 0.138664 | 0.363529 |
| | Ch. 3 | −1.76944 | 2.831363 | 0.662023 | 0.606958 | 0.821825 | 0.662164 | 0.333987 | 0.149804 | 0.301575 |
| | Ch. 4 | −2.75797 | 0.30567 | 0.0143 | 0.001475 | 0.035465 | 0.007053 | 0.123731 | 0.482452 | 0.257418 |
| 0.35 Hz | Ch. 1 | 0.018753 | 3.509863 | 7.273936 | 7.34783 | 2.180097 | 3.866254 | 0.24524 | 0.070939 | 0.238533 |
| | Ch. 2 | 3.274402 | 0.803191 | 1.369094 | 0.078176 | 0.534193 | 0.071027 | 0.107548 | 0.139332 | 0.082864 |
| | Ch. 3 | −0.90199 | 1.629154 | 0.273327 | 1.669854 | 0.251591 | 0.598414 | 0.209169 | 0.224708 | 0.090465 |
| | Ch. 4 | −1.97898 | 0.225348 | 0.011549 | 0.137676 | 0.125243 | 0.00093 | 0.102074 | 0.037346 | 0.163087 |
| 0.4 Hz | Ch. 1 | −0.22939 | 2.239677 | 2.03E−06 | 3.505561 | 1.649424 | 2.21791 | 0.232253 | 0.047118 | 0.024717 |
| | Ch. 2 | 2.787303 | 2.797175 | 0.113407 | 0.512558 | 0.571471 | 0.921616 | 0.19488 | 0.060904 | 0.398591 |
| | Ch. 3 | −1.30066 | 7.041305 | 1.202913 | 6.060707 | 3.563729 | 5.033803 | 0.024659 | 0.160381 | 0.226705 |
| | Ch. 4 | −2.52901 | 0.378352 | 1.00455 | 0.128076 | 0.07971 | 0.121896 | 0.500522 | 0.007617 | 0.064227 |
| 0.45 Hz | Ch. 1 | −0.39279 | 0.587582 | 0.507914 | 0.891184 | 0.364088 | 0.631257 | 0.043513 | 0.064106 | 0.010974 |
| | Ch. 2 | 2.593831 | 0.390173 | 0.004463 | 0.12652 | 0.041256 | 0.389703 | 0.101485 | 0.033881 | 0.068596 |
| | Ch. 3 | −1.59325 | 1.936852 | 1.030809 | 1.955191 | 1.058851 | 2.662929 | 0.068663 | 0.112752 | 0.045901 |
| | Ch. 4 | −2.87677 | 0.023177 | 0.05574 | 0.005609 | 0.011412 | 0.016017 | 0.003629 | 0.00251 | 0.000595 |
| 0.5 Hz | Ch. 1 | −0.71804 | 0.252705 | 0.742829 | 0.490162 | 0.912153 | 0.322248 | 0.095198 | 0.086096 | 0.001373 |
| | Ch. 2 | 1.814917 | 3.64718 | 1.782315 | 1.668601 | 3.054408 | 1.633361 | 0.194115 | 0.278654 | 0.221534 |
| | Ch. 3 | −1.98283 | 1.453982 | 1.013789 | 1.028849 | 1.334105 | 1.114809 | 0.064995 | 0.083836 | 0.032415 |
| | Ch. 4 | −2.6395 | 0.321277 | 0.543137 | 0.290955 | 0.918222 | 0.126992 | 0.040479 | 0.171786 | 0.13903 |

| | | $(\log|Y_{u,c}|-\log|Y_{g,ck}|-L_{ug,k})^2/\sigma_{Lg,c}^2$ | | | | | | | |
|---|---|---|---|---|---|---|---|---|---|
| | | EtOH | | Benzene | | | | | |
| f | c | $k_4$ | $k_5$ | $k_1$ | $k_2$ | $k_3$ | $k_4$ | $k_5$ | $k_1$ |
| 0.05 Hz | Ch. 1 | 0.129918 | 0.19257 | 0.005681 | 0.254404 | 0.009428 | 0.020592 | 0.154662 | 0.025694 |
| | Ch. 2 | 0.045672 | 0.02753 | 0.01543 | 0.688385 | 0.451995 | 0.049012 | 0.017962 | 0.54515 |
| | Ch. 3 | 0.121649 | 0.134252 | 0.0136594 | 0.029386 | 0.196176 | 0.059366 | 0.001191 | 0.777177 |
| | Ch. 4 | 0.176155 | 0.209306 | 0.00335 | 0.020154 | 0.054685 | 0.040003 | 0.137347 | 0.008212 |
| 0.1 Hz | Ch. 1 | 1.04822 | 2.389486 | 0.010416 | 0.3837 | 0.004697 | 0.000966 | 0.037201 | 0.006426 |
| | Ch. 2 | 0.000191 | 0.563498 | 0.020246 | 0.033972 | 0.034033 | 0.000446 | 0.196837 | 0.063312 |
| | Ch. 3 | 0.168064 | 0.040651 | 0.004499 | 0.127939 | 0.001158 | 0.01335 | 0.006817 | 2.054133 |
| | Ch. 4 | 0.113008 | 1.306572 | 0.003767 | 0.068512 | 0.0101483 | 0.021617 | 0.004507 | 0.839865 |
| 0.15 Hz | Ch. 1 | 0.449085 | 5.46E−05 | 0.83263 | 5.071078 | 1.823974 | 2.149327 | 0.505535 | 0.018985 |
| | Ch. 2 | 0.927825 | 0.893489 | 0.405279 | 0.120113 | 0.137552 | 0.169551 | 0.677133 | 1.333721 |
| | Ch. 3 | 0.631304 | 0.522915 | 0.00883 | 0.014472 | 0.001662 | 0.000393 | 2.84E−06 | 0.321398 |
| | Ch. 4 | 2.648471 | 9.802633 | 1.008058 | 1.148153 | 0.768906 | 0.889497 | 0.263335 | 2.635884 |
| 0.2 Hz | Ch. 1 | 3.308204 | 0.415909 | 0.365112 | 0.204256 | 0.523779 | 0.721885 | 0.027649 | 0.03318 |
| | Ch. 2 | 0.185981 | 0.887093 | 1.280496 | 0.145999 | 0.635738 | 0.499149 | 0.661905 | 0.105549 |
| | Ch. 3 | 3.123916 | 2.474397 | 0.000248 | 0.000678 | 0.018019 | 0.048719 | 0.001544 | 0.103095 |
| | Ch. 4 | 0.93983 | 0.061669 | 0.12126 | 0.006775 | 0.021418 | 0.162996 | 0.194906 | 0.020919 |
| 0.25 Hz | Ch. 1 | 1.030527 | 0.073754 | 0.280525 | 0.036379 | 1.689192 | 1.908279 | 0.004014 | 0.037425 |
| | Ch. 2 | 0.140455 | 0.838034 | 0.344118 | 0.086919 | 0.650406 | 0.145179 | 0.043682 | 0.238723 |
| | Ch. 3 | 0.205587 | 0.151938 | 0.048252 | 0.237198 | 0.063683 | 0.043624 | 0.115866 | 0.107224 |
| | Ch. 4 | 0.268079 | 0.896369 | 0.078626 | 0.050648 | 0.323569 | 0.402868 | 0.163037 | 0.754246 |
| 0.3 Hz | Ch. 1 | 0.081925 | 0.149082 | 1.138271 | 0.18309 | 1.626731 | 1.768191 | 0.291885 | 0.139706 |
| | Ch. 2 | 0.30083 | 0.820939 | 0.093386 | 0.014749 | 1.196221 | 0.089453 | 0.121697 | 0.015645 |
| | Ch. 3 | 0.142554 | 0.204773 | 0.073639 | 0.106501 | 0.036552 | 0.161909 | 0.181439 | 0.012882 |
| | Ch. 4 | 0.191341 | 0.642541 | 0.293204 | 0.000675 | 0.091356 | 0.501381 | 0.037843 | 0.362602 |
| 0.35 Hz | Ch. 1 | 2.180926 | 0.121772 | 0.653333 | 1.229187 | 0.274229 | 0.539296 | 0.086954 | 1.176935 |
| | Ch. 2 | 0.030293 | 0.079173 | 4.734412 | 3.996132 | 0.868009 | 8.875554 | 1.553071 | 1.261486 |
| | Ch. 3 | 0.314401 | 0.212764 | 0.041725 | 0.00033 | 0.00137 | 0.034143 | 0.002299 | 0.569627 |
| | Ch. 4 | 0.14168 | 0.026259 | 0.04512 | 0.16573 | 0.056757 | 0.039481 | 0.015105 | 0.478471 |
| 0.4 Hz | Ch. 1 | 0.123288 | 0.017156 | 1.189983 | 0.46167 | 0.993444 | 1.406893 | 1.308758 | 0.642097 |
| | Ch. 2 | 0.204693 | 0.195326 | 1.357562 | 5.007675 | 0.158895 | 1.01518 | 0.093316 | 0.032208 |
| | Ch. 3 | 0.175013 | 0.148673 | 0.040298 | 0.853871 | 2.5E−05 | 0.027678 | 3.6E−05 | 0.066865 |
| | Ch. 4 | 0.132619 | 0.024586 | 0.0827 | 0.09668 | 0.187447 | 0.001271 | 0.347772 | 0.371105 |
| 0.45 Hz | Ch. 1 | 2.65902 | 0.02804 | 0.11418 | 0.58817 | 2.130915 | 3.171912 | 2.505138 | 0.006747 |
| | Ch. 2 | 1.022429 | 0.086402 | 0.010461 | 0.731734 | 0.233398 | 0.25584 | 0.102382 | 0.26102 |
| | Ch. 3 | 0.416703 | 0.05084 | 3.09E−05 | 0.487811 | 0.025555 | 0.022341 | 0.000814 | 0.892044 |
| | Ch. 4 | 0.499422 | 0.068394 | 0.034726 | 0.023977 | 0.113266 | 0.178835 | 0.129471 | 0.165127 |
| 0.5 Hz | Ch. 1 | 27.44248 | 0.018945 | 2.590844 | 0.893281 | 5.931476 | 4.201568 | 0.984 | 0.100162 |
| | Ch. 2 | 0.001367 | 0.242138 | 7.691813 | 4.506969 | 6.289852 | 10.30399 | 7.873357 | 0.18925 |
| | Ch. 3 | 0.278524 | 0.056493 | 0.022386 | 0.246567 | 0.065594 | 0.151168 | 0.629888 | 0.029174 |
| | Ch. 4 | 0.493979 | 0.147993 | 4.23886 | 1.895751 | 0.137853 | 5.342899 | 4.386726 | 0.025865 |

TABLE 13

2-Benzene-2

$(\log|Y_{u,c}| - \log|Y_{g,ck}| - L_{ug,k})^2 / \sigma_{Lg,c}^2$

| Hexane | | | | AcOEt | | | | | THF |
|---|---|---|---|---|---|---|---|---|---|
| $k_2$ | $k_3$ | $k_4$ | $k_5$ | $k_1$ | $k_2$ | $k_3$ | $k_4$ | $k_5$ | $k_1$ |
| 1.750763 | 0.736961 | 0.05617 | 1.073536 | 0.381776 | 0.516799 | 0.475674 | 0.916178 | 0.570547 | 1.718113 |
| 0.590078 | 0.675023 | 0.040918 | 0.806085 | 0.001967 | 0.206415 | 0.202864 | 0.291504 | 0.06684 | 0.72042 |
| 0.14863 | 0.445571 | 1.062908 | 0.390687 | 0.111014 | 0.038691 | 0.26438 | 0.061664 | 0.072878 | 0.045851 |
| 1.03307 | 0.412295 | 0.4552 | 0.491826 | 0.043263 | 0.038601 | 0.154102 | 0.100881 | 0.075925 | 0.003425 |
| 0.04433 | 0.001816 | 0.030914 | 0.265802 | 12.28302 | 10.17914 | 11.23598 | 10.67986 | 12.69904 | 1.638381 |
| 0.174327 | 0.355625 | 0.968322 | 0.510232 | 1.50443 | 0.699792 | 1.291214 | 0.718136 | 1.160436 | 1.400789 |
| 1.882795 | 1.718739 | 2.03958 | 1.245436 | 1.031861 | 1.47927 | 1.293654 | 1.759203 | 1.769911 | 0.004092 |
| 0.241507 | 0.448348 | 0.001639 | 0.297695 | 1.26391 | 1.139969 | 0.949391 | 1.07322 | 1.142861 | 0.002948 |
| 5.321479 | 1.570663 | 2.31225 | 0.106605 | 0.328753 | 0.293681 | 0.761028 | 0.164863 | 0.277162 | 1.517696 |
| 0.001476 | 0.446049 | 0.172361 | 0.119685 | 1.202832 | 0.830486 | 1.354924 | 0.417261 | 0.667897 | 6.98638 |
| 0.003031 | 0.030839 | 0.023229 | 0.402436 | 0.048974 | 0.079499 | 0.090424 | 0.1546 | 0.118706 | 0.048173 |
| 3.35044 | 3.33184 | 3.104777 | 1.593525 | 0.793454 | 0.611491 | 0.613833 | 0.53199 | 0.575023 | 3.59475 |
| 1.129798 | 3.796903 | 0.036314 | 2.704223 | 0.647266 | 0.372552 | 0.822799 | 0.877642 | 0.979795 | 0.966133 |
| 0.1502 | 0.45269 | 0.148142 | 0.638841 | 0.04206 | 0.124714 | 0.000199 | 0.008626 | 0.165683 | 1.657875 |
| 0.081009 | 0.000999 | 0.409842 | 0.015005 | 0.268134 | 0.268574 | 0.348448 | 0.382831 | 0.373753 | 0.188802 |
| 0.423031 | 0.673714 | 0.134083 | 0.362287 | 0.009301 | 0.024609 | 0.661397 | 0.038716 | 0.332644 | 5.58E−05 |
| 0.030091 | 0.814403 | 7.140568 | 6.282477 | 0.362146 | 1.11952 | 0.3184 | 0.365115 | 0.394988 | 2.994367 |
| 0.551023 | 0.199763 | 0.056188 | 0.000327 | 0.435511 | 0.003218 | 0.18898 | 0.280053 | 0.24568 | 1.782473 |
| 0.246921 | 0.030237 | 0.016817 | 0.006121 | 0.000259 | 0.259011 | 0.003806 | 0.008181 | 0.006323 | 0.15899 |
| 2.448146 | 1.469876 | 2.347725 | 1.554391 | 0.003118 | 0.009684 | 0.000539 | 0.002735 | 1.35E−05 | 0.085219 |
| 1.571537 | 1.986436 | 0.011707 | 0.135107 | 1.000731 | 2.832645 | 1.754971 | 0.899532 | 1.901571 | 0.389253 |
| 0.223279 | 0.582517 | 0.004191 | 0.290632 | 0.413451 | 0.064381 | 0.012802 | 0.02549 | 0.054585 | 0.369614 |
| 0.116248 | 1.434053 | 0.236028 | 0.007602 | 0.411595 | 0.393972 | 0.192096 | 0.262128 | 0.541258 | 0.000481 |
| 1.089712 | 0.125927 | 0.315658 | 1.430989 | 0.745236 | 1.409997 | 3.110529 | 1.345902 | 0.344491 | 0.00452 |
| 6.6185 | 2.546881 | 1.084881 | 6.988233 | 10.1689 | 40.09693 | 11.6662 | 18.0399 | 13.79098 | 7.818834 |
| 1.192789 | 0.535371 | 1.42001 | 3.154253 | 0.113335 | 0.34427 | 0.037822 | 0.014136 | 0.00637 | 0.355387 |
| 0.024442 | 0.419448 | 0.258503 | 0.026898 | 0.783093 | 0.689157 | 0.769361 | 1.049629 | 0.89889 | 0.145964 |
| 2.461245 | 1.713854 | 0.197059 | 0.929551 | 0.994121 | 0.3824 | 0.024465 | 0.790727 | 0.16534 | 0.800903 |
| 0.458422 | 0.077147 | 0.007257 | 0.16327 | 0.644621 | 0.23018 | 0.266621 | 1.06247 | 0.375933 | 0.321182 |
| 0.121521 | 0.107791 | 0.93256 | 0.176609 | 0.016951 | 0.046747 | 0.330506 | 0.004235 | 0.108819 | 0.050494 |
| 0.021834 | 0.518471 | 0.009141 | 0.000379 | 0.315102 | 0.28888 | 0.324869 | 0.355797 | 0.221424 | 0.021864 |
| 0.12257 | 0.231601 | 0.481924 | 0.301342 | 0.000216 | 0.009235 | 0.202462 | 0.041271 | 0.143714 | 1.33E−06 |
| 0.71359 | 0.27594 | 0.204419 | 1.202355 | 0.096941 | 0.700824 | 0.083178 | 0.645294 | 0.011508 | 0.436577 |
| 0.226276 | 0.028434 | 0.006557 | 0.003264 | 2.22E−05 | 0.007462 | 0.001685 | 0.039391 | 0.005343 | 0.243056 |
| 0.034067 | 0.471956 | 0.353999 | 0.073705 | 0.030281 | 0.049911 | 0.030243 | 0.338015 | 0.026857 | 0.055126 |
| 0.623909 | 1.604226 | 1.351602 | 2.747685 | 4.95E−06 | 0.052699 | 0.001592 | 0.14795 | 0.001819 | 0.003456 |
| 0.096067 | 0.555556 | 0.206116 | 1.872914 | 0.031549 | 0.09734 | 0.200675 | 0.055272 | 0.031549 | 0.018942 |
| 0.058580 | 0.265386 | 0.142193 | 0.388518 | 0.116028 | 0.820916 | 0.560158 | 0.182715 | 0.499698 | 0.030953 |
| 0.510108 | 0.000635 | 0.044463 | 0.014812 | 0.01457 | 0.97135 | 0.014211 | 0.67814 | 0.135806 | 0.004922 |
| 0.155745 | 0.155491 | 0.210201 | 0.703459 | 0.398886 | 0.22272 | 0.00634 | 0.456094 | 0.553311 | 0.161601 |

| $(\log|Y_{u,c}| - \log|Y_{g,ck}| - L_{ug,k})^2 / \sigma_{Lg,c}^2$ THF | | | | $\arg Y_{u,c}$ Benzene | $H_2O$ | | | |
|---|---|---|---|---|---|---|---|---|
| $k_2$ | $k_3$ | $k_4$ | $k_5$ | $k_6$ | $k_1$ | $k_2$ | $k_3$ | $k_4$ |
| 1.940963 | 1.619131 | 1.874769 | 1.311608 | −3.13673 | 0.00319 | 0.021035 | 0.000173 | 0.012633 |
| 1.555587 | 1.53867 | 0.673 | 1.02185 | −2.75746 | 0.009921 | 0.048492 | 0.000153 | 0.021628 |
| 0.046907 | 0.000206 | 0.027001 | 0.016078 | −3.00932 | 0.007918 | 0.01651 | 0.009852 | 0.010206 |
| 0.628865 | 0.437305 | 0.030222 | 0.293514 | −2.7575 | 0.002409 | 0.003924 | 0.00935 | 0.005438 |
| 1.538497 | 1.540024 | 2.117063 | 2.050695 | −2.70991 | 0.000129 | 1.83E−05 | 0.000166 | 0.000525 |
| 1.644636 | 0.920853 | 1.336526 | 1.22442 | −2.48953 | 0.00272 | 7.51E−05 | 0.001886 | 0.001122 |
| 0.014611 | 0.029216 | 0.015815 | 0.019569 | −2.69715 | 0.005083 | 0.004205 | 0.003624 | 0.003126 |
| 0.049247 | 0.035975 | 0.074126 | 0.086058 | −2.50019 | 0.000101 | 0.002644 | 0.000946 | 0.00413 |
| 1.552249 | 2.360222 | 0.88899 | 1.668148 | −0.75762 | 0.787117 | 0.016294 | 1.665395 | 0.003576 |
| 6.742417 | 7.358866 | 3.894659 | 4.96865 | 1.816123 | 0.10817 | 0.276771 | 0.815531 | 0.220093 |
| 0.026497 | 0.023705 | 0.045855 | 0.055502 | −0.0184 | 3.75413 | 5.91E−07 | 1.02805 | 0.006004 |
| 3.126286 | 2.478208 | 2.083193 | 1.894529 | −1.29491 | 1.125615 | 0.778923 | 0.023261 | 0.713633 |
| 1.477726 | 1.971809 | 1.437160 | 0.566166 | −0.8949 | 0.149651 | 0.315299 | 0.001434 | 0.010323 |
| 2.690761 | 6.311613 | 2.883742 | 0.453163 | 0.127848 | 0.041816 | 1.458265 | 0.019903 | 0.037245 |
| 0.138894 | 0.080631 | 0.252926 | 0.172963 | −0.44731 | 0.167178 | 0.254465 | 0.027567 | 0.036301 |
| 0.024527 | 0.007197 | 0.002448 | 0.016964 | −0.04441 | 0.451447 | 0.53749 | 0.000222 | 0.002766 |
| 1.598081 | 3.681557 | 6.835514 | 2.200373 | −1.42664 | 1.09E−05 | 4.33E−05 | 0.020164 | 4.3E−05 |
| 2.746296 | 3.535513 | 5.426536 | 2.327753 | −1.16375 | 0.000178 | 0.005674 | 0.002555 | 0.00029 |
| 0.043704 | 0.032531 | 0.201659 | 0.001286 | −1.55919 | 0.01924 | 0.012955 | 0.062243 | 0.020763 |
| 0.115195 | 0.014411 | 0.015157 | 0.041761 | −0.61405 | 0.024106 | 0.035927 | 0.004178 | 0.023776 |
| 0.36856 | 0.294301 | 0.0585 | 0.873389 | −0.71197 | 0.124395 | 0.120299 | 0.104771 | 0.057595 |
| 0.403695 | 0.024606 | 0.514114 | 1.358748 | 0.485459 | 0.056596 | 1.15E−07 | 0.051148 | 0.140374 |
| 0.002347 | 0.009046 | 5.04E−05 | 0.028317 | 0.461889 | 0.002429 | 0.016733 | 0.00068 | 0.015993 |
| 0.008577 | 0.153015 | 0.245124 | 0.001231 | 0.785956 | 0.024182 | 0.06288 | 0.013733 | 0.001397 |
| 12.96544 | 8.162422 | 10.4907 | 6.298884 | −1.41551 | 0.106578 | 0.016222 | 0.005798 | 0.031198 |
| 0.366819 | 0.524412 | 1.011352 | 6.53E−05 | −1.35154 | 0.065862 | 0.003399 | 0.001455 | 0.004957 |

TABLE 13-continued

2-Benzene-2

| | | | | | | | | |
|---|---|---|---|---|---|---|---|---|
| 0.132002 | 0.358308 | 0.871285 | 0.375816 | −1.33267 | 0.088298 | 0.015365 | 0.005113 | 0.024384 |
| 2.556515 | 0.195738 | 0.02272 | 1.803551 | −1.19885 | 0.18572 | 0.011435 | 0.00501 | 0.022919 |
| 0.843029 | 0.28549 | 1.051346 | 0.629455 | −1.20868 | 0.004863 | 4.483075 | 0.116932 | 0.012151 |
| 0.000152 | 0.001977 | 0.305012 | 0.042778 | −0.11066 | 0.522811 | 3.114392 | 0.138277 | 0.315288 |
| 0.019052 | 0.033363 | 0.136039 | 0.034737 | −0.97949 | 0.013032 | 0.966871 | 0.000296 | 0.0122 |
| 0.379649 | 0.029157 | 0.095083 | 0.028083 | −0.80251 | 0.022645 | 1.034964 | 0.003621 | 0.004031 |
| 0.264773 | 0.489399 | 0.004913 | 0.614536 | −1.34673 | 0.008706 | 0.02456 | 0.035888 | 0.078036 |
| 0.742473 | 0.308276 | 1.282207 | 0.131779 | −1.4029 | 0.002182 | 0.03077 | 0.002573 | 0.320358 |
| 0.023585 | 0.148018 | 0.020782 | 0.209902 | −1.15544 | 0.022032 | 0.004379 | 0.018812 | 0.122658 |
| 0.605755 | 0.019386 | 3.060805 | 0.078062 | −0.80361 | 0.009058 | 0.005026 | 0.000178 | 0.241983 |
| 1.449268 | 0.187551 | 0.170746 | 0.254348 | −1.44223 | 0.030122 | 6.2E−05 | 0.00071 | 0.037669 |
| 0.723799 | 0.013147 | 0.021435 | 0.169097 | −0.90011 | 0.00018 | 0.000519 | 0.063231 | 0.000104 |
| 0.065085 | 0.079139 | 0.002526 | 0.391917 | −1.37208 | 0.030938 | 0.004198 | 0.01879 | 0.0554943 |
| 1.64E−05 | 0.065644 | 0.462327 | 0.146396 | −1.34722 | 0.000804 | 0.009679 | 0.015774 | 0.000119 |

TABLE 14

2-Benzene-3

$(argY_{u,c} - argY_{g,ck} - \theta_{ug,k})^2 / \sigma_{\theta g,c}^2$

| | EtOH | | | | | Benzene | | | |
|---|---|---|---|---|---|---|---|---|---|
| $k_5$ | $k_1$ | $k_2$ | $k_3$ | $k_4$ | $k_5$ | $k_1$ | $k_2$ | $k_3$ | $k_4$ |
| 0.012711 | 1.496419 | 0.704605 | 1.774922 | 0.007764 | 0.004992 | 0.006924 | 0.005652 | 0.002011 | 0.000163 |
| 0.003346 | 0.634387 | 0.07019 | 0.671971 | 0.000165 | 9.14E−06 | 0.004093 | 2.97E−05 | 0.011243 | 0.00846 |
| 0.001887 | 0.491725 | 0.403619 | 0.670802 | 0.000251 | 0.011426 | 0.000242 | 0.00025 | 0.002154 | 0.001413 |
| 0.011418 | 0.690952 | 0.560377 | 0.816751 | 0.034822 | 0.00082 | 4.8E−05 | 0.004163 | 0.014239 | 0.003544 |
| 0.011747 | 0.061768 | 5.611648 | 0.000074 | 0.000477 | 0.004225 | 0.030411 | 0.197214 | 1.693928 | 0.014207 |
| 0.027289 | 0.000525 | 0.303707 | 0.028894 | 0.000296 | 0.009934 | 0.004066 | 0.403973 | 0.934677 | 0.020155 |
| 0.033934 | 0.003785 | 0.201263 | 0.000158 | 0.001109 | 3.64E−05 | 0.001883 | 0.05597 | 2.468059 | 7.5E−05 |
| 0.006261 | 0.007261 | 0.289664 | 0.008163 | 2.62E−06 | 0.002114 | 0.001112 | 0.029452 | 1.004363 | 0.002812 |
| 0.001937 | 0.065659 | 0.005006 | 0.015479 | 0.011697 | 0.005358 | 0.015902 | 0.002909 | 0.010239 | 0.021912 |
| 0.084751 | 0.3543 | 0.445674 | 0.511017 | 0.473579 | 0.3821 | 0.547618 | 0.290397 | 0.275951 | 0.397488 |
| 0.029504 | 0.000654 | 0.000207 | 0.00067 | 0.000106 | 0.001005 | 0.00604 | 0.010744 | 0.004959 | 0.002995 |
| 0.519697 | 0.13141 | 0.337149 | 0.347706 | 0.317722 | 0.237807 | 0.684435 | 0.587678 | 0.449077 | 0.560651 |
| 0.013542 | 0.007253 | 0.012363 | 0.002684 | 0.016726 | 0.397587 | 0.003814 | 0.023594 | 0.007009 | 0.013599 |
| 0.031433 | 0.017074 | 0.02442 | 0.013765 | 0.009745 | 0.171842 | 0.026383 | 0.00321 | 0.00643 | 0.032328 |
| 0.018223 | 0.003467 | 0.003761 | 0.002158 | 0.001572 | 0.413978 | 0.000184 | 2.45E−06 | 2.09E−05 | 0.005163 |
| 0.001543 | 0.000213 | 0.000314 | 0.000265 | 0.004614 | 2.528622 | 0.009122 | 0.006733 | 7.99E−05 | 5.42E−05 |
| 0.021021 | 3.87E−05 | 0.001016 | 0.004036 | 0.00717 | 0.000303 | 0.030963 | 0.133992 | 0.010653 | 0.015994 |
| 0.131077 | 0.000702 | 4.32E−07 | 0.007595 | 0.00152 | 0.000462 | 3.68E−05 | 0.08848 | 0.015056 | 0.00232 |
| 0.166209 | 0.019604 | 0.022098 | 0.012332 | 0.016639 | 0.019534 | 0.004977 | 0.046411 | 0.005078 | 0.09933 |
| 0.003722 | 0.026846 | 0.012775 | 0.017084 | 0.00687 | 0.02856 | 0.046804 | 0.00355 | 0.000901 | 0.101334 |
| 0.030135 | 0.056776 | 0.110563 | 0.083087 | 0.215918 | 0.153554 | 0.064096 | 0.008362 | 0.050625 | 1.449098 |
| 0.091275 | 0.015106 | 0.013456 | 0.006094 | 0.019728 | 0.000955 | 0.01035 | 0.001252 | 0.005069 | 1.884028 |
| 0.009708 | 0.004414 | 0.006531 | 0.009591 | 0.020022 | 0.005782 | 0.005759 | 0.006855 | 0.015161 | 0.786556 |
| 0.000108 | 0.001866 | 0.014127 | 0.00934 | 0.025073 | 0.090915 | 0.015508 | 0.002772 | 0.003433 | 1.550202 |
| 0.050735 | 0.004312 | 0.003349 | 0.010559 | 0.009284 | 0.005134 | 0.041902 | 0.001647 | 0.009554 | 0.028496 |
| 2.33E−06 | 0.002512 | 2.07E−05 | 0.00702 | 0.004205 | 0.002458 | 0.00181 | 0.004108 | 0.000463 | 0.012296 |
| 0.016633 | 0.000133 | 1.77E−08 | 0.000709 | 2.02E−06 | 0.00033 | 0.001393 | 0.001389 | 0.000312 | 0.007741 |
| 0.023739 | 0.000108 | 0.006324 | 0.04083 | 0.039838 | 0.000124 | 0.051505 | 0.002333 | 0.002972 | 0.101225 |
| 0.002657 | 0.001381 | 0.002943 | 0.000399 | 1.150779 | 0.00377 | 0.033454 | 0.807383 | 0.000202 | 0.017266 |
| 0.218609 | 0.169003 | 0.102227 | 0.081753 | 0.40538 | 0.099001 | 0.019052 | 0.003712 | 0.002625 | 0.034211 |
| 0.015695 | 0.000199 | 0.010001 | 0.008367 | 0.107131 | 0.011594 | 0.000156 | 0.055651 | 5.34E−05 | 0.019043 |
| 0.010813 | 0.120726 | 0.023173 | 0.045231 | 0.077247 | 0.017255 | 2.27E−05 | 0.179388 | 0.002245 | 0.003165 |
| 0.05516 | 0.009696 | 0.00106 | 0.029933 | 1.164686 | 2.19E−05 | 1.07517 | 1.865197 | 0.003683 | 0.030704 |
| 0.038676 | 0.033843 | 0.049895 | 0.0741269 | 0.398949 | 0.001032 | 0.004747 | 0.285161 | 0.000546 | 0.006622 |
| 0.024669 | 0.001685 | 0.006673 | 0.002237 | 0.59274 | 3.63E−06 | 0.000827 | 1.406107 | 0.006603 | 0.091061 |
| 0.00999 | 0.013667 | 0.038108 | 0.000363 | 0.203651 | 0.001603 | 0.065788 | 0.170033 | 7.82E−05 | 0.010067 |
| 0.019414 | 0.001241 | 0.000528 | 0.027659 | 0.330083 | 0.00578 | 0.163546 | 0.877872 | 0.004637 | 0.0232 |
| 0.059715 | 0.035556 | 0.020759 | 0.034438 | 0.221689 | 0.017012 | 0.028938 | 0.121022 | 0.026656 | 0.006913 |
| 0.001265 | 0.008388 | 0.003181 | 0.000928 | 0.268738 | 0.001801 | 0.041411 | 0.001599 | 0.001329 | 5.54E−09 |
| 0.009318 | 0.004258 | 0.004135 | 0.083399 | 1.817549 | 0.02253 | 0.013895 | 0.317817 | 0.007307 | 0.010422 |

$(argY_{u,c} - argY_{g,ck} - \theta_{ug,k})^2 / \sigma_{\theta g,c}^2$

| Benzene | | Hexane | | | | | AcOEt | | |
|---|---|---|---|---|---|---|---|---|---|
| $k_5$ | $k_1$ | $k_2$ | $k_3$ | $k_4$ | $k_5$ | $k_1$ | $k_2$ | $k_3$ | |
| 0.20831 | 0.611193 | 0.091323 | 0.519756 | 4.495983 | 1.00659 | 0.001148 | 0.403093 | 0.052765 | |
| 0.254625 | 0.190978 | 0.092606 | 0.170232 | 0.607432 | 0.389811 | 0.006983 | 2.969084 | 0.434142 | |
| 2.712452 | 0.010792 | 0.009984 | 0.001433 | 0.295752 | 0.023186 | 0.000853 | 0.254842 | 0.385078 | |

TABLE 14-continued

2-Benzene-3

| | | | | | | | | |
|---|---|---|---|---|---|---|---|---|
| 0.199083 | 0.050609 | 0.008443 | 0.067143 | 0.583619 | 0.040214 | 0.03019 | 0.405151 | 3.453952 |
| 0.58337 | 0.23543 | 0.118752 | 0.069081 | 0.057089 | 0.067911 | 0.125223 | 0.266336 | 0.148618 |
| 0.046512 | 0.046364 | 1.542476 | 0.025255 | 0.033776 | 0.054165 | 0.252152 | 0.172124 | 0.057122 |
| 9.63E−05 | 0.001619 | 0.417516 | 1.29E−05 | 0.002346 | 0.000468 | 0.000246 | 0.007728 | 0.006078 |
| 0.11855 | 0.01195 | 0.432194 | 0.000892 | 6.33E−05 | 0.002496 | 0.006008 | 0.006804 | 0.013897 |
| 0.083926 | 0.283105 | 0.314891 | 0.00475 | 2.201073 | 0.215369 | 0.034182 | 0.011683 | 0.050493 |
| 0.827314 | 0.403168 | 0.436122 | 0.409377 | 0.929656 | 0.450706 | 0.534092 | 0.55086 | 0.196563 |
| 0.001669 | 0.03463 | 0.009352 | 0.537282 | 0.311836 | 0.007251 | 0.00082 | 0.00064 | 0.014239 |
| 0.785046 | 0.252205 | 0.162802 | 0.022036 | 0.011108 | 0.299584 | 0.179995 | 0.243415 | 0.065357 |
| 0.016562 | 0.021775 | 0.173852 | 1.024423 | 1.117975 | 1.642973 | 0.02121 | 0.002566 | 0.010823 |
| 0.010272 | 0.019665 | 0.109598 | 0.010659 | 0.745298 | 0.037159 | 0.007086 | 0.000371 | 0.013567 |
| 0.001141 | 0.024802 | 0.000268 | 0.149361 | 0.58851 | 0.178974 | 0.002559 | 0.002578 | 0.003827 |
| 0.002238 | 0.006734 | 0.002932 | 0.102338 | 0.661385 | 0.172933 | 0.014664 | 0.007786 | 0.002756 |
| 0.349631 | 0.014312 | 0.239822 | 0.005288 | 2.376028 | 0.000615 | 8E−05 | 0.026106 | 0.00059 |
| 0.191382 | 0.008386 | 1.920574 | 1.845405 | 10.73338 | 1.384062 | 0.007443 | 0.177352 | 0.00229 |
| 0.003764 | 0.2469 | 0.000218 | 0.786666 | 1.943306 | 0.382473 | 0.010734 | 0.100227 | 0.013072 |
| 0.079162 | 0.613963 | 0.629117 | 0.030134 | 3.64458 | 0.012156 | 0.038038 | 0.851839 | 0.023315 |
| 0.038091 | 1.345213 | 0.234047 | 0.679277 | 0.535957 | 0.159232 | 0.043646 | 0.082963 | 0.06396 |
| 0.006867 | 0.16371 | 0.047164 | 0.010214 | 0.421373 | 0.002313 | 0.016402 | 0.023228 | 0.00018 |
| 0.018495 | 0.094439 | 0.010304 | 0.089407 | 0.038014 | 0.033549 | 0.00165 | 0.004715 | 0.009361 |
| 0.030432 | 0.102191 | 0.01273 | 0.106135 | 0.025044 | 0.015496 | 0.001901 | 0.005072 | 0.020959 |
| 0.00023 | 0.012074 | 0.011975 | 0.174478 | 3.039683 | 0.029321 | 0.424805 | 0.006362 | 0.012222 |
| 0.011662 | 0.017025 | 0.01561 | 0.021129 | 0.362545 | 0.037 | 0.182633 | 0.001615 | 0.004391 |
| 0.002476 | 0.001678 | 0.00056 | 0.012537 | 0.290456 | 0.003226 | 0.387732 | 0.00014 | 0.000321 |
| 0.000881 | 0.003753 | 4.56E−05 | 0.016377 | 0.219098 | 0.006181 | 2.318966 | 0.013743 | 0.000579 |
| 0.039956 | 0.001631 | 0.499224 | 0.364851 | 0.024504 | 0.054339 | 0.004797 | 0.806209 | 0.004474 |
| 0.047372 | 0.114296 | 0.647285 | 1.516928 | 0.152896 | 0.104793 | 0.051395 | 1.663844 | 0.092342 |
| 1E−05 | 0.124995 | 2.376803 | 2.018784 | 0.024238 | 1.383992 | 0.004111 | 1.058064 | 0.00074 |
| 0.00384 | 0.000217 | 0.825446 | 0.283098 | 0.005899 | 0.352482 | 0.004812 | 0.841237 | 0.049969 |
| 0.101035 | 0.056618 | 0.000948 | 0.145142 | 0.131929 | 0.686089 | 0.002737 | 2.368645 | 0.005115 |
| 0.016171 | 0.045256 | 0.001109 | 0.01893 | 0.063811 | 0.63296 | 0.011495 | 1.222675 | 0.024062 |
| 0.031313 | 0.021498 | 0.001358 | 0.002809 | 0.002129 | 1.129758 | 0.000629 | 1.636441 | 0.001734 |
| 0.022314 | 0.144887 | 0.001428 | 0.047719 | 0.005035 | 0.785597 | 0.004842 | 2.048362 | 0.034607 |
| 0.579181 | 0.762288 | 0.831273 | 0.058338 | 0.283175 | 2.38054 | 0.000272 | 0.00036 | 1.550249 |
| 0.004003 | 0.097321 | 0.476692 | 0.077636 | 0.178611 | 0.008534 | 0.014312 | 0.282548 | 0.054352 |
| 0.036226 | 0.247207 | 0.973583 | 7.91E−05 | 3E−05 | 0.166442 | 1.36E−06 | 0.017139 | 0.163999 |
| 0.190559 | 0.120911 | 0.835776 | 0.009666 | 0.005074 | 0.202428 | 0.015382 | 0.404014 | 0.18107 |

TABLE 15

2-Benzene-4

| | | THF | | | | | $\log\sigma_{Lg,c}$ | | |
|---|---|---|---|---|---|---|---|---|---|
| $k_4$ | $k_5$ | $k_1$ | $k_2$ | $k_3$ | $k_4$ | $k_5$ | $H_2O$ | EtOH | Benzene |
| 0.02079 | 0.002363 | 0.147353 | 1.630764 | 0.000437 | 0.003737 | 0.002719 | −0.27945 | 0.398827 | −0.12502 |
| 0.018879 | 0.00025 | 0.270805 | 0.333794 | 0.000806 | 0.011321 | 0.000818 | −0.0226 | 0.248584 | −0.25239 |
| 2E−05 | 0.000752 | 0.290594 | 0.16422 | 0.00066 | 9.88E−05 | 3.76E−05 | −0.55571 | 0.239137 | −0.39623 |
| 4.57E−06 | 0.001152 | 10.41389 | 0.46785 | 0.003548 | 0.017324 | 0.029625 | −0.53188 | −0.1312 | −0.52282 |
| 0.124324 | 0.105967 | 0.012175 | 0.050907 | 0.101678 | 0.611598 | 0.013435 | −0.7076 | −0.13743 | 0.044038 |
| 0.007844 | 0.038553 | 0.061115 | 0.193742 | 5.35836 | 2.142278 | 0.095858 | −0.42382 | −0.15439 | −0.11099 |
| 0.014687 | 0.010048 | 0.000273 | 0.000257 | 0.213738 | 0.827404 | 0.00031 | −0.42179 | −0.09534 | 0.33566 |
| 0.033722 | 0.005038 | 2.37E−05 | 7.53E−05 | 0.24243 | 0.897883 | 0.001098 | −0.40275 | 0.458128 | 0.175373 |
| 0.016761 | 0.025246 | 0.384732 | 0.148719 | 0.07192 | 0.303885 | 0.041603 | −0.91872 | −0.22917 | −0.95407 |
| 0.661534 | 0.784522 | 1.424949 | 0.284301 | 1.210491 | 2.563825 | 1.191637 | −0.17315 | −0.39424 | −0.01421 |
| 0.003476 | 2.11E−11 | 0.024601 | 0.015113 | 0.011524 | 0.001059 | 0.004667 | −0.83614 | −0.65358 | −0.29561 |
| 0.313089 | 0.288362 | 0.782232 | 1.01348 | 1.136804 | 1.476426 | 1.165135 | −0.6724 | −1.1222 | 0.043835 |
| 0.010968 | 0.000894 | 0.010851 | 0.020239 | 0.006032 | 0.002409 | 0.016374 | 0.371859 | −0.99151 | −0.41346 |
| 0.015633 | 0.004915 | 1.55E−05 | 0.015526 | 2.05E−05 | 0.078662 | 0.012333 | −0.16865 | −1.23994 | −0.55346 |
| 0.003335 | 0.001947 | 0.00388 | 0.00362 | 0.001121 | 0.000299 | 0.003165 | −0.0813 | −1.29443 | −0.40318 |
| 0.001566 | 1.02E−05 | 0.028206 | 0.009496 | 0.011301 | 0.069482 | 0.008209 | 0.04032 | −1.12337 | −0.28638 |
| 0.003405 | 3.876116 | 0.00645 | 0.002596 | 0.010078 | 0.010761 | 0.001256 | 0.191785 | −0.22819 | −0.94597 |
| 0.00019 | 0.221491 | 0.052761 | 0.097442 | 0.042867 | 0.012242 | 0.002581 | −0.11037 | −0.07316 | −1.25623 |
| 0.015481 | 0.180868 | 0.019022 | 0.017108 | 0.019041 | 0.012242 | 0.02795 | −0.54554 | −0.75784 | −0.37232 |
| 0.004785 | 0.501782 | 0.06905 | 0.128452 | 0.049863 | 0.106072 | 0.029444 | −0.54083 | −0.73936 | −0.23667 |
| 0.092321 | 0.070388 | 0.12257 | 0.079138 | 0.017063 | 0.306036 | 0.113909 | −1.05253 | −1.09551 | −0.50347 |
| 0.005711 | 0.013207 | 0.000252 | 0.00334 | 0.016059 | 0.050112 | 0.000403 | −1.54038 | −1.18116 | −0.45473 |
| 0.006176 | 0.008153 | 0.013156 | 0.016257 | 0.016312 | 0.006919 | 0.015088 | −0.16437 | −1.13825 | −0.67257 |
| 0.023454 | 0.004028 | 0.046761 | 0.035777 | 0.017318 | 0.026163 | 0.02476 | −0.59311 | −1.11749 | −0.54994 |
| 0.004661 | 0.020035 | 0.004021 | 1.275414 | 0.004007 | 0.02157 | 0.008673 | −0.791 | −0.48094 | −0.13148 |
| 0.018695 | 0.004174 | 0.001474 | 0.096254 | 0.002645 | 0.070291 | 0.01713 | −0.30458 | −0.04454 | −1.15475 |
| 0.000243 | 0.000377 | 6.14E−07 | 0.231887 | 3.46E−06 | 0.002269 | 0.000112 | −0.14548 | −0.29639 | −0.3181 |
| 0.002043 | 0.002683 | 0.001235 | 0.236152 | 0.000372 | 0.002189 | 0.001205 | −0.15455 | −0.13279 | −0.21329 |
| 0.002827 | 0.000407 | 0.003728 | 0.005446 | 0.000237 | 0.003742 | 1.28E−05 | −0.62735 | 0.889626 | −0.60433 |

TABLE 15-continued

2-Benzene-4

| | | | | | | | | | |
|---|---|---|---|---|---|---|---|---|---|
| 0.013398 | 0.038465 | 0.018077 | 0.014862 | 0.002557 | 0.000296 | 0.013756 | −0.90372 | −0.23395 | −0.70282 |
| 0.005095 | 0.002146 | 0.003878 | 0.000145 | 0.002713 | 0.000616 | 0.004312 | −0.75676 | −0.16047 | 0.069012 |
| 0.000294 | 0.010847 | 0.000483 | 0.036486 | 0.000256 | 0.008256 | 0.002689 | −0.97667 | 0.048629 | −0.20526 |
| 0.665286 | 0.01839 | 0.020849 | 0.015685 | 0.023261 | 0.07434 | 0.017168 | −0.10314 | −0.45305 | −0.63388 |
| 0.408568 | 0.026418 | 0.385411 | 0.128921 | 0.546679 | 0.013784 | 0.324628 | −0.20565 | −0.12083 | 0.069844 |
| 0.740894 | 0.005004 | 0.001576 | 0.000469 | 0.002501 | 0.004448 | 0.023821 | −0.25904 | 0.189343 | 0.446272 |
| 0.464961 | 0.069741 | 0.226955 | 0.267121 | 0.344333 | 0.012536 | 0.09732 | −0.1905 | 0.489136 | 0.408102 |
| 0.000636 | 0.038065 | 0.000387 | 0.022299 | 0.024131 | 2.25E−06 | 0.056167 | −0.18367 | −1.36604 | −0.93406 |
| 0.044625 | 0.00295 | 0.019813 | 1.062904 | 0.973702 | 0.015851 | 0.478855 | −0.56828 | 0.228993 | −0.9417 |
| 0.00144 | 0.001152 | 0.002704 | 0.108267 | 0.034224 | 0.001738 | 0.006596 | −0.16197 | 0.020417 | −1.34016 |
| 0.045017 | 0.020357 | 0.004703 | 0.086162 | 0.153398 | 0.002411 | 0.043172 | −0.17728 | 0.066696 | −1.43918 |

| $\log\sigma_{Lg,c}$ | | | $\log\sigma_{\theta g,c}$ | | | | | |
|---|---|---|---|---|---|---|---|---|
| Hexane | AcOEt | THF | $H_2O$ | EtOH | Benzene | Hexane | AcOEt | THF |
| −0.55113 | 0.32871 | −0.08107 | 0.801234 | 1.207714 | 1.079374 | 0.189762 | 0.866507 | 1.150356 |
| −0.32497 | −0.10168 | 0.215972 | 0.729341 | 0.669981 | 1.252097 | 0.229623 | 0.939439 | 1.183314 |
| −0.61155 | 0.447759 | −0.12574 | 0.714165 | 0.547871 | 0.999054 | 0.229044 | 1.090265 | 1.080074 |
| −0.89179 | 0.355916 | −0.55732 | 0.722126 | 0.465178 | 1.1117856 | 0.1627 | 0.785955 | 0.3326 |
| −0.64421 | −1.19739 | −0.06096 | 0.5606 | 0.605007 | 0.795256 | 0.743116 | −0.2618 | 1.272984 |
| −1.14907 | −1.08912 | −0.0579 | 0.53307 | 0.957349 | 1.134892 | 1.126902 | −0.39762 | 0.636763 |
| −1.22368 | −1.29606 | −0.19802 | 0.576843 | 0.985589 | 0.696795 | 0.874959 | −0.37434 | 1.23767 |
| −1.11758 | −1.11766 | −0.44338 | 0.594635 | 0.995588 | 1.106001 | 0.863036 | −0.35685 | 1.205117 |
| −0.36169 | −0.08808 | −0.54633 | 1.378727 | 0.870049 | 0.644553 | 1.15028 | 0.84218 | 0.01585 |
| −0.13507 | 0.117575 | −0.50368 | 1.295079 | 0.951724 | 0.980232 | 1.301856 | 0.750527 | 0.170075 |
| −0.0715 | 0.061467 | −0.58296 | 0.444318 | 0.974456 | 0.722887 | 0.901578 | 0.922287 | 0.046107 |
| −0.11942 | 0.057921 | −0.63334 | 0.472307 | 1.012596 | 0.702096 | 0.794673 | 1.032039 | 0.070549 |
| −0.38187 | −0.37755 | −0.48677 | 0.961614 | 1.035338 | 0.756087 | 0.997163 | 0.862225 | 0.689686 |
| −0.28183 | −0.55965 | −1.19113 | 1.01892 | 1.0191 | 0.857216 | 1.099827 | 0.859037 | 0.505935 |
| −0.17188 | −0.38782 | −0.72924 | 0.654436 | 1.034736 | 0.840677 | 1.216736 | 0.834254 | 0.678971 |
| 0.033897 | −0.15015 | −0.82075 | 0.619903 | 1.091146 | 0.840677 | 1.260704 | 0.774444 | 0.696334 |
| −1.15407 | 0.02776 | −0.90701 | 1.044944 | 0.930337 | −0.16622 | 0.883427 | 0.852136 | 0.731865 |
| −0.34122 | 0.011325 | −0.71451 | 0.951797 | 1.037002 | 0.532775 | −0.79673 | 1.082475 | 0.682279 |
| −0.33503 | 0.564229 | −0.99709 | 1.059034 | 1.038236 | 0.205231 | −0.45793 | 1.088727 | 0.735329 |
| −0.51182 | 0.321599 | −0.41743 | 1.050676 | 1.089144 | 0.128321 | −0.33163 | 1.021132 | 0.783396 |
| 0.125804 | −0.91843 | −0.05209 | 0.656551 | 0.717663 | 1.123837 | 0.642526 | 1.106472 | 0.682546 |
| −0.12365 | −0.52523 | −0.15205 | 0.594556 | 0.691442 | 0.946763 | 0.738585 | 1.084102 | 0.904087 |
| −0.81878 | −1.01393 | −0.17641 | 0.879033 | 0.762743 | 1.111363 | 0.709606 | 1.104812 | 0.776997 |
| −0.24084 | −1.39596 | −0.26371 | 0.860382 | 0.844861 | 0.831881 | 0.830535 | 1.095595 | 0.802764 |
| −0.8441 | −1.78544 | −1.54092 | 0.909549 | 0.899793 | 0.836804 | 0.622138 | 0.89432 | 1.315317 |
| −1.10002 | −0.25395 | −0.86242 | 0.906718 | 0.842321 | 0.733571 | 0.646614 | 0.880259 | 1.176445 |
| −1.07174 | −0.91017 | −1.1134 | 0.706513 | 0.779633 | 0.822822 | 0.725209 | 0.912419 | 1.213009 |
| −0.67837 | −0.81836 | −1.39507 | 0.671983 | 0.655389 | 0.947994 | 0.74445 | 1.008622 | 1.180359 |
| −0.2829 | −0.47458 | −0.25747 | 0.40447 | 0.757171 | 0.997815 | 0.85769 | 1.104346 | 0.999825 |
| −0.41213 | −0.27044 | 0.071537 | 0.071537 | 0.602741 | 1.225844 | 0.825294 | 1.052402 | 1.112113 |
| −0.27628 | −0.31088 | 0.087425 | 0.907564 | 0.618479 | 1.213651 | 0.576452 | 1.166429 | 1.023458 |
| 0.111701 | −0.27363 | −0.07046 | 0.950403 | 0.619702 | 1.220683 | 1.165549 | 1.218396 | 1.152418 |
| 0.038614 | 0.083506 | −0.32954 | 0.634833 | 0.739149 | −0.20836 | 0.812456 | 0.535362 | 0.228705 |
| −0.15347 | 0.56292 | −0.3326 | 0.551091 | 0.864869 | 0.855276 | 0.850432 | 0.930297 | 0.188121 |
| −0.10431 | 0.630582 | −0.87208 | 0.582188 | 0.645764 | 0.006498 | 0.60461 | 0.689769 | 0.163691 |
| −0.21624 | 0.388878 | −0.91419 | 0.584172 | 0.450962 | 0.931221 | 0.69898 | 0.643733 | 0.089592 |
| 0.227763 | 0.666495 | 0.047935 | 0.768615 | 0.7843 | 0.198057 | 0.592487 | 0.754077 | 0.893002 |
| 0.117962 | 0.073392 | 0.670118 | 0.838437 | 0.813008 | 0.568256 | 1.022759 | 0.875654 | 0.682508 |
| 0.391301 | 0.153097 | 0.439682 | 0.683124 | 0.702989 | 0.698645 | 0.987988 | 0.895158 | 0.95815 |
| −0.00175 | −0.09715 | −0.05799 | 0.699085 | 0.915385 | 1.181083 | 1.161702 | 0.945869 | 1.024418 |

TABLE 16

2-Hexane-1

| | | $\log|Y_{u,c}|$ | $(\log|Y_{u,c}|-\log|Y_{g,ck}|-L_{ug,k})^2/\sigma_{Lg,c}^2$ | | | | | | | |
|---|---|---|---|---|---|---|---|---|---|---|
| | | Hexane | $H_2O$ | | | | | EtOH | | |
| f | c | $k_6$ | $k_1$ | $k_2$ | $k_3$ | $k_4$ | $k_5$ | $k_1$ | $k_2$ | $k_3$ |
| 0.05 Hz | Ch. 1 | 0.452503 | 4.210062 | 4.729468 | 4.057809 | 4.154793 | 3.914605 | 0.47778 | 0.159357 | 0.533332 |
| | Ch. 2 | 4.73525 | 0.219407 | 0.279969 | 0.791636 | 0.542156 | 0.216442 | 0.110085 | 0.168746 | 0.175105 |
| | Ch. 3 | −0.44139 | 1.394347 | 1.416809 | 0.602933 | 0.835865 | 1.301916 | 0.011278 | 0.007018 | 0.000284 |
| | Ch. 4 | −1.03361 | 0.502044 | 0.572215 | 0.125346 | 0.255667 | 0.433424 | 0.286759 | 0.001906 | 0.365545 |
| 0.1 Hz | Ch. 1 | −0.55719 | 6.801627 | 5.220871 | 6.777973 | 6.193464 | 7.51995 | 0.995344 | 0.279252 | 0.797982 |
| | Ch. 2 | 3.244214 | 0.034617 | 0.336929 | 0.518136 | 0.556437 | 0.55768 | 0.009227 | 0.07686 | 0.136758 |
| | Ch. 3 | −1.84015 | 0.744895 | 0.295391 | 0.308056 | 0.248914 | 0.351911 | 0.000277 | 0.027729 | 0.014748 |
| | Ch. 4 | −2.16524 | 0.798737 | 0.339789 | 0.451248 | 0.378015 | 0.501876 | 0.238472 | 0.241071 | 0.13092 |

TABLE 16-continued

2-Hexane-1

| f | c | | | | | | | | | |
|---|---|---|---|---|---|---|---|---|---|---|
| 0.15 Hz | Ch. 1 | −1.42047 | 27.5936 | 19.91142 | 33.14208 | 22.88004 | 22.15093 | 3.577634 | 4.221304 | 3.799237 |
| | Ch. 2 | 3.258706 | 0.156235 | 0.123744 | 0.220699 | 2.180408 | 0.327023 | 0.260172 | 0.622079 | 0.556908 |
| | Ch. 3 | −1.60969 | 3.213652 | 2.510558 | 3.385066 | 0.240956 | 1.950829 | 0.088668 | 0.061597 | 0.078937 |
| | Ch. 4 | −1.83119 | 3.736509 | 2.443926 | 4.683333 | 0.791301 | 2.405727 | 9.5349 | 9.287607 | 7.653754 |
| 0.2 Hz | Ch. 1 | −1.3994 | 0.598514 | 0.200277 | 0.84596 | 1.010487 | 1.054269 | 4.452551 | 6.458342 | 6.438304 |
| | Ch. 2 | 2.446857 | 0.481568 | 0.006547 | 0.016757 | 0.000515 | 9.1E−05 | 0.092472 | 0.152728 | 0.033079 |
| | Ch. 3 | −2.10624 | 0.560376 | 0.042101 | 0.370027 | 0.526996 | 0.532761 | 0.014692 | 0.154882 | 0.165686 |
| | Ch. 4 | −2.31954 | 0.956459 | 0.141456 | 0.406601 | 0.602157 | 0.626999 | 6.635773 | 8.501013 | 7.364907 |
| 0.25 Hz | Ch. 1 | −1.34263 | 2.415616 | 2.2415 | 2.847395 | 2.301781 | 0.828291 | 2.12354 | 3.227922 | 2.717185 |
| | Ch. 2 | 3.269495 | 0.000441 | 0.483531 | 0.04262 | 0.373749 | 0.364582 | 0.142301 | 0.081212 | 0.092465 |
| | Ch. 3 | −1.62167 | 2.366039 | 0.744806 | 2.339838 | 0.935272 | 0.076448 | 0.04334 | 0.070853 | 0.063404 |
| | Ch. 4 | −1.86976 | 2.789995 | 1.40769 | 2.791341 | 1.571744 | 0.475634 | 2.22247 | 4.952269 | 3.644581 |
| 0.3 Hz | Ch. 1 | −1.37539 | 11.91728 | 8.835044 | 10.63841 | 10.96909 | 8.993443 | 1.313226 | 2.803796 | 2.059219 |
| | Ch. 2 | 1.944247 | 21.04786 | 0.655351 | 6.79E−05 | 0.642346 | 0.455576 | 1.465446 | 0.641497 | 1.063978 |
| | Ch. 3 | −2.50579 | 2.355024 | 0.443012 | 0.398184 | 0.5753051 | 0.443127 | 0.034534 | 2.54E−05 | 0.024673 |
| | Ch. 4 | −2.78858 | 2.568553 | 1.357447 | 1.184193 | 1.532935 | 1.285593 | 4.516878 | 6.091654 | 5.202521 |
| 0.35 Hz | Ch. 1 | −3.83248 | 49.5958 | 61.87378 | 62.08894 | 44.16241 | 50.91172 | 18.37096 | 16.46141 | 18.31258 |
| | Ch. 2 | 2.731045 | 0.169309 | 6.139315 | 1.056951 | 4.155754 | 2.478072 | 0.462814 | 0.403197 | 0.518959 |
| | Ch. 3 | −1.98824 | 3.111014 | 1.020565 | 3.16716 | 0.978145 | 1.590111 | 1.048924 | 0.183377 | 0.75272 |
| | Ch. 4 | −2.52886 | 2.536351 | 1.020949 | 2.216916 | 0.583677 | 1.31876 | 1.997428 | 1.656534 | 2.242985 |
| 0.4 Hz | Ch. 1 | −2.54399 | 14.77116 | 5.514033 | 17.80069 | 13.18468 | 14.71518 | 2.649351 | 1.857289 | 1.69774 |
| | Ch. 2 | 2.277409 | 0.096666 | 1.050223 | 0.416842 | 0.36676 | 0.161247 | 0.065246 | 0.202588 | 0.004296 |
| | Ch. 3 | −2.47051 | 5.868133 | 0.749352 | 4.976146 | 2.744527 | 4.05012 | 0.000883 | 0.074617 | 0.121676 |
| | Ch. 4 | −2.78031 | 7.653161 | 1.320337 | 6.296127 | 5.922706 | 6.252341 | 2.187837 | 0.737771 | 1.050806 |
| 0.45 Hz | Ch. 1 | −3.97589 | 8.040752 | 7.738212 | 9.078823 | 7.142152 | 8.200205 | 9.887844 | 10.17028 | 9.245557 |
| | Ch. 2 | 1.466546 | 0.009893 | 0.625534 | 0.135722 | 0.271426 | 0.034544 | 0.120165 | 0.231504 | 0.162657 |
| | Ch. 3 | −3.00804 | 3.179118 | 1.978487 | 3.202601 | 2.031058 | 4.093128 | 0.262087 | 0.343036 | 0.215437 |
| | Ch. 4 | −3.61875 | 1.773184 | 0.889769 | 1.573176 | 1.150348 | 1.108414 | 0.4329 | 0.299871 | 0.387011 |
| 0.5 Hz | Ch. 1 | −3.13679 | 2.317057 | 3.539535 | 2.957045 | 3.898875 | 2.519074 | 9.103153 | 1.309796 | 10.81507 |
| | Ch. 2 | 0.162104 | 4.224615 | 2.192358 | 2.066035 | 3.584638 | 2.026802 | 0.256237 | 0.352231 | 0.287604 |
| | Ch. 3 | −3.19734 | 2.637945 | 2.031293 | 2.052587 | 2.475581 | 2.173291 | 0.364253 | 0.407245 | 0.279475 |
| | Ch. 4 | −3.63469 | 1.571251 | 2.026812 | 1.503285 | 2.705768 | 1.087937 | 0.546433 | 0.907235 | 0.829713 |

$(\log|Y_{u,c}| - \log|Y_{g,ck}| - L_{ug,k})^2 / \sigma_{Lg,c}^2$

| | | EtOH | | Benzene | | | | | |
|---|---|---|---|---|---|---|---|---|---|
| f | c | $k_4$ | $k_5$ | $k_1$ | $k_2$ | $k_3$ | $k_4$ | $k_5$ | $k_1$ |
| 0.05 Hz | Ch. 1 | 0.387463 | 0.491193 | 0.134727 | 0.896453 | 0.291086 | 0.343311 | 0.002416 | 0.267492 |
| | Ch. 2 | 0.079207 | 0.108389 | 0.886193 | 2.712121 | 2.218514 | 1.078581 | 0.466681 | 0.019691 |
| | Ch. 3 | 0.000643 | 0.001846 | 0.642955 | 0.611479 | 1.109792 | 0.729656 | 0.416094 | 0.015459 |
| | Ch. 4 | 0.371358 | 0.418847 | 0.04961 | 0.019222 | 0.002167 | 0.230994 | 0.008099 | 0.099359 |
| 0.1 Hz | Ch. 1 | 1.023976 | 2.35281 | 0.008487 | 0.371494 | 0.006157 | 0.000447 | 0.041132 | 0.003647 |
| | Ch. 2 | 0.047259 | 0.269844 | 0.132255 | 0.001374 | 0.001362 | 0.058805 | 0.04941 | 0.139512 |
| | Ch. 3 | 0.015174 | 0.109905 | 0.171017 | 0.000126 | 0.0797621 | 0.213452 | 0.069645 | 0.045992 |
| | Ch. 4 | 0.260943 | 1.736367 | 0.085913 | 0.243526 | 0.073029 | 0.14346 | 0.089321 | 0.0052 |
| 0.15 Hz | Ch. 1 | 4.733641 | 2.244496 | 4.821459 | 0.733356 | 3.089586 | 2.696651 | 14.58688 | 3.447283 |
| | Ch. 2 | 0.107547 | 0.09607 | 0.040875 | 0.007721 | 0.00404 | 0.000514 | 0.150886 | 0.441719 |
| | Ch. 3 | 0.226597 | 0.163705 | 0.016567 | 0.117635 | 0.033094 | 0.041146 | 0.050339 | 0.151281 |
| | Ch. 4 | 15.01134 | 5.621376 | 0.504618 | 0.413278 | 0.701428 | 0.594833 | 1.442936 | 0.155915 |
| 0.2 Hz | Ch. 1 | 11.561 | 4.956015 | 0.080009 | 0.189351 | 0.026692 | 0.001404 | 0.519588 | 0.458811 |
| | Ch. 2 | 0.009518 | 0.369863 | 0.928575 | 0.045853 | 0.396104 | 0.290027 | 0.416814 | 0.038759 |
| | Ch. 3 | 0.589843 | 0.328987 | 0.181181 | 0.190053 | 0.076001 | 0.035794 | 0.13736 | 1.75E−05 |
| | Ch. 4 | 11.01549 | 6.748785 | 1.86485 | 0.87434 | 0.75868 | 0.376559 | 2.128253 | 0.352746 |
| 0.25 Hz | Ch. 1 | 4.607563 | 1.968275 | 3.202454 | 6.299593 | 1.039374 | 0.879434 | 5.676511 | 9.297351 |
| | Ch. 2 | 0.133672 | 0.821344 | 0.309925 | 0.105447 | 0.699539 | 0.123282 | 0.057078 | 0.227162 |
| | Ch. 3 | 0.239337 | 0.125307 | 0.038147 | 0.26151 | 0.076566 | 0.034045 | 0.099881 | 0.123138 |
| | Ch. 4 | 5.696455 | 0.850441 | 0.72272 | 0.819896 | 0.315509 | 0.245832 | 2.354113 | 0.384572 |
| 0.3 Hz | Ch. 1 | 1.567878 | 1.828001 | 0.283609 | 0.011333 | 0.549208 | 0.632539 | 3.5E−05 | 0.007917 |
| | Ch. 2 | 0.954605 | 1.781052 | 0.263022 | 0.10805 | 1.69256 | 0.256392 | 0.309265 | 0.000565 |
| | Ch. 3 | 0.000211 | 0.003652 | 0.267786 | 0.327711 | 0.003017 | 0.420544 | 0.45168 | 0.120218 |
| | Ch. 4 | 4.888371 | 6.631277 | 0.215263 | 0.959344 | 0.494484 | 0.088425 | 1.439953 | 0.018479 |
| 0.35 Hz | Ch. 1 | 27.74685 | 17.13861 | 3.476652 | 2.446664 | 4.619550 | 3.757786 | 5.654828 | 19.0615 |
| | Ch. 2 | 1.397833 | 0.528344 | 0.781697 | 1.125666 | 4.529818 | 0.006532 | 3.289812 | 3.146671 |
| | Ch. 3 | 1.271336 | 1.056956 | 0.613915 | 0.314833 | 0.379802 | 0.583757 | 0.393397 | 3.942215 |
| | Ch. 4 | 2.161539 | 1.577184 | 0.946909 | 0.605918 | 0.897319 | 1.916023 | 1.711934 | 1.429921 |
| 0.4 Hz | Ch. 1 | 0.631441 | 1.630059 | 1.446007 | 2.604673 | 1.681293 | 1.225977 | 1.321014 | 0.74241 |
| | Ch. 2 | 0.059759 | 0.064988 | 0.002641 | 1.263448 | 0.511419 | 0.011276 | 0.653309 | 0.426849 |
| | Ch. 3 | 0.084699 | 0.066702 | 0.009907 | 0.677072 | 0.009257 | 0.071597 | 0.009065 | 0.013372 |
| | Ch. 4 | 0.166047 | 0.862034 | 0.50001 | 0.467522 | 0.31555 | 1.051614 | 0.163999 | 0.013296 |
| 0.45 Hz | Ch. 1 | 20.85334 | 9.630769 | 10.11197 | 18.35918 | 4.235668 | 3.016658 | 3.74452 | 3.525977 |
| | Ch. 2 | 0.119672 | 0.919984 | 0.425123 | 0.093441 | 0.004438 | 0.00193 | 0.052791 | 0.031111 |
| | Ch. 3 | 0.8018 | 0.225992 | 0.035241 | 0.795163 | 0.12471 | 0.11748 | 0.049201 | 1.637598 |
| | Ch. 4 | 1.701476 | 0.113021 | 0.213268 | 0.644816 | 0.0971 | 0.050747 | 0.083139 | 0.646033 |

TABLE 16-continued

2-Hexane-1

| | | | | | | | | | |
|---|---|---|---|---|---|---|---|---|---|
| 0.5 Hz | Ch. 1 | 73.34625 | 11.99461 | 0.30194 | 1.473711 | 0.076376 | 0.011953 | 1.362199 | 0.128976 |
| | Ch. 2 | 0.000821 | 0.311017 | 8.91001 | 5.449959 | 7.395735 | 11.7069 | 9.105322 | 0.258417 |
| | Ch. 3 | 0.768017 | 0.343741 | 1.462709 | 3.443247 | 1.216457 | 0.941367 | 4.634111 | 0.169242 |
| | Ch. 4 | 1.539719 | 0.851406 | 20.10875 | 14.45743 | 7.821612 | 22.43823 | 20.42932 | 0.172478 |

TABLE 17

2-Hexane-2

$(\log|Y_{u,c}|-\log|Y_{g,ck}|-L_{ug,k})^2/\sigma_{Lg,c}^2$

| Hexane | | | | AcOEt | | | | | THF |
|---|---|---|---|---|---|---|---|---|---|
| $k_2$ | $k_3$ | $k_4$ | $k_5$ | $k_1$ | $k_2$ | $k_3$ | $k_4$ | $k_5$ | $k_1$ |
| 0.416894 | 0.032751 | 0.836298 | 0.128612 | 0.808085 | 0.999886 | 0.942349 | 1.533207 | 1.074126 | 3.007358 |
| 0.012211 | 0.003257 | 0.457499 | 0.000367 | 0.558282 | 1.339034 | 0.063722 | 1.544424 | 0.924237 | 1.850521 |
| 0.138172 | 0.008051 | 0.07493 | 0.017475 | 0.004992 | 0.004334 | 0.063326 | 0.000202 | 5.52E-05 | 0.063366 |
| 0.372792 | 0.055823 | 0.072281 | 0.087302 | 0.105324 | 0.097977 | 0.259181 | 0.188493 | 0.15373 | 0.053797 |
| 0.036396 | 0.003891 | 0.024353 | 0.286576 | 12.04327 | 9.960992 | 11.00673 | 10.45638 | 12.45524 | 1.61026 |
| 0.0431 | 0.000829 | 0.128811 | 0.007952 | 3.295347 | 2.03146 | 2.975876 | 2.062631 | 2.77553 | 1.941794 |
| 0.075918 | 0.11335 | 0.052231 | 0.282695 | 0.570864 | 0.308146 | 0.401921 | 0.198035 | 0.194464 | 0.277539 |
| 0.124537 | 0.030535 | 0.646161 | 0.086926 | 3.87554 | 3.656106 | 3.307919 | 3.535773 | 3.661285 | 0.234774 |
| 0.345664 | 0.216821 | 0.03932 | 1.938769 | 3.537461 | 3.420161 | 4.751586 | 2.936004 | 3.36321 | 10.88613 |
| 0.279497 | 0.031549 | 0.005638 | 0.020821 | 0.512567 | 0.281442 | 0.613422 | 0.070309 | 0.190489 | 3.741934 |
| 0.015108 | 5.58E-06 | 0.000653 | 0.208307 | 0.004289 | 0.015912 | 0.020994 | 0.056349 | 0.035617 | 0.005979 |
| 0.035337 | 0.037276 | 0.065723 | 0.571616 | 0.639433 | 0.825239 | 0.822523 | 0.923576 | 0.868816 | 2.185834 |
| 0.041376 | 1.185041 | 0.447491 | 0.616135 | 2.756712 | 2.149674 | 3.107779 | 3.213529 | 3.406433 | 3.753884 |
| 0.067364 | 0.29682 | 0.065988 | 0.450597 | 0.139944 | 0.272647 | 0.033537 | 0.068583 | 0.05666 | 2.577251 |
| 0.001652 | 0.086238 | 0.099174 | 0.041118 | 0.013029 | 0.013126 | 0.034829 | 0.046252 | 0.043132 | 0.017802 |
| 0.00777 | 0.006764 | 0.138669 | 0.018675 | 0.968725 | 0.534252 | 1.289546 | 1.176272 | 2.14491 | 3.039716 |
| 7.194371 | 3.815213 | 0.033678 | 0.12195 | 2.183518 | 3.740206 | 2.074053 | 2.193247 | 2.263124 | 15.68942 |
| 0.533383 | 0.1892 | 0.050652 | 3.72E-05 | 0.424649 | 0.002333 | 0.18173 | 0.271213 | 0.237405 | 1.736319 |
| 0.270786 | 0.038947 | 0.011283 | 0.003001 | 0.000658 | 0.268818 | 0.005075 | 0.009998 | 0.007932 | 0.124788 |
| 0.005783 | 0.076302 | 0.001902 | 0.058496 | 0.34934 | 0.555472 | 0.449039 | 0.353542 | 0.423234 | 2.710805 |
| 0.938601 | 1.264757 | 0.031186 | 0.006851 | 3.274411 | 6.211132 | 4.55362 | 3.089174 | 4.787863 | 0.929575 |
| 0.386102 | 0.831881 | 0.007074 | 0.1523 | 0.176901 | 0.000981 | 0.112594 | 0.14597 | 0.000126 | 0.206864 |
| 0.329678 | 2.047027 | 0.063808 | 0.021326 | 0.087207 | 0.079199 | 0.008471 | 0.027468 | 0.151674 | 0.016363 |
| 0.093507 | 0.146874 | 0.031071 | 0.209889 | 2.183091 | 12.46417 | 16.86499 | 12.27214 | 8.584693 | 0.676361 |
| 8.283862 | 14.8612 | 19.44138 | 7.880864 | 294.502 | 412.2906 | 302.3532 | 331.9708 | 312.8069 | 188.732 |
| 3.257648 | 4.688759 | 2.908399 | 1.256692 | 0.821679 | 3.348397 | 2.06668 | 1.263874 | 1.750134 | 8.29735 |
| 1.924056 | 3.528435 | 3.024807 | 1.137977 | 3.732894 | 3.524252 | 3.70284 | 4.291768 | 3.980993 | 2.773115 |
| 0.101553 | 0.334508 | 2.083971 | 0.852625 | 10.03735 | 7.781359 | 5.417431 | 9.365755 | 6.644766 | 22.65684 |
| 0.971946 | 1.918745 | 2.489302 | 1.584766 | 7.936528 | 6.220398 | 6.404216 | 9.272411 | 6.903418 | 4.787012 |
| 0.234455 | 0.254509 | 3.234587 | 0.170201 | 0.727573 | 0.252 | 0.02187 | 0.620721 | 0.154375 | 0.454718 |
| 2.32E-05 | 0.333049 | 0.002241 | 0.01525 | 0.170867 | 0.151708 | 0.17808 | 0.20116 | 0.104057 | 0.002353 |
| 0.140168 | 0.059166 | 0.000917 | 0.473155 | 1.103279 | 1.348336 | 2.295337 | 1.608412 | 2.085644 | 0.757607 |
| 0.904166 | 1.918745 | 1.804971 | 0.48874 | 4.113371 | 6.52263 | 4.020819 | 6.350873 | 3.327219 | 10.59845 |
| 0.044775 | 0.254509 | 0.367611 | 0.397098 | 0.115909 | 0.178191 | 0.08685 | 0.28539 | 0.068984 | 1.72953 |
| 0.270171 | 0.333049 | 0.865243 | 0.368076 | 0.112068 | 0.147577 | 0.111995 | 0.550773 | 0.105385 | 0.91612 |
| 0.176602 | 0.059166 | 0.00226 | 0.200251 | 0.439523 | 0.792638 | 0.490901 | 0.07623 | 0.382038 | 6.203552 |
| 0.971335 | 0.004864 | 0.049114 | 0.48015 | 0.376129 | 0.559007 | 0.000157 | 0.449937 | 0.376128 | 0.89558 |
| 0.099862 | 0.346302 | 0.202863 | 0.485294 | 0.17413 | 0.965707 | 0.680786 | 0.254129 | 0.613359 | 0.047587 |
| 0.911651 | 0.070646 | 0.203806 | 0.014133 | 0.178724 | 1.662407 | 0.034064 | 0.318304 | 0.451976 | 0.089627 |
| 0.032937 | 0.033054 | 0.013842 | 0.068955 | 1.601183 | 1.222652 | 0.508983 | 1.713876 | 1.897928 | 1.023047 |

| $(\log|Y_{u,c}|-\log|Y_{g,ck}|-L_{ug,k})^2/\sigma_{Lg,c}^2$ THF | | | | $\arg Y_{u,c}$ Hexane | $H_2O$ | | | |
|---|---|---|---|---|---|---|---|---|
| $k_2$ | $k_3$ | $k_4$ | $k_5$ | $k_5$ | $k_1$ | $k_2$ | $k_3$ | $k_4$ |
| 3.299999 | 2.875929 | 3.213514 | 2.460695 | 0.048294 | 0.230223 | 0.153085 | 0.301911 | 0.179691 |
| 3.093357 | 3.069483 | 1.774033 | 2.317789 | −1.49382 | 0.062831 | 0.016914 | 0.131514 | 0.041291 |
| 0.062138 | 0.203855 | 0.090923 | 0.114959 | −1.18279 | 0.028566 | 0.043481 | 0.032145 | 0.032781 |
| 0.252554 | 0.137514 | 0.21558 | 0.063155 | −1.07272 | 0.009833 | 0.007328 | 0.002658 | 0.005551 |
| 1.511251 | 1.512764 | 2.085081 | 2.019219 | −0.84167 | 0.26929 | 0.262107 | 0.244823 | 0.281538 |
| 2.22716 | 1.367834 | 1.865999 | 1.73309 | −2.07799 | 0.078839 | 0.105148 | 0.083813 | 0.134267 |
| 0.220823 | 0.176288 | 0.216255 | 0.203314 | −1.89245 | 0.028608 | 0.026469 | 0.024979 | 0.023642 |
| 0.043399 | 0.384291 | 0.493511 | 0.523595 | −1.66902 | 0.00511 | 0.000906 | 0.002576 | 0.000298 |
| 10.97834 | 12.98714 | 9.062075 | 11.28311 | −0.26175 | 0.518308 | 0.001542 | 1.262452 | 0.011573 |
| 3.563971 | 4.015834 | 1.599519 | 2.311247 | −0.54529 | 0.564824 | 0.005621 | 0.091205 | 0.017404 |
| 0.017963 | 0.020404 | 0.006834 | 0.003748 | −0.13792 | 3.872417 | 0.000965 | 1.090387 | 0.002228 |
| 2.580228 | 5.563864 | 3.729195 | 3.992086 | 0.023157 | 3.947473 | 0.001876 | 1.162928 | 0.006578 |
| 4.709729 | 5.563864 | 4.637099 | 2.913895 | 0.664399 | 0.117603 | 0.366653 | 0.032688 | 0.013705 |
| 3.834354 | 8.009405 | 4.064076 | 0.982023 | 0.251487 | 0.26651 | 2.308404 | 0.029132 | 0.014106 |

TABLE 17-continued

2-Hexane-2

| | | | | | | | | |
|---|---|---|---|---|---|---|---|---|
| 0.038124 | 0.080646 | 0.004228 | 0.023119 | 0.750877 | 0.268839 | 0.377079 | 0.003182 | 0.006546 |
| 3.582007 | 2.726379 | 2.844402 | 3.482898 | 1.023539 | 0.511662 | 0.603021 | 0.003401 | 0.009215 |
| 12.21304 | 17.21671 | 23.47446 | 13.79327 | −1.26384 | 0.079026 | 0.0772 | 0.181809 | 0.084671 |
| 2.688933 | 3.470387 | 5.345779 | 2.274966 | −2.37388 | 0.053442 | 0.085934 | 0.027982 | 0.055148 |
| 0.026756 | 0.018193 | 0.152878 | 9.26E−05 | −1.91124 | 0.001355 | 0.000142 | 0.021781 | 0.00178 |
| 1.030482 | 1.523946 | 2.183425 | 1.322902 | −1.79823 | 0.001088 | 1.7E−06 | 0.015277 | 0.001159 |
| 0.897443 | 0.779227 | 0.338854 | 1.625106 | −1.23493 | 0.070126 | 0.021948 | 0.086333 | 0.142521 |
| 0.23255 | 1.39E−05 | 0.317963 | 1.025193 | −1.94974 | 0.025689 | 0.158275 | 0.02959 | 0.000553 |
| 0.039323 | 0.002996 | 0.024634 | 0.101204 | −1.26602 | 0.00305 | 0.015232 | 0.001025 | 0.017531 |
| 0.718755 | 1.31412 | 0.067642 | 0.624517 | −1.38239 | 0.001358 | 0.003411 | 0.00565 | 0.024021 |
| 211.4847 | 190.4055 | 201.0921 | 180.9433 | 2.635391 | 0.561074 | 0.302447 | 0.248735 | 0.35906 |
| 8.352239 | 9.051261 | 10.82429 | 5.255337 | 1.187858 | 0.025689 | 0.016469 | 0.02205 | 0.013508 |
| 2.711077 | 3.541182 | 4.913497 | 3.595774 | 1.311276 | 0.224269 | 0.090226 | 0.061488 | 0.110606 |
| 2.985419 | 18.55378 | 13.79569 | 27.12276 | 1.573049 | 0.300553 | 0.05027 | 0.035365 | 0.072182 |
| 6.448356 | 4.646214 | 7.00421 | 5.830185 | −3.02483 | 6.919555 | 21.88471 | 8.425787 | 7.134224 |
| 0.19122 | 0.244123 | 1.003801 | 0.430925 | 2.227115 | 1.04275 | 2.151119 | 0.448834 | 0.738912 |
| 0.001495 | 0.006938 | 0.072616 | 0.007572 | 2.675935 | 0.29891 | 2.703331 | 0.414309 | 0.302974 |
| 2.20644 | 1.081613 | 0.314607 | 1.075022 | 3.094332 | 0.331795 | 3.040944 | 0.618853 | 0.439582 |
| 9.668038 | 10.85278 | 7.101573 | 11.41568 | −0.41763 | 0.051139 | 0.026481 | 0.016901 | 0.358555 |
| 2.835109 | 1.897051 | 3.819894 | 1.404515 | 0.816479 | 0.12219 | 0.048775 | 0.119396 | 0.02881 |
| 0.767248 | 1.225636 | 0.334307 | 1.39359 | 0.676227 | 0.000365 | 0.010272 | 0.000922 | 0.268068 |
| 2.734411 | 5.256358 | 0.46566 | 7.351175 | 0.34345 | 0.014244 | 0.02063 | 0.051914 | 0.076949 |
| 4.050461 | 1.542047 | 1.493124 | 1.724099 | −2.42562 | 1.93884 | 1.466504 | 1.551285 | 1.996432 |
| 0.653759 | 0.024609 | 0.035576 | 0.205593 | 0.424035 | 0.078435 | 0.100007 | 0.296942 | 0.080246 |
| 0.000671 | 0.26065 | 0.07811 | 0.731463 | 0.430596 | 0.065181 | 0.020795 | 0.003325 | 0.098478 |
| 0.366517 | 0.749389 | 1.662571 | 0.98422 | 2.09107 | 0.845441 | 0.628436 | 0.586037 | 0.774773 |

TABLE 18

2-Hexane-3

$(argY_{u,c} - argY_{g,ck} - \theta_{ug,k})^2 / \sigma_{\theta g,c}^2$

| | EtOH | | | | | Benzene | | | |
|---|---|---|---|---|---|---|---|---|---|
| $k_5$ | $k_1$ | $k_2$ | $k_3$ | $k_4$ | $k_5$ | $k_1$ | $k_2$ | $k_3$ | $k_4$ |
| 0.179399 | 0.750153 | 0.232555 | 0.950808 | 0.07239 | 0.183033 | 0.239404 | 0.109495 | 0.203328 | 0.175426 |
| 0.08551 | 0.180454 | 0.011396 | 0.200751 | 0.128767 | 0.140407 | 0.07379 | 0.04542 | 0.098406 | 0.089786 |
| 0.015244 | 0.368111 | 0.292465 | 0.524923 | 0.012179 | 0.040563 | 0.00574 | 0.001968 | 0.011363 | 0.000511 |
| 0.001714 | 0.409029 | 0.310139 | 0.507031 | 2.58E−05 | 0.048543 | 0.008625 | 0.001244 | 0.000381 | 0.001622 |
| 0.379544 | 0.538999 | 3.54666 | 0.331185 | 0.257535 | 0.3032 | 0.331646 | 0.715017 | 0.810018 | 0.271119 |
| 0.028137 | 0.057949 | 0.111074 | 0.15039 | 0.040243 | 0.100799 | 0.06059 | 0.669081 | 0.615287 | 0.105206 |
| 0.079559 | 0.016013 | 0.225311 | 0.00275 | 0.009666 | 0.003479 | 0.016949 | 0.022438 | 2.74828 | 0.006104 |
| 0.025807 | 0.019546 | 0.233881 | 0.001278 | 0.002806 | 7.43E−05 | 0.006763 | 0.015063 | 0.908768 | 1.71E−05 |
| 0.015104 | 0.000456 | 0.042783 | 0.023463 | 0.02871 | 0.041777 | 0.010997 | 0.086362 | 0.060821 | 0.039911 |
| 0.096066 | 0.63541 | 0.032298 | 0.017543 | 0.025324 | 0.052516 | 0.006969 | 0.081001 | 0.088912 | 0.037258 |
| 0.040826 | 0.001884 | 0.001037 | 0.00191 | 0.000791 | 0.000192 | 0.010129 | 0.016022 | 0.008713 | 0.00603 |
| 0.042015 | 0.03129 | 0.001701 | 0.002527 | 0.000589 | 0.002677 | 0.008374 | 0.000949 | 0.004311 | 0.000168 |
| 0.010485 | 0.013915 | 0.008453 | 0.0229 | 0.005447 | 0.182684 | 0.109112 | 0.013217 | 0.034167 | 0.023089 |
| 0.01808 | 0.032773 | 0.024159 | 0.037783 | 0.045363 | 0.527423 | 0.279738 | 0.095988 | 0.081959 | 0.034847 |
| 0.000644 | 0.000258 | 0.000185 | 0.000812 | 0.001246 | 0.323155 | 0.01195 | 0.009472 | 0.010067 | 0.000571 |
| 0.006837 | 0.001739 | 0.002008 | 0.000117 | 0.009029 | 2.615531 | 0.016983 | 0.013657 | 0.000669 | 0.000753 |
| 0.184395 | 0.086534 | 0.110397 | 0.132437 | 0.148274 | 0.080079 | 0.606778 | 0.346774 | 1.11971 | 1.169408 |
| 0.020801 | 0.051313 | 0.040276 | 0.082473 | 0.057129 | 0.049074 | 0.113741 | 0.001138 | 0.20602 | 0.14391 |
| 0.093505 | 0.001294 | 0.00199 | 4.91E−05 | 0.000622 | 0.001276 | 0.028485 | 0.000571 | 0.096459 | 0.005753 |
| 0.062126 | 0.000299 | 0.004639 | 0.002543 | 0.009053 | 0.000147 | 0.066113 | 0.171299 | 0.196651 | 0.024067 |
| 0.197061 | 0.117392 | 0.061693 | 0.085646 | 0.01351 | 0.035737 | 0.017908 | 0.087349 | 0.026242 | 0.667148 |
| 0.009227 | 0.056884 | 0.060228 | 0.080284 | 0.048822 | 0.153913 | 0.031769 | 0.099452 | 0.043589 | 1.193829 |
| 0.010914 | 0.003572 | 0.005497 | 0.008329 | 0.018179 | 0.004812 | 0.005067 | 0.006098 | 0.014024 | 0.794928 |
| 0.033119 | 0.023156 | 0.005854 | 0.009746 | 0.00137 | 0.011269 | 0.005386 | 0.021103 | 0.019412 | 1.096529 |
| 0.419683 | 0.242453 | 0.234839 | 0.280356 | 0.109149 | 0.248383 | 0.434557 | 0.171302 | 0.304943 | 0.388476 |
| 0.034265 | 0.062084 | 0.037831 | 0.013285 | 0.06964 | 0.061813 | 0.043458 | 0.024907 | 0.059259 | 0.012327 |
| 0.093262 | 0.030799 | 0.026846 | 0.036331 | 0.026426 | 0.033181 | 0.014333 | 0.014346 | 0.030522 | 0.00477 |
| 0.073631 | 0.016803 | 0.039507 | 0.103235 | 0.006457 | 0.016999 | 0.099816 | 0.018848 | 0.020594 | 0.16577 |
| 6.296198 | 3.373968 | 3.437021 | 3.167328 | 8.250787 | 3.463599 | 2.552541 | 0.26648 | 2.041978 | 2.390614 |
| 0.586222 | 0.343804 | 0.245003 | 0.212681 | 0.659252 | 0.239995 | 0.053829 | 0.001093 | 0.021089 | 0.07781 |
| 0.286872 | 0.753958 | 0.612164 | 0.625596 | 1.463436 | 0.60022 | 0.249099 | 0.06286 | 0.243966 | 0.121541 |
| 0.387521 | 0.440616 | 0.737911 | 0.037711 | 1.561981 | 0.774202 | 0.302142 | 0.017134 | 0.25711 | 0.372953 |
| 0.007154 | 0.035847 | 0.06515 | 0.013177 | 1.86871 | 0.085544 | 3.165636 | 0.388631 | 0.644825 | 0.321593 |
| 0.039842 | 0.008549 | 0.004379 | 0.007464 | 0.848552 | 0.103471 | 0.130492 | 0.058404 | 0.072346 | 0.044504 |
| 0.000109 | 0.039304 | 0.057071 | 0.041821 | 0.859523 | 0.024119 | 0.106721 | 2.201418 | 0.143777 | 0.359624 |
| 0.013127 | 0.01643 | 0.002488 | 0.051098 | 0.484924 | 0.081298 | 0.010999 | 0.318059 | 0.020385 | 0.063479 |
| 1.84471 | 1.525538 | 1.495398 | 1.068241 | 3.148585 | 1.263089 | 6.558163 | 1.487264 | 4.948748 | 4.01668 |
| 0.289265 | 0.239697 | 0.198119 | 0.236779 | 0.028837 | 0.186153 | 0.045963 | 0.536385 | 0.30005 | 0.218694 |

TABLE 18-continued

2-Hexane-3

| | | | | | | | | | |
|---|---|---|---|---|---|---|---|---|---|
| 0.001922 | 0.000189 | 0.00046 | 0.002246 | 0.194082 | 0.001254 | 0.079348 | 0.013965 | 0.013143 | 0.006125 |
| 0.631382 | 0.425812 | 0.427047 | 0.184045 | 4.26819 | 0.322276 | 0.446476 | 0.000181 | 0.216067 | 0.200903 |

$(argY_{u,c} - argY_{g,ck} - \theta_{ug,k})^2/\sigma_{\theta g,c}^2$

| | Benzene | Hexane | | | | | AcOEt | | |
|---|---|---|---|---|---|---|---|---|---|
| | $k_5$ | $k_1$ | $k_2$ | $k_3$ | $k_4$ | $k_5$ | $k_1$ | $k_2$ | $k_3$ |
| | 0.743866 | 0.042717 | 0.47097 | 0.071572 | 1.281204 | 0.00022 | 0.219519 | 0.017553 | 0.535994 |
| | 0.088172 | 0.19688 | 0.074537 | 0.027137 | 0.040826 | 0.002211 | 0.135014 | 2.071371 | 0.140638 |
| | 2.914337 | 0.000682 | 0.052863 | 0.008491 | 0.171257 | 0.000496 | 0.007081 | 0.313334 | 0.319907 |
| | 0.119985 | 0.001185 | 0.28055 | 7.03E−08 | 0.254718 | 0.003463 | 0.001202 | 0.60155 | 3.990256 |
| | 1.357892 | 0.003872 | 0.589199 | 0.02565 | 0.033877 | 0.026371 | 2.278104 | 2.794074 | 2.374625 |
| | 0.158444 | 0.000991 | 2.032941 | 0.000622 | 0.00011 | 0.00239 | 1.813197 | 1.585787 | 1.173766 |
| | 0.005925 | 0.001049 | 0.328937 | 0.005808 | 0.014656 | 0.008886 | 0.056459 | 0.116429 | 0.10974 |
| | 0.154603 | 0.002209 | 0.354125 | 0.001054 | 0.002957 | 0.012609 | 0.017847 | 0.086407 | 0.108234 |
| | 0.003376 | 0.103894 | 0.123483 | 0.077659 | 1.622696 | 0.064683 | 0.010111 | 0.031453 | 0.003688 |
| | 0.007409 | 0.00144 | 0.004018 | 1.529756 | 0.134821 | 0.005526 | 0.093223 | 0.086402 | 0.351395 |
| | 0.000321 | 0.042133 | 0.013428 | 0.5655757 | 0.33616 | 0.010884 | 0.002249 | 0.001943 | 0.019074 |
| | 0.02257 | 0.028404 | 0.071421 | 0.671054 | 0.319609 | 0.015226 | 0.010973 | 0.00127 | 0.074726 |
| | 0.019564 | 0.128593 | 0.042404 | 1.49615 | 0.716239 | 2.22851 | 0.009194 | 0.03643 | 0.018903 |
| | 0.070291 | 0.021696 | 0.001895 | 0.152701 | 1.324418 | 0.230682 | 0.079314 | 0.12009 | 0.062165 |
| | 0.003843 | 0.009027 | 0.002127 | 0.104975 | 0.688265 | 0.130018 | 0.00168 | 0.001666 | 0.000883 |
| | 0.006743 | 0.003503 | 0.005932 | 0.088228 | 0.699107 | 0.154435 | 0.025054 | 0.015732 | 0.008044 |
| | 2.390795 | 0.046074 | 0.02416 | 0.068416 | 1.457221 | 0.09578 | 0.12521 | 0.256525 | 0.136312 |
| | 0.590844 | 1.345731 | 0.018015 | 0.011412 | 4.098826 | 0.00565 | 0.076958 | 0.052897 | 0.057118 |
| | 0.031673 | 0.001043 | 0.202273 | 0.183457 | 3.454114 | 0.023699 | 2.2E−05 | 0.172645 | 0.000238 |
| | 0.036905 | 0.001128 | 0.001866 | 0.33221 | 1.343539 | 0.739977 | 1.32E−06 | 1.247325 | 0.001697 |
| | 0.036797 | 3.190026 | 0.020291 | 0.039185 | 0.011206 | 1.05118 | 0.034172 | 0.011181 | 0.019844 |
| | 0.131655 | 0.561572 | 0.016281 | 0.059392 | 0.092637 | 0.154338 | 0.01345 | 0.008398 | 0.053195 |
| | 0.017237 | 0.098812 | 0.008925 | 0.08525 | 0.03532 | 0.036175 | 0.001287 | 0.004086 | 0.008466 |
| | 0.000551 | 0.268177 | 0.007286 | 0.016282 | 0.127049 | 0.104114 | 0.01176 | 0.006532 | 5.28E−05 |
| | 0.220561 | 0.205582 | 0.205992 | 0.021196 | 1.39281 | 0.153711 | 1.168217 | 0.258909 | 0.291192 |
| | 0.108838 | 0.012454 | 0.013721 | 0.009354 | 0.129629 | 0.002472 | 0.055563 | 0.022939 | 0.066515 |
| | 0.011511 | 0.017475 | 0.038738 | 0.003744 | 0.133801 | 0.013539 | 0.229529 | 0.017361 | 0.026083 |
| | 0.003518 | 0.029017 | 0.01047 | 0.000357 | 0.128882 | 0.035229 | 2.581065 | 0.040395 | 0.011623 |
| | 2.607097 | 2.782051 | 0.848258 | 1.04763 | 3.183029 | 3.462108 | 1.798425 | 0.139805 | 1.79208 |
| | 0.097115 | 0.228827 | 0.441239 | 1.882159 | 0.28228 | 0.215296 | 0.114573 | 1.964713 | 0.172772 |
| | 0.239893 | 0.3212 | 0.386134 | 0.250548 | 0.584624 | 0.065608 | 0.198948 | 0.268809 | 0.288744 |
| | 0.242532 | 0.326193 | 2.23325 | 0.002894 | 0.25914 | 1.391381 | 0.236528 | 0.130669 | 0.110338 |
| | 1.123981 | 0.255434 | 0.088956 | 0.420466 | 0.397757 | 1.200697 | 0.090322 | 1.407035 | 0.07915 |
| | 0.027281 | 0.006564 | 0.10697 | 0.186056 | 0.298513 | 0.251836 | 0.026893 | 0.696457 | 0.013476 |
| | 0.225509 | 0.09637 | 0.040258 | 0.047006 | 0.044083 | 1.504826 | 0.030808 | 1.274177 | 0.011836 |
| | 5.01E−06 | 0.035867 | 0.052463 | 0.000739 | 0.01447 | 0.483144 | 0.017565 | 1.510669 | 0.000259 |
| | 1.947261 | 0.336999 | 0.293618 | 2.873498 | 3.943202 | 0.007973 | 1.488951 | 1.576771 | 6.159357 |
| | 0.200497 | 0.309169 | 0.199239 | 0.273215 | 0.444477 | 0.023008 | 0.161909 | 0.061905 | 0.266134 |
| | 0.072104 | 0.192417 | 0.861476 | 0.002466 | 0.004099 | 0.1221 | 0.003978 | 0.004446 | 0.220157 |
| | 0.012946 | 0.045522 | 2.17648 | 0.214153 | 0.239956 | 0.012357 | 0.327436 | 1.773864 | 1.258361 |

TABLE 19

2-Hexane-4

| | | THF | | | | | $Log\sigma_{Lg,c}$ | | |
|---|---|---|---|---|---|---|---|---|---|
| $k_4$ | $k_5$ | $k_1$ | $k_2$ | $k_3$ | $k_4$ | $k_5$ | $H_2O$ | EtOH | Benzene |
| 0.418089 | 0.303623 | 3.15E−05 | 0.80777 | 0.159332 | 0.193062 | 0.106345 | −0.27945 | 0.398827 | −0.12502 |
| 0.177475 | 0.071863 | 0.551814 | 0.126236 | 0.037658 | 0.108145 | 0.063024 | −0.0226 | 0.248584 | −0.25239 |
| 0.002548 | 0.006784 | 0.353477 | 0.122339 | 0.006588 | 0.004278 | 0.002434 | −0.55571 | 0.239137 | −0.39623 |
| 0.019943 | 0.029937 | 9.049262 | 0.216355 | 0.07752 | 0.00761 | 0.002184 | −0.53188 | −0.1312 | −0.52282 |
| 2.274266 | 2.19335 | 0.129135 | 0.225281 | 0.00488 | 0.284127 | 0.133167 | −0.7076 | −0.13743 | 0.044038 |
| 0.870435 | 1.083165 | 0.299597 | 0.548045 | 4.05891 | 1.353762 | 0.371794 | −0.42382 | −0.15439 | −0.11099 |
| 0.14025 | 0.124997 | 0.001156 | 0.001191 | 0.263014 | 0.921886 | 0.001083 | −0.42179 | −0.09534 | 0.33566 |
| 0.155818 | 0.079568 | 0.01553 | 0.002804 | 0.287987 | 0.81594 | 0.00124 | −0.40275 | 0.48128 | 0.175373 |
| 0.024328 | 0.016014 | 0.00102 | 0.071052 | 0.147469 | 0.010189 | 0.20091 | −0.91872 | −0.22917 | −0.95407 |
| 0.049637 | 0.022623 | 0.432584 | 0.515745 | 0.564302 | 0.062615 | 0.5773 | −0.17315 | −0.39424 | −0.01421 |
| 0.006044 | 0.000353 | 0.040784 | 0.028238 | 0.023242 | 0.000158 | 0.012865 | −0.83614 | −0.65358 | −0.29561 |
| 0.000932 | 6.37E−05 | 0.249234 | 0.142069 | 0.100782 | 0.028423 | 0.092573 | −0.6724 | −1.1222 | 0.043835 |
| 0.018713 | 0.044785 | 0.03343 | 0.020949 | 0.043823 | 0.056608 | 0.025295 | 0.371859 | −0.99151 | −0.41346 |
| 0.057973 | 0.08744 | 0.275266 | 0.156907 | 0.266449 | 0.641899 | 0.167824 | −0.16865 | −1.23994 | −0.55346 |
| 0.001145 | 0.002252 | 0.001995 | 0.002191 | 0.0054 | 0.015442 | 0.002571 | −0.0813 | −1.29443 | −0.40318 |
| 0.005894 | 0.001631 | 0.04331 | 0.018951 | 0.021469 | 0.0923 | 0.017113 | 0.04032 | −1.12337 | −0.28638 |
| 0.162619 | 2.635977 | 0.220245 | 0.193549 | 0.239491 | 0.242775 | 0.180144 | 0.191785 | −0.22819 | −0.94597 |

TABLE 19-continued

2-Hexane-4

| | | | | | | | | |
|---|---|---|---|---|---|---|---|---|
| 0.03145 | 0.077521 | 0.25512 | 0.356836 | 0.242305 | 0.406887 | 0.112902 | −0.11037 | −0.07316 | −1.25623 |
| 0.00065 | 0.274791 | 8.6E−06 | 0.000101 | 8.19E−06 | 0.000912 | 0.000693 | −0.54554 | −0.75784 | −0.37232 |
| 0.015553 | 0.26469 | 0.000284 | 0.012652 | 0.000512 | 0.006363 | 0.005525 | −0.54083 | −0.73936 | −0.23667 |
| 0.008087 | 0.016503 | 0.063285 | 0.102624 | 0.221877 | 0.002348 | 0.069781 | −1.05253 | −1.09551 | −0.50347 |
| 0.028384 | 0.016673 | 0.094905 | 0.122483 | 0.175481 | 0.004668 | 0.074044 | −1.54088 | −1.18116 | −0.45473 |
| 0.005453 | 0.00732 | 0.01169 | 0.014623 | 0.014675 | 0.005868 | 0.13516 | −0.16437 | −1.13825 | −0.67257 |
| 1.23E−06 | 0.007845 | 0.000156 | 0.000214 | 0.005208 | 0.001765 | 0.002154 | −0.59311 | −1.11749 | −0.54994 |
| 0.247345 | 0.325601 | 0.119062 | 0.718601 | 0.118986 | 0.183616 | 0.140452 | −0.791 | −0.48094 | −0.13148 |
| 0.107825 | 0.065661 | 0.032728 | 0.028135 | 0.037613 | 0.166168 | 0.074745 | −0.30458 | −0.04454 | −1.15475 |
| 0.016381 | 0.026572 | 0.011136 | 0.140801 | 0.011701 | 0.003443 | 0.013664 | −0.14548 | −0.29639 | −0.3181 |
| 0.001487 | 0.018374 | 0.011167 | 0.172571 | 0.008071 | 0.000564 | 0.001283 | −0.15455 | −0.13279 | −0.21329 |
| 1.755535 | 1.669188 | 2.169666 | 1.790579 | 1.950328 | 1.82452 | 2.003645 | −0.62735 | 0.089626 | −0.60433 |
| 0.05177 | 0.094807 | 0.057481 | 0.051625 | 0.024295 | 0.015009 | 0.049545 | −0.90372 | −0.23395 | −0.70282 |
| 0.192524 | 0.21514 | 0.27698 | 0.360704 | 0.287804 | 0.376238 | 0.273421 | −0.75676 | −0.16047 | 0.069012 |
| 0.328176 | 0.203904 | 0.326758 | 0.162084 | 0.333649 | 0.252757 | 0.293497 | −0.97667 | 0.048629 | −0.20526 |
| 0.21418 | 0.238597 | 0.112289 | 0.365694 | 0.10691 | 0.565713 | 0.12424 | −0.10314 | −0.45305 | −0.63388 |
| 0.828828 | 0.011809 | 0.002616 | 0.044358 | 0.028801 | 0.47207 | 8.36E−09 | −0.20565 | −0.12083 | 0.069844 |
| 0.504543 | 0.048919 | 0.086607 | 0.076314 | 0.092781 | 0.10322 | 0.167223 | −0.25904 | 0.189343 | 0.446272 |
| 0.781453 | 0.00384 | 0.015531 | 0.027246 | 0.055237 | 0.057508 | 0.001585 | −0.1905 | 0.489136 | 0.408102 |
| 1.592497 | 2.050102 | 1.116489 | 1.502178 | 0.848174 | 1.161664 | 0.70444 | −0.18367 | −1.36604 | −0.93406 |
| 0.244029 | 0.113612 | 0.234011 | 1.887767 | 0.414447 | 0.219858 | 0.121805 | −0.53828 | 0.228993 | −0.9417 |
| 0.010443 | 0.000918 | 6.93E−05 | 0.072211 | 0.06018 | 0.000347 | 0.020033 | −0.16197 | 0.020417 | −1.34016 |
| 0.234327 | 0.703791 | 0.330705 | 0.122579 | 1.071862 | 0.353479 | 0.724927 | −0.17728 | 0.066696 | −1.43918 |

| Logσ$_{Lg,c}$ | | | Logσ$_{\theta g,c}$ | | | | | |
|---|---|---|---|---|---|---|---|---|
| Hexane | AcOEt | THF | H$_2$O | EtOH | Benzene | Hexane | AcOEt | THF |
| −0.55113 | 0.32871 | −0.08107 | 0.801234 | 1.207714 | 1.079374 | 0.189762 | 0.866507 | 1.150356 |
| −0.32497 | −0.10168 | 0.215972 | 0.729341 | 0.669981 | 1.252097 | 0.229623 | 0.939489 | 1.183314 |
| −0.61155 | 0.447759 | −0.12574 | 0.714165 | 0.547871 | 0.999054 | 0.229044 | 1.090265 | 1.080704 |
| −0.89179 | 0.355916 | −0.55732 | 0.722126 | 0.465178 | 1.117856 | 0.1627 | 0.785955 | 0.3326 |
| −0.64421 | −1.19739 | −0.06096 | 0.5606 | 0.605007 | 0.795256 | 0.743116 | −0.2618 | 1.272964 |
| −1.14907 | −1.08912 | −0.0579 | 0.53307 | 0.957349 | 1.134892 | 1.126902 | −0.39762 | 0.636763 |
| −1.22368 | −1.29606 | −0.19802 | 0.576843 | 0.985589 | 0.696795 | 0.874959 | −0.37434 | 1.23767 |
| −1.11758 | −1.11766 | −0.44338 | 0.594635 | 0.995586 | 1.106001 | 0.863036 | −0.35685 | 1.205117 |
| −0.36169 | −0.08808 | −0.54633 | 1.378727 | 0.870049 | 0.844553 | 1.15028 | 0.84218 | 0.01585 |
| −0.13507 | 0.117575 | −0.50368 | 1.295079 | 0.951724 | 0.980232 | 1.301856 | 0.750527 | 0.170075 |
| −0.0715 | 0.061467 | −0.58296 | 0.44318 | 0.974456 | 0.722887 | 0.901578 | 0.99287 | 0.046107 |
| −0.11942 | 0.057921 | −0.63334 | 0.472307 | 1.012596 | 0.702096 | 0.794673 | 1.032039 | 0.070549 |
| −0.38187 | −0.37755 | −0.48677 | 0.961814 | 1.035338 | 0.756087 | 0.997163 | 0.862225 | 0.689656 |
| −0.28183 | −0.55965 | −1.19113 | 1.01892 | 1.0191 | 0.857216 | 1.099827 | 0.859037 | 0.505935 |
| −0.17188 | −0.38782 | −0.72924 | 0.654436 | 1.034736 | 0.789613 | 1.216736 | 0.834254 | 0.678971 |
| 0.033897 | −0.15015 | −0.82075 | 0.619903 | 1.091146 | 0.840677 | 1.260704 | 0.774444 | 0.696334 |
| −1.15407 | 0.02776 | −0.90701 | 1.044944 | 0.990337 | −0.16622 | 0.883427 | 0.852136 | 0.731865 |
| −0.34122 | 0.011325 | −0.71451 | 0.951797 | 1.037002 | 0.532775 | −0.79673 | 1.082475 | 0.682279 |
| −0.33503 | 0.564229 | −0.99709 | 1.059034 | 1.038236 | 0.205231 | −0.45793 | 1.088727 | 0.735329 |
| −0.51182 | 0.321599 | −0.41743 | 1.050676 | 1.089144 | 0.128321 | −0.33163 | 1.021132 | 0.783396 |
| 0.125804 | −0.91843 | −0.05209 | 0.658551 | 0.717663 | 1.123837 | 0.642526 | 1.106472 | 0.682546 |
| −0.12365 | −0.52523 | −0.15205 | 0.594566 | 0.691442 | 0.946736 | 0.738585 | 1.084102 | 0.904087 |
| −0.61878 | −1.01393 | −0.17641 | 0.879033 | 0.762743 | 1.111363 | 0.709606 | 1.104812 | 0.776997 |
| −0.24084 | −1.39596 | −0.26371 | 0.860382 | 0.844861 | 0.831881 | 0.830535 | 1.095595 | 0.802764 |
| −0.8441 | −1.78544 | −1.54092 | 0.909549 | 0.899793 | 0.836804 | 0.622138 | 0.59432 | 1.315317 |
| −1.10002 | −0.25395 | −0.86242 | 0.906718 | 0.842321 | 0.733571 | 0.646614 | 0.880259 | 1.176445 |
| −1.07174 | −0.91017 | −1.11347 | 0.706513 | 0.779633 | 0.822822 | 0.725209 | 0.912419 | 1.213009 |
| −0.67837 | −0.81836 | −1.39507 | 0.671983 | 0.65589 | 0.947994 | 0.74445 | 1.008622 | 1.180359 |
| −0.2829 | −0.47458 | −0.25747 | 0.40447 | 0.757171 | 0.997815 | 0.85769 | 1.104346 | 0.999825 |
| −0.41213 | −0.27044 | 0.204271 | 0.071537 | 0.602741 | 1.225844 | 0.825294 | 1.052402 | 1.112113 |
| −0.27628 | −0.31088 | 0.087425 | 0.907564 | 0.618479 | 1.213651 | 0.576452 | 1.166429 | 1.023458 |
| 0.111701 | −0.27363 | −0.07046 | 0.950403 | 0.619702 | 1.220683 | 1.165549 | 1.218396 | 1.152418 |
| 0.038614 | 0.083506 | −0.32954 | 0.634833 | 0.739149 | −0.20836 | 0.812456 | 0.535362 | 0.228705 |
| −0.15347 | 0.56292 | −0.3326 | 0.551091 | 0.864869 | 0.855276 | 0.850432 | 0.930297 | 0.188121 |
| −0.10431 | 0.630582 | −0.87208 | 0.582188 | 0.645764 | 0.006498 | 0.60461 | 0.689769 | 0.163691 |
| −0.21624 | 0.388878 | −0.91419 | 0.584172 | 0.480962 | 0.931221 | 0.69898 | 0.643733 | 0.089592 |
| 0.227763 | 0.666495 | 0.047935 | 0.768615 | 0.7843 | 0.198057 | 0.592487 | 0.754077 | 0.893002 |
| 0.117962 | 0.073392 | 0.670118 | 0.838437 | 0.813008 | 0.568256 | 1.022759 | 0.875654 | 0.682508 |
| 0.391301 | 0.158097 | 0.439682 | 0.583124 | 0.702989 | 0.698545 | 0.987988 | 0.695158 | 0.95815 |
| −0.00175 | −0.09715 | −0.05799 | 0.699085 | 0.915385 | 1.181083 | 1.161702 | 0.945869 | 1.024418 |

TABLE 20

2-AcOEt-1

| | | $\log|Y_{u,c}|$ | $(\log|Y_{u,c}|-\log|Y_{g,ck}|-L_{ug,k})^2/\sigma_{Lg,c}^2$ | | | | | | | |
|---|---|---|---|---|---|---|---|---|---|---|
| | | AcOEt | H$_2$O | | | | | EtOH | | |
| f | c | k$_5$ | k$_1$ | k$_2$ | k$_3$ | k$_4$ | k$_5$ | k$_1$ | k$_2$ | k$_3$ |
| 0.05 Hz | Ch. 1 | 2.105285 | 0.006185 | 0.001958 | 0.013476 | 0.008493 | 0.023089 | 0.152093 | 0.46514 | 0.123139 |
| | Ch. 2 | 3.772776 | 0.312171 | 0.248014 | 0.018877 | 0.084576 | 0.31573 | 0.203733 | 0.138661 | 0.133009 |
| | Ch. 3 | −0.49463 | 1.030896 | 1.050222 | 0.373313 | 0.560645 | 0.951641 | 0.000989 | 8.16E−05 | 0.003353 |
| | Ch. 4 | −1.50388 | 0.026531 | 0.013221 | 0.267893 | 0.133808 | 0.045405 | 0.002328 | 0.393638 | 0.000435 |
| 0.1 Hz | Ch. 1 | 1.093515 | 1.262077 | 0.640562 | 1.251899 | 1.008217 | 1.581763 | 0.025044 | 0.022547 | 0.002903 |
| | Ch. 2 | 3.6045 | 0.44577 | 0.074671 | 0.017929 | 0.011614 | 0.011435 | 0.309158 | 0.140507 | 0.079677 |
| | Ch. 3 | −0.74179 | 1.29146 | 0.667245 | 0.683225 | 0.596392 | 0.750948 | 0.045739 | 0.000942 | 0.005742 |
| | Ch. 4 | −1.59828 | 0.134663 | 0.003154 | 0.021023 | 0.007757 | 0.033006 | 0.070558 | 0.071976 | 0.019355 |
| 0.15 Hz | Ch. 1 | 0.938779 | 1.403216 | 0.155106 | 2.851129 | 0.511113 | 0.407159 | 0.022519 | 0.001387 | 0.008531 |
| | Ch. 2 | 3.656626 | 4.28E−05 | 0.002504 | 0.004621 | 1.155216 | 0.028916 | 7.81E−05 | 0.08265 | 0.060041 |
| | Ch. 3 | −0.9968 | 2.276937 | 1.691976 | 2.421575 | 0.042915 | 1.238785 | 0.00377 | 0.00014 | 0.001988 |
| | Ch. 4 | −2.25787 | 0.118547 | 0.509804 | 0.012817 | 1.92588 | 0.52747 | 0.233236 | 0.273791 | 0.646844 |
| 0.2 Hz | Ch. 1 | 1.397561 | 0.010222 | 0.182515 | 0.002027 | 0.017027 | 0.023115 | 1.714898 | 0.771448 | 0.778394 |
| | Ch. 2 | 3.721616 | 0.987961 | 0.048004 | 0.029092 | 0.104132 | 0.095822 | 1.392085 | 1.604222 | 1.118623 |
| | Ch. 3 | −0.74977 | 0.316181 | 0.000357 | 0.178097 | 0.291234 | 0.295524 | 0.255475 | 0.054338 | 0.048229 |
| | Ch. 4 | −1.63469 | 0.028144 | 0.188459 | 0.029781 | 0.001172 | 0.000338 | 0.000328 | 0.103389 | 0.014335 |
| 0.25 Hz | Ch. 1 | 2.155453 | 0.071798 | 0.044474 | 0.16052 | 0.053309 | 0.141503 | 0.250377 | 0.017783 | 0.09562 |
| | Ch. 2 | 4.70544 | 0.29349 | 0.017588 | 0.126947 | 0.002363 | 0.001686 | 0.027211 | 0.066156 | 0.058694 |
| | Ch. 3 | 0.193501 | 1.750314 | 0.419674 | 1.727788 | 0.565346 | 0.003757 | 0.003354 | 7.06E−09 | 0.000204 |
| | Ch. 4 | −0.85944 | 0.005456 | 0.168089 | 0.005518 | 0.117481 | 0.822259 | 0.208164 | 0.077465 | 0.001441 |
| 0.3 Hz | Ch. 1 | 1.234063 | 1.626711 | 0.633083 | 1.177099 | 1.288784 | 0.675999 | 1.268646 | 0.357423 | 0.701079 |
| | Ch. 2 | 3.657786 | 27.28305 | 2.0882 | 0.393486 | 2.064934 | 1.717375 | 2.735947 | 1.548652 | 2.175645 |
| | Ch. 3 | −0.67027 | 2.304119 | 0.421091 | 0.377416 | 0.550286 | 0.421203 | 0.020071 | 0.002421 | 0.01275 |
| | Ch. 4 | −1.54843 | 0.249692 | 0.004409 | 0.000218 | 0.018263 | 0.000952 | 0.068596 | 0.365712 | 0.174321 |
| 0.35 Hz | Ch. 1 | 1.211129 | 0.105785 | 1.319757 | 1.351339 | 0.005141 | 0.174776 | 0.409915 | 0.755367 | 0.418693 |
| | Ch. 2 | 3.719332 | 0.917592 | 1.228511 | 0.116486 | 0.447808 | 0.041946 | 0.141014 | 0.17711 | 0.112516 |
| | Ch. 3 | −0.79566 | 0.692462 | 0.006173 | 0.719083 | 0.003289 | 0.10846 | 0.003511 | 0.001812 | 0.046582 |
| | Ch. 4 | −1.7609 | 0.024598 | 0.18091 | 0.002828 | 0.451273 | 0.082589 | 7.16E−05 | 0.013871 | 0.008614 |
| 0.4 Hz | Ch. 1 | −0.21043 | 2.14E−05 | 2.249274 | 0.137738 | 0.047039 | 0.000142 | 0.062997 | 0.266102 | 0.331431 |
| | Ch. 2 | 1.848274 | 4.23724 | 0.522353 | 1.214209 | 1.30402 | 1.811685 | 0.40833 | 0.197441 | 0.687069 |
| | Ch. 3 | −2.54036 | 2.820677 | 0.015059 | 2.213524 | 0.834894 | 1.61177 | 0.144043 | 0.018519 | 0.003651 |
| | Ch. 4 | −3.49997 | 0.013248 | 2.255832 | 0.0202 | 0.047382 | 0.022761 | 0.278922 | 0.008476 | 0.005489 |
| 0.45 Hz | Ch. 1 | 0.45099 | 0.523058 | 0.448055 | 0.811285 | 0.313696 | 0.564309 | 0.021651 | 0.036762 | 0.001875 |
| | Ch. 2 | 3.447455 | 0.318731 | 0.016099 | 0.087392 | 0.02046 | 0.228643 | 0.069368 | 0.01661 | 0.042732 |
| | Ch. 3 | −1.14321 | 0.868926 | 0.308849 | 0.881225 | 0.329829 | 1.374294 | 0.00099 | 0.001789 | 0.00628 |
| | Ch. 4 | −1.80536 | 0.225536 | 0.007495 | 0.158054 | 0.046587 | 0.038459 | 0.050074 | 0.012865 | 0.035315 |
| 0.5 Hz | Ch. 1 | 0.76566 | 0.020734 | 0.046305 | 0.002854 | 0.095097 | 0.006244 | 5.847264 | 3.298382 | 4.608012 |
| | Ch. 2 | 3.013299 | 2.141556 | 0.789753 | 0.714684 | 1.693468 | 0.691687 | 0.05735 | 0.106779 | 0.072666 |
| | Ch. 3 | −1.30108 | 0.802206 | 0.485419 | 0.495857 | 0.713628 | 0.55606 | 1.24E−05 | 0.000967 | 0.006146 |
| | Ch. 4 | −2.22124 | 0.003935 | 0.011542 | 0.008125 | 0.108041 | 0.074629 | 0.085296 | 0.006206 | 0.014492 |

| | | $(\log|Y_{u,c}|-\log|Y_{g,ck}|-L_{ug,k})^2/\sigma_{Lg,c}^2$ | | | | | | |
|---|---|---|---|---|---|---|---|---|
| | | EtOH | | Benzene | | | | |
| f | c | k$_4$ | k$_5$ | k$_1$ | k$_2$ | k$_3$ | k$_4$ | k$_5$ | k$_1$ |
| 0.05 Hz | Ch. 1 | 0.210445 | 0.144671 | 2.127427 | 0.772307 | 1.65405 | 1.536843 | 3.15583 | 5.191035 |
| | Ch. 2 | 0.251725 | 0.206056 | 0.12327 | 0.125582 | 0.038805 | 0.06448 | 0.371291 | 1.561086 |
| | Ch. 3 | 0.00244 | 0.00101 | 0.88914 | 0.852057 | 1.426985 | 0.990616 | 0.618034 | 0.002567 |
| | Ch. 4 | 0.000658 | 0.004024 | 0.410676 | 0.525522 | 0.667179 | 0.146655 | 0.909289 | 0.871851 |
| 0.1 Hz | Ch. 1 | 0.029756 | 0.432289 | 0.369648 | 0.00821 | 0.606187 | 0.460989 | 0.815266 | 1.77686 |
| | Ch. 2 | 0.188954 | 1.372516 | 0.067972 | 0.344941 | 0.345135 | 0.145836 | 0.716842 | 1.931024 |
| | Ch. 3 | 0.005481 | 0.016037 | 0.081441 | 0.019428 | 0.033959 | 0.111452 | 0.018425 | 0.156064 |
| | Ch. 4 | 0.083012 | 1.199036 | 5.64E−08 | 0.039204 | 0.000637 | 0.006935 | 1.14E−05 | 1.319547 |
| 0.15 Hz | Ch. 1 | 0.018 | 0.295244 | 4.076431 | 11.2791 | 6.037229 | 6.61822 | 0.156437 | 0.224806 |
| | Ch. 2 | 0.030028 | 0.036587 | 0.019765 | 0.185442 | 0.165098 | 0.133545 | 0.002086 | 0.077187 |
| | Ch. 3 | 0.057433 | 0.028303 | 0.086412 | 0.258294 | 0.120522 | 0.135491 | 0.151796 | 0.065987 |
| | Ch. 4 | 0.092197 | 1.439673 | 0.161848 | 0.220713 | 0.07571 | 0.116563 | 0.007842 | 0.837442 |
| 0.2 Hz | Ch. 1 | 0.00038 | 1.424292 | 2.675025 | 2.200388 | 3.080134 | 3.537949 | 1.434207 | 1.395657 |
| | Ch. 2 | 0.947381 | 2.202054 | 1.972461 | 0.428961 | 1.145296 | 0.959143 | 1.180328 | 0.283911 |
| | Ch. 3 | 0.019982 | 0.002818 | 0.466042 | 0.480206 | 0.28377 | 0.199106 | 0.393931 | 0.043319 |
| | Ch. 4 | 0.525408 | 1.39E−05 | 0.058714 | 0.035428 | 0.063637 | 0.259734 | 0.112605 | 0.049072 |
| 0.25 Hz | Ch. 1 | 0.035687 | 0.307649 | 4.943233 | 2.258387 | 8.960333 | 9.456222 | 2.657993 | 3.579854 |
| | Ch. 2 | 0.031178 | 0.132565 | 1.471824 | 4.387446 | 6.792701 | 2.012938 | 4.035305 | 0.053943 |
| | Ch. 3 | 0.049784 | 0.384506 | 0.141591 | 0.109169 | 0.009165 | 0.13358 | 0.247022 | 0.031174 |
| | Ch. 4 | 0.193319 | 1.05032 | 0.107346 | 0.074139 | 0.379534 | 0.465058 | 0.127125 | 0.866139 |
| 0.3 Hz | Ch. 1 | 1.040713 | 0.846891 | 3.202611 | 1.323826 | 3.992484 | 4.212428 | 1.595043 | 0.576002 |
| | Ch. 2 | 2.01797 | 3.161548 | 0.529015 | 0.295075 | 2.296687 | 0.519625 | 0.593847 | 0.031615 |
| | Ch. 3 | 0.003443 | 0.000265 | 0.297245 | 0.360218 | 0.006831 | 0.457266 | 0.48971 | 0.139124 |
| | Ch. 4 | 0.120812 | 0.506574 | 0.350959 | 0.005917 | 0.124741 | 0.576108 | 0.02062 | 0.409032 |

TABLE 20-continued

| | | | | | | | | | |
|---|---|---|---|---|---|---|---|---|---|
| | | | | | 2-AcOEt-1 | | | | |
| 0.35 Hz | Ch. 1 | 0.116508 | 0.618588 | 2.58847 | 3.645309 | 1.753641 | 2.356071 | 1.200038 | 7.384823 |
| | Ch. 2 | 0.015997 | 0.108208 | 5.38357 | 4.594225 | 1.157887 | 9.75668 | 1.933781 | 1.587225 |
| | Ch. 3 | 0.001946 | 0.003053 | 0.104766 | 0.298229 | 0.241005 | 0.117761 | 0.23039 | 0.134682 |
| | Ch. 4 | 0.004274 | 0.022195 | 0.301966 | 0.553833 | 0.331013 | 0.019155 | 0.045881 | 1.509042 |
| 0.4 Hz | Ch. 1 | 1.175146 | 0.362328 | 6.542764 | 4.607388 | 6.069995 | 7.039175 | 6.817472 | 3.478451 |
| | Ch. 2 | 0.42248 | 0.408976 | 2.192987 | 6.520428 | 0.510289 | 1.751099 | 0.385897 | 0.172684 |
| | Ch. 3 | 0.013975 | 0.022795 | 0.050983 | 0.247521 | 0.177696 | 0.351535 | 0.176854 | 0.118236 |
| | Ch. 4 | 0.295408 | 0.000508 | 0.269109 | 0.29389 | 0.441073 | 0.03823 | 0.673883 | 0.60461 |
| 0.45 Hz | Ch. 1 | 2.46237 | 0.011235 | 0.169368 | 0.430643 | 2.351325 | 3.439631 | 2.743664 | 0.001985 |
| | Ch. 2 | 0.913865 | 0.121893 | 0.021871 | 0.655786 | 0.19141 | 0.211762 | 0.075275 | 0.206008 |
| | Ch. 3 | 0.123926 | 0.004626 | 0.054081 | 0.222256 | 0.004507 | 0.00601 | 0.039389 | 0.303394 |
| | Ch. 4 | 0.757294 | 0.009603 | 8.13E−05 | 0.110341 | 0.025351 | 0.060299 | 0.033303 | 0.005667 |
| 0.5 Hz | Ch. 1 | 9.790563 | 3.88851 | 8.875539 | 5.357882 | 14.4783 | 11.69194 | 5.576802 | 0.555092 |
| | Ch. 2 | 0.05668 | 0.084663 | 4.515616 | 2.174293 | 3.457904 | 6.561634 | 4.654963 | 0.044228 |
| | Ch. 3 | 0.072529 | 0.000431 | 1.338965 | 0.261083 | 1.596784 | 1.949713 | 0.045736 | 5.7E−05 |
| | Ch. 4 | 0.043927 | 0.011783 | 0.027145 | 0.716975 | 3.431096 | 0.00772 | 0.016681 | 0.474746 |

TABLE 21

2-AcOEt-2

$(\log|Y_{u,c}|-\log|Y_{g,ck}|-L_{ug,k})^2/\sigma_{Lg,c}^2$

| Hexane | | | | AcOEt | | | | | THF |
|---|---|---|---|---|---|---|---|---|---|
| $k_2$ | $k_3$ | $k_4$ | $k_5$ | $k_1$ | $k_2$ | $k_3$ | $k_4$ | $k_5$ | $k_1$ |
| 11.84223 | 8.859876 | 3.53849 | 9.949014 | 0.068019 | 0.025535 | 0.035718 | 0.00616 | 0.015212 | 0.000168 |
| 1.636498 | 1.776061 | 0.503902 | 1.985038 | 0.132839 | 0.002071 | 0.73826 | 0.017186 | 0.022584 | 0.303841 |
| 0.298886 | 0.070081 | 0.009749 | 0.094366 | 9.97E−05 | 0.016003 | 0.036472 | 0.005607 | 0.002835 | 0.129157 |
| 3.457774 | 2.205851 | 2.303698 | 2.385207 | 0.001164 | 0.002083 | 0.022635 | 0.005701 | 0.001118 | 0.438174 |
| 1.44626 | 2.119247 | 1.530982 | 3.719926 | 1.097397 | 0.537772 | 0.800781 | 0.657491 | 1.224173 | 0.241419 |
| 2.41964 | 3.007925 | 4.503 | 3.431013 | 0.023955 | 0.055339 | 0.004155 | 0.050332 | 2.98E−05 | 0.642218 |
| 0.111539 | 0.074437 | 0.145134 | 0.006055 | 0.01006 | 0.01003 | 0.000453 | 0.044203 | 0.045914 | 0.095034 |
| 0.523752 | 0.813355 | 0.0744 | 1.880842 | 0.795565 | 0.697893 | 0.550673 | 0.645886 | 0.700157 | 0.004104 |
| 8.519134 | 3.478909 | 4.547688 | 0.860644 | 0.011648 | 0.005849 | 0.165587 | 0.00353 | 0.003723 | 0.245954 |
| 0.838084 | 0.043754 | 0.213333 | 0.282056 | 0.172637 | 0.052932 | 0.233068 | 0.001245 | 0.018498 | 1.891195 |
| 0.065017 | 0.018072 | 0.024348 | 0.105195 | 0.002514 | 0.000111 | 0.000857 | 0.014824 | 0.005344 | 0.088552 |
| 1.258881 | 1.24749 | 1.110106 | 0.306835 | 0.088482 | 0.035599 | 0.036166 | 0.018517 | 0.027225 | 0.506398 |
| 4.252444 | 8.583467 | 1.415594 | 6.989034 | 0.036249 | 0.14788 | 0.007716 | 0.003375 | 2.58E−05 | 0.016084 |
| 0.354627 | 0.77576 | 0.351461 | 1.014502 | 0.004825 | 0.006178 | 0.067821 | 0.033004 | 0.464564 | 0.594953 |
| 0.059827 | 0.247614 | 0.012315 | 0.165422 | 0.019303 | 0.019191 | 0.004419 | 0.001447 | 0.002063 | 0.239633 |
| 0.52896 | 0.805845 | 0.196304 | 0.460757 | 1.61E−05 | 0.062149 | 0.024136 | 0.010886 | 0.234574 | 0.030018 |
| 5.102961 | 8.927839 | 22.63562 | 21.0864 | 0.001434 | 0.175072 | 0.005683 | 0.001196 | 0.000125 | 0.010293 |
| 0.000461 | 0.075021 | 0.234072 | 0.493885 | 0.023486 | 0.20246 | 0.005179 | 0.000507 | 0.000121 | 0.082978 |
| 0.119731 | 0.000529 | 0.078719 | 0.0525 | 0.002052 | 0.200291 | 9.2E−08 | 0.000844 | 0.000329 | 0.477866 |
| 2.646635 | 1.624547 | 2.54218 | 1.713337 | 0.006867 | 0.005095 | 1.45E−05 | 0.006292 | 0.000545 | 0.055381 |
| 2.685618 | 3.220537 | 0.24342 | 0.566624 | 0.008837 | 0.346539 | 0.053076 | 0.021297 | 0.080988 | 0.026803 |
| 0.601264 | 1.136604 | 0.056715 | 0.055797 | 0.036263 | 0.039537 | 0.320035 | 0.374822 | 0.047934 | 0.08782 |
| 0.360534 | 2.122885 | 0.051227 | 0.029688 | 0.065694 | 0.058769 | 0.002813 | 0.016062 | 0.122818 | 0.020966 |
| 1.169176 | 0.153862 | 0.359072 | 1.521846 | 0.964259 | 1.142198 | 2.705937 | 1.084584 | 0.219246 | 0.00084 |
| 17.68439 | 10.42275 | 7.151414 | 18.28557 | 0.992538 | 4.609955 | 0.592209 | 0.00387 | 0.222324 | 0.231434 |
| 1.510051 | 0.754089 | 1.764472 | 3.658476 | 0.156267 | 0.27888 | 0.018448 | 0.031524 | 0.000448 | 0.238495 |
| 0.931973 | 0.22475 | 0.376129 | 1.653104 | 0.004823 | 0.005966 | 0.01543 | 0.00492 | 3.94E−05 | 0.620119 |
| 4.433341 | 3.407189 | 0.96163 | 2.252542 | 0.144169 | 1.05E−06 | 0.212472 | 0.073912 | 0.044411 | 0.041649 |
| 3.030454 | 1.799637 | 1.320065 | 2.154491 | 0.235833 | 0.654057 | 0.596224 | 0.066434 | 0.456131 | 0.221199 |
| 0.341355 | 0.318549 | 0.532325 | 0.430775 | 0.00558 | 0.181206 | 0.608077 | 0.01955 | 0.285983 | 0.009457 |
| 0.206729 | 0.013832 | 0.256877 | 0.339868 | 0.003882 | 0.607426 | 0.002881 | 0.000738 | 0.023437 | 0.073381 |
| 0.268825 | 0.422023 | 0.744062 | 0.04203 | 0.068775 | 0.022935 | 0.040972 | 0.00197 | 0.017307 | 0.040351 |
| 0.778506 | 0.316841 | 0.23982 | 1.286198 | 0.075854 | 0.641946 | 0.063741 | 0.588849 | 0.005089 | 0.36775 |
| 0.17528 | 0.012455 | 0.000574 | 1.16E−08 | 0.00106 | 0.01305 | 0.000174 | 0.051224 | 0.002047 | 0.31496 |
| 0.043721 | 0.086038 | 0.040526 | 0.014928 | 0.000218 | 0.001199 | 0.000221 | 0.154138 | 0.00062 | 0.375442 |
| 0.210498 | 0.875163 | 0.691401 | 1.759696 | 0.033488 | 0.168375 | 0.048698 | 0.041563 | 0.019078 | 0.524371 |
| 0.014069 | 1.376082 | 0.778913 | 3.229588 | 0.009749 | 0.00127 | 0.524972 | 0.001702 | 0.00975 | 0.140896 |
| 0.000323 | 0.084351 | 0.023214 | 0.158873 | 0.011165 | 0.450346 | 0.263553 | 0.037051 | 0.222716 | 0.002168 |
| 0.287148 | 0.023455 | 0.001057 | 0.090037 | 0.011282 | 0.578154 | 0.118618 | 0.00124 | 0.02054 | 0.009956 |
| 0.851626 | 0.851032 | 0.973514 | 1.868457 | 0.002551 | 0.01191 | 0.251441 | 0.008889 | 0.026499 | 0.024571 |

| $(\log|Y_{u,c}|-\log|Y_{g,ck}|-L_{ug,k})^2/\sigma_{Lg,c}^2$ | | | | $\arg Y_{u,c}$ | | | | |
|---|---|---|---|---|---|---|---|---|
| THF | | | | AcOEt | $H_2O$ | | | |
| $k_2$ | $k_3$ | $k_4$ | $k_5$ | $k_5$ | $k_1$ | $k_2$ | $k_3$ | $k_4$ |
| 0.004825 | 0.002629 | 0.00207 | 0.031851 | −2.37737 | 0.004634 | 0.000419 | 0.018968 | 0.000148 |
| 0.901879 | 0.88901 | 0.273327 | 0.508808 | −2.15067 | 0.025561 | 0.078671 | 0.002293 | 0.042989 |

TABLE 21-continued

| 2-AcOEt-2 | | | | | | | | |
|---|---|---|---|---|---|---|---|---|
| 0.127401 | 0.312662 | 0.167439 | 0.199555 | −2.56138 | 0.011144 | 0.021046 | 0.013419 | 0.013832 |
| 1.950038 | 1.599512 | 0.184542 | 1.311476 | −2.64436 | 0.016895 | 0.013555 | 0.006785 | 0.011093 |
| 0.204045 | 0.204601 | 0.444042 | 0.413933 | 2.203582 | 0.002579 | 0.003346 | 0.005627 | 0.001538 |
| 0.810485 | 0.333445 | 0.598349 | 0.524713 | 2.747895 | 0.031817 | 0.018196 | 0.028782 | 0.008599 |
| 0.063189 | 0.040531 | 0.060757 | 0.053991 | 2.326585 | 0.00497 | 0.004102 | 0.003529 | 0.003038 |
| 0.115787 | 0.005085 | 0.023686 | 0.030624 | 2.414441 | 0.002439 | 6.41E−05 | 0.000821 | 2.35E−05 |
| 0.25998 | 0.640466 | 0.042788 | 0.308645 | 1.704025 | 0.645378 | 0.001919 | 1.456028 | 0.000578 |
| 1.765304 | 2.087314 | 0.497759 | 0.923671 | 2.221704 | 0.641349 | 0.002931 | 0.185862 | 7.89E−06 |
| 0.125515 | 0.131838 | 0.091762 | 0.079226 | 2.066986 | 3.647015 | 0.000733 | 0.972366 | 0.011094 |
| 0.340781 | 0.151996 | 0.067051 | 0.036664 | 2.267702 | 3.822085 | 0.000132 | 1.095334 | 0.00243 |
| 0.011209 | 0.086712 | 0.007935 | 0.127665 | −1.00928 | 0.175967 | 0.279807 | 0.010867 | 0.001642 |
| 1.263602 | 3.984172 | 1.3969 | 0.024624 | −0.27876 | 0.030897 | 1.389737 | 0.028829 | 0.049153 |
| 0.303989 | 0.409703 | 0.177342 | 0.258215 | −0.81289 | 0.222352 | 0.321617 | 0.010685 | 0.016348 |
| 0.000582 | 0.070523 | 0.052993 | 0.002549 | −1.10247 | 0.132656 | 0.181615 | 0.085711 | 0.065071 |
| 0.133093 | 0.083965 | 0.97123 | 0.021201 | 2.839006 | 0.3204 | 0.316711 | 0.505966 | 0.331667 |
| 0.372297 | 0.694326 | 1.6447 | 0.29119 | −2.95412 | 2.980212 | 3.198008 | 2.763676 | 2.992865 |
| 0.2516 | 0.22364 | 0.549981 | 0.107848 | 2.987809 | 0.270653 | 0.297171 | 0.167663 | 0.26508 |
| 0.156811 | 0.031201 | 0.004425 | 0.068093 | 2.951094 | 0.226944 | 0.260783 | 0.148816 | 0.225929 |
| 0.021587 | 0.006778 | 0.047654 | 0.225042 | −1.95659 | 0.007957 | 0.000754 | 0.013975 | 0.040768 |
| 0.104818 | 0.023948 | 0.164352 | 0.729383 | −1.79823 | 0.018142 | 0.010582 | 0.015118 | 0.073691 |
| 0.046302 | 0.005129 | 0.036217 | 0.112228 | −1.83423 | 0.01745 | 0.002166 | 0.011855 | 0.043797 |
| 0.002955 | 0.124548 | 0.284469 | 1.01E−05 | −1.77626 | 0.001716 | 0.002898 | 0.006353 | 0.025459 |
| 0.104628 | 0.17665 | 0.001471 | 0.589111 | −2.17659 | 0.098201 | 0.013053 | 0.003976 | 0.026745 |
| 0.247876 | 0.379923 | 0.806181 | 0.00994 | −1.89527 | 0.109748 | 0.017175 | 0.012721 | 0.021041 |
| 0.649972 | 0.325973 | 0.055744 | 0.309682 | −2.08385 | 0.095052 | 0.018255 | 0.006833 | 0.027993 |
| 0.249899 | 0.43111 | 1.561861 | 0.059512 | −2.05713 | 0.247204 | 0.029991 | 0.018776 | 0.047365 |
| 0.014133 | 0.252742 | 0.000137 | 0.059372 | −2.7724 | 2.546163 | 13.27334 | 3.488997 | 2.677026 |
| 0.019542 | 0.006888 | 0.180471 | 0.0062 | 2.718774 | 7.204734 | 0.038551 | 5.442717 | 6.363571 |
| 0.078807 | 0.055742 | 0.002492 | 0.053999 | −3.0546 | 1.545463 | 0.021232 | 1.313832 | 1.536267 |
| 0.171502 | 0.000978 | 0.26049 | 0.001187 | 2.898461 | 1.0016 | 4.702883 | 1.467624 | 1.183293 |
| 0.211825 | 0.416353 | 0.000249 | 0.532327 | 1.314033 | 0.004119 | 0.016279 | 0.0257 | 0.095158 |
| 0.864668 | 0.388667 | 1.441325 | 0.18595 | 1.840001 | 0.06611 | 0.01649 | 0.064059 | 0.068735 |
| 0.482697 | 0.21493 | 0.985052 | 0.152245 | 1.566154 | 0.021068 | 0.003955 | 0.017922 | 0.124968 |
| 0.012758 | 0.276798 | 1.175415 | 0.892546 | 1.434009 | 0.029379 | 0.038292 | 0.078344 | 0.050779 |
| 0.477292 | 0.006387 | 0.009956 | 7.51E−05 | −2.55087 | 0.041871 | 0.000538 | 0.00332 | 0.050694 |
| 0.960672 | 0.000216 | 0.00029 | 0.079433 | −2.28957 | 0.026831 | 0.016288 | 0.010213 | 0.025788 |
| 0.180668 | 0.012406 | 0.014322 | 0.208027 | −2.50054 | 0.017435 | 0.000438 | 0.032735 | 0.036308 |
| 0.316746 | 0.091528 | 0.014689 | 0.031022 | −1.88718 | 0.07712 | 0.022791 | 0.015316 | 0.656852 |

TABLE 22

| 2-AcOEt-3 | | | | | | | | | |
|---|---|---|---|---|---|---|---|---|---|
| $(argY_{u,c}-argY_{gc,k}-\theta_{ug,k})^2/\sigma_{\theta g,c}^2$ | | | | | | | | | |
| EtOH | | | | | | Benzene | | | |
| k5 | k1 | k2 | k3 | k4 | k5 | k1 | k2 | k3 | k4 | k5 |
| 0.00014 | 1.300352 | 0.572225 | 1.560775 | 2.67E−05 | 0.023595 | 0.031514 | 0.000366 | 0.019363 | 0.011464 | 0.303294 |
| 0.013951 | 0.740363 | 0.108171 | 0.780921 | 0.005899 | 0.003713 | 0.000798 | 0.000917 | 0.004941 | 0.003163 | 0.291965 |
| 0.003602 | 0.464646 | 0.379121 | 0.639109 | 0.001255 | 0.015996 | 0.000786 | 1.13E−05 | 0.003467 | 0.000631 | 2.753686 |
| 0.005215 | 0.359647 | 0.267344 | 0.45187 | 0.002018 | 0.06769 | 0.012909 | 0.003138 | 1.49E−06 | 0.003723 | 0.106042 |
| 0.00214 | 0.03576 | 5.896741 | 0.000926 | 0.001413 | 3.11E−05 | 0.015689 | 0.155989 | 1.824236 | 0.004908 | 0.51073 |
| 0.084924 | 0.003551 | 0.401546 | 0.007639 | 0.009959 | 0.000292 | 2.9E−05 | 0.320856 | 1.07316 | 0.005303 | 0.021468 |
| 0.033642 | 0.00372 | 0.291834 | 0.000172 | 0.001074 | 4.31E−05 | 0.001823 | 0.056305 | 2.465842 | 8.77E−05 | 0.000111 |
| 0.019195 | 0.015627 | 0.248414 | 0.002556 | 0.001457 | 3.82E−05 | 0.004759 | 0.018491 | 0.934211 | 0.000302 | 1.144357 |
| 0.001586 | 0.013643 | 0.004718 | 0.000226 | 0.000979 | 0.004388 | 0.004656 | 0.014586 | 0.005405 | 0.000712 | 0.013223 |
| 0.032699 | 0.004909 | 5.26E−06 | 0.002456 | 0.000523 | 0.002223 | 0.008727 | 0.011602 | 0.01471 | 0.00026 | 0.069155 |
| 0.020714 | 8.46E−05 | 4.06E−06 | 9.02E−05 | 3.69E−05 | 0.002312 | 0.003209 | 0.00682 | 0.002435 | 0.001133 | 0.003834 |
| 0.029986 | 0.025078 | 0.003574 | 0.004734 | 0.001832 | 0.001103 | 0.01364 | 0.003146 | 0.001631 | 0.001463 | 0.030805 |
| 0.000663 | 0.002195 | 0.000434 | 0.006435 | 7.24E−06 | 0.248528 | 0.055839 | 0.000439 | 0.008249 | 0.003356 | 0.002102 |
| 0.04244 | 0.025401 | 0.034217 | 0.021326 | 0.016237 | 0.148863 | 0.016557 | 0.008174 | 0.012984 | 0.045606 | 0.018253 |
| 0.005231 | 0.000257 | 0.000342 | 1.31E−05 | 1.02E−05 | 0.360682 | 0.004665 | 0.003171 | 0.003519 | 0.000293 | 0.00044 |
| 0.072038 | 0.03149 | 0.030398 | 0.043401 | 0.01541 | 1.954692 | 0.022866 | 0.027116 | 0.065366 | 0.064561 | 0.039767 |
| 0.510273 | 0.35412 | 0.40091 | 0.442002 | 0.470564 | 0.340934 | 3.012139 | 2.388468 | 4.05924 | 4.153378 | 6.264065 |
| 1.82501 | 2.558585 | 2.476602 | 2.756316 | 2.598709 | 2.542625 | 6.815207 | 5.3226 | 7.437811 | 7.036789 | 9.253788 |
| 0.063134 | 0.283862 | 0.27473 | 0.315564 | 0.265728 | 0.284129 | 2.181659 | 1.774642 | 2.620667 | 1.518867 | 2.208906 |
| 0.067661 | 0.223592 | 0.178112 | 0.193349 | 0.15358 | 0.228489 | 1.048658 | 0.752176 | 0.70176 | 1.267939 | 1.186043 |
| 0.071988 | 0.03148 | 0.006921 | 0.016245 | 0.002398 | 0.000569 | 0.000565 | 0.034408 | 0.002698 | 0.859044 | 0.006686 |
| 0.039566 | 0.000855 | 0.000498 | 0.000244 | 0.002186 | 0.015521 | 0.000851 | 0.011654 | 1.88E−06 | 1.690081 | 0.024161 |
| 0.032885 | 0.000707 | 0.000149 | 2.41E−05 | 0.00235 | 0.000289 | 0.000105 | 0.000294 | 0.003305 | 0.907301 | 0.00495 |
| 0.034803 | 0.024591 | 0.006586 | 0.010684 | 0.001736 | 0.010305 | 0.006098 | 0.022491 | 0.020744 | 1.086701 | 0.000794 |
| 0.045008 | 0.00275 | 0.001994 | 0.008017 | 0.012006 | 0.003414 | 0.036335 | 0.002988 | 0.007 | 0.02394 | 1.18E−06 |
| 0.005802 | 0.00087 | 0.007082 | 0.026699 | 0.000218 | 0.000902 | 0.010446 | 0.023364 | 0.004521 | 0.039858 | 0.00037 |

TABLE 22-continued

2-AcOEt-3

| | | | | | | | | | | |
|---|---|---|---|---|---|---|---|---|---|---|
| 0.019634 | 0.000479 | 0.000105 | 0.001369 | 8.01E−05 | 0.000815 | 0.000751 | 0.000748 | 0.000761 | 0.006092 | 0.001586 |
| 0.048541 | 0.006044 | 0.021573 | 0.072586 | 0.017488 | 0.006162 | 0.076848 | 0.009715 | 0.010979 | 0.135737 | 0.000424 |
| 2.17362 | 1.23114 | 1.269344 | 1.107609 | 4.601666 | 1.285516 | 1.052566 | 0.003081 | 0.734889 | 0.949533 | 1.087702 |
| 5.898406 | 2.446183 | 2.16872 | 2.070297 | 3.20275 | 2.153767 | 0.572018 | 0.310656 | 0.448266 | 0.645214 | 0.698798 |
| 1.573242 | 2.315165 | 2.583943 | 2.55657 | 1.39275 | 2.608662 | 0.6705 | 1.138958 | 0.678992 | 0.939565 | 0.685833 |
| 1.096825 | 1.575183 | 2.103345 | 1.931661 | 3.5361 | 2.164315 | 0.763622 | 0.207094 | 0.690959 | 0.873998 | 0.666925 |
| 0.042327 | 0.005217 | 3.99E−05 | 0.021541 | 1.222017 | 0.000956 | 1.22012 | 1.684896 | 0.016481 | 0.011565 | 0.148646 |
| 0.011484 | 0.000621 | 1.88E−06 | 0.000355 | 0.728676 | 0.06458 | 0.085874 | 0.096015 | 0.040312 | 0.020382 | 0.009404 |
| 0.023649 | 0.001947 | 0.007186 | 0.002538 | 0.567492 | 1.38E−06 | 0.001197 | 1.419985 | 0.007585 | 0.094618 | 0.033413 |
| 0.027764 | 0.035213 | 0.011957 | 0.081521 | 0.571288 | 0.118748 | 0.004635 | 0.36091 | 0.032243 | 0.083371 | 0.001523 |
| 0.029037 | 0.004332 | 0.002868 | 0.018429 | 0.356162 | 0.002055 | 0.211026 | 0.77789 | 0.015145 | 0.009477 | 0.498537 |
| 0.00883 | 0.001176 | 0.000104 | 0.00098 | 0.390762 | 0.000568 | 0.134809 | 0.02275 | 0.001141 | 0.012974 | 0.017898 |
| 0.006308 | 0.01811 | 0.009878 | 0.005395 | 0.315157 | 0.007299 | 0.025702 | 1.02E−05 | 4.52E−05 | 0.001858 | 0.021655 |
| 0.023354 | 0.018387 | 0.018644 | 0.007733 | 2.399447 | 0.002575 | 0.073909 | 0.167909 | 0.004693 | 0.002693 | 0.079832 |

| $(\arg Y_{u,c} - \arg Y_{gc,k} - \theta_{ug,k})^2 / \sigma_{\theta g,c}^2$ | | | | | | | |
|---|---|---|---|---|---|---|---|
| Hexane | | | | | AcOEt | | |
| k1 | k2 | k3 | k4 | k5 | k1 | k2 | k3 |
| 0.304943 | 0.005274 | 0.241443 | 3.575129 | 0.598639 | 0.006857 | 0.268543 | 0.119987 |
| 0.287678 | 0.162939 | 0.262079 | 0.772157 | 0.523733 | 0.001205 | 3.139814 | 0.500901 |
| 0.005921 | 0.016092 | 0.000119 | 0.267181 | 0.015709 | 0.001648 | 0.266466 | 0.371079 |
| 0.007804 | 0.049027 | 0.002936 | 0.203196 | 0.012718 | 3.32E−05 | 0.647236 | 4.106604 |
| 0.288341 | 0.085756 | 0.098971 | 0.084504 | 0.097569 | 0.045143 | 0.140384 | 0.05959 |
| 0.081239 | 1.3742 | 0.052267 | 0.069708 | 0.091467 | 0.033128 | 0.008976 | 0.006583 |
| 0.001667 | 0.41828 | 8.99E−06 | 0.002289 | 0.000443 | 0.000315 | 0.00737 | 0.005761 |
| 0.004081 | 0.374521 | 0.000243 | 0.001405 | 0.0091 | 0.005831 | 0.056038 | 0.073854 |
| 0.182087 | 0.207746 | 0.030374 | 1.89955 | 0.128679 | 0.001723 | 0.001245 | 0.006614 |
| 0.02752 | 0.036723 | 1.228969 | 0.245445 | 0.04104 | 0.006847 | 0.005093 | 0.137056 |
| 0.028381 | 0.006254 | 0.511756 | 0.292463 | 0.00456 | 0.00013 | 6.46E−05 | 0.010417 |
| 0.021167 | 0.059635 | 0.633831 | 0.294085 | 0.01007 | 0.007495 | 0.000305 | 0.06512 |
| 0.081066 | 0.078288 | 1.320877 | 0.846744 | 2.013395 | 0.000128 | 0.011303 | 0.002802 |
| 0.027794 | 0.127835 | 0.005892 | 0.700273 | 0.02765 | 0.013894 | 0.002805 | 0.022552 |
| 0.014828 | 0.000375 | 0.123031 | 0.644581 | 0.150031 | 3.11E−06 | 2.51E−06 | 9.05E−05 |
| 0.059617 | 0.011654 | 0.232333 | 0.423995 | 0.334036 | 0.020314 | 0.03076 | 0.044574 |
| 0.301967 | 0.032196 | 0.355731 | 0.760885 | 0.415188 | 0.489106 | 0.725893 | 0.510818 |
| 95.08963 | 71.52281 | 71.98586 | 43.12259 | 75.10825 | 2.526221 | 1.170731 | 2.405568 |
| 6.284794 | 8.934046 | 4.48083 | 19.34033 | 5.689632 | 0.287367 | 0.914433 | 0.275983 |
| 4.255744 | 4.295492 | 2.111145 | 10.16632 | 1.366877 | 0.276452 | 0.350697 | 0.23372 |
| 2.585581 | 0.00127 | 0.141407 | 0.080627 | 0.717715 | 0.005311 | 3.9E−05 | 0.000834 |
| 0.24401 | 0.016335 | 0.000137 | 0.313343 | 0.018893 | 0.004201 | 0.007948 | 0.002485 |
| 0.164357 | 1.16E−05 | 0.040365 | 0.009384 | 0.07911 | 0.000648 | 6.7E−06 | 0.000941 |
| 0.273077 | 0.008112 | 0.015102 | 0.130428 | 0.107175 | 0.012556 | 0.00713 | 0.000118 |
| 0.016214 | 0.0161 | 0.189363 | 3.100843 | 0.035603 | 0.407653 | 0.004418 | 0.009459 |
| 0.051656 | 0.049178 | 0.058651 | 0.488514 | 0.083621 | 0.254019 | 0.013649 | 0.000108 |
| 0.000901 | 0.001198 | 0.010205 | 0.278775 | 0.002102 | 0.376507 | 7.57E−06 | 0.000729 |
| 0.015099 | 0.00301 | 0.004403 | 0.165214 | 0.019665 | 2.465292 | 0.027074 | 0.005093 |
| 1.020565 | 0.069322 | 0.133824 | 1.268747 | 1.447103 | 0.684105 | 0.019612 | 0.680194 |
| 1.59003 | 0.014006 | 4.641973 | 1.72635 | 1.554025 | 0.925624 | 4.101797 | 1.080074 |
| 3.708353 | 9.698082 | 8.958054 | 2.985452 | 7.554767 | 0.875406 | 3.610514 | 0.712874 |
| 0.834827 | 3.374427 | 0.157095 | 0.725245 | 2.316858 | 0.658149 | 0.001337 | 0.431772 |
| 0.068819 | 0.003045 | 0.164319 | 0.15024 | 0.727084 | 0.000406 | 2.270645 | 0.001548 |
| 0.000156 | 0.066841 | 0.131636 | 0.228329 | 0.325309 | 0.010146 | 0.806054 | 0.00279 |
| 0.02245 | 0.001605 | 0.003159 | 0.002436 | 1.136591 | 0.000786 | 1.628909 | 0.001498 |
| 0.020443 | 0.075876 | 0.000369 | 0.027789 | 0.420783 | 0.03297 | 1.392515 | 0.004242 |
| 0.698962 | 0.765083 | 0.077609 | 0.323982 | 2.26758 | 0.000226 | 0.002551 | 1.629741 |
| 0.034925 | 0.665056 | 0.23578 | 0.088532 | 0.04729 | 0.000639 | 0.457592 | 0.007785 |
| 0.2804 | 1.038426 | 0.001699 | 0.000721 | 0.193866 | 0.001343 | 0.027686 | 0.136526 |
| 0.036376 | 1.147484 | 0.003444 | 0.007357 | 0.085803 | 0.005012 | 0.689631 | 0.384824 |

TABLE 23

2-AcOEt-4

| THF | | | | | | | log $\sigma_{Lg,c}$ | | | |
|---|---|---|---|---|---|---|---|---|---|---|
| k4 | k5 | k1 | k2 | k3 | k4 | k5 | $H_2O$ | EtOH | Benzene | Hexane |
| 0.068055 | 0.027323 | 0.087626 | 1.414112 | 0.011829 | 0.022196 | 0.001275 | −0.27945 | 0.398827 | −0.12502 | −0.55113 |
| 0.007841 | 0.00418 | 0.23243 | 0.379491 | 0.004446 | 0.004641 | 9.38E−05 | −0.0226 | 0.248584 | −0.25239 | −0.32497 |
| 4.78E−05 | 0.001506 | 0.303118 | 0.155037 | 0.001383 | 0.000459 | 2.87E−05 | −0.55571 | 0.239137 | −0.39623 | −0.61155 |
| 0.028945 | 0.040778 | 8.777602 | 0.1761 | 0.104926 | 0.017618 | 0.008507 | −0.53188 | −0.1312 | −0.52282 | −0.89179 |
| 0.044604 | 0.033902 | 0.006379 | 0.038085 | 0.12204 | 0.660188 | 0.007299 | −0.7076 | −0.13743 | 0.044038 | −0.64421 |

TABLE 23-continued

2-AcOEt-4

| | | | | | | | | | | |
|---|---|---|---|---|---|---|---|---|---|---|
| 0.053624 | 0.015323 | 0.017802 | 0.106517 | 5.898119 | 2.488328 | 0.038345 | −0.42382 | −0.15439 | −0.11099 | −1.14907 |
| 0.014192 | 0.009639 | 0.000287 | 0.00027 | 0.213358 | 0.826656 | 0.000325 | −0.42179 | −0.09534 | 0.33566 | −1.22368 |
| 0.113913 | 0.050558 | 0.000751 | 0.001677 | 0.27525 | 0.837767 | 7.4E−07 | −0.40275 | 0.458128 | 0.175373 | −1.11758 |
| 0.000194 | 0.000241 | 0.085651 | 0.003368 | 0.003531 | 0.05002 | 0.015286 | −0.91872 | −0.22917 | −0.95407 | −0.36169 |
| 4.75E−08 | 0.005208 | 0.067602 | 0.102686 | 0.124957 | 0.02175 | 0.131113 | −0.17315 | −0.39424 | −0.01421 | −0.13507 |
| 0.001739 | 0.000298 | 0.013314 | 0.006638 | 0.004341 | 0.005477 | 0.000721 | −0.83614 | −0.65358 | −0.29561 | −0.0715 |
| 0.002372 | 0.000684 | 0.204029 | 0.108516 | 0.072859 | 0.014654 | 0.065905 | −0.6724 | −1.1222 | 0.043835 | −0.11942 |
| 0.002729 | 0.016148 | 0.006784 | 0.001959 | 0.011852 | 0.018893 | 0.003431 | 0.371859 | −0.99151 | −0.41346 | −0.38187 |
| 0.025194 | 0.010774 | 0.001938 | 0.029779 | 0.002756 | 0.054059 | 0.025287 | −0.16865 | −1.23994 | −0.55346 | −0.28183 |
| 2.91E−05 | 6.77E−05 | 1.29E−06 | 9.73E−07 | 0.000766 | 0.006154 | 2.39E−05 | −0.0813 | −1.29443 | −0.40318 | −0.17188 |
| 0.050196 | 0.067823 | 0.01371 | 0.03519 | 0.031945 | 0.00046 | 0.037805 | 0.04032 | −1.12337 | −0.28638 | 0.033897 |
| 0.560658 | 1.634221 | 0.73783 | 0.688252 | 0.772721 | 0.778613 | 0.662761 | 0.191785 | −0.22819 | −0.94597 | −1.15407 |
| 2.218129 | 1.068267 | 6.113507 | 6.528074 | 6.001997 | 6.736772 | 5.26088 | −0.11037 | −0.07316 | −1.25623 | −0.34122 |
| 0.265484 | 1.134137 | 0.597392 | 0.608448 | 0.597281 | 0.640295 | 0.553013 | −0.54554 | −0.75784 | −0.37232 | −0.33503 |
| 0.159943 | 1.079771 | 0.465525 | 0.605164 | 0.413218 | 0.555335 | 0.349415 | −0.54083 | −0.73936 | −0.23667 | −0.51182 |
| 0.000486 | 0.000272 | 0.006474 | 0.022274 | 0.089961 | 0.015042 | 0.00866 | −1.05253 | −1.09551 | −0.50347 | 0.125804 |
| 0.000152 | 0.00267 | 0.008394 | 0.017829 | 0.040988 | 0.021941 | 0.003098 | −1.54088 | −1.18116 | −0.45473 | −0.12365 |
| 0.000157 | 0.000587 | 0.000529 | 0.001281 | 0.001297 | 7.27E−05 | 0.000969 | −0.16437 | −1.13825 | −0.67257 | −0.61878 |
| 6.27E−06 | 0.008498 | 5.83E−05 | 0.000379 | 0.005931 | 0.002196 | 0.002627 | −0.59311 | −1.11749 | −0.54994 | −0.24084 |
| 0.003022 | 0.016448 | 0.002991 | 1.295199 | 0.002979 | 0.019083 | 0.007124 | −0.791 | −0.48094 | −0.13148 | −0.8441 |
| 0.00361 | 0.000145 | 0.000346 | 0.13487 | 3.1E−05 | 0.043317 | 0.005459 | −0.30458 | −0.04454 | −1.15475 | −1.10002 |
| 4.25E−05 | 0.000812 | 3.53E−05 | 0.225458 | 7.37E−05 | 0.001674 | 0.000299 | −0.14548 | −0.29639 | −0.3181 | −1.07174 |
| 4.47E−06 | 0.009822 | 0.005622 | 0.199015 | 0.003498 | 4.82E−05 | 2.63E−05 | −0.15455 | −0.13279 | −0.21329 | −0.67837 |
| 0.657752 | 0.60532 | 0.814335 | 0.589136 | 0.682223 | 0.608672 | 0.713904 | −0.62735 | 0.089626 | −0.60433 | −0.2829 |
| 0.724436 | 0.867718 | 0.68428 | 0.663689 | 0.55254 | 0.504058 | 0.656178 | −0.90372 | −0.23395 | −0.70282 | −0.41213 |
| 0.889045 | 0.842423 | 1.14006 | 0.986921 | 1.118414 | 0.961659 | 1.147317 | −0.75676 | −0.16047 | 0.069012 | −0.27628 |
| 0.806023 | 0.60292 | 0.844029 | 0.56202 | 0.855082 | 0.722215 | 0.790029 | −0.97667 | 0.048629 | −0.20526 | 0.111701 |
| 0.613835 | 0.028151 | 0.010135 | 0.028548 | 0.011836 | 0.100092 | 0.007622 | −0.10314 | −0.45305 | −0.63388 | 0.038614 |
| 0.717636 | 0.002062 | 0.033869 | 0.006041 | 0.091565 | 0.30712 | 0.017684 | −0.20565 | −0.12083 | 0.069844 | −0.15347 |
| 0.735829 | 0.005429 | 0.001997 | 0.00071 | 0.003025 | 0.005138 | 0.025386 | −0.25904 | 0.189343 | 0.446272 | −0.10431 |
| 0.870568 | 0.000167 | 0.001542 | 0.006353 | 0.0224 | 0.105734 | 0.015668 | −0.1905 | 0.489136 | 0.408102 | −0.21624 |
| 0.00322 | 0.051359 | 6.04E−05 | 0.031245 | 0.01636 | 0.000837 | 0.043916 | −0.18367 | −1.36604 | −0.93406 | 0.227763 |
| 0.004401 | 0.008206 | 0.001226 | 0.73136 | 1.351498 | 0.002487 | 0.753025 | −0.56828 | 0.228993 | −0.9417 | 0.117962 |
| 6.12E−06 | 0.004818 | 0.007277 | 0.131296 | 0.02301 | 0.005625 | 0.002295 | −0.16197 | 0.020417 | −1.34016 | 0.391301 |
| 0.000301 | 0.113905 | 0.012438 | 0.012867 | 0.326913 | 0.01716 | 0.150452 | −0.17728 | 0.066696 | −1.43918 | −0.00175 |

| log $\sigma_{Lg,c}$ | | log $\sigma_{\theta g,c}$ | | | | | |
|---|---|---|---|---|---|---|---|
| AcOEt | THF | H$_2$O | EtOH | Benzene | Hexane | AcOEt | THF |
| 0.32871 | −0.08107 | 0.801234 | 1.207714 | 1.079374 | 1.189762 | 0.866507 | 1.150355 |
| −0.10168 | 0.215972 | 0.729341 | 0.669981 | 1.252097 | 0.229523 | 0.939489 | 1.183314 |
| 0.447759 | −0.12574 | 0.714165 | 0.547871 | 0.999054 | 0.229044 | 1.090265 | 1.080704 |
| 0.355916 | −0.55732 | 0.722126 | 0.465178 | 1.117856 | 0.1627 | 0.785955 | 0.3326 |
| −1.19739 | −0.06096 | 0.5606 | 0.605007 | 0.795256 | 0.743116 | −0.2618 | 1.272964 |
| −1.08912 | −0.0579 | 0.53307 | 0.957349 | 1.134892 | 1.126902 | −0.39762 | 0.636763 |
| −1.29606 | −0.19802 | 0.576843 | 0.985589 | 0.696795 | 0.874959 | −0.37434 | 1.23767 |
| −1.11766 | −0.44338 | 0.594635 | 0.995589 | 1.106001 | 0.863036 | −0.35685 | 1.205117 |
| −0.08808 | −0.54633 | 1.378727 | 0.870049 | 0.644553 | 1.15028 | 0.84218 | 0.01585 |
| 0.117575 | −0.50368 | 1.295079 | 0.951724 | 0.980232 | 1.301856 | 0.750527 | 0.170075 |
| 0.061467 | −0.58296 | 0.444318 | 0.974456 | 0.722887 | 0.901578 | 0.922287 | 0.046107 |
| 0.057921 | −0.63334 | 0.472307 | 1.012596 | 0.702096 | 0.794673 | 1.032039 | 0.070549 |
| −0.37755 | −0.48677 | 0.961614 | 1.035338 | 0.756087 | 0.997163 | 0.862225 | 0.689686 |
| −0.55965 | −1.19113 | 1.01892 | 1.0191 | 0.857216 | 1.099827 | 0.859037 | 0.505935 |
| −0.38782 | −0.72924 | 0.654436 | 1.034736 | 0.789613 | 1.216736 | 0.834254 | 0.678971 |
| −0.15015 | −0.82075 | 0.619903 | 1.091146 | 0.840677 | 1.260704 | 0.774444 | 0.696334 |
| 0.02776 | −0.90701 | 1.044944 | 0.990337 | −0.16622 | 0.883427 | 0.852136 | 0.731865 |
| 0.011325 | −0.71451 | 0.951797 | 1.037002 | 0.532775 | −0.79673 | 1.082475 | 0.682279 |
| 0.564229 | −0.99708 | 1.059034 | 1.038236 | 0.205231 | −0.45793 | 1.088727 | 0.735329 |
| 0.321599 | −0.41743 | 1.050676 | 1.089144 | 0.128321 | −0.33163 | 1.021132 | 0.783396 |
| −0.91843 | −0.05209 | 0.656561 | 0.717663 | 1.123837 | 0.642526 | 1.106472 | 0.682546 |
| −0.52523 | −0.15205 | 0.594566 | 0.691442 | 0.946763 | 0.738585 | 1.084102 | 0.904087 |
| −1.01393 | −0.17641 | 0.879033 | 0.762743 | 1.111363 | 0.709606 | 1.104812 | 0.776997 |
| −1.39596 | −0.26371 | 0.860382 | 0.844861 | 0.831881 | 0.830535 | 1.095595 | 0.802764 |
| −1.78544 | −1.54092 | 0.909549 | 0.899793 | 0.836804 | 0.622138 | 0.89432 | 1.315317 |
| −0.25395 | −0.86242 | 0.906718 | 0.842321 | 0.733571 | 0.646614 | 0.880259 | 1.176445 |
| −0.91017 | −1.11347 | 0.706513 | 0.778633 | 0.822822 | 0.725209 | 0.912419 | 1.213009 |
| −0.81836 | −1.39507 | 0.671983 | 0.655389 | 0.947994 | 0.74445 | 1.008622 | 1.180359 |
| −0.47458 | −0.25747 | 0.40447 | 0.757171 | 0.997815 | 0.85769 | 1.104346 | 0.999825 |
| −0.27044 | 0.204271 | 0.071537 | 0.502741 | 1.225844 | 0.825294 | 1.052402 | 1.112113 |
| −0.31088 | 0.087425 | 0.907564 | 0.618479 | 1.213651 | 0.576452 | 1.166429 | 1.023458 |
| −0.27363 | −0.07046 | 0.950403 | 0.619702 | 1.220683 | 1.165549 | 1.218396 | 1.152418 |
| 0.083506 | −0.32954 | 0.634833 | 0.739149 | −0.20836 | 0.812456 | 0.535362 | 0.228705 |
| 0.56292 | −0.3326 | 0.551091 | 0.864869 | 0.855276 | 0.850432 | 0.930297 | 0.188121 |
| 0.630582 | −0.87208 | 0.582188 | 0.645764 | 0.006498 | 0.60461 | 0.689769 | 0.163691 |
| 0.388878 | −0.91419 | 0.584172 | 0.450962 | 0.931221 | 0.69898 | 0.643733 | 0.089592 |
| 0.666495 | 0.047935 | 0.768615 | 0.7843 | 0.198057 | 0.592487 | 0.754077 | 0.893002 |
| 0.073392 | 0.670118 | 0.838437 | 0.813008 | 0.568256 | 1.022759 | 0.875654 | 0.682508 |

TABLE 23-continued

2-AcOEt-4

| | | | | | | | |
|---|---|---|---|---|---|---|---|
| 0.158097 | 0.439682 | 0.683124 | 0.702989 | 0.698645 | 0.987988 | 0.895158 | 0.95815 |
| −0.09715 | −0.05799 | 0.699085 | 0.915385 | 1.181083 | 1.161702 | 0.945869 | 1.024418 |

TABLE 24

2-THF-1

| | | $\log|Y_{u,c}|$ | $(\log|Y_{u,c}|-\log|Y_{g,ck}|-L_{ug,k})^2/\sigma_{Lg,c}^2$ | | | | | | | |
|---|---|---|---|---|---|---|---|---|---|---|
| | | THF | $H_2O$ | | | | | ETOH | | |
| f | c | k6 | k1 | k2 | k3 | k4 | k5 | k1 | k2 | k3 |
| 0.05 Hz | Ch.1 | 2.237439 | 0.131576 | 0.057525 | 0.160142 | 0.141562 | 0.190133 | 0.285332 | 0.682583 | 0.24511 |
| | Ch.2 | 2.837434 | 2.047422 | 1.877364 | 1.019194 | 1.352519 | 2.056521 | 1.246272 | 1.076137 | 1.060285 |
| | Ch.3 | −0.16256 | 3.021741 | 3.054766 | 1.779499 | 2.166041 | 2.884923 | 0.128154 | 0.112605 | 0.072162 |
| | Ch.4 | −1.36347 | 0.047018 | 0.070085 | 0.018954 | 0.000194 | 0.027767 | 0.042483 | 0.139162 | 0.075745 |
| 0.1 Hz | Ch.1 | 2.445109 | 0.051696 | 0.302983 | 0.053781 | 0.120194 | 0.008689 | 0.366655 | 0.376528 | 0.503947 |
| | Ch.2 | 3.731151 | 2.316683 | 1.271628 | 0.976744 | 0.925778 | 0.924176 | 1.460779 | 1.055653 | 0.873997 |
| | Ch.3 | 0.048693 | 1.679328 | 0.953191 | 0.972273 | 0.868118 | 1.052752 | 0.108186 | 0.021242 | 0.036414 |
| | Ch.4 | −1.12344 | 0.002627 | 0.067369 | 0.029145 | 0.05182 | 0.017966 | 0.017463 | 0.018172 | 3.18E−05 |
| 0.15 Hz | Ch.1 | 1.926522 | 0.01091 | 0.801363 | 0.159604 | 0.329593 | 0.423715 | 0.635049 | 0.371598 | 0.546416 |
| | Ch.2 | 3.370923 | 0.82653 | 0.907504 | 0.696585 | 0.029659 | 0.53662 | 1.247867 | 0.702965 | 0.775962 |
| | Ch.3 | −0.38892 | 3.309877 | 2.595691 | 3.483806 | 0.26782 | 2.025958 | 0.102379 | 0.073106 | 0.091902 |
| | Ch.4 | −1.67426 | 0.016481 | 0.248082 | 0.010531 | 1.373194 | 0.260451 | 0.020843 | 0.034106 | 0.216871 |
| 0.2 Hz | Ch.1 | 1.991851 | 0.088302 | 0.388466 | 0.022811 | 0.004299 | 0.001938 | 4.309674 | 2.70522 | 2.718214 |
| | Ch.2 | 3.46463 | 2.77231 | 0.79239 | 0.708337 | 0.987555 | 0.961604 | 9.852046 | 10.40391 | 9.099758 |
| | Ch.3 | −0.22403 | 0.634235 | 0.064005 | 0.430473 | 0.59869 | 0.604833 | 0.07954 | 0.307325 | 0.32247 |
| | Ch.4 | −1.25822 | 0.053762 | 0.136949 | 0.011765 | 0.000892 | 0.00209 | 0.035022 | 0.277511 | 0.105612 |
| 0.25 Hz | Ch.1 | 0.777946 | 0.05013 | 0.027834 | 0.127516 | 0.034907 | 0.176587 | 0.321969 | 0.040161 | 0.14158 |
| | Ch.2 | 3.038818 | 0.648037 | 0.017066 | 0.38385 | 0.046076 | 0.049371 | 0.175226 | 0.26097 | 0.241817 |
| | Ch.3 | −1.25978 | 1.649506 | 0.371075 | 1.62762 | 0.5087 | 0.000512 | 0.011177 | 6.002278 | 0.003857 |
| | Ch.4 | −2.08552 | 0.181127 | 0.003396 | 0.18147 | 8.02E−05 | 0.308109 | 0.000745 | 0.500236 | 0.152868 |
| 0.3 Hz | Ch.1 | 1.428141 | 0.590202 | 0.083224 | 0.333809 | 0.394468 | 0.099233 | 2.741652 | 1.270806 | 1.868023 |
| | Ch.2 | 3.553512 | 33.52085 | 40.45981 | 1.424888 | 4.01357 | 3.522709 | 4.199817 | 2.688696 | 3.497957 |
| | Ch.3 | −0.52422 | 2.788862 | 0.641555 | 0.587366 | 0.799001 | 0.641694 | 0.296312 | 0.124944 | 0.265831 |
| | Ch.4 | −1.71611 | 0.027364 | 0.071755 | 0.121832 | 0.039654 | 0.092058 | 0.091697 | 0.001601 | 0.02167 |
| 0.35 Hz | Ch.1 | 0.570521 | 0.452002 | 2.237632 | 2.2787 | 0.075825 | 0.58542 | 0.148771 | 0.377709 | 0.154076 |
| | Ch.2 | 2.906373 | 1.974062 | 0.43729 | 0.621581 | 0.04932 | 0.058707 | 0.518752 | 0.586098 | 0.462618 |
| | Ch.3 | −1.16547 | 0.928032 | 0.044002 | 0.958811 | 0.035551 | 0.212091 | 0.008708 | 0.012101 | 0.004001 |
| | Ch.4 | −1.87052 | 0.351541 | 0.000115 | 0.239363 | 0.055553 | 0.022108 | 0.189352 | 0.095423 | 0.269876 |
| 0.4 Hz | Ch.1 | 1.21246 | 0.077125 | 1.482102 | 0.427026 | 0.004285 | 0.073129 | 0.012802 | 0.142887 | 0.191716 |
| | Ch.2 | 3.569667 | 2.868795 | 0.12819 | 0.543475 | 0.604091 | 0.962919 | 0.204613 | 0.066398 | 0.41246 |
| | Ch.3 | −0.69935 | 5.059271 | 0.479571 | 4.233664 | 2.200834 | 3.38321 | 0.004311 | 0.031608 | 0.064235 |
| | Ch.4 | −2.1906 | 0.344287 | 4.858214 | 0.712313 | 0.845542 | 0.727143 | 0.076387 | 0.11821 | 0.031565 |
| 0.45 Hz | Ch.1 | 0.875247 | 0.005467 | 0.000403 | 0.063214 | 0.007957 | 0.010387 | 0.59932 | 0.532265 | 0.770885 |
| | Ch.2 | 2.588143 | 2.021593 | 0.533459 | 1.329144 | 1.000609 | 1.783374 | 1.10445 | 0.839841 | 0.98857 |
| | Ch.3 | −1.01121 | 1.722181 | 0.875905 | 1.739476 | 0.910999 | 2.410129 | 0.044662 | 0.081272 | 0.026746 |
| | Ch.4 | −2.1479 | 0.065406 | 0.01758 | 0.031826 | 1.1E−05 | 0.000531 | 0.012701 | 5.54E−06 | 0.005906 |
| 0.5 Hz | Ch.1 | 0.508622 | 0.000235 | 0.140265 | 0.045267 | 0.218754 | 0.00645 | 3.603717 | 1.680599 | 2.64669 |
| | Ch.2 | 2.948061 | 1.846621 | 0.614937 | 0.548916 | 1.432406 | 0.528784 | 0.037016 | 0.078224 | 0.049499 |
| | Ch.3 | −1.27257 | 1.156682 | 0.768341 | 0.781459 | 1.050039 | 0.856596 | 0.021412 | 0.032744 | 0.005105 |
| | Ch.4 | −2.42522 | 0.024869 | 0.000155 | 0.034265 | 0.054629 | 0.135536 | 0.134295 | 0.023466 | 0.037943 |

| $(\log|Y_{u,c}|-\log|Y_{g,ck}|-L_{ug,k})^2/\sigma_{Lg,c}^2$ | | | | | | | |
|---|---|---|---|---|---|---|---|
| ETOH | | Benzene | | | | | |
| k4 | k5 | k1 | k2 | k3 | k4 | k5 | k1 |
| 0.363508 | 0.275132 | 2.896831 | 1.25944 | 2.339482 | 2.199682 | 4.08001 | 7.028658 |
| 1.361233 | 1.252007 | 2.098349 | 0.552189 | 0.810692 | 1.826278 | 2.913185 | 5.902515 |
| 0.076806 | 0.086884 | 0.106626 | 0.094043 | 0.334268 | 0.143559 | 0.028814 | 0.50957 |
| 0.078404 | 0.100996 | 0.069984 | 0.121546 | 0.194054 | 4.44E−05 | 0.333243 | 0.151722 |
| 0.349604 | 0.004803 | 1.550046 | 0.529445 | 2.003927 | 1.731812 | 2.371421 | 6.764205 |
| 1.18221 | 3.327527 | 0.78429 | 1.469441 | 1.46984 | 1.013591 | 2.165468 | 9.948755 |
| 0.035753 | 0.000371 | 0.044357 | 0.04586 | 0.011993 | 0.067121 | 0.003718 | 0.563424 |
| 0.023913 | 0.92453 | 0.032211 | 0.000437 | 0.040943 | 0.008803 | 0.030177 | 3.218372 |
| 0.26283 | 1.416573 | 11.2522 | 22.03223 | 14.38298 | 15.27249 | 2.996134 | 1.470479 |
| 1.687938 | 1.73501 | 0.829083 | 1.441396 | 1.383622 | 1.269109 | 0.524573 | 0.349323 |
| 0.248221 | 0.182158 | 0.012813 | 0.107232 | 0.027689 | 0.035092 | 0.043617 | 0.161082 |
| 0.412436 | 0.741824 | 0.088092 | 0.132716 | 0.028783 | 0.055655 | 0.037657 | 0.62554 |
| 0.617693 | 3.841096 | 4.26636 | 3.660407 | 4.774214 | 5.340306 | 2.64892 | 2.553513 |
| 8.598182 | 11.85335 | 5.714308 | 2.692782 | 4.227974 | 3.862706 | 4.295038 | 1.649444 |
| 0.862727 | 0.539332 | 0.129381 | 0.136894 | 0.043984 | 0.015187 | 0.092819 | 0.002319 |

TABLE 24-continued

| 2-THF-1 | | | | | | | |
|---|---|---|---|---|---|---|---|
| 0.86509 | 0.043675 | 0.109684 | 0.00987 | 0.026695 | 0.177043 | 0.180153 | 0.024649 |
| 0.014851 | 0.386521 | 5.573265 | 2.690904 | 9.802031 | 10.32038 | 3.125023 | 4.248887 |
| 0.185087 | 0.012199 | 4.166392 | 8.541647 | 11.79419 | 5.047962 | 8.047397 | 0.317957 |
| 0.030735 | 0.446082 | 0.167118 | 0.088741 | 0.003997 | 0.158404 | 0.280399 | 0.021094 |
| 0.754516 | 0.3551 | 0.004647 | 0.000164 | 0.127158 | 0.17849 | 0.379477 | 0.346935 |
| 2.401276 | 2.101683 | 4.336706 | 2.0836 | 5.248736 | 5.500487 | 2.420644 | 0.837322 |
| 3.297233 | 4.723451 | 0.843685 | 0.539309 | 2.912658 | 0.831778 | 0.925027 | 0.099284 |
| 0.118331 | 0.175517 | 0.08552 | 0.1207 | 0.028939 | 0.179311 | 0.199836 | 0.017814 |
| 0.047152 | 0.021614 | 0.832782 | 0.157666 | 0.453383 | 1.164605 | 0.031171 | 0.76489 |
| 0.355062 | 0.282988 | 2.043199 | 2.992215 | 1.31053 | 1.837333 | 0.839047 | 5.529616 |
| 0.047532 | 0.453839 | 11.33322 | 10.17385 | 4.504089 | 17.38724 | 5.938173 | 5.064147 |
| 0.038685 | 0.009454 | 0.028142 | 0.152242 | 0.112226 | 0.035059 | 0.10502 | 0.001275 |
| 0.242123 | 0.077119 | 0.00758 | 0.079383 | 0.012743 | 0.105007 | 0.061629 | 0.2422 |
| 0.895284 | 0.215379 | 5.20737 | 3.499018 | 4.786555 | 5.651213 | 5.452751 | 2.772194 |
| 0.214665 | 0.20597 | 1.39842 | 5.085869 | 0.173072 | 1.050554 | 0.104251 | 0.037049 |
| 0.038282 | 0.026534 | 0.000563 | 0.558048 | 0.029594 | 0.117919 | 0.029251 | 7.32E−05 |
| 0.632444 | 0.075238 | 0.711104 | 0.751045 | 0.977419 | 0.270439 | 1.311978 | 1.028049 |
| 0.419767 | 0.66472 | 2.29662 | 0.168619 | 6.955454 | 8.752962 | 7.619351 | 0.26928 |
| 3.039836 | 0.192211 | 0.25295 | 2.13346 | 1.184473 | 1.234385 | 0.855984 | 1.606707 |
| 0.353814 | 0.030546 | 0.002005 | 0.434571 | 0.014555 | 0.012156 | 0.000114 | 0.768203 |
| 0.576316 | 0.043709 | 0.016761 | 0.044829 | 0.078213 | 0.133958 | 0.091771 | 0.090093 |
| 13.3134 | 2.108783 | 6.978801 | 3.909587 | 12.02421 | 9.498138 | 4.096981 | 0.408902 |
| 0.081315 | 0.05946 | 3.893477 | 1.749642 | 2.916361 | 5.806945 | 4.022945 | 0.024867 |
| 0.175696 | 0.016664 | 0.328284 | 0.00536 | 0.46166 | 0.65958 | 0.137131 | 0.00919 |
| 0.018274 | 0.033474 | 0.250194 | 1.397551 | 4.786286 | 0.061292 | 0.215846 | 0.590895 |

TABLE 25

| 2-THF-2 |
|---|
| $(\log|Y_{u,c}|-\log|Y_{g,ck}|-L_{ug,k})^2/\sigma_{Lg,c}^2$ |

| Hexane | | | | AcOEt | | | | | THF | |
|---|---|---|---|---|---|---|---|---|---|---|
| k2 | k3 | k4 | k5 | k1 | k2 | k3 | k4 | k5 | k1 | k2 |
| 14.54683 | 11.21802 | 5.079906 | 12.43961 | 0.172598 | 0.098874 | 0.118087 | 0.0058 | 0.077275 | 0.06048 | 0.026736 |
| 6.048311 | 6.313984 | 3.585147 | 6.702863 | 1.711908 | 0.80715 | 3.251346 | 0.660598 | 1.197294 | 0.018448 | 0.068975 |
| 0.047433 | 0.249777 | 0.745183 | 0.209137 | 0.075645 | 0.019196 | 0.20796 | 0.036164 | 0.044852 | 0.012307 | 0.012857 |
| 1.729998 | 0.885473 | 0.947855 | 1.000393 | 0.014924 | 0.012241 | 0.094081 | 0.053725 | 0.035991 | 0.074225 | 1.013914 |
| 6.102998 | 7.417901 | 6.275766 | 10.2178 | 1.338374 | 2.164191 | 1.715011 | 1.942093 | 1.205658 | 0.046742 | 0.065448 |
| 11.02287 | 12.24222 | 15.1055 | 13.08161 | 2.271361 | 3.599063 | 2.551494 | 3.55785 | 2.743728 | 0.043601 | 0.094675 |
| 0.475467 | 0.394884 | 0.542478 | 0.18782 | 0.0795 | 0.232715 | 0.162846 | 0.351059 | 0.355851 | 0.032683 | 0.015347 |
| 1.874091 | 2.393608 | 0.842781 | 4.067099 | 0.060823 | 0.03613 | 0.009361 | 0.025075 | 0.036647 | 0.154347 | 0.447669 |
| 13.37549 | 6.799146 | 8.242785 | 2.812069 | 0.205931 | 0.23546 | 0.023962 | 0.385806 | 0.250705 | 0.153909 | 0.143162 |
| 3.183832 | 1.162161 | 1.770871 | 1.959859 | 0.067282 | 0.19786 | 0.036907 | 0.504338 | 0.290386 | 0.014178 | 0.005258 |
| 0.012213 | 0.000101 | 0.000173 | 0.219781 | 0.005829 | 0.018769 | 0.024258 | 0.061621 | 0.039833 | 0.003208 | 0.012847 |
| 0.995587 | 0.985459 | 0.863799 | 0.184658 | 0.037417 | 0.007166 | 0.007422 | 0.001027 | 0.003718 | 0.253977 | 0.141458 |
| 6.14414 | 11.31907 | 2.580455 | 9.365253 | 0.366255 | 0.638958 | 0.252643 | 0.223628 | 0.176293 | 0.347499 | 0.127302 |
| 1.814355 | 2.664228 | 1.807185 | 3.093022 | 1.127004 | 0.834555 | 1.568921 | 1.377833 | 2.801373 | 1.197425 | 0.549822 |
| 0.000137 | 0.058237 | 0.134878 | 0.022631 | 0.032077 | 0.032229 | 0.063291 | 0.078409 | 0.074331 | 0.001767 | 0.010789 |
| 0.439273 | 0.69417 | 0.143294 | 0.377329 | 0.006654 | 0.029495 | 0.05425 | 0.033056 | 0.315715 | 0.000467 | 0.016265 |
| 5.896184 | 9.967794 | 24.27457 | 22.66927 | 0.00806 | 0.13433 | 0.016204 | 0.00748 | 0.003979 | 0.000945 | 0.247014 |
| 0.0962 | 0.366656 | 0.664927 | 1.069964 | 0.006375 | 0.466558 | 0.09306 | 0.044341 | 0.059591 | 0.037489 | 0.016507 |
| 0.099035 | 6.93E−05 | 0.097277 | 0.067836 | 0.003369 | 0.189046 | 0.000155 | 0.000266 | 2.89E−05 | 0.565517 | 0.316213 |
| 1.651723 | 0.870345 | 1.569426 | 0.935651 | 0.004304 | 0.048335 | 0.020925 | 0.004781 | 0.015654 | 0.298348 | 0.007244 |
| 3.221631 | 3.805192 | 0.421826 | 0.826006 | 0.288943 | 0.021067 | 0.045431 | 0.347467 | 0.025263 | 0.000518 | 0.001566 |
| 0.833021 | 1.44818 | 0.140952 | 0.009787 | 0.000216 | 0.163193 | 0.594209 | 0.668077 | 0.179837 | 0.024057 | 0.033311 |
| 0.130264 | 1.482279 | 0.217023 | 0.004519 | 0.374435 | 0.357634 | 0.166987 | 0.23265 | 0.498515 | 8.29E−05 | 0.003755 |
| 1.732568 | 0.393477 | 0.695973 | 2.156949 | 2.986075 | 0.104121 | 0.808046 | 0.087246 | 0.077185 | 0.044727 | 0.034635 |
| 14.74016 | 8.193556 | 5.327894 | 15.28946 | 0.003373 | 9.518864 | 0.028437 | 1.000784 | 0.217784 | 0.064312 | 1.119651 |
| 4.925542 | 3.4555 | 5.37706 | 8.428738 | 0.672949 | 0.010622 | 0.083639 | 0.3631 | 0.163114 | 0.085661 | 0.080183 |
| 0.402082 | 0.020389 | 0.079527 | 0.910951 | 0.04512 | 0.024852 | 0.04187 | 0.123906 | 0.075949 | 0.195426 | 0.212339 |
| 1.874856 | 1.231134 | 0.0597 | 0.584544 | 1.504603 | 0.719022 | 0.148981 | 1.251702 | 0.404734 | 1.699375 | 4.030376 |
| 2.37391 | 1.302875 | 0.900356 | 1.807186 | 0.059187 | 0.320804 | 0.280702 | 0.000237 | 0.187517 | 0.075774 | 0.005801 |
| 0.130763 | 0.116505 | 0.907596 | 0.187717 | 0.014138 | 0.053862 | 0.34362 | 0.002892 | 0.116398 | 0.047385 | 0.000375 |
| 0.010458 | 0.220918 | 0.023846 | 0.053164 | 0.09151 | 0.077642 | 0.096808 | 0.11401 | 0.044827 | 0.000672 | 0.001279 |
| 0.56979 | 0.784965 | 1.207695 | 0.19481 | 0.371766 | 0.24892 | 0.021042 | 0.153558 | 0.046622 | 0.234705 | 0.017041 |
| 2.09035 | 1.26869 | 1.109206 | 2.881782 | 0.069339 | 0.068894 | 0.08195 | 0.05227 | 0.218463 | 0.043195 | 0.125325 |
| 1.518669 | 0.856148 | 0.701632 | 0.662248 | 0.133174 | 0.080234 | 0.168658 | 0.029297 | 0.196014 | 0.169813 | 0.001885 |
| 0.013587 | 0.383138 | 0.277697 | 0.041403 | 0.019994 | 0.036402 | 0.019963 | 0.301156 | 0.017231 | 0.007785 | 4.92E−05 |
| 0.467412 | 1.346474 | 1.11594 | 2.406875 | 0.003626 | 0.082585 | 0.009583 | 0.106703 | 0.000235 | 0.074102 | 0.31908 |
| 0.00017 | 1.141321 | 0.603682 | 2.881221 | 0.000939 | 0.010759 | 0.430939 | 0.00072 | 0.000939 | 0.061985 | 0.667908 |
| 0.0012 | 0.056558 | 0.00995 | 0.199699 | 0.002566 | 0.379539 | 0.210186 | 0.018898 | 0.17382 | 0.000265 | 1.020965 |
| 0.408674 | 0.002474 | 0.018474 | 0.03567 | 0.000593 | 0.793784 | 0.045725 | 0.027485 | 0.075018 | 1.56E−06 | 0.108616 |

TABLE 25-continued

2-THF-2

| 1.005036 | 1.004391 | 1.137096 | 2.092635 | 0.00138 | 0.038726 | 0.347031 | 4.39E-05 | 0.005644 | 0.0581 | 0.418726 |

| | | | $(\log|Y_{u,c}|-\log|Y_{g,ck}|-L_{ug,k})^2/\sigma_{Lg,c}^2$ THF | | | | $\arg Y_{u,c}$ THF | $H_2O$ | | |
|---|---|---|---|---|---|---|---|---|---|---|
| | | | k3 | k4 | k5 | | k6 | k1 | k2 | k3 | k4 |

| | | | k3 | k4 | k5 | k6 | k1 | k2 | k3 | k4 |
|---|---|---|---|---|---|---|---|---|---|---|
| | | | 0.080795 | 0.035146 | 0.169283 | 0.701438 | 0.000329 | 0.004959 | 0.007705 | 0.001428 |
| | | | 0.06545 | 0.026973 | 0.00069 | 1.128613 | 0.041161 | 0.104645 | 0.008262 | 0.062671 |
| | | | 0.007892 | 0.003737 | 0.000557 | 0.722547 | 0.003556 | 0.009828 | 0.004886 | 0.005136 |
| | | | 0.765999 | 0.001606 | 0.571072 | 0.474016 | 0.027166 | 0.022881 | 0.013738 | 0.019645 |
| | | | 0.065134 | 0.001696 | 0.004117 | -2.98042 | 0.185841 | 0.191982 | 0.207321 | 0.175997 |
| | | | 0.000229 | 0.032885 | 0.01737 | -1.07942 | 0.340532 | 0.291673 | 0.330428 | 0.247913 |
| | | | 0.005451 | 0.01416 | 0.010997 | -2.35595 | 0.026576 | 0.024516 | 0.023083 | 0.021798 |
| | | | 0.066303 | 0.030591 | 0.023657 | -1.96292 | 0.00079 | 0.004829 | 0.002385 | 0.00678 |
| | | | 0.007737 | 0.464304 | 0.110684 | 2.039828 | 0.71229 | 0.007128 | 1.555704 | 0.000275 |
| | | | 0.035576 | 0.30318 | 0.08706 | 3.12061 | 0.477184 | 0.026961 | 0.292871 | 0.011502 |
| | | | 0.014923 | 0.003842 | 0.001643 | 2.414849 | 3.290765 | 0.015066 | 0.792842 | 0.0404 |
| | | | 0.033201 | 0.002632 | 0.000243 | 2.67334 | 0.00207 | 0.979268 | 5.94E-05 | |
| | | | 0.028291 | 0.139571 | 0.672352 | 2.153896 | 0.003195 | 1.009969 | 0.336692 | 0.266795 |
| | | | 0.017014 | 0.467439 | 2.919588 | -2.98113 | 3.399043 | 8.103962 | 2.244252 | 2.09141 |
| | | | 0.037093 | 0.000695 | 0.00368 | 2.570142 | 1.520239 | 1.765045 | 0.433057 | 0.40142 |
| | | | 0.012974 | 0.006169 | 0.010236 | 2.725634 | 1.937259 | 2.11148 | 0.540034 | 0.596826 |
| | | | 0.024832 | 0.728162 | 0.077168 | -2.74209 | 0.017576 | 0.018453 | 0.000161 | 0.015057 |
| | | | 0.12361 | 0.641246 | 9.1E-06 | -1.49417 | 0.050638 | 0.026589 | 0.083479 | 0.049004 |
| | | | 0.284768 | 0.643745 | 0.151424 | -2.16233 | 0.000366 | 3.3E-05 | 0.016879 | 0.000602 |
| | | | 0.018021 | 0.142432 | 0.002493 | -2.1567 | 0.00278 | 0.00034 | 0.020547 | 0.002893 |
| | | | 0.010851 | 0.16386 | 0.08288 | 0.6541 | 0.002877 | 0.029003 | 0.000606 | 0.003489 |
| | | | 0.087611 | 0.069781 | 0.508079 | 1.523618 | 0.14073 | 0.018928 | 0.13206 | 0.262049 |
| | | | 0.00677 | 0.000397 | 0.0328 | 0.965009 | 0.028279 | 0.00011 | 0.02101 | 0.060193 |
| | | | 0.012645 | 0.598795 | 0.059358 | 1.036387 | 0.005256 | 0.00518 | 0.01228 | 0.036341 |
| | | | 0.098832 | 0.484854 | 0.00108 | -0.81297 | 0.084288 | 0.008322 | 0.001601 | 0.019738 |
| | | | 0.027113 | 0.013651 | 0.7757 | -0.26477 | 0.173013 | 0.047355 | 0.038988 | 0.052772 |
| | | | 0.050866 | 0.011947 | 0.044557 | -0.69335 | 0.104507 | 0.022524 | 0.009532 | 0.033226 |
| | | | 0.724356 | 0.066531 | 3.068216 | -0.75836 | 0.313085 | 0.055471 | 0.039748 | 0.078388 |
| | | | 0.094671 | 0.033618 | 0.002364 | 0.887472 | 0.000434 | 4.278359 | 0.085876 | 0.00376 |
| | | | 0.001402 | 0.297301 | 0.039921 | 1.573657 | 0.166369 | 4.326137 | 0.003213 | 0.06068 |
| | | | 7.85E-05 | 0.038041 | 0.00158 | 1.158165 | 0.004602 | 1.060113 | 0.000847 | 0.004113 |
| | | | 0.099139 | 0.630391 | 0.101147 | 1.370806 | 0.008522 | 1.156693 | 0.014004 | 2.83E-05 |
| | | | 0.028562 | 0.637573 | 0.007166 | 0.612607 | 0.009843 | 0.026446 | 0.038161 | 0.074771 |
| | | | 0.122405 | 0.051645 | 0.293847 | 1.026178 | 0.0531 | 0.010349 | 0.051263 | 0.083439 |
| | | | 0.056728 | 0.084516 | 0.097091 | 0.694578 | 0.041323 | 0.014647 | 0.036866 | 0.087247 |
| | | | 0.005505 | 2.359554 | 0.242879 | 0.750741 | 0.015482 | 0.022113 | 0.054252 | 0.074159 |
| | | | 0.00216 | 0.000708 | 0.01386 | 1.031278 | 0.029011 | 0.000123 | 0.000548 | 0.036425 |
| | | | 0.002025 | 0.000176 | 0.063277 | 1.349207 | 0.011519 | 0.005062 | 0.024817 | 0.01084 |
| | | | 0.044064 | 0.000447 | 0.307614 | 1.174591 | 0.046812 | 0.01106 | 0.009333 | 0.075552 |
| | | | 0.149633 | 0.001362 | 0.067818 | 1.249439 | 0.008655 | 0.001136 | 0.003711 | 0.002891 |

TABLE 26

2-THF-3
$(\arg Y_{u,c} - \arg Y_{gc,k} - \theta_{ug,k})^2 / \sigma_{\theta g,c}^2$

| EtOH | | | | | | Benzene | | | | |
|---|---|---|---|---|---|---|---|---|---|---|
| k5 | k1 | k2 | k3 | k4 | k5 | k1 | k2 | k3 | k4 | k5 |
| 0.001454 | 1.377316 | 0.623653 | 1.644989 | 0.001476 | 0.014483 | 0.019518 | 0.000349 | 0.010269 | 0.004796 | 0.253072 |
| 0.02596 | 0.82098 | 0.140272 | 0.86366 | 0.014991 | 0.011357 | 7.53E-06 | 0.003111 | 0.002007 | 0.000945 | 0.32017 |
| 0.000198 | 0.541546 | 0.448871 | 0.728792 | 0.000354 | 0.005217 | 4.23E-05 | 0.001437 | 0.000592 | 0.003561 | 2.640211 |
| 0.01146 | 0.307649 | 0.222792 | 0.39334 | 0.008094 | 0.093158 | 0.018789 | 0.006316 | 0.000609 | 0.007135 | 0.091318 |
| 0.111589 | 0.030515 | 7.795878 | 0.111132 | 0.1611 | 0.128318 | 0.030804 | 0.008872 | 2.727145 | 0.053225 | 0.171305 |
| 0.485243 | 0.105467 | 0.807771 | 0.031571 | 0.133135 | 0.061502 | 0.051685 | 0.118667 | 1.582301 | 0.022242 | 0.005692 |
| 0.076144 | 0.015 | 0.229187 | 0.00234 | 0.008883 | 0.003016 | 0.015565 | 0.024093 | 2.730316 | 0.005286 | 0.005119 |
| 0.003727 | 0.005345 | 0.302837 | 0.010496 | 0.000188 | 0.003373 | 0.000507 | 0.033289 | 1.026201 | 0.004078 | 0.111205 |
| 6.23E-07 | 0.033987 | 1.29E-06 | 0.002759 | 0.001315 | 1.73E-06 | 0.023371 | 0.001306 | 0.000124 | 0.003359 | 0.039853 |
| 0.005009 | 0.007239 | 0.024787 | 0.041905 | 0.031592 | 0.011663 | 0.059635 | 0.001855 | 0.00087 | 0.018132 | 0.171196 |
| 0.002329 | 0.002219 | 0.003401 | 0.002191 | 0.003891 | 0.010896 | 0.000246 | 0.000103 | 0.000532 | 0.001502 | 0.018045 |
| 0.013494 | 0.015663 | 0.008647 | 0.010406 | 0.005778 | 2.73E-12 | 0.026273 | 0.010279 | 2.42E-05 | 0.006981 | 0.048758 |
| 0.251757 | 0.239148 | 0.214372 | 0.272892 | 0.197905 | 0.003176 | 0.673907 | 0.366705 | 0.456221 | 0.412867 | 0.39749 |
| 2.137052 | 2.27466 | 2.198093 | 2.31509 | 2.372059 | 4.216464 | 4.365097 | 3.49764 | 3.410166 | 3.052192 | 3.332467 |
| 0.474875 | 0.254547 | 0.252083 | 0.267235 | 0.274324 | 0.006401 | 0.537966 | 0.52052 | 0.524869 | 0.419967 | 0.470778 |
| 0.576439 | 0.215317 | 0.218207 | 0.187616 | 0.267641 | 4.159885 | 0.452716 | 0.434792 | 0.323067 | 0.324865 | 0.390176 |
| 0.000247 | 0.020376 | 0.010952 | 0.005328 | 0.002688 | 0.023694 | 0.372053 | 0.640073 | 0.1094 | 0.094574 | 0.024743 |
| 0.360516 | 0.037026 | 0.047636 | 0.017362 | 0.032374 | 0.038974 | 0.127016 | 0.435485 | 0.057482 | 0.098781 | 0.005627 |

TABLE 26-continued

2-THF-3
$(\arg Y_{u,c} - \arg Y_{gc,k} - \theta_{ug,k})^2/\sigma_{\theta g,c}^2$

| | | | | | | | | | | |
|---|---|---|---|---|---|---|---|---|---|---|
| 0.083014 | 0.000322 | 0.000706 | 0.000122 | 4.78E−05 | 0.000313 | 0.044209 | 0.004274 | 0.123948 | 0.001181 | 0.04816 |
| 0.072356 | 0.001317 | 0.007568 | 0.00482 | 0.013747 | 0.000969 | 0.09411 | 0.214863 | 0.24315 | 0.041937 | 0.058447 |
| 0.015741 | 0.001853 | 0.00262 | 4.79E−05 | 0.033614 | 0.012217 | 0.004323 | 0.009211 | 0.001412 | 1.032998 | 6.01E−05 |
| 0.193037 | 0.061245 | 0.057873 | 0.041062 | 0.070238 | 0.008773 | 0.039298 | 0.003735 | 0.028122 | 2.158252 | 0.000186 |
| 0.047266 | 0.004503 | 0.00278 | 0.001268 | 6.34E−05 | 0.003306 | 0.000337 | 0.000131 | 0.000835 | 0.962581 | 0.001744 |
| 0.047363 | 0.035485 | 0.012704 | 0.018205 | 0.005362 | 0.004893 | 0.012114 | 0.033104 | 0.030977 | 1.021063 | 0.003617 |
| 0.03576 | 0.000851 | 0.000457 | 0.004391 | 0.017648 | 0.001236 | 0.0275 | 0.006313 | 0.003467 | 0.016884 | 0.000562 |
| 0.025869 | 0.01435 | 0.030434 | 0.064361 | 0.011038 | 0.01448 | 0.041159 | 0.064275 | 0.028195 | 0.09019 | 0.006632 |
| 0.024054 | 0.001282 | 0.000583 | 0.002592 | 0.000523 | 0.001803 | 0.000198 | 0.000196 | 0.001674 | 0.004189 | 0.000702 |
| 0.079899 | 0.019917 | 0.044212 | 0.110758 | 0.004741 | 0.020131 | 0.105314 | 0.021279 | 0.023131 | 0.172833 | 0.00461 |
| 0.010091 | 7.78E−06 | 0.000395 | 0.002954 | 1.078216 | 0.000731 | 0.0243 | 0.856671 | 0.000164 | 0.010895 | 0.029884 |
| 0.023221 | 0.05099 | 0.018074 | 0.010128 | 0.203767 | 0.016733 | 0.001495 | 0.025693 | 0.002316 | 0.007327 | 0.013991 |
| 0.006234 | 0.002279 | 0.001456 | 0.000877 | 0.151444 | 0.0021 | 0.00217 | 0.040722 | 0.001715 | 0.010793 | 0.001389 |
| 0.0021 | 0.071019 | 0.005079 | 0.017349 | 0.128806 | 0.00254 | 0.00157 | 0.143757 | 8.94E−06 | 0.01013 | 0.000309 |
| 0.057969 | 0.010772 | 0.001435 | 0.031802 | 1.15323 | 4.13E−07 | 1.046898 | 1.90287 | 0.002206 | 0.035702 | 0.092499 |
| 0.006477 | 2.93E−05 | 0.000435 | 4.15E−07 | 0.695769 | 0.05505 | 0.074724 | 0.108603 | 0.032794 | 0.015149 | 0.005974 |
| 0.044908 | 0.000109 | 0.000913 | 1.75E−05 | 0.516134 | 0.002849 | 0.004731 | 1.184291 | 0.000265 | 0.041706 | 0.006306 |
| 0.014315 | 0.017951 | 0.0031 | 0.053753 | 0.493034 | 0.084638 | 0.010259 | 0.322118 | 0.021422 | 0.065299 | 3.39E−05 |
| 0.018524 | 0.001027 | 0.000392 | 0.028737 | 0.326437 | 0.006274 | 0.158955 | 0.888619 | 0.003891 | 0.024975 | 0.587916 |
| 0.022633 | 0.008505 | 0.002279 | 0.007962 | 0.321694 | 0.001162 | 0.085948 | 0.050546 | 0.001617 | 0.001593 | 0.003575 |
| 2.4E−05 | 0.002695 | 0.00028 | 8.49E−05 | 0.229179 | 7.68E−06 | 0.059215 | 0.006372 | 0.005821 | 0.001594 | 0.052981 |
| 0.001015 | 0.000173 | 0.000149 | 0.056024 | 1.960731 | 0.009605 | 0.024906 | 0.27438 | 0.002074 | 0.003863 | 0.157284 |

| Hexane | | | | | AcOEt | | |
|---|---|---|---|---|---|---|---|
| k1 | k2 | k3 | k4 | k5 | k1 | k2 | k3 |
| 0.415081 | 0.027119 | 0.340379 | 3.931706 | 0.749557 | 0.001297 | 0.319224 | 0.089763 |
| 0.368741 | 0.22519 | 0.339681 | 0.901757 | 0.631355 | 1.9E−08 | 3.264551 | 0.551452 |
| 0.022974 | 0.002728 | 0.007317 | 0.349893 | 0.039983 | 8.2E−05 | 0.2349 | 0.410498 |
| 0.02229 | 0.079736 | 0.013258 | 0.151958 | 0.030181 | 0.000725 | 0.700893 | 4.240138 |
| 0.729035 | 0.000577 | 0.398739 | 0.369127 | 0.395921 | 0.426536 | 0.240971 | 0.386206 |
| 0.258843 | 0.899692 | 0.20463 | 0.237913 | 0.276862 | 0.715076 | 0.870286 | 1.229364 |
| 0.000775 | 0.334167 | 0.005137 | 0.013577 | 0.008051 | 0.049183 | 0.10587 | 0.099496 |
| 0.015161 | 0.450552 | 0.001908 | 0.000474 | 0.001306 | 0.015452 | 0.0013 | 0.005054 |
| 0.228255 | 0.256881 | 0.015188 | 2.042855 | 0.167905 | 0.012314 | 0.001168 | 0.022738 |
| 0.075904 | 0.090569 | 0.998549 | 0.365709 | 0.097281 | 0.011443 | 0.014008 | 0.032576 |
| 0.011644 | 0.000343 | 0.428777 | 0.230628 | 4.86E−05 | 0.002298 | 0.00263 | 0.001827 |
| 0.010857 | 0.041172 | 0.569785 | 0.251002 | 0.003487 | 0.002917 | 0.000228 | 0.049558 |
| 0.553687 | 0.032249 | 2.587835 | 0.212342 | 3.528095 | 0.288456 | 0.3995 | 0.334874 |
| 1.881101 | 1.39407 | 2.608247 | 5.640958 | 2.905425 | 3.382533 | 3.625522 | 3.264772 |
| 0.09745 | 0.205479 | 0.006919 | 1.529571 | 0.002172 | 0.406898 | 0.406668 | 0.392639 |
| 0.088367 | 0.1879 | 0.003531 | 1.422245 | 0.001334 | 0.544582 | 0.497167 | 0.448045 |
| 0.073745 | 0.411705 | 0.050465 | 2.857478 | 0.031232 | 0.021848 | 2.32E−05 | 0.017545 |
| 2.135565 | 7.593511 | 7.443301 | 21.58503 | 6.483372 | 0.015106 | 0.397295 | 0.026027 |
| 0.002326 | 0.281183 | 0.116912 | 3.75989 | 0.005391 | 0.000155 | 0.187189 | 3.01E−06 |
| 0.00203 | 0.001256 | 0.429053 | 1.167408 | 0.881466 | 0.000368 | 1.293153 | 0.003785 |
| 2.140705 | 0.032581 | 0.271338 | 0.183877 | 0.493255 | 0.000332 | 0.009473 | 0.003869 |
| 0.081669 | 0.1129 | 0.048356 | 0.589772 | 0.005005 | 0.045024 | 0.055944 | 0.009511 |
| 0.200825 | 0.001546 | 0.025023 | 0.002932 | 0.104969 | 0.002941 | 0.000686 | 3.6E−06 |
| 0.307564 | 0.014904 | 0.008258 | 0.154579 | 0.129163 | 0.018664 | 0.011881 | 0.001256 |
| 0.024982 | 0.024839 | 0.217043 | 3.209979 | 0.04814 | 0.378319 | 0.001855 | 0.005455 |
| 0.113649 | 0.109944 | 0.123902 | 0.654085 | 0.159193 | 0.349209 | 0.04152 | 0.00947 |
| 0.000235 | 0.002431 | 0.007452 | 0.263476 | 0.000971 | 0.361703 | 8.9E−05 | 0.001535 |
| 0.032712 | 0.012734 | 7.01E−05 | 1.121438 | 0.03929 | 2.60709 | 0.043708 | 0.013431 |
| 8.64E−05 | 0.544116 | 0.403369 | 0.015738 | 0.040813 | 0.002022 | 0.850418 | 0.001815 |
| 0.036008 | 0.90794 | 1.173577 | 0.058903 | 0.030765 | 0.011776 | 1.372917 | 0.034482 |
| 0.083546 | 2.182075 | 1.839646 | 0.008314 | 1.236385 | 0.000804 | 0.985782 | 0.003963 |
| 0.001035 | 0.912877 | 0.235384 | 0.000894 | 0.410378 | 0.000619 | 0.761603 | 0.032057 |
| 0.05429 | 0.000669 | 0.141399 | 0.128362 | 0.677922 | 0.003462 | 2.388767 | 0.006091 |
| 5.31E−05 | 0.057004 | 0.117673 | 0.209816 | 0.348265 | 0.0068 | 0.839181 | 0.001194 |
| 0.008647 | 0.000281 | 4.07E−07 | 5.61E−05 | 1.01862 | 0.000584 | 1.764886 | 0.008263 |
| 0.034174 | 0.054556 | 0.000514 | 0.015579 | 0.476874 | 0.018855 | 1.498937 | 0.000436 |
| 0.769033 | 0.838316 | 0.056491 | 0.279088 | 2.392448 | 0.000391 | 0.000247 | 1.542094 |
| 0.054686 | 0.590656 | 0.040206 | 0.118688 | 0.029058 | 0.000849 | 0.386939 | 0.020347 |
| 0.21843 | 0.915598 | 0.000439 | 0.001247 | 0.142989 | 0.000997 | 0.00964 | 0.191585 |
| 0.09425 | 0.911891 | 0.003317 | 0.000931 | 0.167443 | 0.005401 | 0.470805 | 0.226628 |

TABLE 27

2-THF-4

| | | THF | | | | | log σ$_{Lg,c}$ | | | |
|---|---|---|---|---|---|---|---|---|---|---|
| k4 | k5 | k1 | k2 | k3 | k4 | k5 | H$_2$O | EtOH | Benzene | Hexane |
| 0.045833 | 0.014044 | 0.109721 | 1.499129 | 0.005407 | 0.012941 | 2.27E−07 | −0.27945 | 0.398827 | −0.12502 | −0.55113 |
| 0.002883 | 0.009902 | 0.20684 | 0.413888 | 0.008834 | 0.001685 | 0.001369 | −0.0226 | 0.248584 | −0.25239 | −0.32497 |
| 0.000606 | 5.28E−05 | 0.25907 | 0.181126 | 2.86E−05 | 0.000108 | 0.000701 | −0.5571 | 0.239137 | −0.39623 | −0.61155 |
| 0.041134 | 0.055046 | 8.475501 | 0.13558 | 0.14089 | 0.033916 | 0.02064 | −0.53188 | −0.1312 | −0.52282 | −0.89179 |
| 0.428199 | 0.46436 | 0.011377 | 7.43E−05 | 0.287165 | 0.99811 | 0.010221 | −0.7075 | −0.13743 | 0.044038 | −0.64421 |
| 1.585586 | 1.325767 | 0.053752 | 0.001513 | 7.805723 | 3.774128 | 0.028713 | −0.42382 | −0.15439 | −0.11099 | −1.14907 |
| 0.128637 | 0.114048 | 0.000951 | 0.000983 | 0.259783 | 0.915828 | 0.000885 | −0.42179 | −0.09534 | 0.33565 | −1.22368 |
| 0.018725 | 0.000585 | 0.000216 | 1.29E−06 | 0.232862 | 0.916578 | 0.001844 | −0.40275 | 0.458128 | 0.175373 | −1.11758 |
| 0.003085 | 0.00722 | 0.20374 | 0.04698 | 0.009858 | 0.146204 | 0.00123 | −0.91872 | −0.22917 | −0.95407 | −0.36169 |
| 0.035912 | 0.068586 | 0.006241 | 0.000344 | 0.00021 | 0.236666 | 0.000533 | −0.17315 | −0.39424 | −0.01421 | −0.13507 |
| 0.00031 | 0.005866 | 0.000733 | 0.00372 | 0.005864 | 0.04686 | 0.013365 | −0.83614 | −0.65358 | −0.29561 | −0.0715 |
| 0.006606 | 0.003449 | 0.134329 | 0.059649 | 0.034128 | 0.001286 | 0.029424 | −0.6724 | −1.1222 | 0.043635 | −0.11942 |
| 0.334071 | 0.426172 | 0.500015 | 0.447586 | 0.538195 | 0.580954 | 0.456832 | 0.371859 | −0.99151 | −0.41346 | −0.38187 |
| 3.233939 | 3.434508 | 7.517357 | 6.829003 | 7.470976 | 9.110181 | 6.900001 | −0.16865 | −1.23994 | −0.55346 | −0.28183 |
| 0.397815 | 0.45186 | 0.550334 | 0.553489 | 0.593904 | 0.674751 | 0.559311 | −0.0813 | −1.29443 | −0.40318 | −0.17188 |
| 0.430916 | 0.384473 | 0.697104 | 0.584352 | 0.597975 | 0.86597 | 0.573932 | 0.04032 | −1.12337 | −0.28638 | 0.033897 |
| 0.009683 | 4.517922 | 0.009307 | 0.015834 | 0.005837 | 0.005337 | 0.019978 | 0.191785 | −0.22819 | −0.94597 | −1.15407 |
| 0.049719 | 0.460697 | 0.006794 | 1.06E−09 | 0.011042 | 0.001644 | 0.068286 | −0.11037 | −0.07316 | −1.25623 | −0.34122 |
| 6.98E−05 | 0.293062 | 0.000748 | 0.001188 | 0.000744 | 0.002984 | 3.66E−06 | −0.54554 | −0.75784 | −0.37232 | −0.33503 |
| 0.021038 | 0.244182 | 7.98E−05 | 0.007516 | 0.002343 | 0.002914 | 0.010023 | −0.54083 | −0.73936 | −0.23667 | −0.51182 |
| 0.012801 | 0.005566 | 0.003447 | 0.000101 | 0.025843 | 0.068551 | 0.002127 | −1.05253 | −1.09551 | −0.50347 | 0.125804 |
| 0.0255 | 0.039617 | 0.007195 | 0.001842 | 0.000677 | 0.105342 | 0.014587 | −1.54088 | −1.18116 | −0.45473 | −0.12365 |
| 0.000265 | 2.08E−05 | 0.000287 | 1.72E−05 | 1.54E−05 | 0.002349 | 7.77E−05 | −0.16437 | −1.13825 | −0.67257 | −0.61878 |
| 0.000733 | 0.01363 | 0.000539 | 0.002744 | 0.012084 | 0.006364 | 0.007085 | −0.59311 | −1.11749 | −0.54994 | −0.24084 |
| 0.000997 | 0.010994 | 0.001547 | 1.330396 | 0.001538 | 0.015075 | 0.004767 | −0.791 | −0.46094 | −0.13148 | −0.8441 |
| 0.000721 | 0.009797 | 0.006931 | 0.186535 | 0.004931 | 0.020585 | 8.53E−05 | −0.30458 | −0.04454 | −1.15475 | −1.10002 |
| 3.21E−05 | 0.001655 | 0.000224 | 0.216973 | 0.00031 | 0.001017 | 0.000593 | −0.14548 | −0.29639 | −0.3181 | −1.07174 |
| 0.002175 | 0.020629 | 0.012552 | 0.166964 | 0.00934 | 0.000934 | 0.001817 | −0.15455 | −0.13279 | −0.21329 | −0.67837 |
| 0.000834 | 1.69E−05 | 0.001162 | 0.010153 | 0.001793 | 0.007769 | 0.000547 | −0.62735 | 0.089626 | −0.60433 | −0.2829 |
| 5.93E−06 | 0.006075 | 0.000534 | 0.000112 | 0.003693 | 0.00886 | 3.54E−05 | −0.90372 | −0.23395 | −0.70282 | −0.41213 |
| 0.001259 | 0.000112 | 0.000442 | 0.002838 | 0.000117 | 0.004365 | 0.000596 | −0.75676 | −0.16047 | 0.069012 | −0.27628 |
| 0.003801 | 0.003559 | 0.000652 | 0.020588 | 0.000995 | 0.001878 | 1.88E−05 | −0.97667 | 0.048629 | −0.20526 | 0.111701 |
| 0.67597 | 0.016663 | 0.023487 | 0.013543 | 0.026043 | 0.069584 | 0.01957 | −0.10314 | −0.45305 | −0.63388 | 0.038614 |
| 0.687028 | 0.000737 | 0.04946 | 0.00155 | 0.116252 | 0.266073 | 0.029358 | −0.20565 | −0.12083 | 0.069844 | −0.15347 |
| 0.828113 | 0.000461 | 0.001905 | 0.003806 | 0.001112 | 0.000278 | 0.005039 | −0.25904 | 0.189343 | 0.446272 | −0.10431 |
| 0.78993 | 0.00327 | 0.013526 | 0.024568 | 0.051394 | 0.061569 | 0.002317 | −0.1905 | 0.489136 | 0.408102 | −0.21624 |
| 0.000482 | 0.036796 | 0.000507 | 0.021455 | 0.025026 | 1.83E−06 | 0.057528 | −0.18367 | −1.36604 | −0.93406 | 0.227763 |
| 0.014582 | 0.001309 | 0.00096 | 0.84661 | 1.20239 | 0.00026 | 0.642628 | −0.56828 | 0.228993 | −0.9417 | 0.117962 |
| 0.004996 | 1.45E−06 | 0.000452 | 0.088984 | 0.046542 | 0.00012 | 0.012534 | −0.16197 | 0.020417 | −1.34016 | 0.391301 |
| 0.026127 | 0.03733 | 0.000478 | 0.06092 | 0.192173 | 5.72E−06 | 0.064767 | −0.17728 | 0.066696 | −1.43918 | −0.00175 |

| log σ$_{Lg,c}$ | | log σ$_{θg,c}$ | | | | | |
|---|---|---|---|---|---|---|---|
| AcOEt | THF | H$_2$O | EtOH | Benzene | Hexane | AcOEt | THF |
| 0.32871 | −0.08107 | 0.801234 | 1.207714 | 1.079374 | 0.189762 | 0.866507 | 1.150356 |
| −0.10168 | 0.215972 | 0.729341 | 0.669981 | 1.252097 | 0.229623 | 0.939489 | 1.183314 |
| 0.447759 | −0.12574 | 0.714165 | 0.547705 | 0.999054 | 0.229044 | 1.090265 | 1.080704 |
| 0.355916 | −0.55732 | 0.722126 | 0.465178 | 1.117856 | 0.1627 | 0.785955 | 0.3326 |
| −1.19739 | −0.06096 | 0.5606 | 0.605007 | 0.795256 | 0.743116 | −0.2618 | 1.272964 |
| −1.08912 | −0.0579 | 0.53307 | 0.957349 | 1.134892 | 1.126902 | −0.39762 | 0.636763 |
| −1.29606 | −0.19802 | 0.576843 | 0.985589 | 0.696795 | 0.874959 | −0.37434 | 1.23767 |
| −1.11766 | −0.44338 | 0.594635 | 0.995588 | 1.106001 | 0.863036 | −0.35685 | 1.205117 |
| −0.08808 | −0.54633 | 1.376427 | 0.970049 | 0.644553 | 1.15028 | 0.84218 | 0.01585 |
| 0.117575 | −0.50368 | 1.295079 | 0.951724 | 0.980232 | 1.301856 | 0.750527 | 0.170075 |
| 0.061467 | −0.58296 | 0.444318 | 0.974456 | 0.722887 | 0.901578 | 0.922287 | 0.046107 |
| 0.057921 | −0.63334 | 0.472307 | 1.012566 | 0.702096 | 0.794673 | 1.032039 | 0.070549 |
| −0.37755 | −0.48677 | 0.961614 | 1.035338 | 0.756087 | 0.997163 | 0.862225 | 0.689686 |
| −0.55965 | −1.19113 | 1.01892 | 1.0191 | 0.857216 | 1.099827 | 0.859037 | 0.505935 |
| −0.38782 | −0.72924 | 0.654436 | 1.034736 | 0.789613 | 1.216736 | 0.834254 | 0.678971 |
| −0.15015 | −0.82075 | 0.619903 | 1.091146 | 0.840677 | 1.260704 | 0.774444 | 0.696334 |
| 0.02776 | −0.90701 | 1.044944 | 0.990337 | −0.16622 | 0.883427 | 0.852136 | 0.731865 |
| 0.011325 | −0.71451 | 0.951797 | 1.037002 | 0.532775 | −0.79673 | 1.082475 | 0.682279 |
| 0.564229 | −0.99709 | 1.059034 | 1.038236 | 0.205231 | −0.45793 | 1.088727 | 0.735329 |
| 0.321599 | −0.41743 | 1.050676 | 1.083144 | 0.128321 | −0.33163 | 1.021132 | 0.783396 |
| −0.91843 | −0.05209 | 0.656551 | 0.717663 | 1.123837 | 0.642526 | 1.106472 | 0.582546 |
| −0.52523 | −0.15205 | 0.594566 | 0.691442 | 0.946763 | 0.738585 | 1.094102 | 0.904087 |
| −1.01393 | −0.17641 | 0.879033 | 0.762743 | 1.111363 | 0.709606 | 1.104812 | 0.776997 |
| −1.39596 | −0.26371 | 0.860382 | 0.844861 | 0.831881 | 0.830535 | 1.095595 | 0.802764 |
| −1.78544 | −1.54092 | 0.909549 | 0.899793 | 0.836804 | 0.622138 | 0.89432 | 1.315317 |
| −0.25395 | −0.88242 | 0.906718 | 0.842321 | 0.733571 | 0.646614 | 0.880259 | 1.176445 |
| −0.91017 | −1.11347 | 0.706513 | 0.779633 | 0.822822 | 0.725209 | 0.912419 | 1.213009 |
| −0.81836 | −1.39507 | 0.671983 | 0.555389 | 0.947994 | 0.74445 | 1.008622 | 1.180359 |
| −0.47458 | −0.25747 | 0.40447 | 0.757171 | 0.997815 | 0.85769 | 1.104346 | 0.999825 |

TABLE 27-continued

2-THF-4

| | | | | | | | |
|---|---|---|---|---|---|---|---|
| −0.27044 | 0.204271 | 0.071537 | 0.602741 | 1.225844 | 0.825294 | 1.052402 | 1.112113 |
| −0.31088 | 0.087425 | 0.907564 | 0.618479 | 1.213651 | 0.576452 | 1.166429 | 1.023458 |
| −0.27363 | −0.07046 | 0.950403 | 0.619702 | 1.220683 | 1.165549 | 1.218396 | 1.152418 |
| 0.083506 | −0.32954 | 0.634833 | 0.739149 | −0.20836 | 0.612456 | 0.535352 | 0.228705 |
| 0.56292 | −0.3326 | 0.551091 | 0.864869 | 0.855276 | 0.850432 | 0.930297 | 0.188121 |
| 0.630582 | −0.87208 | 0.582188 | 0.645764 | 0.006498 | 0.60461 | 0.689769 | 0.163691 |
| 0.388878 | −0.91419 | 0.584172 | 0.450962 | 0.931221 | 0.69898 | 0.643733 | 0.089592 |
| 0.666495 | 0.047935 | 0.768615 | 0.7843 | 0.198057 | 0.592487 | 0.754077 | 0.893002 |
| 0.073392 | 0.670118 | 0.836437 | 0.813008 | 0.568256 | 1.022759 | 0.875654 | 0.682508 |
| 0.158097 | 0.439682 | 0.683124 | 0.702989 | 0.698545 | 0.987988 | 0.895158 | 0.95815 |
| −0.09715 | −0.05799 | 0.699085 | 0.915385 | 1.181083 | 1.161702 | 0.945869 | 1.024418 |

(B) Data in Analysis Example 3

TABLE 28

3-H2O-1

| | | $r_{u,mn}$ | $(r_{u,mn}-r_{g,mnk})^2/\sigma_{rg,mn}^2$ | | | | | | |
|---|---|---|---|---|---|---|---|---|---|
| | | $H_2O$ | $H_2O$ | | | | | EtOH | | |
| f | Ku', mn | k5 | k1 | k2 | k3 | k4 | k5 | k1 | k2 | k3 |
| 0.05 Hz | Ku', 12 | 0.153385 | 2.626306 | 1.157602 | 0.006243 | 0.452793 | 3.271986 | 40.02722 | 55.56901 | 31.28706 |
| | Ku', 13 | 15.15589 | 3.314155 | 5.693374 | 0.321013 | 0.993656 | 1.983925 | 19.80165 | 38.65417 | 22.14679 |
| | Ku', 14 | 21.82819 | 2.904381 | 5.818667 | 0.297363 | 1.074143 | 1.578404 | 0.056373 | 2.734085 | 0.003051 |
| | Ku', 23 | 98.80976 | 3.263832 | 2.672568 | 0.063897 | 0.483386 | 3.036855 | 5.276851 | 1.430714 | 0.227584 |
| | Ku', 24 | 142.3102 | 3.273736 | 2.90949 | 0.063026 | 0.548772 | 2.963684 | 2.905443 | 0.123547 | 2.428759 |
| | Ku', 34 | 1.440245 | 1.945654 | 0.212154 | 0.176485 | 7.41E−08 | 2.771331 | 1.505977 | 0.019668 | 3.132534 |
| 0.1 Hz | Ku', 12 | 0.143238 | 3.206458 | 2.143246 | 0.237177 | 0.434294 | 0.007669 | 110.9124 | 88.19078 | 88.90345 |
| | Ku', 13 | 21.09035 | 0.223076 | 1.704871 | 0.357955 | 1.23458 | 0.017527 | 47.81364 | 59.1995 | 61.88843 |
| | Ku', 14 | 31.75012 | 0.034534 | 2.496805 | 0.391942 | 1.133068 | 0.018623 | 0.005398 | 0.005532 | 0.023559 |
| | Ku', 23 | 147.2399 | 2.410599 | 0.024272 | 0.001205 | 0.021087 | 0.000261 | 0.006015 | 0.612569 | 0.75331 |
| | Ku', 24 | 221.6901 | 2.339706 | 0.002001 | 0.001133 | 0.026802 | 0.000267 | 0.021354 | 0.0111 | 0.001903 |
| | Ku', 34 | 1.505435 | 1.666761 | 1.555537 | 0.006108 | 3.03E−05 | 0.000157 | 0.03697 | 0.07041 | 0.026929 |
| 0.15 Hz | Ku', 12 | 0.125762 | 0.068072 | 0.435684 | 0.021029 | 1.352085 | 0.123384 | 7.884941 | 3.298153 | 5.035944 |
| | Ku', 13 | 11.97089 | 1.017066 | 0.059516 | 2.48889 | 0.041085 | 0.072227 | 8.222862 | 5.969316 | 7.535337 |
| | Ku', 14 | 17.83217 | 0.800718 | 0.014669 | 2.853862 | 0.011847 | 0.054656 | 0.005167 | 0.118809 | 0.00123 |
| | Ku', 23 | 95.18687 | 1.359991 | 1.105564 | 1.156444 | 0.277771 | 0.318679 | 0.168202 | 0.072163 | 0.018352 |
| | Ku', 24 | 141.7931 | 1.38245 | 0.760208 | 1.685297 | 0.219239 | 0.302327 | 1.962601 | 0.877141 | 0.655221 |
| | Ku', 34 | 1.489628 | 0.100344 | 0.363951 | 1.746287 | 0.397788 | 0.0081 | 4.882024 | 5.139427 | 3.230425 |
| 0.2 Hz | Ku', 12 | 0.117152 | 4.0658 | 3.365945 | 0.445342 | 0.459161 | 0.336643 | 16.49582 | 13.86775 | 12.68336 |
| | Ku', 13 | 15.95981 | 0.234341 | 2.372139 | 0.114219 | 0.020804 | 0.051447 | 24.84136 | 19.82688 | 19.77629 |
| | Ku', 14 | 22.97689 | 0.025073 | 2.350345 | 0.186526 | 0.013802 | 0.053716 | 1.818068 | 0.69215 | 0.947449 |
| | Ku', 23 | 136.2321 | 2.683545 | 0.054695 | 0.010684 | 0.179349 | 0.169931 | 4.559317 | 1.71573 | 3.203148 |
| | Ku', 24 | 196.1295 | 2.721231 | 0.020608 | 0.001286 | 0.094896 | 0.098736 | 7.721246 | 15.76239 | 8.160561 |
| | Ku', 34 | 1.439672 | 2.106559 | 0.155728 | 0.123595 | 0.008622 | 8.25E−06 | 24.64722 | 28.53642 | 21.37692 |
| 0.25 Hz | Ku', 12 | 0.069243 | 0.005265 | 1.373469 | 0.371253 | 1.045575 | 0.224053 | 1.53608 | 0.508038 | 1.076767 |
| | Ku', 13 | 10.9113 | 0.876921 | 0.05014 | 1.595929 | 0.109832 | 0.323337 | 4.166046 | 2.164385 | 3.082497 |
| | Ku', 14 | 13.54974 | 1.206918 | 0.246381 | 2.118528 | 0.048232 | 0.167786 | 0.045577 | 0.385763 | 0.031239 |
| | Ku', 23 | 157.5789 | 1.274147 | 0.077981 | 0.604729 | 0.025404 | 0.218065 | 1.710918 | 1.020117 | 1.161097 |
| | Ku', 24 | 195.6826 | 1.807152 | 0.005053 | 0.952918 | 0.002432 | 0.066094 | 0.096964 | 1.34754 | 0.620732 |
| | Ku', 34 | 1.241807 | 1.023885 | 4.457106 | 1.126202 | 3.569365 | 7.063924 | 3.332656 | 10.8336 | 6.651106 |
| 0.3 Hz | Ku', 12 | 0.111851 | 3.517111 | 0.536037 | 0.001257 | 0.179526 | 0.407621 | 108.7315 | 74.60139 | 92.11381 |
| | Ku', 13 | 17.9267 | 2.143988 | 0.034722 | 0.010613 | 0.003411 | 0.030912 | 936.2297 | 853.7375 | 874.3428 |
| | Ku', 14 | 23.68647 | 2.051202 | 0.054713 | 0.001764 | 0.108521 | 0.071954 | 25.75396 | 10.92937 | 17.93603 |
| | Ku', 23 | 180.273 | 2.568881 | 0.001987 | 0.001137 | 0.006163 | 0.001061 | 4.085984 | 13.06678 | 8.772654 |
| | Ku', 24 | 211.768 | 2.812898 | 0.021754 | 0.000239 | 0.031568 | 0.011763 | 6.840723 | 6.057853 | 6.393783 |
| | Ku', 34 | 1.321296 | 1.710909 | 0.119996 | 0.079197 | 0.03155 | 0.069726 | 14.85288 | 29.12633 | 19.00234 |
| 0.35 Hz | Ku', 12 | 0.089726 | 0.094147 | 2.459261 | 0.015467 | 0.078281 | 0.030877 | 1.110903 | 1.407239 | 1.054291 |
| | Ku', 13 | 11.9285 | 0.333627 | 0.021783 | 2.047519 | 0.190354 | 6.36E−06 | 4.876478 | 5.704064 | 5.651321 |
| | Ku', 14 | 16.98813 | 0.50176 | 0.216732 | 1.970047 | 0.255738 | 0.013627 | 0.178951 | 0.572327 | 0.099257 |
| | Ku', 23 | 132.9486 | 1.48283 | 0.195329 | 0.302525 | 0.133935 | 0.019691 | 0.081365 | 0.000406 | 0.898895 |
| | Ku', 24 | 189.3342 | 1.625275 | 0.16185 | 0.215652 | 0.138224 | 0.009527 | 4.268299 | 3.13153 | 4.976963 |
| | Ku', 34 | 1.424115 | 0.03446 | 1.831243 | 0.253761 | 0.008492 | 0.335418 | 6.313895 | 3.659031 | 12.95333 |
| 0.4 Hz | Ku', 12 | 0.094141 | 1.642212 | 2.874699 | 0.032121 | 0.554555 | 0.453153 | 3.379205 | 4.931734 | 9.209386 |
| | Ku', 13 | 8.03614 | 1.647977 | 0.077644 | 2.30217 | 0.283449 | 0.861752 | 2.330129 | 3.285654 | 3.297988 |
| | Ku', 14 | 12.4428 | 1.355995 | 0.17694 | 1.94332 | 0.516758 | 0.915989 | 2.050674 | 0.007697 | 0.0349 |
| | Ku', 23 | 85.36283 | 4.514893 | 0.036436 | 1.22013 | 0.535406 | 1.207197 | 0.150376 | 0.345978 | 4.845989 |
| | Ku', 24 | 132.1721 | 4.600335 | 0.025609 | 1.0607 | 1.01635 | 1.402565 | 4.477761 | 0.384582 | 1.857051 |
| | Ku', 34 | 1.648358 | 2.528207 | 0.586018 | 2.670303 | 0.008895 | 0.946812 | 6.328963 | 0.200851 | 0.328045 |
| 0.45 Hz | Ku', 12 | 0.088401 | 1.40082 | 0.302463 | 1.96E−05 | 0.391111 | 0.855724 | 6.512243 | 4.665191 | 5.711036 |
| | Ku', 13 | 61.23301 | 33.2085 | 42.66764 | 27.90206 | 44.703 | 26.37461 | 33.34524 | 32.57737 | 34.07047 |

TABLE 28-continued

3-H2O-1

|  | Ku', 14 | 41.61707 | 4.212903 | 10.51137 | 2.768546 | 10.36855 | 7.655392 | 0.196203 | 0.228906 | 0.223234 |
|---|---|---|---|---|---|---|---|---|---|---|
|  | Ku', 23 | 692.6718 | 7.714327 | 17.22337 | 10.48352 | 16.06992 | 6.180433 | 12.73916 | 12.89752 | 13.29044 |
|  | Ku', 24 | 470.775 | 0.026509 | 4.214024 | 0.91497 | 2.368298 | 0.999167 | 0.014886 | 0.044549 | 0.024799 |
|  | Ku', 34 | 0.679651 | 5.425678 | 4.81077 | 4.109181 | 8.861737 | 0.620231 | 1.390769 | 0.665791 | 1.388184 |
| 0.5 Hz | Ku', 12 | 0.109345 | 13.33184 | 3.09251 | 4.767134 | 5.512627 | 6.445713 | 0.151179 | 0.142792 | 0.145176 |
|  | Ku', 13 | 18.06198 | 0.602055 | 0.061319 | 0.593568 | 0.536904 | 1.094342 | 1.386342 | 1.214764 | 1.392435 |
|  | Ku', 14 | 23.30611 | 0.362573 | 0.057687 | 0.13821 | 0.901377 | 9.603245 | 0.293231 | 0.171611 | 0.214123 |
|  | Ku', 23 | 165.1828 | 4.383133 | 0.366937 | 0.319856 | 2.60087 | 0.395933 | 8.085191 | 4.624924 | 9.068773 |
|  | Ku', 24 | 213.1422 | 1.579808 | 0.666739 | 0.191158 | 3.832465 | 0.028066 | 0.278082 | 0.807872 | 0.123973 |
|  | Ku', 34 | 1.290341 | 0.268942 | 0.438138 | 0.001153 | 0.867241 | 0.451691 | 3.024732 | 8.826425 | 11.97302 |

| | | $(r_{u,mn} - r_{g,mn})^2 / \sigma_{rg,mn}^2$ | | | | | | | |
|---|---|---|---|---|---|---|---|---|---|
| | | EtOH | | Benzene | | | | | |
| f | Ku', mn | k4 | k5 | k1 | k2 | k3 | k4 | k5 | k1 |
| 0.05 Hz | Ku', 12 | 48.13344 | 39.43968 | 5.370007 | 0.629707 | 2.839072 | 4.277746 | 6.895764 | 65.05191 |
|  | Ku', 13 | 28.44524 | 22.59994 | 204.2142 | 164.2441 | 205.2504 | 193.9052 | 214.1331 | 34.11505 |
|  | Ku', 14 | 0.104393 | 0.001462 | 16.0677 | 8.433925 | 15.33638 | 10.43588 | 22.17737 | 26.52638 |
|  | Ku', 23 | 3.836589 | 2.645587 | 4.466271 | 8.992134 | 9.437696 | 5.463433 | 1.816457 | 6.13931 |
|  | Ku', 24 | 4.469555 | 4.082469 | 0.27815 | 0.5151 | 0.373282 | 0.562506 | 0.324751 | 5.036578 |
|  | Ku', 34 | 3.053633 | 3.182773 | 6.142953 | 4.939213 | 7.612646 | 11.17918 | 2.026536 | 3.245541 |
| 0.1 Hz | Ku', 12 | 93.12673 | 119.8574 | 47.64651 | 39.63376 | 39.46083 | 52.73734 | 65.92533 | 420.6551 |
|  | Ku', 13 | 55.42473 | 37.4336 | 37.7561 | 21.28234 | 38.07935 | 38.94533 | 38.60024 | 489.9639 |
|  | Ku', 14 | 0.003349 | 2.217394 | 13.68496 | 5.19067 | 15.38989 | 13.43411 | 16.10071 | 191.1861 |
|  | Ku', 23 | 0.322115 | 0.659105 | 1.970889 | 0.0385 | 0.631383 | 1.842415 | 0.035853 | 0.435291 |
|  | Ku', 24 | 0.016103 | 2.836836 | 0.005304 | 2.844752 | 0.596245 | 0.375067 | 2.847144 | 0.146424 |
|  | Ku', 34 | 0.038446 | 3.236174 | 4.624128 | 1.044108 | 2.448344 | 8.116553 | 2.128184 | 0.056378 |
| 0.15 Hz | Ku', 12 | 6.44482 | 13.7039 | 13.468 | 17.70311 | 16.08755 | 16.10879 | 6.025828 | 4.255544 |
|  | Ku', 13 | 2.72955 | 12.97271 | 30.98506 | 39.80579 | 34.23307 | 35.07604 | 19.77046 | 2.627042 |
|  | Ku', 14 | 1.521538 | 0.614446 | 0.941121 | 1.622992 | 0.988536 | 1.134802 | 0.232771 | 4.799155 |
|  | Ku', 23 | 1.584243 | 1.323682 | 0.004267 | 0.329667 | 1.01007 | 0.560651 | 0.613614 | 0.016526 |
|  | Ku', 24 | 6.634462 | 1.3496 | 3.572493 | 7.910329 | 14.04618 | 9.968476 | 11.46603 | 0.008883 |
|  | Ku', 34 | 9.056451 | 1.161819 | 1.168743 | 1.658492 | 2.251424 | 1.854609 | 8.132835 | 1.152477 |
| 0.2 Hz | Ku', 12 | 5.732797 | 17.34042 | 226.5979 | 182.9497 | 218.815 | 221.0251 | 188.7496 | 33.36305 |
|  | Ku', 13 | 9.744677 | 21.33301 | 1082.66 | 1055.084 | 1076.627 | 1083.859 | 976.5125 | 37.45839 |
|  | Ku', 14 | 0.164716 | 1.694623 | 10.95154 | 13.63527 | 16.04659 | 18.80357 | 6.140049 | 15.99501 |
|  | Ku', 23 | 1.331651 | 0.076706 | 0.258227 | 5.690402 | 0.947558 | 0.895776 | 1.507391 | 1.107254 |
|  | Ku', 24 | 19.49634 | 12.943 | 3.321463 | 0.12329 | 0.38135 | 0.079172 | 2.329055 | 0.935886 |
|  | Ku', 34 | 31.94915 | 14.61579 | 4.158986 | 1.520582 | 0.849686 | 0.260093 | 4.579098 | 2.518296 |
| 0.25 Hz | Ku', 12 | 0.157614 | 0.0037 | 33.6022 | 32.61441 | 52.8768 | 45.50165 | 33.47484 | 3.18098 |
|  | Ku', 13 | 0.318819 | 5.959491 | 22.8817 | 10.88164 | 22.55481 | 26.41233 | 20.97103 | 8.703589 |
|  | Ku', 14 | 0.736853 | 0.214664 | 1.21934 | 0.486836 | 2.367206 | 2.524592 | 0.016052 | 7.546906 |
|  | Ku', 23 | 0.857854 | 6.913823 | 0.567393 | 0.419289 | 0.365816 | 0.443206 | 0.30858 | 8.574508 |
|  | Ku', 24 | 1.35922 | 0.267595 | 0.18128 | 0.795825 | 0.457445 | 0.024278 | 3.975552 | 0.131687 |
|  | Ku', 34 | 9.907325 | 3.222153 | 0.577613 | 0.078424 | 0.035376 | 0.181072 | 3.683376 | 0.287885 |
| 0.3 Hz | Ku', 12 | 97.09999 | 105.4449 | 54.31022 | 48.31864 | 77.03288 | 68.12158 | 55.7688 | 9.467728 |
|  | Ku', 13 | 955.8103 | 916.2577 | 744.9001 | 678.2071 | 726.6803 | 777.2669 | 702.6498 | 48.7414 |
|  | Ku', 14 | 22.3577 | 14.44809 | 33.83623 | 22.03969 | 33.67595 | 36.89762 | 20.75867 | 61.37965 |
|  | Ku', 23 | 10.2973 | 4.166229 | 1.080463 | 1.497923 | 0.200793 | 1.284027 | 1.227691 | 7.723637 |
|  | Ku', 24 | 6.075401 | 16.06696 | 0.00263 | 0.08281 | 2.186736 | 0.046104 | 0.861356 | 0.298302 |
|  | Ku', 34 | 21.54488 | 30.62325 | 0.823958 | 3.060309 | 0.494761 | 0.713421 | 5.474912 | 0.079623 |
| 0.35 Hz | Ku', 12 | 0.236513 | 1.126226 | 90.73294 | 94.83674 | 72.30768 | 94.4864 | 58.44037 | 124.7194 |
|  | Ku', 13 | 0.568108 | 5.442814 | 369.8437 | 405.6869 | 356.1821 | 364.6115 | 330.5181 | 142.09 |
|  | Ku', 14 | 0.934424 | 0.530802 | 37.31958 | 43.15568 | 33.22981 | 29.76523 | 22.02029 | 70.37638 |
|  | Ku', 23 | 3.310903 | 0.224452 | 0.087214 | 0.045084 | 0.559291 | 0.992499 | 0.327521 | 0.614326 |
|  | Ku', 24 | 0.222006 | 1.70442 | 0.430458 | 0.120711 | 0.012506 | 3.747823 | 0.385639 | 0.008349 |
|  | Ku', 34 | 5.638656 | 3.356578 | 1.073404 | 1.102991 | 1.869329 | 5.420731 | 6.253187 | 0.118633 |
| 0.4 Hz | Ku', 12 | 13.33616 | 7.841902 | 114.837 | 126.7548 | 32.32789 | 113.6806 | 94.39256 | 3.334298 |
|  | Ku', 13 | 11.07806 | 4.624675 | 6.231787 | 1.168561 | 6.848583 | 7.798133 | 7.132512 | 22.2021 |
|  | Ku', 14 | 0.235305 | 0.004859 | 42.18432 | 32.47096 | 45.16828 | 32.20647 | 53.78047 | 19.06172 |
|  | Ku', 23 | 1.871274 | 1.297656 | 0.033331 | 2.498628 | 0.002372 | 0.00016 | 0.00377 | 0.006064 |
|  | Ku', 24 | 0.088062 | 0.862998 | 0.659522 | 3.310006 | 0.049031 | 1.251121 | 0.005687 | 0.022115 |
|  | Ku', 34 | 0.00113 | 0.295954 | 0.147893 | 0.117807 | 0.261021 | 2.615932 | 0.112755 | 0.011808 |
| 0.45 Hz | Ku', 12 | 2.963955 | 0.781621 | 3.774614 | 7.460928 | 12.27661 | 13.09741 | 11.75328 | 16.59533 |
|  | Ku', 13 | 17.68319 | 33.76741 | 51.03854 | 32.09375 | 25.42132 | 53.01501 | 53.2485 | 170.8756 |
|  | Ku', 14 | 1.194168 | 0.302295 | 7.876716 | 2.423902 | 9.961137 | 10.41584 | 10.12718 | 48.22419 |
|  | Ku', 23 | 4.509127 | 15.21533 | 6.660661 | 0.676091 | 5.024205 | 5.003187 | 5.87602 | 30.80371 |
|  | Ku', 24 | 1.84898 | 0.121117 | 0.790028 | 0.643828 | 0.436418 | 0.532432 | 0.626024 | 3.133614 |
|  | Ku', 34 | 5.8563 | 0.350027 | 3.055782 | 1.356987 | 1.935152 | 1.303407 | 3.319713 | 0.642502 |
| 0.5 Hz | Ku', 12 | 1.440098 | 0.141775 | 145.9689 | 117.8813 | 154.8145 | 159.0167 | 134.8251 | 2.890135 |
|  | Ku', 13 | 0.124409 | 0.301572 | 220.1777 | 194.6036 | 234.9808 | 230.5891 | 190.2915 | 3.185549 |
|  | Ku', 14 | 1.237599 | 0.195335 | 48.22778 | 44.66193 | 66.61366 | 51.79701 | 39.32024 | 32.65663 |
|  | Ku', 23 | 16.52467 | 6.91283 | 1.641759 | 2.626233 | 3.229035 | 0.648745 | 0.001584 | 1.804111 |
|  | Ku', 24 | 0.559595 | 0.28175 | 1.57375 | 0.139876 | 0.052657 | 3.705105 | 1.715809 | 11.66643 |
|  | Ku', 34 | 11.86115 | 9.739847 | 4.980458 | 1.422554 | 1.177851 | 7.357202 | 2.099832 | 0.000952 |

TABLE 29

3-H2O-2

| Hexane | | | | AcOEt | | | | |
|---|---|---|---|---|---|---|---|---|
| k2 | k3 | k4 | k5 | k1 | k2 | k3 | k4 | k5 |
| 75.50926 | 72.73314 | 48.00505 | 74.70234 | 0.404819 | 0.001973 | 0.875805 | 0.185024 | 0.024778 |
| 47.86347 | 42.98831 | 27.01763 | 44.63184 | 2.997306 | 3.754951 | 0.134828 | 0.306393 | 2.10107 |
| 44.3195 | 38.83938 | 26.77548 | 40.69478 | 0.052186 | 0.255838 | 1.321648 | 4.267585 | 0.862577 |
| 1.42203 | 4.66003 | 0.867789 | 5.471807 | 0.000443 | 0.22277 | 1.487907 | 0.220735 | 0.068425 |
| 1.112568 | 2.689273 | 0.162713 | 3.043894 | 0.3344 | 0.027721 | 3.621204 | 0.064418 | 0.210606 |
| 1.10517 | 1.112315 | 0.027417 | 1.095686 | 4.096872 | 9.156982 | 3.740809 | 12.72134 | 9.097476 |
| 417.6798 | 450.872 | 452.1924 | 492.0402 | 3.015504 | 11.089 | 5.384837 | 9.970745 | 3.952487 |
| 478.9519 | 507.7038 | 478.8425 | 555.9669 | 359.9688 | 378.6872 | 365.9351 | 353.4723 | 309.9488 |
| 174.9363 | 190.006 | 163.4305 | 214.9345 | 5.058955 | 13.37609 | 11.84205 | 12.27419 | 5.075287 |
| 0.168573 | 0.014804 | 1.326735 | 0.074118 | 59.33554 | 38.73963 | 52.24278 | 35.88745 | 44.1824 |
| 0.033274 | 0.031415 | 2.062564 | 0.031586 | 0.215625 | 3.369415 | 0.063557 | 2.743004 | 0.705036 |
| 0.421772 | 0.156787 | 2.318094 | 0.015781 | 79.38809 | 59.80253 | 57.69171 | 50.68551 | 52.77134 |
| 14.83469 | 12.25226 | 13.38596 | 10.83739 | 0.027834 | 0.359424 | 0.475773 | 1.337494 | 0.61167 |
| 10.44027 | 8.748893 | 9.28832 | 4.150703 | 6.682363 | 5.958982 | 0.764636 | 6.080562 | 4.92549 |
| 13.22153 | 11.24865 | 11.69517 | 4.820348 | 0.119564 | 0.457331 | 4.31544 | 0.169263 | 0.518549 |
| 1.486104 | 0.047923 | 0.307562 | 3.15902 | 0.797615 | 0.130052 | 0.771158 | 0.628415 | 0.003422 |
| 1.432072 | 0.029186 | 0.311583 | 2.583234 | 0.081926 | 0.919505 | 0.125568 | 3.968996 | 1.687271 |
| 0.470136 | 0.000474 | 0.231617 | 0.19887 | 159.4864 | 198.3978 | 181.1388 | 151.3211 | 166.1602 |
| 44.78995 | 52.62521 | 34.47558 | 51.86595 | 11.3449 | 14.05053 | 13.49977 | 9.933302 | 24.73209 |
| 46.80718 | 53.27118 | 32.00374 | 51.55199 | 46.97821 | 56.14697 | 38.46411 | 35.61133 | 33.3589 |
| 27.90592 | 31.42444 | 19.31148 | 29.73693 | 0.241843 | 1.117889 | 0.004572 | 0.014852 | 0.769274 |
| 0.959256 | 0.940665 | 0.308461 | 0.018718 | 4.013117 | 5.062893 | 2.161943 | 2.44212 | 0.170813 |
| 0.470002 | 0.533956 | 0.054802 | 0.242624 | 0.022906 | 0.038311 | 0.260947 | 0.134811 | 2.799951 |
| 0.00458 | 0.000585 | 0.008663 | 0.217144 | 2.124811 | 0.70207 | 2.974067 | 2.294098 | 7.737241 |
| 2.725138 | 5.77822 | 9.576344 | 9.989045 | 3.215222 | 0.452392 | 0.039958 | 0.581811 | 0.475108 |
| 8.637637 | 13.62971 | 19.23126 | 18.76059 | 0.178329 | 1.452721 | 0.158102 | 0.114881 | 0.112702 |
| 14.22111 | 14.42538 | 20.71224 | 19.20444 | 0.145335 | 4.142899 | 0.25479 | 0.156245 | 0.333047 |
| 12.27234 | 13.6909 | 18.5487 | 6.124908 | 0.355399 | 1.209955 | 0.172277 | 0.198145 | 0.189624 |
| 3.412488 | 0.80431 | 1.023897 | 0.000156 | 0.000711 | 3.342426 | 0.350095 | 0.054754 | 0.17993 |
| 1.093164 | 0.035241 | 0.076512 | 0.616957 | 3.485461 | 0.058698 | 3.885622 | 2.151078 | 3.128736 |
| 14.61641 | 15.30891 | 6.665257 | 5.678655 | 0.430173 | 0.240569 | 2.885341 | 4.633641 | 0.978285 |
| 59.00945 | 61.49147 | 36.98074 | 46.98689 | 50.25726 | 32.08541 | 46.65198 | 54.66472 | 37.74178 |
| 68.69874 | 65.84712 | 43.15773 | 59.70001 | 1.847828 | 0.121534 | 0.120795 | 0.219508 | 0.158068 |
| 2.655112 | 5.139577 | 2.991453 | 10.89946 | 15.744 | 9.61833 | 5.829603 | 4.565095 | 8.272037 |
| 0.142118 | 0.761026 | 0.221336 | 1.057457 | 0.360391 | 0.157713 | 1.498998 | 0.828115 | 0.023345 |
| 0.003906 | 2.47274 | 2.96E-05 | 0.038902 | 0.1681 | 2.547368 | 5.253003 | 2.896801 | 1.187372 |
| 152.6549 | 129.6217 | 124.9566 | 180.3676 | 0.319683 | 1.554495 | 0.021912 | 0.068309 | 0.036879 |
| 177.4778 | 155.6518 | 145.8427 | 181.1784 | 6.308259 | 0.59572 | 5.845919 | 3.293673 | 4.812863 |
| 94.1976 | 84.83597 | 65.29024 | 90.0901 | 0.11033 | 2.059469 | 0.150569 | 0.469516 | 0.005014 |
| 6.637416 | 4.872365 | 1.785749 | 2.695711 | 0.123716 | 4.704332 | 2.354073 | 0.522489 | 1.556864 |
| 0.896873 | 0.856872 | 0.298055 | 0.105804 | 2.085456 | 0.048794 | 0.00938 | 0.794955 | 0.035849 |
| 0.114371 | 0.183347 | 1.19208 | 0.923523 | 10.28504 | 5.88271 | 2.031915 | 8.950723 | 3.123096 |
| 3.375439 | 2.603645 | 0.033935 | 3.00456 | 0.022702 | 1.323386 | 2.300558 | 0.011443 | 1.324423 |
| 22.06642 | 9.315197 | 15.50289 | 20.46821 | 0.225291 | 1.806219 | 1.378805 | 0.110921 | 1.491005 |
| 14.32688 | 12.11576 | 13.46761 | 5.893076 | 0.806413 | 0.226072 | 2.563931 | 5.191807 | 2.759235 |
| 0.000825 | 0.816908 | 1.195859 | 0.013342 | 0.01452 | 0.351318 | 2.868085 | 0.005775 | 0.496714 |
| 0.144657 | 0.020672 | 0.582212 | 1.350282 | 0.114242 | 0.733769 | 4.434385 | 0.401119 | 2.144431 |
| 0.192264 | 0.111839 | 0.00543 | 2.043886 | 1.240258 | 2.251589 | 6.825622 | 2.743274 | 7.346474 |
| 32.81959 | 28.57802 | 50.59336 | 31.57508 | 0.049224 | 0.560807 | 0.099073 | 1.163458 | 0.25193 |
| 218.0646 | 204.0805 | 204.2531 | 220.088 | 24.83301 | 19.81352 | 24.97875 | 11.65377 | 26.10314 |
| 70.64888 | 71.13396 | 89.56454 | 76.67379 | 2.208889 | 0.000111 | 2.116144 | 2.316582 | 3.027212 |
| 49.60201 | 45.49346 | 48.96567 | 54.65447 | 419.688 | 425.9393 | 409.226 | 355.489 | 404.0903 |
| 5.897729 | 10.27584 | 10.22856 | 12.20107 | 4.644177 | 2.872556 | 3.380171 | 11.93591 | 3.585809 |
| 3.039933 | 0.001527 | 0.075794 | 0.014096 | 1.875821 | 3.52671 | 2.178111 | 233E-05 | 1.649461 |
| 0.195532 | 4.156898 | 3.147118 | 5.149085 | 0.720591 | 2.168105 | 6.558164 | 0.06485 | 2.375896 |
| 0.129914 | 3.912179 | 3.326711 | 4.353045 | 1.45574 | 0.063374 | 2.704535 | 1.052748 | 1.030263 |
| 23.65322 | 40.12002 | 37.77858 | 45.02775 | 0.37721 | 0.162724 | 4.042041 | 0.112634 | 0.1864 |
| 0.00394 | 2.403081 | 1.832294 | 2.861853 | 0.263203 | 1.39393 | 0.194396 | 0.152088 | 0.010515 |
| 24.94818 | 15.96965 | 22.47331 | 25.36417 | 0.004557 | 1.760508 | 0.003669 | 0.138097 | 2.069904 |
| 3.132783 | 0.006128 | 0.70314 | 0.377518 | 2.309479 | 0.103912 | 0.971791 | 1.445269 | 1.111955 |

| THF | | | | | $\theta_{u,mn}$ $H_2O$ | $H_2O$ | | | |
|---|---|---|---|---|---|---|---|---|---|
| k1 | k2 | k3 | k4 | k5 | k6 | k1 | k2 | k3 | k4 |
| 1.309422 | 7.016431 | 5.099599 | 1.39502 | 1.541547 | −0.37398 | 0.562001 | 3.150712 | 0.019099 | 1.589473 |
| 9.556335 | 7.000541 | 17.10811 | 9.219587 | 17.77164 | −0.46025 | 1.724783 | 3.483425 | 0.228332 | 3.195268 |
| 0.13474 | 0.231365 | 0.306533 | 0.931537 | 0.420442 | −0.53299 | 3.846344 | 9.744341 | 2.777602 | 8.206326 |
| 79.93641 | 103.9613 | 110.3442 | 80.43529 | 94.5719 | −0.08627 | 0.025094 | 1.446623 | 0.258592 | 0.298954 |
| 5.031458 | 11.96857 | 11.48174 | 3.501007 | 9.084046 | −0.15901 | 0.030378 | 0.301264 | 1.560382 | 0.000369 |
| 2.349873 | 0.112423 | 0.98543 | 4.864215 | 0.817211 | −0.07274 | 2.015768 | 8.446304 | 9.294095 | 6.008813 |
| 5.843396 | 7.336144 | 1.709023 | 10.04486 | 7.759786 | −0.171 | 0.029171 | 0.13433 | 0.168825 | 1.628329 |
| 106.1827 | 105.0271 | 98.85126 | 78.7255 | 80.04074 | −0.09946 | 0.057001 | 0.020733 | 6.97E-05 | 0.044309 |

TABLE 29-continued

3-H2O-2

| | | | | | | | | | |
|---|---|---|---|---|---|---|---|---|---|
| 1.52012 | 3.279699 | 1.163077 | 0.02794 | 0.039541 | −0.08766 | 0.238167 | 0.020572 | 0.029744 | 0.032518 |
| 376.2297 | 384.3743 | 316.8103 | 362.2094 | 350.983 | 0.071537 | 0.066351 | 0.000359 | 0.021241 | 0.091506 |
| 27.15509 | 35.22286 | 17.22414 | 21.71517 | 19.58159 | 0.083335 | 0.197214 | 0.000316 | 0.079343 | 0.097839 |
| 8.028178 | 2.741081 | 8.000067 | 11.43215 | 11.51899 | 0.011799 | 2.258589 | 8.61E−06 | 1.17107 | 0.029363 |
| 1.119176 | 1.004458 | 3.033818 | 0.028741 | 0.264049 | −0.07709 | 0.069422 | 0.010731 | 0.291112 | 0.627266 |
| 11.38907 | 12.41094 | 5.865803 | 19.10281 | 9.560676 | −0.37799 | 0.201379 | 0.425829 | 0.070811 | 1.18421 |
| 0.571113 | 1.10575 | 5.341746 | 1.079871 | 4.494331 | −0.32638 | 2.321211 | 0.122003 | 0.162253 | 3.885789 |
| 17.98625 | 16.07299 | 19.89892 | 7.859771 | 11.42757 | −0.3009 | 0.011028 | 0.092206 | 0.348221 | 0.180267 |
| 0.243514 | 0.100701 | 0.064135 | 1.188444 | 0.513529 | −0.24929 | 0.000965 | 0.001323 | 0.215274 | 0.195768 |
| 6.990163 | 10.38227 | 15.34515 | 17.35385 | 18.78079 | 0.05161 | 0.742633 | 3.01327 | 1.022742 | 0.006687 |
| 0.001501 | 0.18325 | 1.975852 | 0.196605 | 0.248341 | −0.38104 | 0.112787 | 2.73229 | 0.038184 | 0.04172 |
| 58.95209 | 50.19698 | 44.41747 | 46.05528 | 70.05625 | −0.37565 | 2.167867 | 0.005836 | 0.038841 | 0.013563 |
| 2.076567 | 0.087751 | 0.056299 | 0.77498 | 3.440896 | −0.36058 | 2.111606 | 0.008236 | 0.058082 | 0.006793 |
| 27.53385 | 32.45946 | 42.36946 | 30.86337 | 20.82701 | 0.005387 | 1.27287 | 0.672355 | 0.006795 | 0.037813 |
| 0.696943 | 0.930095 | 3.653226 | 1.6326 | 0.000997 | 0.020463 | 1.272294 | 0.666141 | 0.014678 | 0.026718 |
| 33.59916 | 48.61644 | 38.16942 | 26.3607 | 43.03644 | 0.015075 | 0.254232 | 0.0868 | 0.651657 | 0.279482 |
| 0.100924 | 0.078941 | 0.665886 | 3.73204 | 0.096003 | −0.33543 | 0.011615 | 0.055854 | 0.207441 | 0.0005 |
| 10.4266 | 13.17084 | 6.869178 | 3.185168 | 9.637601 | 0.134466 | 0.24407 | 0.15366 | 2.005146 | 0.301278 |
| 1.219916 | 2.58E−07 | 0.452198 | 3.177826 | 0.067031 | 0.104801 | 0.426021 | 0.251731 | 2.554373 | 0.485046 |
| 40.83325 | 45.31495 | 50.15025 | 64.06731 | 38.70697 | 0.4698 | 0.152372 | 0.033928 | 0.673588 | 0.156587 |
| 0.957625 | 0.433018 | 0.338847 | 0.502555 | 0.094804 | 0.440235 | 0.241549 | 0.059038 | 0.808296 | 0.235507 |
| 8.410631 | 1.778645 | 2.854441 | 6.451523 | 1.952179 | −0.02967 | 0.637081 | 0.255104 | 0.015679 | 0.434182 |
| 0.035167 | 0.03855 | 0.058823 | 0.007282 | 2.369107 | −0.41946 | 4.013044 | 0.589531 | 2.371564 | 4.788335 |
| 43.22604 | 47.267 | 44.09505 | 62.56337 | 35.65573 | −1.08918 | 0.569343 | 3.210328 | 0.56929 | 0.013521 |
| 0.239288 | 0.231872 | 0.007424 | 2.78765 | 0.031955 | −1.108 | 1.096319 | 3.110262 | 0.662275 | 0.065814 |
| 15.43238 | 16.63079 | 8.169818 | 17.12868 | 23.23165 | −0.58973 | 0.042181 | 2.067091 | 0.09879 | 0.172721 |
| 0.38759 | 0.394357 | 0.324282 | 1.36994 | 1.329129 | −0.68855 | 0.236241 | 2.155146 | 0.146112 | 0.092053 |
| 3.05222 | 4.076849 | 5.925069 | 0.399072 | 4.962399 | −0.01882 | 1.967205 | 0.034896 | 0.072484 | 0.466085 |
| 0.000368 | 0.418462 | 0.060004 | 1.036997 | 0.718255 | −0.27551 | 0.02042 | 0.024281 | 0.211261 | 0.042978 |
| 48.91095 | 36.27333 | 42.53937 | 27.95435 | 47.81954 | −0.32183 | 4.260648 | 0.333653 | 0.279181 | 0.823509 |
| 0.002051 | 1.629875 | 0.119892 | 0.279344 | 0.01372 | −0.35457 | 4.447557 | 0.290731 | 0.089641 | 0.689484 |
| 30.03296 | 30.49653 | 29.25207 | 29.65792 | 15.10035 | −0.04632 | 4.340146 | 0.401575 | 0.133069 | 0.636236 |
| 0.002237 | 0.150169 | 0.164474 | 0.75363 | 0.929681 | −0.07906 | 4.520588 | 0.342387 | 0.176291 | 0.555566 |
| 3.506633 | 8.427069 | 1.721704 | 0.463298 | 3.969711 | −0.03274 | 4.426712 | 0.132283 | 0.338487 | 0.247488 |
| 0.006005 | 0.002737 | 0.045333 | 2.602925 | 0.088779 | −0.22847 | 0.068541 | 1.376049 | 0.10813 | 7.97E−06 |
| 1.199208 | 0.208871 | 1.139071 | 0.418359 | 0.33154 | −0.4174 | 0.000269 | 0.65973 | 1.21291 | 0.017779 |
| 0.063971 | 3.879828 | 0.19087 | 0.118451 | 0.578198 | −0.56509 | 0.037802 | 0.244249 | 1.632969 | 0.08103 |
| 4.557415 | 0.989498 | 1.191587 | 7.067 | 3.618801 | −0.08893 | 0.016797 | 1.558948 | 0.42048 | 0.010345 |
| 0.022218 | 2.407664 | 0.384584 | 0.129928 | 0.120398 | −0.23662 | 0.089514 | 1.087015 | 0.744229 | 0.0412 |
| 0.584215 | 4.243054 | 0.946338 | 0.00858 | 0.921432 | −0.14769 | 0.575307 | 0.855756 | 0.893585 | 0.201248 |
| 5.202749 | 15.6457 | 9.085871 | 6.826092 | 5.001042 | −0.15682 | 0.025173 | 1.938115 | 0.699397 | 0.758363 |
| 717.9564 | 737.9513 | 703.525 | 787.1266 | 687.7563 | −0.88293 | 0.052608 | 0.064871 | 0.00663 | 2.869014 |
| 5.187781 | 9.062035 | 5.667971 | 13.5589 | 3.5327 | −0.47813 | 0.004582 | 0.050497 | 0.184445 | 1.873373 |
| 1164.671 | 1212.907 | 1161.297 | 1251.452 | 1127.005 | −0.72611 | 0.077594 | 0.396439 | 0.09259 | 3.911998 |
| 12.03466 | 19.01315 | 13.68622 | 23.42287 | 9.459084 | −0.32131 | 0.000676 | 0.023129 | 0.044877 | 2.469343 |
| 9.447048 | 4.283648 | 6.558735 | 1.977255 | 9.330285 | 0.404801 | 3.901742 | 9.934964 | 10.88952 | 9.55836 |
| 0.002493 | 2.392427 | 0.000111 | 0.000381 | 0.003052 | −0.03213 | 0.140859 | 1.140768 | 0.08442 | 0.067012 |
| 4.753654 | 2.420565 | 2.318626 | 3.853835 | 0.123214 | −1.11763 | 7.717473 | 3.307501 | 1.711272 | 8.176878 |
| 2.781138 | 0.011437 | 1.850967 | 0.217017 | 0.892488 | −1.05946 | 10.14585 | 2.925567 | 3.081328 | 9.647388 |
| 0.476807 | 1.342703 | 0.327962 | 0.53834 | 0.507856 | −1.0855 | 5.140635 | 3.655049 | 0.680177 | 5.732247 |
| 0.067651 | 2.0371 | 0.304293 | 0.000998 | 0.205398 | −1.02733 | 6.712022 | 4.117788 | 1.12681 | 5.989984 |
| 0.845343 | 1.351593 | 0.048597 | 2.431774 | 0.0227 | 0.058169 | 1.854545 | 2.217684 | 0.054726 | 4.288251 |

TABLE 30

3-H2O-3
$(\theta_{u,mn}-\theta_{g,mnk})^2/\sigma_{\theta g,mn}^2$

| EtOH | | | | | Benzene | | | | |
|---|---|---|---|---|---|---|---|---|---|
| k5 | k1 | k2 | k3 | k4 | k5 | k1 | k2 | k3 | k4 |
| 0.703082 | 0.038695 | 2.125016 | 0.010105 | 0.019075 | 0.011811 | 0.623554 | 0.107613 | 0.716729 | 0.368921 | 0.481641 |
| 5.517547 | 0.210452 | 2.113905 | 0.002946 | 0.182476 | 0.003961 | 0.009731 | 1.662456 | 0.026131 | 0.736466 | 2.98648 |
| 10.36709 | 0.22795 | 2.032554 | 0.02432 | 0.249379 | 0.007376 | 0.042459 | 2.844197 | 0.298648 | 0.772454 | 0.266504 |
| 0.167039 | 0.000118 | 3.259341 | 0.090006 | 0.314669 | 0.09771 | 5.68693 | 3.373224 | 7.158183 | 12.22814 | 3.101577 |
| 0.711054 | 0.019532 | 2.485221 | 5.34E−05 | 0.665107 | 0.050977 | 0.450858 | 0.389401 | 2.211945 | 1.213541 | 0.160873 |
| 3.148104 | 0.103463 | 0.290007 | 0.9637 | 0.831409 | 0.062272 | 0.059211 | 0.002214 | 0.431657 | 0.043605 | 1.733771 |
| 0.135381 | 2.737909 | 2.687996 | 3.709449 | 0.017073 | 1.575957 | 0.045015 | 1.223578 | 0.022335 | 0.065117 | 0.664567 |
| 2.933752 | 2.383761 | 1.425503 | 0.016324 | 0.015153 | 0.002192 | 0.21342 | 0.254264 | 0.048292 | 0.039507 | 3.587579 |
| 3.224654 | 2.814559 | 1.608233 | 0.007643 | 0.107245 | 0.058721 | 0.161054 | 0.149593 | 0.10574 | 0.022135 | 3.536749 |
| 2.339985 | 0.00689 | 0.155021 | 2.705361 | 2.99E−05 | 1.223023 | 0.032314 | 3.538609 | 0.035233 | 0.187083 | 0.361012 |
| 2.375765 | 0.239369 | 0.010743 | 1.523385 | 0.051618 | 0.390988 | 0.000242 | 2.294925 | 0.001031 | 0.102462 | 0.076482 |
| 0.326294 | 3.441102 | 1.794346 | 0.000189 | 0.605556 | 0.46123 | 0.102912 | 0.056615 | 0.199385 | 0.009029 | 3.349599 |
| 3.57241 | 2.18482 | 6.644567 | 2.246986 | 3.858061 | 9.635215 | 0.005165 | 1.24741 | 1.111064 | 0.388375 | 0.312456 |

TABLE 30-continued

3-H2O-3
$(\theta_{u,mn} - \theta_{g,mnk})^2 / \sigma_{\theta g,mn}^2$

| | | | | | | | | | | |
|---|---|---|---|---|---|---|---|---|---|---|
| 0.130826 | 1.024679 | 0.240806 | 0.00019 | 0.038066 | 0.740044 | 2.23543 | 0.065817 | 0.0178 | 0.035738 | 0.370287 |
| 0.836747 | 0.842942 | 0.90297 | 0.603451 | 0.521033 | 0.260645 | 4.871309 | 13.95777 | 3.624999 | 5.526341 | 5.742802 |
| 3.559527 | 14.87257 | 6.711265 | 4.221015 | 4.915529 | 6.894584 | 0.188137 | 1.507116 | 1.402369 | 0.583445 | 0.251381 |
| 2.978015 | 2.311773 | 0.003691 | 0.044073 | 0.002358 | 0.596396 | 0.117702 | 0.211528 | 0.549705 | 0.042514 | 1.078686 |
| 3.250308 | 0.17236 | 1.151425 | 1.481851 | 0.852162 | 0.007832 | 11.0986 | 8.708191 | 2.253864 | 4.82849 | 6.961338 |
| 0.039212 | 0.081878 | 0.502323 | 1.504744 | 0.000824 | 0.011021 | 2.046714 | 0.074714 | 0.171672 | 0.002167 | 0.037795 |
| 0.000338 | 0.000191 | 0.186293 | 0.127725 | 1.292656 | 0.453917 | 0.584523 | 1.297701 | 0.263047 | 0.006413 | 0.31672 |
| 0.005381 | 0.702021 | 0.253144 | 2.533919 | 0.096304 | 1.132877 | 2.655491 | 0.012908 | 1.832303 | 1.109496 | 0.186907 |
| 0.01129 | 0.071126 | 0.051586 | 0.522965 | 1.373495 | 0.344236 | 3.637176 | 0.728626 | 0.575766 | 0.000562 | 0.248038 |
| 0.023321 | 0.750848 | 1.408184 | 1.227433 | 0.175192 | 1.856487 | 1.842426 | 0.140133 | 0.010809 | 0.26924 | 0.00195 |
| 0.944503 | 2.933502 | 2.407645 | 7.583187 | 0.728808 | 1.624447 | 2.864159 | 2.986234 | 11.24928 | 4.278732 | 3.056577 |
| 1.852388 | 0.003216 | 0.003457 | 1.795532 | 1.066625 | 0.052321 | 0.039803 | 0.705457 | 0.044727 | 0.012128 | 1.228396 |
| 4.004248 | 7.36142 | 13.09178 | 12.03207 | 17.94166 | 6.21758 | 0.018441 | 0.009588 | 1.73E−05 | 1.240012 | 1.683999 |
| 4.470387 | 1.764363 | 4.642073 | 5.10791 | 8.425642 | 1.414128 | 0.987225 | 2.131278 | 6.895582 | 3.212738 | 8.828917 |
| 3.770047 | 4.506473 | 6.998289 | 0.58408 | 3.115842 | 4.81899 | 0.087149 | 1.169191 | 6.08061 | 0.235265 | 0.579682 |
| 4.082195 | 5.073629 | 11.76485 | 3.495023 | 11.1052 | 6.044937 | 0.930768 | 3.531071 | 0.964374 | 0.515477 | 0.009789 |
| 0.913859 | 0.03725 | 0.865857 | 1.54514 | 3.152843 | 0.011657 | 2.09432 | 2.098685 | 5.785867 | 0.171079 | 1.668456 |
| 0.393239 | 0.021256 | 0.198853 | 0.010661 | 2.252225 | 0.014507 | 0.242323 | 1.20945 | 0.033457 | 0.113567 | 0.534343 |
| 0.000406 | 2.770842 | 5.509389 | 4.183714 | 12.74057 | 7.218636 | 0.739148 | 2.052918 | 9.848914 | 8.72842 | 8.818535 |
| 0.002287 | 0.142554 | 1.167409 | 0.652767 | 2.120454 | 4.475916 | 1.812272 | 0.000811 | 0.758129 | 0.047044 | 1.486134 |
| 0.017173 | 10.88818 | 12.59639 | 17.45273 | 16.02836 | 26.33087 | 3.217476 | 7.888858 | 5.742022 | 4.069258 | 12.80713 |
| 0.040842 | 0.244511 | 0.775502 | 0.863959 | 0.937494 | 5.482778 | 0.395443 | 0.818208 | 0.261273 | 0.189559 | 2.282266 |
| 0.114177 | 1.123006 | 0.379713 | 0.785158 | 0.537046 | 0.508312 | 0.324139 | 0.987542 | 1.542867 | 5.540568 | 0.524553 |
| 1.829563 | 0.088129 | 0.127605 | 0.471665 | 1.779495 | 0.127534 | 0.433199 | 1.534658 | 0.027711 | 0.022139 | 0.018554 |
| 1.046185 | 0.030505 | 0.104445 | 0.057193 | 2.548686 | 0.005999 | 0.195413 | 1.541957 | 0.006396 | 0.021713 | 0.890145 |
| 1.011076 | 0.004413 | 0.057691 | 0.590109 | 1.339508 | 0.008296 | 1.259667 | 0.017019 | 0.077615 | 1.711684 | 0.047894 |
| 0.167444 | 0.279372 | 0.005861 | 1.004923 | 0.650291 | 0.210002 | 0.142054 | 0.008914 | 0.02046 | 0.000197 | 2.883938 |
| 0.269402 | 0.001538 | 0.167752 | 1.288641 | 0.633748 | 0.001192 | 0.801694 | 0.207764 | 0.05424 | 2.391627 | 0.09799 |
| 0.753057 | 0.068368 | 0.466728 | 1.345484 | 0.56563 | 0.049522 | 1.661295 | 0.269105 | 0.113336 | 3.514316 | 0.052975 |
| 0.033911 | 0.001191 | 0.001565 | 0.027035 | 2.315251 | 0.001308 | 0.011411 | 2.424243 | 0.091191 | 0.013873 | 0.077888 |
| 0.111513 | 0.016422 | 0.003945 | 0.000165 | 2.681615 | 0.004013 | 0.160659 | 3.197587 | 0.019242 | 0.001957 | 0.167242 |
| 0.083761 | 0.041765 | 1.73E−05 | 0.01858 | 2.207378 | 0.000526 | 0.2146 | 3.470813 | 0.000716 | 0.262073 | 0.126787 |
| 0.033271 | 1.79311 | 1.945432 | 3.883764 | 8.897863 | 1.844404 | 1.135069 | 0.558294 | 2.541906 | 0.075856 | 0.208384 |
| 0.030258 | 1.394708 | 0.023987 | 0.000745 | 0.504416 | 0.076492 | 0.664679 | 0.305212 | 1.197578 | 0.813323 | 0.001815 |
| 0.004658 | 3.790096 | 0.144214 | 0.564286 | 0.130307 | 0.04869 | 0.017238 | 1.015234 | 0.103747 | 0.883558 | 0.140925 |
| 4.225527 | 0.113414 | 0.079278 | 0.21276 | 2.845379 | 0.047683 | 0.484986 | 1.516444 | 0.014075 | 0.004769 | 0.009685 |
| 0.000896 | 0.127435 | 0.243527 | 0.070584 | 1.391809 | 0.195285 | 11.31021 | 2.792973 | 2.125714 | 3.371728 | 5.892963 |
| 0.100136 | 0.007001 | 0.027342 | 0.143827 | 2.012521 | 0.012991 | 0.549595 | 1.329153 | 1.22E−05 | 0.057519 | 0.088266 |
| 0.260634 | 3.858632 | 5.112886 | 4.164863 | 0.753747 | 0.599024 | 0.057366 | 4.118574 | 0.181953 | 0.455596 | 0.438091 |
| 0.057709 | 0.044588 | 0.099809 | 0.017543 | 1.9752 | 0.055594 | 0.242958 | 0.025553 | 0.219928 | 0.636275 | 0.875286 |
| 3.338333 | 0.214998 | 0.185075 | 0.33817 | 1.36052 | 0.337259 | 0.007358 | 3.641509 | 0.270023 | 0.701248 | 0.125225 |
| 0.641539 | 0.000864 | 0.268145 | 3.067999 | 1.444156 | 2.158314 | 0.203959 | 2.183448 | 0.039024 | 0.610498 | 3.562823 |
| 4.020221 | 7.878859 | 8.637286 | 3.446782 | 14.14632 | 5.642042 | 3.472273 | 0.000187 | 1.323877 | 0.97864 | 0.230654 |
| 5.976559 | 0.850772 | 0.803984 | 0.016214 | 0.528701 | 0.197159 | 0.669187 | 0.800728 | 0.116698 | 0.039284 | 0.378782 |
| 1.164891 | 0.08304 | 11.27173 | 10.45757 | 22.2575 | 12.49143 | 11.07678 | 2.259128 | 3.885027 | 4.290191 | 7.296606 |
| 1.405798 | 1.228079 | 1.529036 | 0.17514 | 0.225505 | 1.014228 | 1.664393 | 0.340416 | 0.294298 | 0.35384 | 0.001261 |
| 0.56621 | 0.003106 | 0.014030 | 0.460204 | 3.177212 | 0.115546 | 0.007231 | 2.469378 | 0.116712 | 0.106709 | 2.20028 |

| | Hexane | | | | | AcOEt | | |
|---|---|---|---|---|---|---|---|---|
| | k1 | k2 | k3 | k4 | k5 | k1 | k2 | k3 |
| | 0.305007 | 0.07585 | 0.263798 | 1.03522 | 0.546019 | 0.019844 | 0.14118 | 1.330645 |
| | 0.779286 | 0.128747 | 0.615655 | 5.033844 | 1.185308 | 0.124198 | 0.135549 | 3.104745 |
| | 0.731789 | 0.154828 | 0.695468 | 5.146606 | 1.010837 | 0.295322 | 0.05577 | 2.567276 |
| | 0.269599 | 1.190903 | 0.729764 | 0.070246 | 2.689974 | 2.611467 | 6.097091 | 2.9994 |
| | 0.272927 | 0.229905 | 0.052232 | 0.103343 | 2.619084 | 3.555534 | 2.532949 | 2.87276 |
| | 0.132801 | 0.195857 | 0.400837 | 0.065788 | 1.186357 | 0.881853 | 0.057843 | 0.339931 |
| | 12.88792 | 13.5457 | 4.758537 | 5.340480 | 7.135278 | 1.000324 | 12.11375 | 5.910958 |
| | 8.266832 | 4.749893 | 2.270789 | 1.27646 | 1.938237 | 3.00382 | 13.51898 | 6.827522 |
| | 5.854624 | 2.214627 | 1.098783 | 0.696548 | 0.413191 | 6.751244 | 19.44085 | 14.66047 |
| | 3.632028 | 11.37475 | 2.565111 | 6.545504 | 7.828339 | 5.630287 | 3.015077 | 1.418246 |
| | 2.192781 | 8.93 | 2.225574 | 4.097506 | 7.93339 | 1.085817 | 0.363432 | 0.000484 |
| | 0.121361 | 2.287112 | 0.952805 | 0.309317 | 4.31315 | 10.86464 | 16.60725 | 22.04085 |
| | 1.364688 | 1.718217 | 0.876293 | 0.178124 | 1.222896 | 1.592892 | 2.678583 | 6.333851 |
| | 1.732142 | 1.491104 | 0.524527 | 0.185534 | 0.946835 | 0.249172 | 0.027694 | 2.695904 |
| | 0.907946 | 1.343903 | 0.42004 | 0.412716 | 0.552865 | 0.027293 | 0.191392 | 1.168351 |
| | 1.569725 | 0.067922 | 0.002347 | 0.025908 | 0.350641 | 1.020188 | 0.922072 | 5.252444 |
| | 0.109928 | 0.023276 | 0.878064 | 2.609023 | 1.526216 | 0.402645 | 0.169659 | 3.025003 |
| | 1.674202 | 0.122646 | 0.893387 | 2.071817 | 0.542498 | 0.010283 | 0.356808 | 0.306672 |
| | 0.101609 | 0.590329 | 1.767524 | 0.035889 | 0.665619 | 0.139633 | 3.294992 | 0.210304 |
| | 0.255329 | 0.255037 | 1.185979 | 0.204926 | 0.434082 | 1.167378 | 0.226222 | 0.048751 |
| | 0.386837 | 0.192204 | 1.926525 | 0.299842 | 0.201792 | 0.195653 | 0.449925 | 0.237238 |
| | 7.981079 | 12.48691 | 5.792178 | 15.25511 | 4.237329 | 2.852799 | 6.795424 | 0.949795 |
| | 38.80849 | 52.46762 | 54.93527 | 55.35809 | 67.00447 | 0.931579 | 1.773835 | 0.001734 |
| | 0.936805 | 0.893991 | 1.772377 | 0.564802 | 6.326122 | 0.073249 | 0.585894 | 1.273138 |
| | 0.075252 | 1.639134 | 0.342956 | 0.467159 | 0.203358 | 0.086796 | 1.846985 | 0.033239 |

TABLE 30-continued

3-H2O-3
$(\theta_{u,mn}-\theta_{g,mnk})^2/\sigma_{\theta g,mn}^2$

| | | | | | | | |
|---|---|---|---|---|---|---|---|
| 0.000347 | 0.665794 | 0.07255 | 1.357347 | 0.053743 | 0.284138 | 0.814056 | 0.412734 |
| 0.001824 | 0.29694 | 0.161443 | 1.873285 | 0.272102 | 0.042208 | 1.575153 | 0.081186 |
| 0.922675 | 2.505046 | 7.770877 | 2.236761 | 4.950400 | 0.402662 | 3.521811 | 1.842224 |
| 0.558965 | 2.77921 | 5.553499 | 3.058209 | 6.505771 | 0.022945 | 1.35223 | 0.110237 |
| 0.015828 | 1.267738 | 0.590071 | 20.87905 | 4.06784 | 0.002549 | 2.020884 | 0.013413 |
| 1.191684 | 0.070425 | 0.198233 | 0.770458 | 0.530821 | 0.735776 | 4.025329 | 0.099472 |
| 1.988172 | 0.190087 | 0.765559 | 0.508549 | 0.258984 | 9.271155 | 20.40835 | 19.53729 |
| 1.620708 | 0.115509 | 0.68769 | 0.075775 | 0.381889 | 1.314607 | 4.571213 | 0.193013 |
| 1.498055 | 0.354313 | 2.123292 | 0.129299 | 0.317728 | 2.182774 | 2.311386 | 10.21183 |
| 0.172491 | 0.025401 | 0.585891 | 1.220497 | 0.028295 | 0.111511 | 0.129148 | 3.485463 |
| 0.624182 | 0.232708 | 0.099975 | 4.130213 | 0.173878 | 3.027219 | 3.069098 | 0.923492 |
| 0.16305 | 0.167502 | 0.591451 | 1.092646 | 0.296957 | 1.30998 | 0.18786 | 0.698691 |
| 0.111372 | 0.061943 | 0.021908 | 1.13069 | 0.181975 | 0.939225 | 0.132131 | 0.141632 |
| 0.017175 | 0.047691 | 0.528875 | 1.375684 | 0.031954 | 1.159638 | 0.391331 | 0.107474 |
| 0.715823 | 2.575039 | 0.013488 | 0.003105 | 1.886084 | 2.753433 | 0.014679 | 0.186885 |
| 2.515844 | 1.094136 | 0.082305 | 0.096302 | 4.53199 | 1.608482 | 0.386431 | 0.000652 |
| 2.136872 | 0.03116 | 0.085395 | 1.128345 | 3.180736 | 0.937479 | 0.920504 | 0.067556 |
| 0.008795 | 3.755593 | 0.654086 | 0.22475 | 0.250006 | 0.066247 | 0.392646 | 0.769596 |
| 0.022486 | 0.789419 | 1.192903 | 0.014786 | 0.345736 | 0.535763 | 3.094724 | 3.304859 |
| 0.011189 | 0.516888 | 2.861392 | 0.020697 | 1.781678 | 0.054113 | 1.213179 | 0.47552 |
| 0.053756 | 0.000685 | 0.989299 | 0.012284 | 0.982284 | 0.440938 | 2.490108 | 1.279344 |
| 0.00275 | 0.083596 | 1.662688 | 0.010146 | 1.004765 | 0.003759 | 0.327003 | 0.924818 |
| 0.098658 | 0.138317 | 0.202955 | 6.44E-07 | 1.730018 | 0.008341 | 0.072805 | 1.88679 |
| 0.067937 | 0.13975 | 2.089962 | 2.834048 | 0.050828 | 0.036483 | 1.879832 | 0.151872 |
| 0.528093 | 0.161921 | 0.639958 | 0.559816 | 0.749833 | 0.112044 | 0.849653 | 0.062323 |
| 0.422456 | 0.001417 | 0.419741 | 0.221793 | 3.547839 | 0.000105 | 0.000209 | 0.006131 |
| 0.532624 | 0.075314 | 0.022103 | 0.000272 | 1.369919 | 0.236968 | 0.198256 | 0.230176 |
| 0.173352 | 0.033294 | 0.004601 | 0.094172 | 2.02304 | 0.003514 | 0.235275 | 0.048544 |
| 0.389812 | 4.697475 | 0.994847 | 2.827508 | 4.899301 | 0.604276 | 4.144433 | 0.135723 |
| 0.309791 | 1.008997 | 0.102231 | 0.550107 | 1.543049 | 0.012954 | 0.593635 | 1.416292 |
| 0.394493 | 1.040331 | 0.241406 | 0.463944 | 1.343028 | 0.34123 | 0.197146 | 0.854759 |
| 0.451612 | 0.758811 | 0.175233 | 0.437898 | 1.382911 | 0.073887 | 1.385028 | 0.493238 |
| 0.553558 | 0.909502 | 0.764947 | 0.209336 | 0.686181 | 2.386474 | 9.310995 | 5.833449 |
| 1.059998 | 0.004395 | 0.619514 | 0.021384 | 0.359638 | 0.157644 | 0.752367 | 0.845998 |
| 0.089514 | 2.834095 | 0.62507 | 0.474788 | 0.809988 | 0.078483 | 1.726577 | 0.000227 |

TABLE 31

3-H2O-4

| | | THF | | | | | $\log\sigma_{rg,mn}$ | | | |
|---|---|---|---|---|---|---|---|---|---|---|
| k4 | k5 | k1 | k2 | k3 | k4 | k5 | H2O | EtOH | Benzene | Hexane |
| 0.506541 | 0.006697 | 1.454593 | 0.812675 | 0.002749 | 1.792552 | 0.026299 | −3.47051 | −4.20695 | −3.01438 | −4.10649 |
| 1.17E-05 | 0.021431 | 0.004399 | 1.244932 | 0.067259 | 0.029141 | 0.63559 | 1.423286 | 0.497692 | −0.08048 | 0.689939 |
| 0.029319 | 0.001033 | 0.208306 | 1.565294 | 2.57E-05 | 0.024992 | 0.37508 | 1.749126 | 2.144489 | 1.309926 | 1.072453 |
| 5.967249 | 0.563048 | 0.657141 | 0.409295 | 0.093951 | 1.405165 | 0.659402 | 4.210396 | 2.883662 | 3.146059 | 3.374514 |
| 1.600051 | 0.012172 | 0.008898 | 0.935482 | 0.000439 | 0.744422 | 0.379139 | 4.511755 | 4.725985 | 4.151946 | 4.422189 |
| 0.409691 | 0.312067 | 1.486895 | 1.850245 | 0.36577 | 0.011993 | 0.019346 | −3.37465 | −0.12163 | −0.1564 | −1.31552 |
| 3.329441 | 4.294 | 2.982998 | 10.23715 | 2.405786 | 2.147197 | 3.954124 | −3.53899 | −4.81517 | −4.14667 | −5.16409 |
| 7.057286 | 5.323331 | 1.011734 | 7.11271 | 2.189624 | 1.059644 | 1.146231 | 1.382603 | 0.58021 | 1.121638 | −0.22856 |
| 15.89517 | 10.40369 | 2.621372 | 9.604085 | 4.115589 | 2.124751 | 1.898864 | 1.741738 | 4.397142 | 1.667993 | 0.658653 |
| 0.302473 | 0.951418 | 4.186826 | 10.05379 | 1.9404 | 2.560819 | 5.872169 | 4.20986 | 3.877253 | 4.065613 | 2.946359 |
| 0.332651 | 0.00152 | 1.749826 | 5.529267 | 0.380364 | 1.079087 | 4.024572 | 4.502093 | 7.334288 | 4.599096 | 4.283216 |
| 25.16501 | 14.01379 | 10.84179 | 14.94614 | 11.59379 | 6.541651 | 4.400057 | −2.81705 | 2.017158 | −0.07503 | −1.28754 |
| 1.322414 | 0.373975 | 0.651133 | 1.889027 | 2.745504 | 0.004819 | 3.214202 | −2.54699 | −3.73822 | −3.60914 | −3.45323 |
| 0.097552 | 0.000737 | 2.502592 | 0.338476 | 0.007452 | 0.362015 | 0.090667 | 2.232661 | 0.673325 | 0.52533 | 1.248007 |
| 0.432568 | 0.197732 | 2.486404 | 0.257079 | 0.000538 | 0.120314 | 0.064031 | 2.82399 | 2.29138 | 2.377234 | 1.521438 |
| 0.738047 | 0.157743 | 3.840375 | 4.160531 | 4.369593 | 0.202624 | 4.090122 | 4.526049 | 3.418593 | 3.245467 | 4.290344 |
| 0.004684 | 0.000551 | 4.03858 | 3.570045 | 3.384476 | 0.102071 | 3.355054 | 4.977347 | 4.815047 | 4.288023 | 4.912251 |
| 1.742104 | 0.569184 | 1.624454 | 0.032797 | 0.130905 | 0.263497 | 0.003218 | −1.65188 | −0.43421 | 0.255924 | −1.43277 |
| 0.140894 | 2.387451 | 0.837507 | 0.099005 | 0.991368 | 4.362121 | 0.176855 | −3.21894 | −4.00041 | −4.99092 | −4.18508 |
| 0.088581 | 0.503314 | 0.067354 | 3.519394 | 0.115545 | 1.46854 | 2.120226 | 1.990366 | 0.825083 | −0.84597 | 0.734052 |
| 0.343633 | 2.398548 | 0.151483 | 0.009952 | 0.751934 | 0.949155 | 0.142809 | 2.337258 | 2.032124 | 1.48009 | 1.36182 |
| 0.820912 | 3.760873 | 0.930998 | 0.270587 | 1.114815 | 5.173887 | 0.341483 | 4.824302 | 2.611209 | 3.155974 | 3.225993 |
| 0.06623 | 0.00092 | 0.720966 | 0.058144 | 0.375769 | 3.858538 | 0.065591 | 5.461588 | 3.586953 | 5.32421 | 4.055777 |
| 1.932737 | 4.687337 | 0.085442 | 0.52670 | 0.939639 | 0.288129 | 0.766701 | −1.65006 | −1.31919 | 0.433949 | −0.61674 |
| 0.001166 | 0.091369 | 2.042003 | 2.872356 | 2.019195 | 4.792616 | 0.070052 | −3.2759 | −3.9933 | −4.83793 | −3.99619 |
| 0.671556 | 0.427732 | 55.50974 | 38.59073 | 68.16059 | 53.53207 | 47.94885 | 2.395255 | 1.121161 | 0.586189 | 0.784868 |
| 0.199176 | 0.102275 | 4.909461 | 1.080019 | 7.691403 | 3.342819 | 7.173396 | 2.671958 | 2.476318 | 1.833904 | 0.952827 |
| 5.81672 | 0.963497 | 0.057503 | 0.493506 | 0.015105 | 1.040792 | 0.703822 | 4.960104 | 3.724711 | 4.348747 | 2.499667 |
| 0.429712 | 0.102424 | 0.005189 | 0.560067 | 0.027638 | 0.58356 | 0.870595 | 5.213834 | 5.060598 | 5.343589 | 3.978408 |
| 0.072751 | 0.026147 | 0.078441 | 0.571405 | 0.546978 | 0.022637 | 1.036548 | −1.9216 | −0.48259 | 0.760752 | −0.9561 |

TABLE 31-continued

3-H2O-4

| 1.805964 | 1.805348 | 0.019983 | 0.171136 | 0.895014 | 0.976778 | 0.004729 | −3.33665 | −4.93122 | −4.45787 | −3.59592 |
| --- | --- | --- | --- | --- | --- | --- | --- | --- | --- | --- |
| 23.72601 | 20.26641 | 5.240801 | 4.001084 | 1.453242 | 10.10734 | 5.152823 | 2.617672 | −0.84792 | −0.52142 | 0.80426 |
| 9.24335 | 3.440837 | 2.84825 | 1.60097 | 0.121545 | 5.243944 | 1.827228 | 1.895491 | 0.827266 | 1.224621 | 1.003504 |
| 5.708407 | 4.475308 | 3.623905 | 4.658228 | 6.196169 | 0.398079 | 3.118108 | 6.047699 | 2.645935 | 4.198668 | 3.45203 |
| 2.213134 | 0.32356 | 3.789145 | 4.156043 | 4.528642 | 0.17614 | 2.176892 | 5.744713 | 3.834929 | 4.787592 | 5.019523 |
| 0.243742 | 5.150199 | 0.365204 | 1.807449 | 5.97867 | 1.100395 | 3.436956 | −1.07522 | −1.18013 | 0.031744 | 0.484981 |
| 1.198426 | 1.232855 | 0.056222 | 1.856623 | 0.092167 | 3.606465 | 0.791116 | −1.96114 | −3.01957 | −4.77763 | −5.02916 |
| 0.301643 | 0.593458 | 0.001499 | 2.45165 | 0.000512 | 1.144171 | 1.077313 | 2.302229 | 1.172873 | −0.60568 | −0.18678 |
| 0.024563 | 0.334909 | 2.348577 | 6.552299 | 1.341284 | 3.426572 | 0.47878 | 2.531087 | 2.180185 | 0.824372 | 0.492859 |
| 1.440345 | 0.167101 | 0.088095 | 1.514657 | 0.130212 | 4.043176 | 0.638656 | 5.313679 | 3.296982 | 4.056546 | 2.583292 |
| 0.230571 | 0.006719 | 0.01236 | 0.773277 | 0.002816 | 2.69868 | 0.659256 | 5.661962 | 4.329304 | 5.29199 | 4.232906 |
| 0.001157 | 0.170887 | 2.410847 | 0.975782 | 1.259548 | 0.602235 | 0.114455 | −1.57645 | −0.82074 | −0.38181 | −0.89466 |
| 0.64685 | 0.181120 | 0.277995 | 2.632811 | 3.188589 | 5.719507 | 1.191132 | −3.49631 | −3.94273 | −4.91018 | −3.25608 |
| 0.208923 | 0.147423 | 2.907912 | 0.0396 | 0.000189 | 0.73654 | 0.020552 | 2.424872 | 0.445572 | 0.883886 | 0.257281 |
| 0.433608 | 0.053385 | 0.261320 | 1.675304 | 0.017744 | 0.348928 | 8.08E−05 | 2.589026 | 2.778786 | 0.220413 | 0.796696 |
| 6.614954 | 2.565042 | 1.243050 | 3.392151 | 3.826382 | 8.366207 | 1.542097 | 5.021767 | 3.336671 | 5.535133 | 3.892615 |
| 0.814444 | 0.000397 | 1.192005 | 0.012964 | 3.085665 | 2.038197 | 0.978055 | 5.199181 | 5.413236 | 5.249664 | 4.686197 |
| 0.164839 | 0.134288 | 0.02556 | 2.055968 | 0.019535 | 0.687613 | 0.00053 | −1.63969 | 0.909739 | 0.495249 | 0.162628 |
| 0.321925 | 0.001759 | 0.618956 | 0.004761 | 0.911441 | 0.584171 | 0.491025 | −3.75061 | −4.03684 | −3.85018 | −4.34306 |
| 3.93588 | 0.298285 | 2.79434 | 6.691395 | 2.813741 | 11.15909 | 4.525603 | 1.981951 | 2.272385 | 2.102403 | 1.395306 |
| 2.735785 | 0.088529 | 0.94375 | 5.415616 | 1.958616 | 2.004918 | 0.155672 | 1.953076 | 4.092013 | 2.495732 | 1.534185 |
| 4.339931 | 0.393664 | 4.681844 | 2.532569 | 5.891644 | 0.497422 | 5.236576 | 4.897952 | 5.078273 | 5.504239 | 4.403683 |
| 2.099039 | 0.089337 | 1.41506 | 0.746657 | 2.268752 | 0.127007 | 0.810631 | 4.935532 | 6.916974 | 5.854076 | 4.753436 |
| 0.152743 | 0.207362 | 0.677881 | 0.399927 | 0.25568 | 4.319418 | 3.032869 | −1.17559 | 0.833256 | −0.31503 | −0.61998 |
| 0.000501 | 0.00024 | 0.010593 | 0.486958 | 1.095459 | 0.008971 | 0.819524 | −3.97889 | −1.75606 | −4.84518 | −3.09943 |
| 0.477282 | 0.636771 | 6.552293 | 2.867712 | 12.34446 | 8.285974 | 4.318133 | 1.369908 | 2.462408 | 0.091022 | 2.128556 |
| 0.044169 | 0.6065 | 1.342898 | 0.607805 | 7.168436 | 1.763702 | 2.37324 | 2.397467 | 3.352771 | 0.918106 | 1.222062 |
| 1.92713 | 2.603305 | 0.152884 | 0.210122 | 1.86401 | 0.163299 | 1.151966 | 4.568042 | 3.121787 | 3.407953 | 3.974758 |
| 0.037094 | 0.613014 | 0.113352 | 0.214805 | 0.349753 | 0.133006 | 1.31492 | 5.043107 | 3.956618 | 5.072329 | 3.311061 |
| 0.25642 | 0.066369 | 0.113877 | 0.010922 | 1.640601 | 0.073304 | 0.478909 | −1.06582 | −1.14587 | −0.12107 | −0.74758 |

| $\log\sigma_{rg,mn}$ | | $\log\sigma\theta_{g,mn}$ | | | | | |
| --- | --- | --- | --- | --- | --- | --- | --- |
| AcOEt | THF | H2O | EtOH | Benzene | Hexane | AcOEt | THF |
| −2.38023 | −1.65628 | −0.82928 | 0.823367 | −0.51055 | 0.992277 | −0.01687 | −0.89727 |
| 1.180556 | 0.570003 | −1.55647 | 0.340158 | −0.76989 | 0.467301 | −0.07627 | −0.43568 |
| 2.454608 | 2.150339 | −1.63936 | 0.400977 | −1.08067 | 0.466282 | 0.123082 | −0.0921 |
| 4.503642 | 2.094256 | −1.14966 | −0.67501 | −1.52378 | −1.6571 | −1.24557 | −0.59128 |
| 5.309541 | 3.505918 | −1.1801 | −0.63757 | −0.50805 | −1.42174 | −0.9164 | −0.22346 |
| −0.58079 | −0.29805 | −2.61649 | −1.8355 | −0.74507 | −2.09105 | −1.17806 | −1.17675 |
| −4.20663 | −2.91238 | −2.16383 | −1.07598 | 1.084797 | −0.78634 | −1.58827 | −0.63991 |
| −0.39937 | 0.259949 | −1.37948 | −1.06307 | −0.17791 | −0.971 | −2.29371 | −1.39058 |
| 0.724481 | 2.016578 | −1.37216 | −0.73084 | 0.417273 | −0.73216 | −2.03317 | −1.17522 |
| 2.288464 | 1.814887 | −1.17288 | −0.98772 | 0.319091 | −1.48448 | −1.58917 | −1.13088 |
| 3.001095 | 3.289227 | −1.13063 | −0.69726 | 0.469739 | −1.13058 | −1.40378 | −1.16917 |
| −1.63629 | −0.70151 | −3.16176 | −1.91056 | −0.36615 | −2.02085 | −2.98339 | −2.57999 |
| −2.96846 | −2.63055 | −0.40833 | −1.46006 | −0.15372 | 0.262191 | −0.86764 | −0.58837 |
| 0.90212 | 0.207069 | −1.49237 | −1.15723 | −1.7426 | 0.300856 | −1.27126 | −1.29522 |
| 1.683112 | 1.784406 | −2.05044 | −0.51846 | −1.86177 | 0.407925 | −0.48163 | −1.06233 |
| 3.604589 | 2.58891 | −0.3419 | −1.76309 | −0.29631 | −1.57369 | −0.42624 | −0.79534 |
| 4.56719 | 4.147205 | −0.4135 | −0.61661 | −0.19836 | −1.35308 | −0.02066 | −0.70174 |
| −2.33187 | −0.66004 | −2.20351 | −0.95833 | −1.7064 | −1.3211 | −0.98294 | −2.43581 |
| −4.57644 | −2.66352 | −0.25239 | −1.97182 | −0.41206 | 0.666055 | −1.33803 | −0.7309 |
| 0.285807 | 0.234313 | 0.394229 | −1.83933 | −1.48248 | 0.686205 | −1.9322 | −3.00454 |
| 2.258278 | 1.282089 | 0.427422 | −1.40014 | −1.40448 | 0.639888 | −1.32376 | −1.9627 |
| 3.283066 | 2.743929 | 0.533222 | −1.84778 | −0.65336 | −1.99667 | −1.85619 | −0.75504 |
| 5.115025 | 3.888008 | 0.556183 | −1.64801 | −0.58531 | −2.40852 | −1.49817 | −0.53901 |
| −0.16786 | −1.41821 | −2.43387 | −2.10459 | −2.01139 | −1.70592 | −1.94335 | −1.94459 |
| −4.57673 | −2.58564 | −0.82216 | −1.35865 | 0.057138 | 0.385252 | −0.37197 | −0.95689 |
| 2.366694 | 0.470495 | −0.2301 | −1.96415 | −0.60879 | 0.362595 | −0.47755 | −2.79221 |
| 2.335711 | 2.321066 | −0.34122 | −1.17207 | −0.99518 | 0.428725 | 0.658463 | −1.47053 |
| 4.966157 | 2.71242 | 0.119395 | −1.68121 | −0.2457 | −0.8037 | −1.60442 | −0.95537 |
| 4.951408 | 4.257231 | 0.039661 | −1.65995 | −0.27385 | −0.4667 | 0.24632 | −0.59658 |
| −0.20126 | 0.059249 | −2.41235 | −1.76205 | −0.90936 | −1.20675 | 0.271423 | −1.67284 |
| −3.69173 | −2.1596 | −1.79439 | −1.19371 | −0.6264 | 0.809715 | −1.30587 | −0.12794 |
| 0.42360 | 0.51278 | −0.45931 | −1.11443 | −1.16205 | 0.870868 | −1.51448 | −0.98185 |
| 2.133735 | 2.193251 | −0.46491 | −0.64042 | −0.69015 | 0.84193 | −1.12517 | −0.76481 |
| 3.075531 | 3.315992 | −0.35884 | −1.72029 | −0.99729 | −0.29057 | −1.21759 | −0.66615 |
| 4.940724 | 4.681185 | −0.40388 | −0.70956 | −0.41013 | 0.18832 | −0.87095 | −0.76053 |
| −0.02916 | −0.18164 | −2.05213 | −1.116 | −0.82419 | −0.6464 | −1.76629 | −2.12582 |
| −2.67317 | −3.5853 | −1.36913 | −1.49909 | −1.03902 | 0.499386 | −1.34106 | −0.46286 |
| 0.836193 | −0.03587 | −0.56432 | −1.20381 | −1.08981 | 0.459324 | −1.59999 | −1.97602 |
| 2.038741 | 1.658616 | −0.32969 | −0.42158 | −0.19039 | 0.488639 | −0.50208 | −1.97447 |
| 3.546491 | 2.6235 | −0.54307 | −1.49349 | −1.49594 | −1.82025 | −1.1087 | −0.65216 |
| 4.911158 | 4.373398 | −0.31415 | −0.54561 | −0.31769 | −1.25587 | −0.23396 | −0.55993 |
| −0.59548 | −0.03484 | −1.81485 | −0.9873 | −0.51292 | −1.53594 | −0.75271 | −1.96259 |
| −3.40032 | −2.58689 | −0.83757 | 0.556473 | 0.611169 | 0.037197 | −1.06393 | −0.99593 |

TABLE 31-continued

3-H2O-4

| | | | | | | | |
|---|---|---|---|---|---|---|---|
| 0.484046 | 0.909823 | −0.51511 | 0.632718 | 0.594448 | 0.835504 | −1.34173 | −2.24377 |
| 1.443826 | 2.481656 | −0.43515 | 0.690223 | 0.321458 | 0.671697 | −0.5567 | −0.69441 |
| 3.480733 | 2.713015 | −0.22912 | −2.0043 | −0.69921 | 0.647753 | −1.88841 | −1.08793 |
| 4.999752 | 5.020012 | −0.23107 | −0.92487 | −0.61209 | 0.73669 | −0.3206 | −0.8862 |
| −0.47691 | 0.577207 | −1.72139 | −1.09882 | −0.40671 | 0.565064 | −0.45378 | −0.76466 |
| −2.56695 | −4.43024 | −1.2803 | 0.314511 | 0.553145 | −0.03673 | −0.25352 | −0.0916 |
| 2.397084 | 0.725282 | 0.085808 | 0.458979 | −0.76659 | 0.722195 | 0.667138 | −1.08915 |
| 2.81233 | 2.262165 | 0.038463 | 0.046601 | 0.655338 | 0.643474 | 0.757237 | −1.25364 |
| 3.380728 | 2.933968 | 0.054007 | −0.66324 | 0.366502 | 0.534097 | 0.497352 | −0.52911 |
| 4.669018 | 4.459714 | 0.009472 | 0.57047 | −0.84925 | 0.8618 | 0.756353 | −0.1815 |
| 0.343869 | −0.14069 | −1.81933 | 0.339932 | 0.45126 | −0.87872 | −0.14241 | −1.07022 |
| −3.29933 | −0.12005 | −0.81177 | −1.34576 | −0.35306 | 0.785952 | 0.817846 | 0.998936 |
| 2.322421 | 1.823127 | −0.45072 | −1.0943 | 0.04527 | 1.088347 | 0.547119 | −1.11656 |
| 2.309211 | 1.954408 | −0.82505 | −0.04856 | 0.911424 | 0.943053 | 0.808506 | −0.46843 |
| 5.190598 | 4.924648 | −0.15758 | −1.09899 | −0.38398 | −0.14212 | −0.19413 | 1.07302 |
| 4.635536 | 4.926917 | −0.30587 | −0.23342 | 0.514798 | −0.71994 | 0.782028 | 1.093496 |
| 0.103346 | 0.236609 | −1.29184 | 0.090747 | 0.241204 | −0.75044 | 0.355101 | −0.89061 |

TABLE 32

3-EtOH-1

| | | $r_{u,mn}$ EtOH | H$_2$O | | | | | EtOH | | |
|---|---|---|---|---|---|---|---|---|---|---|
| f | Ku', mn | k5 | k1 | k2 | k3 | k4 | k5 | k1 | k2 | k3 |
| 0.05 Hz | Ku', 12 | 0.07274 | 0.945545 | 2.301472 | 6.353262 | 3.686708 | 0.614838 | 0.830474 | 4.157764 | 0.031713 |
| | Ku', 13 | 7.230348 | 13.91224 | 18.45139 | 6.13062 | 8.4463 | 11.00878 | 0.135637 | 1.957354 | 0.012579 |
| | Ku', 14 | 22.90291 | 2.302207 | 4.951823 | 0.128442 | 0.721628 | 1.143668 | 0.131994 | 3.166217 | 0.004991 |
| | Ku', 23 | 99.39997 | 3.23228 | 2.644006 | 0.059546 | 0.471283 | 3.008404 | 5.093239 | 1.335886 | 0.19047 |
| | Ku', 24 | 314.8502 | 0.007244 | 0.03562 | 2.700786 | 1.330943 | 0.029902 | 0.030765 | 1.385843 | 0.000859 |
| | Ku', 34 | 3.167609 | 2689.288 | 2593.262 | 2589.139 | 2546.59 | 2717.35 | 0.523576 | 3.277999 | 0.032715 |
| 0.1 Hz | Ku', 12 | 0.054169 | 1.628616 | 2.569122 | 6.655486 | 5.797602 | 8.875987 | 0.208697 | 2.55147 | 2.431928 |
| | Ku', 13 | 6.297896 | 17.50671 | 5.789245 | 9.693874 | 7.290707 | 12.81213 | 1.865391 | 0.34389 | 0.171077 |
| | Ku', 14 | 17.98575 | 6.747379 | 0.891575 | 3.217443 | 1.815167 | 5.176861 | 0.009217 | 0.009044 | 0.000251 |
| | Ku', 23 | 116.2645 | 4.050349 | 0.379126 | 0.180817 | 0.099052 | 0.196938 | 0.516936 | 0.019949 | 0.051305 |
| | Ku', 24 | 332.0322 | 0.093667 | 1.389642 | 1.580826 | 1.924525 | 1.538859 | 0.005488 | 0.001109 | 0.000806 |
| | Ku', 34 | 2.855835 | 570.239 | 563.1481 | 507.7322 | 510.4956 | 509.6804 | 0.000159 | 0.007345 | 0.000242 |
| 0.15 Hz | Ku', 12 | 0.059508 | 0.342302 | 0.034562 | 0.982053 | 4.03513 | 0.244739 | 0.000567 | 0.937253 | 0.291718 |
| | Ku', 13 | 6.821765 | 2.435793 | 0.633878 | 4.533464 | 0.122158 | 0.673969 | 0.058299 | 0.033447 | 0.01415 |
| | Ku', 14 | 19.05989 | 0.675574 | 0.002325 | 2.421673 | 0.032695 | 0.025886 | 0.002733 | 0.048634 | 0.025355 |
| | Ku', 23 | 114.6365 | 0.913317 | 0.707193 | 0.748001 | 0.54398 | 0.12532 | 0.051537 | 0.820423 | 0.596928 |
| | Ku', 24 | 320.2924 | 0.00297 | 0.128433 | 0.004612 | 2.884919 | 0.452988 | 0.02129 | 0.260618 | 0.406545 |
| | Ku', 34 | 2.793982 | 63.90877 | 79.46564 | 48.85444 | 58.98797 | 67.58597 | 0.038395 | 0.064235 | 0.046762 |
| 0.2 Hz | Ku', 12 | 0.038927 | 0.003707 | 0.014603 | 1.659345 | 1.632979 | 1.89141 | 0.044371 | 0.300529 | 0.505206 |
| | Ku', 13 | 4.770282 | 1.091835 | 0.000125 | 1.418559 | 2.799712 | 3.082891 | 0.006541 | 0.202947 | 0.2081 |
| | Ku', 14 | 13.05074 | 0.640709 | 0.329815 | 0.277625 | 1.158354 | 1.417424 | 0.002253 | 0.219899 | 0.107269 |
| | Ku', 23 | 122.5131 | 3.056712 | 0.015296 | 0.045564 | 0.284824 | 0.272922 | 1.271615 | 0.091362 | 0.611739 |
| | Ku', 24 | 335.1767 | 1.121711 | 0.538834 | 0.307634 | 0.07978 | 0.076333 | 1.145905 | 0.014642 | 0.985083 |
| | Ku', 34 | 2.735844 | 28.07065 | 40.38539 | 50.42611 | 46.81861 | 45.51799 | 0.013555 | 0.243828 | 0.050471 |
| 0.25 Hz | Ku', 12 | 0.046083 | 0.292055 | 3.185973 | 1.493977 | 2.6749 | 0.019498 | 0.003191 | 0.221025 | 0.021091 |
| | Ku', 13 | 4.41475 | 2.336447 | 0.665981 | 3.442724 | 0.852973 | 0.000554 | 0.005798 | 0.417382 | 0.130705 |
| | Ku', 14 | 10.32989 | 1.745421 | 0.516837 | 2.81589 | 0.660412 | 0.034995 | 0.033266 | 0.795197 | 0.200149 |
| | Ku', 23 | 95.79906 | 2.439824 | 0.023704 | 1.466172 | 0.074981 | 0.00114 | 0.033166 | 0.230521 | 0.176233 |
| | Ku', 24 | 224.156 | 1.41464 | 0.051076 | 0.674465 | 0.011151 | 0.169748 | 0.017114 | 0.960918 | 0.368606 |
| | Ku', 34 | 2.339856 | 42.11878 | 29.0584 | 41.4806 | 31.50009 | 23.42755 | 0.002156 | 2.287105 | 0.639757 |
| 0.3 Hz | Ku', 12 | 0.053456 | 0.054355 | 0.828298 | 2.814696 | 1.484862 | 1.00762 | 5.463156 | 0.299328 | 2.272538 |
| | Ku', 13 | 4.883584 | 5.837177 | 0.585916 | 0.720406 | 1.020497 | 0.602129 | 0.028921 | 1.523851 | 0.781354 |
| | Ku', 14 | 10.33059 | 11.84968 | 3.142604 | 3.859857 | 5.457235 | 3.022055 | 0.585098 | 6.420104 | 2.574928 |
| | Ku', 23 | 91.35166 | 3.139564 | 0.043039 | 0.016683 | 0.058266 | 0.038204 | 8.22445 | 1.624126 | 5.29936 |
| | Ku', 24 | 193.2427 | 3.015239 | 0.042752 | 0.00192 | 0.056278 | 0.028134 | 8.7479 | 8.188021 | 8.577836 |
| | Ku', 34 | 2.115371 | 13.21444 | 3.923355 | 4.185011 | 4.620471 | 4.258352 | 1.611341 | 7.90917 | 3.149242 |
| 0.35 Hz | Ku', 12 | 0.029429 | 0.014616 | 3.987045 | 0.305723 | 0.50175 | 0.365146 | 0.032774 | 0.002377 | 0.043365 |
| | Ku', 13 | 4.180779 | 1.829777 | 0.851333 | 4.86645 | 0.11478 | 0.604678 | 0.035772 | 9.11E−05 | 0.000425 |
| | Ku', 14 | 8.936653 | 1.81991 | 1.223725 | 4.178996 | 0.018217 | 0.573968 | 0.237127 | 0.02355 | 0.353943 |
| | Ku', 23 | 142.0655 | 1.375521 | 0.237023 | 0.25516 | 0.168806 | 0.034304 | 0.386892 | 0.127268 | 1.650457 |
| | Ku', 24 | 303.673 | 0.769929 | 0.639541 | 0.004486 | 0.591657 | 0.245036 | 0.3129 | 0.06917 | 0.52461 |
| | Ku', 34 | 2.137557 | 10.66564 | 4.402565 | 15.64369 | 12.55719 | 8.25017 | 1.380319 | 0.330875 | 5.113013 |
| 0.4 Hz | Ku', 12 | 0.062631 | 0.0585 | 0.430169 | 1.485584 | 0.086984 | 0.12893 | 0.045461 | 0.355388 | 1.988308 |
| | Ku', 13 | 7.794387 | 1.70336 | 0.06618 | 2.367546 | 0.306685 | 0.901928 | 1.881405 | 2.748316 | 2.759597 |
| | Ku', 14 | 7.240452 | 2.418429 | 0.000899 | 3.185111 | 1.231027 | 1.816378 | 3.080582 | 0.168815 | 0.26005 |
| | Ku', 23 | 124.4496 | 3.486191 | 0.004464 | 0.717243 | 0.224696 | 0.707335 | 0.973154 | 0.638012 | 0.663256 |
| | Ku', 24 | 115.6058 | 5.017761 | 0.06514 | 1.265849 | 1.217356 | 1.701883 | 4.795712 | 0.481617 | 2.06375 |
| | Ku', 34 | 0.928937 | 2.567034 | 5.888937 | 2.427751 | 10.80138 | 4.924794 | 4.641352 | 0.48659 | 0.675928 |

TABLE 32-continued

3-EtOH-1

| | | | | | | | | | | |
|---|---|---|---|---|---|---|---|---|---|---|
| 0.45 Hz | Ku', 12 | 0.042992 | 0.560171 | 6.160199 | 3.749791 | 1.707254 | 1.013957 | 0.000652 | 0.174331 | 0.000172 |
| | Ku', 13 | 4.007042 | 4.507403 | 1.832501 | 6.778243 | 1.439318 | 7.563076 | 0.015258 | 0.036252 | 0.003729 |
| | Ku', 14 | 10.72892 | 5.42214 | 1.297232 | 7.38312 | 1.348064 | 2.605792 | 0.005337 | 0.001411 | 0.001895 |
| | Ku', 23 | 93.2038 | 2.875297 | 0.10435 | 1.525843 | 0.350054 | 3.948527 | 0.027517 | 0.020669 | 0.008006 |
| | Ku', 24 | 249.5546 | 2.035491 | 0.214349 | 0.401056 | 0.002591 | 0.348391 | 0.009445 | 5.6E−05 | 0.003808 |
| | Ku', 34 | 2.577516 | 17.19297 | 18.33898 | 19.79038 | 14.87072 | 32.35564 | 0.014095 | 0.059842 | 0.013836 |
| 0.5 Hz | Ku', 12 | 0.031437 | 0.255154 | 5.749703 | 3.892849 | 3.270704 | 2.616521 | 0.003873 | 0.005355 | 0.004905 |
| | Ku', 13 | 3.386219 | 8.75399 | 12.15924 | 8.786498 | 19.95743 | 7.288184 | 0.005637 | 0.022605 | 0.005256 |
| | Ku', 14 | 6.435392 | 0.869033 | 3.148254 | 1.351624 | 6.169106 | 0.574065 | 0.002377 | 0.030976 | 0.016263 |
| | Ku', 23 | 107.0767 | 7.271834 | 1.465171 | 1.365622 | 4.9096 | 1.518495 | 0.079653 | 0.168657 | 0.202699 |
| | Ku', 24 | 204.7047 | 1.719658 | 0.758631 | 0.241738 | 4.048632 | 4.048632 | 0.049276 | 0.133915 | 1.124041 | 0.26367 |
| | Ku', 34 | 1.911757 | 5.394943 | 1.304588 | 3.378482 | 0.761864 | 6.131494 | 0.046346 | 1.03319 | 2.267237 |

| | | $(r_{u,mn}-r_{g,mnk})^2/\sigma_{rg,mn}^2$ | | | | | | |
|---|---|---|---|---|---|---|---|---|
| | | EtOH | | Benzene | | | | |
| f | Ku', mn | k4 | k5 | k1 | k2 | k3 | k4 | k5 | k1 |
|---|---|---|---|---|---|---|---|---|---|
| 0.05 Hz | Ku', 12 | 2.317773 | 0.751839 | 0.454375 | 0.722013 | 0.001739 | 0.180639 | 0.965747 | 10.03412 |
| | Ku', 13 | 0.265446 | 0.004129 | 32.49714 | 17.8595 | 32.91131 | 28.46498 | 36.52463 | 3.464521 |
| | Ku', 14 | 0.201582 | 0.007682 | 18.47672 | 10.20243 | 17.69188 | 12.39367 | 24.99288 | 30.44956 |
| | Ku', 23 | 3.680267 | 2.516053 | 4.57424 | 9.145063 | 9.594352 | 5.58278 | 1.885546 | 6.039578 |
| | Ku', 24 | 0.342221 | 0.241451 | 4.784994 | 11.78252 | 11.06115 | 3.860668 | 4.600996 | 0.029676 |
| | Ku', 34 | 0.041389 | 0.027801 | 0.192198 | 0.033248 | 0.516973 | 1.69894 | 0.380108 | 21.55021 |
| 0.1 Hz | Ku', 12 | 1.790532 | 0.001631 | 1.616501 | 0.441303 | 4.325805 | 2.659574 | 6.191204 | 24.34065 |
| | Ku', 13 | 0.698488 | 4.575257 | 1.758322 | 0.042149 | 1.828622 | 2.02219 | 1.944148 | 12.40125 |
| | Ku', 14 | 0.012456 | 2.75084 | 2.476336 | 0.023294 | 3.230338 | 2.370295 | 3.560344 | 44.93386 |
| | Ku', 23 | 0.005458 | 2.112025 | 0.761392 | 0.529284 | 0.069322 | 0.68236 | 0.116934 | 0.935851 |
| | Ku', 24 | 0.003009 | 2.55933 | 1.076546 | 0.331999 | 0.114431 | 0.248022 | 0.332818 | 3.631282 |
| | Ku', 34 | 0.00672 | 2.622097 | 0.482697 | 0.188181 | 0.011904 | 1.941402 | 1.03E−05 | 26.32843 |
| 0.15 Hz | Ku', 12 | 0.060288 | 0.842131 | 1.494617 | 3.099175 | 2.445687 | 2.463973 | 5.92E−05 | 0.000954 |
| | Ku', 13 | 0.948612 | 0.951916 | 6.357796 | 10.655 | 7.873182 | 8.280113 | 1.963964 | 0.020342 |
| | Ku', 14 | 1.23066 | 0.707951 | 1.175175 | 1.926288 | 1.22808 | 1.39054 | 0.135809 | 6.045837 |
| | Ku', 23 | 0.386295 | 0.263552 | 0.47921 | 0.033637 | 0.061232 | 7.52E−05 | 2.37439 | 0.019019 |
| | Ku', 24 | 1.273917 | 0.08142 | 0.314785 | 0.130588 | 1.681334 | 0.49817 | 0.87421 | 1.980422 |
| | Ku', 34 | 0.9923 | 0.875545 | 0.004946 | 0.07728 | 0.24073 | 0.12391 | 3.392891 | 42.7806 |
| 0.2 Hz | Ku', 12 | 3.526218 | 0.011657 | 12.60286 | 4.091611 | 10.81936 | 11.31512 | 4.997462 | 0.406363 |
| | Ku', 13 | 3.174056 | 0.080922 | 46.64134 | 41.05876 | 45.39583 | 46.89241 | 26.7791 | 0.562197 |
| | Ku', 14 | 2.912967 | 0.001452 | 1.102393 | 2.054163 | 3.050114 | 4.170647 | 0.047765 | 2.120971 |
| | Ku', 23 | 0.021451 | 0.533833 | 0.00581 | 3.243862 | 0.151354 | 0.131095 | 0.413931 | 0.25745 |
| | Ku', 24 | 0.320676 | 0.083275 | 1.311071 | 0.106497 | 0.002629 | 0.156886 | 0.720222 | 2.077254 |
| | Ku', 34 | 0.646726 | 1.050841 | 1.438827 | 0.154682 | 0.006713 | 0.108804 | 1.69009 | 0.680779 |
| 0.25 Hz | Ku', 12 | 2.496106 | 1.546861 | 8.772626 | 8.258618 | 18.91046 | 14.61175 | 8.195537 | 0.274418 |
| | Ku', 13 | 2.410552 | 0.104958 | 1.365425 | 0.100004 | 1.286492 | 2.323566 | 0.930157 | 0.00018 |
| | Ku', 14 | 2.523449 | 0.037126 | 0.347795 | 0.034104 | 1.048734 | 1.154337 | 0.411127 | 2.296318 |
| | Ku', 23 | 0.318018 | 1.297958 | 0.002036 | 2.090668 | 1.968994 | 0.017594 | 0.058991 | 4.59958 |
| | Ku', 24 | 0.970785 | 0.487019 | 0.083928 | 0.571573 | 0.291904 | 0.00039 | 3.45147 | 0.802418 |
| | Ku', 34 | 1.872695 | 0.000253 | 0.060947 | 0.054332 | 0.103948 | 0.007675 | 1.977054 | 5.51668 |
| 0.3 Hz | Ku', 12 | 3.111106 | 4.746028 | 8.880132 | 3.654791 | 13.98966 | 10.33089 | 5.897323 | 0.610911 |
| | Ku', 13 | 0.214324 | 0.033666 | 28.33212 | 16.58398 | 24.85111 | 34.9215 | 20.58869 | 1.312762 |
| | Ku', 14 | 1.235119 | 4.156251 | 3.579704 | 0.592535 | 3.527698 | 4.820178 | 0.398523 | 5.161052 |
| | Ku', 23 | 2.823311 | 8.111546 | 2.08E−05 | 0.035723 | 2.199263 | 0.009654 | 0.005346 | 0.354771 |
| | Ku', 24 | 7.03876 | 19.43762 | 0.010825 | 0.195479 | 2.667095 | 0.003643 | 1.171709 | 0.179573 |
| | Ku', 34 | 4.231609 | 8.6982 | 0.01917 | 0.960615 | 0.004339 | 0.005682 | 2.466749 | 0.042743 |
| 0.35 Hz | Ku', 12 | 2.963067 | 0.021284 | 5.572934 | 6.624128 | 1.792059 | 6.531776 | 1.22809 | 3.818635 |
| | Ku', 13 | 2.70317 | 0.004209 | 25.33067 | 35.32291 | 21.85025 | 23.97514 | 15.85469 | 6.661058 |
| | Ku', 14 | 3.521772 | 0.032914 | 6.647737 | 9.233355 | 4.890201 | 2.705996 | 1.350066 | 12.04506 |
| | Ku', 23 | 4.649151 | 0.65669 | 0.018912 | 0.136996 | 0.820217 | 0.702985 | 0.533039 | 2.167781 |
| | Ku', 24 | 1.072126 | 0.040432 | 0.006524 | 0.051935 | 0.214826 | 1.85125 | 0.002086 | 2.457687 |
| | Ku', 34 | 1.074778 | 0.244252 | 8.26E−05 | 2.59E−05 | 0.103744 | 1.646357 | 2.118487 | 1.176395 |
| 0.4 Hz | Ku', 12 | 4.109734 | 1.382309 | 41.49205 | 48.7731 | 28.45124 | 40.7981 | 29.60245 | 1.016861 |
| | Ku', 13 | 10.07135 | 3.98271 | 5.743061 | 0.982584 | 6.33576 | 7.250246 | 6.608961 | 20.47561 |
| | Ku', 14 | 0.026227 | 0.154324 | 5.390379 | 2.32594 | 6.489801 | 2.255546 | 9.987434 | 4.08318 |
| | Ku', 23 | 0.008889 | 0.051409 | 2.034849 | 0.041181 | 0.027845 | 0.046493 | 0.823472 |
| | Ku', 24 | 0.137338 | 1.00564 | 0.808328 | 3.633993 | 0.095104 | 1.453222 | 0.026366 | 1.85E−05 |
| | Ku', 34 | 0.080094 | 0.629503 | 0.580727 | 0.001173 | 0.790449 | 3.979505 | 0.508763 | 0.174542 |
| 0.45 Hz | Ku', 12 | 0.732429 | 2.867405 | 0.036654 | 0.356625 | 1.875557 | 2.20477 | 1.674479 | 0.336239 |
| | Ku', 13 | 2.865979 | 0.007584 | 0.023488 | 1.757568 | 0.062195 | 0.084259 | 0.093813 | 1.223705 |
| | Ku', 14 | 2.588187 | 0.001143 | 0.06773 | 0.978953 | 0.37189 | 0.463841 | 0.404526 | 0.080607 |
| | Ku', 23 | 2.597286 | 0.027425 | 0.019968 | 2.61559 | 0.039225 | 0.041108 | 0.000239 | 3.178051 |
| | Ku', 24 | 2.493122 | 0.016597 | 0.064688 | 2.064653 | 0.000682 | 0.009059 | 0.02456 | 0.018814 |
| | Ku', 34 | 1.847946 | 0.21992 | 0.010122 | 2.47359 | 1.813239 | 2.547199 | 0.038424 | 8.479686 |
| 0.5 Hz | Ku', 12 | 2.726119 | 0.005554 | 4.742411 | 0.908632 | 6.443233 | 7.322924 | 2.91497 | 0.000804 |
| | Ku', 13 | 2.828924 | 0.012465 | 2.019775 | 0.28392 | 3.65531 | 3.125687 | 0.142446 | 0.001289 |
| | Ku', 14 | 2.899306 | 0.021991 | 0.043507 | 0.001454 | 2.032562 | 0.212497 | 0.216648 | 0.553701 |

TABLE 32-continued

3-EtOH-1

| | | | | | | | | |
|---|---|---|---|---|---|---|---|---|
| Ku', 23 | 2.251521 | 0.004625 | 0.41283 | 0.091969 | 0.016098 | 1.25078 | 3.549567 | 0.063361 |
| Ku', 24 | 0.344182 | 0.479129 | 1.709234 | 0.182231 | 0.079725 | 3.911494 | 1.856944 | 9.856646 |
| Ku', 34 | 2.218703 | 1.360494 | 2.34182 | 0.24139 | 0.147375 | 4.044213 | 0.559035 | 1.804186 |

TABLE 33

3-EtOH-2

| Hexane | | | | AcOEt | | | | | THF | |
|---|---|---|---|---|---|---|---|---|---|---|
| k2 | k3 | k4 | k5 | k1 | k2 | k3 | k4 | k5 | k1 | k2 |
| 14.37772 | 13.18096 | 4.420724 | 14.02885 | 0.055367 | 0.839009 | 0.004133 | 3.14829 | 0.510002 | 2.468381 | 9.459704 |
| 8.63888 | 6.641243 | 1.484408 | 7.296592 | 0.49382 | 0.246241 | 4.271691 | 3.536163 | 0.96922 | 1.934191 | 3.371742 |
| 49.35097 | 43.55813 | 30.71841 | 45.52176 | 0.01853 | 0.170973 | 1.117914 | 3.894695 | 0.699624 | 0.058527 | 0.367417 |
| 1.374243 | 4.573193 | 0.830648 | 5.377477 | 0.000211 | 0.228979 | 1.472012 | 0.226917 | 0.071885 | 81.24153 | 105.4489 |
| 1.034659 | 0.18668 | 2.784186 | 0.107118 | 0.076018 | 0.471455 | 1.102133 | 0.359176 | 0.155396 | 55.09951 | 74.63882 |
| 29.0738 | 29.04235 | 43.68338 | 29.12771 | 1.131023 | 0.003784 | 1.330432 | 0.229566 | 0.005093 | 0.030805 | 3.967531 |
| 23.62896 | 32.00723 | 32.35975 | 43.63561 | 17.97009 | 6.999298 | 13.39137 | 7.941043 | 15.90054 | 16.45271 | 18.90001 |
| 10.85033 | 15.53382 | 10.98471 | 24.87977 | 9.509169 | 6.728926 | 8.55255 | 10.5823 | 19.79001 | 1.214021 | 1.341083 |
| 37.24192 | 44.36268 | 32.03853 | 56.80502 | 19.54248 | 9.075553 | 10.42432 | 10.02838 | 19.51042 | 0.3591 | 0.000449 |
| 1.480077 | 2.2685 | 7.722841 | 1.635791 | 20.806 | 9.501928 | 16.69801 | 8.116896 | 12.28774 | 205.9827 | 212.0203 |
| 1.797009 | 1.810892 | 0.00753 | 2.882249 | 25.24792 | 13.34856 | 27.42598 | 14.691 | 21.61159 | 86.97463 | 100.9395 |
| 18.0136 | 20.11781 | 11.36468 | 25.23278 | 3.897657 | 0.635941 | 0.435277 | 0.033718 | 0.108003 | 0.012084 | 1.140318 |
| 3.089655 | 1.978353 | 2.44933 | 1.435769 | 0.999787 | 0.321727 | 3.446565 | 0.000105 | 0.147945 | 3.910954 | 3.693809 |
| 3.072833 | 2.189399 | 2.463279 | 0.312634 | 0.055172 | 0.143808 | 3.784888 | 0.125326 | 0.360683 | 0.658171 | 0.439742 |
| 15.24335 | 13.11912 | 13.60098 | 6.069621 | 0.013848 | 0.200845 | 3.419761 | 0.033603 | 0.242063 | 0.202067 | 0.714757 |
| 0.907436 | 0.002261 | 0.063012 | 2.316838 | 2.02236 | 0.791445 | 1.980099 | 0.068885 | 0.221377 | 32.50966 | 32.62623 |
| 0.013533 | 1.30459 | 0.569754 | 0.086565 | 2.458197 | 0.801353 | 2.249124 | 0.019153 | 0.308182 | 10.99112 | 9.85425 |
| 22.54801 | 30.11163 | 24.54383 | 25.19715 | 0.643765 | 0.428021 | 0.000764 | 1.276624 | 0.292493 | 0.014434 | 0.487767 |
| 2.414666 | 4.476245 | 0.537262 | 4.256763 | 18.03629 | 14.94901 | 15.53094 | 19.92213 | 5.980158 | 1.173707 | 2.403127 |
| 2.163986 | 3.717889 | 0.082172 | 3.274084 | 2.41439 | 0.836799 | 4.866224 | 5.955418 | 6.928366 | 1.378686 | 3.123028 |
| 7.455578 | 9.380313 | 3.427911 | 8.468847 | 0.297906 | 0.000389 | 0.940839 | 0.628532 | 3.665946 | 1.724102 | 6.041043 |
| 0.188834 | 0.180636 | 1.210568 | 0.166508 | 2.216041 | 3.02721 | 0.913392 | 1.098491 | 0.01027 | 19.05242 | 23.18382 |
| 9.573725 | 8.918982 | 4.728361 | 3.671089 | 0.467508 | 1.062601 | 0.105147 | 0.218956 | 0.7026 | 13.5672 | 14.5385 |
| 6.097515 | 5.625851 | 8.16963 | 3.746753 | 0.005085 | 0.483266 | 0.036664 | 0.00034 | 1.558801 | 0.156834 | 2.62353 |
| 0.15321 | 1.308992 | 3.366806 | 3.613285 | 16.35518 | 8.54773 | 4.207234 | 9.083077 | 8.645542 | 0.383128 | 0.339017 |
| 0.000606 | 0.530335 | 2.021356 | 1.867574 | 0.030611 | 3.249142 | 0.039851 | 0.066723 | 0.068402 | 0.687783 | 0.184225 |
| 5.397633 | 6.534879 | 10.9517 | 9.86307 | 0.479865 | 5.507964 | 0.666262 | 0.499527 | 0.789603 | 2.018069 | 0.100234 |
| 2.453968 | 1.884492 | 0.586862 | 6.749781 | 0.27408 | 2.342669 | 0.000241 | 0.000211 | 2.36E−05 | 5.241312 | 6.921838 |
| 5.655269 | 2.044111 | 2.386309 | 0.270837 | 0.030532 | 2.846561 | 0.152321 | 0.001062 | 0.049629 | 0.331035 | 1.126286 |
| 15.45162 | 7.276956 | 6.805324 | 4.409346 | 0.274674 | 1.211254 | 0.388469 | 0.015329 | 0.181457 | 3.479077 | 0.089268 |
| 2.872391 | 3.162929 | 0.20556 | 0.06463 | 2.844147 | 3.429374 | 0.414358 | 0.036004 | 1.831293 | 0.481146 | 0.493449 |
| 3.407805 | 4.023687 | 0.060242 | 1.038282 | 2.101493 | 8.26269 | 2.94461 | 1.311776 | 5.738207 | 1.527549 | 0.875145 |
| 11.50773 | 10.35848 | 2.799897 | 2.011236 | 0.049246 | 3.724438 | 3.720341 | 1.238204 | 1.401112 | 1.001449 | 1.016797 |
| 0.306989 | 0.00698 | 0.206057 | 1.249737 | 0.617986 | 0.006487 | 0.588757 | 1.092347 | 0.09342 | 2.035465 | 2.484966 |
| 0.064809 | 0.989582 | 0.121141 | 0.820687 | 0.218912 | 0.280452 | 1.840854 | 1.08671 | 0.08136 | 0.203287 | 0.208196 |
| 0.182525 | 1.174136 | 0.233749 | 0.470462 | 0.166118 | 0.006019 | 2.17326 | 0.782206 | 0.074023 | 0.631738 | 1.138233 |
| 9.870327 | 4.715414 | 3.860233 | 11.90237 | 0.094891 | 4.49542 | 0.526237 | 0.374653 | 0.464318 | 4.812526 | 7.960548 |
| 15.86295 | 9.339528 | 7.492743 | 16.9827 | 0.704206 | 6.652091 | 0.870788 | 2.359744 | 1.339042 | 1.076289 | 4.03345 |
| 22.91615 | 18.42281 | 9.996813 | 20.91339 | 1.505509 | 6.166912 | 0.435877 | 3.004862 | 0.955367 | 2.218331 | 7.894325 |
| 10.65936 | 8.386294 | 4.10009 | 5.430815 | 0.377654 | 5.913386 | 3.229559 | 0.971471 | 2.281736 | 37.71982 | 39.23912 |
| 6.791807 | 6.680932 | 1.239033 | 1.779843 | 0.362558 | 1.129713 | 0.881416 | 0.002462 | 0.425949 | 2.216896 | 1.111146 |
| 3.12312 | 3.449334 | 0.11372 | 0.219068 | 3.659253 | 1.279878 | 0.01725 | 1.801795 | 0.223838 | 1.285648 | 3.227161 |
| 1.039638 | 0.63357 | 0.40119 | 0.838862 | 0.630123 | 0.042399 | 0.327509 | 1.105544 | 0.042585 | 0.247054 | 0.222657 |
| 20.34532 | 8.209194 | 14.06594 | 18.80999 | 0.107022 | 1.431403 | 1.054151 | 0.230933 | 1.152532 | 0.995516 | 0.129381 |
| 2.07303 | 1.289326 | 1.754405 | 0.00677 | 4.519323 | 2.901351 | 8.179715 | 12.29466 | 8.346066 | 0.473155 | 5.782415 |
| 0.736729 | 0.005513 | 3.700206 | 0.893158 | 1.752385 | 0.372779 | 0.24036 | 1.270774 | 0.2485 | 22.351 | 12.87094 |
| 0.284204 | 0.087941 | 0.372415 | 1.728661 | 0.202183 | 0.937515 | 4.917089 | 0.555011 | 2.483896 | 0.066806 | 2.759175 |
| 0.931087 | 0.036874 | 0.204993 | 3.826305 | 4.465647 | 6.25087 | 13.04752 | 7.053393 | 13.76366 | 1.236814 | 5.796775 |
| 4.995061 | 1.854821 | 1.090177 | 4.516881 | 0.136635 | 1.796511 | 0.07659 | 2.789379 | 0.008025 | 37.12583 | 80.33573 |
| 0.346756 | 0.011561 | 0.012896 | 0.43104 | 0.049867 | 0.605059 | 0.043559 | 3.214205 | 0.009498 | 0.834358 | 0.294721 |
| 3.044464 | 3.145818 | 2.822839 | 4.392826 | 0.136205 | 3.481339 | 0.160477 | 0.111062 | 0.013316 | 0.880882 | 0.042396 |
| 0.08407 | 0.345865 | 0.112406 | 0.003606 | 0.00824 | 0.058943 | 0.027515 | 2.374697 | 0.086152 | 5.039342 | 8.6694 |
| 0.271606 | 1.685402 | 1.666327 | 2.514249 | 0.014582 | 0.115204 | 0.03832 | 2.017991 | 0.001431 | 0.629082 | 3.24665 |
| 3.891928 | 13.50356 | 11.82324 | 12.92457 | 0.002199 | 0.212939 | 0.003591 | 1.992822 | 0.017474 | 0.598955 | 0.052893 |
| 1.642501 | 0.096345 | 0.00208 | 0.292417 | 1.577875 | 0.40757 | 0.202508 | 1.678315 | 0.324301 | 0.001437 | 2.671893 |
| 1.927069 | 0.052439 | 0.005625 | 0.113885 | 0.054837 | 2.964406 | 0.041548 | 0.171958 | 0.181218 | 0.037391 | 0.668865 |
| 0.011455 | 1.859268 | 1.382837 | 3.026851 | 1.127327 | 1.619356 | 0.111925 | 1.79646 | 1.548009 | 0.521336 | 6.233273 |
| 1.332231 | 0.210434 | 0.068731 | 0.360294 | 0.034673 | 2.272478 | 0.013014 | 0.003989 | 0.050304 | 0.072014 | 0.54257 |
| 21.9683 | 13.60448 | 19.64991 | 22.35876 | 0.022308 | 1.984417 | 0.000442 | 0.205631 | 2.312127 | 0.036576 | 1.866251 |
| 9.500695 | 1.93387 | 4.626317 | 3.712475 | 0.920247 | 0.779259 | 0.180959 | 0.411896 | 0.244126 | 0.209312 | 0.490925 |

TABLE 33-continued

| | | | | | | | |
|---|---|---|---|---|---|---|---|
| | | | 3-EtOH-2 | | | | |
| | THF | | | $\theta_{u,mn}$ EtOH | | $H_2O$ | |
| | k3 | k4 | k5 | k6 | k1 | k2 | k3 | k4 |

| k3 | k4 | k5 | k6 | k1 | k2 | k3 | k4 |
|---|---|---|---|---|---|---|---|
| 7.209428 | 2.585401 | 2.783555 | −0.49172 | 1.039367 | 4.181415 | 0.017328 | 2.342642 |
| 0.119807 | 2.090068 | 0.070991 | −0.3649 | 0.741633 | 2.000148 | 0.000661 | 1.783299 |
| 0.46077 | 0.705627 | 0.593396 | −0.59058 | 5.098292 | 11.68493 | 3.85472 | 9.994442 |
| 11.8767 | 81.74446 | 95.99102 | 0.12682 | 0.690808 | 3.517475 | 0.028967 | 1.487189 |
| 73.4155 | 49.71535 | 67.13817 | −0.09888 | 0.000461 | 0.554475 | 1.109645 | 0.031169 |
| 1.780819 | 0.014802 | 2.025397 | −0.22568 | 12.34242 | 24.99653 | 26.44039 | 20.65419 |
| 8.679969 | 23.11923 | 19.57639 | −1.10111 | 68.34178 | 59.74677 | 72.36901 | 46.51314 |
| 1.998733 | 6.419063 | 6.050502 | −0.5856 | 2.865023 | 3.194788 | 3.762564 | 2.961461 |
| 0.567466 | 2.772321 | 2.664494 | −0.60611 | 2.423329 | 3.614329 | 3.505262 | 3.475374 |
| 162.6803 | 195.6432 | 187.416 | 0.51551 | 2.863514 | 2.004093 | 2.497486 | 1.281664 |
| 69.31269 | 77.00671 | 73.12572 | 0.495001 | 2.955889 | 1.581069 | 2.423816 | 0.926809 |
| 0.011017 | 0.432529 | 0.449157 | −0.02051 | 0.547511 | 0.577477 | 0.101957 | 0.872854 |
| 7.083517 | 0.571801 | 2.05509 | −0.56247 | 0.216431 | 0.390765 | 0.03578 | 0.008364 |
| 3.112214 | 0.034088 | 1.196865 | −0.49892 | 0.007937 | 1.417054 | 0.646334 | 0.302906 |
| 4.43148 | 0.89398 | 3.682988 | −0.75811 | 3.354406 | 9.03463 | 8.715777 | 1.914243 |
| 35.06446 | 18.18387 | 23.43695 | 0.063551 | 0.166463 | 0.043832 | 0.005943 | 0.007821 |
| 9.456028 | 2.998634 | 4.431889 | −0.19563 | 0.01259 | 0.002004 | 0.14739 | 0.130551 |
| 1.941951 | 2.696315 | 3.275855 | −0.25918 | 3.814351 | 1.16407 | 3.25258 | 7.470084 |
| 6.389649 | 2.450878 | 0.38911 | −0.46577 | 0.197929 | 3.104708 | 0.007457 | 0.098162 |
| 4.795371 | 4.26748 | 0.232547 | −0.39172 | 2.199879 | 0.004299 | 0.034689 | 0.011157 |
| 6.334312 | 3.510943 | 0.808408 | −0.51368 | 2.411769 | 8.28E−05 | 0.01876 | 0.000304 |
| 31.6611 | 21.83804 | 13.55197 | 0.074052 | 1.18359 | 0.740045 | 0.01506 | 0.055103 |
| 22.65644 | 17.0261 | 7.93527 | −0.04791 | 1.362272 | 0.603683 | 0.006716 | 0.015439 |
| 0.661158 | 0.047764 | 1.457812 | −0.12196 | 4.271793 | 1.80782 | 0.570576 | 4.373443 |
| 1.248373 | 4.9869 | 0.573481 | −0.20442 | 0.036228 | 0.26583 | 0.567661 | 0.076037 |
| 2.066234 | 5.169474 | 0.909931 | −0.38049 | 0.023766 | 0.065639 | 0.589573 | 0.009682 |
| 0.977223 | 4.404689 | 0.330618 | −0.88994 | 0.557371 | 0.805593 | 0.039587 | 0.493961 |
| 8.886271 | 15.23736 | 4.497766 | −0.17607 | 0.033461 | 0.15138 | 0.061232 | 0.031529 |
| 0.970875 | 1.236846 | 0.505702 | −0.68552 | 0.348673 | 0.703894 | 0.033253 | 0.358016 |
| 0.432419 | 2.265339 | 0.131278 | −0.50945 | 20.75998 | 23.51675 | 27.34526 | 22.04829 |
| 0.069477 | 0.177061 | 4.163289 | −0.48078 | 5.633158 | 1.292155 | 3.643935 | 6.539004 |
| 1.369326 | 0.009823 | 3.383208 | −0.21482 | 0.396325 | 0.166177 | 0.396369 | 1.607344 |
| 1.970457 | 0.032303 | 2.754407 | −0.47533 | 0.001593 | 0.572229 | 0.037377 | 0.563391 |
| 0.127149 | 2.679753 | 5.374108 | 0.265958 | 1.288415 | 0.009635 | 1.047933 | 3.080655 |
| 0.549304 | 0.967503 | 0.962724 | 0.005456 | 0.30615 | 0.183773 | 0.431791 | 1.802996 |
| 2.196044 | 0.102733 | 1.626653 | −0.2605 | 10.83091 | 2.871491 | 4.625001 | 6.574388 |
| 5.854056 | 10.19453 | 1.761085 | −1.05313 | 10.24292 | 10.32592 | 12.37062 | 8.123911 |
| 2.276655 | 7.528948 | 1.245261 | −0.66408 | 12.33745 | 0.1412 | 0.61828 | 0.002109 |
| 1.408409 | 1.008997 | 2.722997 | −0.99537 | 1.483211 | 0.123803 | 0.393324 | 0.003684 |
| 36.84406 | 37.29937 | 20.67821 | 0.169055 | 6.192404 | 1.079213 | 0.592805 | 1.446719 |
| 3.412061 | 5.334902 | 0.227932 | 0.057766 | 5.35223 | 0.596701 | 0.366687 | 0.869909 |
| 0.328788 | 0.003373 | 1.571706 | −0.13129 | 2.246464 | 0.05829 | 0.000546 | 0.011593 |
| 0.0427 | 4.00647 | 0.514822 | −2.08878 | 18.71071 | 27.46477 | 19.3289 | 16.52268 |
| 0.940793 | 0.554887 | 0.228931 | −1.39282 | 6.178603 | 2.745697 | 12.749 | 6.773489 |
| 0.780078 | 0.602464 | 1.425671 | −1.77334 | 2.797405 | 1.884453 | 9.89008 | 4.469062 |
| 13.57534 | 27.5757 | 20.203 | 0.196186 | 0.236733 | 2.582707 | 0.084066 | 0.065943 |
| 0.532375 | 0.063023 | 0.208297 | 0.315442 | 0.98955 | 3.021241 | 0.027928 | 0.242648 |
| 1.743934 | 0.19386 | 1.710064 | 0.119275 | 5.089119 | 0.322521 | 0.299958 | 1.090716 |
| 46.55472 | 41.27834 | 36.58368 | −0.69846 | 3.204223 | 0.309329 | 1.237422 | 1.161745 |
| 1.402084 | 0.12085 | 2.199278 | −0.59644 | 0.001127 | 6.78E−05 | 0.032946 | 2.047428 |
| 0.698016 | 0.217173 | 1.788701 | −0.85775 | 0.088569 | 0.019763 | 0.004118 | 2.751901 |
| 4.819708 | 12.20418 | 2.850942 | 0.102024 | 0.256078 | 0.024014 | 0.2307 | 1.423912 |
| 1.301718 | 5.203679 | 0.267291 | −0.15929 | 0.024781 | 7.09E−05 | 0.138638 | 1.990683 |
| 0.069312 | 0.798403 | 0.569826 | −0.26131 | 4.550189 | 0.914743 | 0.653627 | 1.03376 |
| 0.005974 | 0.004668 | 0.001063 | −0.57675 | 0.724429 | 0.025084 | 2.301283 | 0.936212 |
| 0.724124 | 0.168543 | 4.091074 | −0.54389 | 3.525334 | 0.843104 | 0.166227 | 4.53217 |
| 1.059572 | 3.701235 | 2.08801 | −0.56806 | 4.240792 | 0.341625 | 0.396181 | 3.920713 |
| 0.022857 | 0.097069 | 1.287766 | 0.032871 | 0.917859 | 0.363092 | 0.234758 | 1.177147 |
| 0.240556 | 0.008604 | 0.264577 | 0.010706 | 0.756194 | 0.094308 | 0.435137 | 0.527479 |
| 0.058309 | 1.204495 | 0.413128 | −0.02217 | 1.143831 | 1.432489 | 0.003409 | 3.163037 |

TABLE 34

3-EtOH-3

$(\theta_{u,mn} - \theta_{g,mnk})^2 / \sigma_{\theta g,mn}^2$

| | EtOH | | | | | Benzene | | | | |
|---|---|---|---|---|---|---|---|---|---|---|
| k5 | k1 | k2 | k3 | k4 | k5 | k1 | k2 | k3 | k4 | k5 |
| 1.228388 | 0.052369 | 2.278368 | 0.002386 | 0.036022 | 0.003249 | 0.352209 | 0.274813 | 0.423041 | 0.159091 | 0.792431 |
| 3.597915 | 0.277311 | 2.315814 | 0.014915 | 0.12911 | 0.017105 | 0.011503 | 1.173894 | 0.001956 | 0.425466 | 2.31723 |
| 12.36596 | 0.192608 | 1.924064 | 0.013777 | 0.299389 | 0.002238 | 0.00132 | 3.445448 | 1.714256 | 1.099586 | 0.470538 |
| 0.069713 | 0.18428 | 1.923354 | 0.014043 | 0.020289 | 0.011221 | 1.978995 | 0.737313 | 2.881553 | 6.344916 | 0.613347 |
| 0.419237 | 0.064285 | 2.139405 | 0.014664 | 0.492457 | 0.012543 | 0.326607 | 0.274634 | 1.924591 | 1.00329 | 0.251056 |
| 14.95916 | 0.281273 | 0.176468 | 0.000529 | 3.498747 | 0.502871 | 0.006185 | 0.07295 | 0.958815 | 0.012852 | 0.989116 |
| 71.64024 | 1.151867 | 1.18462 | 0.643076 | 8.745697 | 2.16838 | 0.010015 | 2.01784 | 0.027193 | 0.003501 | 0.250858 |
| 0.047766 | 0.018613 | 0.045812 | 1.637755 | 1.849722 | 1.8515 | 0.014121 | 0.005861 | 0.130357 | 0.151095 | 1.72472 |
| 0.061984 | 0.361119 | 0.036645 | 0.978737 | 0.561376 | 0.695239 | 0.003569 | 0.002043 | 0.000269 | 0.037172 | 2.368666 |
| 6.78711 | 1.23013 | 0.637426 | 0.204321 | 1.408144 | 0.007433 | 0.020427 | 2.428719 | 0.01822 | 0.012066 | 0.077372 |
| 7.9329 | 1.731785 | 0.865588 | 0.166085 | 1.110733 | 0.040581 | 0.053467 | 1.581411 | 0.083793 | 0.005401 | 0.286062 |
| 0.036722 | 2.678856 | 1.257161 | 0.053848 | 0.31346 | 0.212373 | 0.075189 | 0.036613 | 0.159946 | 0.002345 | 3.181221 |
| 1.348802 | 0.374598 | 0.237703 | 0.349591 | 0.015995 | 1.028007 | 0.244198 | 0.303426 | 0.238188 | 0.003268 | 1.265652 |
| 0.809427 | 1.95147 | 0.011243 | 0.158786 | 0.020554 | 0.226335 | 4.778195 | 0.188551 | 0.310644 | 0.778707 | 1.688142 |
| 5.955147 | 2.3314 | 0.050711 | 0.00268 | 1.04E−05 | 0.04502 | 0.326134 | 0.917428 | 0.7643 | 0.182644 | 0.145749 |
| 1.886931 | 2.99878 | 0.21695 | 0.004928 | 0.008495 | 0.250826 | 0.003053 | 0.543901 | 0.481729 | 0.074904 | 0.98313 |
| 2.704558 | 2.019353 | 0.001494 | 0.09702 | 0.002586 | 0.452733 | 0.16688 | 0.155622 | 0.45626 | 0.019812 | 1.218683 |
| 1.024091 | 1.501869 | 0.069011 | 0.165626 | 0.01272 | 0.522703 | 2.622016 | 1.534556 | 0.044481 | 0.235409 | 0.657925 |
| 0.094295 | 0.104025 | 1.845601 | 0.391938 | 0.336351 | 0.2537 | 2.816469 | 0.021143 | 0.082024 | 0.030217 | 0.004419 |
| 5.69E−05 | 0.013206 | 0.28377 | 0.055691 | 1.532729 | 0.327928 | 0.48135 | 1.46389 | 0.340621 | 0.022748 | 0.401354 |
| 0.000702 | 0.047045 | 0.013885 | 0.942558 | 0.867586 | 0.196643 | 1.011887 | 0.540931 | 0.532877 | 0.184529 | 0.036601 |
| 0.021474 | 0.028564 | 0.439369 | 0.082622 | 0.542048 | 1.045382 | 3.146511 | 0.51883 | 0.391244 | 0.024651 | 0.133033 |
| 0.012884 | 0.261336 | 0.691868 | 0.634851 | 0.598865 | 0.86959 | 2.190771 | 0.247117 | 0.000353 | 0.156909 | 0.026694 |
| 0.348999 | 0.346374 | 0.208103 | 2.655424 | 0.072827 | 0.022598 | 0.446502 | 0.495473 | 5.428056 | 1.090636 | 0.524368 |
| 1.12979 | 0.205356 | 0.323384 | 3.421924 | 2.379755 | 0.079035 | 0.005741 | 0.512911 | 0.112376 | 0.054633 | 1.517978 |
| 1.830248 | 0.917512 | 0.002788 | 0.040939 | 0.318883 | 1.386634 | 1.669205 | 1.572437 | 1.327134 | 0.001816 | 0.020026 |
| 0.513332 | 3.519022 | 1.117601 | 0.905629 | 0.095492 | 4.090679 | 1.632662 | 1.515605 | 0.004231 | 0.807441 | 0.078413 |
| 1.872484 | 1.815347 | 0.680239 | 7.322125 | 2.903228 | 1.62672 | 0.400879 | 0.06523 | 1.231677 | 0.116179 | 2.519369 |
| 0.88075 | 13.45393 | 6.202285 | 16.4014 | 6.59767 | 13.50076 | 0.265875 | 0.158978 | 0.248371 | 0.581295 | 2.494299 |
| 39.82237 | 6.767485 | 3.47423 | 2.406862 | 1.037991 | 7.21716 | 0.065536 | 0.055955 | 1.474296 | 0.6046 | 0.010102 |
| 0.992192 | 0.003197 | 0.420242 | 0.009817 | 2.900457 | 0.006705 | 0.368528 | 0.970262 | 0.088592 | 0.204059 | 0.380614 |
| 1.860383 | 1.00061 | 0.100924 | 0.23261 | 0.818126 | 0.000478 | 0.026026 | 1.855255 | 0.117718 | 0.025336 | 0.030528 |
| 1.11511 | 0.677003 | 0.014936 | 0.153997 | 0.320487 | 0.837781 | 0.007164 | 1.529805 | 0.152322 | 2.185849 | 0.001806 |
| 2.16275 | 3.725954 | 2.825287 | 1.107444 | 1.504192 | 0.009729 | 0.551799 | 0.074064 | 0.019638 | 0.269955 | 1.086068 |
| 1.541191 | 0.40215 | 0.261416 | 0.231966 | 0.196134 | 0.865683 | 0.180654 | 0.019973 | 0.285931 | 2.194126 | 0.216078 |
| 2.352242 | 0.10366 | 0.014774 | 0.022003 | 2.42E−05 | 2.10458 | 0.000335 | 0.195992 | 0.477481 | 3.254681 | 0.030005 |
| 2.906836 | 10.14427 | 14.73862 | 17.37765 | 23.19241 | 9.764089 | 2.363979 | 11.7959 | 4.117804 | 5.496649 | 4.23999 |
| 0.004822 | 3.927444 | 4.538176 | 2.458528 | 11.58435 | 3.550647 | 1.369856 | 8.146585 | 2.348529 | 3.096952 | 6.53282 |
| 0.013104 | 0.828795 | 0.54261 | 0.043524 | 4.554725 | 0.784516 | 0.116239 | 0.8315 | 0.252823 | 0.277625 | 1.000513 |
| 0.663168 | 0.269866 | 0.943785 | 4.204555 | 0.058388 | 0.347844 | 0.453881 | 1.311108 | 0.82358 | 1.133479 | 0.338079 |
| 0.498953 | 0.038769 | 0.416312 | 1.878032 | 0.313568 | 0.040637 | 1.28207 | 0.41448 | 0.177144 | 3.008415 | 0.015636 |
| 0.069158 | 4.75E−05 | 0.175276 | 0.901803 | 1.033474 | 0.001762 | 1.264075 | 0.125423 | 0.029602 | 2.524271 | 0.004298 |
| 10.70237 | 1.066292 | 0.920567 | 0.696547 | 6.353486 | 0.927072 | 1.128205 | 5.311685 | 0.426892 | 1.151615 | 1.523734 |
| 4.559579 | 0.831202 | 0.716337 | 0.594016 | 5.861922 | 0.717252 | 1.476096 | 6.771986 | 0.907907 | 0.736777 | 1.495916 |
| 2.48889 | 0.161224 | 0.362078 | 0.217189 | 4.374865 | 0.395424 | 1.79333 | 7.50268 | 0.815126 | 1.926601 | 1.518222 |
| 0.031011 | 0.603058 | 0.519626 | 0.020998 | 0.752198 | 0.573882 | 0.241809 | 0.030115 | 1.106158 | 0.720926 | 0.013727 |
| 0.247442 | 6.620443 | 1.530746 | 1.862549 | 0.464882 | 1.245472 | 0.041161 | 2.466847 | 0.005769 | 0.013529 | 1.125211 |
| 2.029859 | 7.550926 | 1.394367 | 2.450677 | 1.35038 | 1.043943 | 0.283257 | 1.983992 | 0.522804 | 0.290546 | 0.602747 |
| 0.011431 | 0.003447 | 0.012977 | 0.004327 | 1.66757 | 0.376807 | 1.012795 | 0.84911 | 0.183705 | 0.058037 | 0.166775 |
| 0.08577 | 0.030821 | 0.097382 | 0.007099 | 1.85279 | 0.067842 | 7.542811 | 1.111552 | 1.332055 | 1.487372 | 3.27934 |
| 0.002387 | 0.077614 | 0.27838 | 0.000268 | 3.171593 | 0.062305 | 0.880803 | 0.913486 | 0.040246 | 0.001824 | 0.244253 |
| 0.075171 | 0.145957 | 0.427312 | 0.187597 | 0.546553 | 0.694742 | 0.111901 | 2.118903 | 0.021747 | 0.010191 | 0.007837 |
| 0.006357 | 0.014297 | 0.050328 | 0.00167 | 2.241024 | 0.107171 | 0.013021 | 0.290147 | 0.718705 | 1.384078 | 0.30999 |
| 5.20428 | 0.00011 | 0.001831 | 0.011529 | 2.605108 | 0.011361 | 0.114523 | 2.202483 | 0.009109 | 0.170741 | 0.004946 |
| 4.110383 | 4.254323 | 2.478015 | 0.115892 | 0.792578 | 0.387976 | 0.104733 | 0.49336 | 0.333748 | 3.69E−05 | 1.23719 |
| 1.220146 | 1.194864 | 1.500942 | 0.020379 | 4.191692 | 0.437534 | 1.729387 | 0.315844 | 0.362608 | 0.075875 | 0.004534 |
| 1.735887 | 0.163556 | 0.143413 | 0.416394 | 1.550201 | 0.005465 | 0.358615 | 1.24103 | 0.014985 | 0.00044 | 0.696615 |
| 0.052918 | 0.263482 | 9.33E−07 | 0.01502 | 1.253443 | 0.031665 | 2.843569 | 0.01926 | 0.108344 | 0.184373 | 1.08706 |
| 0.266759 | 0.03599 | 0.003765 | 0.773345 | 3.142719 | 0.08457 | 0.448582 | 1.449142 | 0.006062 | 0.000659 | 0.430149 |
| 0.211741 | 0.000311 | 0.002035 | 0.365047 | 2.921051 | 0.071052 | 0.00048 | 22.74992 | 0.07757 | 0.069457 | 2.017016 |

| Hexane | | | | | AcOEt | | |
|---|---|---|---|---|---|---|---|
| k1 | k2 | k3 | k4 | k5 | k1 | k2 | k3 |
| 0.355126 | 0.101811 | 0.310542 | 0.9483 | 0.612433 | 0.000446 | 0.065533 | 1.621244 |
| 0.677362 | 0.089438 | 0.525459 | 4.769294 | 1.058773 | 0.062258 | 0.070367 | 2.752704 |
| 0.794912 | 0.184565 | 0.758018 | 5.31185 | 1.084796 | 0.354359 | 0.082417 | 2.733065 |
| 3.549724 | 6.032561 | 4.924424 | 1.200566 | 9.024264 | 0.766579 | 2.938546 | 0.982911 |
| 0.595501 | 0.531073 | 0.228299 | 0.005214 | 3.48801 | 3.011032 | 2.076397 | 2.38561 |
| 0.763307 | 2.823664 | 3.500398 | 2.343077 | 0.022087 | 2.061624 | 0.065669 | 1.165971 |
| 31.71836 | 32.74562 | 17.83658 | 18.94757 | 22.21355 | 1.630507 | 0.965388 | 4.128121 |
| 16.29535 | 11.16205 | 7.120646 | 5.250265 | 6.521619 | 9.519184 | 1.303375 | 4.854225 |

TABLE 34-continued

| | 3-EtOH-3 | | | | | | |
|---|---|---|---|---|---|---|---|
| | $(\theta_{u,mn}-\theta_{g,mnk})^2/\sigma_{\theta g,mn}^2$ | | | | | | |

| | | | | | | | |
|---|---|---|---|---|---|---|---|
| 12.27582 | 6.616299 | 4.54663 | 3.691214 | 2.992024 | 1.854354 | 0.201704 | 0.017204 |
| 14.93736 | 28.42752 | 12.57856 | 20.40815 | 22.62521 | 0.039004 | 0.192659 | 0.969094 |
| 7.595128 | 13.17685 | 7.840589 | 10.98572 | 16.74241 | 0.142373 | 1.151027 | 2.734759 |
| 0.01095 | 1.60926 | 0.536356 | 0.097599 | 3.360103 | 6.903475 | 11.81276 | 16.4555 |
| 2.37661 | 2.836678 | 1.714898 | 0.002363 | 2.188277 | 0.006874 | 0.209254 | 1.788979 |
| 1.975763 | 1.717717 | 0.895094 | 0.116436 | 1.129042 | 0.855497 | 0.070085 | 4.297621 |
| 1.537527 | 2.092005 | 0.874624 | 0.126253 | 1.062255 | 0.74657 | 0.06236 | 3.167473 |
| 0.255415 | 4.075924 | 2.923508 | 3.683448 | 5.524485 | 0.204201 | 0.161675 | 3.005589 |
| 0.290227 | 0.003032 | 1.310285 | 3.322867 | 2.062328 | 0.336126 | 0.127532 | 2.837453 |
| 0.016691 | 2.294994 | 0.048191 | 0.075441 | 0.19333 | 0.531636 | 0.054386 | 1.916345 |
| 0.075754 | 0.648543 | 1.885158 | 0.021291 | 0.738538 | 0.002573 | 2.225853 | 0.018389 |
| 0.24722 | 0.263272 | 1.203662 | 0.197663 | 0.444806 | 1.419374 | 0.13301 | 0.110037 |
| 0.292922 | 0.269517 | 1.196651 | 0.217763 | 0.280851 | 1.035524 | 0.009117 | 0.007781 |
| 11.07036 | 16.31642 | 13.21266 | 19.46095 | 6.574888 | 1.414526 | 4.697624 | 0.286408 |
| 29.74006 | 42.0335 | 44.24518 | 44.62788 | 55.13801 | 1.01556 | 2.682241 | 0.069811 |
| 0.045498 | 0.036453 | 0.332609 | 0.000103 | 3.099592 | 0.470818 | 0.036622 | 0.029422 |
| 0.034297 | 1.418364 | 0.246511 | 0.596936 | 0.130918 | 0.234395 | 1.36654 | 0.138654 |
| 0.115409 | 1.380434 | 0.00792 | 0.650779 | 0.016007 | 0.058289 | 3.001319 | 0.035245 |
| 0.366274 | 1.422863 | 0.060574 | 0.51949 | 0.001438 | 0.095778 | 3.13282 | 0.052897 |
| 0.232723 | 0.019533 | 1.808097 | 0.002767 | 0.611467 | 6.651925 | 1.787676 | 3.440234 |
| 1.097533 | 0.016429 | 0.315074 | 0.002162 | 0.570583 | 0.530707 | 4.173148 | 0.300255 |
| 2.172704 | 0.228288 | 0.698182 | 0.03104 | 0.170697 | 0.09938 | 3.194497 | 0.062461 |
| 1.252008 | 0.025654 | 0.223278 | 0.819109 | 0.491802 | 1.175316 | 4.984812 | 0.104764 |
| 1.089998 | 0.004896 | 0.265047 | 0.120499 | 0.765451 | 0.866667 | 0.293555 | 0.197445 |
| 1.000928 | 0.004524 | 0.309875 | 7.11E−06 | 0.793143 | 0.644091 | 0.035692 | 0.291019 |
| 0.000742 | 0.430262 | 0.042422 | 2.594573 | 0.472673 | 2.835683 | 2.694138 | 0.001148 |
| 0.025458 | 0.172641 | 0.036313 | 2.821183 | 0.165377 | 1.753402 | 1.686681 | 0.043617 |
| 0.108088 | 0.000446 | 0.021051 | 2.468067 | 0.001963 | 0.106452 | 0.114422 | 0.204879 |
| 0.766908 | 0.754821 | 1.540074 | 0.296114 | 1.03385 | 2.64901 | 11.60325 | 4.586975 |
| 0.457333 | 0.349781 | 1.279502 | 0.519552 | 0.591553 | 13.35785 | 9.297632 | 5.333156 |
| 0.274739 | 0.373915 | 1.255169 | 0.608054 | 0.327023 | 4.560619 | 0.187672 | 0.534162 |
| 5.286043 | 9.349954 | 2.46243 | 2.276465 | 7.588676 | 0.895025 | 0.696301 | 0.078954 |
| 4.269435 | 2.329842 | 0.58669 | 1.728751 | 6.808025 | 1.199641 | 0.631273 | 0.021712 |
| 1.007923 | 0.079146 | 0.027432 | 0.365282 | 1.757245 | 1.396364 | 0.562837 | 0.002572 |
| 3.203448 | 13.20573 | 5.249072 | 4.709387 | 4.822595 | 28.71154 | 32.80476 | 35.73892 |
| 0.229887 | 2.352662 | 2.999608 | 0.579505 | 0.002677 | 40.04883 | 54.80245 | 55.79858 |
| 0.522592 | 1.785352 | 5.330377 | 0.579255 | 3.810373 | 5.479792 | 10.30229 | 2.012695 |
| 0.145175 | 0.015079 | 0.714818 | 0.0676 | 1.277185 | 1.399906 | 0.072262 | 0.512287 |
| 0.044873 | 0.306252 | 1.051 | 0.133222 | 0.644807 | 0.469172 | 0.035673 | 2.966809 |
| 0.026364 | 0.274194 | 0.069269 | 0.022778 | 2.152167 | 0.261742 | 0.022636 | 3.218019 |
| 0.675602 | 0.875612 | 4.030378 | 5.041702 | 0.619938 | 0.257037 | 4.280811 | 0.095009 |
| 0.345221 | 0.0693 | 0.436728 | 0.403648 | 1.005691 | 0.035235 | 0.600231 | 0.010532 |
| 0.721553 | 0.026192 | 0.718003 | 0.44947 | 4.339085 | 0.028143 | 0.037015 | 0.065704 |
| 0.05971 | 0.044529 | 0.110423 | 0.251956 | 2.741968 | 0.000283 | 0.003406 | 0.000569 |
| 0.121045 | 0.062954 | 0.018569 | 0.140861 | 1.633034 | 0.000281 | 0.314837 | 0.020815 |
| 0.959485 | 0.317514 | 0.367918 | 0.006028 | 0.371556 | 8.63E−05 | 1.607132 | 0.159724 |
| 0.095115 | 1.569181 | 0.322529 | 0.979849 | 2.22122 | 0.016021 | 0.280992 | 2.046247 |
| 0.674225 | 0.683831 | 0.088988 | 0.23825 | 0.932896 | 0.063593 | 0.012553 | 1.578801 |
| 0.746789 | 0.460972 | 0.053458 | 0.220514 | 0.967909 | 0.0027 | 0.915945 | 0.850326 |
| 4.133811 | 0.112545 | 0.171847 | 0.931598 | 0.212333 | 0.032761 | 2.867633 | 1.117819 |
| 5.917751 | 4.2164 | 1.775801 | 3.694785 | 2.310357 | 0.006058 | 1.801682 | 0.19794 |
| 0.220272 | 2.290181 | 0.384984 | 0.269264 | 0.532652 | 0.050082 | 1.877765 | 0.005094 |

TABLE 35

| | 3-EtOH-4 | | | | | | | |
|---|---|---|---|---|---|---|---|---|
| | | | THF | | | | log $\sigma_{rg,mn}$ | |
| k4 | k5 | k1 | k2 | k3 | k4 | k5 | H2O | EtOH | Benzene |
| 0.35043 | 0.001437 | 0.841358 | 0.375372 | 0.116447 | 1.10269 | 0.203381 | −3.47051 | −4.20695 | −3.01438 |
| 0.009897 | 0.001891 | 0.04568 | 1.595598 | 0.021901 | 0.000543 | 0.422285 | 1.423286 | 0.497692 | −0.08048 |
| 0.014523 | 0.000353 | 0.154848 | 1.411259 | 0.004655 | 0.048947 | 0.456422 | 1.749126 | 2.144489 | 1.309926 |
| 2.89795 | 0.00011 | 0.18126 | 1.049923 | 0.006144 | 0.640801 | 0.182446 | 4.210396 | 2.683662 | 3.146059 |
| 1.342924 | 0.001604 | 0.000366 | 1.086617 | 0.009245 | 0.620303 | 0.29218 | 4.511755 | 4.725985 | 4.151946 |
| 0.020537 | 0.003826 | 0.511167 | 0.746711 | 0.011811 | 0.366781 | 0.403481 | −3.37465 | −0.12163 | −1.1664 |
| 6.960881 | 5.716054 | 0.001344 | 2.061398 | 0.045258 | 0.089082 | 0.05049 | −3.53898 | −4.81517 | −4.14667 |
| 4.673879 | 6.306308 | 0.896983 | 0.509831 | 0.223922 | 0.852948 | 0.778489 | 1.382603 | 0.58021 | 1.121638 |
| 0.000719 | 0.539618 | 0.003616 | 2.015977 | 0.122148 | 0.049081 | 0.090723 | 1.741738 | 4.397142 | 1.867993 |
| 2.641767 | 1.439809 | 0.449685 | 3.222632 | 0.000302 | 0.050469 | 1.097577 | 4.20996 | 3.877253 | 4.065613 |
| 5.073631 | 2.679881 | 6.11E−06 | 1.052998 | 0.502038 | 0.082077 | 0.463558 | 4.502093 | 7.334288 | 4.599096 |
| 19.16902 | 9.642697 | 8.215798 | 11.83124 | 8.87205 | 4.542433 | 2.793126 | −2.91705 | 2.017158 | −0.07503 |
| 0.000954 | 0.322231 | 0.003733 | 0.247275 | 0.612705 | 0.647675 | 0.843859 | −2.54699 | −3.73822 | −3.60914 |

TABLE 35-continued

3-EtOH-4

| | | | | | | | | | |
|---|---|---|---|---|---|---|---|---|---|
| 0.552766 | 0.210029 | 4.094808 | 1.047331 | 0.278774 | 1.088437 | 0.019739 | 2.232681 | 0.673325 | 0.52533 |
| 0.001692 | 0.064601 | 7.988992 | 3.085914 | 1.504191 | 2.548845 | 0.993219 | 2.82389 | 2.29136 | 2.377234 |
| 0.090564 | 0.025917 | 1.327916 | 1.518817 | 1.646148 | 0.127431 | 1.476395 | 4.526049 | 3.418593 | 3.245467 |
| 0.000187 | 0.006122 | 3.615234 | 3.172714 | 2.997917 | 0.044622 | 2.97023 | 4.977347 | 4.815047 | 4.289023 |
| 0.239461 | 0.005791 | 23.28425 | 13.92733 | 10.16989 | 9.226503 | 12.20879 | −1.55189 | −0.4342 | 0.255924 |
| 0.002747 | 1.493751 | 0.546302 | 0.01923 | 0.671904 | 3.685483 | 0.059812 | −3.21894 | −4.00041 | −4.99092 |
| 0.166911 | 0.358231 | 0.340654 | 4.841213 | 0.440971 | 2.355784 | 3.169244 | 1.990366 | 0.825083 | −0.84597 |
| 0.000119 | 0.947594 | 2.187622 | 1.025563 | 0.049601 | 4.258385 | 0.506878 | 2.337258 | 2.032124 | 1.48009 |
| 0.217752 | 2.241795 | 0.670411 | 0.139938 | 0.827648 | 4.530604 | 0.19208 | 4.824302 | 2.611209 | 3.155974 |
| 0.002353 | 0.075292 | 0.933751 | 0.128409 | 0.533208 | 4.332756 | 0.139367 | 5.461588 | 3.586953 | 5.32421 |
| 0.187856 | 1.448643 | 1.56323 | 0.053913 | 0.000129 | 2.23432 | 0.006785 | −1.65006 | −1.31919 | 0.433949 |
| 0.050263 | 0.24238 | 3.133229 | 4.144926 | 3.104889 | 6.402474 | 0.356968 | −3.2759 | −3.9333 | −4.83793 |
| 0.000114 | 0.031035 | 0.906585 | 4.798247 | 0.072209 | 1.178553 | 2.184847 | 2.395255 | 1.121161 | 0.586189 |
| 0.004711 | 0.033073 | 4.464618 | 10.82051 | 2.419135 | 6.251785 | 2.723736 | 2.671959 | 2.476318 | 1.833904 |
| 0.643045 | 4.982316 | 3.682895 | 5.67292 | 3.247895 | 7.287197 | 0.706185 | 4.960104 | 3.724711 | 4.348747 |
| 0.050378 | 0.31353 | 4.478689 | 7.798789 | 3.526912 | 7.685797 | 1.234762 | 5.213634 | 5.050598 | 5.343589 |
| 0.009219 | 0.041632 | 5.179622 | 10.95845 | 3.299208 | 7.32465 | 2.364957 | −1.9216 | −0.48259 | 0.760752 |
| 2.466723 | 2.464835 | 0.005136 | 0.118329 | 0.768 | 1.119398 | 8.57E−07 | −3.33665 | −4.93122 | −4.45787 |
| 0.80172 | 0.276983 | 0.002001 | 0.111384 | 1.27353 | 0.714349 | 0.0041 | 2.617672 | −0.84793 | −0.52142 |
| 1.190556 | 0.008867 | 0.107792 | 0.008848 | 1.021566 | 0.86603 | 5.79E−05 | 1.895491 | 0.827268 | 1.224621 |
| 0.59673 | 1.094573 | 0.008057 | 0.11861 | 0.456051 | 1.418327 | 0.002312 | 8.047899 | 2.645935 | 4.198668 |
| 0.029047 | 1.186567 | 0.213282 | 0.306795 | 0.413851 | 1.134348 | 8.68E−05 | 5.744713 | 3.834929 | 4.787592 |
| 0.84625 | 0.732364 | 2.01899 | 0.463615 | 0.159491 | 0.953121 | 0.029353 | −1.07522 | −1.10013 | 0.031744 |
| 3.544846 | 3.469225 | 0.996452 | 0.016191 | 0.86815 | 0.440542 | 0.119639 | −1.96114 | −3.01957 | −4.77763 |
| 10.46473 | 3.668531 | 15.66783 | 5.540242 | 15.18598 | 8.121858 | 8.303673 | 2.302225 | 1.172873 | −0.60568 |
| 1.477248 | 0.230384 | 9.504978 | 4.226213 | 11.9535 | 7.642024 | 15.39440 | 2.531087 | 2.180185 | 0.824372 |
| 0.237027 | 0.092726 | 0.024038 | 0.606628 | 0.008281 | 2.430214 | 0.120624 | 5.313679 | 3.298982 | 4.056546 |
| 0.094425 | 0.06176 | 0.122985 | 0.409401 | 0.034764 | 1.969107 | 0.327675 | 5.661962 | 4.329305 | 5.29199 |
| 0.03069 | 0.04169 | 0.724437 | 0.081948 | 0.177026 | 0.005548 | 1.081317 | −1.57645 | −0.62874 | −0.38181 |
| 16.45123 | 21.85879 | 17.95923 | 9.875253 | 8.910418 | 5.633674 | 13.49604 | −3.49631 | −3.94273 | −4.91018 |
| 37.21934 | 36.33248 | 243.8201 | 199.0491 | 193.9583 | 218.0849 | 197.4823 | 2.424872 | 0.445572 | 0.883836 |
| 7.654979 | 3.523965 | 8.589316 | 1.266111 | 6.516579 | 3.344692 | 5.897819 | 2.589026 | 2.778786 | 0.220413 |
| 0.525816 | 0.060147 | 0.07222 | 0.991205 | 1.23194 | 4.187153 | 0.15652 | 5.021767 | 3.338671 | 5.535133 |
| 0.020093 | 0.548782 | 0.061236 | 2.11152 | 0.174188 | 0.007816 | 0.122697 | 5.159181 | 5.413236 | 5.249664 |
| 0.000204 | 0.619949 | 0.171101 | 4.029587 | 0.188310 | 1.967687 | 0.355855 | −1.63969 | 0.909739 | 0.495249 |
| 1.601053 | 0.547428 | 0.037276 | 0.275211 | 0.130386 | 1.843934 | 0.011476 | −3.75061 | −4.03884 | −3.85018 |
| 3.374146 | 0.159308 | 0.658845 | 3.11597 | 0.568282 | 6.153308 | 1.608331 | 1.981951 | 2.272385 | 2.102403 |
| 3.356399 | 0.241986 | 5.35767 | 13.47142 | 7.321207 | 7.612895 | 3.019772 | 1.953076 | 4.092013 | 2.495732 |
| 2.495222 | 0.015327 | 0.574644 | 0.034485 | 1.043599 | 0.490591 | 0.779076 | 4.987952 | 5.078273 | 5.504239 |
| 1.884456 | 0.049559 | 0.991228 | 0.448661 | 1.721254 | 0.303218 | 0.498547 | 4.935532 | 5.916974 | 5.854076 |
| 0.142308 | 0.097775 | 1.252278 | 1.716074 | 2.061382 | 0.018478 | 0.04035 | −1.17599 | 0.633256 | −0.31503 |
| 0.069052 | 0.06548 | 0.009535 | 0.807115 | 0.715833 | 0.011206 | 0.496607 | −3.97888 | −1.75605 | −4.84516 |
| 0.128798 | 0.217163 | 0.785422 | 0.003474 | 3.101456 | 1.268244 | 0.10604 | 1.369905 | 2.462408 | 0.091022 |
| 9.33E−05 | 0.311718 | 0.137357 | 0.00084 | 3.569035 | 0.291427 | 0.566074 | 2.397461 | 3.352771 | 0.918108 |
| 0.000914 | 0.075065 | 7.31E−05 | 0.707019 | 0.965964 | 0.000772 | 0.477265 | 4.568042 | 3.121787 | 3.407953 |
| 0.079681 | 0.094911 | 0.000123 | 0.658137 | 0.882069 | 0.000286 | 0.638263 | 5.043107 | 3.956616 | 5.073329 |
| 0.202551 | 0.098561 | 0.020083 | 0.008324 | 2.180357 | 0.005625 | 0.768146 | −1.06582 | −1.14587 | −0.12107 |

| | log $\sigma_{rg,mn}$ | | | | | log $\sigma_{\theta g,mn}$ | | |
|---|---|---|---|---|---|---|---|---|
| Hexane | AcOEt | THF | H2O | EtOH | Benzene | Hexane | AcOEt | THF |
| −4.10649 | −2.38023 | −1.68628 | −0.82928 | 0.823367 | −0.51055 | 0.992277 | −0.01687 | −0.89727 |
| 0.688928 | 1.180556 | 0.570003 | −1.55647 | 0.340158 | −0.76988 | 0.467301 | −0.07627 | −0.43568 |
| 1.072453 | 2.454608 | 2.150339 | −1.63936 | 0.400977 | −1.08067 | 0.465262 | 0.123082 | −0.0921 |
| 3.37414 | 4.503542 | 2.094256 | −1.14966 | −0.67501 | −1.52378 | −1.8571 | −1.24557 | −0.59128 |
| 4.422139 | 5.309541 | 3.505918 | −1.1801 | −0.63757 | −0.50805 | −1.42174 | −0.9164 | −0.22345 |
| −1.31652 | −0.58079 | −0.29805 | −2.61649 | −1.8355 | −0.74507 | −2.09105 | −1.17806 | −1.17675 |
| −5.16409 | −4.20603 | −2.91236 | −2.16383 | −1.07596 | 1.084797 | −0.75634 | −1.56927 | −0.63991 |
| −0.22856 | −0.39937 | 0.259949 | −1.37949 | −1.06307 | −0.17781 | −0.871 | −2.29371 | −1.35059 |
| 0.658653 | 0.724481 | 2.016576 | −1.37216 | −0.73084 | 0.417273 | −0.73762 | −2.03317 | −1.17522 |
| 2.946359 | 2.288464 | 1.814887 | −1.17286 | −0.98772 | 0.319091 | −1.48448 | −1.58917 | −1.13088 |
| 4.283216 | 3.001095 | 3.289227 | −1.13063 | −0.69725 | 0.469739 | −1.13058 | −1.40378 | −1.16917 |
| −1.28754 | −1.63629 | −0.70151 | −3.16176 | −1.91056 | −0.36615 | −2.02085 | −2.98339 | −2.57999 |
| −3.45323 | −2.86846 | −2.63055 | −0.40633 | −1.46006 | −0.15372 | 0.262191 | −0.88764 | −0.58837 |
| 1.248007 | 0.60212 | 0.207069 | −1.49237 | −1.15723 | −1.74261 | 0.300856 | −1.27126 | −1.29522 |
| 1.521438 | 1.683112 | 1.784486 | −2.05044 | −0.51846 | −1.86177 | 0.407925 | −0.48163 | −1.06283 |
| 4.290344 | 3.604588 | 2.58891 | −0.3419 | −1.76309 | −0.29631 | −1.57369 | −0.42624 | −0.79534 |
| 4.912251 | 4.56719 | 4.147205 | −0.4135 | −0.61661 | −0.19836 | −1.35308 | −0.02066 | −0.70174 |
| −1.43277 | −2.33187 | −0.66004 | −2.20351 | −0.95833 | −1.7084 | −1.3211 | −0.98294 | −2.43581 |
| −4.18508 | −4.57844 | −2.68352 | −0.25239 | −1.97182 | −0.41208 | 0.666055 | −1.33803 | −0.7309 |
| 0.734052 | 0.285807 | 0.234313 | 0.394229 | −1.83933 | −1.48248 | 0.686205 | −1.9322 | −3.00454 |
| 1.36182 | 2.258278 | 1.282089 | 0.427422 | −1.40018 | −1.40448 | 0.639868 | −1.32376 | −1.9627 |
| 3.225993 | 3.283066 | 2.743929 | 0.533222 | −1.84778 | −0.66336 | −1.98667 | −1.65619 | −0.75504 |
| 4.055777 | 5.115025 | 3.888008 | 0.566183 | −1.64801 | −0.58531 | −2.40852 | −1.49817 | −0.53901 |
| −0.61674 | −0.16786 | −1.41821 | −2.43387 | −2.10459 | −2.01139 | −1.70592 | −1.94335 | −1.94459 |
| −3.99619 | −4.57673 | −2.56564 | −0.82216 | −1.35886 | 0.057138 | 0.385252 | −0.37197 | −0.95689 |
| 0.794856 | 2.396694 | 0.470495 | −0.2301 | −1.96415 | −0.80879 | 0.362596 | −0.47755 | −2.79221 |

TABLE 35-continued

| \multicolumn{8}{c}{3-EtOH-4} |
|---|---|---|---|---|---|---|---|
| 0.952827 | 2.335711 | 2.321066 | −0.34122 | −1.17207 | −0.99618 | 0.428725 | 0.658463 | −1.47053 |
| 2.499667 | 4.966157 | 2.71242 | 0.119395 | −1.68121 | −0.2457 | −0.8037 | −1.60442 | −0.95537 |
| 3.978408 | 4.951408 | 4.257231 | 0.039681 | −1.65995 | −0.27385 | −0.4667 | 0.24636 | −0.59658 |
| −0.9661 | −0.20126 | 0.059249 | −2.41235 | −1.76205 | −0.90936 | −1.20675 | 0.271423 | −1.67284 |
| −3.59592 | −3.69173 | −2.1596 | −1.79439 | −1.19371 | −0.6264 | 0.809715 | −1.30587 | −0.12794 |
| 0.80426 | 0.42363 | 0.51278 | −0.45931 | −1.11443 | −1.16205 | 0.870868 | −1.51448 | −0.98185 |
| 1.003504 | 2.133733 | 2.193251 | −0.46491 | −0.64042 | −0.69015 | 0.84193 | −1.12517 | −0.76481 |
| 3.45203 | 3.07553 | 3.315992 | −0.35884 | −1.72089 | −0.99729 | −0.29057 | −1.21759 | −0.66195 |
| 5.019523 | 4.340724 | 4.681185 | −0.40388 | −0.70966 | −0.41013 | 0.18832 | −0.87095 | −0.76053 |
| 0.484981 | −0.02916 | −0.18164 | −2.05213 | −1.116 | −0.82419 | −0.6464 | −1.76629 | −2.12582 |
| −5.02916 | −2.67317 | −3.5853 | −1.36913 | −1.49909 | −1.03802 | 0.499388 | −1.34106 | −0.46286 |
| −0.18678 | 0.838193 | −0.03587 | −0.56432 | −1.20378 | −1.08981 | 0.459324 | −1.59999 | −1.97802 |
| 0.492859 | 2.038741 | 1.658616 | −0.32969 | −0.42158 | −0.19839 | 0.458639 | −0.50208 | −1.97447 |
| 2.583292 | 3.546491 | 2.6235 | −0.54307 | −1.49349 | −1.49594 | −1.82025 | −1.1087 | −0.65216 |
| 4.232906 | 4.911158 | 4.373398 | −0.31415 | −0.54561 | −0.31769 | −1.25567 | −0.23396 | −0.55993 |
| −0.68466 | −0.58548 | −0.03464 | −1.81488 | −0.9873 | −0.51292 | −1.52594 | −0.75271 | −1.96269 |
| −3.25608 | −3.40032 | −2.52899 | −0.83757 | 0.566743 | 0.611169 | 0.037197 | −1.06393 | −0.99583 |
| 0.257281 | 0.494046 | 0.909833 | −0.51511 | 0.632718 | 0.594448 | 0.835504 | −1.34173 | −2.24377 |
| 0.796696 | 1.443826 | 2.481656 | −0.43515 | 0.690223 | 0.321458 | 0.611697 | −0.5567 | −0.69441 |
| 3.852615 | 3.490733 | 2.713015 | −0.22912 | −2.0043 | −0.69921 | 0.647753 | −1.86841 | −1.08793 |
| 4.688197 | 4.999752 | 5.020012 | −0.23107 | −0.92487 | −0.61209 | 0.73669 | −0.3206 | −0.8862 |
| 0.162628 | −0.47851 | 0.577207 | −1.72139 | −1.09882 | −0.40671 | 0.565064 | −0.45378 | −0.76466 |
| −4.34306 | −2.56696 | −4.43024 | −1.2803 | 0.314511 | 0.558145 | −0.03673 | −0.25352 | −0.0916 |
| 1.395306 | 2.357084 | 0.725282 | 0.085208 | 0.456879 | −0.76659 | 0.722195 | 0.667138 | −1.09915 |
| 1.534186 | 2.81233 | 2.262165 | 0.038463 | 0.046801 | 0.655339 | 0.643474 | 0.757237 | −1.26364 |
| 4.403683 | 3.380728 | 2.933968 | 0.054007 | −0.66324 | 0.366502 | 0.534097 | 0.497352 | −0.52911 |
| 4.753436 | 4.689019 | 4.459714 | 0.009472 | 0.57047 | −0.84925 | 0.8618 | 0.766353 | −0.1815 |
| −0.61998 | 0.343889 | −0.14069 | −1.81933 | 0.339932 | 0.45126 | −0.87872 | −0.14241 | −1.07022 |
| −3.09943 | −3.29933 | −0.12005 | −0.81177 | −1.34576 | −0.35308 | 0.785952 | 0.817846 | 0.998936 |
| 2.128556 | 2.322421 | 1.823127 | −0.45072 | −1.0943 | 0.04527 | 1.089347 | 0.547118 | −1.11656 |
| 1.222062 | 2.309211 | 1.954408 | −0.32505 | −0.04856 | 0.811424 | 0.943053 | 0.808506 | −0.46843 |
| 3.974758 | 5.180598 | 4.924648 | −0.15758 | −1.09839 | −0.38398 | −1.14212 | −0.19413 | 1.07302 |
| 3.311061 | 4.635536 | 4.926917 | −0.50567 | −0.22342 | 0.514798 | −0.71394 | 0.782028 | 1.093496 |
| −0.74758 | 0.103346 | 0.236609 | −1.29164 | 0.090747 | 0.241204 | −0.75044 | 0.355101 | −0.89061 |

TABLE 36

3-Benzene-1

| | | $r_{u,mn}$ | | | | $(r_{u,mn}-r_{g,mnk})^2/\sigma_{r_{g,mn}}^2$ | | | | | | | | |
|---|---|---|---|---|---|---|---|---|---|---|---|---|---|---|
| | | Benzene | | | | | H$_2$O | | | | | EtOH | | | |
| f | Ku', mn | k5 | k1 | k2 | k3 | k4 | k5 | k1 | k2 | k3 | k4 | k5 | k1 | k2 | k3 |
| 0.05 Hz | Ku', 12 | 0.038457 | 4.300327 | 0.855977 | 13.11816 | 9.128931 | 3.554914 | 1.928802 | 0.068151 | 4.503036 |
| | Ku', 13 | 2.395338 | 23.95574 | 29.81557 | 13.25589 | 16.57391 | 20.09552 | 10.94053 | 2.372537 | 9.311743 |
| | Ku', 14 | 7.713047 | 17.29906 | 23.68945 | 9.001798 | 12.18988 | 13.77401 | 2.004623 | 5.27E-08 | 2.919007 |
| | Ku', 23 | 62.23715 | 5.519508 | 4.74173 | 0.632876 | 1.532681 | 5.223112 | 22.9969 | 13.64928 | 8.853161 |
| | Ku', 24 | 200.4052 | 1.372442 | 1.140385 | 0.149602 | 0.0106 | 1.174408 | 1.415386 | 0.026881 | 1.089126 |
| | Ku', 34 | 3.220025 | 2850.453 | 2751.566 | 2747.318 | 2703.484 | 2879.342 | 0.812746 | 3.495851 | 0.057032 |
| 0.1 Hz | Ku', 12 | 0.026953 | 4.898543 | 6.451301 | 12.3687 | 11.18845 | 15.33782 | 14.54963 | 24.551 | 24.17717 |
| | Ku', 13 | 2.19881 | 27.17186 | 11.7968 | 17.15667 | 13.90315 | 21.23335 | 13.38841 | 8.300179 | 7.33437 |
| | Ku', 14 | 6.513115 | 21.23143 | 8.075803 | 14.46972 | 11.27258 | 18.38515 | 0.056293 | 0.055863 | 0.024684 |
| | Ku', 23 | 81.57956 | 6.688579 | 1.276591 | 0.884056 | 0.688471 | 0.919285 | 2.065611 | 0.33293 | 0.241803 |
| | Ku', 24 | 241.6478 | 1.710944 | 0.031276 | 0.065148 | 0.14845 | 0.056895 | 0.017711 | 0.008521 | 0.000935 |
| | Ku', 34 | 2.882109 | 658.3 | 656.0533 | 591.005 | 593.9861 | 593.1067 | 2.28E-06 | 0.005121 | 0.00881 |
| 0.15 Hz | Ku', 12 | 0.020035 | 1.186035 | 0.475992 | 2.235023 | 6.314049 | 0.997452 | 2.673094 | 6.90056 | 4.835085 |
| | Ku', 13 | 3.389683 | 3.720148 | 1.355433 | 6.236303 | 0.514917 | 1.413773 | 2.276914 | 3.73757 | 2.6816 |
| | Ku', 14 | 29.93788 | 0.030594 | 0.357189 | 0.828629 | 0.68343 | 0.235216 | 1.327895 | 0.773583 | 1.585833 |
| | Ku', 23 | 160.1896 | 0.133392 | 0.06275 | 0.075308 | 1.763578 | 0.055905 | 4.056574 | 7.251436 | 6.552008 |
| | Ku', 24 | 1494.298 | 66.35932 | 71.40251 | 64.37991 | 95.84603 | 76.94898 | 91.46267 | 100.5804 | 103.1257 |
| | Ku', 34 | 8.832089 | 2158.26 | 2245.612 | 2086.897 | 2130.183 | 2180.387 | 83.27147 | 82.22539 | 90.96414 |
| 0.2 Hz | Ku', 12 | 0.042299 | 0.021009 | 0.001353 | 1.449852 | 1.425214 | 1.667269 | 0.000729 | 0.132908 | 0.277875 |
| | Ku', 13 | 2.772165 | 1.738972 | 0.068568 | 2.14349 | 3.787956 | 4.118231 | 0.631541 | 1.75847 | 1.773564 |
| | Ku', 14 | 9.687664 | 1.266278 | 0.062224 | 0.725475 | 1.963125 | 2.296447 | 0.154674 | 0.827534 | 0.590246 |
| | Ku', 23 | 65.53739 | 4.866363 | 0.11153 | 0.450389 | 0.982739 | 0.980512 | 9.345023 | 15.07272 | 11.5769 |
| | Ku', 24 | 229.0283 | 2.279801 | 0.080237 | 0.010786 | 0.028338 | 0.030453 | 3.489394 | 9.380339 | 3.786716 |
| | Ku', 34 | 3.49462 | 85.55068 | 106.2165 | 122.1538 | 116.5021 | 114.4448 | 7.407513 | 5.495822 | 9.380519 |
| 0.25 Hz | Ku', 12 | 0.024232 | 1.251567 | 5.585127 | 3.24231 | 4.901221 | 0.515518 | 1.122765 | 2.51611 | 1.590926 |
| | Ku', 13 | 3.308039 | 2.655011 | 0.840802 | 3.827243 | 1.049481 | 0.015477 | 0.190816 | 1.013505 | 0.521587 |
| | Ku', 14 | 10.17518 | 1.773789 | 0.532325 | 2.85189 | 0.677905 | 0.031109 | 0.004921 | 0.818557 | 0.211953 |
| | Ku', 23 | 138.518 | 1.629361 | 0.01731 | 0.856229 | 0.000137 | 0.101947 | 0.640048 | 0.252022 | 0.324389 |
| | Ku', 24 | 419.815 | 0.015452 | 1.666866 | 0.058449 | 1.370488 | 2.181783 | 1.233518 | 0.068222 | 0.402163 |
| | Ku', 34 | 3.078894 | 132.6748 | 108.5583 | 131.54 | 113.2317 | 97.38226 | 1.313644 | 0.102236 | 0.154234 |
| 0.3 Hz | Ku', 12 | 0.043797 | 0.001491 | 1.396792 | 3.80038 | 2.220993 | 1.627037 | 0.997275 | 0.62682 | 0.028491 |
| | Ku', 13 | 3.77258 | 6.235494 | 0.716602 | 0.964801 | 1.190866 | 0.734521 | 5.99918 | 14.69869 | 12.08581 |
| | Ku', 14 | 10.13803 | 12.04969 | 3.246015 | 3.974372 | 5.59324 | 3.123479 | 0.720991 | 8.853855 | 2.852223 |
| | Ku', 23 | 88.13844 | 3.183376 | 0.064368 | 0.020018 | 0.064368 | 0.043172 | 10.48238 | 2.703502 | 7.057525 |
| | Ku', 24 | 231.4787 | 2.805326 | 0.007127 | 0.006166 | 0.013199 | 0.00206 | 4.544041 | 4.143108 | 4.421705 |
| | Ku', 34 | 2.687287 | 28.20936 | 13.37239 | 13.85188 | 14.63529 | 13.98143 | 0.350567 | 0.904119 | 0.007545 |
| 0.35 Hz | Ku', 12 | 0.038556 | 0.003232 | 3.732189 | 0.238194 | 0.414056 | 0.290955 | 3.49E-05 | 0.019096 | 0.000453 |
| | Ku', 13 | 2.511168 | 2.309527 | 1.18744 | 5.831241 | 0.255847 | 0.862327 | 0.498209 | 0.276938 | 0.288709 |
| | Ku', 14 | 7.372299 | 2.171261 | 1.514624 | 4.703429 | 0.067314 | 0.777727 | 0.440578 | 0.106074 | 0.595575 |
| | Ku', 23 | 65.13076 | 2.407572 | 0.011673 | 0.781355 | 0.001027 | 0.03748 | 4.922368 | 6.168968 | 2.420489 |
| | Ku', 24 | 191.2112 | 1.608684 | 0.167142 | 0.209635 | 0.143118 | 0.010843 | 4.166716 | 3.044606 | 4.867221 |
| | Ku', 34 | 2.935804 | 50.80212 | 35.52114 | 61.10459 | 54.83914 | 45.34734 | 0.103709 | 0.949513 | 0.584138 |
| 0.4 Hz | Ku', 12 | 0.048983 | 0.043717 | 0.041992 | 2.788228 | 0.556342 | 0.656135 | 0.24115 | 0.01179 | 0.49754 |

TABLE 36-continued

3-Benzene-1

| | | | k4 | k5 | k1 | k2 | k3 | k4 | k5 | k1 |
|---|---|---|---|---|---|---|---|---|---|---|
| 0.45 Hz | Ku', 13 | 2.919094 | 3.015572 | 0.030331 | 3.881275 | 0.970626 | 1.907467 | 3.065221 | 2.145099 | 2.135154 |
| | Ku', 14 | 2.970384 | 1.522881 | 0.055216 | 2.495426 | 0.818157 | 1.305842 | 2.514082 | 0.058229 | 0.115863 |
| | Ku', 23 | 59.61853 | 5.26499 | 0.13004 | 1.623902 | 0.8126 | 1.808976 | 1.726555 | 2.255144 | 9.702451 |
| | Ku', 24 | 203.6315 | 3.007485 | 0.062803 | 0.383493 | 0.357015 | 0.637971 | 3.231236 | 0.080986 | 1.090412 |
| | Ku', 34 | 3.415574 | 125.7294 | 107.9187 | 126.7197 | 90.79349 | 112.2735 | 1.32984 | 0.092193 | 0.032057 |
| 0.5 Hz | Ku', 12 | 0.050457 | 0.18561 | 4.684427 | 2.620567 | 0.978117 | 0.47518 | 0.158566 | 3.84E-05 | 0.190848 |
| | Ku', 13 | 3.321647 | 4.917359 | 2.097129 | 7.278953 | 1.674858 | 8.091477 | 0.0377 | 0.068142 | 0.017347 |
| | Ku', 14 | 11.98887 | 4.621818 | 0.922087 | 6.443693 | 0.96502 | 2.060773 | 0.002705 | 0.000273 | 0.000505 |
| | Ku', 23 | 65.83064 | 3.609712 | 0.278032 | 2.072173 | 0.63347 | 4.80199 | 0.113169 | 0.098788 | 0.067614 |
| | Ku', 24 | 237.6034 | 2.287945 | 0.142198 | 0.517218 | 0.018712 | 0.45716 | 0.011887 | 0.000389 | 0.00541 |
| | Ku', 34 | 3.609313 | 51.36172 | 53.329 | 55.78456 | 47.28661 | 75.83745 | 0.141326 | 0.546537 | 0.142151 |
| | Ku', 12 | 0.079423 | 4.222775 | 0.028313 | 0.344512 | 0.56484 | 0.888308 | 0.046476 | 0.041879 | 0.043174 |
| | Ku', 13 | 3.542322 | 8.49117 | 11.84913 | 8.523186 | 19.5597 | 6.989547 | 0.003609 | 0.018317 | 0.003305 |
| | Ku', 14 | 6.830891 | 0.803263 | 3.021903 | 1.269281 | 5.991718 | 0.520853 | 0.001219 | 0.026297 | 0.012925 |
| | Ku', 23 | 44.60043 | 11.18922 | 3.455279 | 3.301467 | 8.203397 | 3.536911 | 6.108916 | 10.01424 | 5.306705 |
| | Ku', 24 | 86.00594 | 4.315588 | 2.879885 | 1.581837 | 7.718191 | 0.976191 | 3.627084 | 11.09318 | 7.750226 |
| | Ku', 34 | 1.928365 | 2.521262 | 1.417062 | 3.558064 | 0.848363 | 6.372514 | 0.071568 | 0.929724 | 2.112658 |

| | | | | EtOH | | | $(r_{u,mn}-r_{g,mnk})^2/\sigma_{r_{g,mn}}^2$ | Benzene | | | |
|---|---|---|---|---|---|---|---|---|---|---|---|
| f | Ku', mn | k4 | k5 | k1 | k2 | k3 | k4 | k5 | k1 |
| 0.05 Hz | Ku', 12 | 0.604807 | 2.063574 | 0.00057 | 2.395261 | 0.430683 | 0.074492 | 0.081097 | 1.182421 |
| | Ku', 13 | 5.876474 | 9.021692 | 0.211985 | 1.28498 | 0.248652 | 0.009037 | 0.645394 | 0.320788 |
| | Ku', 14 | 1.789375 | 2.881206 | 0.03985 | 0.818496 | 0.011522 | 0.33451 | 0.810821 | 0.102799 |
| | Ku', 23 | 19.86585 | 17.01476 | 0.291548 | 2.031441 | 2.246044 | 0.58389 | 0.050915 | 13.91247 |
| | Ku', 24 | 2.557748 | 2.267059 | 0.1495 | 2.66263 | 2.325887 | 0.026912 | 0.119482 | 2.392075 |
| | Ku', 34 | 0.068875 | 0.051045 | 0.141751 | 0.014505 | 0.431784 | 1.541393 | 0.460274 | 23.40385 |
| 0.1 Hz | Ku', 12 | 22.04933 | 11.54606 | 0.201822 | 1.11589 | 0.12902 | 0.008072 | 0.589133 | 0.03034 |
| | Ku', 13 | 9.799066 | 19.86328 | 8.54E-05 | 2.373337 | 0.000289 | 0.00753 | 0.003489 | 2.687367 |
| | Ku', 14 | 0.06394 | 3.239361 | 0.039251 | 2.621597 | 0.000653 | 0.053908 | 0.013255 | 0.586195 |
| | Ku', 23 | 0.62745 | 4.715607 | 0.077088 | 1.748872 | 0.109985 | 0.053417 | 0.877755 | 7.780808 |
| | Ku', 24 | 0.012962 | 2.793056 | 0.016452 | 2.206843 | 0.326125 | 0.169195 | 2.208949 | 0.433555 |
| | Ku', 34 | 0.004602 | 2.57651 | 0.336644 | 0.30069 | 2.97E-05 | 1.635299 | 0.012396 | 30.42897 |
| 0.15 Hz | Ku', 12 | 3.626391 | 0.549224 | 0.055397 | 0.091528 | 0.011227 | 0.011795 | 2.103123 | 1.834112 |
| | Ku', 13 | 7.422153 | 0.600212 | 0.241938 | 1.524245 | 0.802878 | 0.718973 | 0.394611 | 0.710051 |
| | Ku', 14 | 8.62E-05 | 3.769307 | 4.383236 | 5.747865 | 4.484886 | 4.790734 | 0.877755 | 23.37315 |
| | Ku', 23 | 1.358509 | 1.822323 | 7.936125 | 5.328098 | 2.524876 | 4.551969 | 13.43786 | 0.783754 |
| | Ku', 24 | 70.37189 | 96.09523 | 278.3076 | 248.3816 | 219.7757 | 237.6433 | 230.6299 | 100.865 |
| | Ku', 34 | 69.3077 | 105.2055 | 21.20035 | 19.33113 | 17.50642 | 18.68575 | 8.024357 | 1013.823 |
| 0.2 Hz | Ku', 12 | 2.970258 | 0.005726 | 16.35811 | 6.336489 | 14.31672 | 14.86818 | 7.452713 | 0.736786 |
| | Ku', 13 | 7.080499 | 1.345691 | 4.723421 | 3.068135 | 4.332806 | 4.803547 | 0.2691 | 0.043773 |
| | Ku', 14 | 4.011741 | 0.229307 | 0.080914 | 0.445077 | 0.962288 | 1.630017 | 0.299148 | 0.353732 |
| | Ku', 23 | 16.30674 | 24.15979 | 6.286075 | 0.391772 | 4.153229 | 4.283891 | 3.181282 | 3.081682 |
| | Ku', 24 | 12.28324 | 7.219527 | 2.762897 | 0.036419 | 0.216496 | 0.014652 | 1.865505 | 0.157956 |
| | Ku', 34 | 4.136803 | 14.9244 | 0.501074 | 0.009678 | 0.167862 | 0.674853 | 0.653493 | 4.931251 |
| 0.25 Hz | Ku', 12 | 7.268413 | 5.568753 | 0.013434 | 0.000904 | 2.53048 | 1.133498 | 0.011006 | 0.441808 |
| | Ku', 13 | 3.680617 | 0.001347 | 0.305487 | 0.808732 | 0.268738 | 0.825375 | 0.12538 | 0.268613 |
| | Ku', 14 | 2.58493 | 0.032265 | 0.319249 | 0.025585 | 0.998715 | 1.10183 | 0.443439 | 2.090244 |

TABLE 36-continued

3-Benzene-1

| | | | | | | | | |
|---|---|---|---|---|---|---|---|---|
| | Ku, 23 | 0.174902 | 4.50044 | 0.231443 | 0.845854 | 0.769125 | 0.154895 | 0.080276 | 1.437278 |
| | Ku, 24 | 0.065625 | 3.760991 | 0.417016 | 0.032201 | 0.156175 | 0.838549 | 0.850714 | 20.78891 |
| | Ku, 34 | 0.030938 | 1.384538 | 0.009426 | 0.332991 | 0.44405 | 0.185253 | 1.12809 | 18.3426 |
| 0.3 Hz | Ku, 12 | 0.180736 | 0.705324 | 4.605586 | 1.161779 | 8.442061 | 5.665719 | 2.542585 | 0.184405 |
| | Ku, 13 | 4.541204 | 7.714198 | 11.91226 | 4.844249 | 9.695198 | 16.30690 | 7.108082 | 0.420799 |
| | Ku, 14 | 1.429349 | 4.506631 | 3.36878 | 0.50862 | 3.318335 | 4.380118 | 0.33028 | 4.845302 |
| | Ku, 23 | 4.202878 | 10.35487 | 0.005434 | 0.01226 | 2.437567 | 0.000399 | 2.68E−05 | 0.1853 |
| | Ku, 24 | 3.338137 | 12.83647 | 0.046451 | 0.015259 | 1.727969 | 0.143609 | 0.583472 | 0.457534 |
| | Ku, 34 | 0.038265 | 1.183304 | 0.172715 | 0.18153 | 0.384299 | 0.229124 | 1.033358 | 0.312344 |
| 0.35 Hz | Ku, 12 | 2.354408 | 0.001686 | 11.86964 | 13.38291 | 5.871927 | 10.25151 | 4.808022 | 11.21458 |
| | Ku, 13 | 4.569218 | 0.338239 | 3.894355 | 8.31608 | 2.607834 | 2.374185 | 0.850541 | 0.323109 |
| | Ku, 14 | 4.216527 | 0.128325 | 3.680431 | 5.535 | 2.395964 | 1.535397 | 0.226517 | 6.325077 |
| | Ku, 23 | 0.468264 | 4.1214 | 2.158427 | 0.924501 | 0.18146 | 4.709251 | 0.361855 | 18.61958 |
| | Ku, 24 | 0.199311 | 1.640453 | 0.418155 | 0.114238 | 0.010483 | 3.711344 | 0.373998 | 0.004114 |
| | Ku, 34 | 0.211777 | 1.005385 | 1.388781 | 1.355557 | 0.717889 | 0.012934 | 0.081865 | 7.201351 |
| 0.4 Hz | Ku, 12 | 1.74911 | 0.221848 | 21.04219 | 25.31196 | 12.10841 | 20.54884 | 12.8634 | 0.42738 |
| | Ku, 13 | 0.002613 | 1.26856 | 0.146018 | 1.067567 | 0.252756 | 0.460057 | 0.309631 | 0.571026 |
| | Ku, 14 | 0.109889 | 0.049853 | 20.36456 | 13.80113 | 22.44289 | 13.62888 | 28.62437 | 10.57139 |
| | Ku, 23 | 4.857728 | 4.213421 | 0.080739 | 2.83008 | 0.002795 | 0.007909 | 0.001614 | 0.21952 |
| | Ku, 24 | 0.00473 | 0.372672 | 0.190968 | 2.085805 | 0.023618 | 0.55268 | 0.089813 | 0.652357 |
| | Ku, 34 | 0.515789 | 0.043173 | 0.567536 | 2.1938 | 0.392291 | 0.229887 | 0.543409 | 2.875161 |
| 0.45 Hz | Ku, 12 | 0.186703 | 1.611915 | 0.025416 | 0.898812 | 2.959728 | 3.369507 | 2.705671 | 1.332299 |
| | Ku, 13 | 3.110148 | 0.024873 | 0.004834 | 1.986584 | 0.027443 | 0.04266 | 0.049533 | 1.628236 |
| | Ku, 14 | 2.520906 | 0.003099 | 0.13258 | 0.784191 | 0.509358 | 0.616106 | 0.547436 | 0.30869 |
| | Ku, 23 | 3.176104 | 2.4E−05 | 0.000894 | 2.988311 | 0.095757 | 0.098687 | 0.016096 | 4.493988 |
| | Ku, 24 | 2.530657 | 0.013686 | 0.048425 | 2.164336 | 6.06E−05 | 0.003709 | 0.014991 | 0.057699 |
| | Ku, 34 | 0.747771 | 0.928546 | 1.383514 | 8.120231 | 6.88224 | 8.25316 | 4.80702 | 21.56761 |
| 0.5 Hz | Ku, 12 | 1.885889 | 0.041329 | 58.52487 | 49.75154 | 74.62554 | 77.55172 | 60.95836 | 1.073745 |
| | Ku, 13 | 2.77866 | 0.009339 | 2.502628 | 0.481113 | 4.295854 | 3.72005 | 0.289681 | 0.003231 |
| | Ku, 14 | 2.852374 | 0.018078 | 0.134319 | 0.014347 | 2.507764 | 0.383021 | 0.094582 | 0.74069 |
| | Ku, 23 | 1.562537 | 7.213752 | 7.349744 | 5.525372 | 4.819785 | 10.15637 | 15.62267 | 0.849771 |
| | Ku, 24 | 2.835062 | 8.777153 | 4.208068 | 1.370928 | 1.053365 | 7.407615 | 4.438091 | 1.493265 |
| | Ku, 34 | 2.085815 | 1.241364 | 2.284797 | 0.223321 | 0.133334 | 3.969168 | 0.531354 | 1.899642 |

TABLE 37

| 3-Benzene-2 |||||||||||
| --- | --- | --- | --- | --- | --- | --- | --- | --- | --- | --- |
| Hexane |||| AcOEt ||||| THF ||
| k2 | k3 | k4 | k5 | k1 | k2 | k3 | k4 | k5 | k1 | |
| 2.929309 | 2.403354 | 0.000496 | 2.772117 | 0.385609 | 1.654196 | 0.09357 | 4.598979 | 1.175751 | 3.070858 | |
| 0.261279 | 0.022308 | 1.462502 | 0.074812 | 4.785564 | 3.924743 | 12.81441 | 11.3255 | 6.097735 | 17.01617 | |
| 3.339887 | 1.965841 | 0.118852 | 2.400929 | 2.076159 | 2.952387 | 5.579404 | 10.74699 | 4.584725 | 4.042927 | |
| 5.976404 | 11.63417 | 4.768883 | 12.89762 | 0.181362 | 0.004513 | 2.639344 | 0.004227 | 0.020514 | 19.68134 | |
| 0.127581 | 0.887932 | 0.086566 | 1.096371 | 0.084202 | 0.014578 | 2.61053 | 0.001117 | 0.029476 | 15.8966 | |
| 31.22056 | 31.18807 | 46.30629 | 31.27652 | 1.33908 | 0.02409 | 1.555344 | 0.148564 | 0.027244 | 0.747953 | |
| 0.010307 | 0.8065 | 0.863271 | 3.408773 | 38.78438 | 19.99447 | 30.08875 | 21.58567 | 33.79617 | 20.76595 | |
| 3.451051 | 1.485036 | 3.375907 | 0.028905 | 84.54758 | 75.78221 | 81.64485 | 87.69059 | 111.511 | 18.1697 | |
| 0.027217 | 0.522574 | 0.07594 | 2.557669 | 99.60149 | 73.47804 | 77.22963 | 76.13961 | 99.52909 | 4.521469 | |
| 9.233092 | 11.0723 | 21.16935 | 10.08288 | 1.088994 | 0.189478 | 0.323202 | 0.447285 | 0.000154 | 75.75012 | |
| 0.00872 | 0.009712 | 1.346454 | 0.205679 | 0.280565 | 0.708065 | 0.550467 | 0.438459 | 0.023648 | 35.47691 | |
| 21.43103 | 23.7209 | 14.10961 | 29.25021 | 2.040381 | 0.063318 | 0.012979 | 0.131152 | 0.047172 | 0.010901 | |
| 0.260469 | 0.025314 | 0.100808 | 0.002421 | 2.873054 | 1.593464 | 6.510702 | 0.49751 | 1.165863 | 6.378422 | |
| 0.589333 | 0.244424 | 0.341306 | 0.181589 | 4.470861 | 5.102171 | 14.63106 | 4.988931 | 6.15113 | 12.97033 | |
| 39.43869 | 35.97339 | 36.76847 | 23.41989 | 3.622997 | 2.474127 | 0.029527 | 3.377445 | 2.338132 | 1.629922 | |
| 0.042109 | 0.631928 | 0.21093 | 0.600202 | 8.444068 | 5.633041 | 8.357482 | 1.491501 | 3.815204 | 96.01573 | |
| 76.60128 | 95.61063 | 88.1858 | 60.58335 | 189.4032 | 171.3403 | 187.5318 | 145.3501 | 162.5536 | 478.4981 | |
| 904.8903 | 947.9528 | 917.2293 | 919.3698 | 3956.192 | 3784.849 | 3862.339 | 4007.553 | 3933.32 | 133.6975 | |
| 3.14963 | 5.459693 | 0.909861 | 5.217091 | 15.36208 | 12.52492 | 13.05705 | 17.10718 | 5.35765 | 1.07152 | |
| 0.262177 | 0.939283 | 0.452068 | 0.723225 | 9.334436 | 5.837866 | 13.74446 | 15.53757 | 17.08648 | 7.589498 | |
| 3.492745 | 4.844365 | 0.979823 | 4.195462 | 0.805239 | 0.110108 | 1.746396 | 1.605942 | 5.135708 | 5.045243 | |
| 3.342743 | 3.37771 | 11.31081 | 7.13382 | 0.450808 | 0.157964 | 1.396223 | 1.186455 | 5.011677 | 0.49055 | |
| 1.576126 | 1.317356 | 0.112744 | 0.005976 | 0.002138 | 0.154698 | 0.098123 | 0.028758 | 2.177754 | 2.276472 | |
| 15.01741 | 14.2718 | 15.12576 | 11.16608 | 0.946443 | 2.53647 | 0.498405 | 0.83887 | 0.123245 | 7.235395 | |
| 0.635292 | 0.001973 | 0.417768 | 0.507412 | 38.04504 | 25.47789 | 17.43118 | 26.39624 | 25.64655 | 0.815851 | |
| 0.280347 | 0.049899 | 0.940874 | 0.742581 | 0.078564 | 3.626287 | 0.090825 | 0.129637 | 0.131973 | 2.312474 | |
| 6.099383 | 6.233408 | 10.56038 | 9.49189 | 0.500824 | 5.578437 | 0.690939 | 0.520908 | 0.816425 | 2.061449 | |
| 3.146467 | 3.883895 | 6.643295 | 0.555762 | 0.201925 | 1.554439 | 0.071969 | 0.089008 | 0.083328 | 24.92158 | |
| 36.52852 | 25.94305 | 27.12823 | 17.50893 | 2.431801 | 0.05863 | 0.989845 | 1.82317 | 1.350043 | 4.828281 | |
| 34.39729 | 21.45219 | 20.63673 | 16.27243 | 0.141403 | 4.002797 | 0.07665 | 0.602672 | 0.22482 | 1.327489 | |
| 1.802655 | 2.050318 | 0.010242 | 0.009596 | 4.301708 | 5.015149 | 1.063584 | 0.333324 | 3.030554 | 0.604345 | |
| 1.819851 | 2.276578 | 0.063321 | 0.272361 | 4.739253 | 12.9731 | 5.969795 | 3.506848 | 9.751789 | 3.614696 | |
| 11.03379 | 9.909075 | 2.568844 | 7.61662 | 0.059884 | 3.912952 | 3.308806 | 1.28946 | 1.455602 | 1.044902 | |
| 0.517287 | 0.006651 | 0.36328 | 0.907741 | 0.297518 | 0.103098 | 1.016012 | 1.653341 | 0.298462 | 1.531326 | |
| 0.25728 | 0.550751 | 0.360847 | 1.342283 | 0.515446 | 0.065644 | 1.173788 | 0.691497 | 0.000141 | 0.648422 | |
| 0.607408 | 0.536007 | 0.698245 | 1.07752 | 0.992846 | 0.03596 | 1.784157 | 0.087369 | 0.100331 | 0.011678 | |
| 20.57885 | 12.71767 | 11.28578 | 23.47078 | 0.030916 | 3.952254 | 0.351894 | 0.230279 | 0.301614 | 1.476562 | |
| 3.882305 | 1.26411 | 0.525252 | 4.445903 | 2.437538 | 10.8983 | 2.739959 | 5.099637 | 3.531625 | 7.661976 | |
| 14.68003 | 11.13256 | 4.867075 | 13.08623 | 2.509275 | 7.219937 | 0.746284 | 3.752439 | 1.394988 | 3.188308 | |
| 6.480215 | 8.494902 | 14.33096 | 12.11098 | 2.570105 | 0.04582 | 0.176898 | 1.517966 | 0.500059 | 0.313768 | |
| 0.9492 | 0.908037 | 0.289072 | 0.088645 | 2.045736 | 0.55031 | 0.012248 | 0.770498 | 0.030806 | 0.005036 | |
| 11.33087 | 11.945 | 3.748638 | 4.272337 | 0.216203 | 0.100251 | 1.73344 | 0.011158 | 0.850285 | 0.094443 | |
| 0.44219 | 0.194762 | 0.97624 | 0.314869 | 1.448377 | 0.041523 | 0.026439 | 2.134904 | 0.04134 | 0.461087 | |
| 0.54944 | 0.817518 | 0.000356 | 0.322297 | 7.009419 | 3.162211 | 3.794550 | 11.9386 | 3.614229 | 0.931215 | |
| 7.131469 | 5.598731 | 0.529141 | 1.723864 | 2.194998 | 1.121519 | 4.903339 | 8.191373 | 5.038418 | 0.211261 | |
| 0.267966 | 2.103172 | 0.299875 | 0.185663 | 0.451632 | 1.918935 | 6.180583 | 0.754308 | 2.241951 | 0.182346 | |
| 0.077639 | 0.265428 | 2.022097 | 0.253049 | 0.020625 | 0.15062 | 2.637997 | 0.023022 | 0.995853 | 0.10426 | |
| 1.319015 | 3.691728 | 2.757759 | 0.024749 | 3.607752 | 2.287487 | 0.160386 | 1.840894 | 0.091604 | 0.080677 | |
| 7.892473 | 3.74901 | 2.519564 | 7.288309 | 0.074201 | 1.545382 | 0.032222 | 2.474015 | 5.87E-05 | 29.86133 | |
| 0.175602 | 0.00368 | 0.003164 | 0.235901 | 0.081606 | 0.70586 | 0.073477 | 3.441691 | 0.025542 | 1.550752 | |
| 4.066367 | 4.183373 | 3.809408 | 5.60549 | 0.086072 | 3.204659 | 0.105571 | 0.066349 | 0.001578 | 0.651832 | |
| 0.390353 | 0.851499 | 0.44904 | 0.075507 | 0.706498 | 0.474069 | 1.204478 | 6.112799 | 1.500198 | 0.622552 | |
| 0.17482 | 1.428471 | 1.410915 | 2.198087 | 0.000118 | 0.201385 | 0.093424 | 1.71783 | 0.021824 | 0.596471 | |
| 13.70751 | 29.23374 | 26.73509 | 28.37885 | 0.500621 | 0.03968 | 0.361574 | 4.284545 | 0.628593 | 0.089187 | |
| 0.047095 | 1.890556 | 1.232518 | 2.577105 | 0.001938 | 0.437911 | 3.063098 | 2.17E-05 | 0.533903 | 0.000262 | |
| 1.870145 | 0.062477 | 0.009206 | 0.128469 | 0.047049 | 2.806285 | 0.048884 | 0.157937 | 0.166815 | 0.0272 | |
| 9.01E-05 | 2.190614 | 1.070462 | 3.445977 | 1.04544 | 1.520906 | 0.139757 | 1.692685 | 1.451787 | 0.443575 | |
| 5.418509 | 0.51096 | 0.830613 | 0.328674 | 0.027291 | 2.455438 | 0.056325 | 0.083097 | 0.331421 | 0.03443 | |
| 0.127597 | 0.411399 | 0.010608 | 0.158943 | 1.692192 | 6.554513 | 1.374792 | 2.575866 | 7.139868 | 0.437567 | |
| 9.718152 | 2.032654 | 4.778433 | 3.84887 | 0.891735 | 0.805927 | 0.16844 | 0.392895 | 0.229549 | 0.198168 | |

| | | | $\theta_{u,mn}$ | | | | | |
| --- | --- | --- | --- | --- | --- | --- | --- | --- |
| THF |||| Benzene | H$_2$O ||||
| k2 | k3 | k4 | k5 | k6 | k1 | k2 | k3 | k4 |
| 10.60768 | 8.215782 | 3.201234 | 3.421315 | −0.37926 | 0.580287 | 3.193809 | 0.015901 | 1.82016 |
| 20.88988 | 9.489141 | 17.47257 | 9.004536 | −0.1274 | 0.070255 | 0.08296 | 1.211157 | 0.04376 |
| 1.351707 | 1.198054 | 6.805812 | 0.990459 | −0.37922 | 1.366637 | 5.426177 | 0.764639 | 4.295221 |
| 32.39645 | 36.0016 | 19.92927 | 27.25317 | 0.251858 | 1.502846 | 5.154045 | 0.312455 | 2.605843 |
| 27.07658 | 26.34189 | 12.06867 | 22.03798 | 3.72E-05 | 0.117886 | 1.137455 | 0.535112 | 0.248432 |
| 4.253835 | 1.974278 | 0.036972 | 2.231392 | −0.25192 | 14.98444 | 28.70226 | 30.24801 | 24.03436 |
| 23.50492 | 11.88147 | 26.18568 | 24.25853 | −0.22038 | 0.360751 | 0.004009 | 0.706801 | 0.706103 |
| 18.6522 | 20.52635 | 32.42767 | 31.59252 | −0.01276 | 0.340133 | 0.238584 | 0.112973 | 0.307978 |

TABLE 37-continued

3-Benzene-2

| | | | | | | | | |
|---|---|---|---|---|---|---|---|---|
| 2.397271 | 2.500354 | 10.18984 | 9.982141 | −0.20972 | 4.4E−05 | 0.114217 | 0.095434 | 0.090637 |
| 79.42863 | 50.49492 | 89.53243 | 84.86326 | 0.207021 | 0.486246 | 0.177057 | 0.342773 | 0.018831 |
| 44.62346 | 23.96486 | 29.22026 | 26.84888 | 0.010656 | 0.047941 | 0.059005 | 0.003197 | 0.28902 |
| 1.644009 | 0.011962 | 0.196547 | 0.207808 | −0.19697 | 11.74086 | 24.29662 | 14.8009 | 26.01783 |
| 6.100254 | 10.30043 | 1.700718 | 3.82634 | −2.57374 | 12.14387 | 13.28328 | 10.29554 | 9.573514 |
| 11.9252 | 20.74169 | 6.788778 | 15.08678 | −0.73922 | 1.340584 | 5.106736 | 3.508978 | 0.208712 |
| 0.962004 | 0.077761 | 0.986439 | 0.007677 | 0.537287 | 67.82192 | 49.85976 | 50.8144 | 75.40054 |
| 96.21599 | 100.3716 | 69.91083 | 75.8916 | 1.834526 | 9.415031 | 7.302044 | 5.835998 | 6.663138 |
| 470.8233 | 468.0464 | 411.7235 | 427.0224 | 3.11103 | 26.13451 | 25.44952 | 21.30812 | 21.51725 |
| 120.6597 | 105.8714 | 100.8192 | 97.47597 | 1.276504 | 142.9366 | 164.5955 | 146.5287 | 124.8862 |
| 2.255906 | 6.148121 | 2.302178 | 0.33126 | −1.02274 | 1.349712 | 6.144932 | 0.397562 | 1.061286 |
| 11.20875 | 14.18999 | 13.29715 | 4.255843 | −0.44758 | 2.313028 | 0.000778 | 0.022077 | 0.004619 |
| 11.49864 | 11.90193 | 7.878475 | 3.357053 | −0.85048 | 3.142278 | 0.052331 | 0.006838 | 0.056212 |
| 1.323519 | 3.95064 | 1.017261 | 0.000282 | 0.57516 | 0.630314 | 1.332326 | 0.173858 | 0.279573 |
| 2.684294 | 6.893819 | 3.80913 | 0.142866 | 0.172262 | 1.083514 | 0.815797 | 0.043344 | 0.062749 |
| 2.291583 | 5.327815 | 11.23644 | 3.709978 | −0.4029 | 27.77849 | 19.99438 | 15.67268 | 28.03476 |
| 0.750863 | 1.96442 | 6.337344 | 0.801746 | −0.26288 | 0.003284 | 0.181133 | 0.385084 | 0.020369 |
| 1.255677 | 4.531769 | 8.791242 | 2.706875 | 0.13255 | 0.241692 | 0.151774 | 1.99832 | 0.298636 |
| 0.110081 | 1.00748 | 4.768667 | 0.348313 | −0.81259 | 0.406744 | 0.622111 | 0.094724 | 0.352854 |
| 28.44834 | 32.30496 | 43.64276 | 23.26687 | 0.395435 | 0.105147 | 0.01395 | 0.56948 | 0.108653 |
| 14.89572 | 14.11929 | 15.08823 | 12.13381 | −0.54971 | 0.211557 | 0.501903 | 0.002685 | 0.217285 |
| 0.15696 | 0.001304 | 0.658384 | 0.109807 | −0.94514 | 88.71207 | 94.31913 | 101.8417 | 91.35455 |
| 0.618125 | 0.120641 | 0.254556 | 4.53289 | −1.19743 | 44.68398 | 29.97965 | 38.68942 | 47.17383 |
| 2.562519 | 3.368975 | 0.320586 | 6.273245 | −1.17398 | 0.789584 | 3.708615 | 0.789522 | 0.062659 |
| 1.060579 | 2.031224 | 0.025043 | 2.856555 | −1.49792 | 2.781392 | 5.684846 | 2.057792 | 0.769549 |
| 0.924179 | 0.028006 | 2.096025 | 4.532567 | 0.023569 | 0.619658 | 0.198181 | 0.457879 | 1.982917 |
| 0.657168 | 0.149597 | 1.830944 | 1.783715 | −0.3005 | 0.009045 | 0.786573 | 0.039564 | 0.782437 |
| 0.145198 | 0.633733 | 1.012743 | 0.347594 | −0.32407 | 14.33261 | 4.79328 | 6.998089 | 9.355659 |
| 6.211451 | 4.369561 | 9.200904 | 0.99579 | −0.06397 | 0.474534 | 0.456897 | 0.138483 | 1.079676 |
| 13.97959 | 10.49399 | 20.02094 | 8.102543 | −0.08264 | 6.171955 | 0.995691 | 0.344924 | 1.762761 |
| 9.656869 | 2.204092 | 1.696103 | 3.794732 | −0.21265 | 5.253173 | 0.534305 | 0.207628 | 1.044725 |
| 0.362744 | 0.238568 | 0.276492 | 1.069501 | −0.01886 | 4.539303 | 0.463709 | 0.169784 | 0.713867 |
| 0.132365 | 0.18423 | 0.795279 | 0.884604 | −0.15269 | 4.102055 | 0.234574 | 0.101799 | 0.415449 |
| 0.94067 | 0.064084 | 0.782561 | 0.182439 | −0.13383 | 2.200025 | 0.066052 | 0.001516 | 0.015189 |
| 0.427526 | 1.151031 | 4.768133 | 8.0091 | −1.09802 | 4.146042 | 8.710053 | 4.439702 | 3.152064 |
| 2.569782 | 0.985862 | 7.331409 | 2.203096 | −0.22918 | 0.08919 | 1.270751 | 0.618242 | 0.033015 |
| 4.736863 | 0.414212 | 0.300254 | 0.932737 | −0.40616 | 0.193603 | 0.54725 | 1.065647 | 2.15E−05 |
| 0.508448 | 0.379893 | 0.903525 | 0.037635 | 0.868935 | 1.775373 | 6.017007 | 0.309065 | 1.215885 |
| 1.165784 | 0.021987 | 0.692899 | 0.015616 | 0.891855 | 2.158034 | 4.994871 | 0.09434 | 0.934812 |
| 1.023113 | 0.005712 | 0.913458 | 0.007826 | −0.17769 | 0.353683 | 1.18559 | 1.230044 | 0.375014 |
| 50.99236 | 38.39521 | 23.61805 | 29.39515 | 0.056172 | 0.855511 | 4.660413 | 2.568256 | 2.680194 |
| 0.765174 | 2.298123 | 0.000248 | 3.2937 | −0.19129 | 0.164352 | 0.144454 | 0.306189 | 1.121583 |
| 0.005582 | 0.496012 | 0.35666 | 1.453191 | −0.54312 | 2.65E−05 | 0.0253 | 0.134637 | 1.83909 |
| 2.2158 | 0.546942 | 4.151892 | 0.054124 | −0.24746 | 0.0306 | 0.031028 | 0.022261 | 2.323766 |
| 2.757639 | 1.005417 | 4.592164 | 0.143473 | −0.5993 | 0.062413 | 0.18271 | 0.004035 | 3.410586 |
| 1.696637 | 0.654956 | 3.865543 | 0.100531 | −0.35193 | 7.243842 | 2.294448 | 1.868124 | 2.480819 |
| 2.497936 | 0.000538 | 0.000202 | 0.000462 | −0.54212 | 0.597713 | 0.006458 | 2.070671 | 0.791326 |
| 0.623149 | 0.676524 | 0.145997 | 3.976818 | −0.07015 | 1.266136 | 0.03052 | 0.112761 | 1.919282 |
| 5.956677 | 0.947377 | 3.488818 | 1.929246 | −0.09501 | 0.969011 | 0.240539 | 0.198475 | 0.819286 |
| 0.079911 | 0.092043 | 0.020263 | 2.523986 | 0.471966 | 0.157145 | 0.007838 | 0.997115 | 0.325956 |
| 0.255715 | 0.136871 | 0.908558 | 1.890063 | 0.447111 | 0.021314 | 0.172667 | 1.913387 | 7.15E−05 |
| 0.473777 | 0.064424 | 1.177549 | 0.429151 | −0.02486 | 1.122991 | 1.409155 | 0.004847 | 3.128318 |

TABLE 38

3-Benzene-3
$(\theta_{u,mn} - \theta_{g,mnk})^2 / \sigma_{\theta_{g,mn}}^2$

| EtOH | | | | | | Benzene | | | |
|---|---|---|---|---|---|---|---|---|---|
| k5 | k1 | k2 | k3 | k4 | k5 | k1 | k2 | k3 | k4 |
| 0.723519 | 0.0774 | 2.131778 | 0.009645 | 0.01972 | 0.011313 | 0.609739 | 0.113462 | 0.701912 | 0.358313 |
| 0.593751 | 0.483891 | 2.858802 | 0.084765 | 0.036214 | 0.089884 | 0.384572 | 0.325559 | 0.310399 | 0.01943 |
| 5.893336 | 0.336878 | 2.336762 | 0.067039 | 0.15714 | 0.035685 | 0.434476 | 1.521233 | 0.471269 | 0.181307 |
| 0.434006 | 0.455594 | 1.302492 | 0.13256 | 0.010638 | 0.12356 | 0.693712 | 0.081114 | 1.262596 | 3.783206 |
| 0.106016 | 0.19417 | 1.627072 | 0.094985 | 0.264864 | 0.005641 | 0.165748 | 0.129371 | 1.49554 | 0.701021 |
| 17.85488 | 0.481921 | 0.34098 | 0.019839 | 4.138571 | 0.762108 | 0.017879 | 0.105728 | 1.059688 | 0.02837 |
| 0.836442 | 2.279601 | 2.234078 | 3.172549 | 0.000201 | 1.233307 | 0.039041 | 1.260779 | 0.017625 | 0.056878 |
| 4.23245 | 3.221922 | 2.087695 | 0.143484 | 0.13997 | 0.088711 | 0.319857 | 0.369459 | 0.104549 | 0.08682 |
| 1.727499 | 2.028251 | 1.029542 | 0.027581 | 0.005474 | 0.000125 | 0.102975 | 0.093853 | 0.059907 | 0.004673 |
| 3.875645 | 0.079748 | 0.000802 | 1.536858 | 0.129554 | 0.548345 | 0.006538 | 3.176279 | 0.007885 | 0.111305 |
| 1.732448 | 0.117853 | 0.00178 | 1.904985 | 0.0066 | 0.594796 | 0.003721 | 2.434654 | 0.000178 | 0.141592 |
| 18.99232 | 0.197513 | 0.00505 | 2.028765 | 0.399956 | 0.535029 | 0.000389 | 0.003986 | 0.021157 | 0.042456 |
| 3.452656 | 85.98829 | 56.80438 | 85.60331 | 77.21856 | 58.47717 | 8.063491 | 3.220676 | 3.450005 | 5.236321 |

TABLE 38-continued

| 3-Benzene-3 |
|---|
| $(\theta_{u,mn} - \theta_{g,mnk})^2 / \sigma_{\theta g,mn}^2$ |

| | | | | | | | | | |
|---|---|---|---|---|---|---|---|---|---|
| 3.874698 | 4.671449 | 0.43345 | 1.352297 | 0.824682 | 0.083323 | 12.66315 | 3.264701 | 3.724818 | 5.085331 |
| 58.18493 | 0.420749 | 5.763533 | 4.960908 | 4.718852 | 3.845609 | 60.29395 | 86.37516 | 55.67781 | 62.54644 |
| 1.252637 | 73.85458 | 97.2154 | 108.0719 | 104.7224 | 96.52552 | 5.93903 | 2.703606 | 2.848313 | 4.44398 |
| 11.25893 | 22.13732 | 38.00388 | 41.44206 | 38.15433 | 29.73755 | 19.71942 | 13.23255 | 11.2638 | 15.14292 |
| 166.3187 | 7.720313 | 18.20518 | 19.45714 | 16.94382 | 10.76543 | 101.5983 | 94.07072 | 68.05143 | 80.02062 |
| 1.048481 | 18.69424 | 28.72645 | 11.44565 | 20.98659 | 20.29359 | 0.603051 | 0.483833 | 0.307568 | 1.029856 |
| 0.000907 | 0.217577 | 0.781869 | 0.009069 | 2.526724 | 0.048893 | 0.200492 | 2.119772 | 0.688333 | 0.157494 |
| 0.080591 | 1.320572 | 2.20194 | 0.156183 | 5.278515 | 0.851217 | 0.133965 | 4.44121 | 0.412104 | 0.887841 |
| 0.194081 | 11.21512 | 14.76663 | 8.366254 | 5.971425 | 17.65956 | 0.641668 | 0.063756 | 0.12062 | 1.276463 |
| 0.057481 | 2.740199 | 3.904301 | 3.767414 | 0.137108 | 4.312527 | 1.176789 | 0.01036 | 0.141771 | 0.626384 |
| 14.39849 | 2.945346 | 3.417152 | 0.455881 | 6.628573 | 4.641482 | 2.049028 | 1.948126 | 0.052978 | 1.113691 |
| 1.430286 | 0.050911 | 0.116377 | 2.631912 | 1.729536 | 0.002873 | 0.017157 | 0.59505 | 0.078405 | 0.031915 |
| 3.994599 | 7.287469 | 12.9931 | 11.93748 | 17.8261 | 6.149632 | 0.019629 | 0.010428 | 1.91E-08 | 1.230467 |
| 0.681087 | 2.644402 | 0.651910 | 0.492665 | 0.003513 | 3.142815 | 1.141702 | 1.044171 | 0.020796 | 0.475169 |
| 3.517784 | 2.988085 | 5.041801 | 0.132655 | 1.856707 | 3.221062 | 0.009513 | 0.972365 | 0.143736 | 0.151971 |
| 1.142793 | 8.724316 | 3.154795 | 11.12622 | 3.510831 | 8.762035 | 0.113589 | 0.3333 | 0.102252 | 0.340853 |
| 124.8336 | 26.41001 | 19.3737 | 16.7202 | 12.64831 | 27.29127 | 0.68179 | 0.680441 | 0.017556 | 3.456868 |
| 28.18702 | 5.861058 | 9.076268 | 6.068847 | 16.54453 | 5.984442 | 3.793948 | 0.126538 | 2.684306 | 3.212946 |
| 0.023769 | 3.696608 | 6.787465 | 5.956847 | 14.64949 | 8.671987 | 10.41266 | 2.90178 | 11.61882 | 10.39876 |
| 0.327007 | 1.248468 | 3.304892 | 2.395455 | 6.29137 | 8.153432 | 4.510142 | 0.643548 | 2.718485 | 0.314279 |
| 1.262501 | 0.331133 | 0.106294 | 0.091484 | 0.01648 | 1.578025 | 0.00735 | 0.883494 | 0.267066 | 0.018913 |
| 0.513473 | 0.085754 | 0.008392 | 0.019733 | 0.032121 | 2.410297 | 0.001299 | 0.10224 | 0.005424 | 1.040771 |
| 4.154503 | 0.015366 | 0.099593 | 0.002089 | 0.039584 | 2.70521 | 0.016037 | 0.088674 | 0.298194 | 2.752764 |
| 4.771506 | 1.547683 | 0.348071 | 0.067816 | 0.149602 | 1.701228 | 1.57625 | 0.411527 | 0.583351 | 0.201168 |
| 2.082388 | 0.386894 | 0.224037 | 1.072582 | 0.63993 | 0.517405 | 1.328861 | 0.282012 | 0.625174 | 0.317369 |
| 1.433501 | 0.075536 | 0.202871 | 0.957283 | 0.397089 | 0.090784 | 1.66544 | 0.001422 | 0.1996 | 2.180004 |
| 0.208357 | 0.165079 | 0.002089 | 1.264985 | 0.468059 | 0.112897 | 0.064696 | 0.047078 | 0.000422 | 0.018658 |
| 0.174916 | 0.027648 | 0.079813 | 1.014529 | 0.8522 | 0.026111 | 0.710865 | 0.125773 | 0.017352 | 2.088954 |
| 0.06121 | 0.000186 | 0.169523 | 0.789659 | 1.04736 | 0.00238 | 1.254569 | 0.122441 | 0.028162 | 2.909802 |
| 0.96441 | 0.222079 | 0.157752 | 0.074154 | 3.835059 | 0.160452 | 0.275025 | 3.899217 | 0.013379 | 0.285685 |
| 0.421166 | 0.000794 | 0.001381 | 0.012724 | 2.364196 | 0.001341 | 0.088181 | 2.838901 | 0.001214 | 0.003557 |
| 0.286214 | 0.080691 | 0.007033 | 0.048204 | 1.976914 | 0.003222 | 0.121112 | 3.054714 | 0.00783 | 0.157365 |
| 1.044438 | 33.2742 | 32.63451 | 26.38587 | 17.01165 | 33.05516 | 0.742674 | 1.092376 | 0.091075 | 4.851446 |
| 0.9442 | 12.40584 | 4.780235 | 5.354106 | 2.660044 | 4.26484 | 0.804782 | 5.129478 | 0.382081 | 0.65696 |
| 0.053836 | 3.455658 | 0.085193 | 0.457665 | 0.074586 | 0.017631 | 0.007623 | 0.928533 | 0.077347 | 0.969181 |
| 7.963045 | 0.242343 | 0.191036 | 0.380409 | 3.394212 | 0.00395 | 0.330075 | 1.831495 | 1.05E-05 | 0.036461 |
| 0.441826 | 0.006562 | 0.00308 | 0.029691 | 2.61707 | 1.52E-05 | 3.51326 | 0.033216 | 0.079579 | 0.120777 |
| 0.064466 | 0.000469 | 0.0517 | 0.100631 | 2.192341 | 0.002564 | 0.600836 | 1.252474 | 0.001387 | 0.04247 |
| 0.003242 | 1.124496 | 1.774412 | 1.235443 | 0.00371 | 0.024056 | 0.008513 | 2.882843 | 0.006983 | 0.117786 |
| 0.265833 | 0.133638 | 0.223784 | 0.083859 | 1.558216 | 0.006186 | 1.305999 | 0.240142 | 0.032736 | 0.021837 |
| 8.063389 | 0.005611 | 0.011497 | 0.001844 | 2.401256 | 0.001777 | 0.156864 | 2.0347 | 0.001428 | 0.126424 |
| 3.800131 | 3.723075 | 2.078762 | 0.042956 | 0.573344 | 0.239909 | 0.075246 | 0.565088 | 0.279201 | 0.003068 |
| 0.130389 | 0.103684 | 0.036088 | 1.61885 | 0.399757 | 0.567908 | 0.743544 | 1.029761 | 0.02232 | 0.031442 |
| 0.058853 | 0.008112 | 0.013407 | 1.299084 | 3.026064 | 0.323095 | 0.151783 | 1.751036 | 0.007541 | 0.053007 |
| 0.55365 | 3.352882 | 1.734007 | 2.07458 | 0.001903 | 1.299224 | 1.085029 | 0.613862 | 0.099531 | 0.046334 |
| 1.585338 | 0.540764 | 0.368464 | 2.030785 | 5.375105 | 0.699573 | 0.167246 | 2.145077 | 0.114694 | 0.082071 |
| 0.302829 | 0.000404 | 0.001819 | 0.36308 | 2.91266 | 0.069749 | 0.000392 | 2.268621 | 0.076397 | 0.068347 |

| Benzene | Hexane | | | | | AcOEt | | |
|---|---|---|---|---|---|---|---|---|
| k5 | k1 | k2 | k3 | k4 | k5 | k1 | k2 | k3 |
| 0.493928 | 0.307182 | 0.076942 | 0.265812 | 1.031241 | 0.548915 | 0.01836 | 0.137174 | 1.343061 |
| 1.018805 | 0.454519 | 0.022567 | 0.331828 | 4.141353 | 0.774624 | 4.64E-05 | 8E-05 | 1.967857 |
| 0.003988 | 0.576059 | 0.088221 | 0.544717 | 4.718245 | 0.826177 | 0.166789 | 0.01004 | 2.150031 |
| 0.043806 | 7.208979 | 10.60812 | 9.120324 | 3.612606 | 14.47745 | 0.194522 | 1.675141 | 0.310161 |
| 0.442795 | 1.396069 | 1.296442 | 0.787964 | 0.114015 | 5.186952 | 2.214026 | 1.425331 | 1.682909 |
| 0.882616 | 1.177741 | 3.579436 | 4.336801 | 3.035522 | 0.129731 | 2.312653 | 0.116394 | 1.356542 |
| 0.637635 | 13.87804 | 14.35543 | 5.243255 | 5.853294 | 7.72619 | 8.560562 | 10.52052 | 4.81495 |
| 3.99051 | 7.118495 | 3.889532 | 1.689362 | 0.851276 | 1.404335 | 6.721166 | 20.57697 | 12.05714 |
| 3.240743 | 7.154847 | 3.039388 | 1.698982 | 1.1877 | 0.806442 | 2.775517 | 12.08849 | 8.390127 |
| 0.251939 | 6.281438 | 15.78583 | 4.849192 | 3.978836 | 11.54918 | 2.91062 | 1.144107 | 0.274715 |
| 0.053415 | 1.576737 | 7.635208 | 1.689639 | 3.238787 | 6.715898 | 2.541591 | 0.807662 | 0.101026 |
| 2.338203 | 1.504736 | 0.003938 | 0.35875 | 1.038182 | 0.251741 | 0.738848 | 0.002389 | 0.325691 |
| 12.04421 | 9.542077 | 10.44352 | 8.162108 | 2.245363 | 9.160802 | 23.07143 | 19.61373 | 12.59295 |
| 7.139101 | 2.507413 | 2.215573 | 1.381581 | 0.026688 | 1.538659 | 3.193555 | 1.257686 | 8.683738 |
| 63.26975 | 0.143259 | 0.34211 | 0.005437 | 1.480592 | 0.028623 | 1.519873 | 3.368757 | 0.100574 |
| 11.37908 | 81.88943 | 111.5724 | 105.1388 | 109.4769 | 118.6861 | 5.109152 | 5.336754 | 0.957591 |
| 25.38031 | 177.7759 | 165.1122 | 194.3016 | 213.6886 | 202.7082 | 7.81715 | 9.111726 | 2.860179 |
| 88.10594 | 34.52443 | 17.97874 | 30.64214 | 36.35756 | 28.37573 | 11.38867 | 14.98182 | 7.395805 |
| 0.599867 | 0.000119 | 1.191279 | 2.752766 | 0.019662 | 1.312212 | 4.294018 | 0.397739 | 3.949312 |
| 0.773818 | 0.22004 | 0.292929 | 1.266172 | 0.173448 | 0.483116 | 2.487312 | 0.000443 | 0.514755 |
| 2.443758 | 0.132208 | 0.485486 | 1.616797 | 0.083543 | 0.500658 | 5.2128 | 1.369052 | 1.832662 |
| 0.369739 | 49.24707 | 59.74934 | 53.6605 | 65.84024 | 35.119958 | 4.069927 | 1.080236 | 7.137304 |
| 0.053798 | 62.42888 | 79.7641 | 82.8007 | 83.31647 | 97.48101 | 0.08186 | 0.426174 | 0.519433 |
| 1.892051 | 1.77866 | 1.838845 | 0.941374 | 2.361839 | 0.045637 | 7.01032 | 4.635021 | 3.204145 |
| 1.384966 | 0.05061 | 1.515196 | 0.287586 | 0.537061 | 0.161281 | 0.159881 | 1.572011 | 0.082688 |

TABLE 38-continued

3-Benzene-3

$(\theta_{u,mn} - \theta_{g,mnk})^2 / \sigma_{\theta g,mn}^2$

| | | | | | | | | |
|---|---|---|---|---|---|---|---|---|
| 1.67285 | 0.000299 | 0.668974 | 0.071834 | 1.354242 | 0.053127 | 0.280854 | 0.819641 | 0.408774 |
| 0.239391 | 0.307829 | 1.305206 | 0.038312 | 0.594655 | 0.000155 | 0.072598 | 2.992681 | 0.036082 |
| 0.73372 | 0.630784 | 2.006168 | 5.871151 | 1.766877 | 4.237873 | 0.069745 | 2.268595 | 0.973818 |
| 1.962057 | 0.690633 | 0.007817 | 0.605134 | 0.028931 | 0.944703 | 0.387298 | 3.75067 | 0.19518 |
| 0.962744 | 8.586988 | 3.740903 | 5.252894 | 2.665148 | 1.088248 | 0.419089 | 4.492029 | 0.338778 |
| 0.523888 | 2.057347 | 0.374008 | 0.628342 | 1.498034 | 0.145222 | 13.90684 | 23.79231 | 8.813409 |
| 10.4993 | 2.089381 | 0.222228 | 0.828839 | 0.560356 | 0.224165 | 11.76404 | 24.03527 | 23.08917 |
| 3.986307 | 2.076705 | 0.257935 | 0.994564 | 0.196498 | 0.202475 | 5.512184 | 11.1508 | 13.61476 |
| 2.887411 | 0.038141 | 0.110107 | 0.280991 | 1.655463 | 0.132054 | 0.748654 | 0.676246 | 0.727483 |
| 0.857326 | 0.008813 | 0.026255 | 0.197131 | 2.034062 | 0.023479 | 0.35187 | 0.322338 | 0.883262 |
| 0.0008 | 0.043034 | 0.010042 | 0.070975 | 2.101593 | 0.027432 | 0.002072 | 0.001124 | 0.579581 |
| 0.538591 | 0.075851 | 0.072082 | 0.410464 | 1.309849 | 0.17344 | 4.6401 | 0.14086 | 2.704771 |
| 0.054191 | 0.033396 | 0.009586 | 0.406577 | 1.474564 | 0.07596 | 0.046058 | 0.672806 | 2.433875 |
| 0.002568 | 0.002158 | 0.017898 | 0.412996 | 1.581276 | 0.008865 | 0.720833 | 0.728172 | 0.308777 |
| 2.278613 | 1.031381 | 3.147782 | 0.081592 | 0.050727 | 2.380399 | 2.484216 | 0.041765 | 0.121867 |
| 0.171562 | 1.761926 | 0.62015 | 0.000805 | 0.3317 | 3.498148 | 1.853151 | 0.279412 | 0.014062 |
| 0.003761 | 0.984404 | 0.085914 | 0.031474 | 0.351178 | 1.726146 | 1.39907 | 0.554789 | 0.002055 |
| 0.485381 | 0.697611 | 7.179092 | 1.786229 | 1.477502 | 1.541208 | 6.18684 | 8.159984 | 9.654793 |
| 0.093076 | 0.053627 | 0.660127 | 1.021273 | 0.001592 | 0.448382 | 0.000142 | 1.079804 | 1.223486 |
| 0.058001 | 0.0006 | 0.406739 | 2.59323 | 0.003929 | 1.571532 | 0.001998 | 0.679189 | 0.934885 |
| 2.162925 | 0.537249 | 0.225386 | 0.243557 | 0.374489 | 2.196583 | 30.69534 | 21.40323 | 25.73825 |
| 3.079925 | 0.15368 | 0.538151 | 0.714017 | 0.297229 | 0.311278 | 1.483741 | 0.500634 | 5.022636 |
| 0.109845 | 0.109388 | 0.126214 | 0.218228 | 0.000304 | 1.686511 | 0.002045 | 0.099811 | 1.762259 |
| 0.000551 | 0.001575 | 0.02337 | 1.49992 | 2.138922 | 2.02E-05 | 0.2166 | 1.202578 | 0.441104 |
| 0.881432 | 0.152705 | 0.004419 | 0.215369 | 0.192333 | 1.440276 | 0.000408 | 0.3213 | 0.011085 |
| 0.109458 | 0.468017 | 1.21E-05 | 0.465158 | 0.255127 | 3.677659 | 0.000408 | 0.002011 | 0.011833 |
| 0.109413 | 0.201804 | 3.78E-05 | 0.017401 | 0.088250 | 2.10546 | 0.038301 | 0.023769 | 0.0356 |
| 2.513692 | 0.284917 | 0.004231 | 0.002459 | 0.035893 | 2.37085 | 0.036008 | 0.125722 | 0.123064 |
| 0.016377 | 1.433999 | 0.119384 | 0.679843 | 0.019691 | 0.153343 | 0.009042 | 1.353382 | 0.254049 |
| 1.349328 | 0.105102 | 1.529879 | 0.304847 | 0.948844 | 2.174414 | 0.012384 | 0.297437 | 2.002733 |
| 0.271283 | 0.961371 | 0.445633 | 0.0193 | 0.108061 | 0.650414 | 0.000481 | 0.026268 | 2.342786 |
| 1.089699 | 1.097495 | 0.245525 | 0.002282 | 0.081879 | 0.640607 | 0.024933 | 0.558285 | 1.281412 |
| 0.158389 | 6.448184 | 0.708337 | 0.847677 | 1.789639 | 0.934984 | 0.124025 | 1.346147 | 0.274677 |
| 0.840271 | 16.32478 | 8.670284 | 4.845015 | 8.206323 | 5.813582 | 0.076994 | 2.377495 | 0.080152 |
| 2.011017 | 0.225652 | 2.272871 | 0.377947 | 0.263384 | 0.524398 | 0.049242 | 1.882937 | 0.005367 |

TABLE 39

3-Benzene-4

| | | | | THF | | | | log $\sigma_{rg,mn}$ | |
|---|---|---|---|---|---|---|---|---|---|
| k4 | k5 | k1 | k2 | k3 | k4 | k5 | H2O | EtOH | Benzene |
| 0.498927 | 0.005847 | 1.423524 | 0.789496 | 0.004276 | 1.758143 | 0.030666 | -3.47051 | -4.20695 | -3.01438 |
| 0.126598 | 0.045298 | 0.337455 | 2.65804 | 0.048044 | 0.118252 | 0.079893 | 1.423286 | 0.497692 | -0.08048 |
| 0.094492 | 0.028255 | 0.390631 | 2.015593 | 0.026741 | 0.00011 | 0.196993 | 1.749126 | 2.144489 | 1.309526 |
| 1.607415 | 0.179769 | 0.039956 | 1.563783 | 0.09256 | 0.330217 | 0.040515 | 4.210396 | 2.683662 | 3.146059 |
| 0.752173 | 0.082557 | 0.010928 | 1.359721 | 0.048317 | 0.440805 | 0.173785 | 4.511755 | 4.725985 | 4.151946 |
| 0.003411 | 0.000531 | 0.397108 | 0.607356 | 0.00057 | 0.476678 | 0.518393 | -3.37455 | -0.12163 | -0.1664 |
| 2.520883 | 3.368143 | 2.668303 | 9.646694 | 2.124066 | 1.881533 | 3.59043 | -3.53899 | -4.81517 | -4.14667 |
| 12.36172 | 10.02737 | 1.833735 | 9.091859 | 3.341739 | 1.893043 | 2.013352 | 1.382603 | 0.58021 | 1.121638 |
| 9.330258 | 5.258527 | 1.49751 | 7.310041 | 2.667846 | 1.128515 | 0.965612 | 1.741738 | 4.397142 | 1.867993 |
| 0.013641 | 0.095258 | 2.639104 | 7.557715 | 0.943503 | 1.389132 | 4.00645 | 4.20986 | 3.877253 | 4.065613 |
| 0.078912 | 0.112112 | 2.42359 | 6.684385 | 0.723715 | 1.619942 | 5.018102 | 4.502063 | 7.334288 | 4.599096 |
| 0.796376 | 0.144938 | 0.289035 | 1.234222 | 0.422365 | 0.038968 | 0.432224 | -2.81705 | 2.017158 | -0.07503 |
| 24.16124 | 29.74433 | 13.56825 | 9.766517 | 8.063643 | 19.60004 | 7.310492 | -2.54699 | -3.73822 | -3.60914 |
| 2.550663 | 1.72928 | 8.416209 | 3.613417 | 1.975423 | 3.589431 | 1.03633 | 2.232561 | 0.673325 | 0.52533 |
| 4.226051 | 3.395571 | 0.852132 | 3.971703 | 6.36214 | 4.635753 | 7.578938 | 2.62389 | 2.29138 | 2.377234 |
| 5.814321 | 8.255385 | 7.676738 | 7.239555 | 6.969721 | 18.31857 | 7.333129 | 4.526049 | 3.418593 | 3.245467 |
| 11.30316 | 11.92958 | 22.74343 | 23.90401 | 24.39308 | 41.72055 | 24.4723 | 4.977347 | 4.815047 | 4.288023 |
| 21.0974 | 16.22273 | 151.796 | 190.8086 | 206.102 | 210.4753 | 197.4355 | -1.85188 | -0.43421 | 0.255924 |
| 4.287046 | 0.811331 | 0.174417 | 1.036602 | 0.113644 | 0.582096 | 0.83219 | -3.21894 | -4.00041 | -4.99092 |
| 0.63804 | 0.045274 | 2.927157 | 11.07229 | 3.208705 | 7.036701 | 8.453363 | 1.990366 | 0.825083 | -0.34597 |
| 1.574089 | 0.85325 | 15.0281 | 11.6298 | 6.865761 | 19.90171 | 9.668998 | 2.337258 | 2.032124 | 1.48009 |
| 7.50818 | 2.92233 | 0.081217 | 0.479034 | 0.024478 | 1.128514 | 0.394305 | 4.824302 | 2.611209 | 3.155974 |
| 0.876888 | 0.503263 | 0.346785 | 0.000365 | 0.124446 | 2.903911 | 1.7E-05 | 5.451588 | 3.586953 | 5.32421 |
| 2.335143 | 0.57448 | 10.33144 | 4.823098 | 3.812653 | 11.9328 | 4.187496 | -1.65006 | -1.31919 | 0.433549 |
| 0.019424 | 0.166521 | 2.617521 | 3.548294 | 2.591623 | 5.655328 | 0.205718 | -3.2759 | -3.9333 | -4.83793 |
| 0.586504 | 0.423701 | 55.04474 | 38.20318 | 65.65284 | 53.07544 | 47.51675 | 2.395255 | 1.121161 | 0.596189 |
| 0.000818 | 0.02405 | 3.155467 | 8.719348 | 1.485366 | 4.681841 | 1.725001 | 2.671959 | 2.476318 | 1.833904 |
| 4.167006 | 0.373462 | 0.187819 | 0.802965 | 0.100163 | 1.47325 | 0.415487 | 4.960104 | 3.724711 | 4.348747 |
| 0.013992 | 0.205911 | 3.495644 | 6.482137 | 2.661402 | 6.561482 | 0.747484 | 5.213834 | 5.060598 | 5.343589 |
| 0.183303 | 0.287471 | 21.13179 | 31.72978 | 17.1183 | 25.27539 | 14.89108 | -1.9216 | -0.48259 | 0.760752 |

TABLE 39-continued

3-Benzene-4

| | | | | | | | | | |
|---|---|---|---|---|---|---|---|---|---|
| 17.77168 | 17.7661 | 0.551731 | 0.221335 | 0.003832 | 3.506138 | 0.664842 | −3.33665 | −4.93122 | −4.45787 |
| 27.6272 | 23.88338 | 6.326778 | 4.950412 | 2.04929 | 11.59562 | 6.230077 | 2.617672 | −0.84793 | −0.52142 |
| 17.99057 | 9.340299 | 6.377894 | 4.422894 | 1.40756 | 9.782752 | 4.794011 | 1.895491 | 0.827268 | 1.224621 |
| 0.002168 | 0.051609 | 0.313208 | 0.663064 | 1.311494 | 0.519907 | 0.177924 | 5.047699 | 2.645935 | 4.198668 |
| 0.314207 | 0.128395 | 1.246303 | 1.460341 | 1.68446 | 0.168513 | 0.41633 | 5.744713 | 3.834929 | 4.787592 |
| 1.658515 | 0.234247 | 3.816405 | 1.472508 | 0.017765 | 2.276866 | 0.485585 | −1.07522 | −1.18013 | 0.031744 |
| 3.605786 | 3.682874 | 0.32852 | 2.88536 | 0.409146 | 4.995782 | 1.501855 | −1.98114 | −3.01957 | −4.77763 |
| 0.402625 | 3.818545 | 2.852247 | 10.84615 | 3.063206 | 7.824515 | 7.648053 | 2.302229 | 1.172873 | −0.60568 |
| 0.005058 | 0.650537 | 6.379917 | 12.6243 | 4.628786 | 8.090744 | 2.84011 | 2.531007 | 2.180185 | 0.824372 |
| 1.247546 | 0.105997 | 0.059534 | 1.387694 | 0.09495 | 3.83398 | 0.557167 | 5.313679 | 3.298982 | 4.056546 |
| 0.328581 | 0.000303 | 0.000314 | 1.016585 | 0.03311 | 3.138789 | 0.885185 | 5.661962 | 4.329304 | 5.29199 |
| 0.032605 | 0.03952 | 0.694031 | 0.071938 | 0.16216 | 0.003185 | 1.119189 | −1.57645 | −0.62874 | −0.38181 |
| 2.032546 | 3.255713 | 2.420758 | 0.212094 | 0.091856 | 0.095122 | 0.98355 | −3.49831 | −3.94273 | −4.91018 |
| 0.069151 | 0.112956 | 0.004813 | 2.482629 | 3.100719 | 0.839815 | 2.661055 | 2.424872 | 0.445572 | 0.883886 |
| 0.145294 | 0.258437 | 0.037227 | 2.600452 | 0.034244 | 0.82621 | 0.095847 | 2.589026 | 2.778786 | 0.220413 |
| 13.19443 | 21.18571 | 2.985371 | 1.001938 | 0.786119 | 0.002469 | 2.562995 | 5.021767 | 3.338871 | 5.535133 |
| 0.142077 | 1.586829 | 1.346996 | 5.598141 | 0.245803 | 0.880191 | 1.596243 | 5.159161 | 5.413236 | 5.249664 |
| 0.204401 | 0.102624 | 0.049635 | 1.872506 | 0.04108 | 0.587231 | 0.001592 | −1.63969 | 0.909739 | 0.495249 |
| 0.085811 | 0.05406 | 1.040594 | 0.091458 | 1.411618 | 0.281844 | 0.872642 | −3.75061 | −4.03884 | −3.85018 |
| 2.65355 | 0.036565 | 0.163546 | 0.301523 | 0.158894 | 1.598925 | 0.002633 | 1.981951 | 2.272385 | 2.102403 |
| 2.637541 | 0.118593 | 1.44344 | 6.538823 | 2.536168 | 2.709039 | 0.390022 | 1.953076 | 4.092013 | 2.495732 |
| 3.21185 | 0.113125 | 1.825958 | 0.60673 | 2.607563 | 0.011491 | 2.178224 | 4.897952 | 5.078273 | 5.504239 |
| 2.494139 | 0.18436 | 2.320087 | 1.433767 | 3.383924 | 0.000532 | 1.52191 | 4.935532 | 6.916974 | 5.854076 |
| 0.231954 | 0.173945 | 1.912739 | 2.477337 | 2.889039 | 0.016392 | 0.216076 | −1.17599 | 0.633256 | −0.31503 |
| 0.061249 | 0.057888 | 0.007206 | 0.784353 | 0.737585 | 0.008663 | 0.514752 | −3.977688 | −1.75606 | −4.84518 |
| 0.007186 | 0.036824 | 0.314397 | 2.267715 | 0.099686 | 0.102905 | 1.257344 | 1.369908 | 2.452408 | 0.091022 |
| 0.04819 | 0.12142 | 0.145832 | 0.523464 | 1.292069 | 0.045223 | 1.85E−08 | 2.397467 | 3.352771 | 0.918108 |
| 0.252954 | 0.067181 | 0.020053 | 0.982088 | 0.693348 | 0.014974 | 0.29234 | 4.568042 | 3.121787 | 3.407953 |
| 0.23225 | 0.011757 | 0.02475 | 0.91675 | 1.178093 | 0.018719 | 0.428018 | 5.043107 | 3.956618 | 5.072329 |
| 0.200857 | 0.095745 | 0.018268 | 0.009563 | 2.199756 | 0.004685 | 0.799627 | −1.06582 | −1.14587 | −0.12107 |

| | log $\sigma_{rg,mn}$ | | | | | log $\sigma_{\theta g,mn}$ | | | |
|---|---|---|---|---|---|---|---|---|---|
| | Hexene | AcOEt | THF | H2O | EtOH | Benzene | Hexene | AcOEt | THF |
| | −4.10649 | −2.38023 | −1.66628 | −0.82928 | 0.823367 | −0.51055 | 0.992277 | −0.01887 | −0.69727 |
| | 0.688938 | 1.180556 | 0.570003 | −1.55647 | 0.340158 | −0.76968 | 0.467301 | −0.07627 | −0.43568 |
| | 1.072453 | 2.454608 | 2.150339 | −1.63936 | 0.400977 | −1.08067 | 0.466282 | 0.123082 | −0.0921 |
| | 3.374414 | 4.503642 | 2.094256 | −1.14966 | −0.67501 | −1.52378 | −1.8571 | −1.24557 | −0.59128 |
| | 4.422189 | 5.309541 | 3.505918 | −1.1801 | −0.50805 | −1.42174 | −0.9164 | −0.22346 | |
| | −1.31652 | −0.58079 | −0.29805 | −2.61649 | −1.8365 | −0.74507 | −2.09105 | −1.17806 | −1.17675 |
| | −5.16409 | −4.20603 | −2.91236 | −2.16383 | −1.07598 | 1.084797 | −0.78634 | −1.56827 | −0.63991 |
| | −0.22856 | −0.39937 | 0.259942 | −1.37949 | −1.06307 | −0.17791 | −0.871 | −2.29371 | −1.39059 |
| | 0.658653 | 0.724481 | 2.016576 | −1.37216 | −0.73084 | 0.417273 | −0.73762 | −2.03317 | −1.17522 |
| | 2.946359 | 2.288464 | 1.814887 | −1.17288 | −0.98772 | 0.319091 | −1.48446 | −1.58917 | −1.13088 |
| | 4.283216 | 3.001095 | 3.289227 | −1.13083 | −0.69725 | 0.469739 | −1.13058 | −1.40378 | −1.16917 |
| | −1.28754 | −1.83629 | −0.70151 | −3.16176 | −1.91056 | −0.35615 | −2.02085 | −2.98339 | −2.57999 |
| | −3.45323 | −2.86846 | −2.63055 | −0.40633 | −1.46006 | −0.15372 | 0.262191 | −0.88764 | −0.58837 |
| | 1.248007 | 0.60212 | 0.207069 | −1.49237 | −1.15723 | −1.74261 | 0.300856 | −1.27126 | −1.29522 |
| | 1.521438 | 1.683112 | 1.784486 | −2.05044 | −0.51846 | −1.85177 | 0.407925 | −0.48163 | −1.06283 |
| | 4.290344 | 3.604588 | 2.58891 | −0.3419 | −1.78309 | −0.29631 | −1.57369 | −0.42624 | −0.79534 |
| | 4.912251 | 4.56719 | 4.147205 | −0.4135 | −0.61661 | −0.19836 | −1.3508 | −0.02066 | −0.70174 |
| | −1.43277 | −2.33187 | −0.68004 | −2.20351 | −0.95833 | −1.7064 | −1.3211 | −0.98294 | −2.43591 |
| | −4.18508 | −4.57844 | −2.66352 | −0.25239 | −1.97182 | −0.41206 | 0.666055 | −1.33803 | −0.7309 |
| | 0.734052 | 0.285807 | 0.234313 | 0.394229 | −1.83923 | −1.48248 | 0.686205 | −1.9322 | −3.00454 |
| | 1.36182 | 2.258278 | 1.262069 | 0.427422 | −1.40018 | −1.40448 | 0.839868 | −1.32376 | −1.9627 |
| | 3.225993 | 3.283056 | 2.743929 | 0.533222 | −1.84778 | −0.66338 | −1.99667 | −1.85619 | −0.75504 |
| | 4.055777 | 5.115025 | 3.88808 | 0.556182 | −1.64801 | −0.58531 | −2.40852 | −1.49817 | −0.53901 |
| | −0.61674 | −0.10786 | −1.41821 | −2.43387 | −2.10459 | −2.01139 | −1.70592 | −1.94335 | −1.94459 |
| | −3.99619 | −4.57673 | −2.56564 | −0.82216 | −1.35806 | 0.057138 | 0.385252 | −0.37197 | −0.95589 |
| | 0.784866 | 2.336694 | 0.470495 | −0.2301 | −1.96474 | −0.805879 | 0.362596 | −0.47755 | −2.79221 |
| | 0.952827 | 2.335711 | 2.321066 | −0.34122 | −1.17207 | −0.99518 | 0.428725 | 0.658463 | −1.47053 |
| | 2.499667 | 4.966157 | 2.71242 | 0.119395 | −1.88121 | −0.2457 | −0.8037 | −1.60442 | −0.95537 |
| | 3.978408 | 4.951408 | 4.257231 | 0.039681 | −1.65995 | −0.27385 | −0.4687 | 0.24632 | −0.59658 |
| | −0.9661 | −0.20126 | 0.059249 | −2.41235 | −1.76205 | −0.90936 | −1.20675 | 0.271423 | −1.67284 |
| | −3.59592 | −3.69173 | −2.1596 | −1.79439 | −1.19371 | −0.6264 | 0.809715 | −1.30587 | −0.12794 |
| | 0.80426 | 0.42363 | 0.51278 | −0.48931 | −1.11443 | −1.16205 | 0.870868 | −1.51448 | −0.98185 |
| | 1.003504 | 2.133733 | 2.193251 | −0.46491 | −0.64042 | −0.69015 | 0.34193 | −1.12448 | −0.76481 |
| | 3.45203 | 3.075531 | 3.315992 | −0.35884 | −1.72089 | −0.99729 | −0.29057 | −1.21759 | −0.68195 |
| | 5.019523 | 4.940724 | 4.681185 | −0.40388 | −0.70986 | −0.41013 | 0.18832 | −0.87095 | −0.76053 |
| | 0.484981 | −0.02918 | −0.18164 | −2.05213 | −1.118 | −0.82419 | −0.8464 | −1.76629 | −2.12592 |
| | −5.02918 | −2.67317 | −3.5853 | −1.36913 | −1.49909 | −1.03802 | 0.499368 | −1.34103 | −0.48288 |
| | −0.18678 | 0.838193 | −0.03567 | −0.55432 | −1.20373 | −1.08981 | 0.459324 | −1.59959 | −1.97802 |
| | 0.492859 | 2.38741 | 1.658616 | −0.32969 | −0.42158 | −0.19839 | 0.488639 | −0.50208 | −1.97447 |
| | 2.583292 | 3.546491 | 2.6235 | −0.54307 | −1.49349 | −1.49594 | −1.82025 | −1.1087 | −0.85210 |
| | 4.332906 | 4.911158 | 4.373398 | −0.31415 | −0.54561 | −0.31769 | −1.25587 | −0.23396 | −0.55993 |
| | −0.69466 | −0.59548 | −0.03484 | −1.81488 | −0.9873 | −0.51292 | −1.53594 | −0.75271 | −1.96269 |
| | −3.25508 | −3.40032 | −2.58889 | −0.83757 | 0.566473 | 0.611169 | 0.037197 | −1.06393 | −0.99583 |

TABLE 39-continued

3-Benzene-4

| | | | | | | | | |
|---|---|---|---|---|---|---|---|---|
| 0.257281 | 0.494046 | 0.909333 | −0.51511 | 0.632718 | 0.594448 | 0.835504 | −1.34173 | −2.24377 |
| 0.796890 | 1.443826 | 2.481650 | −0.43515 | 0.690223 | 0.321458 | 0.571697 | −0.5567 | −0.69441 |
| 3.852815 | 3.480733 | 2.713015 | −0.22912 | −2.0043 | −0.69921 | 0.647753 | −1.86841 | −1.08793 |
| 4.886197 | 4.99752 | 5.020012 | −0.23107 | −0.92487 | −0.61209 | 0.73669 | −0.3206 | −0.8862 |
| 0.162829 | −0.47851 | 0.577207 | −1.72139 | −1.09882 | −0.40871 | 0.565064 | −0.45376 | −0.76466 |
| −4.34306 | −2.56696 | −4.43024 | −1.2803 | 0.314511 | 0.558145 | −0.03573 | −0.25352 | −0.0916 |
| 1.395306 | 2.397084 | 0.725282 | 0.085808 | 0.456879 | −0.76859 | 0.722195 | 0.987138 | −1.09915 |
| 4.534136 | 2.81233 | 2.262165 | 0.038463 | 0.046801 | 0.655338 | 0.643474 | 0.757237 | −1.26364 |
| 4.403683 | 3.330728 | 2.933988 | 0.054007 | −0.86324 | 0.366502 | 0.534097 | 0.497352 | −0.52911 |
| 4.753436 | 4.689018 | 4.459714 | 0.009472 | 0.57047 | −0.84925 | 0.8618 | 0.756353 | −0.1815 |
| −0.61998 | 0.343889 | −0.14069 | −1.81933 | 0.339932 | 0.45126 | −0.87872 | −0.14241 | −1.07022 |
| −3.09943 | −3.29933 | −0.12005 | −0.81177 | −1.34576 | −0.35308 | 0.785952 | 0.817846 | 0.998936 |
| 2.128556 | 2.322421 | 1.823127 | −0.45072 | −1.0943 | 0.04527 | 1.089347 | 0.547119 | −1.11656 |
| 1.22062 | 2.309211 | 1.954408 | −0.82505 | −0.04856 | 0.811424 | 0.943053 | 0.808508 | −0.46843 |
| 3.974758 | 5.180598 | 4.924648 | −0.15758 | −1.09899 | −0.38398 | −0.14212 | −0.19413 | 1.07302 |
| 3.311061 | 4.635538 | 4.926917 | −0.50567 | −0.22342 | 0.514798 | −0.71394 | 0.762028 | 1.093496 |
| −0.74758 | 0.103346 | 0.296609 | −1.29164 | 0.090747 | 0.241204 | −0.75044 | 0.355101 | −0.89061 |

TABLE 40

3-Hexane-1

| | | $r_{u,mn}$ | $(r_{u,mn}-r_{g,mnk})^2/\sigma_{rg,mn}^2$ | | | | | | | |
|---|---|---|---|---|---|---|---|---|---|---|
| | | Hexane | H$_2$O | | | | | EtOH | | |
| f | Ku,mn' | k5 | k1 | k2 | k3 | k4 | k5 | k1 | k2 | k3 |
| 0.05 Hz | Ku', 12 | 0.013805 | 8.221674 | 11.64185 | 19.49684 | 14.55449 | 7.177422 | 9.279648 | 3.680791 | 14.28467 |
| | Ku', 13 | 2.444641 | 23.8426 | 29.65899 | 13.16954 | 16.47734 | 19.93917 | 10.74315 | 2.281101 | 9.129716 |
| | Ku', 14 | 4.419905 | 22.39161 | 29.59299 | 12.76678 | 16.51741 | 18.3535 | 3.24564 | 0.148602 | 4.685798 |
| | Ku', 23 | 177.0877 | 0.415928 | 0.223838 | 0.826106 | 0.217551 | 0.337531 | 9.303895 | 17.23283 | 23.71993 |
| | Ku', 24 | 320.1741 | 0.020578 | 0.061047 | 2.89595 | 1.468962 | 0.053483 | 0.016463 | 1.499975 | 0.008316 |
| | Ku', 34 | 1.807997 | 147.342 | 125.5338 | 124.6279 | 115.4304 | 153.9663 | 0.659129 | 0.075664 | 1.734891 |
| 0.1 Hz | Ku', 12 | 0.022339 | 5.626958 | 7.283505 | 13.5113 | 12.2764 | 16.60732 | 19.2157 | 30.51536 | 30.09842 |
| | Ku', 13 | 3.607286 | 23.61223 | 9.493948 | 14.35379 | 11.39246 | 18.10115 | 8.24807 | 4.378828 | 3.885502 |
| | Ku', 14 | 4.993026 | 23.75686 | 5.560529 | 15.56695 | 13.132 | 20.71869 | 0.065524 | 0.065061 | 0.030915 |
| | Ku', 23 | 161.4771 | 1.798845 | 0.003092 | 0.060571 | 0.127172 | 0.051784 | 0.047204 | 1.160977 | 1.351994 |
| | Ku', 24 | 223.5096 | 2.277438 | 0.000537 | 0.002932 | 0.033931 | 0.001402 | 0.021003 | 0.010847 | 0.001799 |
| | Ku', 34 | 1.38415 | 0.544265 | 0.610839 | 4.345162 | 4.09362 | 4.16898 | 0.043435 | 0.079233 | 0.032484 |
| 0.15 Hz | Ku', 12 | 0.009287 | 1.503859 | 0.684195 | 2.664203 | 7.022586 | 1.290415 | 4.354031 | 9.477552 | 7.025438 |
| | Ku', 13 | 1.208307 | 4.677293 | 1.954872 | 7.459431 | 0.905379 | 2.024811 | 6.872094 | 9.276915 | 7.52934 |
| | Ku', 14 | 1.507895 | 3.474776 | 1.18889 | 6.751236 | 0.741881 | 1.447288 | 2.987693 | 3.982049 | 2.610629 |
| | Ku', 23 | 130.1126 | 0.621217 | 0.453528 | 0.486321 | 0.819121 | 0.034783 | 0.538741 | 1.995849 | 1.637338 |
| | Ku', 24 | 162.3726 | 1.06902 | 0.532980 | 1.33714 | 0.372188 | 0.166464 | 1.522982 | 0.592471 | 0.412961 |
| | Ku', 34 | 1.247941 | 3.447533 | 0.877405 | 8.187918 | 4.711882 | 2.656837 | 6.669993 | 6.970296 | 4.710814 |
| 0.2 Hz | Ku', 12 | 0.02136 | 0.143318 | 0.313942 | 2.98486 | 2.949263 | 3.293305 | 1.370608 | 2.274943 | 2.791798 |
| | Ku', 13 | 2.027578 | 2.015511 | 0.132204 | 2.451763 | 4.194352 | 4.539431 | 1.25658 | 2.730246 | 2.749061 |
| | Ku', 14 | 2.509646 | 3.307416 | 0.19704 | 2.387904 | 4.386746 | 4.878548 | 1.779596 | 3.424045 | 2.920691 |
| | Ku', 23 | 94.92582 | 3.880628 | 0.009586 | 0.189263 | 0.570439 | 0.553543 | 0.807319 | 2.971852 | 1.547613 |
| | Ku', 24 | 117.4949 | 3.934516 | 0.036252 | 0.136755 | 0.412162 | 0.420123 | 24.55718 | 37.78555 | 25.33589 |
| | Ku', 34 | 1.237755 | 6.264233 | 2.091117 | 0.489639 | 0.918899 | 1.111586 | 32.71659 | 37.17584 | 28.93099 |
| 0.25 Hz | Ku', 12 | 0.009931 | 2.241854 | 7.517415 | 4.748671 | 6.720398 | 1.202307 | 3.204192 | 5.369843 | 3.967024 |
| | Ku', 13 | 1.321849 | 3.277767 | 1.205588 | 4.568367 | 1.453186 | 0.093297 | 1.175311 | 2.735821 | 1.875563 |
| | Ku', 14 | 1.694064 | 3.678812 | 1.73131 | 5.176354 | 1.986793 | 0.167943 | 0.6131 | 2.615621 | 1.376491 |
| | Ku', 23 | 133.1079 | 1.690978 | 0.01159 | 0.901054 | 0.000149 | 0.087249 | 0.515206 | 0.176204 | 0.237461 |
| | Ku', 24 | 170.5894 | 2.192859 | 0.004283 | 1.238106 | 0.034539 | 0.014535 | 0.221395 | 1.742325 | 0.896811 |
| | Ku', 34 | 1.281597 | 0.54775 | 3.38345 | 0.623241 | 2.616326 | 5.711115 | 3.101484 | 10.41347 | 6.322814 |
| 0.3 Hz | Ku', 12 | 0.036166 | 0.064122 | 1.950136 | 4.683196 | 2.906728 | 2.220597 | 0.003433 | 3.418149 | 0.785324 |
| | Ku', 13 | 3.096902 | 6.484172 | 0.802511 | 0.958727 | 1.300911 | 0.821468 | 16.21615 | 29.22496 | 25.55818 |
| | Ku', 14 | 4.109059 | 19.15889 | 7.330505 | 8.406539 | 10.69929 | 7.145769 | 12.14685 | 27.60566 | 18.7054 |
| | Ku', 23 | 85.63005 | 3.187665 | 0.048832 | 0.020539 | 0.064977 | 0.043573 | 10.1721 | 2.823399 | 7.250443 |
| | Ku', 24 | 113.6164 | 3.964956 | 0.213021 | 0.089158 | 0.24207 | 0.178514 | 21.88219 | 20.99131 | 21.61274 |
| | Ku', 34 | 1.326829 | 1.753594 | 0.109024 | 0.070333 | 0.026052 | 0.061425 | 14.71438 | 28.93226 | 18.84565 |
| 0.35 Hz | Ku', 12 | 0.001411 | 0.102947 | 4.821938 | 0.585586 | 0.823512 | 0.645465 | 0.569882 | 0.387666 | 0.6117 |
| | Ku', 13 | 0.154816 | 3.080372 | 1.755846 | 6.8038 | 0.549376 | 1.692439 | 2.056483 | 1.573654 | 1.601544 |
| | Ku', 14 | 0.271545 | 4.155664 | 3.224629 | 7.473463 | 0.679758 | 2.093557 | 2.150013 | 1.283224 | 2.478316 |
| | Ku', 23 | 112.0887 | 1.743522 | 0.115091 | 0.42606 | 0.069307 | 0.001415 | 0.235148 | 0.56253 | 0.031661 |
| | Ku', 24 | 192.4625 | 1.59767 | 0.170717 | 0.205671 | 0.146428 | 0.011755 | 4.099674 | 2.987338 | 4.794741 |
| | Ku', 34 | 1.717056 | 1.516696 | 0.004089 | 3.689949 | 2.278068 | 0.702286 | 3.854986 | 1.859841 | 9.30091 |
| 0.4 Hz | Ku', 12 | 0.008056 | 2.429724 | 1.310457 | 9.117196 | 4.391347 | 4.56427 | 6.76109 | 4.918283 | 1.970582 |
| | Ku', 13 | 0.929159 | 3.658148 | 0.122672 | 4.606103 | 1.348599 | 2.424869 | 9.152122 | 7.502593 | 7.493994 |
| | Ku', 14 | 1.266581 | 4.014932 | 0.175239 | 4.987574 | 2.427726 | 3.226802 | 4.520794 | 0.61142 | 0.776184 |
| | Ku', 23 | 115.3444 | 3.713959 | 4.6E−05 | 0.822524 | 0.28521 | 0.811911 | 0.440097 | 0.226261 | 1.293891 |

TABLE 40-continued

3-Hexane-1

|  | f | Ku,mn' |  |  |  |  |  |  |  |  |  |
|---|---|---|---|---|---|---|---|---|---|---|---|
|  |  | Ku', 24 | 157.2315 | 4.003351 | 0.000257 | 0.784821 | 0.746733 | 1.135001 | 4.017529 | 0.258524 | 1.565106 |
|  |  | Ku', 34 | 1.363148 | 0.403925 | 0.035708 | 0.461888 | 1.099977 | 0.000344 | 3.918632 | 0.27325 | 0.419026 |
| 0.45 Hz |  | Ku', 12 | 0.004329 | 5.728601 | 17.03195 | 12.62672 | 8.71208 | 7.032884 | 4.928737 | 6.822963 | 4.758589 |
|  |  | Ku', 13 | 0.379899 | 6.879528 | 3.435535 | 9.630637 | 2.888424 | 10.55202 | 0.247368 | 0.318362 | 0.18914 |
|  |  | Ku', 14 | 0.699676 | 14.0705 | 6.561176 | 17.13718 | 6.674886 | 9.221941 | 0.057889 | 0.042069 | 0.044551 |
|  |  | Ku', 23 | 87.75817 | 3.014753 | 0.132254 | 1.627882 | 0.399789 | 4.111687 | 0.039625 | 0.031577 | 0.015229 |
|  |  | Ku', 24 | 161.6262 | 4.237841 | 0.028533 | 1.600893 | 0.466213 | 1.493631 | 0.033968 | 0.009071 | 0.022151 |
|  |  | Ku', 34 | 1.841746 | 2.066207 | 2.475563 | 3.026304 | 1.316176 | 8.875582 | 0.316292 | 0.039621 | 0.31506 |
| 0.5 Hz |  | Ku', 12 | 0.036924 | 0.045121 | 4.431631 | 2.823477 | 2.297646 | 1.755244 | 0.000929 | 0.001715 | 0.001465 |
|  |  | Ku', 13 | 1.06242 | 12.56121 | 16.58505 | 12.60014 | 25.53117 | 10.71903 | 0.073676 | 0.120201 | 0.07228 |
|  |  | Ku', 14 | 1.645262 | 1.871074 | 4.884033 | 2.554393 | 8.523022 | 1.424022 | 0.046805 | 0.118057 | 0.087096 |
|  |  | Ku', 23 | 28.77315 | 12.31511 | 4.092925 | 3.925366 | 9.17131 | 4.181728 | 10.04422 | 14.91635 | 9.007614 |
|  |  | Ku', 24 | 44.55906 | 5.498509 | 3.627223 | 2.32624 | 9.276009 | 1.576317 | 7.27539 | 17.0028 | 12.79297 |
|  |  | Ku', 34 | 1.548599 | 1.608771 | 0.007719 | 0.614243 | 0.032935 | 2.021678 | 0.859184 | 4.659819 | 7.01157 |

| | | | $(r_{u,mn} - r_{g,mnk})^2 / \sigma_{rg,mn}^2$ | | | | | | | |
|---|---|---|---|---|---|---|---|---|---|---|
| | | | EtOH | | Benzene | | | | | |
| | f | Ku,mn' | k4 | k5 | k1 | k2 | k3 | k4 | k5 | k1 |
| | 0.05 Hz | Ku', 12 | 5.930026 | 9.551197 | 0.27754 | 4.204991 | 1.343729 | 0.601985 | 0.047598 | 0.169465 |
| | | Ku', 13 | 5.732055 | 9.842536 | 0.264058 | 0.92297 | 0.302583 | 0.022051 | 0.734104 | 0.293357 |
| | | Ku', 14 | 2.944305 | 4.31488 | 0.474718 | 0.216028 | 0.610402 | 2.152059 | 0.00014 | 0.649934 |
| | | Ku', 23 | 11.48293 | 13.84467 | 30.04112 | 40.52992 | 41.46981 | 32.54727 | 22.23483 | 0.040938 |
| | | Ku', 24 | 0.289342 | 0.197389 | 5.157763 | 12.36349 | 11.62427 | 4.196213 | 4.966663 | 0.011763 |
| | | Ku', 34 | 1.774776 | 1.873388 | 4.178614 | 3.197308 | 5.404556 | 8.463419 | 0.97858 | 0.18462 |
| | 0.1 Hz | Ku', 12 | 27.7186 | 15.73807 | 0.548982 | 1.817221 | 0.004557 | 0.145565 | 0.226446 | 0.400227 |
| | | Ku', 13 | 5.484532 | 13.45709 | 0.202106 | 1.170201 | 0.226396 | 0.29765 | 0.268192 | 0.019604 |
| | | Ku', 14 | 0.073755 | 3.307082 | 0.187378 | 3.436897 | 0.043763 | 0.218027 | 0.014309 | 0.000445 |
| | | Ku', 23 | 0.743861 | 0.267325 | 2.716188 | 0.002303 | 1.079103 | 2.56499 | 0.187968 | 1.98149 |
| | | Ku', 24 | 0.015799 | 2.832773 | 0.002941 | 2.782365 | 0.56787 | 0.362635 | 2.78473 | 0.166594 |
| | | Ku', 34 | 0.077149 | 3.294486 | 5.203477 | 1.328373 | 2.87456 | 8.378557 | 2.526714 | 0.040836 |
| | 0.15 Hz | Ku', 12 | 5.550642 | 1.422695 | 0.39986 | 0.008919 | 0.084693 | 0.083159 | 3.412122 | 2.617897 |
| | | Ku', 13 | 14.7217 | 3.561739 | 0.036975 | 0.003066 | 0.263841 | 0.195413 | 3.679334 | 2.157568 |
| | | Ku', 14 | 8.319345 | 0.871557 | 0.296907 | 0.0581 | 0.271186 | 0.202262 | 3.989885 | 1.888212 |
| | | Ku', 23 | 0.013122 | 4.1E-05 | 1.677152 | 0.618116 | 0.126272 | 0.373896 | 4.595471 | 0.122455 |
| | | Ku', 24 | 5.802838 | 0.989799 | 2.584062 | 6.400539 | 12.00776 | 8.262006 | 9.632026 | 0.060335 |
| | | Ku', 34 | 11.44353 | 2.105343 | 1.605982 | 2.175446 | 2.847958 | 2.399262 | 9.235079 | 0.003696 |
| | 0.2 Hz | Ku', 12 | 8.053725 | 1.140735 | 0.931109 | 0.316224 | 0.495852 | 0.606349 | 0.122238 | 0.267641 |
| | | Ku', 13 | 8.900897 | 2.209135 | 0.192082 | 0.000273 | 0.12004 | 0.203509 | 1.479441 | 0.321026 |
| | | Ku', 14 | 9.537133 | 2.015232 | 1.820842 | 0.933349 | 0.426249 | 0.127534 | 4.755819 | 1.548065 |
| | | Ku', 23 | 3.533297 | 7.599984 | 1.565894 | 0.3918 | 0.61794 | 0.651072 | 0.282767 | 0.346063 |
| | | Ku', 24 | 43.45806 | 33.34422 | 4.864709 | 0.539122 | 1.017482 | 0.441557 | 3.645225 | 5.426186 |
| | | Ku', 34 | 41.05738 | 20.96088 | 4.709726 | 1.86036 | 1.107999 | 0.410656 | 5.156142 | 3.84568 |
| | 0.25 Hz | Ku', 12 | 11.74035 | 9.549586 | 2.852609 | 3.149933 | 0.045873 | 0.54792 | 2.389375 | 2.080855 |
| | | Ku', 13 | 6.556549 | 0.467869 | 0.30527 | 4.150433 | 0.344338 | 0.038691 | 0.572413 | 2.028746 |
| | | Ku', 14 | 5.356429 | 0.284278 | 0.624578 | 1.428578 | 0.122613 | 0.093332 | 4.084828 | 3.330504 |
| | | Ku', 23 | 0.11287 | 4.159225 | 0.190984 | 0.928855 | 0.849363 | 0.122419 | 0.057246 | 0.844296 |
| | | Ku', 24 | 1.755603 | 0.128279 | 0.297769 | 1.02415 | 0.634029 | 0.076025 | 4.468115 | 0.011394 |
| | | Ku', 34 | 9.505734 | 2.994915 | 0.549703 | 0.068358 | 0.029631 | 0.165597 | 3.612367 | 0.186642 |
| | 0.3 Hz | Ku', 12 | 0.39955 | 0.047261 | 2.212664 | 0.175811 | 5.052706 | 2.964309 | 0.876074 | 0.022689 |
| | | Ku', 13 | 13.75383 | 18.96546 | 5.351231 | 1.129594 | 3.902872 | 8.409545 | 2.334651 | 0.119973 |
| | | Ku', 14 | 14.68174 | 22.64813 | 0.004057 | 1.120536 | 0.00249 | 0.103133 | 1.432881 | 8.05E-05 |
| | | Ku', 23 | 4.352049 | 10.58827 | 0.006618 | 0.010628 | 2.461461 | 0.000152 | 0.000164 | 0.171693 |
| | | Ku', 24 | 19.12507 | 37.58424 | 0.587616 | 1.222386 | 5.274414 | 0.363765 | 3.048307 | 0.010482 |
| | | Ku', 34 | 21.37798 | 30.42425 | 0.814255 | 3.041583 | 0.487249 | 0.704394 | 5.449856 | 0.077712 |
| | 0.35 Hz | Ku', 12 | 5.268058 | 0.518053 | 0.937859 | 0.570629 | 3.96193 | 0.598153 | 4.932599 | 5.415301 |
| | | Ku', 13 | 8.346566 | 1.715545 | 5.46849 | 2.039558 | 7.27368 | 6.125609 | 11.48969 | 5.142935 |
| | | Ku', 14 | 8.156588 | 1.347356 | 1.491865 | 0.579267 | 2.45193 | 3.514285 | 6.958076 | 3.322309 |
| | | Ku', 23 | 1.101289 | 0.087854 | 0.430833 | 0.022121 | 0.149613 | 1.842266 | 0.044621 | 0.626725 |
| | | Ku', 24 | 0.18486 | 1.598489 | 0.410052 | 0.110021 | 0.009233 | 3.687124 | 0.366337 | 0.002114 |
| | | Ku', 34 | 3.331563 | 1.845476 | 0.368346 | 0.385761 | 0.880026 | 3.806815 | 4.291113 | 0.058728 |
| | 0.4 Hz | Ku', 12 | 0.618739 | 2.683475 | 0.92635 | 0.176508 | 4.284622 | 1.033402 | 3.853721 | 0.166224 |
| | | Ku', 13 | 1.496587 | 5.765847 | 0.193659 | 3.442589 | 0.102043 | 0.02071 | 0.070621 | 0.612866 |
| | | Ku', 14 | 0.04373 | 0.583549 | 6.10325 | 10.67389 | 5.038614 | 10.82638 | 2.663111 | 0.452184 |
| | | Ku', 23 | 0.0524 | 0.005667 | 0.004131 | 2.138635 | 0.027891 | 0.017146 | 0.032291 | 0.510088 |
| | | Ku', 24 | 0.034246 | 0.66795 | 0.463169 | 2.848683 | 0.008079 | 0.974152 | 0.00315 | 0.144248 |
| | | Ku', 34 | 0.011703 | 0.382649 | 0.247044 | 0.053066 | 0.389945 | 0.046805 | 2.993776 | 0.201295 | 0.002376 |
| | 0.45 Hz | Ku', 12 | 9.304786 | 15.11571 | 4.034827 | 1.488533 | 0.200458 | 0.11055 | 0.273758 | 5.735983 |
| | | Ku', 13 | 4.27148 | 0.212448 | 0.084008 | 3.128773 | 0.037524 | 0.023356 | 0.018717 | 4.019477 |
| | | Ku', 14 | 3.155343 | 0.017885 | 0.320947 | 3.298518 | 0.047065 | 0.021232 | 0.036385 | 3.529526 |
| | | Ku', 23 | 2.707801 | 0.017338 | 0.014194 | 2.687072 | 0.048494 | 0.050585 | 0.001417 | 3.419087 |
| | | Ku', 24 | 2.775829 | 0.00174 | 4.6E-06 | 2.852988 | 0.051108 | 0.024652 | 0.009115 | 0.801502 |
| | | Ku', 34 | 3.251058 | 0.000639 | 1.552165 | 0.182768 | 0.040528 | 0.20317 | 0.052714 | 1.845222 |
| | 0.5 Hz | Ku', 12 | 2.622234 | 0.001628 | 9.268726 | 2.724629 | 10.47064 | 11.58432 | 5.783121 | 0.008716 |
| | | Ku', 13 | 3.527981 | 0.094863 | 0.465363 | 2.466541 | 0.038663 | 0.112495 | 2.978881 | 0.058782 |
| | | Ku', 14 | 3.498128 | 0.099785 | 2.903584 | 3.805264 | 0.237066 | 2.107141 | 5.655018 | 0.445111 |

TABLE 40-continued

3-Hexane-1

| | | | | | | | | |
|---|---|---|---|---|---|---|---|---|
| Ku', 23 | 3.79336 | 11.44796 | 10.46565 | 8.385721 | 7.395272 | 13.771 | 20.03973 | 1.486272 |
| Ku', 24 | 6.133384 | 14.10325 | 5.341388 | 2.046767 | 1.654112 | 8.889445 | 5.600156 | 7.474238 |
| Ku', 34 | 6.926021 | 5.329654 | 3.76437 | 0.812185 | 0.630107 | 5.860856 | 1.340001 | 0.332069 |

TABLE 41

3-Hexane-2

| Hexane | | | | AcOEt | | | | | THF |
|---|---|---|---|---|---|---|---|---|---|
| k2 | k3 | k4 | k5 | k1 | k2 | k3 | k4 | k5 | k1 |
| 0.045143 | 0.002625 | 2.180087 | 0.027528 | 0.760795 | 2.411526 | 0.327922 | 5.814254 | 1.825414 | 3.545767 |
| 0.2872 | 0.030316 | 1.403239 | 0.088967 | 4.719547 | 12.50708 | 11.22382 | 0.023186 | 16.78691 |
| 0.491015 | 0.075934 | 0.611616 | 0.176662 | 2.971344 | 4.004488 | 6.995744 | 12.68165 | 5.876104 | 5.73208 |
| 2.21297 | 0.271842 | 3.057401 | 0.116245 | 0.71465 | 1.79135 | 0.12487 | 1.785571 | 1.272405 | 345.275 |
| 1.168452 | 0.245891 | 3.001199 | 0.152958 | 0.091195 | 0.508225 | 1.047659 | 0.391358 | 0.1768 | 67.49316 |
| 0.102476 | 0.100616 | 2.263739 | 0.105699 | 1.867965 | 5.6108 | 1.630185 | 8.464353 | 5.564242 | 1.076367 |
| 0.497443 | 0.008324 | 0.014958 | 1.08049 | 40.6347 | 32.85838 | 33.58026 | 24.522828 | 37.49081 | 21.54685 |
| 0.007664 | 0.313342 | 0.004517 | 2.580636 | 50.34035 | 43.63153 | 48.10834 | 52.77215 | 71.57152 | 10.09035 |
| 0.386463 | 0.004074 | 1.132306 | 0.660242 | 114.8467 | 86.64877 | 90.71872 | 89.53723 | 114.7689 | 5.422909 |
| 1.342039 | 0.756131 | 0.163177 | 1.040675 | 83.66618 | 58.79949 | 75.20154 | 55.27297 | 65.46347 | 471.5524 |
| 0.02462 | 0.023025 | 1.989955 | 0.041302 | 0.138703 | 3.040106 | 0.025657 | 2.446953 | 0.56 | 27.87805 |
| 1.185835 | 0.718961 | 3.849639 | 0.096087 | 90.87657 | 69.92501 | 67.54263 | 59.94325 | 62.20974 | 9.474147 |
| 0.029135 | 0.032604 | 0.000487 | 0.1512919 | 3.550523 | 2.107141 | 7.512436 | 0.800342 | 1.610427 | 7.154309 |
| 0.020011 | 0.017379 | 0.001765 | 1.10745 | 10.9501 | 11.92617 | 25.19725 | 11.7527 | 13.50398 | 28.88863 |
| 0.005035 | 0.04464 | 0.02113 | 1.875953 | 11.41594 | 13.75838 | 26.11548 | 11.86377 | 14.08553 | 12.22408 |
| 0.548442 | 0.067379 | 0.00579 | 1.716337 | 3.396744 | 1.717569 | 3.341909 | 0.025112 | 0.794658 | 47.11459 |
| 1.092672 | 0.000379 | 0.165483 | 2.119532 | 0.005251 | 0.55524 | 0.019774 | 3.163848 | 1.77628 | 0.670446 |
| 2.884585 | 0.982001 | 2.232058 | 2.127776 | 228.5384 | 274.6998 | 254.322 | 218.7429 | 236.514 | 9.681585 |
| 0.159291 | 0.923342 | 0.177937 | 0.825164 | 35.50105 | 31.11135 | 31.9484 | 38.12792 | 18.95173 | 1.783706 |
| 0.02392 | 0.374292 | 1.060349 | 0.243102 | 13.0662 | 8.85453 | 18.20593 | 20.26135 | 22.02469 | 11.18206 |
| 0.000895 | 0.133161 | 0.720981 | 0.043916 | 2.714822 | 1.171039 | 4.292493 | 4.070622 | 9.099456 | 17.95856 |
| 0.437075 | 0.449776 | 4.822085 | 2.261175 | 0.205892 | 0.49703 | 0.006268 | 0.000174 | 1.291013 | 6.711066 |
| 0.457709 | 0.615 | 2.547875 | 3.439828 | 0.388894 | 0.075471 | 0.966475 | 0.704645 | 4.603475 | 0.602309 |
| 0.093913 | 0.163118 | 0.085554 | 0.705791 | 2.878093 | 1.159321 | 3.854819 | 3.074584 | 9.122862 | 43.56138 |
| 2.480452 | 0.676102 | 0.017287 | 0.00429 | 57.12409 | 41.44198 | 30.96977 | 42.61099 | 41.65702 | 1.186541 |
| 2.060774 | 0.466053 | 0.000117 | 0.001965 | 0.210956 | 4.355059 | 0.234225 | 0.294466 | 0.297982 | 7.625556 |
| 0.641667 | 0.599161 | 0.000444 | 0.03604 | 2.335479 | 10.12734 | 2.728127 | 2.378426 | 2.972312 | 5.145438 |
| 2.231495 | 2.858637 | 5.278274 | 0.216676 | 0.18113 | 1.61427 | 0.059781 | 0.075391 | 0.070171 | 22.71289 |
| 1.99795 | 0.182502 | 0.294032 | 0.232422 | 0.041684 | 4.022938 | 0.591644 | 0.169326 | 0.362016 | 1.779398 |
| 1.322666 | 0.006922 | 0.029612 | 0.463677 | 3.306182 | 0.037492 | 3.676693 | 2.010745 | 2.959003 | 8.19458 |
| 1.133151 | 1.33116 | 0.031304 | 0.141446 | 5.665147 | 6.479845 | 1.788648 | 0.780472 | 4.190003 | 0.711555 |
| 1.095432 | 1.455685 | 0.306864 | 0.048209 | 6.860905 | 16.35531 | 8.327074 | 5.359264 | 12.71019 | 5.316977 |
| 1.235516 | 0.879264 | 0.35903 | 0.30211 | 0.918741 | 7.110093 | 7.104431 | 3.420065 | 3.687479 | 2.872204 |
| 0.540714 | 0.009549 | 0.403482 | 0.87731 | 0.272485 | 0.11072 | 1.063876 | 1.714247 | 0.324656 | 1.485996 |
| 0.073749 | 2.313204 | 0.031716 | 0.144228 | 0.010282 | 1.20749 | 3.709715 | 2.597691 | 0.730201 | 0.082429 |
| 0.003397 | 2.462037 | 4.15E-06 | 0.040156 | 0.163461 | 2.529215 | 5.226921 | 2.877441 | 1.174988 | 3.029079 |
| 1.298474 | 4.450889 | 5.366015 | 0.690947 | 0.509654 | 6.381178 | 1.27979 | 1.036213 | 1.182147 | 10.26675 |
| 0.749738 | 2.930616 | 4.45809 | 0.529547 | 6.650844 | 18.65305 | 7.144466 | 10.73151 | 8.392164 | 27.11205 |
| 0.256277 | 1.002279 | 4.543487 | 0.518693 | 6.292744 | 13.04264 | 3.198169 | 8.188677 | 4.433399 | 9.844427 |
| 1.001739 | 0.39929 | 0.057163 | 0.004411 | 0.062282 | 2.457513 | 0.870485 | 0.01477 | 0.417887 | 15.73609 |
| 0.984903 | 0.94297 | 0.250565 | 0.078163 | 2.019461 | 0.059502 | 0.014373 | 0.754406 | 0.027656 | 0.007525 |
| 0.955545 | 1.030144 | 0.25508 | 0.140049 | 7.159184 | 3.587481 | 0.799392 | 4.431266 | 1.527358 | 2.462621 |
| 0.157193 | 0.384562 | 4.20044 | 0.250317 | 5.903121 | 2.044675 | 1.131133 | 7.221473 | 2.043386 | 1.49747 |
| 0.635652 | 5.966722 | 2.425483 | 0.942469 | 14.91269 | 8.95461 | 9.998697 | 21.80323 | 9.704953 | 3.119199 |
| 1.570642 | 2.426272 | 1.873052 | 6.816554 | 12.50224 | 9.692733 | 18.2329 | 24.17055 | 18.48089 | 1.409703 |
| 0.442332 | 0.071555 | 2.994087 | 0.565267 | 1.088843 | 0.109069 | 0.553772 | 0.717384 | 0.04761 | 17.00474 |
| 0.022275 | 0.007623 | 0.988271 | 0.866623 | 0.028597 | 0.472948 | 3.751618 | 0.215713 | 1.676311 | 0.000271 |
| 0.355083 | 0.031334 | 2.518743 | 0.007009 | 1.995249 | 3.238197 | 8.476068 | 3.822601 | 9.055678 | 0.753992 |
| 0.547436 | 2.801794 | 3.727745 | 0.721747 | 0.762616 | 3.400388 | 0.609001 | 4.725321 | 0.351907 | 87.21576 |
| 0.095971 | 0.625885 | 0.816367 | 0.05862 | 0.30616 | 1.22736 | 0.290214 | 4.5064 | 0.182728 | 7.127043 |
| 0.174539 | 0.151299 | 0.232837 | 0.00445 | 0.943743 | 6.092207 | 1.00601 | 0.87547 | 0.51525 | 3.93168 |
| 0.127135 | 0.428429 | 0.161509 | 4.31E-05 | 0.00893 | 0.003307 | 0.12352 | 2.980368 | 0.229241 | 3.822904 |
| 0.056142 | 0.294738 | 0.283833 | 0.684815 | 0.473054 | 1.317818 | 1.006619 | 0.374561 | 0.716351 | 0.011318 |
| 0.173606 | 4.499145 | 3.552825 | 4.167624 | 0.297758 | 1.110958 | 0.424985 | 0.670941 | 0.211949 | 3.01353 |
| 1.345322 | 0.186724 | 0.027999 | 0.438876 | 1.226509 | 0.239861 | 0.358401 | 1.315246 | 0.177088 | 0.001007 |
| 2.784453 | 0.002041 | 0.03967 | 0.004006 | 0.211625 | 3.679966 | 0.000485 | 0.410282 | 0.424517 | 0.319765 |
| 2.305258 | 0.002278 | 0.055383 | 0.107917 | 2.364231 | 3.056662 | 0.019965 | 3.298474 | 2.958535 | 1.96154 |
| 6.890974 | 1.024371 | 1.460901 | 0.757942 | 0.064629 | 3.794329 | 0.106505 | 0.142333 | 0.441846 | 0.090326 |
| 1.333346 | 4.636773 | 1.985054 | 1.239295 | 2.899952 | 8.774988 | 2.479356 | 4.028179 | 9.450306 | 0.925322 |
| 5.360956 | 0.388991 | 1.915295 | 1.345213 | 1.655846 | 0.308308 | 0.56685 | 0.939529 | 0.675014 | 0.529189 |

TABLE 41-continued

| 3-Hexane-2 |||||||||
| --- | --- | --- | --- | --- | --- | --- | --- | --- |
| THF |||| $\theta_{u,mn}$ Hexane | H$_2$O ||||
| k2 | k3 | k4 | k5 | k6 | k1 | k2 | k3 | k4 |
| 11.47567 | 8.981711 | 3.68575 | 3.921633 | 1.54211 | 13.25978 | 6.84367 | 20.51423 | 9.798919 |
| 20.63578 | 9.31814 | 17.24025 | 8.837978 | 1.231079 | 44.98442 | 37.8712 | 56.88948 | 38.84807 |
| 2.39042 | 2.171048 | 8.953644 | 1.900778 | 1.121013 | 43.03404 | 29.15623 | 46.98595 | 31.99684 |
| 393.5066 | 405.835 | 346.311 | 375.0292 | −0.31103 | 0.303812 | 0.243201 | 1.483819 | 0.026515 |
| 77.42056 | 76.17457 | 51.99031 | 69.77775 | −0.4211 | 1.055384 | 0.092507 | 4.419152 | 0.780793 |
| 0.025649 | 0.247247 | 2.924265 | 0.166912 | −0.11007 0 | 3.72758 | 11.67705 | 12.67031 | 8.774657 |
| 24.33526 | 12.47391 | 29.09426 | 25.10196 | 1.236316 | 145.9024 | 159.1714 | 140.16 | 182.949 |
| 10.45071 | 12.16942 | 21.23635 | 20.56152 | 1.050778 | 23.12157 | 22.21926 | 20.80632 | 22.85067 |
| 3.064781 | 6.164136 | 11.52258 | 11.30164 | 6.7828 | 16.7828 | 14.07818 | 14.29689 | 14.35643 |
| 480.6551 | 404.7251 | 455.8401 | 443.2353 | −0.18554 | 0.328438 | 0.721868 | 0.469143 | 1.284099 |
| 36.04561 | 17.80091 | 22.36526 | 20.29781 | −0.40897 | 1.168303 | 2.380061 | 1.545769 | 3.37619 |
| 3.510864 | 9.443607 | 13.14609 | 13.23705 | −0.22343 0 | 18.41386 | 30.81725 | 19.9997 | 32.78337 |
| 6.859524 | 11.28039 | 2.112128 | 4.53988 | 0.283539 | 0.647851 | 0.416027 | 1.168471 | 1.85387 |
| 27.31805 | 40.03957 | 19.17483 | 32.00787 | −0.12383 | 2.493773 | 0.22835 | 0.747034 | 4.922317 |
| 14.38018 | 25.52065 | 14.28646 | 23.62503 | −0.28491 | 3.407139 | 0.451022 | 0.525767 | 5.261453 |
| 47.2548 | 50.18032 | 29.44706 | 36.04147 | −0.40737 | 0.064965 | 0.205881 | 0.547554 | 0.329986 |
| 0.413024 | 0.334763 | 0.584952 | 0.153095 | −0.56845 | 0.203878 | 0.269328 | 0.898038 | 0.855721 |
| 13.61452 | 19.22754 | 21.46856 | 23.05262 | −0.16108 0 | 1.133203 | 0.036254 | 0.837179 | 3.402857 |
| 3.24857 | 7.728134 | 3.30405 | 0.767313 | 0.412911 | 0.470666 | 0.398256 | 1.481808 | 0.688526 |
| 15.49998 | 16.98642 | 17.94014 | 7.033226 | −0.08648 | 1.631789 | 0.073634 | 0.153696 | 0.096933 |
| 28.97192 | 29.61002 | 23.02517 | 14.62159 | −0.35914 | 2.108885 | 0.008407 | 0.056527 | 0.006948 |
| 9.245384 | 14.84164 | 8.402942 | 3.636512 | −0.49939 | 2.02884 | 0.274381 | 0.045679 | 0.010344 |
| 0.417966 | 0.090255 | 0.111012 | 2.697783 | −0.77205 | 2.503935 | 0.130864 | 0.111089 | 0.084661 |
| 60.94002 | 49.16816 | 35.61854 | 54.67237 | −0.27266 0 | 14.32824 | 8.918778 | 6.11988 | 14.5139 |
| 1.107889 | 2.520529 | 7.308631 | 1.169517 | 1.11004 | 10.12046 | 12.42827 | 14.02126 | 10.6712 |
| 5.575783 | 11.3539 | 17.68643 | 8.329096 | 0.6474 | 1.298867 | 1.076694 | 4.250508 | 1.428908 |
| 1.355747 | 3.37205 | 8.681882 | 2.024251 | 0.534389 | 1.580024 | 1.223269 | 4.851128 | 1.691924 |
| 26.08504 | 29.78319 | 40.70337 | 21.13431 | −0.46264 | 0.191179 | 0.413954 | 4.71E−05 | 0.18652 |
| 0.091618 | 0.051415 | 0.125 | 0.002252 | −0.57564 | 0.235116 | 0.537855 | 0.005891 | 0.241153 |
| 1.68005 | 2.738942 | 6.262475 | 1.848819 | −0.11301 0 | 0.017418 | 0.180688 | 0.647924 | 0.073565 |
| 0.7265 | 0.170961 | 0.325672 | 4.8189 | 0.714806 | 23.22257 | 36.67123 | 27.91535 | 21.48564 |
| 4.021663 | 5.01804 | 0.942467 | 8.46383 | 0.031085 | 1.037984 | 0.000338 | 1.038055 | 2.745922 |
| 2.898156 | 4.400612 | 0.264508 | 5.582294 | 0.14742 | 0.905304 | 0.055194 | 1.403573 | 3.034515 |
| 1.873325 | 0.02217 | 2.042933 | 4.454333 | −0.68372 | 0.050812 | 2.125105 | 0.11285 | 0.156469 |
| 0.079351 | 2.187821 | 0.068003 | 0.05915 | −0.56735 | 0.092741 | 1.855156 | 0.040294 | 0.235143 |
| 4.050097 | 5.89281 | 0.390732 | 4.93288 | 0.116374 0 | 0.127636 | 1.53568 | 0.813389 | 0.13669 |
| 14.68326 | 11.76452 | 17.66788 | 5.463851 | 1.447533 | 43.98376 | 43.81252 | 39.88294 | 46.75162 |
| 38.16824 | 32.24419 | 47.79553 | 27.93599 | 1.324115 | 24.58292 | 12.05208 | 9.370143 | 14.45107 |
| 19.8875 | 8.046414 | 7.045545 | 10.89004 | 1.062342 | 16.63984 | 6.297431 | 4.991512 | 7.843501 |
| 16.07214 | 15.17227 | 15.46495 | 5.629032 | −0.12342 | 3.804834 | 0.250997 | 0.053862 | 0.442146 |
| 0.121153 | 0.198023 | 0.823668 | 0.855175 | −0.38519 | 2.913969 | 0.02756 | 5.51E−07 | 0.10643 |
| 4.981109 | 1.017698 | 0.142381 | 2.853014 | −0.26177 0 | 0.486644 | 1.08713 | 0.679932 | 0.826089 |
| 1.43648 | 0.871059 | 7.443531 | 2.08565 | 1.027637 | 8.289501 | 3.843884 | 7.886887 | 9.837331 |
| 5.780104 | 3.218206 | 12.31159 | 5.223116 | 0.576817 | 2.726069 | 6.149041 | 0.32545 | 2.353621 |
| 8.433865 | 1.880384 | 1.627238 | 2.867811 | 0.160421 | 1.7305 | 2.609102 | 0.024593 | 0.763899 |
| 8.901903 | 9.489288 | 21.59697 | 15.13723 | −0.44882 | 0.105309 | 0.633638 | 1.21222 | 0.307219 |
| 1.921443 | 0.206775 | 0.276633 | 0.032935 | −0.86722 | 0.245354 | 0.081543 | 2.746342 | 0.995008 |
| 4.682268 | 1.159489 | 0.039657 | 1.131883 | −0.4184 0 | 0.570579 | 5.948388 | 6.047433 | 3.851264 |
| 121.2961 | 101.3836 | 93.52173 | 86.38374 | −1.23411 | 13.81706 | 6.166629 | 9.238505 | 9.029658 |
| 5.285872 | 8.645461 | 1.984112 | 10.49252 | −1.09386 | 0.178882 | 0.200953 | 0.075627 | 3.562258 |
| 1.562988 | 3.533521 | 0.334402 | 5.669011 | −0.76102 | 0.041853 | 0.002262 | 0.024711 | 2.451923 |
| 7.047758 | 3.621923 | 10.28449 | 1.956792 | 0.140252 | 0.294045 | 0.038551 | 0.268803 | 1.338789 |
| 0.616097 | 0.015376 | 1.598277 | 0.249926 | 0.473029 | 0.660728 | 0.402932 | 0.997392 | 0.615537 |
| 0.525889 | 1.501363 | 0.004692 | 2.947741 | 0.332777 0 | 2.344129 | 7.331909 | 8.155022 | 7.008895 |
| 2.651707 | 0.005056 | 0.003861 | 0.000698 | 2.433528 | 35.13746 | 43.83024 | 27.68677 | 33.7705 |
| 1.415984 | 1.495888 | 0.612539 | 5.734826 | −2.85622 | 30.32324 | 20.6777 | 16.29556 | 33.15407 |
| 10.08168 | 2.916816 | 8.772348 | 4.509289 | 1.766493 | 10.65084 | 22.45238 | 22.02849 | 11.17433 |
| 0.088122 | 0.179038 | 0.066223 | 2.902578 | 0.992438 | 0.02771 | 0.272424 | 2.588983 | 0.001564 |
| 0.042121 | 0.449447 | 1.571587 | 2.806441 | −0.66704 | 3.973471 | 2.050146 | 0.215401 | 3.422647 |
| 0.942081 | 0.000811 | 1.869901 | 0.138981 | −1.66047 | 23.93055 | 22.70065 | 35.2376 | 17.4966 |

TABLE 42

3-Hexane-3
$(\theta_{u,mn}-\theta_{g,mnk})^2/\sigma_{\theta g,mn}^2$

| | EtOH | | | | | Benzene | | | |
|---|---|---|---|---|---|---|---|---|---|
| k5 | k1 | k2 | k3 | k4 | k5 | k1 | k2 | k3 | k4 |
| 12.62072 | 1.25798 | 3.80285 | 0.886603 | 0.494152 | 0.902024 | 15.85839 | 8.205711 | 16.31517 | 14.43996 |
| 32.16485 | 2.763566 | 7.0627 | 1.582363 | 0.602914 | 1.604229 | 12.62953 | 5.584167 | 12.16569 | 7.807975 |
| 28.10534 | 2.512444 | 5.41763 | 1.595522 | 0.369967 | 1.424463 | 25.80486 | 10.159 | 13.94433 | 15.95922 |
| 1.250908 | 0.185389 | 5.048169 | 0.54976 | 1.00481 | 0.588568 | 11.671 | 8.226512 | 13.7421 | 20.50069 |
| 2.877317 | 0.126797 | 4.294432 | 0.238669 | 1.719727 | 0.520742 | 1.225597 | 1.12281 | 3.697422 | 2.383032 |
| 5.222246 | 0.037772 | 0.092794 | 0.559065 | 1.312839 | 0.000242 | 0.027194 | 0.000704 | 0.541165 | 0.016946 |
| 141.1786 | 33.43298 | 33.25797 | 36.64431 | 16.13165 | 28.97489 | 0.475672 | 0.397561 | 0.390724 | 0.534093 |
| 39.47071 | 23.7576 | 29.46819 | 11.95776 | 11.9255 | 11.40446 | 3.371562 | 3.528587 | 2.540716 | 2.450086 |
| 20.20744 | 12.8019 | 10.03921 | 3.951079 | 4.963063 | 4.590881 | 1.008337 | 0.979344 | 0.861226 | 0.564936 |
| 0.488628 | 0.597957 | 1.175055 | 5.452567 | 0.48405 | 3.226249 | 0.1344 | 4.278473 | 0.140287 | 0.383625 |
| 0.000269 | 0.249406 | 0.783241 | 4.941347 | 0.579828 | 2.604727 | 0.104543 | 3.322156 | 0.075989 | 0.407837 |
| 24.8307 | 0.070543 | 0.062445 | 2.570163 | 0.658121 | 0.628613 | 0.00034 | 0.010262 | 0.01151 | 0.059642 |
| 5.912158 | 9.1873 | 17.06225 | 9.313711 | 12.36567 | 21.68771 | 0.242479 | 2.38368 | 2.174536 | 1.089412 |
| 0.590714 | 0.041515 | 1.688006 | 0.631578 | 1.101413 | 2.785379 | 0.001675 | 2.918561 | 2.513016 | 1.588004 |
| 1.530244 | 0.536097 | 1.040191 | 0.716513 | 0.826435 | 0.336913 | 0.120581 | 16.0231 | 4.712457 | 6.85232 |
| 4.147484 | 20.04693 | 10.31348 | 7.158207 | 8.053404 | 10.53981 | 0.334163 | 1.878184 | 1.761999 | 0.82269 |
| 4.676536 | 4.459428 | 0.425153 | 0.143805 | 0.409405 | 1.359272 | 0.002125 | 0.720974 | 1.276258 | 0.354464 |
| 0.015233 | 0.940347 | 0.268834 | 0.439257 | 0.135846 | 0.218266 | 4.664446 | 3.165898 | 0.108812 | 1.051976 |
| 0.678759 | 35.87603 | 24.53853 | 48.02766 | 32.85846 | 33.7987 | 8.56881 | 2.167195 | 2.502198 | 1.329184 |
| 0.045511 | 3.260674 | 1.926411 | 4.739131 | 0.465968 | 6.216557 | 4.153517 | 0.018035 | 0.578506 | 1.4242 |
| 0.00552 | 0.711815 | 0.259039 | 2.552496 | 0.092811 | 1.14541 | 2.074589 | 0.011234 | 1.848174 | 1.121953 |
| 0.035064 | 12.0401 | 8.856845 | 15.41611 | 19.14179 | 6.845835 | 8.335111 | 3.361786 | 3.023126 | 0.914339 |
| 0.09103 | 10.57474 | 8.59256 | 8.798666 | 20.58396 | 8.012153 | 7.730384 | 3.23042 | 1.739836 | 0.617415 |
| 5.332384 | 0.419615 | 0.609603 | 0.154634 | 2.26857 | 1.179385 | 0.209948 | 0.178423 | 1.446463 | 0.006718 |
| 3.717247 | 31.01036 | 32.31014 | 48.51647 | 44.33133 | 29.12398 | 1.358837 | 0.275922 | 2.485936 | 2.176587 |
| 7.005092 | 40.57445 | 52.92374 | 50.7705 | 52.28955 | 37.82399 | 1.031907 | 1.110521 | 1.335856 | 5.131106 |
| 7.398588 | 7.41369 | 12.54256 | 13.30112 | 18.4015 | 6.636653 | 6.632452 | 6.874948 | 14.34945 | 8.72927 |
| 1.241155 | 9.333598 | 5.58951 | 18.02335 | 10.51922 | 7.923539 | 0.999063 | 0.012316 | 2.17914 | 0.500175 |
| 1.090104 | 9.548931 | 3.65809 | 12.05505 | 4.040745 | 9.588391 | 0.13775 | 0.295071 | 0.125234 | 0.381853 |
| 3.557616 | 0.085516 | 0.198095 | 0.573959 | 1.664587 | 0.142484 | 1.538224 | 1.540251 | 4.833217 | 0.042722 |
| 38.39437 | 15.11711 | 10.66592 | 14.78811 | 5.024492 | 14.92063 | 2.655679 | 10.38 | 3.760251 | 3.186413 |
| 3.073815 | 3.05179 | 1.138868 | 1.517303 | 0.024028 | 0.529445 | 0.390281 | 4.614457 | 0.196205 | 0.397277 |
| 4.191765 | 4.017833 | 1.899936 | 2.477559 | 0.378823 | 0.070932 | 1.339117 | 6.143941 | 2.663845 | 7.400065 |
| 0.012324 | 11.41054 | 13.15776 | 18.11243 | 16.60082 | 27.13978 | 3.35502 | 8.103416 | 5.925283 | 4.222742 |
| 0.147153 | 0.061524 | 0.402196 | 0.466567 | 0.521604 | 4.389429 | 0.19201 | 0.521135 | 0.107911 | 0.281967 |
| 1.932995 | 2.168015 | 1.058549 | 1.686854 | 1.312245 | 0.090157 | 0.770151 | 1.695209 | 2.403406 | 7.093516 |
| 66.05688 | 64.19192 | 54.13872 | 49.39758 | 40.71899 | 55.16103 | 30.50803 | 13.15089 | 25.31784 | 22.24478 |
| 15.34144 | 23.20437 | 26.64889 | 32.7709 | 15.12413 | 29.24906 | 28.47949 | 13.34289 | 24.74599 | 22.536 |
| 8.855361 | 4.956432 | 5.760432 | 8.573688 | 1.005067 | 5.066912 | 3.123565 | 2.55163 | 4.025775 | 9.215215 |
| 0.07645 | 0.760091 | 0.176259 | 0.434522 | 1.321768 | 0.642459 | 0.519889 | 0.062352 | 0.23739 | 0.108959 |
| 0.009982 | 0.322048 | 0.014091 | 0.367261 | 1.753941 | 0.316751 | 0.274243 | 0.001239 | 0.035238 | 1.267595 |
| 0.289704 | 0.127529 | 0.004684 | 0.297262 | 1.868186 | 0.153818 | 0.621525 | 0.018558 | 0.002105 | 2.226418 |
| 15.44343 | 0.540384 | 0.954772 | 0.872446 | 0.565459 | 0.649307 | 0.395844 | 0.674067 | 1.077364 | 0.362168 |
| 4.005696 | 0.160793 | 0.217459 | 0.293728 | 1.228612 | 0.216956 | 0.022188 | 1.533636 | 0.168972 | 0.255577 |
| 1.989428 | 0.322833 | 0.135411 | 0.25369 | 1.258673 | 0.116202 | 0.003946 | 1.757431 | 0.249311 | 0.0002 |
| 0.403184 | 16.07854 | 18.52947 | 21.54321 | 31.96394 | 16.23141 | 3.202535 | 2.164695 | 5.520442 | 0.201375 |
| 0.98537 | 0.167359 | 3.044621 | 2.61587 | 5.291358 | 0.482367 | 3.913589 | 0.37276 | 5.09517 | 4.263584 |
| 2.50306 | 1.287175 | 6.187077 | 0.002294 | 0.203671 | 0.350017 | 0.075773 | 0.361233 | 0.007134 | 1.813167 |
| 3.313063 | 0.202328 | 0.25504 | 0.105833 | 0.810443 | 1.009913 | 1.723732 | 0.37815 | 0.540432 | 0.299983 |
| 0.026781 | 0.240639 | 0.393196 | 0.169397 | 1.094493 | 0.331151 | 14.56996 | 4.515393 | 4.948693 | 5.245119 |
| 0.001951 | 0.034723 | 0.169543 | 0.11932 | 2.851523 | 0.024761 | 0.7891 | 1.011961 | 0.022625 | 0.009632 |
| 0.096343 | 0.094766 | 0.335807 | 0.128826 | 0.661773 | 0.823944 | 0.13033 | 2.042463 | 0.30264 | 0.005543 |
| 0.2998 | 0.056573 | 0.017711 | 0.100209 | 3.438901 | 0.46894 | 1.860976 | 4.068034 | 5.410503 | 7.04771 |
| 1.912364 | 0.170082 | 0.144473 | 0.281171 | 4.145032 | 0.28034 | 0.001593 | 3.468559 | 0.224459 | 0.526533 |
| 22.57592 | 90.2558 | 99.77483 | 125.944 | 113.9052 | 119.6842 | 15.69238 | 24.87397 | 13.7439 | 18.41316 |
| 22.40763 | 64.0033 | 66.13328 | 49.70056 | 80.18253 | 57.28385 | 12.42592 | 2.71584 | 7.90253 | 6.177385 |
| 16.04283 | 4.176726 | 4.284548 | 9.572216 | 13.64331 | 6.363213 | 0.19126 | 4.623331 | 0.834964 | 1.117552 |
| 1.834811 | 11.53347 | 8.304916 | 9.032119 | 2.314594 | 7.316178 | 0.076213 | 2.399628 | 1.168702 | 0.952036 |
| 0.346053 | 0.432567 | 0.617879 | 0.001023 | 0.858296 | 0.309804 | 1.155184 | 0.638034 | 0.107042 | 0.143912 |
| 30.26357 | 2.291642 | 2.105615 | 0.794174 | 0.045337 | 1.511981 | 1.50091 | 0.048894 | 1.017423 | 1.047841 |

| | Benzene | | Hexane | | | | AcOEt | | |
|---|---|---|---|---|---|---|---|---|---|
| | k5 | k1 | k2 | k3 | k4 | k5 | k1 | k2 | k3 |
| | 8.24301 | 0.2499 | 0.189163 | 0.038708 | 2.98534 | 0.000817 | 4.366259 | 5.402981 | 0.632274 |
| | 3.70296 | 0.031389 | 0.491591 | 0.075793 | 1.401102 | 0.000828 | 2.169614 | 2.123456 | 0.004013 |
| | 18.98827 | 0.033187 | 0.414896 | 0.041248 | 1.515379 | 0.001637 | 6.842907 | 1.503805 | 0.019549 |
| | 7.79909 | 0.847145 | 0.121347 | 0.34266 | 2.905912 | 0.039826 | 5.745794 | 10.58422 | 8.31473 |
| | 0.001191 | 0.317832 | 0.368092 | 0.735557 | 1.981506 | 0.283203 | 6.456221 | 5.048206 | 5.523529 |
| | 1.532879 | 0.003848 | 0.554519 | 0.874635 | 0.35402 | 0.619522 | 1.12426 | 0.014224 | 0.496006 |
| | 1.658267 | 0.250437 | 0.349175 | 0.824701 | 0.806199 | 0.175011 | 98.31825 | 104.7194 | 84.34807 |
| | 10.68177 | 0.016118 | 0.323564 | 1.540921 | 2.619359 | 1.838862 | 172.4981 | 227.3315 | 196.383 |

TABLE 42-continued

3-Hexane-3
$(\theta_{u,mn}-\theta_{g,mnk})^2/\sigma_{\theta g,mn}^2$

| | | | | | | | | |
|---|---|---|---|---|---|---|---|---|
| 6.167622 | 0.256443 | 0.180683 | 0.74823 | 1.163457 | 1.613997 | 91.91758 | 129.9197 | 117.0281 |
| 0.620451 | 0.593059 | 5.009835 | 0.218291 | 2.027936 | 2.767353 | 13.19437 | 8.975901 | 6.004874 |
| 0.000975 | 0.001944 | 7.141584 | 7.73E−09 | 0.249335 | 1.668571 | 10.90549 | 8.795453 | 4.104493 |
| 2.222934 | 2.034494 | 0.08887 | 0.637815 | 1.484959 | 0.091241 | 1.907767 | 0.326838 | 0.002292 |
| 0.019162 | 0.793409 | 1.067818 | 0.43382 | 0.489304 | 0.686232 | 4.571945 | 6.313883 | 11.51129 |
| 0.711186 | 1.272344 | 1.06705 | 0.518268 | 0.387891 | 0.616112 | 0.185647 | 1.150435 | 0.541331 |
| 7.093119 | 0.856147 | 1.280718 | 0.385051 | 0.445913 | 0.512612 | 0.009619 | 0.254532 | 1.027732 |
| 0.128302 | 3.120624 | 0.064021 | 0.315943 | 0.124286 | 0.006163 | 1.376158 | 1.261802 | 6.026412 |
| 2.421744 | 0.516888 | 1.92511 | 0.088726 | 0.144649 | 2.32E−07 | 0.922295 | 0.544223 | 4.264523 |
| 2.151242 | 0.246857 | 1.31623 | 0.021942 | 0.412572 | 0.003662 | 0.218057 | 0.000839 | 1.259228 |
| 1.941034 | 0.528004 | 0.125257 | 0.849366 | 0.356791 | 0.168445 | 11.59895 | 23.43897 | 12.14355 |
| 0.505092 | 0.423664 | 0.129162 | 0.890065 | 0.35794 | 0.263431 | 0.839439 | 6.112217 | 3.1537 |
| 0.191999 | 0.38778 | 0.191541 | 1.024991 | 0.300472 | 0.201113 | 0.190968 | 0.457193 | 0.242524 |
| 2.184354 | 0.802623 | 0.033763 | 0.345962 | 0.035475 | 2.752126 | 23.60954 | 34.07089 | 17.68033 |
| 2.142154 | 0.745481 | 2.456512 | 1.957052 | 1.978587 | 0.390818 | 20.34459 | 23.78713 | 12.27569 |
| 0.161739 | 0.380103 | 0.408195 | 0.064062 | 0.671889 | 0.865326 | 3.021946 | 1.5465 | 0.775609 |
| 8.118317 | 0.502888 | 0.088186 | 0.158166 | 2.778276 | 0.283472 | 5.718832 | 0.544286 | 5.194348 |
| 5.999155 | 0.141044 | 0.21127 | 0.392233 | 2.316442 | 0.346838 | 1.849491 | 0.005876 | 2.159012 |
| 17.08281 | 0.104018 | 0.070266 | 0.464587 | 2.717486 | 0.791759 | 0.16303 | 1.066421 | 0.25736 |
| 3.816706 | 1.260111 | 0.250374 | 0.496351 | 0.345188 | 0.02012 | 16.03835 | 7.6325 | 10.77193 |
| 2.058797 | 9.76111 | 0.002213 | 0.542477 | 0.016566 | 0.865989 | 0.41295 | 3.829831 | 0.21351 |
| 1.17871 | 0.022162 | 0.717996 | 0.239877 | 1.320109 | 3.021675 | 0.00017 | 2.205558 | 0.002733 |
| 8.143724 | 0.344486 | 0.05729 | 0.00354 | 0.139149 | 1.52104 | 11.08019 | 4.753025 | 16.72107 |
| 0.373722 | 0.885659 | 0.001087 | 0.184892 | 0.059031 | 0.956162 | 4.198686 | 0.332193 | 0.454034 |
| 1.649524 | 0.535998 | 0.040435 | 0.093128 | 0.070585 | 1.343121 | 7.404937 | 2.991948 | 1.902156 |
| 13.0812 | 1.544215 | 0.376942 | 2.17816 | 0.116191 | 0.339175 | 2.324742 | 2.457422 | 10.5183 |
| 1.783758 | 0.099177 | 0.003479 | 0.442277 | 1.452405 | 0.004599 | 0.001988 | 0.004672 | 2.488096 |
| 1.086079 | 1.098498 | 0.548249 | 0.329746 | 5.245626 | 0.455652 | 8.40426 | 6.465107 | 3.058657 |
| 25.01608 | 0.412058 | 0.421012 | 0.076541 | 4.25111 | 0.250875 | 62.92845 | 37.87133 | 55.10501 |
| 15.61109 | 0.498492 | 0.625492 | 0.063078 | 4.423042 | 0.375988 | 51.59835 | 60.56598 | 72.73831 |
| 2.277057 | 0.544589 | 0.423587 | 0.020158 | 4.170198 | 0.476738 | 1.597948 | 8.799819 | 7.122473 |
| 3.905308 | 0.136991 | 1.274083 | 0.129459 | 0.176595 | 0.805341 | 3.583365 | 0.01265 | 0.443467 |
| 0.538238 | 0.261215 | 0.000829 | 0.6208 | 0.057768 | 1.111021 | 2.739336 | 0.055134 | 0.170849 |
| 0.023216 | 0.158214 | 0.797694 | 0.595706 | 3.27E−06 | 0.517563 | 2.115352 | 0.223956 | 0.0512 |
| 0.208789 | 1.470907 | 0.398593 | 0.506292 | 0.693082 | 0.650582 | 13.4856 | 10.91011 | 9.317112 |
| 0.019832 | 0.338687 | 0.213525 | 0.435848 | 0.09641 | 1.040416 | 9.491645 | 4.210719 | 3.940332 |
| 0.028897 | 0.070193 | 0.121331 | 1.74482 | 0.051419 | 0.92963 | 1.067767 | 0.027052 | 3.824093 |
| 1.392956 | 0.001697 | 0.046065 | 1.399344 | 0.005001 | 0.628305 | 8.972537 | 15.28337 | 11.98869 |
| 1.255299 | 0.125529 | 0.000162 | 2.532288 | 0.040456 | 1.701051 | 0.865349 | 2.075834 | 0.008611 |
| 0.00097 | 0.21897 | 0.047552 | 0.385241 | 0.023916 | 1.349977 | 0.112109 | 0.484389 | 0.89766 |
| 0.511101 | 1.899547 | 2.224345 | 6.570315 | 7.845914 | 1.803767 | 1.433277 | 7.613289 | 0.995886 |
| 8.303264 | 0.687478 | 0.25485 | 0.514401 | 0.76699 | 0.580266 | 0.196223 | 1.060915 | 0.128683 |
| 0.197155 | 0.637834 | 0.01233 | 0.634497 | 0.383939 | 4.13004 | 0.014987 | 0.021626 | 0.044518 |
| 0.003848 | 0.049261 | 0.054489 | 0.129018 | 0.274955 | 2.816683 | 0.001605 | 0.00686 | 0.002219 |
| 0.849193 | 0.006533 | 0.266321 | 0.162899 | 0.412685 | 1.181146 | 0.098522 | 0.735985 | 0.023262 |
| 0.094867 | 0.203335 | 3.97581 | 0.678807 | 0.274357 | 4.161656 | 0.482058 | 3.813194 | 0.081429 |
| 29.13059 | 2.82292 | 0.014179 | 0.646144 | 0.145828 | 0.014073 | 1.445077 | 3.455038 | 0.01038 |
| 4.587751 | 0.001963 | 2.575673 | 1.158325 | 1.502963 | 3.04089 | 2.528488 | 2.102458 | 0.008633 |
| 3.499939 | 3.14194 | 0.05264 | 0.458562 | 0.192539 | 0.005591 | 0.57465 | 0.08675 | 3.846842 |
| 0.135129 | 9.962329 | 2.031484 | 2.315978 | 3.759259 | 2.45879 | 0.970958 | 0.277767 | 0.011903 |
| 0.062913 | 3.116234 | 0.448133 | 0.002839 | 6.347582 | 0.018503 | 0.053926 | 1.08547 | 0.569958 |
| 0.047697 | 15.51696 | 3.827857 | 8.118821 | 8.707924 | 7.507462 | 0.355315 | 6.345049 | 1.488391 |

TABLE 43

3-Hexane-4

| | | THF | | | | | log $\sigma_{rg,mn}$ | | |
|---|---|---|---|---|---|---|---|---|---|
| k4 | k5 | k1 | k2 | k3 | k4 | k5 | H2O | EtOH | Benzane |
| 7.077777 | 4.123053 | 34.88145 | 31.37649 | 21.59975 | 36.46815 | 20.5918 | −3.47051 | −4.20695 | −3.01438 |
| 3.319534 | 2.818996 | 7.189548 | 13.91728 | 5.979738 | 5.973698 | 3.303609 | 1.423286 | 0.497692 | −0.08048 |
| 2.669804 | 2.233765 | 5.1528 | 9.392321 | 3.270674 | 2.74063 | 1.442725 | 1.749126 | 2.144489 | 1.309926 |
| 10.39308 | 2.347023 | 1.480189 | 0.05485 | 0.50766 | 2.532505 | 1.483582 | 4.210396 | 2.683662 | 3.146059 |
| 3.887276 | 0.586177 | 0.178124 | 0.408943 | 0.094109 | 1.417327 | 0.890118 | 4.511755 | 4.725985 | 4.151946 |
| 0.269185 | 0.191301 | 1.188079 | 1.535506 | 0.233973 | 0.053173 | 0.067689 | −3.37465 | −0.12163 | −0.1664 |
| 73.5725 | 77.87996 | 19.32345 | 34.43652 | 17.80845 | 17.09029 | 21.68958 | −3.53859 | −4.81517 | −4.14667 |
| 197.6064 | 187.9075 | 31.65853 | 53.11068 | 37.21585 | 31.92398 | 32.39161 | 1.382603 | 0.58021 | 1.121638 |
| 120.471 | 104.3366 | 21.00069 | 36.75551 | 24.92284 | 19.54735 | 18.84931 | 1.741738 | 4.397142 | 1.867993 |
| 3.274503 | 4.995179 | 8.080891 | 15.73938 | 4.793909 | 5.744522 | 10.36694 | 4.20986 | 3.877253 | 4.065613 |
| 2.036888 | 4.173602 | 8.454672 | 15.49463 | 4.847123 | 6.883662 | 12.89539 | 4.502093 | 7.334288 | 4.599096 |
| 0.136588 | 0.816126 | 0.035476 | 0.580168 | 0.090377 | 0.29855 | 1.013456 | −2.81705 | 2.017158 | −0.07503 |
| 4.10498 | 2.213095 | 2.139239 | 4.084368 | 5.3198 | 0.516862 | 5.964986 | −2.546395 | −3.73822 | −3.60914 |

TABLE 43-continued

3-Hexane-4

| | | | | | | | | | |
|---|---|---|---|---|---|---|---|---|---|
| 0.352641 | 0.772691 | 0.427474 | 0.119963 | 0.708557 | 0.10658 | 1.511062 | 2.232661 | 0.673325 | 0.52533 |
| 0.525379 | 0.261941 | 2.122238 | 0.149759 | 0.020516 | 0.051448 | 0.129193 | 2.82389 | 2.29138 | 2.377234 |
| 1.044792 | 0.313849 | 4.820366 | 5.178281 | 5.41122 | 0.470879 | 6.099696 | 4.526049 | 3.418593 | 3.245467 |
| 0.155442 | 0.091419 | 7.04076 | 6.417495 | 6.16785 | 0.927959 | 6.128109 | 4.977347 | 4.815047 | 4.288023 |
| 0.564775 | 0.034622 | 13.72349 | 6.817741 | 4.277344 | 6.673597 | 5.632342 | −1.85186 | −0.43421 | 0.255924 |
| 11.5704 | 20.89685 | 6.57486 | 3.8559 | 6.994277 | 14.02303 | 4.282981 | −3.21894 | −4.00041 | −4.99092 |
| 2.886723 | 7.32302 | 31.08201 | 15.66982 | 30.19208 | 21.38075 | 18.17171 | 1.990356 | 0.825083 | −0.84597 |
| 0.349988 | 2.415291 | 0.14363 | 0.007634 | 0.769767 | 0.928351 | 0.150639 | 2.337258 | 2.032124 | 1.48009 |
| 17.10869 | 26.69674 | 4.157093 | 2.541449 | 4.536306 | 11.21333 | 2.750217 | 4.824302 | 2.611209 | 3.155974 |
| 10.81069 | 12.35505 | 4.873991 | 2.559188 | 3.887263 | 11.04187 | 2.607327 | 5.461588 | 3.586953 | 5.32421 |
| 0.382903 | 0.022916 | 5.307523 | 1.65304 | 1.086081 | 6.493722 | 1.290241 | −1.65006 | −1.31819 | 0.433949 |
| 4.540919 | 5.755532 | 26.98124 | 29.79236 | 26.87798 | 35.43392 | 16.22565 | −3.2759 | −3.9333 | −4.83793 |
| 2.710634 | 2.193143 | 250.274 | 212.6262 | 272.3649 | 246.0545 | 233.9067 | 2.395255 | 1.121161 | 0.586189 |
| 0.447116 | 0.293958 | 16.6881 | 8.460053 | 21.5549 | 13.6731 | 20.68155 | 2.671959 | 2.476316 | 1.833904 |
| 4.962018 | 13.79927 | 7.097183 | 9.775604 | 6.488017 | 11.88422 | 2.513224 | 4.960104 | 3.724711 | 4.348747 |
| 0.019201 | 0.224727 | 3.674027 | 6.724245 | 2.817333 | 6.805054 | 0.831165 | 5.213834 | 5.060588 | 5.343589 |
| 0.042514 | 0.009636 | 0.026874 | 1.439808 | 0.087364 | 0.353387 | 0.329555 | −1.9216 | −0.48259 | 0.760752 |
| 8.078283 | 8.0817 | 2.046137 | 2.899379 | 4.995772 | 0.090451 | 1.84373 | −3.33685 | −4.93122 | −4.45787 |
| 0.049631 | 0.350318 | 0.491836 | 0.980449 | 3.186019 | 0.035829 | 0.519069 | 2.617572 | −0.84793 | −0.52142 |
| 0.664717 | 4.051425 | 1.01968 | 2.051121 | 5.517025 | 0.168088 | 1.810958 | 1.895491 | 0.827268 | 1.224621 |
| 5.936612 | 4.677623 | 3.727934 | 4.773073 | 6.33197 | 0.422617 | 3.214657 | 6.047929 | 2.645935 | 4.198668 |
| 1.435422 | 0.077968 | 2.846901 | 3.166059 | 3.49228 | 0.025726 | 1.478979 | 5.744713 | 3.634928 | 4.787592 |
| 1.649877 | 9.364679 | 3.017963 | 6.13712 | 12.65583 | 4.780519 | 8.92105 | −1.07522 | −1.18013 | 0.031744 |
| 58.94473 | 59.25516 | 8.84684 | 16.80852 | 9.246722 | 21.49548 | 13.15295 | −1.96114 | −3.01957 | −4.77763 |
| 57.80738 | 79.61453 | 140.6334 | 181.2628 | 142.0921 | 168.1501 | 167.3284 | 2.302229 | 1.172873 | −0.60568 |
| 4.770901 | 8.524516 | 137.7864 | 162.9576 | 229.1377 | 145.3673 | 118.7594 | 2.531087 | 2.180185 | 0.824372 |
| 2.055708 | 0.412681 | 0.197853 | 1.900649 | 0.258927 | 4.660262 | 0.897109 | 5.313679 | 3.298982 | 4.056546 |
| 0.751704 | 0.096849 | 0.180393 | 2.002971 | 0.346883 | 4.746595 | 1.816695 | 5.661952 | 4.329304 | 5.29199 |
| 0.204458 | 0.0053 | 0.008039 | 0.412917 | 0.258173 | 0.729941 | 3.875841 | −1.57645 | −0.62874 | −0.38181 |
| 22.41016 | 18.96822 | 17.62476 | 28.02142 | 29.71325 | 36.75369 | 22.67972 | −3.49631 | −3.94273 | −4.01018 |
| 11.25003 | 11.7459 | 59.10267 | 84.53127 | 87.972 | 72.84396 | 85.55745 | 2.424872 | 0.445572 | 0.883886 |
| 0.369008 | 2.241012 | 0.868722 | 7.54709 | 1.741465 | 4.176149 | 2.084761 | 2.589026 | 2.778786 | 0.220413 |
| 24.04277 | 15.4632 | 4.768063 | 8.468017 | 9.146515 | 15.68572 | 5.335185 | 5.021767 | 3.338671 | 5.535133 |
| 3.137855 | 0.790056 | 6.872553 | 2.064792 | 10.80024 | 8.746333 | 6.344012 | 5.159181 | 5.413236 | 5.249664 |
| 0.692439 | 0.003564 | 0.549694 | 0.726461 | 0.520284 | 0.061348 | 0.311945 | −1.63969 | 0.909739 | 0.495249 |
| 3.824113 | 2.045159 | 0.155202 | 1.235725 | 0.051047 | 3.782794 | 0.239302 | −3.75061 | −4.03884 | −3.85016 |
| 4.377076 | 0.428234 | 5.311826 | 10.61625 | 5.338562 | 15.78976 | 7.62013 | 1.981951 | 2.272385 | 2.102403 |
| 3.192342 | 0.199438 | 3.89121 | 11.07755 | 5.587191 | 5.842365 | 1.947979 | 1.953076 | 4.092013 | 2.495732 |
| 2.422318 | 0.010112 | 0.480477 | 0.014596 | 0.915235 | 0.5857 | 0.668739 | 4.897952 | 5.078273 | 5.504239 |
| 1.157694 | 0.005469 | 0.056382 | 0.007803 | 0.306706 | 1.71298 | 0.002712 | 4.935532 | 6.916974 | 5.854076 |
| 0.094726 | 0.138624 | 0.376151 | 0.178399 | 0.087979 | 3.490533 | 2.34546 | −1.17599 | 0.633256 | −0.31503 |
| 1.136161 | 1.150891 | 1.02203 | 0.044187 | 3.820747 | 1.005497 | 3.288034 | −3.97688 | −1.75606 | −4.34518 |
| 2.879228 | 3.254244 | 63.1838 | 49.051 | 77.8573 | 67.05557 | 54.58582 | 1.269908 | 2.462408 | 0.091022 |
| 1.100116 | 0.231254 | 11.26013 | 13.66958 | 3.374714 | 10.15537 | 8.643891 | 2.397457 | 3.352771 | 0.918108 |
| 1.290827 | 0.796365 | 0.10236 | 1.367341 | 0.428168 | 0.09042 | 0.131301 | 4.568042 | 3.121787 | 3.407953 |
| 0.000771 | 0.362081 | 0.046641 | 0.341271 | 0.507105 | 0.059529 | 1.052648 | 5.043107 | 3.956618 | 5.072329 |
| 0.487955 | 2.139102 | 14.82412 | 16.6722 | 29.90478 | 15.34227 | 23.81146 | −1.06582 | −1.14587 | −0.12107 |

| log $\sigma_{rg,mn}$ | | | log $\sigma_{\theta g,mn}$ | | | | | | |
|---|---|---|---|---|---|---|---|---|---|
| Hexane | AcOEt | THF | H2O | EtOH | Benzane | Hexane | AcOEt | THF | |
| −4.10849 | −2.38023 | −1.66628 | −0.82928 | 0.823367 | −0.51055 | 0.992277 | −0.01587 | −0.89727 | |
| 0.688938 | 1.180556 | 0.570093 | −1.55647 | 0.340158 | −0.76988 | 0.467301 | −0.07627 | −0.43568 | |
| 1.072453 | 2.454603 | 2.150339 | −1.63936 | 0.400977 | −1.08067 | 0.466282 | 0.123082 | −0.0921 | |
| 3.374414 | 4.503642 | 2.094256 | −1.14956 | −0.67501 | −1.52378 | −1.8571 | −1.24557 | −0.59128 | |
| 4.422189 | 5.309541 | 3.505918 | −1.1801 | −0.63757 | −0.90805 | −1.42174 | −0.9164 | −0.22346 | |
| −1.31652 | −0.58079 | −0.29805 | −2.61649 | −1.8355 | −0.74507 | −2.09105 | −1.17806 | −1.17675 | |
| −5.16409 | −4.20603 | −2.91236 | −2.16383 | −1.07598 | 1.084797 | −0.78634 | −1.56827 | −0.63991 | |
| −0.22856 | −0.39937 | 0.259949 | −1.37949 | −1.06307 | −0.17781 | −0.871 | −2.29371 | −1.39059 | |
| 0.658653 | 0.724481 | 2.016578 | −1.37216 | −0.73084 | 0.417273 | −0.73762 | −2.03317 | −1.17522 | |
| 2.946359 | 2.288464 | 1.814887 | −1.17288 | −0.98772 | 0.319081 | −1.48448 | −1.58917 | −1.13088 | |
| 4.283216 | 3.001095 | 3.289227 | −1.13063 | −0.69725 | 0.469729 | −1.13058 | −1.40378 | −1.18917 | |
| −1.28754 | −1.63629 | −0.70151 | −3.16176 | −1.91058 | −0.36615 | −2.02085 | −2.98339 | −2.57999 | |
| −3.45323 | −2.88846 | −2.63055 | −0.40623 | −1.46006 | −0.15372 | 0.262191 | −0.88764 | −0.58837 | |
| 1.248007 | 0.60212 | 0.207069 | −1.49237 | −1.15723 | −1.74261 | 0.300858 | −1.27126 | −1.29522 | |
| 1.521438 | 1.683112 | 1.794486 | −2.05044 | −0.51846 | −1.86177 | 0.407925 | −0.48163 | −1.06263 | |
| 4.290344 | 3.604588 | 2.58891 | −0.3419 | −1.76309 | −0.29631 | −1.57368 | −0.42674 | −0.79534 | |
| 4.912251 | 4.56718 | 4.147205 | −0.41308 | −0.61661 | −0.19836 | −1.4308 | −0.02069 | −0.70174 | |
| −1.43277 | −2.33187 | −0.66004 | −2.20351 | −0.95833 | −1.7064 | −1.3211 | −0.98294 | −2.42581 | |
| −4.18508 | −4.57844 | −2.66352 | −0.25239 | −1.97182 | −0.41206 | 0.666055 | −1.33803 | −0.7309 | |
| 0.734052 | 0.285807 | 0.234313 | 0.394229 | −1.83933 | −1.48248 | 0.686205 | −1.9322 | −3.00454 | |
| 1.36182 | 2.258278 | 1.282089 | −1.40018 | −1.40448 | 0.639868 | −1.32276 | −1.9627 | | |
| 3.225993 | 3.283066 | 2.743929 | 0.533222 | −1.84778 | −0.66336 | −1.99687 | −1.35819 | −0.75504 | |
| 4.055777 | 5.115025 | 3.888008 | 0.556183 | −1.64801 | −0.58531 | −2.40852 | −1.49817 | −0.53901 | |
| −0.61674 | −0.16786 | −1.41821 | −2.43387 | −2.10459 | −2.01139 | −1.70592 | −1.94335 | −1.94459 | |
| −3.99619 | −4.57673 | −2.56564 | −0.82216 | −1.35886 | 0.057138 | 0.385252 | −0.37197 | −0.95689 | |
| 0.784866 | 2.386694 | 0.470485 | −0.2301 | −1.96415 | −0.80879 | 0.362596 | −0.47755 | −2.79221 | |

TABLE 43-continued

3-Hexane-4

| | | | | | | | | |
|---|---|---|---|---|---|---|---|---|
| 0.952827 | 2.335711 | 2.321066 | −0.34122 | −1.17207 | −0.99518 | 0.428725 | 0.658453 | −1.47053 |
| 2.499667 | 4.966157 | 2.71242 | 0.119395 | −1.68121 | −0.2457 | −0.8037 | −1.60442 | −0.95527 |
| 3.978408 | 4.951408 | 4.257231 | 0.039681 | −1.65995 | −0.27385 | −0.4667 | 0.24632 | −0.59658 |
| −0.9661 | −0.20126 | 0.059249 | −2.41235 | −1.76205 | −0.90938 | −1.20675 | 0.271423 | −1.67284 |
| −3.59592 | −3.69173 | −2.1598 | −1.79439 | −1.19371 | −0.6264 | 0.809715 | −1.30587 | −0.12794 |
| 0.80426 | 0.42363 | 0.51278 | −0.45931 | −1.11443 | −1.15205 | 0.870868 | −1.51448 | −0.98185 |
| 1.003504 | 2.133733 | 2.193251 | −0.46491 | −0.64042 | −0.68015 | 0.84193 | −1.12517 | −0.76481 |
| 3.45203 | 3.075531 | 3.315992 | −0.35854 | −1.72089 | −0.98728 | −0.29057 | −1.21759 | −0.66195 |
| 5.019523 | 4.940727 | 4.881186 | −0.40368 | −0.70966 | −0.41013 | 0.18832 | −0.87095 | −0.76053 |
| 0.484981 | −0.02916 | −0.18164 | −2.06213 | −1.116 | −0.82419 | −0.6464 | −1.76629 | −2.12582 |
| −5.02916 | −2.57317 | −3.5853 | −1.36913 | −1.49906 | −1.03802 | 0.499368 | −1.34106 | −0.46288 |
| −0.18678 | 0.838193 | −0.03587 | −0.56432 | −1.20378 | −1.08981 | 0.459324 | −1.59999 | −1.97802 |
| 0.492859 | 2.038741 | 1.658616 | −0.32969 | −0.42158 | −0.19839 | 0.488539 | −0.50208 | −1.97447 |
| 2.583292 | 3.546491 | 2.6235 | −0.54307 | −1.49349 | −1.49594 | −1.82025 | −1.1087 | −0.65216 |
| 4.232906 | 4.911158 | 4.373398 | −0.31415 | −0.54561 | −0.31769 | −1.25587 | −0.23396 | −0.55993 |
| −0.69466 | −0.59548 | −0.03484 | −1.81488 | −0.9873 | −0.51292 | −1.53994 | −0.75271 | −1.96289 |
| −3.25608 | −3.40032 | −2.58889 | −0.83757 | 0.566473 | 0.611169 | 0.037197 | −1.06393 | −0.99583 |
| 0.257281 | 0.494046 | 0.909833 | −0.51511 | 0.632718 | 0.594448 | 0.835504 | −1.34173 | −2.24377 |
| 0.796696 | 1.443826 | 2.481656 | −0.43515 | 0.390223 | 0.321458 | 0.671697 | −0.5557 | −0.69441 |
| 3.852615 | 3.480733 | 2.713015 | −0.22912 | −2.0043 | −0.69921 | 0.647753 | −1.86641 | −1.08793 |
| 4.685197 | 4.999752 | 5.020012 | −0.23107 | −0.92487 | −0.61209 | 0.73669 | −0.3206 | −0.8662 |
| 3.162628 | −0.47851 | 0.577207 | −1.72139 | −1.09882 | −0.49671 | 0.585064 | −0.45378 | −0.76466 |
| −4.34306 | −2.56696 | −4.43024 | −1.2803 | 0.314511 | 0.558145 | −0.03573 | −0.25352 | −0.0916 |
| 1.395306 | 2.397084 | 0.725282 | 0.086808 | 0.458879 | −0.76659 | 0.722195 | 0.667138 | −1.09915 |
| 1.534186 | 2.81233 | 2.262165 | 0.038483 | 0.046801 | 0.655328 | 0.643474 | 0.757237 | −1.28364 |
| 4.403583 | 3.380728 | 2.933988 | 0.054007 | −0.66324 | 0.368502 | 0.534097 | 0.497352 | −0.52911 |
| 4.753436 | 4.689018 | 4.459714 | 0.009472 | 0.57047 | −0.84925 | 0.8618 | 0.755353 | −0.1815 |
| −0.61998 | 0.343889 | −0.14096 | −1.81933 | 0.339932 | 0.45126 | −0.87872 | −0.14241 | −1.07022 |
| −3.09943 | −3.29933 | −0.12005 | −0.81177 | −1.34576 | −0.35308 | 0.785952 | 0.817846 | −0.998936 |
| 2.128556 | 2.322421 | 1.823127 | −0.45072 | −1.0943 | 0.04527 | 1.089347 | 0.547119 | −1.11656 |
| 1.222052 | 2.309211 | 1.954408 | −0.82505 | −0.04856 | 0.811424 | 0.943053 | 0.806506 | −0.46843 |
| 3.974758 | 5.180598 | 4.924648 | −0.16758 | −1.09899 | −0.38398 | −0.14212 | −0.19413 | 1.07302 |
| 3.311051 | 4.635538 | 4.926917 | −0.50567 | −0.22342 | 0.514798 | −0.71394 | 0.782028 | 1.093496 |
| −0.74758 | 0.103346 | 0.296609 | −1.29164 | 0.090747 | 0.241204 | −0.75044 | 0.355101 | −0.89061 |

TABLE 44

3-AcOEt-1

| | | $r_{u,mn}$ | $(r_{u,mn} - r_{g,mnk})^2 / \sigma_{rg,mn}^2$ | | | | | | | |
|---|---|---|---|---|---|---|---|---|---|---|
| | | AcOEt | H$_2$O | | | | | EtOH | | |
| f | Ku,mn' | k5 | k1 | k2 | k3 | k4 | k5 | k1 | k2 | k3 |
| 0.005 Hz | Ku', 12 | 0.18872 | 7.599574 | 4.893225 | 1.460607 | 3.272638 | 8.573069 | 76.6818 | 96.57552 | 63.46203 |
| | Ku', 13 | 13.45263 | 4.965875 | 7.806557 | 0.949693 | 1.973365 | 3.299531 | 11.69593 | 26.91388 | 13.51774 |
| | Ku', 14 | 36.93533 | 0.85248 | 0.046368 | 4.335612 | 2.531645 | 1.680129 | 4.027637 | 11.71675 | 2.938599 |
| | Ku', 23 | 71.33655 | 4.90323 | 4.171867 | 0.436254 | 1.216555 | 4.624106 | 17.42149 | 9.442654 | 5.540493 |
| | Ku', 24 | 195.715 | 1.495744 | 1.253016 | 0.11242 | 0.023855 | 1.288667 | 1.51601 | 0.01483 | 1.177605 |
| | Ku', 34 | 2.743545 | 1557.856 | 1484.979 | 1481.859 | 1449.713 | 1579.232 | 0.059867 | 1.773201 | 0.088826 |
| 0.1 Hz | Ku', 12 | 0.081188 | 0.119604 | 0.452275 | 2.720612 | 2.182966 | 4.158094 | 8.274343 | 3.013755 | 3.146668 |
| | Ku', 13 | 6.267037 | 17.57157 | 5.826567 | 9.742152 | 7.332584 | 12.66763 | 1.912876 | 0.364439 | 0.185665 |
| | Ku', 14 | 14.75821 | 10.00512 | 1.951961 | 5.58601 | 3.659790 | 8.070075 | 0.018426 | 0.018181 | 0.006091 |
| | Ku', 23 | 77.19149 | 6.722205 | 1.430191 | 1.010829 | 0.800844 | 1.048476 | 2.335066 | 0.44605 | 0.339427 |
| | Ku', 24 | 181.7779 | 3.887745 | 0.237028 | 0.165844 | 0.077514 | 0.180777 | 0.02964 | 0.017263 | 0.004852 |
| | Ku', 34 | 2.354894 | 240.2579 | 238.9014 | 200.3213 | 202.0585 | 201.5457 | 0.006284 | 0.023208 | 0.002611 |
| 0.15 Hz | Ku', 12 | 0.066017 | 0.25196 | 0.010567 | 0.824237 | 3.708139 | 0.169415 | 0.088411 | 0.482457 | 0.071066 |
| | Ku', 13 | 6.928022 | 2.400333 | 0.615853 | 4.485041 | 0.114318 | 0.655378 | 0.087423 | 0.016554 | 0.02999 |
| | Ku', 14 | 24.45044 | 0.251875 | 0.073898 | 1.52797 | 0.250879 | 0.025335 | 0.356894 | 0.105364 | 0.496125 |
| | Ku', 23 | 104.9443 | 1.124927 | 0.894632 | 0.940459 | 0.400243 | 0.210597 | 0.008188 | 0.346061 | 0.207124 |
| | Ku', 24 | 370.3572 | 0.159705 | 0.494923 | 0.076849 | 4.176451 | 1.051782 | 0.204382 | 0.839892 | 1.069011 |
| | Ku', 34 | 3.529179 | 160.7524 | 184.9293 | 136.285 | 152.8903 | 168.5542 | 0.881733 | 0.777055 | 1.825768 |
| 0.2 Hz | Ku', 12 | 0.097876 | 2.354561 | 1.829858 | 0.034378 | 0.038294 | 0.00966 | 9.051965 | 7.134704 | 6.292641 |
| | Ku', 13 | 8.561955 | 0.277512 | 0.280151 | 0.452819 | 1.334301 | 1.531905 | 3.036897 | 1.466545 | 1.452811 |
| | Ku', 14 | 20.74802 | 0.003243 | 1.736577 | 0.046914 | 0.110737 | 0.199862 | 1.115663 | 0.291435 | 0.464117 |
| | Ku', 23 | 87.4777 | 4.119908 | 0.02488 | 0.244894 | 0.654386 | 0.646141 | 2.089592 | 5.157164 | 3.207909 |
| | Ku', 24 | 211.983 | 2.503637 | 0.044468 | 0.00099 | 0.057949 | 0.060958 | 5.474884 | 12.47024 | 5.845775 |
| | Ku', 34 | 2.423281 | 13.47303 | 22.34772 | 29.95945 | 27.1943 | 26.20508 | 1.552593 | 2.765203 | 0.891974 |
| 0.25 Hz | Ku', 12 | 0.078083 | 0.039947 | 0.879846 | 0.140892 | 0.621685 | 0.500262 | 2.858986 | 1.355442 | 2.217539 |
| | Ku', 13 | 7.113198 | 1.645017 | 0.325031 | 2.590477 | 0.459147 | 0.049476 | 0.645262 | 0.054465 | 0.268217 |
| | Ku', 14 | 20.0869 | 0.391921 | 0.000567 | 0.986197 | 0.013818 | 0.77824 | 0.621207 | 0.002155 | 0.158352 |
| | Ku', 23 | 31.09829 | 2.543886 | 0.034941 | 1.547084 | 0.0912 | 6.38E−07 | 0.037319 | 0.352253 | 0.276651 |
| | Ku', 24 | 2610.938 | 0.976966 | 0.182303 | 0.384757 | 0.93984 | 0.375739 | 0.010698 | 0.556536 | 0.139161 |
| | Ku', 34 | 2.866087 | 101.7057 | 80.74118 | 100.7126 | 84.77841 | 71.15313 | 0.549908 | 0.435229 | 0.002783 |

TABLE 44-continued

3-AcOEt-1

| f | Ku,mn' | | | | | | | | |
|---|---|---|---|---|---|---|---|---|---|
| 0.3 Hz | Ku', 12 | 0.083591 | 1.491381 | 0.006179 | 0.475584 | 0.053116 | 0.000247 | 51.9096 | 29.31791 | 40.64045 |
| | Ku', 13 | 6.71496 | 5.209281 | 0.399185 | 0.511407 | 0.768351 | 0.412588 | 19.54135 | 9.250685 | 11.50552 |
| | Ku', 14 | 16.15929 | 6.587469 | 0.804627 | 1.185752 | 2.132602 | 0.744211 | 3.18135 | 0.000218 | 0.890934 |
| | Ku', 23 | 785.79712 | 3.271184 | 0.059642 | 0.02753 | 0.077364 | 0.053926 | 15.77085 | 5.654101 | 11.49348 |
| | Ku', 24 | 182.4028 | 3.136895 | 0.058298 | 0.006162 | 0.073927 | 0.040973 | 10.18795 | 9.583015 | 10.00436 |
| | Ku', 34 | 2.406461 | 20.14435 | 8.000562 | 8.40309 | 9.015646 | 8.504056 | 0.103651 | 3.477804 | 0.684215 |
| 0.35 Hz | Ku', 12 | 0.081414 | 0.061387 | 2.648022 | 0.03265 | 0.114825 | 0.055126 | 0.78103 | 1.03233 | 0.733682 |
| | Ku', 13 | 7.439379 | 1.054147 | 0.355052 | 3.534503 | 0.000164 | 0.203974 | 0.671296 | 0.997835 | 0.976846 |
| | Ku', 14 | 19.53149 | 0.255022 | 0.069256 | 1.442893 | 0.501384 | 0.007335 | 0.504774 | 1.989876 | 0.363066 |
| | Ku', 23 | 91.37672 | 2.023239 | 0.055297 | 0.569593 | 0.020011 | 0.004143 | 1.561552 | 2.294377 | 0.344293 |
| | Ku', 24 | 239.9018 | 1.208033 | 0.334158 | 0.083305 | 0.269803 | 0.074727 | 1.959079 | 1.217266 | 2.447959 |
| | Ku', 34 | 2.625415 | 31.65152 | 19.87705 | 39.88364 | 34.8543 | 27.37854 | 0.067609 | 0.115351 | 1.812647 |
| 0.4 Hz | Ku', 12 | 0.127619 | 5.693165 | 7.840228 | 0.856223 | 3.419682 | 3.185583 | 12.70455 | 15.5775 | 22.66503 |
| | Ku', 13 | 10.27717 | 1.176154 | 0.227485 | 1.739716 | 0.111617 | 0.532898 | 8.772039 | 10.54901 | 10.5711 |
| | Ku', 14 | 26.83055 | 0.007065 | 2.253189 | 0.098351 | 0.130727 | 0.015215 | 0.289809 | 0.649545 | 0.499656 |
| | Ku', 23 | 90.53024 | 4.651306 | 0.049614 | 1.291523 | 0.583047 | 1.278225 | 0.327128 | 0.577115 | 5.630382 |
| | Ku', 24 | 210.2398 | 2.877199 | 0.083278 | 0.337903 | 0.013078 | 0.578752 | 3.126211 | 0.074084 | 1.029766 |
| | Ku', 34 | 2.610694 | 49.91263 | 38.94222 | 50.53731 | 28.95013 | 41.57536 | 2.182283 | 0.000418 | 0.021032 |
| 0.45 Hz | Ku', 12 | 0.049963 | 0.204166 | 4.775872 | 2.589074 | 1.020143 | 0.504606 | 0.137017 | 0.000477 | 0.167129 |
| | Ku', 13 | 4.924396 | 3.968623 | 1.506235 | 6.135997 | 1.151982 | 6.863766 | 0.00064 | 0.009168 | 0.001121 |
| | Ku', 14 | 9.548141 | 5.23015 | 1.706763 | 8.321307 | 1.765018 | 3.174543 | 0.009608 | 0.003282 | 0.004001 |
| | Ku', 23 | 98.56017 | 2.741348 | 0.080126 | 1.428698 | 0.304357 | 3.791263 | 0.017559 | 0.012187 | 0.003147 |
| | Ku', 24 | 191.1029 | 3.410588 | 0.001841 | 1.10957 | 0.221217 | 1.020743 | 0.024056 | 0.004361 | 0.014311 |
| | Ku', 34 | 1.938947 | 3.071225 | 3.566254 | 4.221743 | 2.138344 | 10.8521 | 0.260915 | 0.021741 | 0.259796 |
| 0.5 Hz | Ku', 12 | 0.105648 | 11.93043 | 2.43772 | 3.944766 | 4.62536 | 5.483126 | 0.134993 | 0.127074 | 0.129324 |
| | Ku', 13 | 7.898999 | 3.264518 | 5.45266 | 3.284381 | 10.99225 | 2.361176 | 0.096873 | 0.055686 | 0.098489 |
| | Ku', 14 | 19.82423 | 0.081493 | 0.305851 | 0.003036 | 1.602956 | 0.211617 | 0.176137 | 0.08552 | 0.116221 |
| | Ku', 23 | 74.76686 | 9.192746 | 2.389384 | 2.261772 | 6.505021 | 2.457346 | 1.30402 | 3.366651 | 0.946666 |
| | Ku', 24 | 187.6435 | 2.020562 | 0.96256 | 0.362135 | 4.503854 | 0.110283 | 0.001568 | 1.922521 | 0.705315 |
| | Ku', 34 | 2.509715 | 16.47306 | 2.283969 | 12.77396 | 6.806102 | 17.74253 | 4.393096 | 0.746897 | 0.140592 |

| | | $(r_{u,mn} - r_{g,mnk})^2 / \sigma_{rg,mn}^2$ | | | | | | | |
|---|---|---|---|---|---|---|---|---|---|
| | | EtOH | | Benzene | | | | | |
| f | Ku,mn' | k4 | k5 | k1 | k2 | k3 | k4 | k5 | k1 |
| 0.005 Hz | Ku', 12 | 86.68817 | 74.91442 | 9.225425 | 2.290838 | 5.783859 | 7.774518 | 11.19565 | 104.2749 |
| | Ku', 13 | 18.52458 | 13.87227 | 155.1317 | 120.6738 | 156.0351 | 146.1638 | 163.792 | 24.90615 |
| | Ku', 14 | 4.378831 | 2.997173 | 65.36661 | 48.72921 | 63.88289 | 53.39181 | 77.19017 | 106.4933 |
| | Ku', 23 | 14.71096 | 12.27305 | 0.867545 | 3.300597 | 3.572663 | 1.335098 | 0.027498 | 11.68543 |
| | Ku', 24 | 2.692421 | 2.39395 | 0.097881 | 2.42725 | 2.106061 | 0.008146 | 0.073111 | 2.569454 |
| | Ku', 34 | 0.07599 | 0.097452 | 0.882176 | 0.456732 | 1.488026 | 3.255397 | 0.013385 | 9.365399 |
| 0.1 Hz | Ku', 12 | 3.980989 | 10.84361 | 8.878437 | 5.629042 | 14.34978 | 11.14941 | 17.61033 | 93.29122 |
| | Ku', 13 | 0.727661 | 4.750258 | 1.731764 | 0.046378 | 1.801536 | 1.993702 | 1.916217 | 12.1296 |
| | Ku', 14 | 0.022906 | 2.884239 | 1.15605 | 0.11959 | 1.687073 | 1.083964 | 1.927786 | 25.32972 |
| | Ku', 23 | 0.779665 | 5.118411 | 0.040957 | 1.953614 | 0.165574 | 0.02429 | 1.024456 | 9.11994 |
| | Ku', 24 | 0.023388 | 2.925212 | 0.224756 | 4.359297 | 1.37692 | 1.027549 | 4.362257 | 0.028107 |
| | Ku', 34 | 0.022087 | 2.842363 | 1.524571 | 0.011273 | 0.421298 | 3.737698 | 0.295051 | 10.99437 |
| 0.15 Hz | Ku', 12 | 0.000784 | 1.418968 | 2.140225 | 4.003413 | 3.285408 | 3.264966 | 0.061595 | 0.030559 |
| | Ku', 13 | 0.84593 | 1.060663 | 6.678809 | 11.0694 | 8.229962 | 9.645897 | 2.144136 | 0.029979 |
| | Ku', 14 | 0.318348 | 1.922475 | 2.510121 | 3.565257 | 2.587186 | 2.860696 | 0.01736 | 13.22132 |
| | Ku', 23 | 0.881775 | 0.690354 | 0.093057 | 0.027679 | 0.390584 | 0.136047 | 1.353478 | 2.63E-05 |
| | Ku', 24 | 0.52234 | 0.477884 | 1.559218 | 0.106446 | 0.370921 | 0.000331 | 0.061188 | 3.152829 |
| | Ku', 34 | 0.019268 | 4.28763 | 0.248865 | 0.00617 | 0.084798 | 0.047168 | 1.619994 | 92.54151 |
| 0.2 Hz | Ku', 12 | 1.799541 | 9.68035 | 149.286 | 114.2972 | 142.9816 | 144.7693 | 118.891 | 20.33724 |
| | Ku', 13 | 0.01442 | 1.896237 | 245.3916 | 332.3566 | 242.5238 | 245.9671 | 196.2909 | 6.603105 |
| | Ku', 14 | 0.487149 | 0.942211 | 7.851104 | 10.14593 | 12.23944 | 14.39633 | 3.883201 | 11.75361 |
| | Ku', 23 | 5.889064 | 10.91536 | 2.460581 | 0.095278 | 1.2174 | 1.277646 | 0.720845 | 0.781603 |
| | Ku', 24 | 15.81335 | 9.977845 | 3.045877 | 0.075013 | 0.300575 | 0.04167 | 2.089261 | 0.479825 |
| | Ku', 34 | 3.893886 | 0.020735 | 1.965701 | 0.354971 | 0.080917 | 0.016213 | 2.257681 | 0.055502 |
| 0.25 Hz | Ku', 12 | 0.002966 | 0.152599 | 47.78016 | 48.60085 | 70.34435 | 61.79642 | 47.26826 | 5.12706 |
| | Ku', 13 | 0.453154 | 1.44817 | 7.129162 | 1.404936 | 8.94722 | 9.155827 | 6.081064 | 1.482457 |
| | Ku', 14 | 0.552379 | 1.077437 | 4.825657 | 3.210077 | 6.922546 | 7.18989 | 0.932778 | 28.98651 |
| | Ku', 23 | 0.458754 | 1.052465 | 0.011209 | 2.270432 | 2.143168 | 0.0374 | 0.092191 | 6.404208 |
| | Ku', 24 | 0.564051 | 0.868845 | 0.012812 | 0.335832 | 0.132326 | 0.024576 | 2.826766 | 2.518835 |
| | Ku', 34 | 0.266117 | 0.700049 | 9.37E-07 | 0.22944 | 0.322982 | 0.111233 | 1.345997 | 13.92387 |
| 0.3 Hz | Ku', 12 | 43.97447 | 49.64654 | 36.14376 | 24.4408 | 45.86389 | 39.0148 | 29.81656 | 4.252415 |
| | Ku', 13 | 32.45691 | 16.74805 | 70.6877 | 51.22477 | 65.12318 | 80.89646 | 58.09917 | 3.861853 |
| | Ku', 14 | 2.06552 | 0.25996 | 12.99519 | 6.613487 | 12.89593 | 14.91752 | 5.495089 | 19.43532 |
| | Ku', 23 | 7.748955 | 15.61436 | 0.052441 | 0.001985 | 2.946549 | 0.018307 | 0.025741 | 0.010576 |
| | Ku', 24 | 8.336148 | 21.5573 | 0.007403 | 0.283507 | 2.970271 | 0.000898 | 1.375409 | 0.123999 |
| | Ku', 34 | 1.231323 | 4.007337 | 0.020603 | 0.487365 | 0.121011 | 0.4269 | 1.660476 | 0.148973 |
| 0.35 Hz | Ku', 12 | 0.431072 | 0.844387 | 72.89432 | 76.57735 | 56.46708 | 76.26257 | 53.07664 | 97.96626 |
| | Ku', 13 | 0.404079 | 0.890348 | 121.0949 | 141.9592 | 113.3326 | 118.109 | 99.06519 | 42.36288 |
| | Ku', 14 | 0.481323 | 1.032276 | 52.1998 | 59.05267 | 47.33173 | 43.1784 | 33.73116 | 96.85778 |

TABLE 44-continued

3-AcOEt-1

| | | | | | | | | | |
|---|---|---|---|---|---|---|---|---|---|
| | Ku', 23 | 0.081087 | 1.125939 | 1.029972 | 0.257279 | 0.000901 | 2.943962 | 0.021686 | 5.550403 |
| | Ku', 24 | 0.03808 | 0.408601 | 0.161324 | 0.008648 | 0.020338 | 2.827397 | 0.134363 | 0.412639 |
| | Ku', 34 | 0.014851 | 0.176932 | 0.523838 | 0.503511 | 0.154122 | 0.32311 | 0.548613 | 4.25107 |
| 0.4 Hz | Ku', 12 | 28.92239 | 20.4885 | 232.8047 | 249.6488 | 200.236 | 231.1569 | 203.2711 | 7.251286 |
| | Ku', 13 | 22.99245 | 12.85791 | 11.71208 | 4.027795 | 12.55226 | 13.82687 | 12.93552 | 41.53243 |
| | Ku', 14 | 1.900981 | 0.678931 | 325.3193 | 297.2174 | 333.5152 | 296.4191 | 356.2725 | 117.7702 |
| | Ku', 23 | 2.144056 | 1.717748 | 0.040657 | 2.559274 | 0.000879 | 4.13E−05 | 0.001792 | 0.00061 |
| | Ku', 24 | 0.002622 | 0.337578 | 0.161853 | 1.986811 | 0.035484 | 0.502307 | 0.111813 | 0.75451 |
| | Ku', 34 | 0.155327 | 0.013523 | 0.069085 | 0.981365 | 0.013448 | 0.940852 | 0.097106 | 1.023245 |
| 0.45 Hz | Ku', 12 | 0.211727 | 1.683918 | 0.01855 | 0.655316 | 2.880357 | 3.284764 | 2.629808 | 1.245978 |
| | Ku', 13 | 2.554753 | 5.57E−05 | 0.070397 | 1.472987 | 0.13065 | 0.161877 | 0.175022 | 0.772519 |
| | Ku', 14 | 2.652044 | 0.000198 | 0.02654 | 1.181024 | 0.262645 | 0.340729 | 0.290182 | 0.000859 |
| | Ku', 23 | 2.490829 | 0.039592 | 0.026601 | 2.549559 | 0.031066 | 0.032744 | 4E−05 | 2.949736 |
| | Ku', 24 | 2.679369 | 0.005029 | 0.007514 | 2.574549 | 0.020031 | 0.005252 | 0.00012 | 0.411054 |
| | Ku', 34 | 3.067643 | 0.00591 | 1.239024 | 0.314393 | 0.111896 | 0.340983 | 0.009293 | 2.368751 |
| 0.5 Hz | Ku', 12 | 1.491928 | 0.126114 | 134.8345 | 107.8968 | 143.34 | 147.3846 | 124.1318 | 2.617995 |
| | Ku', 13 | 1.676516 | 0.75449 | 30.90924 | 21.82068 | 36.60621 | 34.86534 | 20.39281 | 0.330999 |
| | Ku', 14 | 1.523486 | 0.102493 | 30.85135 | 28.17148 | 45.85315 | 33.71881 | 23.81793 | 21.98447 |
| | Ku', 23 | 0.006347 | 1.839164 | 2.931847 | 1.885154 | 1.431907 | 4.787904 | 8.724784 | 0.126159 |
| | Ku', 24 | 0.067771 | 1.03741 | 2.00281 | 0.284965 | 0.151548 | 4.345916 | 2.159923 | 6.177643 |
| | Ku', 34 | 0.153006 | 0.510209 | 0.731682 | 0.03371 | 0.084693 | 1.78518 | 0.005295 | 0.791302 |

TABLE 45

3-AcOEt-2

| Hexane | | | | AcOEt | | | | | THF |
|---|---|---|---|---|---|---|---|---|---|
| k2 | k3 | k4 | k5 | k1 | k2 | k3 | k4 | k5 | k1 |
| 117.4111 | 113.9429 | 83.65649 | 116.4043 | 1.036601 | 0.113881 | 1.736404 | 0.271342 | 0.290837 | 0.916401 |
| 36.82233 | 32.56237 | 18.90203 | 33.99478 | 1.467147 | 2.01003 | 0.023355 | 0.001123 | 0.863956 | 4.552896 |
| 139.8654 | 129.9897 | 106.9918 | 133.3662 | 1.143219 | 0.627912 | 0.021912 | 0.590066 | 0.136091 | 1.937875 |
| 4.550208 | 9.605927 | 3.505075 | 10.75695 | 0.105722 | 0.028189 | 2.322235 | 0.027468 | 0.001807 | 30.88096 |
| 0.170985 | 0.997242 | 0.056599 | 1.217482 | 0.098197 | 0.009516 | 2.686001 | 0.000105 | 0.037976 | 14.78372 |
| 14.51676 | 14.49453 | 25.27489 | 14.55485 | 0.093333 | 0.485074 | 0.156383 | 1.530468 | 0.471453 | 0.049693 |
| 91.85286 | 107.7985 | 108.4447 | 128.3879 | 5.887335 | 0.693703 | 3.410271 | 1.010538 | 4.729831 | 12.66672 |
| 10.55633 | 15.22961 | 10.72914 | 24.49438 | 9.795033 | 6.969732 | 8.823763 | 10.88375 | 20.20146 | 1.267024 |
| 19.64446 | 24.90133 | 15.91891 | 34.41585 | 35.81637 | 20.94467 | 22.96961 | 22.37703 | 35.77296 | 1.058571 |
| 10.68711 | 12.65951 | 23.34368 | 11.61067 | 0.358191 | 0.775015 | 0.01524 | 1.240667 | 0.20929 | 63.82112 |
| 0.536875 | 0.529328 | 3.946056 | 0.138817 | 5.991762 | 14.58453 | 4.997713 | 13.24708 | 7.973345 | 13.86918 |
| 5.899534 | 7.128581 | 2.420534 | 10.29047 | 20.67625 | 11.3591 | 10.44985 | 7.598253 | 8.418735 | 1.254893 |
| 3.855322 | 2.599312 | 3.135493 | 1.971032 | 0.783704 | 0.204835 | 3.034111 | 0.010898 | 0.072907 | 3.561747 |
| 3.18077 | 2.280653 | 2.560016 | 0.347699 | 0.031209 | 0.103039 | 3.561728 | 0.087491 | 0.294137 | 0.525401 |
| 25.82223 | 23.03344 | 23.67052 | 13.25848 | 0.78121 | 0.306228 | 0.718633 | 0.669494 | 0.259629 | 0.126294 |
| 1.17805 | 0.007265 | 0.17716 | 2.7387 | 1.342079 | 0.391897 | 1.307694 | 0.276755 | 0.042804 | 24.73889 |
| 0.234914 | 2.281708 | 1.261560 | 0.005495 | 4.359729 | 2.003118 | 4.079756 | 0.145725 | 1.156214 | 16.86659 |
| 61.78992 | 73.41229 | 65.04502 | 65.61595 | 70.10363 | 47.83395 | 56.89387 | 75.69556 | 65.79267 | 1.696154 |
| 29.44296 | 35.85531 | 21.20785 | 35.22908 | 2.224559 | 3.504446 | 3.230923 | 1.625599 | 9.58777 | 0.056547 |
| 10.83004 | 14.04777 | 4.437382 | 13.17179 | 1.677705 | 3.741616 | 0.413631 | 0.167053 | 0.047052 | 3.332381 |
| 22.1134 | 25.34848 | 14.61984 | 23.83516 | 0.066973 | 0.6795 | 0.027047 | 0.012347 | 1.232249 | 0.676695 |
| 0.915712 | 0.934057 | 6.208754 | 3.238318 | 0.030398 | 0.181137 | 0.128573 | 0.070861 | 2.004007 | 4.45856 |
| 0.921948 | 0.726753 | 0.001642 | 0.047504 | 0.003151 | 0.084648 | 0.172737 | 0.073958 | 2.490374 | 1.344691 |
| 3.572766 | 3.213949 | 3.625717 | 1.840132 | 0.086608 | 0.10594 | 0.314909 | 0.123374 | 2.618599 | 3.009331 |
| 4.544882 | 8.320708 | 12.78304 | 13.25918 | 0.872294 | 0.034796 | 1.121549 | 0.009288 | 0.028851 | 0.041086 |
| 1.455312 | 3.838549 | 7.036944 | 6.747381 | 0.005346 | 2.416348 | 0.002347 | 0.000105 | 0.000181 | 0.733376 |
| 41.06038 | 41.40696 | 51.66473 | 49.26686 | 0.078516 | 1.887795 | 0.024546 | 0.070842 | 0.007113 | 0.18775 |
| 3.824725 | 3.093232 | 1.327242 | 8.904403 | 0.017633 | 2.444037 | 0.002323 | 0.000332 | 0.000779 | 3.910006 |
| 9.434044 | 4.498769 | 5.00003 | 1.468281 | 0.190105 | 1.864721 | 0.016543 | 0.052297 | 0.001482 | 0.002732 |
| 26.23396 | 16.6488 | 15.93136 | 12.12818 | 0.014264 | 3.041862 | 0.00041 | 0.270103 | 0.047326 | 1.874953 |
| 8.85267 | 9.391818 | 3.006473 | 2.355472 | 0.076823 | 0.195665 | 0.586119 | 1.487288 | 0.00314 | 0.151426 |
| 7.104446 | 7.982351 | 1.133872 | 3.279545 | 0.062857 | 2.807455 | 0.267537 | 0.002874 | 1.431648 | 0.019383 |
| 30.57052 | 28.67832 | 14.51646 | 24.67275 | 0.219184 | 1.537091 | 1.534459 | 0.178642 | 0.243641 | 0.122858 |
| 1.0959 | 0.167476 | 0.896283 | 0.390786 | 0.00463 | 0.637596 | 2.20636 | 3.108983 | 1.048011 | 0.743213 |
| 0.033471 | 1.137218 | 0.076412 | 0.696042 | 0.152398 | 0.368541 | 2.057158 | 1.254294 | 0.131577 | 0.122787 |
| 0.367789 | 0.817847 | 0.439175 | 0.748448 | 0.500244 | 0.229219 | 1.379835 | 0.341287 | 0.000762 | 0.198693 |
| 122.6853 | 102.3164 | 98.17648 | 129.815 | 0.193034 | 1.869205 | 0.000764 | 0.019871 | 0.005133 | 0.101714 |
| 62.5777 | 49.90824 | 44.42305 | 64.78288 | 0.325066 | 1.368547 | 0.226724 | 0.016086 | 0.063577 | 5.476347 |
| 126.7697 | 115.8703 | 92.81202 | 121.9974 | 1.08E−06 | 1.218733 | 0.517183 | 0.12538 | 0.101552 | 0.28042 |
| 0.31742 | 0.869324 | 3.252251 | 2.243576 | 0.716729 | 0.942086 | 0.112677 | 0.226102 | 0.002441 | 6.072549 |
| 2.825014 | 2.753569 | 0.035264 | 0.167098 | 1.14862 | 0.35197 | 0.220176 | 0.269594 | 0.033503 | 0.469054 |
| 7.531897 | 6.034012 | 1.727697 | 2.088725 | 1.056769 | 0.060709 | 0.567891 | 0.2092 | 0.169587 | 0.395276 |
| 7.321939 | 6.16158 | 1.108569 | 6.770753 | 1.332019 | 4.639044 | 6.351499 | 0.803686 | 4.640986 | 0.135618 |
| 41.34678 | 22.8937 | 32.1492 | 39.14524 | 3.393039 | 7.351097 | 6.459715 | 1.069825 | 6.700015 | 3.989221 |
| 105.4998 | 99.34098 | 103.1453 | 79.45567 | 6.239171 | 8.52855 | 3.110578 | 1.248420 | 3.009236 | 0.902418 |

TABLE 45-continued

3-AcOEt-2

| | | | | | | | | |
|---|---|---|---|---|---|---|---|---|
| 0.00545 | 1.012838 | 0.982957 | 0.000167 | 0.000799 | 0.549811 | 3.394122 | 0.050518 | 0.72855 | 3.231429 |
| 0.115313 | 0.331933 | 2.199122 | 0.195453 | 0.0354 | 0.109202 | 2.495307 | 0.01149 | 0.880297 | 0.13435 |
| 0.215876 | 1.530943 | 0.953701 | 0.277472 | 0.360717 | 0.045638 | 0.806999 | 0.003362 | 0.992287 | 0.028182 |
| 7.680302 | 3.603229 | 2.497943 | 7.084477 | 0.077749 | 1.561426 | 0.034574 | 2.494304 | 1.5E−06 | 30.33657 |
| 0.666086 | 0.112094 | 0.116173 | 0.781134 | 0.019557 | 0.48218 | 0.015686 | 2.921901 | 0.000196 | 0.220205 |
| 2.220776 | 2.307461 | 2.031976 | 3.390368 | 0.193585 | 3.751031 | 0.22233 | 0.163364 | 0.034718 | 1.126785 |
| 0.050366 | 0.272915 | 0.072765 | 0.015768 | 0.074538 | 0.180642 | 0.000258 | 1.846503 | 0.012383 | 6.399505 |
| 0.000295 | 0.630947 | 0.619198 | 1.170003 | 0.173679 | 0.768992 | 0.537669 | 0.779786 | 0.33101 | 0.054993 |
| 0.356822 | 5.298302 | 4.266617 | 4.938 | 0.227297 | 0.970429 | 0.33988 | 0.78859 | 0.153244 | 2.637594 |
| 0.133068 | 3.92899 | 2.862842 | 4.783588 | 0.569369 | 1.883212 | 6.055162 | 0.511534 | 2.077172 | 0.002094 |
| 0.720696 | 0.590496 | 0.377539 | 0.76897 | 0.044185 | 1.557704 | 0.420176 | 0.000862 | 0.000349 | 0.290269 |
| 14.72732 | 28.17697 | 26.22044 | 32.31278 | 0.071977 | 0.003307 | 2.770875 | 0.000106 | 0.007371 | 1.379384 |
| 3.10157 | 0.021955 | 0.118844 | 4.43E−05 | 2E−05 | 2.853416 | 0.004577 | 0.01406 | 0.164349 | 0.00113 |
| 16.52167 | 9.400816 | 14.5197 | 10.86051 | 0.099141 | 2.478113 | 0.034797 | 0.383129 | 2.842856 | 0.005664 |
| 18.88018 | 7.040794 | 11.65335 | 10.17349 | 0.17644 | 2.022095 | 0.012963 | 0.010515 | 0.002039 | 0.00017 |

| THF | | | | $\theta_{u,mn}$ AcOEt | H$_2$O | | | |
|---|---|---|---|---|---|---|---|---|
| k2 | k3 | k4 | k5 | k6 | k1 | k2 | k3 | k4 |
| 6.060674 | 4.289945 | 0.988232 | 1.112137 | −0.22671 | 0.169875 | 2.066454 | 0.226295 | 0.852363 |
| 2.850266 | 10.10205 | 4.321398 | 10.61497 | 0.184008 | 3.033822 | 1.413013 | 6.642247 | 1.606723 |
| 5.018269 | 5.349045 | 0.63041 | 5.796349 | 0.266984 | 4.66632 | 0.959567 | 6.02586 | 1.579315 |
| 46.40998 | 50.70626 | 31.19133 | 40.21026 | 0.410715 | 2.964034 | 7.682774 | 1.124674 | 4.476576 |
| 25.63126 | 24.91648 | 12.07054 | 21.31803 | 0.493691 | 3.802859 | 7.14605 | 0.765943 | 4.431552 |
| 2.017973 | 0.592415 | 0.202183 | 0.725852 | 0.062976 | 0.506368 | 0.600438 | 0.841345 | 0.102346 |
| 14.82445 | 5.997685 | 18.58545 | 15.42416 | −0.54431 | 11.69837 | 8.311585 | 13.39836 | 3.894438 |
| 1.396762 | 2.056581 | 6.540204 | 6.168131 | −0.123 | 0.021087 | 0.002546 | 0.01038 | 0.01368 |
| 0.203226 | 1.399306 | 4.387548 | 4.251624 | −0.21086 | 4.62E−06 | 0.117269 | 0.096226 | 0.093358 |
| 67.20117 | 40.84917 | 58.1249 | 53.65069 | 0.42131 | 1.925998 | 1.234923 | 1.628069 | 0.685915 |
| 10.78439 | 7.093045 | 10.07087 | 8.699396 | 0.333454 | 1.485616 | 0.57304 | 1.116086 | 0.213719 |
| 0.003315 | 1.243794 | 2.782101 | 2.824032 | −0.08786 | 0.722829 | 5.523065 | 1.615172 | 6.372937 |
| 3.354685 | 6.610729 | 0.443318 | 1.004199 | −0.51768 | 0.158382 | 0.311211 | 0.014861 | 0.025187 |
| 0.332581 | 2.814726 | 0.073474 | 1.015219 | −0.36296 | 0.265857 | 0.34304 | 0.039698 | 1.334197 |
| 0.003546 | 1.440296 | 0.005174 | 1.017849 | −0.56368 | 0.102738 | 2.2344 | 2.077272 | 0.016234 |
| 24.84059 | 26.9737 | 12.50532 | 16.91898 | 0.154718 | 0.287647 | 0.114034 | 0.002626 | 0.046987 |
| 15.45086 | 14.95118 | 6.366874 | 8.391538 | −0.046 | 0.114551 | 0.073456 | 0.024854 | 0.01824 |
| 0.524326 | 0.000839 | 0.048197 | 0.150098 | −0.20072 | 2.026352 | 0.301823 | 1.62296 | 4.855892 |
| 0.496491 | 2.829777 | 0.518323 | 0.049193 | −0.73052 | 0.617244 | 4.421664 | 0.064722 | 0.427801 |
| 1.518903 | 0.659503 | 0.872093 | 6.337384 | −0.19639 | 1.826573 | 0.03891 | 0.101086 | 0.056321 |
| 0.103805 | 0.145268 | 0.068599 | 1.529056 | 0.093158 | 1.339103 | 0.149531 | 0.28383 | 0.143157 |
| 6.561693 | 11.38011 | 5.855145 | 2.038961 | 0.634131 | 0.669117 | 1.277334 | 0.154175 | 0.254696 |
| 1.662014 | 5.000225 | 2.568036 | 0.085967 | 0.823706 | 0.445404 | 1.630088 | 0.338407 | 0.389415 |
| 8.471159 | 4.477952 | 1.149706 | 6.240969 | 0.289575 | 6.8953 | 11.72873 | 15.50278 | 6.767512 |
| 0.027547 | 0.491441 | 3.300977 | 0.037968 | −0.49005 | 0.211241 | 0.013341 | 0.010737 | 0.140023 |
| 1.57876 | 0.061634 | 0.34568 | 0.535529 | −0.1488 | 0.018899 | 0.001256 | 1.122482 | 0.036991 |
| 0.449824 | 1.59E−06 | 1.235318 | 0.169985 | −0.11209 | 0.120834 | 0.038666 | 1.672237 | 0.153164 |
| 5.377395 | 7.123386 | 12.89879 | 3.271671 | 0.341257 | 0.078277 | 0.004904 | 0.499225 | 0.079267 |
| 2.510196 | 2.275342 | 2.673975 | 1.523301 | 0.377972 | 0.186309 | 0.033539 | 0.70521 | 0.191008 |
| 0.038872 | 0.026129 | 1.018414 | 0.017853 | 0.036715 | 2.368487 | 1.552251 | 0.75001 | 1.959273 |
| 0.158363 | 0.001675 | 0.01352 | 3.030376 | −0.15835 | 0.188146 | 0.644711 | 0.000946 | 0.38128 |
| 0.025932 | 0.005402 | 1.429914 | 0.551557 | −0.12236 | 0.602044 | 0.068265 | 0.602099 | 1.999912 |
| 0.128273 | 0.56779 | 0.668804 | 1.037226 | −0.18033 | 0.184621 | 0.062292 | 0.439469 | 1.488854 |
| 1.023696 | 0.043272 | 1.150034 | 3.075158 | 0.035994 | 0.64798 | 0.162659 | 0.482269 | 2.033331 |
| 0.126608 | 0.708316 | 0.806919 | 0.775869 | −0.02198 | 0.262371 | 0.220687 | 0.379482 | 1.694345 |
| 0.515252 | 1.283318 | 0.448349 | 0.858095 | −0.05797 | 2.939363 | 0.013917 | 0.32948 | 0.975115 |
| 0.896097 | 0.296693 | 1.737303 | 0.300043 | −0.28132 | 0.02747 | 0.031921 | 0.23278 | 0.034029 |
| 1.874867 | 3.492205 | 0.401588 | 5.115244 | −0.09274 | 6.085793 | 0.961249 | 0.324777 | 1.716833 |
| 0.827914 | 0.689747 | 1.025735 | 0.13478 | −0.11946 | 5.933377 | 0.750171 | 0.349074 | 1.339299 |
| 6.281976 | 5.724244 | 5.904556 | 0.756792 | 0.188582 | 6.188352 | 1.077522 | 0.591552 | 1.444761 |
| 0.06253 | 1.088115 | 2.257107 | 0.106685 | 0.161861 | 6.031957 | 0.837188 | 0.562067 | 1.156065 |
| 1.667393 | 0.004658 | 0.317228 | 0.560286 | −0.02672 | 4.583463 | 0.160519 | 0.382819 | 0.285593 |
| 0.154797 | 0.433846 | 1.291197 | 0.021844 | 0.792007 | 5.434462 | 2.005329 | 5.10903 | 6.718314 |
| 1.847544 | 3.878902 | 0.064842 | 2.184528 | 0.282192 | 1.333063 | 3.933194 | 0.004854 | 1.076726 |
| 0.588053 | 0.586748 | 0.742412 | 0.196983 | 0.61232 | 4.055212 | 5.352479 | 0.293169 | 2.472078 |
| 0.454484 | 0.594488 | 5.46532 | 2.50022 | −0.50981 | 0.160974 | 0.51741 | 1.387001 | 0.398129 |
| 1.073443 | 0.010948 | 0.767452 | 0.028429 | −0.17569 | 0.137583 | 1.241738 | 0.625609 | 0.017225 |
| 2.141547 | 0.141627 | 0.253853 | 0.132094 | 0.330128 | 11.7692 | 3.052238 | 2.981977 | 4.944083 |
| 51.58652 | 38.91101 | 34.10081 | 29.84668 | −0.52597 | 1.367594 | 0.00415 | 0.241869 | 0.209078 |
| 0.009744 | 0.547498 | 0.626959 | 1.079154 | −0.25212 | 0.122202 | 0.105133 | 0.247521 | 1.242951 |
| 0.108142 | 0.918572 | 0.117697 | 2.130501 | −0.11998 | 0.170018 | 0.324165 | 0.599248 | 0.900504 |
| 10.42813 | 6.151689 | 14.27573 | 3.894109 | 0.273847 | 0.447335 | 0.100968 | 0.41358 | 1.061906 |
| 1.267455 | 0.216128 | 2.576423 | 0.025291 | 0.405993 | 0.557183 | 0.32304 | 0.869167 | 0.724143 |
| 0.364598 | 1.239696 | 0.001883 | 2.576058 | 0.132145 | 0.086209 | 2.161808 | 2.618762 | 1.988074 |
| 2.40534 | 4.08E−05 | 0.000236 | 0.002609 | −0.26129 | 0.019806 | 0.304728 | 0.6506 | 0.066142 |
| 0.007346 | 0.014118 | 0.103423 | 1.665405 | −0.05033 | 1.216539 | 0.020618 | 0.134623 | 1.834049 |
| 0.360173 | 0.751954 | 0.000748 | 0.203864 | −0.66369 | 5.207995 | 0.651688 | 0.726289 | 4.85261 |

TABLE 45-continued

3-AcOEt-2

| | | | | | | | | |
|---|---|---|---|---|---|---|---|---|
| 0.251856 | 0.007093 | 0.005901 | 1.875635 | 0.210964 | 0.561842 | 0.155301 | 0.480259 | 0.768209 |
| 1.543643 | 0.134536 | 0.046842 | 0.4071 | −0.40239 | 2.416625 | 0.986101 | 0.00064 | 1.991579 |
| 0.065827 | 0.470534 | 0.426425 | 1.182076 | −0.61336 | 1.170047 | 0.910729 | 4.882193 | 0.138901 |

TABLE 46

3-AcOEt-3
$(\theta_{u,mn} - \theta_{g,mnk})^2 / \sigma_{\theta g,mn}^2$

| EtOH | | | | | | Benzene | | | |
|---|---|---|---|---|---|---|---|---|---|
| k5 | k1 | k2 | k3 | k4 | k5 | k1 | k2 | k3 | k4 |
| 0.250994 | 0.119144 | 1.940718 | 0.027282 | 0.005397 | 0.030042 | 1.07132 | 0.006831 | 1.192442 | 0.727235 |
| 0.498649 | 0.841332 | 3.657342 | 0.282927 | 0.000591 | 0.271805 | 1.670913 | 0.010388 | 1.512001 | 0.284205 |
| 0.812846 | 1.028484 | 3.847054 | 0.478396 | 0.00132 | 0.38638 | 6.570557 | 0.449945 | 1.482724 | 2.185549 |
| 1.346345 | 0.974133 | 0.687677 | 0.457101 | 0.172348 | 0.440253 | 0.010779 | 0.197379 | 0.156885 | 1.478578 |
| 1.641202 | 1.889472 | 0.116714 | 1.542884 | 0.175798 | 1.018167 | 0.170863 | 0.212332 | 0.161862 | 0.000282 |
| 0.127496 | 1.972322 | 2.294209 | 3.832783 | 0.004128 | 1.502123 | 0.32669 | 0.144482 | 0.108226 | 0.288203 |
| 13.08583 | 0.313348 | 0.296815 | 0.890736 | 0.929725 | 0.025755 | 0.007763 | 1.518624 | 0.000542 | 0.018644 |
| 2.622123 | 2.177924 | 1.267381 | 0.003552 | 0.003018 | 0.000456 | 0.180222 | 0.226888 | 0.036721 | 0.026649 |
| 1.715728 | 2.021528 | 1.024754 | 0.028371 | 0.00513 | 0.000183 | 0.102494 | 0.093394 | 0.069541 | 0.004571 |
| 7.07516 | 0.733034 | 0.297517 | 0.4979 | 0.871821 | 0.027797 | 0.005544 | 2.646806 | 0.004424 | 0.031785 |
| 5.364453 | 0.983169 | 0.36717 | 0.535765 | 0.531258 | 0.015123 | 0.019826 | 1.845019 | 0.035523 | 0.030445 |
| 3.174926 | 1.396333 | 0.443791 | 0.472116 | 0.010987 | 3.35E−05 | 0.031357 | 0.008378 | 0.091692 | 0.002371 |
| 1.508528 | 0.175687 | 0.463 | 0.158698 | 0.004412 | 1.456366 | 0.1953 | 0.363703 | 0.291905 | 0.011968 |
| 0.087011 | 0.930151 | 0.290026 | 0.001158 | 0.0834 | 0.824924 | 1.986027 | 0.117251 | 0.048088 | 0.011194 |
| 0.863676 | 1.440859 | 0.304402 | 0.143111 | 0.104526 | 0.012547 | 0.452859 | 4.879889 | 0.14208 | 0.878661 |
| 1.56084 | 1.44037 | 0.004325 | 0.362085 | 0.193049 | 0.000944 | 0.031634 | 0.378086 | 0.326563 | 0.022824 |
| 2.01155 | 1.308319 | 0.09978 | 0.34657 | 0.10763 | 0.156526 | 0.349252 | 0.044954 | 0.245564 | 0.00174 |
| 0.23271 | 1.151459 | 0.172347 | 0.312949 | 0.070346 | 0.32551 | 3.768625 | 2.436345 | 0.012366 | 0.64173 |
| 0.419686 | 4.948011 | 10.63045 | 1.648332 | 6.159545 | 5.788775 | 1.483038 | 0.064691 | 0.012848 | 0.328995 |
| 0.019386 | 1.241341 | 0.487936 | 2.206341 | 8.03E−05 | 3.248208 | 2.414905 | 0.122298 | 0.076494 | 0.503216 |
| 0.136381 | 7.173348 | 5.49236 | 11.7805 | 2.340809 | 8.438199 | 12.09601 | 3.015522 | 10.25274 | 8.419807 |
| 0.17345 | 9.539072 | 12.83343 | 6.927897 | 4.766758 | 15.53911 | 0.775618 | 0.029877 | 0.071638 | 1.102829 |
| 0.37612 | 25.40829 | 28.74289 | 28.38938 | 14.10445 | 29.83313 | 0.007207 | 1.140438 | 2.390799 | 3.846069 |
| 18.82608 | 15.71864 | 14.68668 | 25.05689 | 9.648933 | 12.43585 | 14.01656 | 14.28547 | 29.21981 | 16.97481 |
| 2.932893 | 0.433583 | 0.29481 | 0.544957 | 0.185772 | 0.589732 | 0.119401 | 0.972105 | 0.004284 | 0.00129 |
| 2.704398 | 0.48138 | 2.556413 | 2.100815 | 4.912345 | 0.224799 | 0.585859 | 0.53847 | 0.399204 | 0.228079 |
| 3.278478 | 0.403915 | 2.114936 | 2.432986 | 4.8507 | 0.239029 | 0.583108 | 0.78241 | 4.158397 | 1.45387 |
| 3.339739 | 2.049959 | 3.819485 | 0.005354 | 1.156119 | 2.261074 | 0.000789 | 0.840558 | 0.201058 | 0.102764 |
| 3.843966 | 3.705725 | 9.625798 | 2.381225 | 9.030025 | 3.681209 | 0.779488 | 3.230061 | 0.810267 | 0.40461 |
| 0.045309 | 0.335867 | 1.734851 | 2.65579 | 4.675314 | 0.244618 | 2.598483 | 2.601117 | 6.605862 | 0.334571 |
| 0.890345 | 1.014583 | 0.172668 | 0.930675 | 0.408677 | 0.964139 | 1.48E−05 | 2.52507 | 0.093377 | 0.02295 |
| 2.281098 | 1.643845 | 0.359407 | 0.583874 | 0.387734 | 0.057578 | 0.01802 | 2.747785 | 0.002258 | 0.018803 |
| 2.327395 | 1.91128 | 0.464992 | 0.90852 | 4.13E−05 | 0.126439 | 0.253595 | 3.330906 | 0.957479 | 4.27119 |
| 1.302792 | 0.415885 | 0.156402 | 0.054303 | 0.003472 | 1.408364 | 0.014261 | 0.802029 | 0.233387 | 0.010783 |
| 1.440866 | 0.741063 | 0.225344 | 0.181336 | 0.149837 | 0.972597 | 0.147218 | 0.009996 | 0.243425 | 2.073352 |
| 0.001097 | 0.883985 | 0.246705 | 0.587639 | 0.378161 | 0.693015 | 0.230462 | 0.81091 | 1.328886 | 5.134067 |
| 1.768295 | 0.073363 | 0.148864 | 0.508069 | 1.849567 | 0.09632 | 0.411877 | 1.575566 | 0.022519 | 0.027289 |
| 2.032444 | 0.34674 | 0.183886 | 1.005317 | 0.693817 | 0.47102 | 1.26184 | 0.314153 | 0.579477 | 0.285059 |
| 1.775428 | 0.180474 | 0.358303 | 1.269182 | 0.638363 | 0.202028 | 1.985424 | 0.024413 | 0.318581 | 2.544073 |
| 0.961843 | 0.267882 | 0.939697 | 4.195921 | 0.057375 | 0.345384 | 0.45104 | 1.306277 | 0.819752 | 1.126988 |
| 0.7206 | 0.141775 | 0.68115 | 2.402637 | 0.144659 | 0.145327 | 1.626406 | 0.619089 | 0.31799 | 3.525003 |
| 0.819136 | 0.074945 | 0.489043 | 1.38319 | 0.541612 | 0.056967 | 1.687287 | 0.279626 | 0.120199 | 3.552076 |
| 11.46048 | 0.361861 | 0.458239 | 0.640517 | 0.784457 | 0.451679 | 0.251283 | 0.900403 | 0.828246 | 0.240411 |
| 2.264802 | 0.068262 | 0.085341 | 0.147779 | 1.802702 | 0.95008 | 0.000217 | 1.96588 | 0.061189 | 0.11886 |
| 4.446792 | 0.8317 | 0.353542 | 0.53332 | 0.801552 | 0.322051 | 0.152477 | 1.018645 | 0.683894 | 0.116828 |
| 0.506473 | 19.91343 | 20.4138 | 25.94993 | 37.287 | 20.00352 | 3.556877 | 2.541129 | 5.112245 | 0.326591 |
| 0.015978 | 1.754397 | 0.000127 | 0.013518 | 0.321107 | 0.017551 | 0.504495 | 0.432255 | 0.978609 | 0.634559 |
| 6.780228 | 11.42836 | 3.288872 | 4.831887 | 3.221128 | 2.737128 | 0.720668 | 2.976372 | 1.08103 | 0.049439 |
| 0.529266 | 0.004521 | 0.000145 | 0.036758 | 2.008715 | 0.238046 | 0.823852 | 1.040779 | 0.10883 | 0.020219 |
| 0.370724 | 0.001805 | 0.00884 | 0.0179 | 2.493919 | 0.0018 | 4.021238 | 0.098088 | 0.170585 | 0.228927 |
| 0.43703 | 0.181006 | 0.031126 | 0.519876 | 1.158616 | 0.206509 | 0.30848 | 1.702563 | 0.033302 | 0.181314 |
| 0.190937 | 0.002354 | 0.102509 | 0.009921 | 1.361965 | 0.205767 | 1.786353 | 0.071058 | 0.000329 | |
| 0.230613 | 0.039983 | 0.009061 | 0.077854 | 3.299798 | 0.418479 | 1.457943 | 3.460396 | 4.705975 | 8.240152 |
| 0.021153 | 0.072683 | 0.56303 | 0.150112 | 3.58753 | 0.149505 | 0.007718 | 3.008974 | 0.119718 | 0.440592 |
| 1.734509 | 0.723933 | 0.131343 | 0.759215 | 0.103356 | 0.346779 | 0.015732 | 1.325836 | 0.016552 | 0.207139 |
| 0.108889 | 0.145324 | 0.062082 | 1.773044 | 0.328387 | 0.66086 | 0.71123 | 1.068571 | 0.017018 | 0.038519 |
| 2.372672 | 0.258953 | 0.231538 | 0.294633 | 1.305503 | 0.000816 | 0.412438 | 1.146285 | 0.027484 | 0.000501 |
| 0.192308 | 1.087852 | 0.284637 | 0.431698 | 0.603817 | 0.127115 | 2.030136 | 0.15025 | 0.004583 | 0.028199 |
| 0.022337 | 0.1068 | 0.207167 | 0.131687 | 1.578186 | 0.050942 | 0.840225 | 0.91571 | 0.028586 | 0.04893 |
| 2.859598 | 0.310848 | 0.244821 | 0.00424 | 1.367042 | 0.074718 | 0.195867 | 1.089563 | 0.034586 | 0.040377 |

TABLE 46-continued

3-AcOEt-3
$(\theta_{u,mn}-\theta_{g,mn k})^{\wedge}2/\sigma_{\theta g,mn}^{\wedge}2$

| Benzene | Hexane | | | | | AcOEt | | |
|---|---|---|---|---|---|---|---|---|
| k5 | k1 | k2 | k3 | k4 | k5 | k1 | k2 | k3 |
| 0.201253 | 0.24768 | 0.048765 | 0.210693 | 1.149307 | 0.488309 | 0.034476 | 0.276171 | 1.007523 |
| 0.113474 | 0.229461 | 0.002019 | 0.145074 | 3.38513 | 0.489181 | 0.117582 | 0.107027 | 1.137889 |
| 3.389332 | 0.125032 | 0.011743 | 0.110665 | 3.121461 | 0.253589 | 0.026551 | 0.222004 | 0.800923 |
| 0.27017 | 13.70815 | 18.27142 | 16.30129 | 8.515797 | 23.25576 | 0.012314 | 0.550944 | 2.41E−05 |
| 2.207916 | 10.41625 | 10.14092 | 8.605664 | 5.681205 | 18.6914 | 0.064359 | 0.001632 | 0.003869 |
| 2.705222 | 2.638727 | 0.688657 | 0.393324 | 0.835822 | 5.520018 | 0.187744 | 0.556935 | 0.005959 |
| 0.474776 | 19.44398 | 20.25006 | 9.005796 | 9.800083 | 12.18536 | 1.800988 | 2.853338 | 0.409532 |
| 3.481817 | 8.593469 | 4.998251 | 2.443486 | 1.406732 | 2.098029 | 2.249403 | 11.85744 | 5.68259 |
| 3.238045 | 7.107575 | 3.047686 | 1.705187 | 1.192889 | 0.810719 | 2.746646 | 12.02815 | 8.339875 |
| 0.120149 | 11.89708 | 24.16777 | 9.891164 | 16.82528 | 18.84726 | 0.434344 | 0.000512 | 0.273397 |
| 0.187419 | 5.067453 | 14.1665 | 5.2887 | 7.834198 | 12.89788 | 0.078549 | 0.17245 | 0.992264 |
| 2.844189 | 0.18279 | 0.578264 | 0.050287 | 0.038302 | 1.755472 | 1.682279 | 4.43755 | 7.431725 |
| 1.150846 | 2.27154 | 2.721777 | 1.825824 | 0.000901 | 2.087503 | 0.036761 | 0.320557 | 2.091929 |
| 0.273154 | 17.2977 | 1.464053 | 0.804443 | 0.185243 | 0.925305 | 0.198537 | 0.040405 | 2.522773 |
| 0.755867 | 1.233586 | 1.73487 | 0.849494 | 0.234859 | 0.812443 | 0.301748 | 0.002838 | 2.146263 |
| 1.241304 | 0.594327 | 6.045296 | 4.62101 | 5.565153 | 7.785488 | 0.097509 | 0.068889 | 2.54097 |
| 1.855072 | 1.249287 | 0.40202 | 2.97102 | 5.768936 | 4.088545 | 0.162333 | 0.041762 | 2.346152 |
| 1.558378 | 0.121318 | 1.679125 | 1.69E−07 | 0.243817 | 0.043705 | 0.3282 | 0.005923 | 1.506167 |
| 0.111071 | 0.019383 | 0.886105 | 2.277143 | 9.81E−05 | 0.990806 | 0.918478 | 0.233447 | 0.76293 |
| 0.051383 | 0.354689 | 0.172022 | 0.997541 | 0.294786 | 0.323297 | 0.02475 | 2.935746 | 1.034244 |
| 5.201553 | 0.74177 | 0.039046 | 0.596836 | 0.618888 | 0.044065 | 1.59442 | 5.644399 | 4.806306 |
| 0.279219 | 45.09749 | 55.16939 | 49.32496 | 60.33543 | 35.43113 | 3.07649 | 0.603396 | 5.603352 |
| 1.964594 | 229.3294 | 261.5823 | 267.0572 | 257.984 | 292.9465 | 6.507036 | 5.114002 | 13.21288 |
| 14.34884 | 6.147459 | 6.037001 | 8.081683 | 5.181284 | 16.2143 | 4.784021 | 7.193292 | 9.27159 |
| 0.925997 | 0.144028 | 1.919542 | 0.477223 | 0.334433 | 0.309292 | 0.004944 | 2.506857 | 0.001763 |
| 0.437846 | 0.03186 | 1.027573 | 0.005218 | 0.936897 | 0.001205 | 0.005834 | 1.846654 | 0.034513 |
| 5.684609 | 0.009714 | 0.470857 | 0.046878 | 1.508522 | 0.219711 | 0.08681 | 1.869572 | 0.029812 |
| 0.857183 | 0.453194 | 1.677984 | 6.251329 | 1.459788 | 3.754244 | 2.96E−05 | 1.529311 | 0.514506 |
| 0.032695 | 0.420354 | 2.458008 | 5.095375 | 2.720788 | 6.009111 | 0.01057 | 1.467789 | 0.080287 |
| 2.121368 | 0.123627 | 1.818624 | 0.980187 | 2.720637 | 5.012098 | 0.01022 | 1.879577 | 0.027685 |
| 1.488793 | 0.951913 | 0.022258 | 0.108271 | 0.579889 | 0.713623 | 0.011223 | 1.087034 | 0.750528 |
| 0.146003 | 1.010678 | 0.000978 | 0.221146 | 0.095125 | 0.834675 | 1.82613 | 0.014728 | 0.000571 |
| 0.397805 | 0.762752 | 0.003582 | 0.18452 | 0.015485 | 1.035689 | 2.926748 | 0.51823 | 0.138415 |
| 2.774073 | 0.078551 | 0.121409 | 0.263653 | 1.698493 | 0.144405 | 0.823071 | 0.74708 | 0.657628 |
| 0.256225 | 0.018723 | 0.154273 | 0.04545 | 2.745359 | 0.14741 | 1.584112 | 1.520725 | 0.075291 |
| 0.403216 | 0.51169 | 0.186196 | 0.058307 | 3.832063 | 0.117137 | 2.282781 | 2.319166 | 0.535797 |
| 0.014442 | 0.165909 | 0.160313 | 0.596886 | 1.025312 | 0.300711 | 1.750697 | 0.207605 | 0.662057 |
| 0.068756 | 0.034722 | 0.01085 | 0.414593 | 1.459412 | 0.079447 | 0.027412 | 0.594756 | 2.283253 |
| 0.004504 | 0.000174 | 0.005499 | 0.339901 | 1.734798 | 0.001192 | 0.473931 | 1.028039 | 0.513043 |
| 0.340539 | 5.272824 | 9.332104 | 2.453273 | 2.267662 | 7.972176 | 0.39774 | 0.693911 | 0.07815 |
| 0.000323 | 5.913282 | 3.579076 | 1.283063 | 2.823348 | 8.848733 | 0.928985 | 0.857588 | 0.077777 |
| 0.0577 | 2.219334 | 0.041804 | 0.102504 | 1.18848 | 3.281171 | 0.912922 | 0.845163 | 0.074355 |
| 0.108277 | 0.971789 | 0.736795 | 0.234756 | 0.368617 | 0.335891 | 8.836992 | 6.865715 | 5.615004 |
| 0.000523 | 0.205513 | 0.348951 | 0.622236 | 0.033075 | 0.794548 | 3.780848 | 0.841285 | 0.722907 |
| 0.247666 | 0.245806 | 0.013801 | 1.188247 | 0.209493 | 0.537764 | 3.319134 | 0.908259 | 7.529809 |
| 1.698833 | 0.000135 | 0.090808 | 1.473887 | 0.011965 | 0.57873 | 1.149591 | 18.52892 | 14.88106 |
| 0.021786 | 0.000634 | 0.100099 | 1.593145 | 0.016379 | 0.950871 | 0.000294 | 0.243435 | 1.08197 |
| 1.19474 | 0.001809 | 0.414051 | 0.032022 | 0.073308 | 2.513122 | 0.711586 | 0.232701 | 4.519111 |
| 0.095893 | 0.414232 | 0.572734 | 0.343892 | 4.270109 | 0.370186 | 0.081064 | 3.410453 | 0.00739 |
| 1.144427 | 0.176673 | 0.00922 | 0.243684 | 0.21912 | 1.370235 | 0.000121 | 0.357684 | 0.005486 |
| 0.012347 | 0.21323 | 0.051001 | 0.211303 | 0.079948 | 2.874291 | 0.031766 | 0.023591 | 0.008039 |
| 0.000935 | 0.020631 | 0.097183 | 0.191411 | 0.383217 | 3.085683 | 0.014719 | 0.026522 | 0.016473 |
| 0.584909 | 0.011912 | 0.239788 | 0.140658 | 0.377108 | 1.243496 | 0.07958 | 0.682988 | 0.014654 |
| 0.032485 | 0.001034 | 2.282691 | 0.116152 | 1.050648 | 2.424025 | 0.214337 | 2.963224 | 0.002918 |
| 2.437796 | 0.204451 | 1.229692 | 0.179913 | 0.715389 | 1.813389 | 0.000161 | 0.448002 | 1.667271 |
| 0.291378 | 0.974494 | 0.436774 | 0.017491 | 0.10372 | 0.639701 | 0.001118 | 0.030117 | 2.378029 |
| 0.626102 | 0.682024 | 0.514044 | 0.072485 | 0.257967 | 1.044163 | 0.008112 | 1.001091 | 0.772001 |
| 0.610213 | 5.010734 | 0.292429 | 0.384193 | 1.075189 | 0.44367 | 0.001242 | 2.181999 | 0.707315 |
| 0.167266 | 5.316228 | 1.483704 | 0.239161 | 1.276831 | 0.457564 | 0.012354 | 1.330066 | 0.401813 |
| 0.913421 | 2.983322 | 0.058244 | 0.338954 | 0.507571 | 0.272743 | 0.036354 | 3.185511 | 0.236058 |

TABLE 47

3-AcOEt-4

|  | | THF | | | | | log σ$_{rg,mn}$ | | |
|---|---|---|---|---|---|---|---|---|---|
| k4 | k5 | k1 | k2 | k3 | k4 | k5 | H2O | EtOH | Benzene |
| 0.742179 | 0.053647 | 2.456484 | 1.594506 | 0.095369 | 2.890517 | 0.039635 | −3.47051 | −4.20695 | −3.01438 |
| 0.478725 | 0.301322 | 1.128603 | 4.459691 | 0.490892 | 0.681162 | 0.039519 | 1.423286 | 0.497692 | −0.08048 |
| 0.772232 | 0.540806 | 1.778372 | 4.529524 | 0.760521 | 0.517052 | 0.070073 | 1.749125 | 2.144489 | 1.309926 |
| 0.512401 | 0.952593 | 0.007579 | 2.363769 | 0.349493 | 0.082773 | 0.007337 | 4.210396 | 2.683662 | 3.146059 |
| 0.134681 | 2.315253 | 0.520394 | 3.180278 | 0.700695 | 0.002178 | 0.040155 | 4.511755 | 4.725985 | 4.151946 |
| 1.312956 | 1.13294 | 2.945287 | 3.479527 | 1.23188 | 0.1565 | 0.133973 | −3.37465 | −0.12163 | −0.1664 |
| 0.001114 | 0.078903 | 1.038789 | 5.208214 | 0.710874 | 0.573663 | 1.639865 | −3.53899 | −4.81517 | −4.14567 |
| 5.871912 | 4.300937 | 0.830416 | 6.61718 | 1.918567 | 0.873873 | 0.95266 | 1.382503 | 0.58021 | 1.121538 |
| 9.277281 | 5.218759 | 1.438508 | 7.290135 | 2.655826 | 1.120702 | 0.958388 | 1.741738 | 4.397142 | 1.867993 |
| 1.354428 | 0.545188 | 0.926292 | 4.355731 | 0.095635 | 0.266796 | 1.794322 | 4.20986 | 3.877253 | 4.065613 |
| 2.543652 | 0.958715 | 0.267909 | 2.390823 | 0.035523 | 0.05456 | 1.442216 | 4.502093 | 7.334288 | 4.599096 |
| 9.289235 | 3.150091 | 3.910668 | 6.506974 | 4.36734 | 1.543851 | 0.812282 | −2.81705 | 2.017158 | −0.07503 |
| 0.006336 | 0.210526 | 0.000383 | 0.33402 | 0.745514 | 0.524333 | 0.998591 | −2.54899 | −3.73822 | −3.60914 |
| 0.056944 | 0.0007 | 2.331917 | 0.277614 | 0.000992 | 0.298969 | 0.12874 | 2.232861 | 0.673325 | 0.52533 |
| 0.074851 | 0.003658 | 5.124303 | 1.425371 | 0.440453 | 1.058582 | 0.188196 | 2.82389 | 2.29138 | 2.377234 |
| 0.026023 | 0.090357 | 0.90326 | 1.061823 | 1.158712 | 0.312399 | 1.026407 | 4.52849 | 3.418593 | 3.245467 |
| 0.019348 | 0.053362 | 2.558476 | 2.1885 | 2.043745 | 0.008211 | 2.020896 | 4.977347 | 4.815047 | 4.288023 |
| 0.418791 | 0.008424 | 17.28374 | 9.387662 | 6.355556 | 5.614586 | 7.986855 | −1.85188 | −0.43421 | 0.255924 |
| 0.915255 | 0.045407 | 0.035837 | 0.189084 | 0.072808 | 1.8756 | 0.093212 | −3.21894 | −4.00041 | −4.39092 |
| 0.883878 | 3.791665 | 11.2728 | 3.030689 | 10.73943 | 5.790313 | 4.669601 | 1.990366 | 0.825083 | −0.84587 |
| 5.249745 | 10.58692 | 8.070855 | 10.93814 | 15.78765 | 5.091344 | 13.0179 | 2.337258 | 2.032124 | 1.48009 |
| 5.138241 | 2.093588 | 0.025639 | 0.385813 | 0.004783 | 1.321611 | 0.292291 | 4.824302 | 2.611209 | 3.155974 |
| 14.82758 | 13.13081 | 0.278689 | 1.290213 | 0.583707 | 0.344533 | 1.256416 | 5.461588 | 3.586953 | 5.32421 |
| 10.93508 | 16.5219 | 2.646015 | 6.994745 | 8.342345 | 1.910437 | 7.809656 | −1.68006 | −1.31818 | 0.433949 |
| 0.036158 | 0.00608 | 1.053503 | 1.68983 | 1.037096 | 3.192014 | 0.019019 | −3.2729 | −3.9333 | −4.83793 |
| 0.131639 | 0.038946 | 7.999645 | 2.52817 | 12.3327 | 7.260005 | 5.300997 | 2.395255 | 1.121161 | 0.586189 |
| 0.11157 | 0.04307 | 1.617792 | 0.009108 | 3.347188 | 0.782397 | 3.00854 | 2.671859 | 2.476318 | 1.833904 |
| 3.139248 | 0.115579 | 0.329732 | 1.075213 | 0.209148 | 1.834987 | 0.254537 | 4.9501404 | 3.724711 | 4.348747 |
| 0.368273 | 0.07364 | 0.034262 | 0.742078 | 0.002829 | 0.769084 | 0.672389 | 5.213834 | 5.060598 | 5.343589 |
| 0.102608 | 0.045071 | 0.401576 | 0.161835 | 1.1951 | 0.041278 | 1.881661 | −1.9216 | −0.48259 | 0.760752 |
| 0.144796 | 0.144339 | 0.191934 | 0.504705 | 1.544533 | 0.478283 | 0.133588 | −3.33685 | −4.93122 | −4.45787 |
| 0.225858 | 0.011203 | 0.085009 | 0.337063 | 1.891552 | 0.358038 | 0.086633 | 2.617672 | −0.84783 | −0.52142 |
| 0.033257 | 1.005953 | 0.083333 | 0.529813 | 2.704535 | 0.088082 | 0.411433 | 1.895491 | 0.827268 | 1.224621 |
| 2.08E−05 | 0.072446 | 0.286828 | 0.624417 | 1.256906 | 0.555223 | 0.158184 | 6.047699 | 2.645935 | 4.198668 |
| 0.011001 | 1.048066 | 0.270939 | 0.375269 | 0.492813 | 1.012769 | 0.002438 | 5.744713 | 3.834929 | 4.787592 |
| 0.070066 | 4.163231 | 0.078308 | 1.032929 | 4.395371 | 0.519656 | 2.328135 | −1.07522 | −1.18013 | 0.031744 |
| 1.140497 | 1.18403 | 0.051931 | 1.831559 | 0.086649 | 3.571499 | 0.774784 | −1.98114 | −3.01957 | −4.7763 |
| 0.34279 | 3.629274 | 2.615608 | 10.37982 | 2.817785 | 7.42921 | 7.257289 | 2.302229 | 1.172873 | −0.60568 |
| 0.053691 | 0.935381 | 10.40678 | 18.08965 | 8.131541 | 12.56382 | 5.590071 | 2.531087 | 2.180185 | 0.824372 |
| 0.238425 | 0.091855 | 0.023758 | 0.608044 | 0.008117 | 2.433046 | 0.121255 | 5.313679 | 3.298982 | 4.056546 |
| 0.030888 | 0.144437 | 0.283998 | 0.209418 | 0.13592 | 1.490905 | 0.152261 | 5.661962 | 4.329304 | 5.29199 |
| 0.002188 | 0.181605 | 2.545619 | 1.062191 | 1.35747 | 0.670511 | 0.087322 | −1.57645 | −0.62874 | −0.38181 |
| 16.41175 | 13.48694 | 12.67606 | 21.67542 | 23.18638 | 29.42675 | 17.01136 | −3.49631 | −3.94273 | −4.91018 |
| 4.925374 | 5.255286 | 23.92205 | 40.9252 | 43.32971 | 32.92532 | 41.64016 | 2.424872 | 0.445872 | 0.883386 |
| 1.948764 | 5.22361 | 3.409937 | 13.33812 | 4.948826 | 8.693682 | 5.516919 | 2.589026 | 2.778786 | 0.220413 |
| 28.0738 | 18.73237 | 5.589316 | 9.554451 | 10.27435 | 17.15358 | 6.205382 | 5.021767 | 3.338671 | 5.535133 |
| 0.879 | 0.003426 | 0.909497 | 0.06349 | 2.519517 | 1.662914 | 0.72395 | 5.159181 | 5.413235 | 5.249684 |
| 0.119863 | 1.251421 | 0.75101 | 6.053313 | 0.786262 | 3.443651 | 1.101452 | −1.63969 | 0.909739 | 0.495249 |
| 1.087966 | 0.267923 | 0.14501 | 0.112503 | 0.302546 | 1.366263 | 0.087717 | −3.75061 | −4.03884 | −3.85018 |
| 2.756227 | 0.049479 | 0.049203 | 0.535387 | 0.046586 | 2.094031 | 0.05471 | 1.981961 | 2.272385 | 2.102403 |
| 2.208376 | 0.021297 | 0.087483 | 1.123396 | 0.009088 | 0.022114 | 0.761589 | 1.953076 | 4.092013 | 2.495732 |
| 2.176023 | 0.000373 | 0.217525 | 0.011227 | 0.532768 | 0.984021 | 0.349276 | 4.897952 | 5.078273 | 5.504239 |
| 1.226395 | 0.001805 | 0.101013 | 6.33E−05 | 0.402193 | 1.509044 | 0.000801 | 4.935532 | 6.916974 | 5.854076 |
| 0.005643 | 0.019877 | 0.000799 | 0.026451 | 0.083192 | 1.646741 | 0.895761 | −1.17598 | 0.633256 | −0.31503 |
| 0.015261 | 0.013607 | 0.000343 | 0.611854 | 0.925821 | 0.000106 | 0.673847 | −3.97888 | −1.75606 | −4.84518 |
| 0.005373 | 0.032553 | 0.38596 | 2.453731 | 0.064312 | 0.145416 | 1.396791 | 1.359908 | 2.462408 | 0.091022 |
| 0.001145 | 0.362178 | 0.277382 | 0.034205 | 4.182628 | 0.484135 | 0.825043 | 2.397467 | 3.352771 | 0.918108 |
| 0.034604 | 0.003333 | 0.002741 | 0.813148 | 0.849958 | 0.801096 | 0.396825 | 4.558042 | 3.121787 | 3.407953 |
| 0.008704 | 0.247057 | 0.016205 | 0.452728 | 0.641249 | 0.024124 | 0.878567 | 5.043107 | 3.956818 | 5.072329 |
| 0.001265 | 0.530609 | 1.686847 | 2.346218 | 8.503489 | 1.864582 | 5.420867 | −1.06582 | −1.14587 | −0.12107 |

| | log σ$_{rg,mn}$ | | | log σ$_{\theta g,mn}$ | | | | | |
|---|---|---|---|---|---|---|---|---|---|
| | Hexane | AcOEt | THF | H2O | EtOH | Benzene | Hexane | AcOEt | THF |
| | −4.10649 | −2.38020 | −1.85628 | −0.82928 | 0.823367 | −0.51055 | 0.992277 | −0.01687 | −0.89727 |
| | 0.688938 | 1.180556 | 0.570003 | −1.55647 | 0.340158 | −0.76988 | 0.467301 | −0.07627 | −0.43588 |
| | 1.072453 | 2.454608 | 2.150339 | −1.63936 | 0.400977 | −1.08067 | 0.485282 | 0.123082 | −0.0921 |
| | 3.374414 | 4.503642 | 2.094255 | −1.14365 | −0.67501 | −1.52378 | −1.8571 | −1.24557 | −0.59128 |
| | 4.422189 | 5.309541 | 3.505918 | −1.1801 | −0.63757 | −0.50805 | −1.42174 | −0.9184 | −0.22346 |
| | −1.31652 | −0.58079 | −0.29805 | −2.61649 | −1.8353 | −0.74507 | −2.09108 | −1.17808 | −1.17675 |
| | −5.18409 | −4.20603 | −2.91236 | −2.16383 | −1.07598 | 1.084797 | −0.78634 | −1.56827 | −0.63991 |
| | −0.22858 | −0.39937 | 0.259849 | −1.37949 | −1.08307 | −0.17791 | −0.871 | −2.29371 | −1.39059 |
| | 0.658653 | 0.724481 | 2.016578 | −1.37216 | −0.73084 | 0.417273 | −0.73762 | −2.03317 | −1.17522 |

TABLE 47-continued

3-AcOEt-4

| | | | | | | | | |
|---|---|---|---|---|---|---|---|---|
| 2.948359 | 2.288464 | 1.814887 | −1.17288 | −0.98772 | 0.319091 | −1.48448 | −1.58917 | −1.13088 |
| 4.283216 | 3.001095 | 3.289227 | −1.13063 | −0.69725 | 0.469739 | −1.13058 | −1.40378 | −1.16917 |
| −1.28754 | −1.63629 | −0.70151 | −3.16176 | −1.91056 | −0.38615 | −2.02085 | −2.98339 | −2.57999 |
| −3.45323 | −2.86846 | −2.63055 | −0.40833 | −1.46006 | −0.15372 | 0.262191 | −0.88764 | −0.58837 |
| 1.248007 | 0.60212 | 0.207069 | −1.49237 | −1.15723 | −1.74261 | 0.300856 | −1.27126 | −1.29522 |
| 1.521438 | 1.683112 | 1.784486 | −2.05044 | −0.51846 | −1.86177 | 0.407925 | −0.48163 | −1.06283 |
| 4.290344 | 3.604588 | 2.58891 | −0.3419 | −1.76309 | −0.29831 | −1.57369 | −0.42624 | −0.79534 |
| 4.912251 | 4.56719 | 4.147205 | −0.4135 | −0.61561 | −0.19836 | −1.35308 | −0.02066 | −0.70174 |
| −1.43277 | −2.33187 | −0.66004 | −2.20351 | −0.95833 | −1.7064 | −1.3211 | −0.98294 | −2.43581 |
| −4.18508 | −4.57844 | −2.66352 | −0.25239 | −1.97182 | −0.41206 | 0.566055 | −1.33803 | −0.7308 |
| 0.734052 | 0.285807 | 0.234313 | 0.394228 | −1.83933 | −1.48248 | 0.686205 | −1.9322 | −3.00454 |
| 1.36182 | 2.258278 | 1.282089 | 0.427422 | −1.40018 | −1.40448 | 0.839858 | −1.32376 | −1.9627 |
| 3.225993 | 3.283066 | 2.743928 | 0.533222 | −1.84778 | −0.56338 | −1.98657 | −1.85619 | −0.75504 |
| 4.055777 | 5.115025 | 3.888008 | 0.556183 | −1.64801 | −0.58531 | −2.40852 | −1.49817 | −0.53901 |
| −0.61674 | −0.16786 | −1.41821 | −2.43387 | −2.10459 | −2.01139 | −1.70592 | −1.94335 | −1.94459 |
| −3.99619 | −4.57673 | −2.56564 | −0.82216 | −1.35886 | 0.057138 | 0.385252 | −0.37197 | −0.95689 |
| 0.784886 | 2.386694 | 0.470495 | −0.2301 | −1.96415 | −0.86879 | 0.362596 | −0.47755 | −2.79221 |
| 0.952827 | 2.335711 | 2.321066 | −0.34122 | −1.17207 | −0.99518 | 0.428725 | 0.656463 | −1.47053 |
| 2.499667 | 4.986157 | 2.71242 | 0.119395 | −1.68121 | −0.2457 | −0.8037 | −1.60442 | −0.95537 |
| 3.978408 | 4.951408 | 4.257231 | 0.039681 | −1.65995 | −0.27385 | −0.4667 | 0.24632 | −0.59658 |
| −0.9661 | −0.20126 | 0.059249 | −2.41235 | −1.76205 | −0.90836 | −1.20675 | 0.271423 | −1.67284 |
| −3.59592 | −3.69173 | −2.1596 | −1.79439 | −1.19371 | −0.6284 | 0.809715 | −1.30587 | −0.12794 |
| 0.80426 | 0.42383 | 0.51278 | −0.45931 | −1.11443 | −1.16205 | 0.870868 | −1.51448 | −0.98185 |
| 1.003504 | 2.133733 | 2.193251 | −0.46491 | −8.54042 | −0.69015 | 0.84193 | −1.12517 | −0.76481 |
| 3.45203 | 3.075531 | 3.315992 | −0.35834 | −1.72089 | −0.99729 | −0.29057 | −1.21759 | −0.56195 |
| 5.019523 | 4.940724 | 4.691185 | −0.40388 | −0.70966 | −0.41013 | 0.18832 | −0.87095 | −0.76053 |
| 0.484981 | −0.02916 | −0.18164 | −2.05213 | −1.116 | −0.82419 | −0.6464 | −1.76629 | −2.12582 |
| −5.02918 | −2.07317 | −3.5853 | −1.36913 | −1.49909 | −1.03802 | 0.499388 | −1.34106 | −0.46286 |
| −0.18678 | 0.838193 | −0.03587 | −0.56432 | −1.20378 | −1.08991 | 0.459324 | −1.59999 | −1.97802 |
| 0.492859 | 2.038741 | 1.658616 | −0.32909 | −0.42158 | −0.19839 | 0.48639 | −0.50208 | −1.97447 |
| 2.583292 | 3.546491 | 2.6235 | −0.54307 | −1.49349 | −1.43594 | −1.82025 | −1.1087 | −0.65216 |
| 4.232906 | 4.911158 | 4.373398 | −0.31415 | −0.54561 | −0.31769 | −1.25587 | −0.23396 | −0.55993 |
| −0.69466 | −0.59548 | −0.03484 | −1.81488 | −0.9873 | −0.51292 | −1.53594 | −0.75271 | −1.96269 |
| −3.25609 | −3.40032 | −2.58869 | −0.83752 | 0.565473 | 0.611169 | 0.037197 | −1.06293 | −0.59583 |
| 0.257281 | 0.494048 | 0.969833 | −0.51511 | 0.632718 | 0.594448 | 0.835504 | −1.34173 | −2.24377 |
| 0.756698 | 1.443826 | 2.481655 | −0.43515 | 0.690223 | 0.321458 | 0.671697 | −0.5567 | −0.69441 |
| 3.852815 | 3.480733 | 2.713015 | −0.22912 | −2.0043 | −0.69921 | 0.647753 | −1.85841 | −1.08793 |
| 4.686197 | 4.999752 | 5.020012 | −0.23107 | −0.92487 | −0.61209 | 0.73689 | −0.3206 | −0.8862 |
| 0.162828 | −0.47851 | 0.577207 | −1.72139 | −1.09882 | −0.40571 | 0.565064 | −0.45378 | −0.76465 |
| −4.34306 | −2.56596 | −4.43024 | −1.2803 | 0.314511 | 0.558145 | −0.03673 | −0.25352 | −0.0916 |
| 1.395306 | 2.397084 | 0.725282 | 0.085808 | 0.456879 | −0.78658 | 0.722195 | 0.667138 | −1.09915 |
| 1.534186 | 2.81233 | 2.262165 | 0.038403 | 0.046801 | 0.655338 | 0.643474 | 0.757237 | −1.28364 |
| 4.403683 | 3.380728 | 2.933988 | 0.054007 | −0.66324 | 0.366502 | 0.534097 | 0.497352 | −0.52911 |
| 4.753436 | 4.689018 | 4.459714 | 0.009472 | 0.57047 | −0.84925 | 0.8618 | 0.758353 | −0.1815 |
| −0.61998 | 0.343889 | −0.14069 | −1.81933 | 0.339932 | 0.45126 | −0.87872 | −0.14241 | −1.07022 |
| −3.09943 | −3.29933 | −0.12005 | −0.81177 | −1.34576 | −0.35308 | 0.785952 | 0.817846 | 0.998935 |
| 2.1285056 | 2.322421 | 1.823127 | −0.45072 | −1.0943 | 0.04527 | 1.089347 | 0.547119 | −1.11656 |
| 1.222062 | 2.309211 | 1.954408 | −0.82505 | −0.04856 | 0.811424 | 0.943053 | 0.808506 | −0.46843 |
| 3.974758 | 5.180598 | 4.924648 | −0.15758 | −1.09899 | −0.38398 | −0.14212 | −0.19413 | 1.07302 |
| 3.311061 | 4.635536 | 4.926917 | −0.50587 | −0.22342 | 0.514798 | −0.71394 | 0.782028 | 1.093496 |
| −0.74758 | 0.103346 | 0.296609 | −1.29154 | 0.090747 | 0.241204 | −0.75044 | 0.355101 | −0.89061 |

TABLE 48

3-THF-1

| | | $r_{u,mn}$ | $(r_{u,mn}-r_{g,mnk})^2/\sigma_{rg,mn}^2$ | | | | | | | |
|---|---|---|---|---|---|---|---|---|---|---|
| | | THF | H$_2$O | | | | | EtOH | | |
| f | K$_{u,mn'}$ | k5 | k1 | k2 | k3 | k4 | k5 | k1 | k2 | k3 |
| 0.05 Hz | Ku', 12 | 0.548814 | 205.4892 | 190.1703 | 163.5002 | 179.2173 | 210.9225 | 1081.118 | 1156.662 | 1033.439 |
| | Ku', 13 | 11.02315 | 7.930676 | 11.43619 | 2.440604 | 3.970002 | 5.780093 | 3.753821 | 13.7257 | 4.811929 |
| | Ku', 14 | 36.63164 | 0.757736 | 0.026411 | 4.118444 | 2.366355 | 1.738072 | 3.686132 | 11.47451 | 2.817914 |
| | Ku', 23 | 20.0854 | 8.850124 | 7.857409 | 2.01949 | 3.472884 | 8.47372 | 58.90568 | 43.21731 | 34.28009 |
| | Ku', 24 | 66.74693 | 6.96416 | 6.427977 | 1.167853 | 2.4662 | 6.508408 | 5.636716 | 1.042713 | 4.964378 |
| | Ku', 34 | 3.323156 | 3181.245 | 3076.728 | 3072.236 | 3025.872 | 3211.76 | 0.808651 | 3.944947 | 0.127118 |
| 0.1 Hz | Ku', 12 | 0.276563 | 40.63258 | 36.57498 | 25.71251 | 27.48645 | 21.82117 | 726.5639 | 666.3807 | 668.3372 |
| | Ku', 13 | 10.98374 | 9.04991 | 1.513614 | 3.754696 | 2.323601 | 5.777337 | 1.58069 | 4.147883 | 4.881599 |
| | Ku', 14 | 35.46508 | 0.216299 | 4.977544 | 1.610178 | 2.942494 | 0.619966 | 0.014211 | 0.014428 | 0.039744 |
| | Ku', 23 | 39.74396 | 9.914685 | 3.069306 | 2.438068 | 2.105217 | 2.496365 | 5.306304 | 2.08317 | 1.8440306 |
| | Ku', 24 | 128.3291 | 6.575469 | 1.165076 | 1.001993 | 0.758546 | 1.035734 | 0.042871 | 0.027649 | 0.01093 |
| | Ku', 34 | 3.22887 | 907.1879 | 904.5502 | 827.8739 | 831.4015 | 830.361 | 0.001369 | 0.001301 | 0.004248 |

TABLE 48-continued

3-THF-1

| | | | | | | | | | | |
|---|---|---|---|---|---|---|---|---|---|---|
| 0.15 Hz | Ku', 12 | 0.235887 | 2.779056 | 4.269217 | 1.59045 | 0.059221 | 3.086472 | 55.29133 | 41.52362 | 47.22289 |
| | Ku', 13 | 10.12939 | 1.454397 | 0.194875 | 3.14876 | 2.71E−05 | 0.217377 | 3.718619 | 2.262128 | 3.261187 |
| | Ku', 14 | 36.62681 | 0.048833 | 0.989541 | 0.263316 | 1.497795 | 0.778165 | 3.344372 | 2.420995 | 2.747003 |
| | Ku', 23 | 42.94165 | 2.99863 | 2.614452 | 2.692386 | 0.001477 | 1.276865 | 4.501182 | 2.081798 | 2.483788 |
| | Ku', 24 | 155.2725 | 1.172811 | 0.606832 | 1.452712 | 0.314872 | 0.208792 | 1.688287 | 0.634396 | 0.490254 |
| | Ku', 34 | 3.615895 | 175.0686 | 200.2622 | 149.4909 | 166.8996 | 181.121 | 1.151055 | 1.030984 | 2.205416 |
| 0.2 Hz | Ku', 12 | 0.229287 | 23.23201 | 21.51316 | 12.04726 | 12.11669 | 11.45001 | 103.7637 | 97.00056 | 93.82466 |
| | Ku', 13 | 3.169456 | 0.196943 | 0.374918 | 0.347989 | 1.149414 | 1.333308 | 4.034428 | 2.182167 | 2.165407 |
| | Ku', 14 | 25.79207 | 0.185132 | 3.258053 | 0.49535 | 0.023653 | 0.001612 | 2.94914 | 1.442169 | 1.801818 |
| | Ku', 23 | 39.99114 | 5.813766 | 0.290683 | 0.76783 | 1.431654 | 1.404815 | 24.33673 | 33.16176 | 27.86519 |
| | Ku', 24 | 112.488 | 4.019323 | 0.044801 | 0.152934 | 0.439617 | 0.44814 | 25.95012 | 39.50878 | 26.75044 |
| | Ku', 34 | 2.812824 | 32.47903 | 45.64101 | 56.27997 | 52.46526 | 51.08969 | 0.029414 | 0.042375 | 0.262753 |
| 0.25 Hz | Ku', 12 | 0.10425 | 0.998676 | 0.060108 | 0.100791 | 0.009169 | 1.960343 | 9.19788 | 6.25616 | 7.987054 |
| | Ku', 13 | 7.673139 | 1.516701 | 0.28944 | 2.42879 | 0.392584 | 9.074785 | 0.971737 | 0.172941 | 0.480535 |
| | Ku', 14 | 17.52225 | 0.679027 | 0.049195 | 1.394639 | 0.099568 | 0.468108 | 0.299633 | 0.082486 | 0.024698 |
| | Ku', 23 | 73.59841 | 2.950435 | 0.095864 | 1.867445 | 0.184484 | 0.014866 | 0.515013 | 1.031557 | 0.898937 |
| | Ku', 24 | 168.0635 | 2.233748 | 0.006271 | 1.268877 | 0.039836 | 0.01141 | 0.236726 | 1.784869 | 0.927405 |
| | Ku', 34 | 2.283584 | 37.27651 | 25.06139 | 36.67628 | 27.33246 | 19.85377 | 0.018936 | 2.571193 | 0.793924 |
| 0.3 Hz | Ku', 12 | 0.115389 | 4.3572 | 0.891401 | 0.031168 | 0.404114 | 0.723259 | 131.6015 | 93.73221 | 113.2506 |
| | Ku', 13 | 7.045305 | 5.099823 | 0.369305 | 0.47751 | 0.726671 | 0.382201 | 26.95534 | 14.53722 | 17.33284 |
| | Ku', 14 | 23.20223 | 2.2754 | 0.025971 | 0.000946 | 0.161748 | 0.038215 | 23.64979 | 9.574258 | 16.18746 |
| | Ku', 23 | 59.0115 | 3.416253 | 0.020592 | 0.042268 | 0.101005 | 0.073923 | 26.64523 | 12.73484 | 20.98517 |
| | Ku', 24 | 194.342 | 3.003036 | 0.04131 | 0.001624 | 0.054621 | 0.026967 | 5.607986 | 8.052677 | 8.439294 |
| | Ku', 34 | 3.293289 | 50.22873 | 29.51534 | 30.22565 | 31.37774 | 30.41686 | 6.576672 | 1.043592 | 4.240625 |
| 0.35 Hz | Ku', 12 | 0.096728 | 0.127166 | 2.305542 | 0.005565 | 0.052908 | 0.015863 | 1.433816 | 1.768096 | 1.369399 |
| | Ku', 13 | 5.674566 | 1.447636 | 0.597908 | 4.229486 | 0.035857 | 0.394608 | 0.074615 | 0.204981 | 0.195082 |
| | Ku', 14 | 11.48504 | 1.31391 | 0.816203 | 3.391042 | 0.004498 | 0.307611 | 0.039576 | 0.018107 | 0.094194 |
| | Ku', 23 | 58.66515 | 2.507379 | 0.005807 | 0.838649 | 4.66E−08 | 0.050819 | 6.0386 | 7.411766 | 3.220233 |
| | Ku', 24 | 118.7353 | 2.311138 | 0.024626 | 0.503763 | 0.015978 | 0.021838 | 6.977497 | 7.289319 | 9.993007 |
| | Ku', 34 | 2.02395 | 7.377672 | 2.398238 | 11.59815 | 5.964087 | 5.394965 | 1.976290 | 0.621352 | 6.121855 |
| 0.4 Hz | Ku', 12 | 0.094684 | 1.683461 | 2.935812 | 0.026017 | 0.581587 | 0.487875 | 3.482989 | 5.05695 | 9.380207 |
| | Ku', 13 | 6.765355 | 1.949337 | 0.027621 | 2.656058 | 0.415832 | 1.063176 | 0.507786 | 0.997507 | 1.004308 |
| | Ku', 14 | 30.05602 | 0.025014 | 3.039002 | 0.005098 | 0.364541 | 0.133633 | 0.114236 | 1.01262 | 0.82303 |
| | Ku', 23 | 71.45171 | 4.913059 | 0.07985 | 1.431157 | 0.678035 | 1.417146 | 0.799405 | 1.170343 | 7.262949 |
| | Ku', 24 | 317.434 | 1.166939 | 0.81823 | 0.001203 | 0.003186 | 0.02096 | 1.64936 | 0.042272 | 0.288357 |
| | Ku', 34 | 4.442637 | 272.4471 | 245.903 | 273.9039 | 219.6805 | 252.4597 | 0.547099 | 0.514317 | 0.35114 |
| 0.45 Hz | Ku', 12 | 0.180343 | 25.96305 | 11.30214 | 15.26779 | 20.58637 | 23.39546 | 60.36174 | 54.44321 | 60.98401 |
| | Ku', 13 | 6.595964 | 3.119854 | 0.9939 | 5.047895 | 0.710585 | 5.728129 | 0.020536 | 0.005942 | 0.042339 |
| | Ku', 14 | 20.55597 | 0.87368 | 0.064964 | 1.751253 | 0.054186 | 0.046579 | 0.008301 | 0.016028 | 0.014554 |
| | Ku', 23 | 36.57457 | 4.486692 | 0.555907 | 2.74833 | 5.806406 | 0.259072 | 0.246617 | 0.19564 | |
| | Ku', 24 | 113.9827 | 5.764863 | 0.251456 | 2.584366 | 1.051054 | 2.447827 | 0.053598 | 0.020293 | 0.038432 |
| | Ku', 34 | 3.116447 | 31.01553 | 32.54848 | 34.47288 | 27.86763 | 50.56525 | 0.013052 | 0.228138 | 0.013314 |
| 0.5 Hz | Ku', 12 | 0.08721 | 6.102592 | 0.333641 | 1.004686 | 1.3613 | 1.843904 | 0.067945 | 0.062361 | 0.06394 |
| | Ku', 13 | 5.936958 | 5.314923 | 8.029898 | 5.340259 | 14.54714 | 4.142144 | 0.020742 | 0.004727 | 0.021493 |
| | Ku', 14 | 18.79978 | 0.036979 | 0.422259 | 0.00145 | 1.847564 | 0.134576 | 0.147336 | 0.065841 | 0.093068 |
| | Ku', 23 | 63.07372 | 9.618597 | 2.608855 | 2.475433 | 6.867095 | 2.67985 | 2.064472 | 4.535766 | 1.609939 |
| | Ku', 24 | 215.5695 | 1.540672 | 0.641403 | 0.177705 | 3.771377 | 0.023063 | 0.329204 | 0.726567 | 0.053434 |
| | Ku', 34 | 3.166568 | 35.58948 | 22.89732 | 30.04197 | 20.3928 | 37.4452 | 17.32141 | 8.585838 | 5.957917 |

| | | $(r_{u,mn}-r_{g,mnk})^2/\sigma_{rg,mn}^2$ | | | | | | | |
|---|---|---|---|---|---|---|---|---|---|
| | | EtOH | | | Benzane | | | | |
| f | Ku,mn' | k4 | k5 | k1 | k2 | k3 | k4 | k5 | k1 |
| 0.05 Hz | Ku', 12 | 1121.68 | 1078.213 | 107.6363 | 78.34027 | 94.91471 | 102.5305 | 114.1359 | 1029.202 |
| | Ku', 13 | 7.957939 | 5.024379 | 96.26114 | 69.50055 | 96.97302 | 89.22518 | 103.108 | 14.18067 |
| | Ku', 14 | 4.231233 | 2.875279 | 64.04827 | 47.59186 | 62.57968 | 52.20097 | 75.75697 | 104.3595 |
| | Ku', 23 | 53.82548 | 49.08146 | 1.62173 | 0.150651 | 0.099064 | 1.101299 | 4.157794 | 26.76139 |
| | Ku', 24 | 7.749392 | 7.236692 | 2.94567 | 0.222022 | 0.334001 | 3.759334 | 3.0933255 | 9.932518 |
| | Ku', 34 | 0.143573 | 0.117238 | 0.06487 | 1.87E−06 | 0.266547 | 1.253786 | 0.64038 | 27.27423 |
| 0.1 Hz | Ku', 12 | 679.8313 | 749.1879 | 234.6774 | 216.4451 | 260.1002 | 245.818 | 273.4386 | 1917.602 |
| | Ku', 13 | 3.194414 | 0.21235 | 8.13626 | 1.745285 | 8.286691 | 8.693258 | 8.530622 | 88.56052 |
| | Ku', 14 | 0.010734 | 2.083265 | 18.25876 | 8.133975 | 20.22034 | 17.96363 | 21.03394 | 248.0517 |
| | Ku', 23 | 2.75041 | 9.228472 | 0.193545 | 4.161742 | 1.100873 | 0.236648 | 2.737276 | 24.87082 |
| | Ku', 24 | 0.035277 | 3.045777 | 1.023815 | 6.89402 | 2.928123 | 2.40695 | 6.897743 | 0.819318 |
| | Ku', 34 | 0.001046 | 2.463843 | 0.085653 | 0.698724 | 0.085846 | 0.982563 | 0.159108 | 42.02869 |
| 0.15 Hz | Ku', 12 | 51.35823 | 69.38354 | 59.86151 | 68.47437 | 65.25967 | 65.30244 | 42.53875 | 30.72609 |
| | Ku', 13 | 0.508303 | 7.089349 | 20.04768 | 27.25044 | 22.67584 | 23.36287 | 11.27221 | 1.192825 |
| | Ku', 14 | 0.445068 | 6.853345 | 7.367898 | 9.109715 | 7.499516 | 7.893537 | 1.592163 | 29.63208 |
| | Ku', 23 | 8.821742 | 8.190977 | 4.411226 | 6.807597 | 9.241556 | 7.749935 | 1.586592 | 0.712884 |
| | Ku', 24 | 6.083471 | 1.107645 | 2.907038 | 6.903391 | 12.693 | 8.832026 | 10.24674 | 0.037405 |
| | Ku', 34 | 0.074353 | 4.859933 | 0.320355 | 0.128403 | 0.021224 | 0.080837 | 1.453603 | 99.66455 |
| 0.2 Hz | Ku', 12 | 72.57795 | 105.8661 | 585.0928 | 901.0691 | 978.7086 | 983.3766 | 913.8856 | 172.7452 |
| | Ku', 13 | 0.021352 | 2.700255 | 291.7471 | 277.518 | 288.6194 | 292.3745 | 237.9618 | 8.18652 |
| | Ku', 14 | 0.001362 | 2.66255 | 15.60324 | 18.77817 | 21.59091 | 24.42693 | 9.726259 | 22.28414 |

TABLE 48-continued

3-THF-1

|  |  |  |  |  |  |  |  |  |  |
|---|---|---|---|---|---|---|---|---|---|
|  | Ku', 23 | 34.98042 | 46.12481 | 12.89819 | 2.938171 | 9.77275 | 9.942113 | 8.247277 | 7.673376 |
|  | Ku', 24 | 45.30473 | 34.96418 | 4.972916 | 0.575542 | 1.067292 | 0.474573 | 3.738872 | 5.837774 |
|  | Ku', 34 | 0.26652 | 1.724079 | 1.321653 | 0.117918 | 0.001028 | 0.144198 | 1.562838 | 0.916542 |
| 0.25 Hz | Ku', 12 | 1.936153 | 2.984726 | 104.3677 | 102.6212 | 135.6788 | 124.6528 | 104.1432 | 13.60194 |
|  | Ku', 13 | 0.240789 | 1.920676 | 8.890085 | 2.240636 | 3.686774 | 11.13847 | 7.714821 | 2.169717 |
|  | Ku', 14 | 0.93826 | 0.635555 | 3.02412 | 1.779371 | 4.723386 | 4.944659 | 0.258131 | 18.31123 |
|  | Ku', 23 | 1.208814 | 0.384514 | 0.110257 | 3.002729 | 2.85655 | 0.176037 | 0.280694 | 15.74323 |
|  | Ku', 24 | 1.798307 | 0.117061 | 0.311088 | 1.048726 | 0.653397 | 0.082827 | 4.519288 | 0.023721 |
|  | Ku', 34 | 2.130551 | 0.011467 | 0.074622 | 0.042764 | 0.087682 | 0.003759 | 2.051697 | 4.843942 |
| 0.3 Hz | Ku', 12 | 118.7721 | 127.9833 | 75.16699 | 57.78563 | 88.92886 | 79.28307 | 65.90802 | 10.14216 |
|  | Ku', 13 | 30.36193 | 23.65589 | 90.35395 | 59.49943 | 74.41361 | 91.21559 | 66.23147 | 4.46461 |
|  | Ku', 14 | 20.46024 | 12.88332 | 32.20095 | 20.72361 | 32.04459 | 35.18907 | 19.4822 | 45.88627 |
|  | Ku', 23 | 15.79625 | 26.4428 | 0.231404 | 0.087972 | 3.875374 | 0.150039 | 0.170145 | 0.183999 |
|  | Ku', 24 | 6.913314 | 19.22878 | 0.00862 | 0.187463 | 2.63726 | 0.004832 | 1.151963 | 0.165782 |
|  | Ku', 34 | 3.157021 | 0.732548 | 1.00532 | 0.025922 | 1.455814 | 1.135793 | 0.184449 | 0.868621 |
| 0.35 Hz | Ku', 12 | 0.11758 | 1.519221 | 107.2764 | 111.7347 | 87.14979 | 111.3544 | 82.89955 | 149.7634 |
|  | Ku', 13 | 1.396746 | 0.157938 | 60.37771 | 75.35384 | 54.93444 | 58.2748 | 45.14692 | 19.19709 |
|  | Ku', 14 | 2.523709 | 0.011363 | 13.65904 | 17.27347 | 11.23167 | 5.257352 | 5.195737 | 25.27424 |
|  | Ku', 23 | 0.851953 | 5.147627 | 2.499781 | 1.152233 | 0.289328 | 5.207489 | 0.509018 | 23.29482 |
|  | Ku', 24 | 1.964023 | 4.998782 | 1.022785 | 0.493745 | 0.218419 | 5.249433 | 0.953031 | 1.244955 |
|  | Ku', 34 | 1.56169 | 0.500217 | 0.024755 | 0.029419 | 0.238651 | 2.10114 | 2.830831 | 0.734549 |
| 0.4 Hz | Ku', 12 | 13.54156 | 7.999592 | 116.4223 | 128.4201 | 93.74994 | 115.2579 | 95.83037 | 3.385986 |
|  | Ku', 13 | 6.32265 | 1.786556 | 3.88602 | 4.376146 | 5.141365 | 4.503687 | 13.90844 |
|  | Ku', 14 | 2.493579 | 1.04923 | 425.351 | 393.1267 | 434.7154 | 392.2051 | 460.6437 | 151.4448 |
|  | Ku', 23 | 3.191235 | 2.665945 | 0.056386 | 2.675168 | 3.82E-05 | 0.001785 | 4.24E-05 | 0.047254 |
|  | Ku', 24 | 0.279836 | 0.010656 | 0.025723 | 0.717155 | 0.564097 | 0.021329 | 0.804748 | 3.44896 |
|  | Ku', 34 | 1.280767 | 0.386021 | 1.902361 | 4.439701 | 1.568113 | 0.021446 | 2.039297 | 6.59739 |
| 0.45 Hz | Ku', 12 | 48.16739 | 37.24359 | 39.24066 | 49.74297 | 61.23374 | 63.0505 | 60.05793 | 124.277 |
|  | Ku', 13 | 2.033733 | 0.032308 | 0.220457 | 1.019017 | 0.31997 | 0.367894 | 0.38758 | 0.216028 |
|  | Ku', 14 | 2.08692 | 0.039195 | 1.145657 | 0.032151 | 2.016207 | 2.223557 | 2.091286 | 5.774091 |
|  | Ku', 23 | 3.859053 | 0.035057 | 0.007948 | 3.414107 | 0.183616 | 0.187664 | 0.06048 | 6.127651 |
|  | Ku', 24 | 2.935653 | 3.02E-05 | 0.018093 | 3.333309 | 0.131571 | 0.08624 | 0.053884 | 1.705811 |
|  | Ku', 34 | 1.268733 | 0.492759 | 0.250587 | 4.727275 | 3.794821 | 4.828827 | 2.301652 | 13.89733 |
| 0.5 Hz | Ku', 12 | 1.764108 | 0.06169 | 85.89225 | 64.69501 | 92.70708 | 95.95533 | 77.39473 | 1.46158 |
|  | Ku', 13 | 2.139894 | 0.011547 | 14.19984 | 8.293846 | 18.1388 | 16.93357 | 7.422901 | 0.116844 |
|  | Ku', 14 | 1.613252 | 0.080828 | 26.47474 | 23.9967 | 40.4808 | 29.13572 | 15.59273 | 15.24518 |
|  | Ku', 23 | 0.04632 | 2.72596 | 3.739454 | 2.54247 | 2.011086 | 5.805322 | 10.08239 | 0.231222 |
|  | Ku', 24 | 0.631214 | 0.234617 | 1.53581 | 0.128728 | 0.045906 | 3.646768 | 1.675986 | 12.27912 |
|  | Ku', 34 | 6.037262 | 7.729607 | 0.012994 | 0.855613 | 1.065877 | 0.353685 | 0.447056 | 15.94569 |

TABLE 49

3-THF-2

| Hexane | | | | AcOET | | |
|---|---|---|---|---|---|---|
| k2 | k2 | k4 | k5 | k1 | k2 | k3 |
| 1069.638 | 1059.117 | 961.9966 | 1066.595 | 24.10615 | 17.68553 | 27.13777 |
| 23.45714 | 20.08349 | 9.751647 | 21.21174 | 0.213514 | 0.446989 | 0.813618 |
| 137.4184 | 127.6311 | 104.853 | 130.977 | 1.088118 | 0.586397 | 0.01487 |
| 15.11551 | 23.55218 | 13.15462 | 25.34644 | 0.796427 | 0.159507 | 4.372979 |
| 3.849997 | 6.488523 | 1.718026 | 7.033282 | 0.904416 | 0.291702 | 5.182662 |
| 35.66796 | 35.63312 | 51.69025 | 35.72766 | 1.799695 | 0.115294 | 2.049123 |
| 1911.244 | 1981.523 | 1984.29 | 2066.342 | 113.8022 | 150.3397 | 126.5064 |
| 84.32938 | 96.63709 | 84.70329 | 110.3109 | 15.22659 | 19.29019 | 16.49682 |
| 229.4923 | 246.7073 | 216.2854 | 275.0057 | 16.39745 | 29.78426 | 27.47219 |
| 27.41838 | 30.52741 | 46.22194 | 28.88617 | 10.23691 | 21.88703 | 13.50237 |
| 2.161572 | 2.146402 | 7.420062 | 1.232306 | 26.07122 | 41.9536 | 23.74676 |
| 31.31603 | 34.07194 | 22.30658 | 40.64131 | 0.003401 | 1.250977 | 1.577975 |
| 53.75526 | 48.72792 | 53.96578 | 45.86317 | 4.435795 | 6.445588 | 1.561334 |
| 7.303456 | 5.901026 | 6.345485 | 2.276108 | 2.485454 | 2.051193 | 0.017972 |
| 59.92071 | 55.6308 | 55.61847 | 39.69295 | 9.898364 | 7.928062 | 2.001047 |
| 3.743564 | 0.973636 | 1.613796 | 6.271773 | 0.278686 | 1.124389 | 0.294679 |
| 1.204591 | 0.005138 | 0.210704 | 2.274338 | 0.021379 | 0.670591 | 0.045955 |
| 67.6344 | 79.771 | 71.03815 | 71.63474 | 85.85349 | 60.98256 | 71.16149 |
| 197.6754 | 213.7884 | 175.2851 | 212.2553 | 204.0891 | 215.1061 | 212.9253 |
| 12.83415 | 16.31847 | 5.750815 | 15.37324 | 3.068505 | 5.715956 | 1.209169 |
| 35.93694 | 40.0307 | 26.17053 | 38.12298 | 0.61787 | 1.826751 | 0.130961 |
| 8.082205 | 8.136526 | 19.16453 | 13.5831 | 2.582501 | 1.8381 | 4.579335 |
| 0.582586 | 0.756555 | 2.832279 | 3.769066 | 0.427303 | 0.094006 | 1.026506 |
| 6.822284 | 6.322827 | 6.89538 | 4.319284 | 0.027705 | 0.518148 | 0.010086 |
| 12.84286 | 18.56182 | 24.99117 | 25.6552 | 2.593149 | 7.457428 | 12.98395 |
| 2.136851 | 4.904699 | 8.457283 | 8.139845 | 0.015524 | 2.25896 | 0.009985 |
| 28.12273 | 28.40969 | 37.00372 | 34.97877 | 9.48E-06 | 2.726141 | 0.01451 |

TABLE 49-continued

| 3-THF-2 | | | | | | |
|---|---|---|---|---|---|---|
| 11.51117 | 10.21365 | 6.703856 | 19.54653 | 0.000117 | 2.84033 | 0.028997 |
| 1.759536 | 0.144347 | 0.245001 | 0.280236 | 0.048299 | 4.094926 | 0.619448 |
| 14.31101 | 6.90107 | 6.055714 | 3.810221 | 0.351543 | 1.054513 | 0.478988 |
| 16.79263 | 17.53219 | 8.159343 | 7.061204 | 0.918227 | 0.828603 | 4.003982 |
| 7.914202 | 8.839371 | 1.470489 | 3.944817 | 0.001187 | 2.129508 | 0.090469 |
| 65.78753 | 82.99763 | 40.85684 | 56.98829 | 1.695248 | 0.164794 | 0.163934 |
| 2.492112 | 0.885538 | 2.185898 | 0.006712 | 0.48866 | 2.475807 | 5.10892 |
| 0.06856 | 0.975183 | 0.126251 | 0.8339 | 0.226326 | 0.272189 | 1.819989 |
| 1.328221 | 0.128394 | 1.461031 | 1.951365 | 2.625543 | 0.188621 | 0.068429 |
| 180.2403 | 155.1308 | 150.0233 | 188.6127 | 0.444676 | 1.211840 | 0.002232 |
| 33.44746 | 24.27741 | 20.59193 | 35.06479 | 0.037285 | 3.736934 | 0.082432 |
| 40.2442 | 34.20999 | 22.26447 | 37.57526 | 1.099606 | 4.629151 | 0.107866 |
| 9.204803 | 11.57884 | 18.26657 | 15.74816 | 3.202417 | 0.000766 | 0.36841 |
| 0.005986 | 0.009747 | 2.466025 | 1.820797 | 3.8573 | 0.089397 | 0.176959 |
| 2.370603 | 2.655855 | 0.012026 | 0.057835 | 4.490117 | 1.78561 | 0.113847 |
| 3.427444 | 2.649344 | 0.039328 | 3.053738 | 0.027875 | 1.361123 | 2.35023 |
| 13.80109 | 4.283129 | 8.731212 | 12.54188 | 0.090435 | 0.323244 | 0.159083 |
| 137.4851 | 130.4412 | 134.7954 | 107.493 | 10.92185 | 13.55457 | 6.375483 |
| 0.071025 | 1.437799 | 0.538014 | 0.032308 | 0.094712 | 1.042387 | 4.502015 |
| 1.763621 | 2.448124 | 6.108094 | 0.298566 | 0.829188 | 0.153657 | 0.734802 |
| 4.086027 | 7.808087 | 6.41892 | 1.061308 | 12.65049 | 10.04755 | 4.234644 |
| 163.9183 | 142.3235 | 134.8435 | 161.1222 | 2.015028 | 0.201405 | 2.287384 |
| 1.513598 | 0.560922 | 0.570003 | 1.664703 | 0.00015 | 0.294009 | 0.00072 |
| 14.9294 | 15.15284 | 14.4332 | 17.76561 | 0.04853 | 1.627089 | 0.035873 |
| 0.965998 | 1.840023 | 1.056724 | 0.400249 | 3.370540 | 2.835509 | 4.380051 |
| 0.419573 | 0.019725 | 0.014874 | 0.173669 | 1.267704 | 2.515704 | 2.080618 |
| 7.762236 | 20.16586 | 18.10005 | 19.45691 | 0.128236 | 0.022574 | 0.061435 |
| 0.001961 | 2.395427 | 1.545909 | 3.161581 | 0.085022 | 0.761634 | 3.846064 |
| 1.171916 | 0.286157 | 0.145116 | 0.413975 | 0.000319 | 2.07484 | 0.207807 |
| 12.50182 | 25.06375 | 23.22047 | 28.97245 | 0.027728 | 0.001959 | 2.442424 |
| 3.559992 | 0.074988 | 0.221231 | 0.01751 | 0.001099 | 2.98106 | 0.011085 |
| 25.34052 | 16.68515 | 23.32063 | 26.26385 | 0.001932 | 1.698577 | 0.007118 |
| 32.85955 | 16.32679 | 23.04957 | 20.94695 | 0.029692 | 4.057663 | 0.49874 |

| AcOET | | THF | | | | |
|---|---|---|---|---|---|---|
| k4 | k5 | k1 | k2 | k3 | k4 | k5 |
| 11.36203 | 19.63339 | 0.899543 | 0.309203 | 0.027369 | 0.831169 | 0.724545 |
| 0.512183 | 0.032512 | 0.56877 | 0.095289 | 3.235643 | 0.4889 | 3.528882 |
| 0.630822 | 0.117525 | 1.840671 | 4.861087 | 5.186724 | 0.575507 | 5.527326 |
| 0.161238 | 0.371841 | 0.570211 | 0.2503 | 0.653907 | 0.526917 | 0.000839 |
| 0.39364 | 0.693087 | 0.000538 | 1.416987 | 1.254671 | 0.15781 | 0.555956 |
| 0.040441 | 0.122079 | 1.007595 | 4.84527 | 2.384034 | 0.109709 | 2.665784 |
| 146.1425 | 119.2328 | 0.001036 | 0.057095 | 1.304639 | 0.518197 | 0.122987 |
| 13.93553 | 8.438612 | 6.30707 | 6.027824 | 4.637574 | 1.165595 | 1.330418 |
| 28.12837 | 16.42684 | 2.984 | 5.315276 | 2.475499 | 0.437777 | 0.482119 |
| 24.12637 | 18.10919 | 3.573043 | 4.406092 | 0.085716 | 2.36863 | 1.508348 |
| 39.66284 | 30.05125 | 2.997705 | 6.028096 | 0.449611 | 1.39409 | 0.915327 |
| 3.000879 | 2.519486 | 0.412687 | 3.313092 | 0.419091 | 0.008961 | 0.006747 |
| 9.583963 | 7.405964 | 0.221638 | 0.27717 | 0.045407 | 2.863618 | 1.029899 |
| 2.124031 | 1.465158 | 3.52576 | 4.104058 | 0.855313 | 8.257618 | 2.543914 |
| 9.469678 | 7.683121 | 5.758019 | 4.425809 | 0.712481 | 4.478044 | 1.071895 |
| 4.894995 | 2.188903 | 0.100682 | 0.107271 | 0.298466 | 1.254811 | 0.295113 |
| 3.451655 | 1.343137 | 0.49923 | 0.28135 | 0.217474 | 0.769248 | 0.253531 |
| 92.03033 | 81.07548 | 2.161334 | 0.795462 | 0.038711 | 0.002679 | 0.048243 |
| 197.9499 | 252.5204 | 2.714352 | 1.394063 | 0.041262 | 1.358108 | 4.439954 |
| 0.748573 | 0.453461 | 5.31802 | 2.934507 | 1.671075 | 2.000702 | 8.988115 |
| 0.173173 | 0.339669 | 4.937821 | 1.160615 | 1.037069 | 2.760319 | 5.948794 |
| 4.19252 | 10.22079 | 0.886628 | 0.242675 | 0.101915 | 0.49254 | 2.644783 |
| 0.756035 | 4.733419 | 0.772043 | 0.561115 | 0.039145 | 0.189885 | 3.045258 |
| 0.011989 | 1.339735 | 0.015813 | 1.694743 | 0.257469 | 0.287789 | 0.791193 |
| 6.973113 | 7.366605 | 0.019 | 0.020472 | 0.129955 | 2.179528 | 0.021224 |
| 0.001701 | 0.001445 | 1.454836 | 2.580129 | 0.357667 | 0.056718 | 1.169836 |
| 0.00012 | 0.03717 | 0.51054 | 0.151697 | 0.079794 | 1.939524 | 0.01718 |
| 0.1966 | 0.022467 | 0.665316 | 1.339149 | 2.27184 | 5.903851 | 0.418701 |
| 0.184349 | 0.383834 | 1.876106 | 0.071243 | 0.036473 | 0.100987 | 0.006926 |
| 0.37105 | 0.244822 | 3.679735 | 0.123773 | 0.504962 | 2.427799 | 0.172523 |
| 6.026806 | 1.66784 | 0.014932 | 0.017163 | 0.094783 | 0.0227 | 2.172253 |
| 0.072834 | 0.960889 | 0.003429 | 0.128887 | 0.015455 | 1.942149 | 0.29686 |
| 0.169073 | 0.115767 | 0.189357 | 0.182767 | 0.001033 | 2.610185 | 0.054186 |
| 6.44216 | 3.235086 | 0.063915 | 0.162001 | 0.667986 | 0.214472 | 1.309487 |
| 1.070386 | 0.076938 | 0.212578 | 0.217597 | 0.634506 | 1.017958 | 0.982821 |
| 0.107816 | 0.884891 | 0.381577 | 0.11948 | 0.004812 | 3.00349 | 0.016806 |
| 0.131621 | 0.086126 | 0.054451 | 0.155512 | 5.74E−05 | 0.586441 | 1.210078 |
| 0.792271 | 0.261244 | 0.261015 | 0.211505 | 0.001559 | 1.429348 | 0.186993 |
| 1.984688 | 0.416982 | 1.005024 | 5.403143 | 0.492167 | 0.269642 | 1.357068 |
| 2.011952 | 0.798384 | 0.008295 | 0.017746 | 0.000375 | 0.003221 | 2.259721 |

TABLE 49-continued

3-THF-2

| | | | | | | |
|---|---|---|---|---|---|---|
| 1.992302 | 0.503 | 0.710364 | 1.63238 | 0.234817 | 0.000485 | 3.438551 |
| 2.397486 | 0.461296 | 1.56625 | 3.663645 | 0.47753 | 0.003547 | 1.880496 |
| 0.008224 | 1.362175 | 0.004936 | 0.002032 | 0.048456 | 2.480085 | 0.08452 |
| 1.228598 | 0.198643 | 0.340445 | 0.002979 | 0.308764 | 1.343713 | 0.00412 |
| 3.529188 | 5.230159 | 1.487475 | 0.24719 | 1.07259 | 1.279834 | 0.508038 |
| 0.254762 | 1.283762 | 1.458924 | 0.005172 | 0.028487 | 3.012185 | 0.958384 |
| 0.378538 | 0.046567 | 1.154543 | 0.107658 | 0.364 | 2.509082 | 0.768372 |
| 9.085031 | 3.94168 | 0.740798 | 0.189078 | 0.425413 | 2.348275 | 0.44239 |
| 0.014165 | 2.888566 | 29.56838 | 14.16145 | 22.162222 | 26.07078 | 30.05598 |
| 2.425099 | 0.019068 | 0.115664 | 0.505014 | 0.00482 | 2.563716 | 0.052656 |
| 0.065049 | 0.225489 | 0.007172 | 0.668042 | 0.035256 | 2.217891 | 0.095242 |
| 12.02548 | 4.929288 | 0.588214 | 0.004545 | 0.986534 | 0.231986 | 1.781191 |
| 0.030234 | 1.649986 | 0.432228 | 0.054693 | 0.182373 | 0.508622 | 1.104555 |
| 2.968324 | 0.196597 | 0.07219 | 0.540557 | 0.058549 | 1.95657 | 0.052314 |
| 0.048498 | 0.886713 | 0.000624 | 2.470261 | 0.000208 | 2.96E−05 | 0.000917 |
| 0.026458 | 0.030161 | 0.049221 | 0.1621 | 0.18986 | 2.2E−05 | 2.583782 |
| 0.012555 | 0.000253 | 1.059581 | 0.555408 | 0.521342 | 0.029744 | 0.093881 |
| 0.024399 | 0.196822 | 0.000225 | 0.205433 | 0.017642 | 0.000796 | 2.011132 |
| 0.12115 | 2.002704 | 0.077114 | 2.087635 | 0.324014 | 0.000198 | 0.189759 |
| 0.23992 | 0.406428 | 0.225851 | 0.053863 | 1.378784 | 0.027143 | 2.482183 |

| $\theta_{u,mn}$ THF | $H_2O$ | | | |
|---|---|---|---|---|
| k6 | k1 | k2 | k3 | k4 |
| −0.42718 | 0.759633 | 3.596329 | 0.000266 | 1.911706 |
| −0.02111 | 0.591536 | 0.046869 | 2.574585 | 0.086962 |
| 0.227422 | 3.827282 | 0.533554 | 5.066731 | 1.108567 |
| 0.406067 | 2.93355 | 7.801838 | 1.093763 | 4.414693 |
| 0.654597 | 6.119398 | 10.22024 | 1.956873 | 6.910727 |
| 0.24853 | 8.866339 | 2.223573 | 1.81925 | 3.78742 |
| −1.90099 | 231.9335 | 215.8555 | 239.3039 | 189.9575 |
| −0.52446 | 3.411493 | 3.770517 | 4.38533 | 3.516655 |
| −1.0175 | 10.10676 | 12.41651 | 12.21273 | 12.15782 |
| 1.276528 | 17.23295 | 15.01351 | 16.31686 | 12.89652 |
| 0.883496 | 8.542032 | 6.055592 | 7.619072 | 4.692054 |
| −0.39303 | 64.9003 | 91.31711 | 71.85568 | 94.67964 |
| −1.08078 | 1.545938 | 1.969104 | 0.935651 | 0.47153 |
| −0.37502 | 0.21342 | 0.408749 | 0.06395 | 1.21316 |
| −0.63351 | 0.745194 | 4.15144 | 3.936223 | 0.172477 |
| 0.705761 | 1.721318 | 1.239553 | 0.68377 | 0.984913 |
| 0.447269 | 1.175783 | 1.034076 | 0.345897 | 0.373091 |
| −0.25849 | 3.789885 | 1.150572 | 3.229891 | 7.43583 |
| −1.14816 | 1.750852 | 6.97131 | 0.627189 | 1.419943 |
| −0.41625 | 2.24921 | 0.002404 | 0.028802 | 0.007937 |
| −0.57174 | 2.530514 | 0.002206 | 0.009821 | 0.003058 |
| 0.731917 | 0.492737 | 1.553103 | 0.25877 | 0.38529 |
| 0.576425 | 0.654764 | 1.588134 | 0.193546 | 0.232558 |
| −0.15549 | 5.598458 | 2.723628 | 1.294379 | 6.118601 |
| −1.24792 | 4.770084 | 3.385396 | 2.627065 | 4.404285 |
| −0.57976 | 0.164012 | 0.257073 | 0.267303 | 0.122581 |
| −0.55539 | 0.101228 | 0.220091 | 0.393598 | 0.075303 |
| 0.668161 | 0.320691 | 0.129704 | 0.993354 | 0.326792 |
| 0.662533 | 0.497202 | 0.208508 | 1.239344 | 0.488517 |
| −0.00563 | 1.137291 | 0.598059 | 0.154827 | 0.85968 |
| −0.85952 | 22.20275 | 12.07758 | 18.04093 | 23.96787 |
| −0.31091 | 0.227952 | 0.312317 | 0.227985 | 1.24481 |
| −0.38229 | 0.011705 | 0.370082 | 0.116581 | 0.807662 |
| 0.558809 | 2.412367 | 0.102926 | 2.081278 | 4.726958 |
| 0.487231 | 1.625182 | 0.08575 | 1.900611 | 4.261232 |
| −0.07136 | 3.308059 | 0.049426 | 0.460164 | 1.192091 |
| −0.5482 | 1.476446 | 1.508018 | 2.346481 | 0.748019 |
| −0.11983 | 5.85479 | 0.970789 | 0.273131 | 1.595187 |
| −0.05461 | 6.380801 | 0.914503 | 0.463769 | 1.55514 |
| 0.428574 | 8.414258 | 2.105783 | 1.39764 | 2.608472 |
| 0.493586 | 8.469082 | 1.874556 | 1.449317 | 2.33697 |
| 0.065012 | 7.312574 | 0.929148 | 1.39712 | 1.20491 |
| −0.68619 | 1.176224 | 3.998542 | 1.334985 | 0.678582 |
| −0.27068 | 0.052511 | 1.118935 | 0.732329 | 0.012594 |
| −0.48333 | 0.102888 | 0.38508 | 1.326053 | 0.014571 |
| 0.415493 | 0.581186 | 3.545246 | 0.0002 | 0.283658 |
| 0.202852 | 0.727444 | 2.548217 | 0.095465 | 0.123015 |
| −0.21264 | 0.156251 | 1.659852 | 1.712174 | 0.659038 |
| −0.41357 | 0.585317 | 0.219774 | 0.007642 | 0.002795 |
| −0.08197 | 0.255766 | 0.230786 | 0.427291 | 0.919135 |
| −0.13813 | 0.155913 | 0.304573 | 0.572501 | 0.933971 |
| 0.3316 | 0.523521 | 0.136735 | 0.48695 | 0.952132 |

TABLE 49-continued

3-THF-2

| | | | | |
|---|---|---|---|---|
| 0.275435 | 0.380837 | 0.192755 | 0.644752 | 0.960974 |
| −0.05616 | 0.753132 | 0.095397 | 0.208679 | 0.061775 |
| −0.31793 | 0.071958 | 0.18019 | 0.872602 | 0.148005 |
| −0.14331 | 1.559748 | 0.083821 | 0.048832 | 2.250602 |
| −0.21816 | 1.601276 | 0.043655 | 0.027052 | 1.407014 |
| 0.174616 | 0.627442 | 0.190649 | 0.423093 | 0.844609 |
| 0.099768 | 0.521168 | 0.025727 | 0.651772 | 0.334781 |
| −0.07485 | 0.770538 | 1.010364 | 0.062539 | 2.51792 |

TABLE 50

3-THF-3
$(\theta_{u,mn} - \theta_{g,mnk})^2 / \sigma_{\theta g,mn}^2$

| EtOH | | | | | | Benzane | | | | |
|---|---|---|---|---|---|---|---|---|---|---|
| k5 | k1 | k2 | k3 | k4 | k5 | k1 | k2 | k3 | k4 | k5 |
| 0.922372 | 0.06814 | 2.193636 | 0.005956 | 0.02607 | 0.007281 | 0.491434 | 0.173618 | 0.574515 | 0.26911 | 0.612517 |
| 0.071034 | 0.594855 | 3.120328 | 0.134536 | 0.013146 | 0.140985 | 0.721964 | 0.116302 | 0.618887 | 0.008128 | 0.608107 |
| 0.486865 | 0.973501 | 3.743827 | 0.442448 | 9.69E−05 | 0.354146 | 5.986497 | 0.307139 | 1.212407 | 1.854451 | 2.973679 |
| 1.312505 | 0.956196 | 0.702901 | 0.44484 | 0.164851 | 0.428222 | 0.015663 | 0.178379 | 0.172975 | 1.530914 | 0.248448 |
| 3.257285 | 2.819025 | 0.001385 | 2.391797 | 0.523738 | 1.725169 | 0.463474 | 0.539318 | 0.018226 | 0.062321 | 3.074198 |
| 6.880711 | 5.96402 | 6.514772 | 8.972961 | 1.214386 | 5.122762 | 0.846995 | 0.53126 | 0.000391 | 0.784289 | 3.974086 |
| 237.9772 | 11.69084 | 11.79468 | 9.909004 | 24.43507 | 14.58078 | 0.137204 | 2.858947 | 0.189432 | 0.108575 | 0.053141 |
| 0.139084 | 0.000572 | 0.106327 | 1.93838 | 1.951398 | 2.17034 | 0.02731 | 0.015125 | 0.168037 | 0.190239 | 1.604932 |
| 3.502151 | 0.064232 | 0.439493 | 3.399165 | 2.571601 | 2.65198 | 0.044647 | 0.051004 | 0.08262 | 0.215145 | 1.607851 |
| 29.41297 | 9.938426 | 8.075851 | 2.530431 | 10.43333 | 4.535313 | 0.484468 | 1.010668 | 0.473475 | 0.196487 | 0.075601 |
| 16.15997 | 4.393881 | 2.926 | 0.138868 | 3.363926 | 0.963602 | 0.234908 | 1.029552 | 0.283389 | 0.028691 | 0.603397 |
| 80.77895 | 0.775081 | 1.948469 | 7.557874 | 3.830759 | 4.228239 | 0.069188 | 0.119644 | 0.018854 | 0.238937 | 1.553402 |
| 0.146876 | 8.083279 | 3.042924 | 7.970507 | 5.562136 | 1.48362 | 1.206914 | 0.002872 | 0.013546 | 0.299503 | 2.990976 |
| 0.121533 | 1.005624 | 0.250176 | 1.88E−05 | 0.062713 | 0.756706 | 2.184943 | 0.074818 | 0.02262 | 0.030517 | 0.34991 |
| 2.166956 | 1.736185 | 0.186738 | 0.066125 | 0.042444 | 2.78E−05 | 0.05322 | 3.09619 | 0.005252 | 0.14018 | 0.176403 |
| 0.220585 | 4.050846 | 10.74916 | 14.55093 | 13.33856 | 10.52058 | 0.844472 | 0.015927 | 0.028776 | 0.348117 | 3.441876 |
| 0.452154 | 0.052886 | 1.512234 | 2.257658 | 1.542364 | 0.268548 | 1.421974 | 0.151685 | 0.011657 | 0.413707 | 3.564483 |
| 1.011359 | 1.497445 | 0.069963 | 0.167095 | 0.01313 | 0.520095 | 2.634389 | 1.544025 | 0.042886 | 0.239127 | 0.865009 |
| 1.405124 | 27.29709 | 39.19616 | 16.3537 | 30.05332 | 29.22288 | 0.344793 | 0.786144 | 0.553478 | 1.450077 | 0.929072 |
| 8.09E−05 | 0.072505 | 0.472036 | 0.010395 | 1.93873 | 0.174976 | 0.343125 | 1.736962 | 0.478384 | 0.067004 | 0.549697 |
| 0.004142 | 0.000346 | 0.124837 | 0.540772 | 1.361728 | 0.043246 | 0.592014 | 0.944748 | 0.243525 | 0.03732 | 0.163026 |
| 0.283574 | 18.86714 | 23.40113 | 15.11018 | 11.82248 | 2.700945 | 0.246742 | 0.310939 | 0.424602 | 2.058694 | 0.832424 |
| 0.222309 | 14.10483 | 16.51554 | 16.33185 | 6.103697 | 17.4469 | 0.128957 | 0.389264 | 1.214885 | 2.301705 | 0.917069 |
| 0.946933 | 0.098228 | 0.0328 | 1.834599 | 0.296958 | 0.015562 | 0.1744 | 0.205483 | 4.323175 | 0.630022 | 0.224237 |
| 11.81505 | 13.01669 | 12.19657 | 4.899332 | 6.342248 | 14.28762 | 1.126393 | 2.895871 | 0.422919 | 0.565026 | 0.06077 |
| 1.2145 | 5.656816 | 2.17074 | 2.633714 | 0.732403 | 6.750084 | 3.025396 | 2.894701 | 2.558088 | 0.2401 | 0.093561 |
| 1.310752 | 0.79672 | 0.005454 | 0.001003 | 0.454675 | 1.079996 | 0.205948 | 0.165822 | 0.57584 | 0.005579 | 1.218618 |
| 4.484265 | 10.16275 | 13.76773 | 3.346364 | 8.016649 | 10.62646 | 0.199112 | 1.781614 | 0.000927 | 0.545412 | 0.257951 |
| 4.991178 | 11.707 | 21.15145 | 9.239446 | 20.26372 | 11.6634 | 1.580273 | 4.715153 | 1.623971 | 1.020692 | 0.037398 |
| 0.472995 | 0.110894 | 1.14601 | 1.912802 | 3.669634 | 0.061489 | 2.270614 | 2.273077 | 6.076531 | 0.224009 | 1.826191 |
| 11.11982 | 1.793178 | 3.72806 | 1.90892 | 8.913989 | 1.861712 | 1.780454 | 0.066434 | 1.050452 | 1.390041 | 0.012173 |
| 1.468601 | 0.500484 | 0.000617 | 0.03589 | 1.433653 | 0.099043 | 0.219455 | 1.112906 | 0.422905 | 0.217442 | 0.232186 |
| 1.449873 | 0.988849 | 0.089244 | 0.323701 | 0.151783 | 0.545749 | 0.010177 | 2.023151 | 0.331553 | 2.768843 | 0.051991 |
| 3.570613 | 12.71668 | 11.00004 | 7.22601 | 8.192346 | 3.008174 | 2.359868 | 0.271657 | 0.871734 | 1.723776 | 0.061895 |
| 3.853234 | 3.595669 | 2.280338 | 2.135137 | 2.0234 | 0.002418 | 1.324983 | 0.752333 | 1.588542 | 4.872187 | 0.068227 |
| 0.005073 | 0.608713 | 0.20773 | 0.526577 | 0.327641 | 0.762819 | 0.202051 | 0.763737 | 1.259356 | 4.996495 | 0.365334 |
| 0.078627 | 0.853996 | 2.490725 | 3.639563 | 6.527833 | 0.746269 | 0.012496 | 4.035189 | 0.364212 | 0.844113 | 0.401178 |
| 1.899891 | 0.249244 | 0.123006 | 0.833663 | 0.651117 | 0.356057 | 1.08861 | 0.41017 | 0.464146 | 0.206077 | 0.117077 |
| 2.02386 | 0.274234 | 0.488415 | 1.501681 | 0.490175 | 0.300661 | 2.214524 | 0.055377 | 0.415218 | 2.802584 | 0.021589 |
| 1.504624 | 2.515269 | 4.153307 | 9.715574 | 1.71117 | 2.743208 | 3.037386 | 4.902412 | 3.907012 | 4.552901 | 0.23781 |
| 1.697928 | 0.900551 | 1.953736 | 4.504952 | 0.036903 | 0.909468 | 2.99664 | 1.544046 | 1.039748 | 5.444166 | 0.22444 |
| 2.156011 | 0.270369 | 0.894018 | 2.022938 | 0.239839 | 0.235115 | 2.108787 | 0.465133 | 0.249907 | 4.153057 | 0.154777 |
| 0.000924 | 0.056419 | 0.026718 | 0.001489 | 2.974263 | 0.027835 | 0.090575 | 3.066473 | 0.01163 | 0.097295 | 0.223903 |
| 0.335814 | 0.002525 | 0.000228 | 0.008235 | 2.432482 | 0.000212 | 0.102311 | 2.914592 | 0.003336 | 0.001349 | 0.107578 |
| 0.172846 | 0.060204 | 0.00204 | 0.032709 | 2.087232 | 0.000325 | 0.163189 | 3.253439 | 0.001058 | 0.20489 | 0.088083 |
| 0.204214 | 5.780025 | 5.515224 | 3.141782 | 0.578067 | 5.668943 | 0.002542 | 0.071709 | 0.37261 | 1.665123 | 0.311906 |
| 0.126435 | 5.240081 | 0.908844 | 1.168424 | 0.158347 | 0.692403 | 2.27E−05 | 1.857692 | 0.080506 | 0.008342 | 0.727799 |
| 0.186152 | 3.069276 | 0.034178 | 0.324335 | 0.027589 | 0.000664 | 0.001139 | 0.828184 | 0.050425 | 1.076447 | 0.077212 |
| 1.281171 | 0.022292 | 0.008854 | 0.074963 | 2.249078 | 0.164699 | 0.711223 | 1.176159 | 0.070528 | 0.006064 | 0.060194 |
| 0.585273 | 0.02257 | 0.000189 | 0.058341 | 2.845849 | 0.004268 | 2.686537 | 0.002814 | 0.00219 | 0.012595 | 0.494972 |
| 0.414233 | 0.166562 | 0.025312 | 0.495188 | 1.197236 | 0.191061 | 0.319043 | 1.767404 | 0.029949 | 0.173373 | 0.014532 |
| 0.241748 | 0.004042 | 0.043292 | 0.000156 | 1.404024 | 1.636185 | 0.243687 | 1.680948 | 0.094004 | 0.003385 | 0.004985 |
| 0.123127 | 0.015916 | 0.000458 | 0.04197 | 3.037128 | 0.328444 | 0.814007 | 2.417977 | 3.474855 | 4.808372 | 0.211199 |
| 1.032264 | 0.018375 | 0.010658 | 0.064211 | 3.097616 | 0.063815 | 0.043169 | 2.607317 | 0.051113 | 0.295774 | 0.003638 |
| 2.086701 | 1.141442 | 0.336345 | 0.42744 | 0.010806 | 0.137893 | 0.002008 | 1.146684 | 0.043794 | 0.140257 | 2.192558 |
| 0.226494 | 0.010706 | 0.000816 | 1.11052 | 0.723854 | 0.286294 | 0.869018 | 0.892742 | 0.048101 | 0.011534 | 0.203336 |
| 0.274186 | 0.001538 | 0.000132 | 1.021099 | 2.593 | 0.19284 | 0.197403 | 1.609245 | 0.001032 | 0.030809 | 0.978476 |

TABLE 50-continued

3-THF-3

$(\theta_{u,mn}-\theta_{g,mnk})^2/\sigma_{\theta g,mn}^2$

| 0.156797 | 0.881159 | 0.180141 | 0.300253 | 0.876126 | 0.061231 | 2.185048 | 0.120314 | 0.014655 | 0.048969 | 0.69643 |
| 0.456727 | 0.090643 | 0.02983 | 0.981604 | 3.549947 | 0.161738 | 0.380117 | 1.580122 | 0.017184 | 0.006225 | 0.5028 |
| 0.072068 | 0.004323 | 9.02E−06 | 0.310144 | 2.758908 | 0.047718 | 0.000379 | 2.151843 | 0.056227 | 0.049353 | 1.901159 |

| Hexane | | | | | AcOEt | | |
|---|---|---|---|---|---|---|---|
| k1 | k2 | k3 | k4 | k5 | k1 | k2 | k3 |
| 0.327178 | 0.087112 | 0.284444 | 0.995479 | 0.575551 | 0.007529 | 0.103453 | 1.45838 |
| 0.389136 | 0.00699 | 0.25952 | 3.674666 | 0.681803 | 0.014789 | 0.011188 | 1.659158 |
| 0.1432 | 0.00698 | 0.127793 | 3.209775 | 0.27918 | 0.016382 | 0.190263 | 0.684759 |
| 13.48858 | 18.01779 | 16.06177 | 8.342923 | 22.9695 | 0.00899 | 0.575182 | 0.000443 |
| 15.16534 | 14.83275 | 12.92681 | 9.304798 | 24.90214 | 0.022087 | 0.195988 | 0.11513 |
| 8.787184 | 4.65531 | 3.859316 | 5.323547 | 13.61148 | 0.010908 | 1.648694 | 0.212036 |
| 54.58128 | 55.92628 | 35.75259 | 37.31853 | 41.8497 | 26.40234 | 23.23847 | 34.45532 |
| 17.05358 | 11.79107 | 7.624765 | 5.684377 | 7.004457 | 12.04424 | 2.331172 | 6.71153 |
| 15.04334 | 11.78135 | 8.954835 | 7.721892 | 6.692745 | 20.28597 | 7.252964 | 10.71522 |
| 52.17165 | 75.51354 | 47.86983 | 62.02577 | 65.85522 | 12.46971 | 17.3695 | 22.21397 |
| 15.67585 | 29.88569 | 16.02764 | 20.2743 | 28.03806 | 3.836561 | 7.045047 | 10.4659 |
| 7.322242 | 23.77894 | 4.319101 | 6.241002 | 0.955603 | 22.38871 | 15.38325 | 10.90702 |
| 3.765131 | 4.336941 | 2.918322 | 0.12261 | 3.527075 | 1.383615 | 0.642784 | 0.006136 |
| 1.726356 | 1.485735 | 0.320536 | 0.187434 | 0.942558 | 0.238704 | 0.631334 | 2.661213 |
| 1.338909 | 1.859181 | 0.726509 | 0.192001 | 0.898323 | 0.438722 | 0.003573 | 2.490266 |
| 12.98641 | 26.18545 | 23.11789 | 25.17542 | 29.68835 | 0.282654 | 0.338085 | 0.562688 |
| 9.158637 | 6.465117 | 13.19341 | 18.58015 | 15.44981 | 0.005861 | 0.089524 | 1.057097 |
| 0.017369 | 2.287135 | 0.047058 | 0.078874 | 0.181114 | 0.52894 | 0.053526 | 1.911223 |
| 0.005675 | 1.338079 | 2.970721 | 0.041883 | 1.463979 | 6.503732 | 1.229229 | 6.077841 |
| 0.235091 | 0.278093 | 1.230913 | 0.188839 | 0.461432 | 1.851629 | 0.038158 | 0.25109 |
| 0.260716 | 0.302246 | 1.264577 | 0.190129 | 0.314241 | 1.527123 | 0.01505 | 0.093863 |
| 68.78258 | 78.9291 | 71.90647 | 85.67912 | 54.89328 | 9.123667 | 4.17172 | 13.50343 |
| 153.6233 | 180.2136 | 184.7627 | 185.5337 | 206.3974 | 2.316223 | 1.334502 | 6.394543 |
| 0.000822 | 3.96E−05 | 0.153734 | 0.030448 | 2.483654 | 0.846902 | 0.131035 | 0.003917 |
| 0.801144 | 3.612924 | 1.455329 | 0.003937 | 1.148536 | 1.059915 | 7.196806 | 1.30264 |
| 0.22885 | 1.725497 | 0.051827 | 0.446284 | 0.070321 | 0.382391 | 4.21758 | 0.259061 |
| 0.165516 | 0.988269 | 0.00226 | 0.844792 | 0.025746 | 0.023052 | 2.599582 | 0.005233 |
| 1.969626 | 4.103084 | 10.43615 | 3.757604 | 7.117286 | 2.627291 | 8.19668 | 5.49256 |
| 1.214719 | 4.086865 | 7.350007 | 4.423773 | 8.439866 | 0.105782 | 0.978299 | 0.255817 |
| 0.04413 | 1.455129 | 0.719966 | 2.273764 | 4.936404 | 0.004736 | 1.969123 | 0.017994 |
| 1.66904 | 0.216828 | 0.416676 | 1.162144 | 0.279105 | 6.344908 | 13.45025 | 3.092186 |
| 1.175598 | 0.012142 | 0.301606 | 0.15004 | 0.696692 | 0.24403 | 0.957871 | 0.776602 |
| 0.92232 | 0.000738 | 0.26635 | 0.0014 | 0.865155 | 1.186323 | 0.009547 | 0.063923 |
| 0.175197 | 1.096782 | 0.03436 | 4.008395 | 1.1639 | 7.145832 | 6.918232 | 0.912012 |
| 0.312072 | 0.66354 | 0.043481 | 4.321062 | 0.649223 | 6.126653 | 6.00137 | 0.687743 |
| 0.475741 | 0.145988 | 0.046605 | 3.732586 | 0.100278 | 2.952 | 2.086505 | 0.42716 |
| 0.324069 | 0.316249 | 0.873369 | 0.723534 | 0.504586 | 0.091708 | 2.178404 | 0.042698 |
| 0.04243 | 0.014676 | 0.436754 | 1.418664 | 0.08831 | 0.00106 | 0.407092 | 1.898545 |
| 0.002805 | 0.001181 | 0.295098 | 1.841173 | 2.76E−05 | 0.337897 | 1.256776 | 0.678 |
| 14.27162 | 20.57901 | 9.289408 | 8.924774 | 18.53358 | 0.048497 | 2.434469 | 1.013698 |
| 12.93387 | 9.342128 | 5.277903 | 8.09361 | 17.13403 | 0.296867 | 1.809639 | 0.487277 |
| 3.670704 | 0.397668 | 0.557004 | 2.299286 | 5.006699 | 0.57873 | 1.361705 | 0.21847 |
| 0.192225 | 5.210201 | 0.883041 | 0.670315 | 0.713447 | 1.674297 | 2.766152 | 3.662732 |
| 0.045614 | 0.689701 | 1.057929 | 0.003352 | 0.424599 | 0.029142 | 1.43505 | 1.600003 |
| 0.004085 | 0.458576 | 2.721749 | 0.010424 | 1.671925 | 0.008093 | 0.919264 | 0.692625 |
| 0.245793 | 0.05643 | 0.533842 | 0.140443 | 1.549733 | 6.778667 | 2.854788 | 4.564794 |
| 0.024944 | 0.249504 | 1.184412 | 0.096783 | 0.627274 | 0.296223 | 0.001138 | 2.456426 |
| 0.123205 | 0.112225 | 0.237574 | 0.001422 | 1.634262 | 0.000119 | 0.138435 | 1.61536 |
| 0.277734 | 0.409841 | 2.931036 | 3.801738 | 0.241875 | 0.019566 | 2.836492 | 0.003466 |
| 0.114031 | 0.000179 | 0.168907 | 0.148581 | 1.570536 | 0.005822 | 0.280848 | 0.026046 |
| 0.222133 | 0.046782 | 0.220166 | 0.085435 | 2.906734 | 0.028803 | 0.021048 | 0.006584 |
| 0.012052 | 0.119437 | 0.22218 | 0.405189 | 3.205767 | 0.024474 | 0.039195 | 0.026723 |
| 0.026991 | 0.18682 | 0.102334 | 0.312416 | 1.36953 | 0.048761 | 0.585455 | 0.003573 |
| 0.235785 | 1.118179 | 0.01268 | 0.328719 | 1.217735 | 0.050435 | 2.252831 | 0.026605 |
| 0.181779 | 1.287594 | 0.202472 | 0.760254 | 1.883561 | 0.000152 | 0.415163 | 1.73245 |
| 0.91371 | 0.479101 | 0.026744 | 0.124849 | 0.69072 | 0.000416 | 0.014338 | 2.214993 |
| 0.889308 | 0.295354 | 0.009163 | 0.111626 | 0.719679 | 0.010618 | 0.64329 | 1.160204 |
| 4.824914 | 0.24887 | 0.334009 | 0.990055 | 0.389609 | 7.9E−05 | 2.314336 | 0.7835 |
| 11.09632 | 4.996366 | 2.253567 | 4.5457 | 2.856306 | 0.01406 | 1.912721 | 0.163346 |
| 0.337455 | 1.964922 | 0.258972 | 0.165917 | 0.382261 | 0.034915 | 1.980356 | 0.011731 |

TABLE 51

<table>
<tr><th colspan="10">3-THF-4</th></tr>
<tr><th colspan="7">THF</th><th colspan="3">log σ$_{rg,mn}$</th></tr>
<tr><th>k4</th><th>k5</th><th>k1</th><th>k2</th><th>k3</th><th>k4</th><th>k5</th><th>H2O</th><th>EtOH</th><th>Benzene</th></tr>
<tr><td>0.432462</td><td>0.000765</td><td>1.156888</td><td>0.594453</td><td>0.033457</td><td>1.460283</td><td>0.085642</td><td>−3.47051</td><td>−4.20695</td><td>−3.01438</td></tr>
<tr><td>0.221395</td><td>0.107292</td><td>0.555388</td><td>3.22089</td><td>0.14709</td><td>0.258279</td><td>0.014</td><td>1.423286</td><td>0.497692</td><td>−0.08048</td></tr>
<tr><td>0.711975</td><td>0.496296</td><td>1.664556</td><td>4.346759</td><td>0.686742</td><td>0.456549</td><td>0.048989</td><td>1.749126</td><td>2.144489</td><td>1.309926</td></tr>
<tr><td>0.935786</td><td>0.921324</td><td>0.006187</td><td>2.338022</td><td>0.339636</td><td>0.087975</td><td>0.005969</td><td>4.210396</td><td>2.683662</td><td>3.146059</td></tr>
<tr><td>0.59182</td><td>3.701409</td><td>0.851921</td><td>2.936359</td><td>1.078007</td><td>0.023679</td><td>0.161269</td><td>4.511755</td><td>4.725985</td><td>4.151946</td></tr>
<tr><td>2.834445</td><td>2.566821</td><td>5.076963</td><td>5.771414</td><td>2.712374</td><td>0.869795</td><td>0.815501</td><td>−3.37465</td><td>−0.12163</td><td>−0.1664</td></tr>
<tr><td>41.94422</td><td>38.79938</td><td>2.413311</td><td>0.006571</td><td>2.991377</td><td>3.29527</td><td>1.669577</td><td>−3.53899</td><td>−4.81517</td><td>−4.14667</td></tr>
<tr><td>6.487611</td><td>8.38913</td><td>1.21705</td><td>0.311271</td><td>0.396034</td><td>1.165866</td><td>1.078334</td><td>1.382803</td><td>0.58021</td><td>1.121638</td></tr>
<tr><td>9.70594</td><td>15.02985</td><td>1.939192</td><td>0.007845</td><td>0.966129</td><td>2.414783</td><td>2.668706</td><td>1.741738</td><td>4.397142</td><td>1.867993</td></tr>
<tr><td>28.68633</td><td>24.29173</td><td>2.84718</td><td>0.3167</td><td>5.478174</td><td>4.550869</td><td>1.716825</td><td>4.20986</td><td>3.877253</td><td>4.065613</td></tr>
<tr><td>14.69851</td><td>10.3563</td><td>1.570407</td><td>0.050413</td><td>3.836591</td><td>2.362914</td><td>0.324712</td><td>4.502093</td><td>7.334285</td><td>4.599096</td></tr>
<tr><td>8.895603</td><td>16.09522</td><td>4.202096</td><td>2.180245</td><td>3.754368</td><td>7.755803</td><td>10.52975</td><td>−2.81705</td><td>2.017156</td><td>−0.07503</td></tr>
<tr><td>1.659994</td><td>3.337326</td><td>0.989238</td><td>0.190302</td><td>0.022725</td><td>3.021641</td><td>0.000222</td><td>−2.54699</td><td>−3.73822</td><td>−3.60914</td></tr>
<tr><td>0.091043</td><td>0.000274</td><td>0.468364</td><td>0.325963</td><td>0.005705</td><td>0.34907</td><td>0.097322</td><td>2.232661</td><td>0.673325</td><td>0.52533</td></tr>
<tr><td>0.025774</td><td>0.002755</td><td>6.08035</td><td>1.948909</td><td>0.749628</td><td>1.527386</td><td>0.4044445</td><td>2.82389</td><td>2.29138</td><td>2.377234</td></tr>
<tr><td>0.465942</td><td>1.309943</td><td>0.073043</td><td>0.036182</td><td>0.019487</td><td>3.166949</td><td>0.043076</td><td>4.526049</td><td>3.418593</td><td>3.245487</td></tr>
<tr><td>0.41301</td><td>0.539584</td><td>0.365393</td><td>0.234558</td><td>0.188834</td><td>1.178656</td><td>0.181933</td><td>4.977347</td><td>4.815047</td><td>4.288023</td></tr>
<tr><td>0.241276</td><td>0.005513</td><td>23.20794</td><td>13.86832</td><td>10.11548</td><td>9.178488</td><td>12.15355</td><td>−1.85188</td><td>−0.43421</td><td>0.255924</td></tr>
<tr><td>6.495151</td><td>1.901032</td><td>0.459849</td><td>1.634895</td><td>0.357127</td><td>0.252469</td><td>1.375306</td><td>−3.21894</td><td>−4.00041</td><td>−4.99092</td></tr>
<tr><td>0.33399</td><td>0.184173</td><td>1.163377</td><td>7.264164</td><td>1.343262</td><td>4.120055</td><td>5.176411</td><td>1.990366</td><td>0.825093</td><td>−0.84597</td></tr>
<tr><td>0.042948</td><td>0.570452</td><td>3.581035</td><td>2.033481</td><td>0.404512</td><td>6.134965</td><td>1.266198</td><td>2.337258</td><td>2.032124</td><td>1.48009</td></tr>
<tr><td>14.01185</td><td>7.358291</td><td>0.337504</td><td>1.051965</td><td>0.240065</td><td>0.531127</td><td>0.924421</td><td>4.824302</td><td>2.611209</td><td>3.155974</td></tr>
<tr><td>7.532004</td><td>6.337489</td><td>0.010815</td><td>0.506887</td><td>0.115652</td><td>1.022576</td><td>0.486787</td><td>5.461589</td><td>3.585953</td><td>5.32421</td></tr>
<tr><td>0.039725</td><td>0.939898</td><td>2.204316</td><td>0.21771</td><td>0.049747</td><td>2.990015</td><td>0.100347</td><td>−1.65006</td><td>−1.31919</td><td>0.433949</td></tr>
<tr><td>1.662812</td><td>1.043206</td><td>0.896362</td><td>0.46389</td><td>0.91162</td><td>0.034799</td><td>4.456651</td><td>−3.2759</td><td>−3.9333</td><td>−4.83793</td></tr>
<tr><td>0.110183</td><td>0.247418</td><td>17.6702</td><td>29.61467</td><td>12.39156</td><td>18.81407</td><td>22.36882</td><td>2.395255</td><td>1.211161</td><td>0.586189</td></tr>
<tr><td>0.007924</td><td>0.001404</td><td>0.620424</td><td>3.857927</td><td>0.052929</td><td>1.380772</td><td>0.105677</td><td>2.671959</td><td>2.476318</td><td>1.833904</td></tr>
<tr><td>11.54724</td><td>3.872687</td><td>0.075958</td><td>0.035006</td><td>0.154056</td><td>0.254813</td><td>1.634246</td><td>4.960104</td><td>3.72471</td><td>4.348747</td></tr>
<tr><td>0.687719</td><td>0.243839</td><td>0.10998</td><td>0.118823</td><td>0.324805</td><td>0.129774</td><td>1.786635</td><td>5.213834</td><td>5.060598</td><td>5.343589</td></tr>
<tr><td>0.082971</td><td>0.032408</td><td>0.166569</td><td>0.394206</td><td>0.752791</td><td>0.000502</td><td>1.313695</td><td>−1.9216</td><td>−0.48259</td><td>0.760752</td></tr>
<tr><td>9.032248</td><td>9.028635</td><td>0.136992</td><td>0.009565</td><td>0.188847</td><td>2.249422</td><td>0.195998</td><td>−3.33665</td><td>−4.93122</td><td>−4.45787</td></tr>
<tr><td>1.774997</td><td>0.927743</td><td>0.04484</td><td>0.005968</td><td>0.760418</td><td>1.213699</td><td>0.03704</td><td>2.617672</td><td>−0.84793</td><td>−0.52142</td></tr>
<tr><td>0.647285</td><td>0.145008</td><td>0.01649</td><td>0.066417</td><td>1.465622</td><td>0.533928</td><td>0.043061</td><td>1.895491</td><td>0.827268</td><td>1.224621</td></tr>
<tr><td>3.102399</td><td>4.141623</td><td>0.22807</td><td>0.049698</td><td>0.011661</td><td>3.091487</td><td>0.378724</td><td>6.047699</td><td>2.645935</td><td>4.198668</td></tr>
<tr><td>1.746309</td><td>5.019138</td><td>0.32363</td><td>0.227357</td><td>0.150077</td><td>4.392243</td><td>1.08166</td><td>5.744713</td><td>0.834929</td><td>4.767592</td></tr>
<tr><td>0.034705</td><td>3.849415</td><td>0.026866</td><td>0.817217</td><td>3.936985</td><td>0.370322</td><td>1.957961</td><td>−1.07522</td><td>−1.18013</td><td>0.031744</td></tr>
<tr><td>0.002269</td><td>0.004601</td><td>0.038448</td><td>0.863757</td><td>0.016797</td><td>2.148791</td><td>0.208167</td><td>−1.56114</td><td>−0.301957</td><td>−4.77763</td></tr>
<tr><td>0.20459</td><td>3.139625</td><td>2.024755</td><td>9.16532</td><td>2.203089</td><td>8.407543</td><td>6.247952</td><td>2.302229</td><td>1.172873</td><td>−0.60568</td></tr>
<tr><td>0.11482</td><td>1.154096</td><td>13.6385</td><td>22.26098</td><td>11.01354</td><td>16.09316</td><td>8.136569</td><td>2.531087</td><td>2.180185</td><td>0.824372</td></tr>
<tr><td>0.057113</td><td>1.061618</td><td>0.378032</td><td>0.101802</td><td>0.303382</td><td>1.208053</td><td>0.012654</td><td>5.313879</td><td>3.298982</td><td>4.056546</td></tr>
<tr><td>0.059251</td><td>0.638747</td><td>1.240139</td><td>0.015149</td><td>0.901312</td><td>0.410017</td><td>0.036288</td><td>5.661962</td><td>4.329304</td><td>5.29199</td></tr>
<tr><td>0.058326</td><td>0.385489</td><td>5.055756</td><td>2.834601</td><td>3.30551</td><td>2.166337</td><td>0.127805</td><td>−1.57645</td><td>−0.62874</td><td>−0.38181</td></tr>
<tr><td>0.053956</td><td>0.373284</td><td>0.194535</td><td>0.428083</td><td>0.658921</td><td>2.0256</td><td>0.015148</td><td>−3.49631</td><td>−3.94273</td><td>−4.91018</td></tr>
<tr><td>0.010851</td><td>0.031432</td><td>0.103687</td><td>1.402467</td><td>1.875552</td><td>0.275663</td><td>1.537342</td><td>2.424872</td><td>0.445572</td><td>0.883886</td></tr>
<tr><td>0.266078</td><td>0.139661</td><td>0.120741</td><td>2.125939</td><td>0.000931</td><td>0.569155</td><td>0.023942</td><td>2.589026</td><td>2.778786</td><td>0.220413</td></tr>
<tr><td>0.483946</td><td>2.775702</td><td>0.146114</td><td>0.118753</td><td>0.210627</td><td>1.948768</td><td>0.065209</td><td>5.021767</td><td>3.338671</td><td>5.535133</td></tr>
<tr><td>0.088146</td><td>0.342991</td><td>0.000659</td><td>1.39234</td><td>0.476777</td><td>0.13071</td><td>0.005952</td><td>5.159181</td><td>5.413236</td><td>5.249664</td></tr>
<tr><td>0.258314</td><td>0.089807</td><td>0.089639</td><td>1.675321</td><td>0.078004</td><td>0.475688</td><td>0.013573</td><td>−1.63969</td><td>0.909739</td><td>0.495249</td></tr>
<tr><td>0.806805</td><td>0.138965</td><td>0.255321</td><td>0.045106</td><td>0.453352</td><td>1.09347</td><td>0.175858</td><td>−3.75061</td><td>−4.03884</td><td>−3.85018</td></tr>
<tr><td>2.473924</td><td>0.018258</td><td>0.536623</td><td>0.048828</td><td>0.52817</td><td>0.876748</td><td>0.076633</td><td>1.981951</td><td>2.272385</td><td>2.102403</td></tr>
<tr><td>2.233758</td><td>0.023854</td><td>0.053605</td><td>1.263719</td><td>0.025466</td><td>0.04535</td><td>0.653578</td><td>1.953076</td><td>4.092013</td><td>2.495732</td></tr>
<tr><td>2.073639</td><td>0.00025</td><td>0.135693</td><td>0.04161</td><td>0.399272</td><td>1.188339</td><td>0.243015</td><td>4.397952</td><td>5.078273</td><td>5.504239</td></tr>
<tr><td>1.365877</td><td>0.000353</td><td>0.225024</td><td>0.022077</td><td>0.825251</td><td>1.14895</td><td>0.034166</td><td>4.935532</td><td>6.916974</td><td>5.854076</td></tr>
<tr><td>0.019795</td><td>0.005798</td><td>0.27128</td><td>0.506835</td><td>0.70148</td><td>0.538962</td><td>0.157874</td><td>−1.17599</td><td>0.633256</td><td>−0.31503</td></tr>
<tr><td>0.022062</td><td>0.020063</td><td>5.42E−06</td><td>0.644923</td><td>0.886217</td><td>0.000111</td><td>0.64004</td><td>−3.97688</td><td>−1.75606</td><td>−4.84518</td></tr>
<tr><td>0.016155</td><td>0.054862</td><td>0.113744</td><td>1.644657</td><td>0.289008</td><td>0.009475</td><td>0.806156</td><td>1.369908</td><td>2.462408</td><td>0.091022</td></tr>
<tr><td>0.027111</td><td>0.162667</td><td>0.034279</td><td>0.277492</td><td>1.778023</td><td>0.000254</td><td>0.03865</td><td>3.397467</td><td>3.352771</td><td>0.918108</td></tr>
<tr><td>0.020132</td><td>0.010377</td><td>0.001594</td><td>0.790885</td><td>0.873031</td><td>0.000428</td><td>0.41264</td><td>4.568042</td><td>3.121787</td><td>3.407953</td></tr>
<tr><td>0.104344</td><td>0.071486</td><td>0.001677</td><td>0.707443</td><td>0.93901</td><td>0.000167</td><td>0.591474</td><td>5.043107</td><td>3.956618</td><td>5.072329</td></tr>
<tr><td>0.170669</td><td>0.123117</td><td>0.000178</td><td>0.048228</td><td>2.575928</td><td>0.002848</td><td>1.032545</td><td>−1.06582</td><td>−1.14587</td><td>−0.12107</td></tr>
</table>

<table>
<tr><th colspan="3">log σ$_{rg,mn}$</th><th colspan="6">log σ$_{θg,mn}$</th></tr>
<tr><th>Hexane</th><th>AcOEt</th><th>THF</th><th>H2O</th><th>EtOH</th><th>Benzen</th><th>Hexane</th><th>AcOEt</th><th>THF</th></tr>
<tr><td>−4.10649</td><td>−2.38023</td><td>−1.68628</td><td>−0.82928</td><td>0.823367</td><td>−0.51055</td><td>0.992277</td><td>−0.01687</td><td>−0.89727</td></tr>
<tr><td>0.688938</td><td>1.180656</td><td>0.570003</td><td>−1.55647</td><td>0.340158</td><td>−0.76988</td><td>0.467301</td><td>−0.07627</td><td>−0.43568</td></tr>
<tr><td>1.072453</td><td>2.454608</td><td>2.150339</td><td>−1.63936</td><td>0.400977</td><td>−1.08067</td><td>0.466282</td><td>0.123082</td><td>−0.0921</td></tr>
<tr><td>3.374414</td><td>4.503642</td><td>2.094256</td><td>−1.14968</td><td>−0.67501</td><td>−1.52378</td><td>−1.8571</td><td>−1.24577</td><td>−0.59128</td></tr>
<tr><td>4.422189</td><td>5.309541</td><td>3.505918</td><td>−1.1801</td><td>−0.63757</td><td>−0.50805</td><td>−1.42174</td><td>−0.9164</td><td>−0.22346</td></tr>
<tr><td>−1.31652</td><td>−0.58078</td><td>−0.29805</td><td>−2.61649</td><td>−1.8355</td><td>−0.74507</td><td>−2.09105</td><td>−1.17806</td><td>−1.17675</td></tr>
<tr><td>−5.16409</td><td>−4.20603</td><td>−2.91236</td><td>−2.16383</td><td>−1.07598</td><td>1.064797</td><td>−0.78634</td><td>−1.56727</td><td>−0.63991</td></tr>
<tr><td>−0.22856</td><td>−0.39937</td><td>0.259949</td><td>−1.37949</td><td>−1.06307</td><td>−0.17791</td><td>−0.871</td><td>−2.29371</td><td>−1.39059</td></tr>
<tr><td>0.658853</td><td>0.724481</td><td>2.016578</td><td>−1.37216</td><td>−0.73084</td><td>0.417273</td><td>−0.73662</td><td>−2.03317</td><td>−1.17522</td></tr>
</table>

TABLE 51-continued

| 3-THF-4 | | | | | | | | |
|---|---|---|---|---|---|---|---|---|
| 2.946359 | 2.288464 | 1.814887 | −1.17286 | −0.98772 | 0.319091 | −1.48448 | −1.58917 | −1.13088 |
| 4.283216 | 3.001095 | 3.289227 | −1.13063 | −0.69725 | 0.469739 | −1.13058 | −1.40370 | −1.16917 |
| −1.28754 | −1.63629 | −0.70151 | −3.16176 | −1.91056 | −0.36615 | −2.02085 | −2.98339 | −2.57999 |
| −3.45323 | −2.86846 | −2.63055 | −0.40633 | −1.46006 | −0.15372 | 0.262191 | −0.88764 | −0.58837 |
| 1.248007 | 0.60212 | 0.207069 | −1.49237 | −1.15723 | −1.74261 | 0.300956 | −1.27126 | −1.29522 |
| 1.521438 | 1.683112 | 1.784486 | −2.05044 | −0.51046 | −1.86177 | 0.407925 | −0.48163 | −1.06283 |
| 4.290344 | 3.604588 | 2.58891 | −0.3419 | −1.76308 | −0.29631 | −1.57369 | −0.42624 | −0.79534 |
| 4.912251 | 4.56719 | 4.147205 | −0.4135 | −0.61681 | −0.19836 | −1.35308 | −0.02068 | −0.70174 |
| −1.43277 | −2.33187 | −0.66004 | −2.20351 | −0.95633 | −1.7064 | −1.3211 | −0.98294 | −2.43581 |
| −4.18508 | −4.57844 | −2.66352 | −0.25239 | −1.97182 | −0.41206 | 0.666055 | −1.33803 | −0.7309 |
| 0.734052 | 0.285807 | 0.234313 | 0.394229 | −1.83933 | −1.48248 | 0.686205 | −1.9322 | −3.00454 |
| 1.36182 | 2.258278 | 1.282089 | 0.427422 | −1.40018 | −1.40448 | 0.639868 | −1.32376 | −1.9627 |
| 3.225993 | 3.283066 | 2.743929 | 0.533222 | −1.64778 | −0.66336 | −1.99667 | −1.85819 | −0.75504 |
| 4.055777 | 5.115025 | 3.888008 | 0.556183 | −1.64801 | −0.58531 | −2.40852 | −1.49817 | −0.53901 |
| −0.61674 | −0.16786 | −1.41821 | −2.43387 | −2.10459 | −1.70592 | −1.94335 | −1.94459 | |
| −3.99619 | −4.57673 | −2.56564 | −0.82216 | −1.35886 | 0.057138 | 0.385252 | −0.37197 | −0.95689 |
| 0.784866 | 2.386694 | 0.470495 | −0.2301 | −1.96415 | −0.80879 | 0.382596 | −0.47755 | −2.79221 |
| 0.952827 | 2.335711 | 2.321086 | −0.34122 | −1.17207 | −0.99518 | 0.428725 | 0.658463 | −1.47053 |
| 2.499667 | 4.966157 | 2.71242 | 0.119395 | −1.68121 | −0.2457 | −0.8037 | −1.60442 | −0.95537 |
| 3.978408 | 4.951408 | 4.257231 | 0.039681 | −1.65995 | −0.27385 | −0.4667 | 0.24632 | −0.59658 |
| −0.9661 | −0.20126 | 0.059249 | −2.41235 | −1.76205 | −0.90636 | −1.20675 | 0.271423 | −1.67284 |
| −3.59592 | −3.69173 | −2.1596 | −1.79439 | −1.19371 | −0.6264 | 0.808715 | −1.30587 | −0.12794 |
| 0.80428 | 0.42363 | 0.51278 | −0.45931 | −1.11443 | −1.16205 | 0.870868 | −1.51448 | −0.98185 |
| 1.003504 | 2.133733 | 2.193251 | −0.46491 | −0.64042 | −0.69015 | 0.84193 | −1.12517 | −0.76481 |
| 3.45203 | 3.075531 | 3.315992 | −0.35884 | −1.72099 | −0.99729 | −0.29057 | −1.21759 | −0.66195 |
| 5.019523 | 4.940724 | 4.681165 | −0.40388 | −0.70966 | −0.41013 | 0.18832 | −0.87095 | −0.76053 |
| 0.484981 | −0.02916 | −0.18164 | −2.05213 | −1.116 | −0.62419 | −0.8464 | −1.76629 | −2.12562 |
| −5.02916 | −2.67317 | −3.5853 | −1.36913 | −1.49909 | −1.03802 | 0.499388 | −1.34106 | −0.46286 |
| −0.18678 | 0.838193 | −0.03587 | −0.56432 | −1.20378 | −1.08981 | 0.459324 | −1.59999 | −1.97802 |
| 0.492859 | 2.039741 | 1.658616 | −0.32969 | −0.42158 | −0.19839 | 0.488639 | −0.50208 | −1.97447 |
| 2.583292 | 3.546491 | 2.6235 | −0.54307 | −1.49349 | −1.49594 | −1.82025 | −1.1087 | −0.65216 |
| 4.232906 | 4.911158 | 4.373398 | −0.31415 | −0.54561 | −0.31769 | −1.25587 | −0.23396 | −0.55993 |
| −0.69466 | −0.59548 | −0.03484 | −1.81488 | −0.9873 | −0.51292 | −1.53594 | −0.75271 | −1.96269 |
| −3.25608 | −3.40032 | −2.58889 | −0.83757 | 0.566473 | 0.611169 | 0.037197 | −1.06393 | −0.99583 |
| 0.257281 | 0.494046 | 0.909833 | −0.51511 | 0.632718 | 0.594448 | 0.835504 | −1.34173 | −2.24377 |
| 0.796686 | 1.443826 | 2.481656 | −0.43515 | 0.690223 | 0.321458 | 0.671697 | −0.5567 | −0.69441 |
| 3.852615 | 3.480733 | 2.713015 | −0.22912 | −2.0043 | −0.69921 | 0.6347753 | −1.86841 | −1.08793 |
| 4.686197 | 4.999752 | 5.020012 | −0.23107 | −0.92487 | −0.61209 | 0.73689 | −0.3208 | −0.8862 |
| 0.162628 | −0.47851 | 0.577207 | −1.72139 | −1.09882 | −0.40671 | 0.565064 | −0.45378 | −0.76466 |
| −4.34306 | −2.56696 | −4.43024 | −1.2803 | 0.314511 | 0.558145 | −0.03673 | −0.25352 | −0.0918 |
| 1.395306 | 2.397084 | 0.725282 | 0.085808 | 0.456879 | −0.76659 | 0.722195 | 0.667138 | −1.09915 |
| 1.534188 | 2.81233 | 2.262165 | 0.038463 | 0.046801 | 0.655338 | 0.643474 | 0.757237 | −1.26364 |
| 4.403653 | 3.380728 | 2.933988 | 0.054007 | −0.66324 | 0.365502 | 0.534097 | 0.497352 | −0.52911 |
| 4.753636 | 4.689018 | 4.459714 | 0.009472 | 0.57047 | −0.84925 | 0.8618 | 0.756353 | −0.1815 |
| −0.61998 | 0.343889 | −0.14069 | −1.81933 | 0.339932 | 0.45126 | −0.87872 | −0.14241 | −1.07022 |
| −3.09943 | −3.29933 | −0.12005 | −0.81177 | −1.34576 | −0.35308 | 0.785952 | 0.817846 | 0.998938 |
| 2.128556 | 2.322421 | 1.823127 | −0.45072 | −1.0943 | 0.04527 | 1.089347 | 0.547119 | −1.11858 |
| 1.222062 | 2.309211 | 1.954408 | −0.82505 | −0.04856 | 0.811424 | 0.943053 | 0.806506 | −0.46843 |
| 3.974758 | 5.180598 | 4.924648 | −0.15758 | −1.09899 | −0.36398 | −0.14212 | −0.19413 | 1.07302 |
| 3.311061 | 4.635536 | 4.926917 | −0.50567 | −0.22342 | 0.514798 | −0.71394 | 0.782028 | 1.093496 |
| −0.74758 | 0.103346 | 0.296609 | −1.29164 | 0.090747 | 0.241204 | −0.75044 | 0.355101 | −0.89061 |

Example 4

Example of Generating Input Functions by Manual Operation

It has been discussed earlier that the sample identification device according to the present invention did not always require a pump for providing the sample to the chemical sensor, instruments for controlling flow rates thereof, and so forth. Moreover, it has also been discussed in general terms that any of a source of the sample and the chemical sensor might be held at a proper position by hand instead of completely fixing a positional relationship therebetween with a fixture or the like, and that the input function might be optimized for example by moving the hand or the sample when appropriate, and furthermore, that these measures were sufficiently practical. Now, a specific example of a mode of generating the input function by a manual operation will be described.

Figure 8:
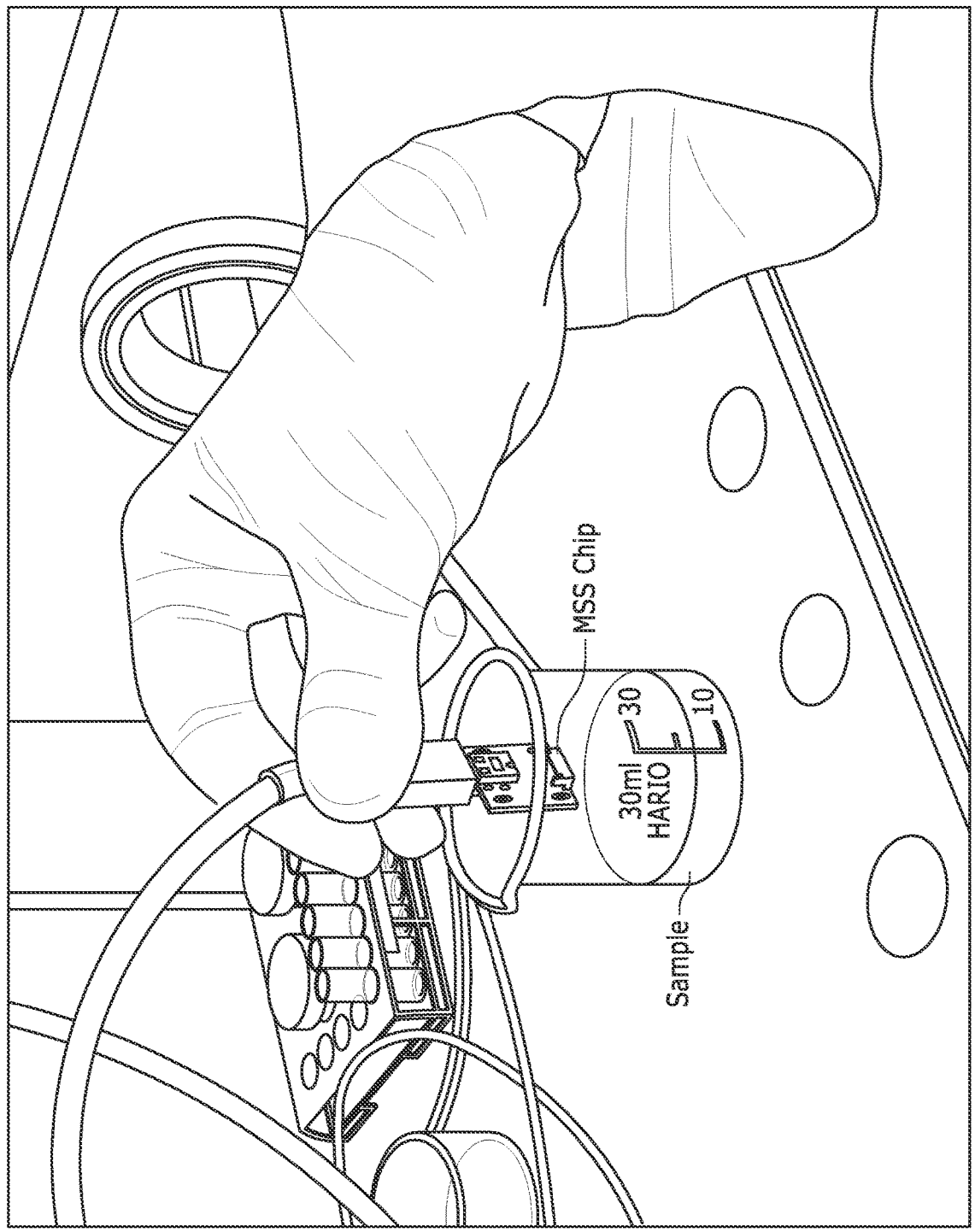
FIG. 8 is a photograph showing an example of an aspect in which an input function is generated by a manual operation.

FIG. 8 shows an example of an aspect designed to generate an input function as appropriate by moving the hand holding the chemical sensor. Here, a beaker is prepared which contains any one of liquids including, but without limitation to, water, ethanol, hexane, benzene, ethyl acetate, tetrahydrofuran, and the like. These liquids may evaporate and exist in the beaker or above the beaker at temporally and spatially heterogeneous concentrations. The chemical sensor, in which the four-channel MSS chip as used in the above-described example is fitted to a tip end, is moved by hand. Accordingly, the chemical sensor is swung in an upper space inside the beaker or moved up and down between this upper space and an external space further above the beaker. Thus, the MSS chip is moved inside the space or spaces having unevenness in the concentration of the vapor of the sample. In this way, the change in concentration of the vapor of the sample, which is equivalent to the case of changing the concentration of the vapor of the sample by providing the sample to the MSS chip using the pump and the like, occurs on a surface of the MSS chip.

While the vapor obtained by the evaporation of the liquid was provided as the sample to the chemical sensor in the aspect shown in FIG. 8, it is of course possible to provide a sample which is in a gas state from the beginning. In the latter case, it is also possible to generate the input functions by conducting a moving operation as appropriate, such as an operation to shake sensor chip portions of the chemical sensor around an outlet of the sample gas, for instance. Meanwhile, the chemical sensor was made freely movable in this aspect by fitting the chemical sensor to a flexible cable. Instead, a portion around the outlet of the sample gas may be formed from a flexible tube and the like so as to make the outlet easily movable, for instance. In this way, the outlet of the sample gas may be moved in the vicinity of each sensor chip of the chemical sensor or a direction of ejection of the sample gas may be changed instead of moving the chemical sensor (or at the same time as the movement of the chemical sensor).

In the meantime, the input functions generated by the aforementioned manual operation preferably comply with the principle of the sample identification method of the present invention described earlier, such that the functions include the frequency components in a certain range, and the like. As for the adjustment of the manual operation as to how to move the hand in order to generate an appropriate function can be learned relatively easily by carrying out actual measurements several times. Alternatively, it is also easily possible to assist an untrained operator by judging whether or not a manual operation is inappropriate based on a change in signals outputted from the chemical sensor while conducting the manual operation, and giving a warning to the operator by using a result of the judgment, and the like.

INDUSTRIAL APPLICABILITY

As described above, according to the present invention, in a measurement of various samples such as a gas measurement using a chemical sensor provided with multiple channels having different characteristics, it is possible to identify a sample only from responses of sensor signals without controlling or monitoring a change in sample introduction with time. Thus, it is not necessary to provide components such as pumps, mass flow controllers, flowmeters, and the like for controlling and monitoring the change in sample introduction with time, so that significant reduction in size of a measurement system can be realized. Meanwhile, the analysis method provided by the present invention is designed to identify an unknown sample by comparing measurement data of the unknown sample with measurement data of a known sample. Accordingly, accuracy of identification is improved more as an amount of the data of known samples (the training data) is larger. As a consequence, it is possible to identify the sample at high accuracy by establishing an environment accessible to a large amount of training data through a network while saving the training data on a cloud storage and so forth.

Therefore, according to the present invention, it is possible to identify a sample only by using a simple and small measurement system that does not need to control or monitor introduction of the sample. Moreover, accumulation of a large amount of training data and access to a database thereof are enabled in combination with cloud computing and the like, whereby accuracy of identification can be dramatically improved. Thus, the present invention is expected to be applied to wide fields including food, safety, environment, medical care, and the like.

What is claimed is:

1. A sample identification method using a chemical sensor, comprising:
    inputting an unknown sample, according to an identical time-varying first function, to a chemical sensor comprising a plurality of channels each having a peculiar transfer function, thereby obtaining, from the plurality of channels, a plurality of time-varying sensor signals each descriptive of the unknown sample through the corresponding transfer function;
    inputting a known sample, according to an identical time-varying second functions, to the same chemical sensor comprising the plurality of same channels each having the same corresponding transfer function, thereby obtaining, from the plurality of channels, a plurality of time-varying sensor signals each descriptive of the known sample through the corresponding transfer function;
    performing one of a first comparison and a second comparison, wherein the first comparison (a) determines a relationship between a sensor signal descriptive of the unknown sample from a respective at least some channels and a sensor signal descriptive of the known sample from the corresponding channel, and (b) compares a determined relationship with another determined relationship among at least some of the determined relationships, and
    the second comparison (a) determines a relationship between a sensor signal descriptive of the unknown sample from one channel among at least some of the channels and a sensor signal descriptive of the unknown sample from another channel from the at least some of the channels, (b) similarly determines a relationship between a sensor signal descriptive of the known sample from one channel among the at least some of the channels and a sensor signal descriptive of the known sample from another channel from the at least some of the channels, and (c) compares a respective at least some of the determined relationships between sensor signals descriptive of the unknown sample with the corresponding, determined relationship between sensor signals descriptive of the known sample; and
    estimating the unknown sample to be the known sample, based on similarity between the relationships compared in one of the first and the second comparisons.

2. The sample identification method using a chemical sensor according to claim 1, wherein each of the channels of the chemical sensor is configured to describe a sensor signal as a function of a multiplication or an addition of an input function of a channel and a transfer function (h) of the channel.

3. The sample identification method using a chemical sensor according to claim 1, wherein the sensor signals descriptive of the unknown sample and the sensor signals descriptive of the known samples are expressed by a formula (1) below using the transfer functions for the plurality of channels, $$y_{q,c}(t) = h_{q,c}(t) * x_q(t) \qquad (1),$$

where $x_q(t)$ represents: one of the first function when the unknown sample is sensed, and the second function when the known ample is sensed, both being expressed as a function of time; $y_{q,c}(t)$ represents one of the sensor signals descriptive of the unknown sample and the sensor signals descriptive of the known sample, both being expressed as a function of time; $h_{q,c}(t)$ represents the transfer functions expressed as a function of time; a suffix q is used to distinguish the unknown sample and the known sample; a number "c" is used to identify a channel within a range from 1 to C, and a symbol "*" represents a convolution operation, and each of the first and second comparisons comprises comparing the formula (1) broken down into a number (C) of polynomials in which the suffix q identifies the unknown sample, and the formula (1) broken down into the number (C) of polynomials in which the suffix q identifies the known sample, in order to determine whether or not the transfer function in the formula (1) in which the suffix q identifies the unknown sample and the transfer function in the formula (1) in which the suffix q identifies the known sample are identical to each other.

4. The sample identification method using a chemical sensor according to claim 3, further including transforming the formula (1) into polynomials expressed by a formula (2) shown below that includes a multiplication of H and X:

$$Y=HX \qquad (2),$$

where X and Y are a collection of inputs to and a collection of sensor signals from the channel, respectively, and H is a collection of variables or constants corresponding to the transfer functions defining the relationship between X and Y.

5. The sample identification method using a chemical sensor according to claim 4, wherein in the first comparison comprises, determining a relationship between a sensor signal descriptive of the unknown sample and a sensor signal descriptive of the known sample comprises determining a ratio between a sensor signal descriptive of the unknown sample and a sensor signal descriptive of the known sample comprises determining; and comparing a determined relationship with another determined relationship comprises comparing a determined ratio with another determined ratio.

6. The sample identification method using a chemical sensor according to claim 4, wherein in the second comparison comprises, determining a relationship between a sensor signal descriptive of the unknown sample from one channel and a sensor signal descriptive of the unknown sample from another channel comprises determining a ratio between a sensor signal descriptive of the unknown sample from one channel and a sensor signal descriptive of the unknown sample from another channel;

determining a relationship between a sensor signal descriptive of the known sample from one channel and a sensor signal descriptive of the known sample from another channel comprises determining a ratio between a sensor signal descriptive of the known sample from one channel and a sensor signal descriptive of the known sample from another channel; and comparing a respective at least some of the determined relationships between sensor signals descriptive of the unknown sample with the corresponding, determined relationship between sensor signals descriptive of the known sample comprises comparing a respective at least some of the determined ratios between sensor signals descriptive of the unknown sample with the corresponding, determined ratio between sensor signals descriptive of the known sample.

7. The sample identification method using a chemical sensor according to claim 4, wherein transforming the formula (1) into polynomials comprises transforming the convolution operation in the formula (1) into a multiplication of matrices or vectors.

8. The sample identification method using a chemical sensor according to claim 4, wherein transforming the formula (1) into polynomials comprises transforming the formula (1) from a function in a time domain into a function in a frequency domain.

9. The sample identification method using a chemical sensor according to claim 1, wherein the first function and the second function are determined independently of each other.

10. The sample identification method using a chemical sensor according to claim 1, wherein at least one of the first function and the second function is a random function.

11. The sample identification method using a chemical sensor according to claim 1, wherein the sensor signals descriptive of the unknown sample and the sensor signals descriptive of the known sample are subjected to time discretization.

12. A sample evaluation method, comprising:

providing a sensor having a plurality of channels, wherein a behavior of each channel is expressed by a combination of a uniform sample input function and a transfer function that is unique to each channel and responds differently to a different sample;

subjecting a known sample to the sensor and obtaining a first response of a transfer function to the known sample with respect to a respective at least some of the channels;

subjecting an unknown sample to the sensor and obtaining a second response of a transfer function to the unknown sample with respect to the respective at least some of the channels;

performing one of a first comparison and a second comparison to evaluate whether the unknown sample is identical to the known sample, wherein the first comparison comprises:

relating a first response and a second response of a corresponding channel to determine a first relationship between them with respect to a respective at least some of the channels subjected to with the unknown sample and the known sample; and comparing a determined first relationship and another determined first relationship with respect to a respective at least some of the determined first relationships to determine correlations among the at least some of the determined first relationships;

the second comparison comprises:

relating a first response to another first response to determine a second relationship between a pair of channels with respect to a respective at least some of the channels subjected to with the identified sample;

relating a second response to another second response to determine a third relationship between a pair of channels with respect to the respective at least some of the channels subjected to with the unknown sample; and comparing a determined second relationship and a determined third relationship of a corresponding pair of channels to determine correlations among at least some of pairs of the channels; and evaluating the correlations from one of the first and second comparisons to determine whether the unknown sample is identical to the known sample.

13. The sample evaluation method according to claim 12, wherein comparing comprises comparing in one of a time domain and a frequency domain.

\* \* \* \* \*